US012419948B2

(12) United States Patent
Sabeti et al.

(10) Patent No.: US 12,419,948 B2
(45) Date of Patent: Sep. 23, 2025

(54) IMMUNOGENIC COMPOSITIONS AND USE THEREOF

(71) Applicants: THE BROAD INSTITUTE, INC., Cambridge, MA (US); PRESIDENT AND FELLOWS OF HARVARD COLLEGE, Cambridge, MA (US); THE GENERAL HOSPITAL CORPORATION, Boston, MA (US); TRUSTEES OF BOSTON UNIVERSITY, Boston, MA (US)

(72) Inventors: Pardis Sabeti, Cambridge, MA (US); Shira Weingarten-Gabbay, Cambridge, MA (US); Susan Klaeger, Cambridge, MA (US); Jenn Abelin, Cambridge, MA (US); Mohsan Saeed, Boston, MA (US); Nir Hacohen, Boston, MA (US); Siranush Sarkizova, Cambridge, MA (US); Steven Carr, Cambridge, MA (US); Karl Clauser, Cambridge, MA (US)

(73) Assignees: The Broad Institute, Inc., Cambridge, MA (US); President and Fellows of Harvard College, Cambridge, MA (US); The General Hospital Corporation, Boston, MA (US); Trustees of Boston University, Boston, MA (US)

( * ) Notice: Subject to any disclaimer, the term of this patent is extended or adjusted under 35 U.S.C. 154(b) by 169 days.

(21) Appl. No.: 17/463,429

(22) Filed: Aug. 31, 2021

(65) Prior Publication Data

US 2022/0088180 A1 Mar. 24, 2022

Related U.S. Application Data

(60) Provisional application No. 63/186,742, filed on May 10, 2021, provisional application No. 63/072,898, filed on Aug. 31, 2020.

(51) Int. Cl.

| | |
|---|---|
| ***A61K 39/215*** | (2006.01) |
| ***A61K 39/00*** | (2006.01) |
| ***A61K 45/06*** | (2006.01) |
| ***A61P 31/14*** | (2006.01) |
| ***G01N 33/569*** | (2006.01) |
| ***G01N 33/68*** | (2006.01) |

(52) U.S. Cl.

CPC ............ *A61K 39/215* (2013.01); *A61K 45/06* (2013.01); *A61P 31/14* (2018.01); *G01N 33/56983* (2013.01); *G01N 33/6818* (2013.01); *A61K 2039/53* (2013.01); *G01N 2333/165* (2013.01); *G01N 2800/26* (2013.01)

(58) Field of Classification Search

CPC ....... A61K 39/215; A61K 39/12; A61P 31/14; G01N 33/56983; G01N 2800/26; G01N 2333/70539; G01N 2500/10; C12N 2770/20034

See application file for complete search history.

(56) References Cited

U.S. PATENT DOCUMENTS

| | | | |
|---|---|---|---|
| 8,278,036 | B2 | 10/2012 | Kariko et al. |
| 8,404,658 | B2 | 3/2013 | Hajjar et al. |
| 8,454,972 | B2 | 6/2013 | Nabel et al. |
| 8,691,966 | B2 | 4/2014 | Kariko et al. |
| 8,748,089 | B2 | 6/2014 | Kariko et al. |
| 9,750,824 | B2 | 9/2017 | Kariko et al. |
| 9,868,692 | B2 | 1/2018 | Benenato |
| 10,064,959 | B2 | 9/2018 | Schrum et al. |
| 10,232,055 | B2 | 3/2019 | Kariko et al. |
| 10,266,485 | B2 | 4/2019 | Benenato |
| 10,272,150 | B2 | 4/2019 | Ciaramella et al. |
| 10,442,756 | B2 | 10/2019 | Benenato et al. |
| 10,577,403 | B2 | 3/2020 | De Fougerolles et al. |
| 10,702,600 | B1 | 7/2020 | Ciaramella et al. |
| 10,703,789 | B2 | 7/2020 | De Fougerolles et al. |
| 2013/0197068 | A1 | 8/2013 | Kariko et al. |
| 2013/0261172 | A1 | 10/2013 | Kariko et al. |
| 2015/0038558 | A1 | 2/2015 | Kariko et al. |
| 2017/0043037 | A1 | 2/2017 | Kariko et al. |

(Continued)

FOREIGN PATENT DOCUMENTS

| | | | |
|---|---|---|---|
| WO | 2013/151663 | A1 | 10/2013 |
| WO | 2013/151664 | A1 | 10/2013 |

(Continued)

OTHER PUBLICATIONS

TopuzoĞullari M, Acar T, Pelit Arayici P, UÇar B, UĞurel E, Abamor EŞ, ArasoĞlu T, Turgut-Balik D, Derman S. An insight into the epitope-based peptide vaccine design strategy and studies against COVID-19. Turk J Biol. Jun. 21, 2020;44(3):215-227. (Year: 2020).*

Jiang HW, Zhang HN, Meng QF, Xie J, Li Y, Chen H, Zheng YX, Wang XN, Qi H, Zhang J, Wang PH, Han ZG, Tao SC. SARS-CoV-2 Orf9b suppresses type I interferon responses by targeting TOM70. Cell Mol Immunol. Sep. 2020;17(9):998-1000. doi: 10.1038/s41423-020-0514-8. Epub Jul. 29, 2020. (Year: 2020).*

Olvera A, Noguera-Julian M, Kilpelainen A, Romero-Martín L, Prado JG, Brander C. SARS-CoV-2 Consensus-Sequence and Matching Overlapping Peptides Design for COVID19 Immune Studies and Vaccine Development. Vaccines (Basel). Aug. 6, 2020;8(3):444. (Year: 2020).*

(Continued)

*Primary Examiner* — Nicole Kinsey White
*Assistant Examiner* — Ruixue Wang
(74) *Attorney, Agent, or Firm* — F. Brent Nix, Esq.; Johnson, Marcou, Isaacs & Nix, LLC

(57) ABSTRACT

Immunogenic compositions comprising one or more polypeptides, wherein the one or more polypeptides: is capable of binding to Major Histocompatibility Complex (MHC) class I, and is derived from one or more proteins of SARS-COV-2. Also provided include methods of treating and preventing diseases using the immunogenic compositions.

29 Claims, 56 Drawing Sheets

Specification includes a Sequence Listing.

(56) References Cited

U.S. PATENT DOCUMENTS

| | | | |
|---|---|---|---|
| 2018/0303925 A1 | 10/2018 | Weissman et al. |
| 2019/0274968 A1 | 9/2019 | Weissman et al. |
| 2020/0030460 A1 | 1/2020 | Kariko et al. |
| 2020/0276300 A1 | 9/2020 | Friedman et al. |

FOREIGN PATENT DOCUMENTS

| | | | |
|---|---|---|---|
| WO | 2013/151667 A1 | 10/2013 | |
| WO | 2013/151669 A1 | 10/2013 | |
| WO | 2013/151671 A1 | 10/2013 | |
| WO | 2013/151668 A3 | 12/2013 | |
| WO | 2013/151736 A3 | 12/2013 | |
| WO | 2013/151666 A3 | 1/2014 | |
| WO | 2013/151665 A3 | 2/2014 | |
| WO | 2013/151670 A3 | 2/2014 | |
| WO | 2013/151672 A3 | 3/2014 | |
| WO | 2016/176330 A1 | 11/2016 | |
| WO | 2018/081638 A1 | 5/2018 | |
| WO | 2020/205793 A1 | 10/2020 | |
| WO | WO-2021188969 A2 * | 9/2021 | ............ A61K 39/12 |

OTHER PUBLICATIONS

Poran et al. Sequence-based prediction of SARS-CoV-2 vaccine targets using a mass spectrometry-based bioinformatics predictor identifies immunogenic T cell epitopes. Genome Med. Aug. 13, 2020;12(1):70. (Year: 2020).*
Abelin, et al., "Defining HLA-Il Ligand Processing and Binding Rules with Mass Spectrometry Enhances Cancer Epitope Prediction", Immunity, vol. 51, Oct. 15, 2019, 766-779.
Abelin, et al., "Mass Spectrometry Profiling of HLA-Associated Peptidomes in Mono-allelic Cells Enables More Accurate Epitope Prediction", Immunity, vol. 46, 2017, 315-326.
Acharya, et al., "Dysregulation of Type I Interferon Responses in COVID-19", Nature Reviews Immunology, vol. 20, Jul. 2020, 397-398.
Altman, et al., "MHC-Peptide Tetramers to Visualize Antigen-Specific T Cells", Current Protocols in Immunology, 2003, 17.3.1-17.3.33.
Altmann, et al., "SARS-CoV-2 T cell Immunity: Specificity, Function, Durability, and Role in Protection", Science Immunology, Jul. 17, 2020, 1-7.
Aran, et al., "Reference-Based Analysis of Lung Single-Cell Sequencing Reveals a Transitional Profibrotic Macrophage", Nature Immunology, vol. 20, Feb. 2019, 163-172.
Bassani-Sternberg, et al., "Unsupervised HLA Peptidome Deconvolution Improves Ligand Prediction Accuracy and Predicts Cooperative Effects in Peptide-HLA Interactions", The Journal of Immunology, vol. 197, Aug. 10, 2016, 1-8.
Burdette, et al., "Sting is a Direct Innate Immune Sensor of Cyclic di-GMP", Nature, vol. 478, Oct. 27, 2011, 515-518.
Callaway, E., "The Race for Coronavirus Vaccines: a Graphical Guide", Nature, vol. 580, Apr. 30, 2020, 576-577.
Campbell, et al., "Prediction of SARS-CoV-2 Epitopes Across 9360 HLA Class I Alleles", BioRxiv, 2020, 12 pages.
Chen, et al., "Pervasive Functional Translation of Noncanonical Human Open Reading Frames", Science, vol. 367, Mar. 6, 2020, 1-7.
Chen, et al., "SARS-CoV-2 Desensitizes Host Cells to Interferon Through Inhibition of the JAK-STAT Pathway", BioRxiv, 2020, 50 pages.
Cheng, et al., "Relationship Between the Inhibition Constant (K1) and the Concentration of Inhibitor which Causes 50 Percent Inhibition (150) of an Enzymatic Reaction", Biochemical Pharmacology, vol. 22, 1973, 3099-3108.
Chong, et al., "High-throughput and Sensitive Immunopeptidomics Platform Reveals Profound Interferony-Mediated Remodeling of the Human Leukocyte Antigen (HLA) Ligandome", Molecular & Cellular Proteomics, vol. 17, No. 3, 2018, 533-548.
Croft, et al., "Kinetics of Antigen Expression and Epitope Presentation during Virus Infection", Plos, vol. 9, No. 1, e1003129, Jan. 31, 2013, 1-13.
Dan, et al., "Immunological Memory to SARS-CoV-2 Assessed for up to Eight Months After Infection", BioRxiv, Dec. 18, 2020, 47 pages.
Dawson, et al., "Ramifications of HLA Class I Polymorphism and Population Genetics for Vaccine Development", Genetic Epidemiology, vol. 20, 2001, 87-106.
Demmers, et al., "Pre-Fractionation Extends but also Creates a Bias in the Detectable HLA Class I Ligandome", Journal of Proteome Research, vol. 18, 2019, 1634-1643.
Dominguez Andres, et al., "SARS-CoV-2 ORF9c is a Membrane-Associated Protein that Suppresses Antiviral Responses in Cells", BioRxiv, 2020, 45 pages.
Dutta, et al., "The Nucleocapsid Protein of SARS-CoV-2: a Target for Vaccine Development", Journal of Virology, vol. 94, No. 13, e00647-20, Jul. 2020, 1-2.
Erhard, et al., "Improved Ribo-seq Enables Identification of Cryptic Translation Events", Nature Methods, 2018, pp. 1-10.
Ferretti, et al., "Unbiased Screens Show CD8+ T Cells of COVID-19 Patients Recognize Shared Epitopes in SARS-CoV-2 that Largely Reside outside the Spike Protein", Immunity, vol. 53, Nov. 17, 2020, 1095-1107.
Finkel, et al., "Comprehensive Annotations of Human Herpesvirus 6A and 6B Genomes Reveal Novel and Conserved Genomic Features", eLife, vol. 9, No. e50960, 2020, 1-25.
Finkel, et al., "The Coding Capacity of SARS-CoV-2", BioRxiv, 2020, 35 pages.
Girdlestone, J., "Regulation of HLA class I Loci by Interferons", Immunobiology, vol. 193, 1995, 229-237.
Gordon, et al., "A SARS-CoV-2 Protein Interaction Map Reveals Targets for Drug Repurposing", Nature, vol. 583, Jul. 16, 2020, 459-468.
Gragert, et al., "Six-Locus High Resolution HLA Haplotype Frequencies Derived from Mixed-Resolution DNA Typing for the Entire US Donor Registry", Human Immunology, vol. 74, 2013, 1313-1320.
Grifoni, et al., "A Sequence Homology and Bioinformatic Approach Can Predict Candidate Targets for Immune Responses to SARS-CoV-2", Cell Host & Microbe, vol. 27, Apr. 8, 2020, 671-680.
Grifoni, et al., "Targets of T Cell Responses to SARS-CoV-2 Coronavirus in Humans with COVID-19 Disease and Unexposed Individuals", Cell, vol. 181, Jun. 25, 2020, 1489-1501.
Gulukota, et al., "Two Complementary Methods for Predicting Peptides Binding Major Histocompatibility Complex Molecules", Journal of Molecular Biology, vol. 267, 1997, 1258-1267.
Habel, et al., "Suboptimal SARS-CoV-2-Specific CD8+ T Cell Response Associated with the Prominent HLA-A*02:01 Phenotype", PNAS, vol. 117, No. 39, Sep. 29, 2020, 24384-24391.
Hansen, et al., "MHC Class I Antigen Presentation: Learning from Viral Evasion Strategies", Nature Reviews Immunology, vol. 9, Jul. 2009, 503-513.
Hickman, et al., "Influenza A Virus Negative Strand RNA is Translated for CD8+ T Cell Immunosurveillance", The Journal of Immunology, vol. 201, 2018, 1222-1228.
Hie, et al., "Efficient Integration of Heterogeneous Single-Cell Transcriptomes Using Scanorama", Nature Biotechnology, Vo. 37, No. 6, Jun. 2019, 22 pages.
Ingolia, et al., "Genome-Wide Analysis in Vivo of Translation with Nucleotide Resolution Using Ribosome Profiling", Science, vol. 324, No. 5924, Apr. 10, 2009, 12 pages.
Ingolia, et al., "Ribosome Profiling of Mouse Embryonic Stem Cells Reveals the Complexity and Dynamics of Mammalian Proteomes", Cell, vol. 147, Nov. 11, 2011, 789-802.
Ingolia, et al., "Ribosome Profiling Reveals Pervasive Translation Outside of Annotated Protein-Coding Genes", Cell Reports, vol. 8, Sep. 11, 2014, 1365-1379.
Jackson, et al., "An mRNA Vaccine Against SARS-CoV-2—Preliminary Report", The New England journal of Medicine, Jul. 18, 2020, 1-12.

(56) References Cited

OTHER PUBLICATIONS

Javitt, et al., "Pro-Inflammatory Cytokines Alter the Immunopeptidome Landscape by Modulation of HLA-B Expression", Frontiers in Immunology, vol. 10, No. 141, Feb. 18, 2019, 1-16.
Kared, et al., "SARS-CoV-2-Specific CD8+ T Cell Responses in Convalescent COVID-19 Individuals", The Journal of Clinical Investigation, vol. 131, No. 5, e145476, 2021, 1-13.
Keskin, et al., "Physical Detection of Influenza A Epitopes Identifies a Stealth Subset on Human Lung Epithelium Evading Natural CD8 Immunity", PNAS, vol. 112, No. 7, Feb. 17, 2015, 2151-2156.
Ketteler, R., "On Programmed Ribosomal Frameshifting: the Alternative Proteomes", Frontiers in Genetics, vol. 3, No. 242, Nov. 19, 2012, 1-10.
Kim, et al., "The Architecture of SARS-CoV-2 Transcriptome", Cell, vol. 181, May 14, 2020, 914-921.
Konstantinidou, et al., "Repurposing Current Therapeutic Regimens Against SARS-CoV-2 (Review)", Experimental and Therapeutic Medicine, vol. 20, 2020, 1845-1855.
Angmead, et al., "Ultrafast and Memory-Efficient Alignment of Short DNA Sequences to the Human Genome", Genome Biology, vol. 10, No. R25, Mar. 4, 2009, 10 pages.
Le, et al., "The COVID-19 Vaccine Development Landscape", Nature Reviews Drug Discovery, vol. 19, May 2020, 305-306.
Le Bert, et al., "SARS-CoV-2-Specific T Cell Immunity in Cases of COVID-19 and SARS, and Uninfected Controls", Nature, vol. 584, Aug. 20, 2020, 457-462.
Ledford, Heidi, "How 'Killer' T Cells Could Boost COVID Immunity in Face of New Variants", Nature, 2021.
Lu, et al., "Genomic Characterisation and Epidemiology of 2019 Novel Coronavirus: Implications for Virus Origins and Receptor Binding", Lancet, vol. 395, 2020, 565-574.
Lunemann, et al., "Interactions Between KIR3DS1 and HLA-F Activate Natural Killer Cells to Control HCV Replication in Cell Culture", Gastroenterology, vol. 155, 2018, 1366-1371.
Maness, et al., "CD8+ T Cell Recognition of Cryptic Epitopes is a Ubiquitous Feature of AIDS Virus Infection", Journal of Virology, vol. 84, No. 21, Nov. 2010, pp. 11569-11574.
Marsh, et al., "Nomenclature for Factors of the HLA System, 2010", Tissue Antigens, vol. 75, 2010, 291-455.
McMurtrey, et al., "Epitope Discovery in West Nile Virus Infection: Identification and Immune Recognition of Viral Epitopes", PNAS, vol. 105, No. 8, Feb. 26, 2008, 2981-2986.
Moderbacher, et al., "Antigen-Specific Adaptive Immunity to SARS-CoV-2 in Acute COVID-19 and Associations with Age and Disease Severity", Cell, vol. 183, Nov. 12, 2020, 996-1012.
Monteil, et al., "Inhibition of SARS-CoV-2 Infections in Engineered Human Tissues Using Clinical-Grade Soluble Human ACE2", Cell, vol. 181, May 14, 2020, 905-913.
Mulligan, et al., "Phase I/II Study of COVID-19 RNA Vaccine BNT162b1 in Adults", Nature, Aug. 12, 2020, 1-5.
Neefjes, et al., "Towards a Systems Understanding of MHC Class I and MHC Class II Antigen Presentation", Nature Reviews Immunology, vol. 11, Dec. 2011, 823-836.
Nguyen, et al., "Human Leukocyte Antigen Susceptibility Map for Severe Acute Respiratory Syndrome Coronavirus 2", Journal of Virology, vol. 94, No. 13, e00510-20, Jul. 2020, 1-12.
O'Donnell, et al., "MHCflurry 2.0: Improved Pan-Allele Prediction of MHC Class I-Presented Peptides by Incorporating Antigen Processing", Cell Systems, vol. 11, Jul. 22, 2020, 42-48.
Ouspenskaia, et al., "Thousands of Novel Unannotated Proteins Expand the MHC I Immunopeptidome in Cancer", BioRxiv, 2020, 64 pages.
Poran, et al., "Sequence-Based Prediction of SARS-CoV-2 Vaccine Targets Using a Mass Spectrometry-Based Bioinformatics Predictor Identifies Immunogenic T Cell Epitopes", Genome Medicine, vol. 12, No. 70, 2020, 1-15.
Puelles, et al., "Multiorgan and Renal Tropism of SARS-CoV-2", The New England Journal of Medicine, May 13, 2020, 1-3.
Redd, et al., "CD8+ T Cell Responses in COVID-19 Convalescent Individuals Target Conserved Epitopes From Multiple Prominent SARS-CoV-2 Circulating Variants", MedRxiv, 2021, 10 pages.
Rucevic, et al., "Analysis of Major Histocompatibility Complex-Bound HIV Peptides Identified from Various Cell Types Reveals Common Nested Peptides and Novel T Cell Responses", Journal of Virology, vol. 90, No. 9, Oct. 2016, 8605-8620.
Ruiz Cuevas, et al., "Most Non-Canonical Proteins Uniquely Populate the Proteome or Immunopeptidome", Cells Reports, vol. 34, No. 108815, Mar. 9, 2021, 1-15.
Sarkizova, et al., "A Large Peptidome Dataset Improves HLA Class I Epitope Prediction Across Most of The Human Population", Nature Biotechnology, vol. 38, No. 2, Feb. 2020, 34 pages.
Schellens, et al., "Measles Virus Epitope Presentation by HLA: Novel Insights into Epitope Selection, Dominance, and Microvariation", Frontiers in Immunology, vol. 6, No. 546, Nov. 2, 2015, 1-11.
Schmidt, et al., "The SARS-CoV-2 RNA-Protein Interactome in Infected Human Cells", Nature Microbiology, vol. 6, Dec. 21, 2020, 339-353.
Schwanhausser, et al., "Global Quantification of Mammalian Gene Expression Control", Nature, vol. 473, May 19, 2011, 337-342.
Sekine, et al., "Robust T Cell Immunity in Convalescent Individuals with Asymptomatic or Mild COVID-19", Cell, vol. 183, Oct. 1, 2020, 158-168.
Shomuradova, et al., "SARS-CoV-2 Epitopes are Recognized by a Public and Diverse Repertoire of Human T Cell Receptors", Immunity, vol. 53, Dec. 15, 2020, 1245-1257.
Sidney, et al., "Measurement of MHC/Peptide Interactions by Gel Filtration or Monoclonal Antibody Capture", Current Protocols in Immunology, Unit 18.3, Feb. 2013, 18.3.1-18.3.36.
Solberg, et al., "Balancing Selection and Heterogeneity Across the Classical Human Leukocyte Antigen Loci: a Meta-Analytic Review of 497 Population Studies", Human Immunology, vol. 69, 2008, 443-464.
Sonenberg, et al., "Regulation of Translation Initiation in Eukaryotes: Mechanisms and Biological Targets", Cell, vol. 136, Feb. 20, 2009, 731-745.
Starck, et al., "Nowhere to Hide: Unconventional Translation Yields Cryptic Peptides for Immune Surveillance", Immunological Reviews, vol. 272, 2016, 8-16.
Stern-Ginossar, et al., "Decoding Human Cytomegalovirus", Science, vol. 338, Nov. 23, 2012, 1088-1093.
Stukalov, et al., "Multilevel Proteomics Reveals Host Perturbations by SARS-CoV-2 and SARS-CoV", BioRxiv, 2020, 67 pages.
Su, et al., "Multi-Omics Resolves a Sharp Disease-State Shift between Mild and Moderate COVID-19", Cell, vol. 183, Dec. 10, 2020, 1479-1495.
Takagi, et al., "Identification of HLA-A*02:01-Restricted Candidate Epitopes Derived from the Non-Structural Polyprotein 1a of SARS-CoV-2 that may be Natural Targets of CD8+ T Cell Recognition in Vivo", Journal of Virology, vol. 95, No. 5, e01837-20, Mar. 2021, 1-16.
Tarke, et al., "Comprehensive Analysis of T Cell Immunodominance and Immunoprevalence of SARS-CoV-2 Epitopes in COVID-19 Cases", BioRxiv, 2020, 41 pages.
Tarke, et al., "Negligible Impact of SARS-CoV-2 Variants on CD4 + and CD8 + T Cell Reactivity in COVID-19 Exposed Donors and Vaccinees", BioRxiv, Mar. 1, 2021, 35 pages.
Ternette, et al., "Defining the HLA Class I-Associated Viral Antigen Repertoire from HIV-1-Infected Human Cells", European Journal of Immunology, vol. 46, 2016, 60-69.
Thompson, et al., "Tandem Mass Tags: A Novel Quantification Strategy for Comparative Analysis of Complex Protein Mixtures by MS/MS", Analytical Chemistry, vol. 75, No. 8, Apr. 15, 2003, 1895-1904.
Tyanova, et al., "The Perseus Computational Platform for Comprehensive Analysis of (Prote)omics Data", Nature Methods, Jun. 27, 2016, 1-10.
Van Dijk, et al., "Recovering Gene Interactions from Single-Cell Data Using Data Diffusion", Cell, vol. 174, Jul. 16, 2018, 716-729.

(56) References Cited

OTHER PUBLICATIONS

Wainwright, et al., "HLA-F is a Predominantly Empty, Intracellular, TAP-Associated MHC Class Ib Protein with a Restricted Expression Pattern", The Journal of Immunology, vol. 164, 2000, 319-328.
Weinberg, et al., "Vaccine Epidemiology: Efficacy, Effectiveness, and the Translational Research Roadmap", The Journal of Infectious Diseases, vol. 201, Jun. 1, 2010, 1607-1610.
Weingarten-Gabby, et al., "SARS-CoV-2 Infected Cells Present HLA-I Peptides from Canonical and Out-of-Frame ORFs", bioRxiv, 2020, 37 pages.
Weiskopf, et al., "Phenotype and Kinetics of SARS-CoV-2-Specific T Cells in COVID-19 Patients with Acute Respiratory Distress Syndrome", Science Immunology, Jun. 26, 2020, 1-14.
Wolf, et al., "SCANPY: Large-Scale Single-Cell Gene Expression Data Analysis", Genome Biology, vol. 19, No. 1, Feb. 2018, 6 pages.
Wu, et al., "A New Coronavirus Associated with Human Respiratory Disease in China", Nature, vol. 579, Mar. 12, 2020, 265-269.
Wu, et al., "Quantification of Epitope Abundance Reveals the Effect of Direct and Cross-Presentation on Influenza CTL Responses", Nature Communications, vol. 10, No. 2846, 2019, 1-14.
Yang, et al., "Defining Viral Defective Ribosomal Products: Standard and Alternative Translation Initiation Events Generate a Common Peptide from Influenza A Virus M2 and M1 mRNAs", The Journal of Immunology, vol. 196, Mar. 25, 2016, 1-10.
Zhou, et al., "Discovery of a Novel Coronavirus Associated with the Recent Pneumonia Outbreak in Humans and its Potential Bat Origin", BioRxiv, 2020, 18 pages.
Zhu, et al., "Induction of SARS-Nucleoprotein-Specific Immune Response by Use of DNA Vaccine", Immunology Letters, vol. 92, 2004, 237-243.

* cited by examiner

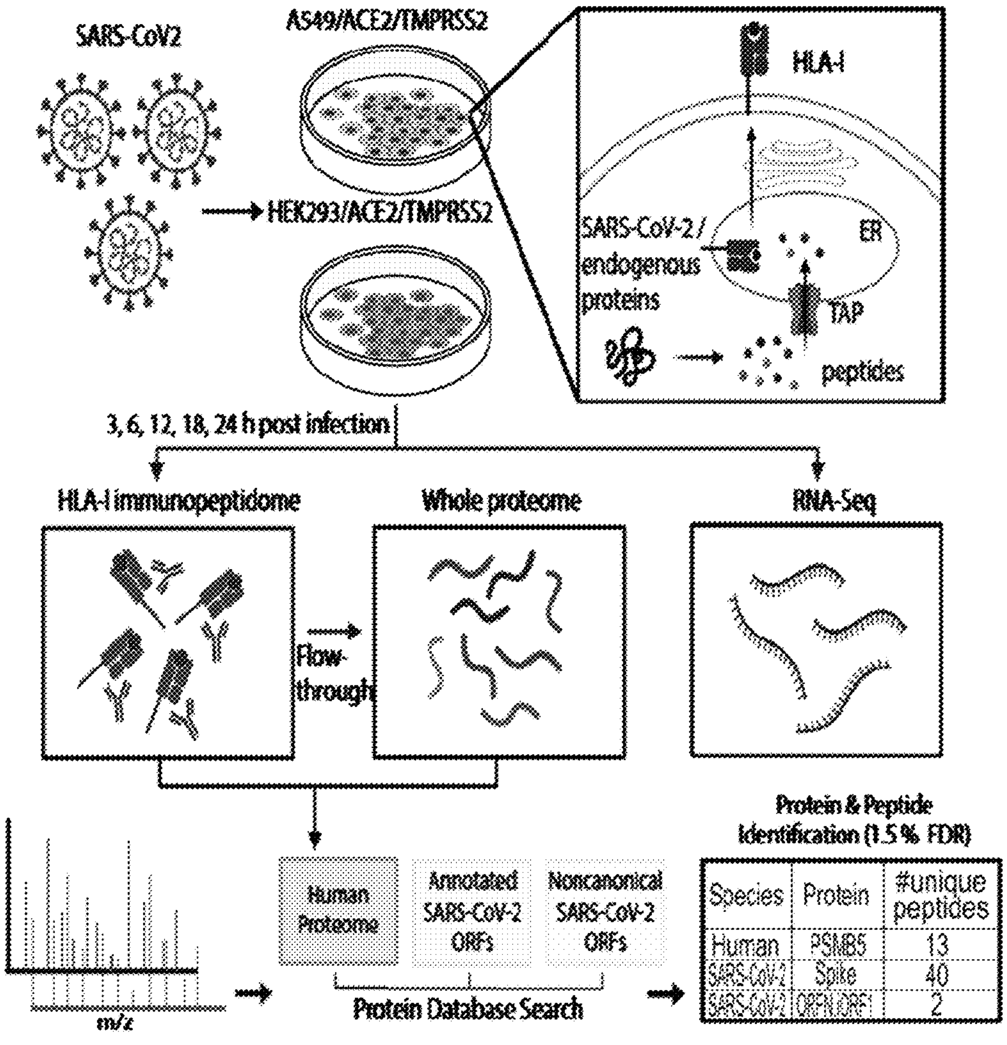
FIG. 1A
| Cell line | Allele | Allele frequency | Phenotypic coverage |
| --- | --- | --- | --- |
| HEK293 | A0201 | 15.28% | 28.23% |
| | B0702 | 4.11% | 8.04% |
| | C0702 | 13.10% | 24.49% |
| A549 | A2501 | 0.45% | 0.90% |
| | A3001 | 2.51% | 4.95% |
| | B1801 | 2.30% | 4.55% |
| | B4403 | 4.47% | 8.75% |
| | C1203 | 1.96% | 3.88% |
| | C1601 | 2.42% | 7.78% |
| Cell line | HLA-I locus | # Allele | Phenotypic coverage |
| --- | --- | --- | --- |
| A549 and HEK293 | A | 3 | 33.15% |
| | B | 3 | 20.57% |
| | C | 3 | 31.90% |
| | ABC | 9 | 63.84% |
FIG. 1B
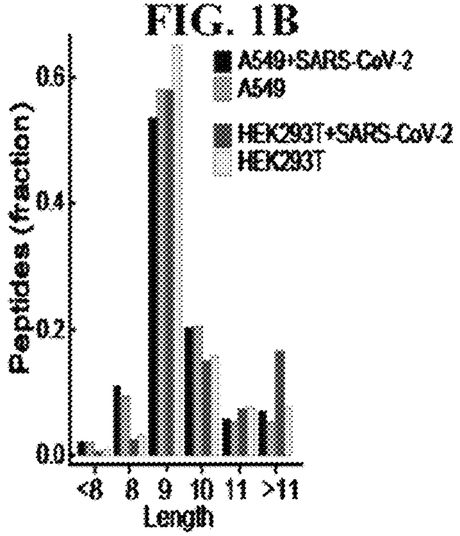
FIG. 1C

| Peptide | HLA Allele | Predicted score |
|---|---|---|
| SEQ ID NO: 4 MLLGSMLYM | A02:01 | 2.16 |
| SEQ ID NO: 221 MSRGSMLFT | A02:01 | 69.12 |
| SEQ ID NO: 6 GPMVLRGLIT | B07:02 | 2.12 |
| SEQ ID NO: 222 ALMERNDSIT | B07:02 | 38.19 |
| SEQ ID NO: 5 GLITLSYHL | A02:01 | 0.23 |
| SEQ ID NO: 223 DSITPSCPS | A02:01 | 91.1 |

| | peptide | viral protein | best predicted prank | best predicted allele | rank within all viral peptides | %rank within all viral proteins | rank within protein | %rank within viral protein | # of alleles with prank <=2 | all alleles with prank <=2 | SEQ ID NO: |
|---|---|---|---|---|---|---|---|---|---|---|---|
| A549 | VAISRILSY | M | 0.0007 | C1601 | 2 | 0.005 | 1 | 0.1171 | 2 | C1203,C1601 | 41 |
| | FAVDAAKAY | nsp10 | 0.0027 | C1601 | 8 | 0.020 | 1 | 0.1916 | 3 | A2501,C1203,C1601 | 28 |
| | FASEAARVV | nsp2 | 0.0049 | C1601 | 18 | 0.045 | 2 | 0.0794 | 2 | C1203,C1601 | 17 |
| | DEFVVVTV | ORF9b | 0.0083 | B1801 | 24 | 0.060 | 2 | 0.5650 | 2 | B1801,B4403 | 11 |
| | NAINVVIKV | S | 0.0180 | C1203 | 45 | 0.113 | 5 | 0.0981 | 2 | C1203,C1601 | 37 |
| | EIKESVQTF | nsp2 | 0.0184 | A2501 | 47 | 0.118 | 3 | 0.1191 | 1 | A2501 | 15 |
| | EEFEPSTQYEY | nsp3 | 0.0194 | B1801 | 49 | 0.123 | 18 | 0.2324 | 3 | A2501,B1801,B4403 | 20 |
| | SEFSSLPSY | nsp8 | 0.0246 | B1801 | 59 | 0.148 | 1 | 0.1319 | 2 | B1801,B4403 | 27 |
| | TVIEVQGY | nsp3 | 0.0528 | A2501 | 128 | 0.321 | 34 | 0.4389 | 1 | A2501 | 22 |
| | LATNNLVVM | nsp2 | 0.0848 | C1203 | 189 | 0.474 | 18 | 0.7149 | 2 | C1203,C1601 | 16 |
| | TTTIKPVTY | nsp3 | 0.0869 | C1601 | 196 | 0.492 | 51 | 0.6584 | 4 | A2501,B1801,C1203,C1601 | 21 |
| | EILDITPCSF | S | 0.0955 | A2501 | 210 | 0.527 | 32 | 0.6279 | 2 | A2501,B1801 | 33 |
| | TAQNSVRVL | nsp2 | 0.1829 | C1601 | 398 | 0.998 | 41 | 1.6283 | 2 | C1203,C1601 | 18 |
| | LEDKAFQL | ORF9b | 0.2740 | B1801 | 613 | 1.537 | 6 | 1.6949 | 2 | B1801,B4403 | 10 |
| | VGYLQPRTF | S | 0.6251 | C1601 | 1473 | 3.694 | 185 | 3.6303 | 1 | C1601 | 39 |
| | QLTPTWRVY | S | 0.7696 | C1601 | 1835 | 4.602 | 238 | 4.6703 | 3 | A2501,C1203,C1601 | 38 |
| | KNIDGYFKIY | S | 0.8731 | B1801 | 2074 | 5.201 | 265 | 5.2002 | 4 | B1801,B4403,C1203,C1601 | 36 |
| | EILDITPCSFG | S | 4.5200 | A2501 | 10633 | 26.666 | 1274 | 25.0000 | 0 | unassigned | 47 |
| HEK293T | YLFDESGEFKL | nsp3 | 0.0052 | A0201 | 6 | 0.015 | 1 | 0.0129 | 2 | A0201,C0702 | 25 |
| | KRVDWTIEY | nsp14 | 0.0180 | C0702 | 13 | 0.033 | 1 | 0.0482 | 1 | C0702 | 29 |
| | APHGHVMVEL | nsp1 | 0.1099 | B0702 | 95 | 0.238 | 3 | 0.4373 | 1 | B0702 | 14 |
| | IRQEEVQEL | ORF7a | 0.1322 | C0702 | 122 | 0.306 | 3 | 0.6667 | 1 | C0702 | 31 |
| | YLNSTNVTI | nsp3 | 0.1354 | A0201 | 126 | 0.316 | 24 | 0.3098 | 1 | A0201 | 24 |
| | SVVSKVVKV | nsp15 | 0.1482 | A0201 | 145 | 0.364 | 5 | 0.3704 | 1 | A0201 | 30 |
| | GLITLSYHL | S.iORF1/2 | 0.2323 | A0201 | 245 | 0.614 | 3 | 3.3333 | 1 | A0201 | 5 |
| | ELPDEFVVVTV | ORF9b | 0.4190 | A0201 | 489 | 1.226 | 9 | 2.5424 | 1 | A0201 | 8 |
| | SLEDKAFQL | ORF9b | 0.4349 | A0201 | 512 | 1.284 | 10 | 2.8249 | 1 | A0201 | 7 |
| | FGDDTVIEV | nsp3 | 0.5348 | A0201 | 629 | 1.577 | 114 | 1.4717 | 1 | A0201 | 23 |
| | KAFQLTPIAV | ORF9b | 0.5696 | A0201 | 682 | 1.710 | 12 | 3.3898 | 1 | A0201 | 13 |
| | ELPDEFVVV | ORF9b | 0.7673 | A0201 | 1006 | 2.523 | 18 | 5.0847 | 1 | A0201 | 12 |
| | NLNESLIDL | S | 0.8444 | A0201 | 1131 | 2.836 | 140 | 2.7473 | 1 | A0201 | 40 |
| | STSAFVETV | nsp2 | 1.3088 | A0201 | 1866 | 4.680 | 84 | 3.3360 | 1 | A0201 | 19 |
| | GPMVLRGLIT | S.iORF1/2 | 2.1237 | B0702 | 3184 | 7.985 | 18 | 20.0000 | 0 | unassigned | 6 |
| | MLLGSMLYM | S.iORF1 | 2.1581 | A0201 | 3238 | 8.120 | 23 | 18.8525 | 0 | unassigned | 4 |
| | APRITFGGP | N | 3.0563 | B0702 | 4781 | 11.990 | 151 | 9.1961 | 0 | unassigned | 42 |
| | AGTDTTITV | nsp5 | 3.4456 | A0201 | 5467 | 13.710 | 129 | 10.8403 | 0 | unassigned | 26 |

FIG. 11A

| sample | hpi | % SARS_CoV_2 |
|---|---|---|
| A549 | 0 | 0.00% |
| HEK293T | 0 | 0.00% |
| A549 | 3 | 0.01% |
| HEK293T | 3 | 0.01% |
| A549 | 6 | 0.38% |
| HEK293T | 6 | 0.48% |
| A549 | 12 | 2.10% |
| HEK293T | 12 | 2.20% |
| A549 | 18 | 2.22% |
| HEK293T | 18 | 2.64% |
| A549 | 24 | 3.05% |
| HEK293T | 24 | 2.58% |

SEQUENCE LISTING

```
<160> NUMBER OF SEQ ID NOS: 239

<210> SEQ ID NO 1
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: N is E, A, V, L, or P
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: N is F, Y, L, or V

<400> SEQUENCE: 1

Xaa Asn Xaa Xaa Xaa Xaa Xaa Xaa Asn
1               5


<210> SEQ ID NO 2
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: N is E, A, V, L, T, S, I, M, G, R, Y, K, D, Q,
      F, or P
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: N is F, Y, L, W, I, K, A, M, or V

<400> SEQUENCE: 2

Xaa Asn Xaa Xaa Xaa Xaa Xaa Xaa Asn
1               5


<210> SEQ ID NO 3
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N is E, D, K, R, N, S, G, L, V, T, F, N, Y, M,
```

or A
<220> FEATURE:
<221> NAME/KEY: MISC_FEATURE
<222> LOCATION: (2)..(2)
<223> OTHER INFORMATION: N is E, A, V, L, T, S, I, M, G, R, Y, K, D, Q, F, or P
<220> FEATURE:
<221> NAME/KEY: MISC_FEATURE
<222> LOCATION: (3)..(3)
<223> OTHER INFORMATION: N is I, V, A, K, R, F, H, L, D, T, S, Q, N, Y, P, or G
<220> FEATURE:
<221> NAME/KEY: MISC_FEATURE
<222> LOCATION: (4)..(4)
<223> OTHER INFORMATION: N is E, D, G, S, P, K, N, A, Q, L, H, or A
<220> FEATURE:
<221> NAME/KEY: MISC_FEATURE
<222> LOCATION: (5)..(5)
<223> OTHER INFORMATION: N is R, P, G, K, A, L, Y, W, F, T, E, S, or V
<220> FEATURE:
<221> NAME/KEY: MISC_FEATURE
<222> LOCATION: (6)..(6)
<223> OTHER INFORMATION: N is I, L, V, Y, F, T, S, P, G, E, A, H, or V
<220> FEATURE:
<221> NAME/KEY: MISC_FEATURE
<222> LOCATION: (7)..(7)
<223> OTHER INFORMATION: N is S, L, P, I, V, Q, H, E, A, K, R, Y, W, N, or M
<220> FEATURE:
<221> NAME/KEY: MISC_FEATURE
<222> LOCATION: (8)..(8)
<223> OTHER INFORMATION: N is S, G, E, A, T, K, Q, N, R, V, D, F or L
<220> FEATURE:
<221> NAME/KEY: MISC_FEATURE
<222> LOCATION: (9)..(9)
<223> OTHER INFORMATION: N is F, Y, L, W, I, K, A, M, T or V

<400> SEQUENCE: 3

Asn Asn Asn Asn Asn Asn Asn Asn Asn
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Met Leu Leu Gly Ser Met Leu Tyr Met
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gly Leu Ile Thr Leu Ser Tyr His Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Gly Pro Met Val Leu Arg Gly Leu Ile Thr

-continued 1 5 10

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Ser Leu Glu Asp Lys Ala Phe Gln Leu
1 5

<210> SEQ ID NO 8
<211> LENGTH: 11
<212> TYPE: PRT
<213> ORGANISM: Unknown
<220> FEATURE:
<223> OTHER INFORMATION: SARS-CoV-2

<400> SEQUENCE: 8

Glu Leu Pro Asp Glu Phe Val Val Val Thr Val
1 5 10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Glu Leu Pro Asp Glu Phe Val Val Thr Val
1 5 10

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Leu Glu Asp Lys Ala Phe Gln Leu
1 5

<210> SEQ ID NO 11
<211> LENGTH: 8
<212> TYPE: PRT
<213> ORGANISM: Unknown
<220> FEATURE:
<223> OTHER INFORMATION: SARS-CoV-2

<400> SEQUENCE: 11

Asp Glu Phe Val Val Val Thr Val
1 5

<210> SEQ ID NO 12
<211> LENGTH: 9
<212> TYPE: PRT
<213> ORGANISM: Unknown
<220> FEATURE:
<223> OTHER INFORMATION: SARS-CoV-2

<400> SEQUENCE: 12

Glu Leu Pro Asp Glu Phe Val Val Val
1 5

```
<210> SEQ ID NO 13
<211> LENGTH: 10
<212> TYPE: PRT
<213> ORGANISM: Unknown
<220> FEATURE:
<223> OTHER INFORMATION: SARS-CoV-2

<400> SEQUENCE: 13

Lys Ala Phe Gln Leu Thr Pro Ile Ala Val
1               5                   10


<210> SEQ ID NO 14
<211> LENGTH: 10
<212> TYPE: PRT
<213> ORGANISM: Unknown
<220> FEATURE:
<223> OTHER INFORMATION: SARS-CoV-2

<400> SEQUENCE: 14

Ala Pro His Gly His Val Met Val Glu Leu
1               5                   10


<210> SEQ ID NO 15
<211> LENGTH: 9
<212> TYPE: PRT
<213> ORGANISM: Unknown
<220> FEATURE:
<223> OTHER INFORMATION: SARS-CoV-2

<400> SEQUENCE: 15

Glu Ile Lys Glu Ser Val Gln Thr Phe
1               5


<210> SEQ ID NO 16
<211> LENGTH: 9
<212> TYPE: PRT
<213> ORGANISM: Unknown
<220> FEATURE:
<223> OTHER INFORMATION: SARS-CoV-2

<400> SEQUENCE: 16

Leu Ala Thr Asn Asn Leu Val Val Met
1               5


<210> SEQ ID NO 17
<211> LENGTH: 9
<212> TYPE: PRT
<213> ORGANISM: Unknown
<220> FEATURE:
<223> OTHER INFORMATION: SARS-CoV-2

<400> SEQUENCE: 17

Phe Ala Ser Glu Ala Ala Arg Val Val
1               5


<210> SEQ ID NO 18
<211> LENGTH: 9
<212> TYPE: PRT
<213> ORGANISM: Unknown
<220> FEATURE:
<223> OTHER INFORMATION: SARS-CoV-2

<400> SEQUENCE: 18

Thr Ala Gln Asn Ser Val Arg Val Leu
1               5
```

<210> SEQ ID NO 19
<211> LENGTH: 9
<212> TYPE: PRT
<213> ORGANISM: Unknown
<220> FEATURE:
<223> OTHER INFORMATION: SARS-CoV-2

<400> SEQUENCE: 19

Ser Thr Ser Ala Phe Val Glu Thr Val
1               5

<210> SEQ ID NO 20
<211> LENGTH: 11
<212> TYPE: PRT
<213> ORGANISM: Unknown
<220> FEATURE:
<223> OTHER INFORMATION: SARS-CoV-2

<400> SEQUENCE: 20

Glu Glu Phe Glu Pro Ser Thr Gln Tyr Glu Tyr
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Thr Thr Thr Ile Lys Pro Val Thr Tyr
1               5

<210> SEQ ID NO 22
<211> LENGTH: 8
<212> TYPE: PRT
<213> ORGANISM: Unknown
<220> FEATURE:
<223> OTHER INFORMATION: SARS-CoV-2

<400> SEQUENCE: 22

Thr Val Ile Glu Val Gln Gly Tyr
1               5

<210> SEQ ID NO 23
<211> LENGTH: 9
<212> TYPE: PRT
<213> ORGANISM: Unknown
<220> FEATURE:
<223> OTHER INFORMATION: SARS-CoV-2

<400> SEQUENCE: 23

Phe Gly Asp Asp Thr Val Ile Glu Val
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Tyr Leu Asn Ser Thr Asn Val Thr Ile
1               5

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Tyr Leu Phe Asp Glu Ser Gly Glu Phe Lys Leu
1 5 10

<210> SEQ ID NO 26
<211> LENGTH: 9
<212> TYPE: PRT
<213> ORGANISM: Unknown
<220> FEATURE:
<223> OTHER INFORMATION: SARS-CoV-2

<400> SEQUENCE: 26

Ala Gly Thr Asp Thr Thr Ile Thr Val
1 5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Ser Glu Phe Ser Ser Leu Pro Ser Tyr
1 5

<210> SEQ ID NO 28
<211> LENGTH: 9
<212> TYPE: PRT
<213> ORGANISM: Unknown
<220> FEATURE:
<223> OTHER INFORMATION: SARS-CoV-2

<400> SEQUENCE: 28

Phe Ala Val Asp Ala Ala Lys Ala Tyr
1 5

<210> SEQ ID NO 29
<211> LENGTH: 9
<212> TYPE: PRT
<213> ORGANISM: Unknown
<220> FEATURE:
<223> OTHER INFORMATION: SARS-CoV-2

<400> SEQUENCE: 29

Lys Arg Val Asp Trp Thr Ile Glu Tyr
1 5

<210> SEQ ID NO 30
<211> LENGTH: 9
<212> TYPE: PRT
<213> ORGANISM: Unknown
<220> FEATURE:
<223> OTHER INFORMATION: SARS-CoV-2

<400> SEQUENCE: 30

Ser Val Val Ser Lys Val Val Lys Val
1 5

<210> SEQ ID NO 31

-continued

<211> LENGTH: 9
<212> TYPE: PRT
<213> ORGANISM: Unknown
<220> FEATURE:
<223> OTHER INFORMATION: SARS-CoV-2

<400> SEQUENCE: 31

Ile Arg Gln Glu Glu Val Gln Glu Leu
1 5

<210> SEQ ID NO 32
<211> LENGTH: 10
<212> TYPE: PRT
<213> ORGANISM: Unknown
<220> FEATURE:
<223> OTHER INFORMATION: SARS-CoV-2
<220> FEATURE:
<221> NAME/KEY: MISC_FEATURE
<222> LOCATION: (8)..(8)
<223> OTHER INFORMATION: C is cysteinylated Cys

<400> SEQUENCE: 32

Glu Ile Leu Asp Ile Thr Pro Cys Ser Phe
1 5 10

<210> SEQ ID NO 33
<211> LENGTH: 10
<212> TYPE: PRT
<213> ORGANISM: Unknown
<220> FEATURE:
<223> OTHER INFORMATION: SARS-CoV-2

<400> SEQUENCE: 33

Glu Ile Leu Asp Ile Thr Pro Cys Ser Phe
1 5 10

<210> SEQ ID NO 34
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: C is cysteinylated Cys

<400> SEQUENCE: 34

Glu Ile Leu Asp Ile Thr Pro Cys Ser Phe Gly
1 5 10

<210> SEQ ID NO 35
<211> LENGTH: 9
<212> TYPE: PRT
<213> ORGANISM: Artificial Sequence
<220> FEATURE:
<223> OTHER INFORMATION: Synthetic

<400> SEQUENCE: 35

His Ala Asp Gln Leu Thr Pro Thr Trp
1 5

<210> SEQ ID NO 36
<211> LENGTH: 10
<212> TYPE: PRT
<213> ORGANISM: Unknown
<220> FEATURE:
<223> OTHER INFORMATION: SARS-CoV-2

<400> SEQUENCE: 36

Lys Asn Ile Asp Gly Tyr Phe Lys Ile Tyr
1 5 10

<210> SEQ ID NO 37
<211> LENGTH: 9
<212> TYPE: PRT
<213> ORGANISM: Unknown
<220> FEATURE:
<223> OTHER INFORMATION: SARS-CoV-2

<400> SEQUENCE: 37

Asn Ala Thr Asn Val Val Ile Lys Val
1 5

<210> SEQ ID NO 38
<211> LENGTH: 9
<212> TYPE: PRT
<213> ORGANISM: Unknown
<220> FEATURE:
<223> OTHER INFORMATION: SARS-CoV-2

<400> SEQUENCE: 38

Gln Leu Thr Pro Thr Trp Arg Val Tyr
1 5

<210> SEQ ID NO 39
<211> LENGTH: 9
<212> TYPE: PRT
<213> ORGANISM: Unknown
<220> FEATURE:
<223> OTHER INFORMATION: SARS-CoV-2

<400> SEQUENCE: 39

Val Gly Tyr Leu Gln Pro Arg Thr Phe
1 5

<210> SEQ ID NO 40
<211> LENGTH: 9
<212> TYPE: PRT
<213> ORGANISM: Unknown
<220> FEATURE:
<223> OTHER INFORMATION: SARS-CoV-2

<400> SEQUENCE: 40

Asn Leu Asn Glu Ser Leu Ile Asp Leu
1 5

<210> SEQ ID NO 41
<211> LENGTH: 9
<212> TYPE: PRT
<213> ORGANISM: Unknown
<220> FEATURE:
<223> OTHER INFORMATION: SARS-CoV-2

<400> SEQUENCE: 41

Val Ala Thr Ser Arg Thr Leu Ser Tyr
1 5

<210> SEQ ID NO 42
<211> LENGTH: 9
<212> TYPE: PRT
<213> ORGANISM: Unknown
<220> FEATURE:
<223> OTHER INFORMATION: SARS-CoV-2

<400> SEQUENCE: 42

Ala Pro Arg Ile Thr Phe Gly Gly Pro
1 5

<210> SEQ ID NO 43
<211> LENGTH: 11
<212> TYPE: PRT
<213> ORGANISM: Artificial Sequence
<220> FEATURE:
<223> OTHER INFORMATION: Synthetic

<400> SEQUENCE: 43

Met Glu Thr Gly Gly Phe Ser Ile Asp Leu Pro
1 5 10

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Leu Ser Asn Pro Val Ile Leu Thr Lys
1 5

<210> SEQ ID NO 45
<211> LENGTH: 11
<212> TYPE: PRT
<213> ORGANISM: Artificial Sequence
<220> FEATURE:
<223> OTHER INFORMATION: Synthetic

<400> SEQUENCE: 45

Leu Ser Ala Ser Leu Ser Asn Phe Leu Ser Ile
1 5 10

<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Met Pro Phe Gln Lys Pro Ile Thr Leu
1 5

<210> SEQ ID NO 47
<211> LENGTH: 11
<212> TYPE: PRT
<213> ORGANISM: Unknown
<220> FEATURE:
<223> OTHER INFORMATION: SARS-CoV-2

<400> SEQUENCE: 47

Glu Ile Leu Asp Ile Thr Pro Cys Ser Phe Gly
1 5 10

<210> SEQ ID NO 48
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 48

Xaa Glu Xaa Xaa Xaa Xaa Xaa Xaa Phe
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 49

Xaa Glu Xaa Xaa Xaa Xaa Xaa Xaa Tyr
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 50

Xaa Glu Xaa Xaa Xaa Xaa Xaa Xaa Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 51

Xaa Glu Xaa Xaa Xaa Xaa Xaa Xaa Val
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 52

Xaa Glu Xaa Xaa Xaa Xaa Xaa Xaa Trp
1 5

<210> SEQ ID NO 53
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 53

Xaa Glu Xaa Xaa Xaa Xaa Xaa Xaa Ile
1 5

<210> SEQ ID NO 54
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 54

Xaa Glu Xaa Xaa Xaa Xaa Xaa Xaa Lys
1 5

<210> SEQ ID NO 55
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 55

Xaa Glu Xaa Xaa Xaa Xaa Xaa Xaa Ala
1 5

<210> SEQ ID NO 56
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 56

Xaa Glu Xaa Xaa Xaa Xaa Xaa Xaa Met
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 57

Xaa Ala Xaa Xaa Xaa Xaa Xaa Xaa Phe
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 58

Xaa Ala Xaa Xaa Xaa Xaa Xaa Xaa Tyr
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 59

Xaa Ala Xaa Xaa Xaa Xaa Xaa Xaa Leu
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 60

Xaa Ala Xaa Xaa Xaa Xaa Xaa Xaa Val
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 61

Xaa Ala Xaa Xaa Xaa Xaa Xaa Xaa Trp
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 62

Xaa Ala Xaa Xaa Xaa Xaa Xaa Xaa Ile
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 63

Xaa Ala Xaa Xaa Xaa Xaa Xaa Xaa Lys
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 64

Xaa Ala Xaa Xaa Xaa Xaa Xaa Xaa Ala
1 5

<210> SEQ ID NO 65
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 65

Xaa Ala Xaa Xaa Xaa Xaa Xaa Xaa Met
1 5

<210> SEQ ID NO 66
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 66

Xaa Val Xaa Xaa Xaa Xaa Xaa Xaa Phe
1 5

<210> SEQ ID NO 67
<211> LENGTH: 9
<212> TYPE: PRT
<213> ORGANISM: Artificial Sequence
<220> FEATURE:

<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 67

Xaa Val Xaa Xaa Xaa Xaa Xaa Xaa Tyr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 68

Xaa Val Xaa Xaa Xaa Xaa Xaa Xaa Leu
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 69

Xaa Val Xaa Xaa Xaa Xaa Xaa Xaa Val
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 70

Xaa Val Xaa Xaa Xaa Xaa Xaa Xaa Trp
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 71

Xaa Val Xaa Xaa Xaa Xaa Xaa Xaa Ile
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 72

Xaa Val Xaa Xaa Xaa Xaa Xaa Xaa Lys
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 73

Xaa Val Xaa Xaa Xaa Xaa Xaa Xaa Ala
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 74

Xaa Val Xaa Xaa Xaa Xaa Xaa Xaa Met
1 5

<210> SEQ ID NO 75
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 75

Xaa Leu Xaa Xaa Xaa Xaa Xaa Xaa Phe
1 5

<210> SEQ ID NO 76
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 76

Xaa Leu Xaa Xaa Xaa Xaa Xaa Xaa Tyr
1 5

<210> SEQ ID NO 77
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 77

Xaa Leu Xaa Xaa Xaa Xaa Xaa Xaa Leu
1 5

<210> SEQ ID NO 78
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:

<221> NAME/KEY: misc_feature
<222> LOCATION: (3)..(8)
<223> OTHER INFORMATION: Xaa can be any naturally occurring amino acid

<400> SEQUENCE: 78

Xaa Leu Xaa Xaa Xaa Xaa Xaa Xaa Val
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 79

Xaa Leu Xaa Xaa Xaa Xaa Xaa Xaa Trp
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 80

Xaa Leu Xaa Xaa Xaa Xaa Xaa Xaa Ile
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 81

Xaa Leu Xaa Xaa Xaa Xaa Xaa Xaa Lys
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 82

Xaa Leu Xaa Xaa Xaa Xaa Xaa Xaa Ala
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 83

Xaa Leu Xaa Xaa Xaa Xaa Xaa Xaa Met
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 84

Xaa Pro Xaa Xaa Xaa Xaa Xaa Xaa Phe
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 85

Xaa Pro Xaa Xaa Xaa Xaa Xaa Xaa Tyr
1               5

<210> SEQ ID NO 86

<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 86

Xaa Pro Xaa Xaa Xaa Xaa Xaa Xaa Leu
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 87

Xaa Pro Xaa Xaa Xaa Xaa Xaa Xaa Val
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 88

Xaa Pro Xaa Xaa Xaa Xaa Xaa Xaa Trp
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 89

Xaa Pro Xaa Xaa Xaa Xaa Xaa Xaa Ile
1 5

<210> SEQ ID NO 90
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 90

Xaa Pro Xaa Xaa Xaa Xaa Xaa Xaa Lys
1 5

<210> SEQ ID NO 91
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 91

Xaa Pro Xaa Xaa Xaa Xaa Xaa Xaa Ala
1 5

<210> SEQ ID NO 92
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 92

Xaa Pro Xaa Xaa Xaa Xaa Xaa Xaa Met
1 5

<210> SEQ ID NO 93
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 93

Xaa Thr Xaa Xaa Xaa Xaa Xaa Xaa Phe
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 94

Xaa Thr Xaa Xaa Xaa Xaa Xaa Xaa Tyr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 95

Xaa Thr Xaa Xaa Xaa Xaa Xaa Xaa Leu
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 96

Xaa Thr Xaa Xaa Xaa Xaa Xaa Xaa Val
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic
<220> FEATURE:

<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 97

Xaa Thr Xaa Xaa Xaa Xaa Xaa Xaa Trp
1 5

<210> SEQ ID NO 98
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 98

Xaa Thr Xaa Xaa Xaa Xaa Xaa Xaa Ile
1 5

<210> SEQ ID NO 99
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 99

Xaa Thr Xaa Xaa Xaa Xaa Xaa Xaa Lys
1 5

<210> SEQ ID NO 100
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 100

Xaa Thr Xaa Xaa Xaa Xaa Xaa Xaa Ala
1 5

<210> SEQ ID NO 101
<211> LENGTH: 9

```
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 101

Xaa Thr Xaa Xaa Xaa Xaa Xaa Xaa Met
1               5


<210> SEQ ID NO 102
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 102

Xaa Ser Xaa Xaa Xaa Xaa Xaa Xaa Phe
1               5


<210> SEQ ID NO 103
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 103

Xaa Ser Xaa Xaa Xaa Xaa Xaa Xaa Tyr
1               5


<210> SEQ ID NO 104
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 104

Xaa Ser Xaa Xaa Xaa Xaa Xaa Xaa Leu
```

1 5

<210> SEQ ID NO 105
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 105

Xaa Ser Xaa Xaa Xaa Xaa Xaa Xaa Val
1 5

<210> SEQ ID NO 106
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 106

Xaa Ser Xaa Xaa Xaa Xaa Xaa Xaa Trp
1 5

<210> SEQ ID NO 107
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 107

Xaa Ser Xaa Xaa Xaa Xaa Xaa Xaa Ile
1 5

<210> SEQ ID NO 108
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)

<223> OTHER INFORMATION: Xaa can be any naturally occurring amino acid

<400> SEQUENCE: 108

Xaa Ser Xaa Xaa Xaa Xaa Xaa Xaa Lys
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 109

Xaa Ser Xaa Xaa Xaa Xaa Xaa Xaa Ala
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 110

Xaa Ser Xaa Xaa Xaa Xaa Xaa Xaa Met
1               5

<210> SEQ ID NO 111
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 111

Xaa Ile Xaa Xaa Xaa Xaa Xaa Xaa Phe
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 112

Xaa Ile Xaa Xaa Xaa Xaa Xaa Xaa Tyr
1               5

<210> SEQ ID NO 113
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 113

Xaa Ile Xaa Xaa Xaa Xaa Xaa Xaa Leu
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 114

Xaa Ile Xaa Xaa Xaa Xaa Xaa Xaa Val
1               5

<210> SEQ ID NO 115
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 115

Xaa Ile Xaa Xaa Xaa Xaa Xaa Xaa Trp
1               5

<210> SEQ ID NO 116
<211> LENGTH: 9
<212> TYPE: PRT

<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 116

Xaa Ile Xaa Xaa Xaa Xaa Xaa Xaa Ile
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 117

Xaa Ile Xaa Xaa Xaa Xaa Xaa Xaa Lys
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 118

Xaa Ile Xaa Xaa Xaa Xaa Xaa Xaa Ala
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 119

Xaa Ile Xaa Xaa Xaa Xaa Xaa Xaa Met
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 120

Xaa Met Xaa Xaa Xaa Xaa Xaa Xaa Phe
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 121

Xaa Met Xaa Xaa Xaa Xaa Xaa Xaa Tyr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 122

Xaa Met Xaa Xaa Xaa Xaa Xaa Xaa Leu
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 123

Xaa Met Xaa Xaa Xaa Xaa Xaa Xaa Val
1 5

<210> SEQ ID NO 124
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 124

Xaa Met Xaa Xaa Xaa Xaa Xaa Xaa Trp
1 5

<210> SEQ ID NO 125
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 125

Xaa Met Xaa Xaa Xaa Xaa Xaa Xaa Ile
1 5

<210> SEQ ID NO 126
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 126

Xaa Met Xaa Xaa Xaa Xaa Xaa Xaa Lys
1 5

<210> SEQ ID NO 127
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 127

Xaa Met Xaa Xaa Xaa Xaa Xaa Xaa Ala
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 128

Xaa Met Xaa Xaa Xaa Xaa Xaa Xaa Met
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 129

Xaa Gly Xaa Xaa Xaa Xaa Xaa Xaa Phe
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 130

Xaa Gly Xaa Xaa Xaa Xaa Xaa Xaa Tyr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 131

Xaa Gly Xaa Xaa Xaa Xaa Xaa Xaa Leu
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 132

Xaa Gly Xaa Xaa Xaa Xaa Xaa Xaa Val
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 133

Xaa Gly Xaa Xaa Xaa Xaa Xaa Xaa Trp
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 134

Xaa Gly Xaa Xaa Xaa Xaa Xaa Xaa Ile
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 135

Xaa Gly Xaa Xaa Xaa Xaa Xaa Xaa Lys
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 136

Xaa Gly Xaa Xaa Xaa Xaa Xaa Xaa Ala
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 137

Xaa Gly Xaa Xaa Xaa Xaa Xaa Xaa Met
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 138

Xaa Arg Xaa Xaa Xaa Xaa Xaa Xaa Phe
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 139

Xaa Arg Xaa Xaa Xaa Xaa Xaa Xaa Tyr
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 140

Xaa Arg Xaa Xaa Xaa Xaa Xaa Xaa Leu
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 141

Xaa Arg Xaa Xaa Xaa Xaa Xaa Xaa Val
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 142

Xaa Arg Xaa Xaa Xaa Xaa Xaa Xaa Trp
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 143

Xaa Arg Xaa Xaa Xaa Xaa Xaa Xaa Ile
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 144

Xaa Arg Xaa Xaa Xaa Xaa Xaa Xaa Lys
1               5

<210> SEQ ID NO 145
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 145

Xaa Arg Xaa Xaa Xaa Xaa Xaa Xaa Ala
1               5

<210> SEQ ID NO 146
<211> LENGTH: 9
<212> TYPE: PRT
<213> ORGANISM: Artificial Sequence
<220> FEATURE:

<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 146

Xaa Arg Xaa Xaa Xaa Xaa Xaa Xaa Met
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 147

Xaa Tyr Xaa Xaa Xaa Xaa Xaa Xaa Phe
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 148

Xaa Tyr Xaa Xaa Xaa Xaa Xaa Xaa Tyr
1               5

<210> SEQ ID NO 149
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 149

Xaa Tyr Xaa Xaa Xaa Xaa Xaa Xaa Leu
1               5

<210> SEQ ID NO 150
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 150

Xaa Tyr Xaa Xaa Xaa Xaa Xaa Xaa Val
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 151

Xaa Tyr Xaa Xaa Xaa Xaa Xaa Xaa Trp
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 152

Xaa Tyr Xaa Xaa Xaa Xaa Xaa Xaa Ile
1               5

<210> SEQ ID NO 153
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 153

```
Xaa Tyr Xaa Xaa Xaa Xaa Xaa Xaa Lys
1               5


<210> SEQ ID NO 154
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 154

Xaa Tyr Xaa Xaa Xaa Xaa Xaa Xaa Ala
1               5


<210> SEQ ID NO 155
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 155

Xaa Tyr Xaa Xaa Xaa Xaa Xaa Xaa Met
1               5


<210> SEQ ID NO 156
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 156

Xaa Lys Xaa Xaa Xaa Xaa Xaa Xaa Phe
1               5


<210> SEQ ID NO 157
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
```

<221> NAME/KEY: misc_feature
<222> LOCATION: (3)..(8)
<223> OTHER INFORMATION: Xaa can be any naturally occurring amino acid

<400> SEQUENCE: 157

Xaa Lys Xaa Xaa Xaa Xaa Xaa Xaa Tyr
1               5

<210> SEQ ID NO 158
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 158

Xaa Lys Xaa Xaa Xaa Xaa Xaa Xaa Leu
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 159

Xaa Lys Xaa Xaa Xaa Xaa Xaa Xaa Val
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 160

Xaa Lys Xaa Xaa Xaa Xaa Xaa Xaa Trp
1               5

<210> SEQ ID NO 161
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 161

Xaa Lys Xaa Xaa Xaa Xaa Xaa Xaa Ile
1               5

<210> SEQ ID NO 162
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 162

Xaa Lys Xaa Xaa Xaa Xaa Xaa Xaa Lys
1               5

<210> SEQ ID NO 163
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 163

Xaa Lys Xaa Xaa Xaa Xaa Xaa Xaa Ala
1               5

<210> SEQ ID NO 164
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 164

Xaa Lys Xaa Xaa Xaa Xaa Xaa Xaa Met
1               5

<210> SEQ ID NO 165

<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 165

Xaa Asp Xaa Xaa Xaa Xaa Xaa Xaa Phe
1               5

<210> SEQ ID NO 166
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 166

Xaa Asp Xaa Xaa Xaa Xaa Xaa Xaa Tyr
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 167

Xaa Asp Xaa Xaa Xaa Xaa Xaa Xaa Leu
1               5

<210> SEQ ID NO 168
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 168

Xaa Asp Xaa Xaa Xaa Xaa Xaa Xaa Val
1 5

<210> SEQ ID NO 169
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 169

Xaa Asp Xaa Xaa Xaa Xaa Xaa Xaa Trp
1 5

<210> SEQ ID NO 170
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 170

Xaa Asp Xaa Xaa Xaa Xaa Xaa Xaa Ile
1 5

<210> SEQ ID NO 171
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 171

Xaa Asp Xaa Xaa Xaa Xaa Xaa Xaa Lys
1 5

<210> SEQ ID NO 172
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 172

Xaa Asp Xaa Xaa Xaa Xaa Xaa Xaa Ala
1               5

<210> SEQ ID NO 173
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 173

Xaa Asp Xaa Xaa Xaa Xaa Xaa Xaa Met
1               5

<210> SEQ ID NO 174
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 174

Xaa Gln Xaa Xaa Xaa Xaa Xaa Xaa Phe
1               5

<210> SEQ ID NO 175
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 175

Xaa Gln Xaa Xaa Xaa Xaa Xaa Xaa Tyr
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic
<220> FEATURE:

<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 176

Xaa Gln Xaa Xaa Xaa Xaa Xaa Xaa Leu
1               5

<210> SEQ ID NO 177
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 177

Xaa Gln Xaa Xaa Xaa Xaa Xaa Xaa Val
1               5

<210> SEQ ID NO 178
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 178

Xaa Gln Xaa Xaa Xaa Xaa Xaa Xaa Trp
1               5

<210> SEQ ID NO 179
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 179

Xaa Gln Xaa Xaa Xaa Xaa Xaa Xaa Ile
1               5

<210> SEQ ID NO 180
<211> LENGTH: 9

<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 180

Xaa Gln Xaa Xaa Xaa Xaa Xaa Xaa Lys
1               5

<210> SEQ ID NO 181
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 181

Xaa Gln Xaa Xaa Xaa Xaa Xaa Xaa Ala
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 182

Xaa Gln Xaa Xaa Xaa Xaa Xaa Xaa Met
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 183

Xaa Phe Xaa Xaa Xaa Xaa Xaa Xaa Phe

-continued 1 5

<210> SEQ ID NO 184
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 184

Xaa Phe Xaa Xaa Xaa Xaa Xaa Xaa Tyr
1 5

<210> SEQ ID NO 185
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 185

Xaa Phe Xaa Xaa Xaa Xaa Xaa Xaa Leu
1 5

<210> SEQ ID NO 186
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 186

Xaa Phe Xaa Xaa Xaa Xaa Xaa Xaa Val
1 5

<210> SEQ ID NO 187
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)

<223> OTHER INFORMATION: Xaa can be any naturally occurring amino acid

<400> SEQUENCE: 187

Xaa Phe Xaa Xaa Xaa Xaa Xaa Xaa Trp
1 5

<210> SEQ ID NO 188
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 188

Xaa Phe Xaa Xaa Xaa Xaa Xaa Xaa Ile
1 5

<210> SEQ ID NO 189
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 189

Xaa Phe Xaa Xaa Xaa Xaa Xaa Xaa Lys
1 5

<210> SEQ ID NO 190
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 190

Xaa Phe Xaa Xaa Xaa Xaa Xaa Xaa Ala
1 5

<210> SEQ ID NO 191
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(8)
<223> OTHER INFORMATION: Xaa can be any naturally occurring amino acid

<400> SEQUENCE: 191

Xaa Phe Xaa Xaa Xaa Xaa Xaa Xaa Met
1               5

<210> SEQ ID NO 192
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Methionine residues are oxidized

<400> SEQUENCE: 192

Ala Pro His Gly His Val Met Val Glu Leu
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Methionine residues are oxidized

<400> SEQUENCE: 193

Gly Pro Met Val Leu Arg Gly Leu Ile Thr
1               5                   10

<210> SEQ ID NO 194
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Methionine residues are oxidized

<400> SEQUENCE: 194

Met Leu Leu Gly Ser Met Leu Tyr Met
1               5

<210> SEQ ID NO 195
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Methionine residues are oxidized

<400> SEQUENCE: 195

Met Leu Leu Gly Ser Met Leu Tyr Met
1               5

```
<210> SEQ ID NO 196
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Methionine residues are oxidized

<400> SEQUENCE: 196

Met Leu Leu Gly Ser Met Leu Tyr Met
1               5


<210> SEQ ID NO 197
<211> LENGTH: 20
<212> TYPE: PRT
<213> ORGANISM: Artificial Sequence
<220> FEATURE:
<223> OTHER INFORMATION: Synthetic

<400> SEQUENCE: 197

Met Glu Thr Pro Ala Gln Leu Leu Phe Leu Leu Leu Leu Trp Leu Pro
1               5                   10                  15

Asp Thr Thr Gly
            20


<210> SEQ ID NO 198
<211> LENGTH: 18
<212> TYPE: PRT
<213> ORGANISM: Artificial Sequence
<220> FEATURE:
<223> OTHER INFORMATION: Synthetic

<400> SEQUENCE: 198

Met Asp Trp Thr Trp Ile Leu Phe Leu Val Ala Ala Ala Thr Arg Val
1               5                   10                  15

His Ser


<210> SEQ ID NO 199
<211> LENGTH: 24
<212> TYPE: PRT
<213> ORGANISM: Artificial Sequence
<220> FEATURE:
<223> OTHER INFORMATION: Synthetic

<400> SEQUENCE: 199

Met Leu Gly Ser Asn Ser Gly Gln Arg Val Val Phe Thr Ile Leu Leu
1               5                   10                  15

Leu Leu Val Ala Pro Ala Tyr Ser
            20


<210> SEQ ID NO 200
<211> LENGTH: 17
<212> TYPE: PRT
<213> ORGANISM: Artificial Sequence
<220> FEATURE:
<223> OTHER INFORMATION: Synthetic

<400> SEQUENCE: 200

Met Lys Cys Leu Leu Tyr Leu Ala Phe Leu Phe Ile Gly Val Asn Cys
1               5                   10                  15

Ala
```

<210> SEQ ID NO 201
<211> LENGTH: 15
<212> TYPE: PRT
<213> ORGANISM: Artificial Sequence
<220> FEATURE:
<223> OTHER INFORMATION: Synthetic

<400> SEQUENCE: 201

Met Trp Leu Val Ser Leu Ala Ile Val Thr Ala Cys Ala Gly Ala
1 5 10 15

<210> SEQ ID NO 202
<211> LENGTH: 22
<212> TYPE: PRT
<213> ORGANISM: Artificial Sequence
<220> FEATURE:
<223> OTHER INFORMATION: Synthetic

<400> SEQUENCE: 202

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 203
<211> LENGTH: 66
<212> TYPE: DNA
<213> ORGANISM: Artificial Sequence
<220> FEATURE:
<223> OTHER INFORMATION: Synthetic

<400> SEQUENCE: 203
ggaagcggag ctactaactt cagcctgctg aagcaggctg gagacgtgga ggagaaccct 60
ggacct 66

<210> SEQ ID NO 204
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Methionine residues are oxidized
<220> FEATURE:
<221> NAME/KEY: MISC_FEATURE
<222> LOCATION: (6)..(6)
<223> OTHER INFORMATION: Methionine residues are oxidized
<220> FEATURE:
<221> NAME/KEY: MISC_FEATURE
<222> LOCATION: (9)..(9)
<223> OTHER INFORMATION: Methionine residues are oxidized

<400> SEQUENCE: 204

Met Leu Leu Gly Ser Met Leu Tyr Met
1 5

<210> SEQ ID NO 205
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)

<223> OTHER INFORMATION: N is deamidated N
<220> FEATURE:
<221> NAME/KEY: MISC_FEATURE
<222> LOCATION: (6)..(6)
<223> OTHER INFORMATION: N is deamidated N

<400> SEQUENCE: 205

Tyr Leu Asn Ser Thr Asn Val Thr Ile
1               5

<210> SEQ ID NO 206
<211> LENGTH: 9
<212> TYPE: PRT
<213> ORGANISM: Influenza A Virus

<400> SEQUENCE: 206

Gly Ile Leu Gly Phe Val Phe Thr Leu
1               5

<210> SEQ ID NO 207
<211> LENGTH: 9
<212> TYPE: PRT
<213> ORGANISM: Unknown
<220> FEATURE:
<223> OTHER INFORMATION: SARS-CoV-2

<400> SEQUENCE: 207

Tyr Leu Gln Pro Arg Thr Phe Leu Leu
1               5

<210> SEQ ID NO 208
<211> LENGTH: 9
<212> TYPE: PRT
<213> ORGANISM: Unknown
<220> FEATURE:
<223> OTHER INFORMATION: SARS-CoV-2

<400> SEQUENCE: 208

Lys Leu Trp Ala Gln Cys Val Gln Leu
1               5

<210> SEQ ID NO 209
<211> LENGTH: 9
<212> TYPE: PRT
<213> ORGANISM: Unknown
<220> FEATURE:
<223> OTHER INFORMATION: SARS-CoV-2

<400> SEQUENCE: 209

Leu Leu Tyr Asp Ala Asn Tyr Phe Leu
1               5

<210> SEQ ID NO 210
<211> LENGTH: 9
<212> TYPE: PRT
<213> ORGANISM: Unknown
<220> FEATURE:
<223> OTHER INFORMATION: EBV

<400> SEQUENCE: 210

Arg Pro Pro Ile Phe Ile Arg Arg Leu
1               5

<210> SEQ ID NO 211
<211> LENGTH: 9
<212> TYPE: PRT
<213> ORGANISM: Unknown

<220> FEATURE:
<223> OTHER INFORMATION: SARS-CoV-2

<400> SEQUENCE: 211

Ser Pro Arg Trp Tyr Phe Tyr Tyr Leu
1 5

<210> SEQ ID NO 212
<211> LENGTH: 9
<212> TYPE: PRT
<213> ORGANISM: Artificial Sequence
<220> FEATURE:
<223> OTHER INFORMATION: Synthetic

<400> SEQUENCE: 212

Gly Pro Met Val Leu Arg Gly Leu Ile
1 5

<210> SEQ ID NO 213
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: N
<222> LOCATION: (8)..(8)
<223> OTHER INFORMATION: N is Leucine (L) or Isoleucine (I)

<400> SEQUENCE: 213

Lys Ile Leu Gly Phe Val Phe Asn Val
1 5

<210> SEQ ID NO 214
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: N
<222> LOCATION: (5)..(5)
<223> OTHER INFORMATION: N is Leucine (L) or Isoleucine (I)

<400> SEQUENCE: 214

Ala Ala Arg Gly Asn Thr Leu Ala Met
1 5

<210> SEQ ID NO 215
<211> LENGTH: 39
<212> TYPE: PRT
<213> ORGANISM: Unknown
<220> FEATURE:
<223> OTHER INFORMATION: SARS-CoV-2

<400> SEQUENCE: 215

Met Leu Leu Gly Ser Met Leu Tyr Met Ser Leu Gly Pro Met Val Leu
1 5 10 15

Arg Gly Leu Ile Thr Leu Ser Tyr His Leu Met Met Val Phe Ile Leu
20 25 30

Leu Pro Leu Arg Ser Leu Thr
35

<210> SEQ ID NO 216
<211> LENGTH: 97
<212> TYPE: PRT
<213> ORGANISM: Unknown

<220> FEATURE:
<223> OTHER INFORMATION: SARS-CoV-2

<400> SEQUENCE: 216

Met Asp Pro Lys Ile Ser Glu Met His Pro Ala Leu Arg Leu Val Asp
1               5                   10                  15

Pro Gln Ile Gln Leu Ala Val Thr Arg Met Glu Asn Ala Val Gly Arg
            20                  25                  30

Asp Gln Asn Asn Val Gly Pro Lys Val Tyr Pro Ile Ile Leu Arg Leu
        35                  40                  45

Gly Ser Pro Leu Ser Leu Asn Met Ala Arg Lys Thr Leu Asn Ser Leu
    50                  55                  60

Glu Asp Lys Ala Phe Gln Leu Thr Pro Ile Ala Val Gln Met Thr Lys
65                  70                  75                  80

Leu Ala Thr Thr Glu Glu Leu Pro Asp Glu Phe Val Val Val Thr Val
                85                  90                  95

Lys

<210> SEQ ID NO 217
<211> LENGTH: 39
<212> TYPE: PRT
<213> ORGANISM: Unknown
<220> FEATURE:
<223> OTHER INFORMATION: SARS-CoV-2

<400> SEQUENCE: 217

Asn Val Thr Trp Phe His Ala Ile His Val Ser Gly Thr Asn Gly Thr
1               5                   10                  15

Lys Arg Phe Asp Asn Pro Val Leu Pro Phe Asn Asp Gly Val Tyr Phe
            20                  25                  30

Ala Ser Thr Glu Lys Ser Asn
        35

<210> SEQ ID NO 218
<211> LENGTH: 39
<212> TYPE: PRT
<213> ORGANISM: Homo sapiens

<400> SEQUENCE: 218

Asn Val Thr Trp Phe His Ala Ile His Val Ser Gly Thr Asn Gly Thr
1               5                   10                  15

Lys Arg Phe Asp Asn Pro Val Leu Pro Phe Asn Asp Gly Val Tyr Phe
            20                  25                  30

Ala Ser Thr Glu Lys Ser Asn
        35

<210> SEQ ID NO 219
<211> LENGTH: 39
<212> TYPE: PRT
<213> ORGANISM: Unknown
<220> FEATURE:
<223> OTHER INFORMATION: SARS-CoV-2

<400> SEQUENCE: 219

Met Leu Leu Gly Ser Met Leu Tyr Met Ser Leu Gly Pro Met Val Leu
1               5                   10                  15

Arg Gly Leu Ile Thr Leu Ser Tyr His Leu Met Met Val Phe Ile Leu
            20                  25                  30

Leu Pro Leu Arg Ser Leu Thr
        35

<210> SEQ ID NO 220
<211> LENGTH: 39
<212> TYPE: PRT
<213> ORGANISM: Homo sapiens

<400> SEQUENCE: 220

```
Met Ser Arg Gly Ser Met Leu Phe Thr Ser Ala Ala Leu Met Glu Arg
1               5                   10                  15

Asn Asp Ser Ile Thr Pro Ser Cys Pro Ser Thr Met Ala Tyr Ile Ser
            20                  25                  30

Arg Gln Gln Arg Lys Val Ile
        35
```

<210> SEQ ID NO 221
<211> LENGTH: 9
<212> TYPE: PRT
<213> ORGANISM: Artificial Sequence
<220> FEATURE:
<223> OTHER INFORMATION: Synthetic

<400> SEQUENCE: 221

```
Met Ser Arg Gly Ser Met Leu Phe Thr
1               5
```

<210> SEQ ID NO 222
<211> LENGTH: 10
<212> TYPE: PRT
<213> ORGANISM: Artificial Sequence
<220> FEATURE:
<223> OTHER INFORMATION: Synthetic

<400> SEQUENCE: 222

```
Ala Leu Met Glu Arg Asn Asp Ser Ile Thr
1               5                   10
```

<210> SEQ ID NO 223
<211> LENGTH: 9
<212> TYPE: PRT
<213> ORGANISM: Artificial Sequence
<220> FEATURE:
<223> OTHER INFORMATION: Synthetic

<400> SEQUENCE: 223

```
Asp Ser Ile Thr Pro Ser Cys Pro Ser
1               5
```

<210> SEQ ID NO 224
<211> LENGTH: 50
<212> TYPE: PRT
<213> ORGANISM: Unknown
<220> FEATURE:
<223> OTHER INFORMATION: SARS-CoV-2

<400> SEQUENCE: 224

```
Asn Gly Pro Gln Asn Gln Arg Asn Ala Pro Arg Ile Thr Phe Gly Gly
1               5                   10                  15

Pro Ser Asp Ser Thr Gly Ser Asn Gln Asn Gly Glu Arg Ser Gly Ala
            20                  25                  30

Arg Ser Lys Gln Arg Arg Pro Gln Gly Leu Pro Asn Asn Thr Ala Ser
        35                  40                  45

Trp Phe
    50
```

```
<210> SEQ ID NO 225
<211> LENGTH: 50
<212> TYPE: PRT
<213> ORGANISM: Homo sapiens

<400> SEQUENCE: 225

Asn Gly Pro Gln Asn Gln Arg Asn Ala Pro Arg Ile Thr Phe Gly Gly
1               5                   10                  15

Pro Ser Asp Ser Thr Gly Ser Asn Gln Asn Gly Glu Arg Ser Gly Ala
            20                  25                  30

Arg Ser Lys Gln Arg Arg Pro Gln Gly Leu Pro Asn Asn Thr Ala Ser
        35                  40                  45

Trp Phe
    50


<210> SEQ ID NO 226
<211> LENGTH: 47
<212> TYPE: PRT
<213> ORGANISM: Unknown
<220> FEATURE:
<223> OTHER INFORMATION: SARS-CoV-2

<400> SEQUENCE: 226

Thr Ala Leu Thr Gln His Gly Lys Glu Asp Leu Lys Phe Pro Arg Gly
1               5                   10                  15

Gln Gly Val Pro Ile Asn Thr Asn Ser Ser Pro Asp Asp Gln Ile Gly
            20                  25                  30

Tyr Tyr Arg Arg Ala Thr Arg Arg Ile Arg Gly Gly Asp Gly Lys
        35                  40                  45


<210> SEQ ID NO 227
<211> LENGTH: 47
<212> TYPE: PRT
<213> ORGANISM: Homo sapiens

<400> SEQUENCE: 227

Thr Ala Leu Thr Gln His Gly Lys Glu Asp Leu Lys Phe Pro Arg Gly
1               5                   10                  15

Gln Gly Val Pro Ile Asn Thr Asn Ser Ser Pro Asp Asp Gln Ile Gly
            20                  25                  30

Tyr Tyr Arg Arg Ala Thr Arg Arg Ile Arg Gly Gly Asp Gly Lys
        35                  40                  45


<210> SEQ ID NO 228
<211> LENGTH: 50
<212> TYPE: PRT
<213> ORGANISM: Unknown
<220> FEATURE:
<223> OTHER INFORMATION: SARS-CoV-2

<400> SEQUENCE: 228

Met Asp Pro Lys Ile Ser Glu Met His Pro Ala Leu Arg Leu Val Asp
1               5                   10                  15

Pro Gln Ile Gln Leu Ala Val Thr Arg Met Glu Asn Ala Val Gly Arg
            20                  25                  30

Asp Gln Asn Asn Val Gly Pro Lys Val Tyr Pro Ile Ile Leu Arg Leu
        35                  40                  45

Gly Ser
    50
```

<210> SEQ ID NO 229
<211> LENGTH: 49
<212> TYPE: PRT
<213> ORGANISM: Homo sapiens

<400> SEQUENCE: 229

```
Thr Ala Pro Lys Thr Asn Gly Met Pro Leu Gly His Leu Val Ala Leu
1               5                   10                  15

Val Ile Pro Gln Glu Val Thr Lys Thr Glu Asn Gly Leu Glu Pro Ala
            20                  25                  30

Leu Asn Arg Gly Asp His Arg Asp Cys Gln Ile Thr Gln Arg His Gly
        35                  40                  45

Leu
```

<210> SEQ ID NO 230
<211> LENGTH: 47
<212> TYPE: PRT
<213> ORGANISM: Unknown
<220> FEATURE:
<223> OTHER INFORMATION: SARS-CoV-2

<400> SEQUENCE: 230

```
Pro Leu Ser Leu Asn Met Ala Arg Lys Thr Leu Asn Ser Leu Glu Asp
1               5                   10                  15

Lys Ala Phe Gln Leu Thr Pro Ile Ala Val Gln Met Thr Lys Leu Ala
            20                  25                  30

Thr Thr Glu Glu Leu Pro Asp Glu Phe Val Val Val Thr Val Lys
        35                  40                  45
```

<210> SEQ ID NO 231
<211> LENGTH: 44
<212> TYPE: PRT
<213> ORGANISM: Homo sapiens

<400> SEQUENCE: 231

```
Gln Pro Leu Asn Met Glu Arg Arg Thr Asn Phe His Glu Asp Arg Val
1               5                   10                  15

Tyr Gln Thr Gln Thr Val Val Gln Thr Ile Arg Ser Gly Ile Ile Glu
            20                  25                  30

Gly Pro Arg Asp Ala Ser Glu Val Glu Met Val Lys
        35                  40
```

<210> SEQ ID NO 232
<211> LENGTH: 9
<212> TYPE: PRT
<213> ORGANISM: Unknown
<220> FEATURE:
<223> OTHER INFORMATION: SARS-CoV-2

<400> SEQUENCE: 232

```
Phe Ala Ser Glu Ala Arg Arg Val Val
1               5
```

<210> SEQ ID NO 233
<211> LENGTH: 27
<212> TYPE: PRT
<213> ORGANISM: Artificial Sequence
<220> FEATURE:
<223> OTHER INFORMATION: Synthetic

<400> SEQUENCE: 233

```
Cys Ala Gly Thr Tyr Gly Gly Ser Gln Gly Asn Leu Ile Phe Cys Ala
1               5                   10                  15
```

Ser Ser Arg Arg Ser Thr Gly Glu Leu Phe Phe
20 25

<210> SEQ ID NO 234
<211> LENGTH: 26
<212> TYPE: PRT
<213> ORGANISM: Artificial Sequence
<220> FEATURE:
<223> OTHER INFORMATION: Synthetic

<400> SEQUENCE: 234

Cys Val Val Thr Asp Ser Trp Gly Lys Leu Gln Phe Cys Ala Ser Ser
1 5 10 15

Val Thr Val Ser Thr Asp Thr Gln Tyr Phe
20 25

<210> SEQ ID NO 235
<211> LENGTH: 26
<212> TYPE: PRT
<213> ORGANISM: Artificial Sequence
<220> FEATURE:
<223> OTHER INFORMATION: Synthetic

<400> SEQUENCE: 235

Cys Ala Leu Ile Arg Thr Ser Gly Thr Tyr Lys Tyr Ile Phe Cys Ala
1 5 10 15

Ser Thr Gly Arg Asp Asn Glu Gln Phe Phe
20 25

<210> SEQ ID NO 236
<211> LENGTH: 38
<212> TYPE: PRT
<213> ORGANISM: Artificial Sequence
<220> FEATURE:
<223> OTHER INFORMATION: Synthetic

<400> SEQUENCE: 236

Met Leu Leu Gly Ser Met Leu Tyr Met Ser Leu Gly Pro Met Val Leu
1 5 10 15

Arg Gly Leu Thr Leu Ser Tyr His Leu Met Met Val Phe Ile Leu Leu
20 25 30

Pro Leu Arg Ser Leu Thr
35

<210> SEQ ID NO 237
<211> LENGTH: 39
<212> TYPE: PRT
<213> ORGANISM: Artificial Sequence
<220> FEATURE:
<223> OTHER INFORMATION: Synthetic

<400> SEQUENCE: 237

Met Leu Leu Gly Ser Met Leu Tyr Met Ser Leu Gly Pro Met Val Leu
1 5 10 15

Arg Gly Leu Leu Thr Leu Ser Tyr His Leu Met Met Val Phe Ile Leu
20 25 30

Leu Pro Leu Arg Ser Leu Thr
35

<210> SEQ ID NO 238
<211> LENGTH: 37
<212> TYPE: PRT
<213> ORGANISM: Artificial Sequence -continued

```
<220> FEATURE:
<223> OTHER INFORMATION: Synthetic

<400> SEQUENCE: 238

Met Leu Leu Gly Ser Met Leu Ser Leu Gly Pro Met Val Leu Arg Gly
1               5                   10                  15

Leu Ile Thr Leu Ser Tyr His Leu Met Met Val Phe Ile Leu Leu Pro
            20                  25                  30

Leu Arg Ser Leu Thr
        35


<210> SEQ ID NO 239
<211> LENGTH: 37
<212> TYPE: PRT
<213> ORGANISM: Artificial Sequence
<220> FEATURE:
<223> OTHER INFORMATION: Synthetic

<400> SEQUENCE: 239

Met Leu Leu Gly Ser Met Leu Ser Leu Gly Pro Met Val Leu Arg Gly
1               5                   10                  15

Leu Ile Thr Leu Ser Tyr His Leu Met Met Val Phe Ile Leu Leu Pro
            20                  25                  30

Leu Arg Ser Leu Thr
        35
```

IMMUNOGENIC COMPOSITIONS AND USE THEREOF

CROSS-REFERENCE TO RELATED APPLICATIONS

This application claims the benefit of and priority to U.S. Provisional Patent Application No. 63/072,898, filed on Aug. 31, 2020, and U.S. Provisional Patent Application No. 63/186,742, filed on May 10, 2021, the contents of which are incorporated by reference in their entireties herein.

STATEMENT REGARDING FEDERALLY SPONSORED RESEARCH

This invention was made with government support under Grant No. AI110818, AI082630, CA210986, CA214125, and CA216772 awarded by the National Institutes of Health. The government has certain rights in the invention.

SEQUENCE LISTING

This application contains a sequence listing filed in electronic form as an ASCII.txt file entitled BROD-5255US.txt, created on Aug. 31, 2021, and having a size of 80,900 bytes. The content of the sequence listing is incorporated herein in its entirety.

TECHNICAL FIELD

The subject matter disclosed herein is generally directed to immunogenic compositions and use thereof.

BACKGROUND

Severe acute respiratory syndrome coronavirus 2 (SARS-COV-2) is the virus causing the ongoing Coronavirus Disease 19 (COVID19) pandemic. Deciphering how infected host cells interact with the immune system is important for the development of effective vaccines and therapeutics. When viruses infect cells, their proteins are being processed and presented on the host cell surface by class I Major Histocompatibility Complex (MHC-I). Cytotoxic T cells recognize the foreign antigens and initiate an immune response resulting in the infected cell death. Thus, there is a need to identify the repertoire of SARS-COV-2 derived MHC-I peptides, which will allow development of novel vaccines, therapeutics, and assays based on the viral signature as seen by cytotoxic T cells in infected patients.

SUMMARY

Described in exemplary embodiments herein are immunogenic compositions comprising one or more polypeptides, wherein the one or more polypeptides: is capable of binding to Major Histocompatibility Complex (MHC) class I, and is derived from one or more proteins of SARS-COV-2.

In certain example embodiments, the MHC class I is Human Leukocyte Antigen class I (HLA-I). In some embodiments, the HLA-I is encoded by an HLA allele having a ranking cut-off of 0.1% or greater as determined by a machine learning predictor of HLA-I epitope binding. In some embodiments, the HLA-1 is encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, HLA-C*07:02; HLA-A*01:01; HLA-A*02:06; HLA-A*26:01; HLA-A*02:07; HLA-A*29:02; HLA-A*02:03; HLA-A*30:02; HLA-A*32:01; HLA-A*68:02; HLA-A*02:05; HLA-A*02:02; HLA-A*36:01; HLA-A*02:11; HLA-A*02:04; HLA-B*35:01; HLA-B*51:01; HLA-B*40:01; HLA-B*40:02; HLA-B*07:02; HLA-B*07:04; HLA-B*08:01; HLA-B*13:01; HLA-B*46:01; HLA-B*52:01; HLA-B*44:02; HLA-B*40:06; HLA-B*13:02; HLA-B*56:01; HLA-B*54:01; HLA-B*15:02; HLA-B*35:07; HLA-B*27:05; HLA-B*15:03; HLA-B*42:01; HLA-B*55:02; HLA-B*45:01; HLA-B*50:01; HLA-B*35:03; HLA-B*49:01; HLA-B*58:02; HLA-B*15:17; HLA-C*57:02; HLA-C*04:01; HLA-C*03:04; HLA-C*01:02; HLA-C*07:01; HLA-C*06:02; HLA-C*03:03; HLA-C*08:01; HLA-C*15:02; HLA-C*12:02; HLA-C*02:02; HLA-C*05:01; HLA-C*03:02; HLA-C*16:01; HLA-C*08:02; HLA-C*04:03; HLA-C*17:01; or HLA-C*17:04. In some embodiments, the HLA-1 is encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, or HLA-C*07:02.

In certain example embodiments, the one or more peptides comprises a motif of $XN_1XXXXXXN_2$ (SEQ ID NO: 1), wherein $N_1$ is E, A, V, L, or P, wherein $N_2$ is F, Y, L, or V, and wherein X is any amino acid. In some embodiments, the one or more peptides comprises a motif of $XN_1XXXXXXN_2$ (SEQ ID NO: 2), wherein in some embodiments Ni is E, A, V, L, T, S, I, M, G, R, Y, K, D, Q, F, or P, wherein in some embodiments $N_2$ is F, Y, L, W, I, K, A, M, or V, and wherein X is any amino acid. In some embodiments, the one or more polypeptides comprises a motif of $N_3N_1N_4N_5N_6N_7N_8N_9N_2$ (SEQ ID NO: 3), wherein $N_1$ is optionally E, A, V, L, T, S, I, M, G, R, Y, K, D, Q, F, or P, wherein $N_2$ is optionally F, Y, L, W, I, K, A, M, T or V, wherein $N_3$ is optionally E, D, K, R, N, S, G, L, V, T, F, N, Y, M, or A, wherein $N_4$ is optionally I, V, A, K, R, F, H, L, D, T, S, Q, N, Y, P, or G, wherein $N_5$ is optionally E, D, G, S, P, K, N, A, Q, L, H, or A, wherein $N_6$ is optionally R, P, G, K, A, L, Y, W, F, T, E, S, or V, wherein $N_7$ is optionally I, L, V, Y, F, T, S, P, G, E, A, H, or V, wherein $N_8$ is optionally S, L, P, I, V, Q, H, E, A, K, R, Y, W, N, or M, and wherein $N_9$ is optionally S, G, E, A, T, K, Q, N, R, V, D, F or L. In some embodiments, the one or more polypeptides is selected from Table 1, Table 2, Table 4, Tables 8A-8B, and/or Tables 9A, 9B, or 9C. In some embodiments, two or more polypeptides are selected from Table 1, Table 2 Table 4, Tables 8A-8B, and/or Tables 9A, 9B, or 9C. In some embodiments, at least one of the one or more polypeptides is derived from expression of an internal out-of-frame open reading frame (ORF) of SARS-COV-2. In some embodiments, the internal out-of-frame ORF is S.iORF1 or S.iORF2. In some embodiments, the internal out-of-frame ORF is ORF9b.

In certain example embodiments the internal out-of-frame ORF is S.iORF1 or S.iORF2. In some embodiments, the polypeptide derived from S.iORF1 is MLLGSMLYM (SEQ ID NO: 4), and the polypeptide derived from S.iORF1 or S.iORF2 is GLITLSYHL (SEQ ID NO: 5) or GPMVLRGLIT (SEQ ID NO: 6). In some embodiments, the internal out-of-frame ORF is ORF9b. In some embodiments, the polypeptide derived from ORF9b is SLEDKAFQL (SEQ ID NO: 7), ELPDEFVVVTV (SEQ ID NO: 8), ELPDEFVVTV (SEQ ID NO: 9), LEDKAFQL (SEQ ID NO: 10), DEFVVVTV (SEQ ID NO: 11), ELPDEFVVV (SEQ ID NO: 12), KAFQLTPIAV (SEQ ID NO: 13), or a combination thereof. In some embodiments, at least one of the one or more the polypeptide is derived from expression of a canonical open reading frame (ORF) of SARS-CoV-2. In some embodiments, the canonical ORF is nsp1, nsp2, nsp3, nsp5 nsp8, nsp10, nsp14, nsp15 ORF7a, S protein, M protein, or N protein. In some embodiments, the polypeptide derived from nsp1 is APHGHVMVEL (SEQ ID NO: 14). In some embodiments, the polypeptide derived from nsp2 is EIKESVQTF (SEQ ID NO: 15), LATNNLVVM (SEQ ID NO: 16), FASEAARVV (SEQ ID NO: 17), TAQNSVRVL (SEQ ID NO: 18), or STSAFVETV (SEQ ID NO: 19). In some embodiments, the polypeptide derived from nsp3 is EEFEPSTQYEY (SEQ ID NO: 20), TTTIKPVTY (SEQ ID NO: 21), TVIEVQGY (SEQ ID NO: 22), FGDDTVIEV (SEQ ID NO: 23), YLNSTNVTI (SEQ ID NO: 24), or YLFDESGEFKL (SEQ ID NO: 25). In some embodiments, the polypeptide is derived from nsp5. In some embodiments, the polypeptide derived from nsp5 is AGTDTTITV (SEQ ID NO: 26). In some embodiments, the polypeptide derived from nsp8 is SEFSSLPSY (SEQ ID NO: 27). In some embodiments, the polypeptide derived from nsp10 is FAVDAAKAY (SEQ ID NO: 28). In some embodiments, the polypeptide derived from nsp14 is KRVDWTIEY (SEQ ID NO: 29). In some embodiments, the polypeptide is derived from nsp15. In some embodiments, the polypeptide derived from nsp15 is SVVSKVVKV (SEQ ID NO: 30). In some embodiments, the polypeptide derived from ORF7a is IRQEEVQEL (SEQ ID NO: 31). In some embodiments, the polypeptide derived from S protein is EILDITPcSF (SEQ ID NO: 32) (cysteinylated Cys), EILDITPCSF (SEQ ID NO: 33), EILDITPcSFG (SEQ ID NO: 34) (cysteinylated Cys), HADQLTPTW (SEQ ID NO: 35), KNIDGYFKIY (SEQ ID NO: 36), NATNVVIKV (SEQ ID NO: 37), QLTPTWRVY (SEQ ID NO: 38), VGYLQPRTF (SEQ ID NO: 39), NLNESLIDL (SEQ ID NO: 40), or a combination thereof. In some embodiments, the polypeptide derived from Mis VATSRTLSY (SEQ ID NO: 41). In one example embodiment, the polypeptide derived from N protein is APRITFGGP (SEQ ID NO: 42).

In certain example embodiments at least one of the one or more the polypeptides is derived from expression of an alternative ORF. In one example embodimentIn, the alternative ORF is F3 R196, F2 R32, F6 R325, or F3 683. In one example embodiment, the one or more polypeptides derived from alternative ORF F3 R196 is METGGFSIDLP (SEQ ID NO: 43). In one example embodiment, the one or more polypeptides derived from alternative ORF F2 R32 is LSNPVILTK (SEQ ID NO: 44). In one example embodiment, the one or more polypeptides derived from alternative ORF F6 R325 is LSASLSNFLSI (SEQ ID NO: 45). In one example embodiment, the one or more polypeptides derived from alternative ORF F3 R683 is MPFQKPITL (SEQ ID NO: 46). In some embodiments, the polypeptide is derived from R196 peptide. In some embodiments, the polypeptide derived from R196 peptide is METGGFSIDLP (SEQ ID NO: 43). In some embodiments, the polypeptide is derived from R32 peptide. In some embodiments, the polypeptide derived from R32 peptide is LSNPVILTK (SEQ ID NO: 44). In some embodiments, the polypeptide is derived from R325 peptide. In some embodiments, the polypeptide derived from R325 peptide is LSASLSNFLSI (SEQ ID NO: 45). In some embodiments, the polypeptide is derived from R683 peptide. In some embodiments, the polypeptide derived from R683 peptide is MPFQKPITL (SEQ ID NO: 46).

In certain example embodiments, the one or more polypeptides are expressed and/or is bound by MHC-I 0-12, 0-11, 0-10, 0-9, 0-8, 0-7, 0-6, 0-5, 0-4, 0-3, 0-2, or 0-1 hours post infection.

Described in certain exemplary embodiments herein are polynucleotides encoding the one or more polypeptides described herein herein.

Described in certain exemplary embodiments herein are vectors comprising the polynucleotide(s) described herein. In certain exemplary embodiments, the vector is a synthetic mRNA vaccine.

Described in certain exemplary embodiments herein are immunogenic compositions comprising: the one or more polypeptides described herein or one or more polynucleotides described herein; and one or more antigenic components capable of stimulating production of an antibody targeting SARS-COV-2. In some exemplary embodiments, the one or more antigenic components comprises one or more antigenic polypeptides from a nucleocapsid phosphoprotein of SARS-COV-2, a spike glycoprotein of SARS-COV-2, a combination thereof, or one or more polynucleotides encoding the one or more antigenic polypeptides.

Described in certain exemplary embodiments herein are therapeutic compositions comprising the immunogenic composition herein and an anti-viral therapeutic. In some embodiments, the one or more polynucleotides encoding the one or more antigenic polypeptides is a synthetic mRNA vaccine.

Described in certain exemplary embodiments herein are methods of inducing a T cell response to SARS-COV-2 in a subject in need thereof comprising administering the immunogenic composition herein or the vector herein.

Described in certain exemplary embodiments herein are methods of inducing an antibody and T cell response to SARS-COV-2 in a subject in need thereof, comprising administering the immunogenic component herein.

Described in certain exemplary embodiments herein are methods of treating a SARS-CoV-2 infection comprising administering the immunogenic composition herein in combination with an anti-viral therapeutic.

Described in certain exemplary embodiments herein are methods of determining an infection status of a subject comprising contacting immune cells derived from the subject with the immunogenic composition herein; and detecting cross-reactivity of the immune cells to the immunogenic composition.

Described in certain exemplary embodiments herein are methods of identifying immunogenic peptides comprising: (a) lysing cells having a potential to express the immunogenic peptides of interest with a lysis buffer comprising a cell membrane disrupting detergent; (b) enzymatic shearing of nucleic acids in the lysed cells; (c) isolating HLA-I from the lysed cells, wherein the HLA-I is in complex with one or more polypeptides or proteins from the lysed cells; and (d) determining sequences of the one or more polypeptides or proteins in complex with the HLA-I from (c).

In certain example embodiments, the method further comprises (e) identifying HLA alleles that bind the polypeptides identified in using a HLA-I epitope binding predictor, and (f) selecting a subset of polypeptides that bind a defined percentage of HLA-I alleles. In some embodiments, the method further comprises selecting immunogenic peptides demonstrating a relative abundance above a defined threshold as determine by analysis of the complete cellular transcriptome and/or proteome. In some embodiments, the method further comprises ribosome sequencing to identify actively translated polypeptides and selecting immunogenic peptides that are being actively translated at one or more time points. In some embodiments, the nucleic acids in the lysed cells are enzymatically sheared using an endonuclease from *Serratia marcescens* and $MgCl_2$. In some embodiments, the cell membrane disrupting agent is Triton-X. In some embodiments, (d) is performed by liquid chromatography tandem mass spectrometry analysis. In some embodiments, isolating HLA-1 comprises immunoprecipitation of the HLA-I complex with an anti-HLA-1 antibody. In some embodiments, the immunogenic peptides of interest are expressed by a pathogen and wherein the cells have been infected with the pathogen. In some embodiments, the infected cells are engineered to express one or more cell surface receptors used by the pathogen to infect the cells. In some embodiments, the cells are treated with one or more cell signaling molecules related to infection by the pathogen.

In some embodiments, the pathogen is a virus. In some embodiments, the virus is SARS-Cov-2. In some embodiments, the cells are engineered to express ACE2 and TMPRSS2. In some embodiments, the cells are engineered to increase or decrease HLA presentation. In some embodiments, the cells are engineered to increase or decrease expression of one or more of CITA, proteasome subunits, TPA, POMP, or ubiquitin-proteasome genes.

Described in certain exemplary embodiments herein are methods of designing an immunogenic composition, comprising: identifying immunogenic peptides derived from expression of out-of-frame ORFs and/or alternative ORFs; and codon optimizing nucleic-acid based vaccines directed to immunogenic peptides derived from in-frame ORFs such that expression of immunogenic peptides derived from out-of-frame ORFs and/or alternative ORFs is maintained.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIGS. 1A-1E-Experimental design and measurements of HLA-I immunopeptidome, whole proteome and RNA-seq in SARS-COV-2 infected cells. (FIG. 1A) Schematic representation of the experiment and the antigen presentation pathway. A549/ACE2/TMPRSS2 and HEK293T/ACE2/TMPRSS2 cells were infected with SARS-COV-2 (Washington strain, accession number MN985325) at Multiplicity of Infection (MOI) of 3 in the BSL3 facility and harvested at 12, 18 and 24hpi (hours post infection). For HLA-I immunopeptidome measurements cells were lysed and HLA-I peptide complexes were immunoprecipitated. The flow-through after immunoprecipitation was collected for whole proteome measurements. For RNA-seq Trizol was added to infected cells, RNA was purified, and strand-specific short reads sequencing was performed. MS/MS spectra of immunopeptidome and proteome analysis were searched against a protein database including the human proteome, SARS-COV-2 canonical ORFs and non-canonical ORFs identified experimentally by Ribo-seq (Finkel et al., 2020b) or in-silico 6-frames translation. Peptides were filtered at 1.5% FDR. (FIG. 1B) Population frequency of the 9 endogenous HLA-I alleles expressed in A549 and HEK293T cells. (FIG. 1C) Length distribution of HLA peptides in infected and naive cells. (FIG. 1D) Motif of 9-mer sequences identified in infected and naive cells. (FIG. 1E) Fraction of observed peptides assigned to alleles using HLAthena prediction (rank cutoff <0.5) for immunopeptidome of infected and naive cells.

(FIG. 2A) Summary of peptides location across SARS-COV-2 genome from HLA-I immunopeptidome and whole proteome mass-spectrometry. Individual tracks represent: (i) Canonical ORFs according to NC_045512.2. Colors represent Ribo-seq translation measurements in Vero cells. (ii) Position of 23 internal out-of-frame ORFs identified by Ribo-seq. (iii) HLA-I peptides detected in HEK293T cells. (iv and v) two biological replicates of HLA-I peptides detected in A549 cells. (vi and vii) Tryptic peptides from whole proteome mass-spectrometry in HEK293T and A549 cells. Blue bars indicate peptides mapped to internal out-of-frame ORFs. (FIG. 2B) Comparison between SARS-COV-2 proteins intensity (iBAQ) in A549 and HEK293T cells. (FIGS. 2C-2D) Comparison between our protein intensity measurements and ribo-seq in A549 (FIG. 2C) and HEK293T (FIG. 2D). nsps are not indicated since expression measurements are not comparable between ORF1a and 1b polyproteins (Ribo-seq) and individual cleaved nsps proteins (MS).

(FIG. 3A (SEQ ID NO: 215)) HLA-I peptides derived from S.iORF1/2. Prediction rank scores were computed with HLAthena. Underscored Methionines (M) represent the start codons of S.iORF1 and S.iORF2. (FIG. 3B (SEQ ID NO: 216) HLA-I peptides derived from ORF9b (N.iORF1) and N.iORF2 and the computed prediction scores for the assigned alleles. (FIG. 3C (SEQ ID NO: 5-7, 10)) Spectra plots of synthetic peptides confirming the sequences of four HLA-I peptides that were identified in S.iORF1/2 and ORF9b. For each peptide, peaks from HLA-IP samples are presented on the positive y-axis and peaks from synthetic peptides are presented on the negative y-axis. (FIG. 3D (SEQ ID NO: 4-6, 217-223)) Biochemical HLA-A*02:01/peptide binding measurements. Purified MHC complexes were incubated with a high-affinity radiolabeled A*02:01 ligand and a binding competition assay was performed with increasing concentration of individual SARS-COV-2 derived HLA-I peptides. The concentration of peptide yielding 50% inhibition of the binding of the radiolabeled A*02:01 ligand ($IC_{50}$) was used to calculate peptide affinity. (FIG. 3E (SEQ ID NO: 217-220)) The effect of human codon optimization on HLA-I peptides derived from S.iORF1/2. Needleman-Wunsch pairwise global alignment between SASR-CoV-2 sequence (NC_045512.2) and the human optimized S from the Krogan library (Gordon et al., 2020) in the S.iORF1/2 coding region, canonical and +1 reading frames. Purple boxes indicate the position of the HLA-I peptides in the out-of-frame ORFs. (FIG. 3F (SEQ ID NO: 224-231)) similar to (FIG. 3E), comparing the sequences of SARS-COV-2 and the human optimized Nucleocapsid from the Krogan library in the ORF9b coding region. (FIG. 3G) Bichemical HLA-A*02:01/peptide binding measurments. The concentration of peptide yielding 50% inhibition of the binding of the radiolabeled A*02:01 ligand ($IC_{50}$) was used to calculated peptide affinity.

(FIG. 4A) Relative abundance of RNA, proteins and HLA-presented peptides mapping to SARS-CoV-2 and human sequences in non-infected A549 cells and 12, 18 and 24 h post infection. (FIG. 4B (SEQ ID NO: 11, 15, 28, 32-33, 36-39, 233)) Dynamics of TMT-labeled HLA peptides at 12, 18 and 24 h after infection with SARS-COV-2. Intensity values were normalized to the 12 h time point.

(FIG. 5A) Venn-diagram showing the overlap between total HLA-I peptides in A549+/− SARS-COV-2 infection. (FIG. 5B) Distribution of protein and HLA-I peptide abundances ranked by protein intensity (iBAQ) and total HLA peptide intensity. Proteins and peptides mapped to SARS-COV2 are highlighted in blue and annotated with the respective sequence and gene name. (C (SEQ ID NO: 10-11, 16-17, 20, 28, 33, 36-37, 39, 41, 47)) Same as (B) but for HLA-I peptides intensity. (FIG. 5D) Heatmap showing iBAQ intensity of major proteins involved in antigen presentation. (FIG. 5E) Volcano plot comparing changes on the protein level across infected and naive A549 and HEK293T cells. Significant proteins involved in proteasomal degradation are highlighted. (FIG. 5F) Volcano plot for genes with function related to ubiquitin-mediated degradation.

(FIG. 6A (SEQ ID NO: 5-8, 10-11, 14-17, 20, 24, 27-29, 31, 33, 35-39, 41, 47)) HLAthena predictions of estimated population coverage at 0.1% (green), 0.5% (purple), and 1% (orange) cutoffs for the LC-MS/MS observed SARS-COV-2 peptides. iORF peptide sequences are marked as red. (FIG. 6B (SEQ ID NO: 5-8, 10-11, 14-17, 20, 24, 27-29, 31, 33, 36-39, 41, 47)) HLAthena predictions using a 1% cutoff demonstrating the number of unique HLA-A,-B, and -C alleles that LC-MS/MS observed SARS-COV-2 peptides are predicted to strongly bind to achieve high population coverage.

(FIG. 7A) Summary of peptides location across SARS-COV-2 genome from HLA-I immunopeptidome, whole proteome, and predictions. Individual tracks represent: (i) Canonical ORFs according to NC_045512.2. Colors represent Ribo-seq translation measurements in Vero cells (Finkel et al., 2020b). (ii) Position of 23 non-canonical ORFs identified by Ribo-seq (Finkel et al., 2020b). (iii, iv) HLA-I peptides detected in HEK293T cells mapped to canonical and non-canonical ORFs . . . (v, vi) HLA-I peptides detected in A549 cells mapped to canonical and non-canonical ORFs. (vii, viii) Tryptic peptides from whole proteome mass-spectrometry in HEK293T and A549 cells. (ix, x) Predicted HLA-I peptides according to HLAthena, rank threshold=0.5. Black and blue bars indicate peptides from canonical and non-canonical ORFs, respectively. (FIG. 7B) In-vitro binding of HLA-I peptides and purified MHC complexes. Shown are the fractions of peptides that were confirmed to bind the assigned alleles ($IC_{50}$<500 nM, Table 4). (FIG. 7C) SARS-COV-2 proteins abundance in A549 and HEK293T cells 24hpi. iBAQ-intensity-based absolute quantification. (FIGS. 7D and 7E) Comparison between our protein abundance measurements 24hpi and Ribo-seq (Finkel et al., 2020b) in A549 (FIG. 7D) and HEK293T (FIG. 7E). Nsps are not indicated since expression measurements are not comparable between polyproteins (measured by Ribo-seq) and individual cleaved nsps proteins (measured by mass spectrometry). (FIG. 7F) SARS-COV-2 ORFs HLA-I presentation potential in A549 cells. ORFs were ranked according to the ratio between the number of peptides predicted to bind any of the six HLA-I alleles in A549 and the total number of 8-11mers. (FIG. 7G) Similar to (FIG. 7F) for HEK293T cells. (FIG. 7H) Presentation potential across 92 HLA-I alleles. Showing box plots of the ratio between the number of peptides predicted to bind each of the 92 HLA-I alleles and total number of peptides. ORFs are ranked according to the median across alleles.

(FIGS. 8A and 8B) Dynamics of TMT-labeled HLA-I peptides from human proteins (grey), canonical SARS-CoV-2 proteins (blue) and out-of-frame SARS-COV-2 ORFs (purple) 3, 6, 12, 18 and 24 h post infection in A549 cells (FIG. 8A (SEQ ID NO: 11, 15, 17-18, 22, 28, 36-37, 39, 41)) and HEK293T (FIG. 8B (SEQ ID NO: 6-7, 12-14, 19, 23, 26, 29, 30-31, 40, 42)). TMT-intensity values of peptides detected in two independent experiments (3, 6, 24hpi and 12, 18, 24hpi) were normalized to the respective abundance at 24 h present in both experiments. Dashed lines indicate detection in the 3|6|24 h plex only. (FIG. 8C) Dynamics of SARS-COV-2 proteins expression according to whole proteome analysis 3, 6 and 24 h post infection in A549 and HEK293T cells. (FIG. 8D) Venn diagram showing SARS-COV-2 proteins according to their earliest expression time (red circle 3hpi, green circle 6-24hpi) and the source proteins for HLA-I presented peptides (blue circle) in A549 and HEK293T cells. Hypergeometric p-value ($p<0.0375$) represents the enrichment of early expressed proteins (3hpi) in the group of proteins presented on HLA-I. (FIG. 8E) CD8+ responses to SARS-COV-2 proteins in convalescence COVID-19 patients. Viral proteins were divided according to their earliest expression time. Shown are % of responses per protein according to a recent study (Tables 5A-5B in (Tarke et al., 2020)).

(FIG. 9A) Rank plot of the protein abundances represented by log 10 protein iBAQ values for each human (gray), canonical SARS-COV-2 (blue, represented in greyscale), and noncanonical SARS-COV-2 proteins detected in the whole proteome analysis of A549 cells 24hpi. SARS-COV2 proteins are annotated with their respective gene names. (FIG. 9B SEQ ID NO: 10-11, 16-17, 20, 28, 33, 36-37, 39, 41, 47)) Similar rank plot to (FIG. 9A) but for observed HLA-I peptides and their abundances represented by log 2 peptide intensities in A549 cells 24hpi. Peptides mapped to SARS-COV-2 are annotated with their respective amino acid sequence and source protein name. (FIG. 9C) Venn-diagram showing the overlap between total HLA-I peptides in uninfected (gray) and 24 hours post SARS-COV-2 infection (blue, represented in greyscale) A549 cells. (FIG. 9D) Heatmap of log 10 iBAQ values for canonical antigen presentation pathway proteins observed across uninfected and infected A549 and HEK293T cells 24hpi. (FIG. 9E) Volcano plot comparing protein levels across uninfected and infected A549 and HEK293T cells 24hpi. Proteins from SARS-COV-2 (red, represented in greyscale), ubiquitination pathways (teal, represented in greyscale), proteasomal function (purple, represented in greyscale), antigen processing (pink, represented in greyscale), and IFN pathways (orange, represented in greyscale) are shaded accordingly. Significantly changing proteins are shown above the dashed line (p-value <0.01, moderated t-test) with annotations of specific proteins involved in the above pathways. (FIG. 9F) Similar to (FIG. 9E), a volcano plot representing publically available whole proteome data from A549/ACE2 cells 2hpi (PXD020019, (Stukalov et al., 2020)) with identical shading to indicate associated pathway annotation.

(FIG. 10A (SEQ ID NO: 4-5, 7-8, 12-13, 19, 23-24)) HLA-A2 transgenic mice immunization with HLA-I peptides. Five transgenic mice were immunized with a pool of nine HLA-I peptides detected on A*02:01 in HEK293T cells. 10 days post vaccination, mice were euthanized and spleens were removed for ELISpot assays. Red blood cell-depleted mouse splenocytes were incubated with individual peptides in triplicate for 18 h and IFNγ secretion was monitored using a specific antibody. HLA-A*02:01 restricted HIV-Gag peptide and non-stimulated wells were used as negative controls. AntiCD3 and PHA were used as a positive control. Dashed line represents the threshold for positive responses, x3 the median of the HIV-Gag negative control. (FIG. 10B (SEQ ID NO: 4-5, 8, 24)) Images from a developed ELISpot plate from one of the five vaccinated mice. (FIG. 10C) INFγ ELISpot assay with peptide pools and PBMCs from convalescent COVID-19 patients. PBMCs from patients expressing A*02:01 alleles were incubated with a pool of HLA-I peptides from canonical ORFs (15 peptides) or out-of-frame ORFs (7 peptides) for 16-20 h. A pool of 102 peptides tiling the entire nucleocapsid (NC) protein (15aa, 11aa overlap) that was evaluated in the same samples (Gallagher et al. in preparation) served as positive control. Each pool was tested in two replicates and the average number of detected spots is indicated after subtraction of background. (FIG. 10D) Images from developed ELISpot plates of two patients with positive T cell responses to the pool of non-canonical HLA-I peptides from out-of-frame ORFs. (FIG. 10E (SEQ ID NO: 8, 206-207, 241-243)) Illustration of multiplexed pMHC tetramer assay and T cells single cell profiling. CD8+ enriched PBMCs are stained with barcoded pMHC tetramer pool, sorted by flow cytometry and subjected to single cell sequencing uncovering the reactive peptide (unique tetramer's barcode), TCR and transcriptomics. (FIG. 10F (SEQ ID NO: 4-8, 10-17, 19-20, 23-24, 27-29, 31, 33, 35-39, 41-42, 206-209)) CD8+ T cell reactivity detected in convalescent COVID-19 patients and unexposed subjects expressing A*02:01 to individual peptides that bind HLA-A*02:01 or other alleles. The score in the heatmap indicates the fraction of peptide-specific reacting T cells from total CD8+ cells in the sample. (FIG. 10G (SEQ ID NO: 9)) Identification of phenotypic features of reacting T cells by single cell transcriptomics. (upper panel) shown are UMAP embedding of all tetramer positive cells colored by unsupervised clustering; (middle panel) expression levels of 14 genes associated with different states of T cells as previously characterized (Su et al., 2020) in the six clusters: naïve T cells (TCF7, LEF1, CCR7), effector (GZMB, PRF1, GNLY), memory (AQP3, CD69, GZMK), exhaustion (PDCD1, TIGIT, LAG3) and proliferation (MKI67, TYMS). (lower panel) expression level of these 14 genes in individual T cells reactive to ELPDEFVVTV (SEQ ID NO: 9) peptides from ORF9b.

FIGS. 11A-11D-Presentation prediction and population coverage estimates of MS-identified SARS-COV-2 HLA-I peptides. (FIG. 11A (SEQ ID NO: 4-8, 10-12, 14-31, 33, 36-40, 42, 47)) Summary of LC-MS/MS identified SARS-COV-2 epitopes with corresponding HLAthena predictions for the 6 HLA-I alleles expressed by A549 (HLA-A*25:01, A*30:01, B*18:01, B*44:03, C*12:03, C*16:01; top) and the 3 HLA-I alleles in HEK293T (HLA-A*02:01, B*07:02, C*07:02; bottom). (FIG. 11B (SEQ ID NO: 4-8, 10-16, 18-24, 26-31, 33, 36-42, 47)) HLAthena predictions for 92 HLA-I alleles using percentile rank cutoff values of 0.1, 0.5, 1, and 2%, demonstrating the number of unique HLA-A,-B, and -C alleles that LC-MS/MS observed SARS-CoV-2 peptides are predicted to strongly bind (left) to achieve a high estimated population coverage (right). Alleles are colored and ordered according to loci and world population frequency (high to low color intensity). Peptides are ordered according to their estimated coverage at % rank cutoff of 0.5. (FIG. 11C) In-vitro binding of HLA-I peptides and five HLA alleles that were not profiled in our cell lines. Shown are the fractions of peptides that were confirmed to bind the predicted alleles ($IC_{50}$<500 nM, Table 4) at % rank<0.5 and 2. (FIG. 11D) $IC_{50}$ affinity measurements of HLA-I peptides that were predicted to bind the five alleles tested or not at % rank<2. Lower $IC_{50}$ indicates higher affinity. Ranksum p-value is indicated.

(FIG. 13A) Cultured media of infected A549 cells. As expected, plaques were observed in all three dilutions, confirming the presence of infectious virus. (FIG. 13B) Infected A549 cells were treated with a lysis buffer containing 1.5% Triton-X and Benzonase. Lysates were incubated for 3 hours in the BSL3 prior dilution for plaque assay. When adding the 1:10 dilution, cells died immediately due to the relatively high Triton-X concentration. No plaques were observed in the 1:102 and 1:103 dilutions. (FIG. 13C) Same as (FIG. 13B) but for non-infected A549 cells. Here too, 1:10 dilution leads to immediate cell death confirming that the observed cell death in the infected sample was not due to the virus. As expected, no plaques were observed.

(FIG. 14A) Logo plots for individual alleles of peptides identified and assigned to cell line specific alleles with HLAthena percentile rank <0.5 for naive and 24 h post SARS-COV-2 infected A549 (left) and HEK293 (right) cells. (FIG. 14B) Peptide logo plots aggregated over all alleles for label free time course experiments in A549 and HEK293 samples. (FIG. 14C) Allele assignment for peptides identified in time course experiments using HLAthena with a percentile rank <0.5 cutoff. (FIG. 14D) Expression level of HLA-A,-B, and -C alleles as measured by RNA-seq in A549 and HEK293T cell lines pre- and 24 hr post-infection. (FIG. 14E) Scored human derived 9-mer peptides for each alle to estimate the contribution of the range of peptides in each allele that can bind to the obtained surface representation.

(FIG. 15A) Table showing the percentage of the total whole proteome abundance represented by SARS-COV-2 derived proteins at 0, 3, 6, 12, 18, 24hpi. identified in singleshot whole proteome LC-MS/MS analyses. (FIG. 15B) Rank plot of the protein abundances represented by log 10 protein iBAQ values for each human (gray), canonical SARS-COV-2 (blue, as represented in greyscale), and noncanonical SARS-COV-2 proteins detected in the whole proteome analysis of HEK293T cells 24hpi. SARS-COV2 proteins are annotated with their respective gene names. (FIG. 15C (SEQ ID NO: 5-8, 14, 29)) Similar rank plot to (FIG. 15A) but for observed HLA-I peptides and their abundances represented by log 2 peptide intensities in HEK293T cells 24hpi. Peptides mapped to SARS-COV-2 are annotated with their respective amino acid sequence and source protein name. (FIG. 15D) Heatmap of iBAQ values for antigen presentation pathway proteins observed across uninfected and 24hpi. in A549 and HEK293T cells. (FIG. 15E) Volcano plot comparing protein levels across uninfected and infected A549/ACE2 cells 6hpi reported in publicly available whole proteome data (PXD020019). Proteins from SARS-CoV-2 (red, represented in greyscale), ubiquitination pathways (teal, represented in greyscale), proteasomal function (purple, represented in greyscale), antigen processing (pink), and IFN pathways (orange, represented in greyscale) are shaded accordingly. Significantly changing proteins are shown above the dashed line (p-value <0.01) along with annotations of specific proteins involved in the above pathways.

(FIG. 16A) The number of unique CD8+ clones reacting to HLA-I peptides that were found to bind HLA-A*02:01 in biochemical binding measurement and HLA-I peptides that did not bind HLA-A*02:01. Wilcoxon ranksum p-value is indicated. (FIG. 16B (SEQ ID NO: 8)) Network plot showing the relationship of unique clonotypes within and across subjects. Clonotypes, shown as nodes, are connected to other clonotypes with similar alpha or beta CDR3 with edges. (FIG. 16C) CDR3 size distributions for alpha and beta TCR chains. (FIG. 16D) TCR a/b sequence logo for related clonotypes represented in the interconnected cluster at the bottom of the network shown in (FIG. 16B).

(FIG. 17A (SEQ ID NO: 4-8, 10-17, 19-20, 23-24, 27-29, 31, 33, 35-39, 41-42, 47, 210-211)) The number of unique CD8+ clones reacting to HLA-I peptides that were found to bind HLA-B*07:02 in biochemical binding measurement and HLA-I peptides that did not bind HLA-B*07:02. Wilcoxon ranksum p-value is indicated. (FIG. 17B) CD8+ T cell reactivity detected in convalescent COVID-19 patients and unexposed subjects expressing B*07:02 to individual peptides that bind HLA-B*07:02 or other alleles. The score in the heatmap indicates the fraction of peptide-specific reacting T cells from total CD8+ cells in the sample.

(FIGS. 19B and 19C) Mutations in the S.iORF1/2 region of B.1.351 (FIG. 19B (SEQ ID NO: 219, 244-245)) and B.1.1.7 (FIG. 19C (SEQ ID NO: 219, 246-247)) variants in comparison to the SARS-COV-2 RefSeq sequence NC_045512.2 isolated from Wuhan. The position of the three HLA-I peptides is indicated.

Figure 1D:
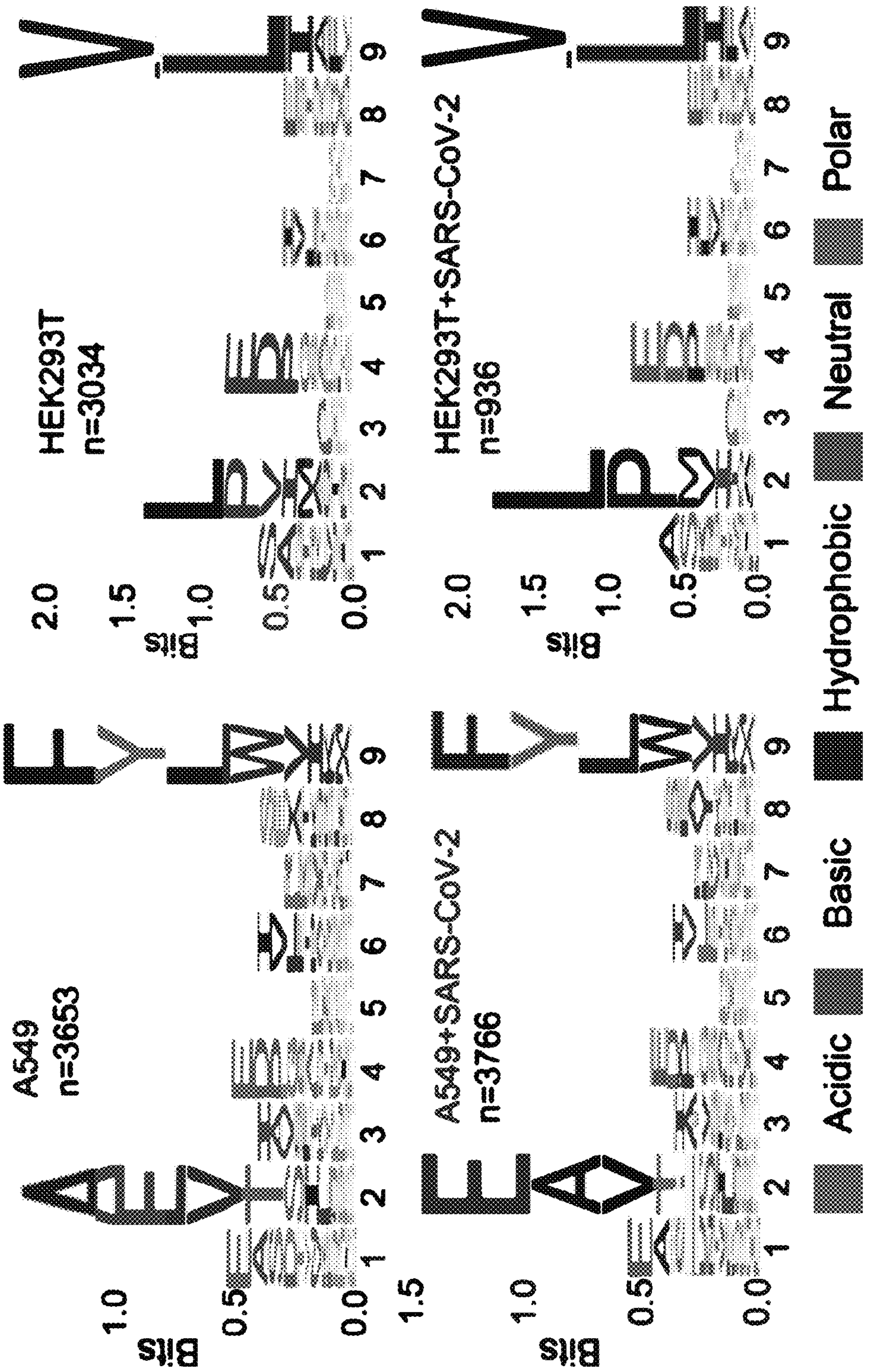

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.); PCR 2: A Practical Approach (1995) (M. J. MacPherson, B. D. Hames, and G. R. Taylor eds.); Antibodies, A Laboratory Manual (1988) (Harlow and Lane, eds.); Antibodies, A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology $2^{nd}$ ed., J. Wiley & Sons (New York, N.Y. 1994), March, Advanced Organic Chemistry Reactions, Mechanisms and Structure $4^{th}$ ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids.

Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The term "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

A protein or nucleic acid derived from a species means that the protein or nucleic acid has a sequence identical to an endogenous protein or nucleic acid or a portion thereof in the species. The protein or nucleic acid derived from the species may be directly obtained from an organism of the species (e.g., by isolation), or may be produced, e.g., by recombination production or chemical synthesis.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

OVERVIEW

T cell-mediated immunity plays an important role in controlling SARS-COV-2 infection, but the repertoire of naturally processed and presented viral epitopes on class I human leukocyte antigen (HLA-I) remains uncharacterized. Applicants disclose herein the first HLA-I immunopeptidome of SARS-COV-2 in twoo cell lines at different times post infection using mass spectroscopy. Disclosed herein aare HLA-I peptides derived not only from canonical open reading frames (ORFs) but also from internal out-of-frame ORFs in spike and nucleocapsid not captured by existing vaccines. Whole-proteome analysis of infected cells revealed that early expressed viral proteins contribute more to HLA-I presentation and immunogenicity. These discoveries, along with the out-of-frame ORF epitopes, help facilitate selection of peptides for immune monitoring and vaccine use.

Accordingly, the present disclosure provides compositions for activating T cell-mediated immunity targeting cells infected by a virus (e.g., SARS-COV-2) in a subject and the application thereof. In one aspect, the composition comprises one or more polypeptides that are a) capable of binding to Major Histocompatibility Complex (MHC) class I and b) derived from one or more proteins of a virus. In some embodiments, the one or more polypeptides may be derived from internal out-of-frame open reading frames of a nucleic acid in the virus. In some embodiments, the composition may further comprise one or more antigenic components capable of stimulating production of an antibody targeting a virus.

In another aspect, the present disclosure provides methods of immunizing a subject against a virus infection or treating a subject infected by a virus. In some embodiments, the methods comprise administering the compositions herein to a subject, e.g., a subject in need thereof.

In another aspect, the present disclosure provides methods of determining an infection status of a subject. In some embodiments, the methods comprise contacting immune cells derived from the subject with the immunogenic composition; and detecting cross-reactivity of the immune cells to the composition.

In another aspect, the present disclosure provides methods of identifying viral immunogenic peptides comprising: lysing cells having a potential to express the immunogenic peptides of interest with a lysis buffer comprising a cell membrane disrupting detergent; enzymatic shearing of nucleic acids in the lysed cells; isolating MHC-I from the lysed cells, wherein the HLA-I is in complex with one or more polypeptides or proteins from the lysed cells; and determining sequences of the one or more polypeptides or proteins in complex with the HLA-I.

COMPOSITIONS

In one aspect, the present disclosure provides compositions comprising one or more polypeptides for inducing immunity in a subject, e.g., to protect from or treat the infection of a virus. In some cases, the present disclosure includes one or more polynucleotides encoding the one or more polypeptides herein.

In some embodiments, the compositions may comprise immunogenic composition(s). The immunogenic compositions may elicit an immunological response in the host to which the immunogenic compositions are administered. Such immunological response may be a T cell-mediated (e.g., cytotoxic T cell-mediated) immune response to the immunogenic compositions. In certain embodiments, the immunogenic compositions may be combined with one or more antigenic components and/or anti-viral therapeutics. In some examples, such combination may elicit cellular and/or antibody-mediated immune response, e.g., production or activation of antibodies, B cells, helper T cells, suppressor T cells, and/or cytotoxic T cells and/or gamma-delta T cells.

In some embodiments, the composition may be used to treat viral infection of a subject. For example, the composition may be used to remove infected cells in the subject. Alternatively or additionally, the composition may be used to prevent viral infection or reduce the impact of viral infection on the subject (e.g., clinical signs normally dis-played by an infected host, a quicker recovery time and/or a lowered duration of infectivity or lowered pathogen titer in the tissues or body fluids or excretions of the infected subject). In some cases, the subject displays a protective immunological response such that resistance to new infection may be enhanced and/or the clinical severity of the disease may be reduced.

Polypeptides

The immunogenic compositions may comprise one or more polypeptides. The one or more polypeptides is each capable of binding to Major Histocompatibility Complex (MHC) class I and is derived from one or more proteins of a virus. In an embodiment the MHC class I is a Human Leukocyte Anticgen class I (HLA-I). In an aspect, the one or more polypeptides are derived from a virus that related to a viral infection targeted for prevention, treatment or reduction of impact in a subject. The one or more polypeptides may be derived from viral proteins expressed from one or more open reading frames (ORFs) in a viral genome. In an aspect, the one or more polypeptides is derived from a protein of SARS-Co-V-2, and may optionally be derived from expression of internal out-of-frame open reading frame (ORF) of SARS-COV-2.

Major Histocompatibility Complex (MHC) Class I

The polypeptide(s) may bind, or may be capable of binding, to Major Histocompatibility Complex (MHC) class I, e.g., Human Leukocyte Antigen class I. In some cases, after binding, the MHC class I may present the one or more polypeptides to activate cytotoxic T cells. As used herein, MHC refers to protein complexes capable of binding peptides resulting from the proteolytic cleavage of protein antigens and representing potential T-cell epitopes, transporting them to the cell surface and presenting them there to specific cells, in particular cytotoxic T-lymphocytes or T-helper cells.

MHC class I, or MHC-I, function mainly in antigen presentation to CD8+T lymphocytes or cytotoxic T cells and may be heterodimers comprising two polypeptide chains, an alpha chain and β2-microglobulin.

In some embodiments, the MHC class I may be Human Leukocyte Antigen (HLA) class I, which is the MHC class I in human. HLA class I may comprises an alpha chain and β2-microglobulin. The alpha chain may be HLA-A, HLA-B, or HLA-C. In one example, the one or more peptides binds, or is capable of binding, to HLA-A. In another example, the one or more peptides binds, or is capable of binding, to HLA-B. In another example, the one or more peptides binds, or is capable of binding, to HLA-C. In another example, the one or more peptides binds, or is capable of binding, to β2-microglobulin of HLA-1.

HLA Alleles

The one or more peptides may bind, or may be capable of binding, to proteins encoded by certain HLA alleles. HLA genes may be polymorphic and have many different alleles, allowing them to fine-tune the immune system. The nomenclature of HLA genes are well known in the art, e.g., as described in Marsh SGE et al., Nomenclature for factors of the HLA system, 2010, Tissue Antigens. 2010 April; 75 (4): 291-455, which is incorporated by reference in its entirety.

The HLA alleles may encode HLA protein capable of epitope binding. In some cases, the HLA alleles may have a ranking cut-off as determined by a machine learning predictor of HLA (e.g., HLA-I) epitope binding. For example, the HLA alleles may have a ranking cut-off of at least 0.1%, 0 at least 0.5%, or at least 1.0% as determined by HLAthena. Examples of methods for determining the ranking include those described in Sarkizova S. et al., A large peptidome dataset improves HLA class I epitope prediction across most of the human population, Nat Biotechnol. 2020 February; 38 (2): 199-209; and Abelin J G et al., Mass Spectrometry Profiling of HLA-Associated Peptidomes in Mono-allelic Cells Enables More Accurate Epitope Prediction, Immunity. 2017 Feb. 21; 46 (2): 315-326, which are incorporated by reference herein in their entireties.

In some embodiments, the proteins encoded by HLA alleles include HLA proteins encoded by encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, HLA-C*07:02; HLA-A*01:01; HLA-A*02:06; HLA-A*26:01; HLA-A*02:07; HLA-A*29:02; HLA-A*02:03; HLA-A*30:02; HLA-A*32:01; HLA-A*68:02; HLA-A*02:05; HLA-A*02:02; HLA-A*36:01; HLA-A*02:11; HLA-A*02:04; HLA-B*35:01; HLA-B*51:01; HLA-B*40:01; HLA-B*40:02; HLA-B*07:02; HLA-B*07:04; HLA-B*08:01; HLA-B*13:01; HLA-B*46:01; HLA-B*52:01; HLA-B*44:02; HLA-B*40:06; HLA-B*13:02; HLA-B*56:01; HLA-B*54:01; HLA-B*15:02; HLA-B*35:07; HLA-B*27:05; HLA-B*15:03; HLA-B*42:01; HLA-B*55:02; HLA-B*45:01; HLA-B*50:01; HLA-B*35:03; HLA-B*49:01; HLA-B*58:02; HLA-B*15:17; HLA-C*57:02; HLA-C*04:01; HLA-C*03:04; HLA-C*01:02; HLA-C*07:01; HLA-C*06:02; HLA-C*03:03; HLA-C*08:01; HLA-C*15:02; HLA-C*12:02; HLA-C*02:02; HLA-C*05:01; HLA-C*03:02; HLA-C*16:01; HLA-C*08:02; HLA-C*04:03; HLA-C*17:01; or HLA-C*17:04. In some embodiments, the HLA-1 is encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, or HLA-C*07:02. In some embodiments, the proteins encoded by HLA alleles include HLA proteins encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, HLA-C*07:02, or a combination thereof.

Figure 11B:
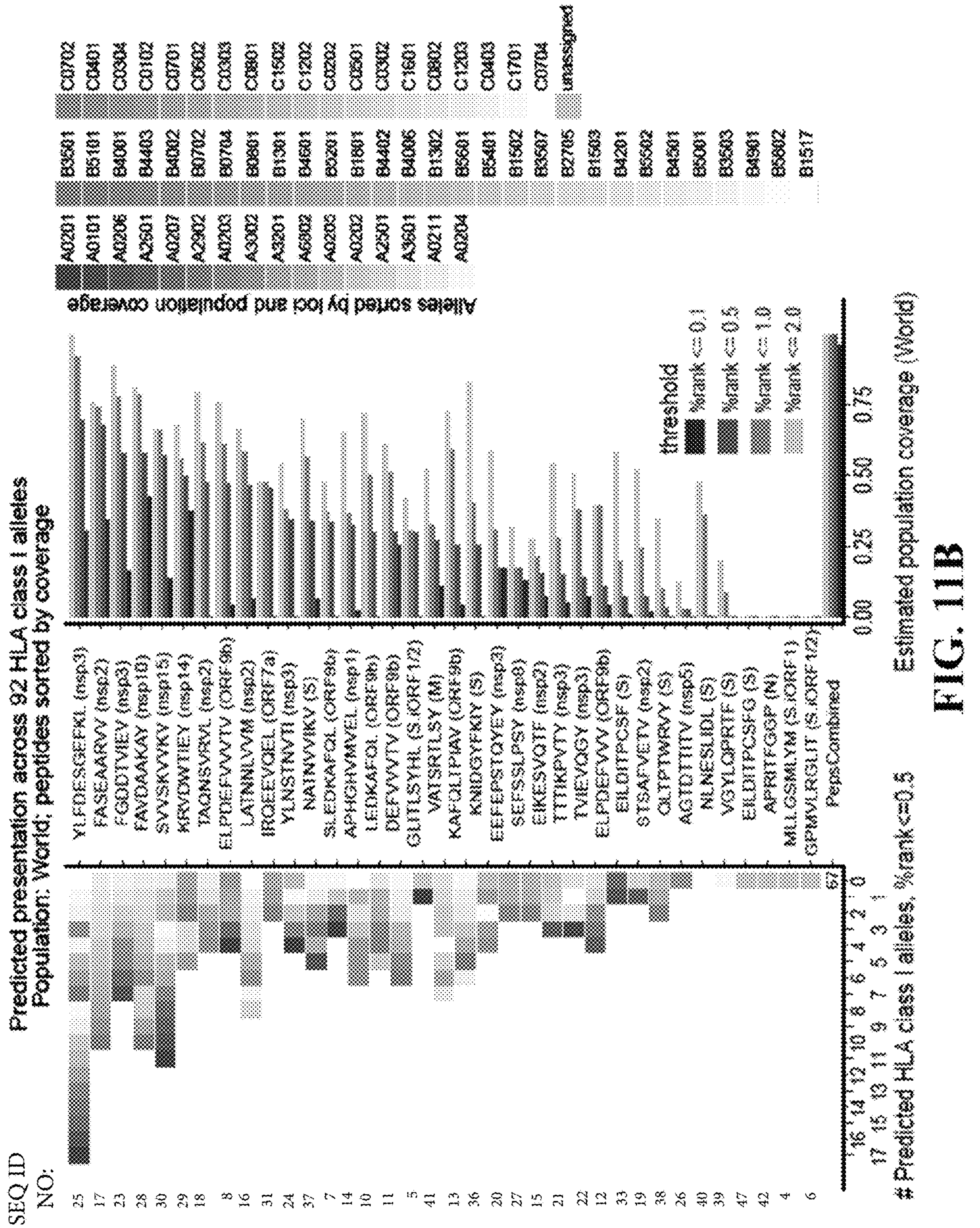

In one example, the one or more polypeptides binds, or is capable of binding, to an HLA protein encoded by HLA-A*02:01. In another example, the one or more polypeptides binds, or is capable of binding, to an HLA protein encoded by HLA-A*25:01. In another example, the one or more polypeptides binds, or is capable of binding, to an HLA protein encoded by HLA-A*30:01. In another example, the one or more polypeptides binds, or is capable of binding, to an HLA protein encoded by HLA-B*18:01. In another example, the one or more polypeptides binds, or is capable of binding, to an HLA protein encoded by HLA-B*44:03. In another example, the one or more polypeptides binds, or is capable of binding, to an HLA protein encoded by HLA-C*12:03. In another example, the one or more polypeptides binds, or is capable of binding, to an HLA protein encoded by HLA-B*16:01. In another example, the one or more polypeptides binds, or is capable of binding, to an HLA protein encoded by HLA-A*02:01. In another example, the one or more polypeptides binds, or is capable of binding, to an HLA protein encoded by HLA-B*07:02. In another example, the one or more polypeptides binds, or is capable of binding, to an HLA protein encoded by HLA-C*07:02. In another example, the one or more polypeptides binds, or is capable of binding, to an HLA protein encoded by HLA-A*01:01. In another example, the one or more polypeptides binds, or is capable of binding, to an HLA protein encoded by HLA-A*02:06. In another example, the one or more polypeptides binds, or is capable of binding, to an HLA protein encoded by HLA-A*26:01. In another example, the one or more polypeptides binds, or is capable of binding, to an HLA protein encoded by HLA-A*02:07. In another example, the one or more polypeptides binds, or is capable of binding, to an HLA protein encoded by HLA-A*29:02. In another example, the one or more polypeptides binds, or is capable of binding, to an HLA protein encoded by HLA-A*02:03. In another example, the one or more polypeptides binds, or is capable of binding, to an HLA protein encoded by HLA-A*30:02. In another example, the one or more polypeptides binds, or is capable of binding, to an HLA protein encoded by HLA-A*32:01. In another example, the one or more polypeptides binds, or is capable of binding, to an HLA protein encoded by HLA-A*68:02. In another example, the one or more polypeptides binds, or is capable of binding, to an HLA protein encoded by HLA-A*02:05. In another example, the one or more polypeptides binds, or is capable of binding, to an HLA protein encoded by HLA-A*02:02. In another example, the one or more polypeptides binds, or is capable of binding, to an HLA protein encoded by HLA-A*36:01. In another example, the one or more polypeptides binds, or is capable of binding, to an HLA protein encoded by HLA-A*02:11. In another example, the one or more polypeptides binds, or is capable of binding, to an HLA protein encoded by HLA-A*02:04. In another example, the one or more polypeptides binds, or is capable of binding, to an HLA protein encoded by HLA-B*35:01. In another example, the one or more polypeptides binds, or is capable of binding, to an HLA protein encoded by HLA-B*51:01. In another example, the one or more polypeptides binds, or is capable of binding, to an HLA protein encoded by HLA-B*40:01. In another example, the one or more polypeptides binds, or is capable of binding, to an HLA protein encoded by HLA-B*40:02. In another example, the one or more polypeptides binds, or is capable of binding, to an HLA protein encoded by HLA-B*07:02. In another example, the one or more polypeptides binds, or is capable of binding, to an HLA protein encoded by HLA-B*07:04. In another example, the one or more polypeptides binds, or is capable of binding, to an HLA protein encoded by HLA-B*08:01. In another example, the one or more polypeptides binds, or is capable of binding, to an HLA protein encoded by HLA-B*13:01. In another example, the one or more polypeptides binds, or is capable of binding, to an HLA protein encoded by HLA-B*46:01. In another example, the one or more polypeptides binds, or is capable of binding, to an HLA protein encoded by HLA-B*52:01. In another example, the one or more polypeptides binds, or is capable of binding, to an HLA protein encoded by HLA-B*44:02. In another example, the one or more polypeptides binds, or is capable of binding, to an HLA protein encoded by HLA-B*40:06. In another example, the one or more polypeptides binds, or is capable of binding, to an HLA protein encoded by HLA-B*13:02. In another example, the one or more polypeptides binds, or is capable of binding, to an HLA protein encoded by HLA-B*56:01. In another example, the one or more polypeptides binds, or is capable of binding, to an HLA protein encoded by HLA-B*54:01. In another example, the one or more polypeptides binds, or is capable of binding, to an HLA protein encoded by HLA-B*15:02. In another example, the one or more polypeptides binds, or is capable of binding, to an HLA protein encoded by HLA-B*35:07. In another example, the one or more polypeptides binds, or is capable of binding, to an HLA protein encoded by HLA-B*27:05. In another example, the one or more polypeptides binds, or is capable of binding, to an HLA protein encoded by HLA-B*15:03. In another example, the one or more polypeptides binds, or is capable of binding, to an HLA protein encoded by HLA-B*42:01. In another example, the one or more polypeptides binds, or is capable of binding, to an HLA protein encoded by HLA-B*55:02. In another example, the one or more polypeptides binds, or is capable of binding, to an HLA protein encoded by HLA-B*45:01. In another example, the one or more polypeptides binds, or is capable of binding, to an HLA protein encoded by HLA-B*50:01. In another example, the one or more polypeptides binds, or is capable of binding, to an HLA protein encoded by HLA-B*35:03. In another example, the one or more polypeptides binds, or is capable of binding, to an HLA protein encoded by HLA-B*49:01. In another example, the one or more polypeptides binds, or is capable of binding, to an HLA protein encoded by HLA-B*58:02. In another example, the one or more polypeptides binds, or is capable of binding, to an HLA protein encoded by HLA-B*15:17. In another example, the one or more polypeptides binds, or is capable of binding, to an HLA protein encoded by HLA-C*57:02. In another example, the one or more polypeptides binds, or is capable of binding, to an HLA protein encoded by HLA-C*04:01. In another example, the one or more polypeptides binds, or is capable of binding, to an HLA protein encoded by HLA-C*03:04. In another example, the one or more polypeptides binds, or is capable of binding, to an HLA protein encoded by HLA-C*01:02. In another example, the one or more polypeptides binds, or is capable of binding, to an HLA protein encoded by HLA-C*07:01. In another example, the one or more polypeptides binds, or is capable of binding, to an HLA protein encoded by HLA-C*06:02. In another example, the one or more polypeptides binds, or is capable of binding, to an HLA protein encoded by HLA-C*03:03. In another example, the one or more polypeptides binds, or is capable of binding, to an HLA protein encoded by HLA-C*08:01. In another example, the one or more polypeptides binds, or is capable of binding, to an HLA protein encoded by HLA-C*15:02. In another example, the one or more polypeptides binds, or is capable of binding, to an HLA protein encoded by HLA-C*12:02. In another example, the one or more polypeptides binds, or is capable of binding, to an HLA protein encoded by HLA-C*02:02. In another example, the one or more polypeptides binds, or is capable of binding, to an HLA protein encoded by HLA-C*05:01. In another example, the one or more polypeptides binds, or is capable of binding, to an HLA protein encoded by HLA-C*03:02. In another example, the one or more polypeptides binds, or is capable of binding, to an HLA protein encoded by HLA-C*16:01. In another example, the one or more polypeptides binds, or is capable of binding, to an HLA protein encoded by HLA-C*08:02. In another example, the one or more polypeptides binds, or is capable of binding, to an HLA protein encoded by HLA-C*04:03. In another example, the one or more polypeptides binds, or is capable of binding, to an HLA protein encoded by HLA-C*17:01. In another example, the one or more polypeptides binds, or is capable of binding, to an HLA protein encoded by HLA-C*17:04. Additional examples of HLA alleles include those described in e.g., FIGS. 6B and 11B.

Viral Proteins

The one or more polypeptides may be derived from one or more proteins of a virus. A polypeptide derived from a protein has an amino acid sequence that is a portion or the full-length of the protein's amino acid sequence. In some examples, the one or more polypeptides may be peptides resulting from digestion or degradation of a viral protein in cells infected by the virus. The virus may be a DNA virus, a RNA virus, or a retrovirus.

The one or more proteins of a virus may be protein(s) of a coronavirus. The coronavirus may be a positive-sense single stranded RNA family of viruses, infecting a variety of animals and humans. In one example, the one or more proteins are protein(s) of SARS-COV-2. SARS-COV is one type of coronavirus infection, as well as MERS-COV. Example sequences of the SARS-COV-2 are available at GISAID accession no. EPI_ISL_402124 and EPI_ISL_402127-402130, and described in DOI: 10.1101/2020.01.22.914952. Further deposits of the example SARS-COV2 are deposited in the GISAID platform include EP_ISL_402119-402121 and EP_ISL 402123-402124; see also GenBank Accession No. MN908947.3.

The one or more polypeptides may be derived from proteins of other viruses. Examples of such viruses include Ebola, measles, SARS, Chikungunya, hepatitis, Marburg, yellow fever, MERS, Dengue, Lassa, influenza, rhabdovirus or HIV. A hepatitis virus may include hepatitis A, hepatitis B, or hepatitis C. An influenza virus may include, for example, influenza A or influenza B. An HIV may include HIV 1 or HIV 2. In certain example embodiments, the viral sequence may be a human respiratory syncytial virus, Sudan ebola virus, Bundibugyo virus, Tai Forest ebola virus, Reston ebola virus, Achimota, *Aedes* flavivirus, Aguacate virus, Akabane virus, Alethinophid reptarenavirus, Allpahuayo mammarenavirus, Amapari mmarenavirus, Andes virus, Apoi virus, Aravan virus, Aroa virus, Arumwot virus, Atlantic salmon paramyxovirus, Australian bat lyssavirus, Avian bornavirus, Avian metapneumovirus, Avian paramyxoviruses, penguin or Falkland Islands virus, BK polyomavirus, Bagaza virus, Banna virus, Bat herpesvirus, Bat sapovirus, Bear Canon mammarenavirus, Beilong virus, Betacoronavirus, Betapapillomavirus 1-6, Bhanja virus, Bokeloh bat lyssavirus, Borna disease virus, Bourbon virus, Bovine hepacivirus, Bovine parainfluenza virus 3, Bovine respiratory syncytial virus, Brazoran virus, Bunyamwera virus, Caliciviridae virus. California encephalitis virus, Candiru virus, Canine distemper virus, Canine pneumovirus, Cedar virus, Cell fusing agent virus, Cetacean morbillivirus, Chandipura virus, Chaoyang virus, Chapare mammarenavirus, Chikungunya virus, Colobus monkey papillomavirus, Colorado tick fever virus, Cowpox virus, Crimean-Congo hemorrhagic fever virus, *Culex* flavivirus, Cupixi mammarenavirus, Dengue virus, Dobrava-Belgrade virus, Donggang virus, Dugbe virus, Duvenhage virus, Eastern equine encephalitis virus, Entebbe bat virus, Enterovirus A-D, European bat lyssavirus 1-2, Eyach virus, Feline morbillivirus, Fer-de-Lance paramyxovirus, Fitzroy River virus, Flaviviridae virus, Flexal mammarenavirus, GB virus C, Gairo virus, Gemycircularvirus, Goose paramyxovirus SF02, Great Island virus, Guanarito mammarenavirus, Hantaan virus, Hantavirus Z10, Heartland virus, Hendra virus, Hepatitis A/B/C/E, Hepatitis delta virus, Human bocavirus, Human coronavirus, Human endogenous retrovirus K, Human enteric coronavirus, Human genital-associated circular DNA virus-1, Human herpesvirus 1-8, Human immunodeficiency virus 1/2, Human mastadenovirus A-G, Human papillomavirus, Human parainfluenza virus 1-4, Human parechovirus, Human picornavirus, Human smacovirus, Ikoma lyssavirus, Ilheus virus, Influenza A-C, Ippy mammarenavirus, Irkut virus, J-virus, JC polyomavirus, Japanese encephalitis virus, Junin mammarenavirus, KI polyomavirus, Kadipiro virus, Kamiti River virus, Kedougou virus, Khujand virus, Kokobera virus, Kyasanur forest disease virus, Lagos bat virus, Langat virus, Lassa mammarenavirus, Latino mammarenavirus, Leopards Hill virus, Liao ning virus, Ljungan virus, Lloviu virus, Louping ill virus, Lujo mammarenavirus, Luna mammarenavirus, Lunk virus, Lymphocytic choriomeningitis mammarenavirus, Lyssavirus Ozernoe, MSSI2\0.225 virus, Machupo mammarenavirus, Mamastrovirus 1, Manzanilla virus, Mapuera virus, Marburg virus, Mayaro virus, Measles virus, Menangle virus, Mercadeo virus, Merkel cell polyomavirus, Middle East respiratory syndrome coronavirus, Mobala mammarenavirus, Modoc virus, Mojiang virus, Mokola virus, Monkeypox virus, Montana *myotis* leukoenchalitis virus, Mopeia lassa virus reassortant 29, Mopeia mammarenavirus, Morogoro virus, Mossman virus, Mumps virus, Murine pneumonia virus, Murray Valley encephalitis virus, Nariva virus, Newcastle disease virus, Nipah virus, Norwalk virus, Norway rat hepacivirus, Ntaya virus, O'nyong-nyong virus, Oliveros mammarenavirus, Omsk hemorrhagic fever virus, Oropouche virus, Parainfluenza virus 5, Parana mammarenavirus, Parramatta River virus, Peste-des-petits-ruminants virus, Pichande mammarenavirus, Picornaviridae virus, Pirital mammarenavirus, Piscihepevirus A, Porcine parainfluenza virus 1, porcine rubulavirus, Powassan virus, Primate T-lymphotropic virus 1-2, Primate erythroparvovirus 1, Punta Toro virus, Puumala virus, Quang Binh virus, Rabies virus, Razdan virus, Reptile bornavirus 1, Rhinovirus A-B, Rift Valley fever virus, Rinderpest virus, Rio Bravo virus, Rodent Torque Teno virus, Rodent hepacivirus, Ross River virus, Rotavirus A-I, Royal Farm virus, Rubella virus, Sabia mammarenavirus, Salem virus, Sandfly fever Naples virus, Sandfly fever Sicilian virus, Sapporo virus, Sathuperi virus, Seal anellovirus, Semliki Forest virus, Sendai virus, Seoul virus, Sepik virus, Severe acute respiratory syndrome-related coronavirus, Severe fever with thrombocytopenia syndrome virus, Shamonda virus, Shimoni bat virus, Shuni virus, Simbu virus, Simian torque teno virus, Simian virus 40-41, Sin Nombre virus, Sindbis virus, Small anellovirus, Sosuga virus, Spanish goat encephalitis virus, Spondweni virus, St. Louis encephalitis virus, Sunshine virus, TTV-like mini virus, Tacaribe mammarenavirus, Taila virus, Tamana bat virus, Tamiami mammarenavirus, Tembusu virus, Thogoto virus, Thottapalayam virus, Tick-borne encephalitis virus, Tioman virus, Togaviridae virus, Torque teno *canis* virus, Torque teno douroucouli virus, Torque teno *felis* virus, Torque teno midi virus, Torque teno sus virus, Torque teno tamarin virus, Torque teno virus, Torque teno *zalophus* virus, Tuhoko virus, Tula virus, Tupaia paramyxovirus, Usutu virus, Uukuniemi virus, Vaccinia virus, Variola virus, Venezuelan equine encephalitis virus, Vesicular stomatitis Indiana virus, WU Polyomavirus, Wesselsbron virus, West Caucasian bat virus, West Nile virus, Western equine encephalitis virus, Whitewater Arroyo mammarenavirus, Yellow fever virus, Yokose virus, Yug Bogdanovac virus, Zaire ebolavirus, Zika virus, or *Zygosaccharomyces bailii* virus Z viral sequence. Examples of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

Open Reading Frames (ORFs)

The one or more viral proteins may be expressed from one or more open reading frames (ORFs) in a viral genome. An ORF refers to a polynucleotide that encodes a protein, or a portion of a protein. An open reading frame usually begins with a start codon and is read in codon-triplets until the frame ends with a STOP codon.

In some embodiments, the ORFs are canonical ORFs. A canonical ORF is an ORF that is most prevalent, most similar to orthologous sequences found in other species, by virtue of its length or amino acid composition, allows for the clearest description of domains, isoforms, polymorphisms, post-translational modifications, or in the absence of other information is the longest sequence. In some examples, the ORFs are canonical ORFs of SARS-COV-2, such as of nsp1, nsp2, nsp3, nsp5, nsp8, nsp10, nsp14, ORF7a, S protein, or M protein. In one example, the ORF is nsp1 ORF. In another example, the ORF is nsp2 ORF. In another example the ORF is nsp3 ORF. In another example, the ORF is nsp5 ORF. In another example, the ORF is nsp8 ORF. In another example the ORF is nsp10 ORF. In another example, the ORF is nsp14 ORF. In another example, the ORF is ORF7a. In another example, the ORF is spike(S) protein ORF. In another example, the ORF is membrane (M) protein ORF. In another example, the ORF is nucleocapsid (N) protein ORF. In other example embodiments, polypeptides are derived from non-canonical translation of ORF, such as via internal ribosome entry, leaky scanning, non-AUD initiation, ribosome shunting, reinitiation, ribosomal frameshifting and stop-codon readthrough.

In some embodiments, the ORFs are alternative ORFs of a SARS-COV-2 genome. In some embodiments, alternative ORFs can be identified using in silico 6-frame translation analysis. In some embodiments, the alternative ORF is F3 R196, F2 R32, F6 R325, or F3 R683.

In some embodiments, the ORFs are out-of-frame ORFs. As used herein, the term "out-of-frame ORF" refers to ORFs that are out of frame with a canonical ORF. In certain example embodiments, the out-of-frame ORF is an internal out-of-frame ORF, which is an ORF found within a canonical ORF but out of frame with the canonical ORF. In some examples, the ORFs are internal out-of-frame ORFs of SARS-COV-2, such as ORFORF9b, ORFS.iORF1, or ORF-S.iORF2. In one example, the ORF is ORFORF9b. In another example, the ORF is ORFS.iORF1. In another example, the ORF is ORFS.iORF2.

Other examples of the ORFs include those described in Finkel Y et al., The coding capacity of SARS-COV-2, doi: doi.org/10.1101/2020.05.07.082909, which is incorporated by reference in its entirety.

In some embodiments, the sequence, ORFs, and other annotations are based on the sequence of 2019-nCOV/USA-WA1/2020 isolate (NCBI accession number: MN985325) of SARS-COV-2.

Examples of Polypeptides

In some embodiments, the one or more polypeptides comprises GPMVLRGLIT (SEQ ID NO: 6), GLITLSYHL (SEQ ID NO: 5), SLEDKAFQL (SEQ ID NO: 7), ELPDEFVVVTV (SEQ ID NO: 8), LEDKAFQL (SEQ ID NO: 10), DEFVVVTV (SEQ ID NO: 11), or a combination thereof. In one example, the one or more polypeptides comprises GPMVLRGLIT (SEQ ID NO: 6). In another example, the one or more polypeptides comprises GLITLSYHL (SEQ ID NO: 5). In another example, the one or more polypeptides comprises SLEDKAFQL (SEQ ID NO: 7). In another example, the one or more polypeptides comprises ELPDEFVVVTV (SEQ ID NO: 8). In another example, the one or more polypeptides comprises LEDKAFQL (SEQ ID NO: 10). In another example, the one or more polypeptides comprises DEFVVVTV (SEQ ID NO: 11).

In some embodiments, the one or more polypeptides comprises KRVDWTIEY (SEQ ID NO: 29), FASEAARVV (SEQ ID NO: 17), or a combination thereof. In one example, the one or more polypeptides comprises KRVDWTIEY (SEQ ID NO: 29). In another example, the one or more polypeptides comprises FASEAARVV (SEQ ID NO: 17).

In certain examples, the polypeptide derived from S.iORF1 is MLLGSMLYM (SEQ ID NO: 4). In certain example embodiments, the polypeptide is derived from both S.iORF1 and S.iORF2 and has a sequence of GPMVLRGLIT (SEQ ID NO: 6) or GLITLSYHL (SEQ ID NO: 5). In certain examples, the polypeptide derived from ORF9b is SLEDKAFQL (SEQ ID NO: 7), ELPDEFVVVTV (SEQ ID NO: 8), LEDKAFQL (SEQ ID NO: 10), DEFVVVTV (SEQ ID NO: 11), ELPDEFVVV (SEQ ID NO: 12), KAFQLTPIAV (SEQ ID NO: 13), or a combination thereof. In certain examples, the polypeptide derived from nsp1 is APHGHVMVEL (SEQ ID NO: 14). In certain examples, the polypeptide derived from nsp2 is EIKESVQTF (SEQ ID NO: 15), FASEAARVV (SEQ ID NO: 17), TAQNSVRVL (SEQ ID NO: 18), LATNNLVVM (SEQ ID NO: 16), or STSAFVETV (SEQ ID NO: 19). In certain examples, the polypeptide derived from nsp3 is EEFEPSTQYEY (SEQ ID NO: 20), TTTIKPVTY (SEQ ID NO: 21), TVIEVQGY (SEQ ID NO: 22), FGDDTVIEV (SEQ ID NO: 23), YLNSTNVTI (SEQ ID NO: 24), or YLFDESGEFKL (SEQ ID NO: 25). In some embodiments, the polypeptide derived from nsp5 is AGTDTTITV (SEQ ID NO: 26). In certain examples, the polypeptide derived from nsp8 is SEFSSLPSY (SEQ ID NO: 27). In certain examples, the polypeptide derived from nsp10 is FAVDAAKAY (SEQ ID NO: 28). In certain examples, the polypeptide derived from nsp14 is KRVDWTIEY (SEQ ID NO: 29). In some embodiments, the polypeptide derived from nsp15 is SVVSKVVKV (SEQ ID NO: 30). In certain examples, the polypeptide derived from ORF7a is IRQEEVQEL (SEQ ID NO: 31). In certain examples, the polypeptide derived from S is EILDITPcSF (SEQ ID NO: 32) (cysteinylated Cys), EILDITPCSF (SEQ ID NO: 33), EILDITPcSFG (SEQ ID NO: 34) (cysteinylated Cys), HADQLTPTW (SEQ ID NO: 35), KNIDGYFKIY (SEQ ID NO: 36), NATNVVIKV (SEQ ID NO: 37), QLTPTWRVY (SEQ ID NO: 38), VGYLQPRTF (SEQ ID NO: 39) or a combination thereof. In certain examples, the polypeptide derived from M is VATSRTLSY (SEQ ID NO: 41). In certain examples, the polypeptide derived from N protein is APRITFGGP (SEQ ID NO: 42).

In some embodiments, the polypeptide is derived from an alternative ORF. In some embodiments, the alternative ORF is F3 R196, F2 R32, F6 R325, or F3 R683. In some embodiments, the alternative ORF produces a peptide. In some embodiments, the F3 R196 alternative ORF produces an R196 peptide. In some embodiments, the F2 R32 alternative ORF produces R32 peptide. In some embodiments the F6 R325 alternative ORF produces R325 peptide. In some embodiments, the F3 R683 alternative ORF produces R683 peptide.

In these notations above and elsewhere herein, the indications of "F3 R196", "F2 R32", "F6 R325", "F3 R683", and the like refer to the translation frame (designated with "F" such that "F3" refers to frame 3, "F6" refers to frame 6 and the like) and the position of the chromosome of the alternative ORF from which the peptide is derived (i.e., the transition position of the chromosome). Thus, F3 R196 indicates that the peptide is derived from position 10695-10727 on the (+) strand, F2 R32 indicates that the peptide is derived from position 14666-14692 on the (+) strand, F6 R325 is derived from position 12370-12402 on the (−) strand, and F3 R683 is derived from position 25788-25814 on the (+) strand.

In some embodiments, the polypeptide is or is derived from F3 R196 peptide/ORF. In some embodiments, the polypeptide that is or is derived from F3 R196 peptide/ORF is METGGFSIDLP (SEQ ID NO: 43). In some embodiments, the polypeptide that is or is derived from F2 R32 peptide/ORF. In some embodiments, the polypeptide that is or is derived from F2 R32 peptide/ORF is LSNPVILTK (SEQ ID NO: 44). In some embodiments, the polypeptide is or is derived from F6 R325 peptide/ORF. In some embodiments, the polypeptide that is or is derived from F6 R325 peptide/ORF is LSASLSNFLSI (SEQ ID NO: 45). In some embodiments, the polypeptide is or is derived from F3 R683 peptide/ORF. In some embodiments, the polypeptide that is or is derived from F3 R683 peptide/ORF is MPFQKPITL (SEQ ID NO: 46).

In one example embodiment at least one of the one or more the polypeptides is derived from expression of an alternative ORF. In one example embodiment, the alternative ORF is F3 R196, F2 R32, F6 R325, or F3 683. In one example embodiment, the one or more polypeptides derived from alternative ORF F3 R196 is METGGFSIDLP (SEQ ID NO: 43). In one example embodiment, the one or more polypeptides derived from alternative ORF F2 R32 is LSNPVILTK (SEQ ID NO: 44). In one example embodiment, the one or more polypeptides derived from alternative ORF F6 R325 is LSASLSNFLSI (SEQ ID NO: 45). In one example embodiment, the one or more polypeptides derived from alternative ORF F3 R683 is MPFQKPITL (SEQ ID NO: 46). In some embodiments, the polypeptide is derived from F3 R196 peptide. In some embodiments, the polypeptide derived from F3 R196 peptide is METGGFSIDLP (SEQ ID NO: 43). In some embodiments, the polypeptide is derived from F2 R32 peptide. In some embodiments, the polypeptide derived from F2 R32 peptide is LSNPVILTK (SEQ ID NO: 44). In some embodiments, the polypeptide is derived from F6 R325 peptide. In some embodiments, the polypeptide derived from F6 R325 peptide is LSASLSNFLSI (SEQ ID NO: 45). In some embodiments, the polypeptide is derived from F3 R683 peptide. In some embodiments, the polypeptide derived from F3 R683 peptide is MPFQKPITL (SEQ ID NO: 46).

As is demonstrated in the Working Examples below, in some embodiments, one or more of the polypeptides is expressed and/or bound with an MHC-I molecule almost immediately post infection. In some embodiments, these early expressed and/or MHC-I presented/bound polypeptides are more highly expressed within about 0, 1, 2, 3, 4, 5, 6, 7, 8, 9, 10, 11, or 12 hours post infection as compared to a later time point (e.g., after 12 hours post infection). In one example embodiment, the one or more polypeptides are expressed and/or is bound by MHC-I 0-12, 0-11, 0-10, 0-9, 0-8, 0-7, 0-6, 0-5, 0-4, 0-3, 0-2, or 0-1 hours post infection.

The one or more polypeptides include those in Table 1 Table 2, Table 4, Tables 8A-8B, and/or Tables 9A, 9B, or 9C. In some examples, the one or more polypeptides include at least 2, at least 4, at least 6, at least 8, at least 10, at least 12, at least 14, at least 16, at least 18, at least 20, at least 22, at least 24, at least 26, or at least 28, polypeptides in Table 1 Table 2, Table 4, Tables 8A-8B, and/or Tables 9A, 9B, or 9C.

The one or more polypeptides include one or more of those in FIGS. 1D, 3A-3G, 4B, 5C, 6A-6B, 8A-8B, 9B, 10A-10B, 10F, 11A-11B, 14A-14B, 15C, 16D, 17A, and/or 18-18E. In one example embodiment, the one or more polypeptides include at least 2, at least 4, at least 6, at least 8, at least 10, at least 12, at least 14, at least 16, at least 18, at least 20, at least 22, at least 24, at least 26, or at least 28, polypeptides in FIGS. 1D, 3A-3G, 4B, 5C, 6A-6B, 8A-8B, 9B, 10A-10B, 10F, 11A-11B, 14A-14B, 15C, 16D, 17A, and/or 18-18E.

In one example embodiment, the one or more polypeptides comprises FAVDAAKAY (SEQ ID NO: 28). In another example embodiment, the one or more polypeptides comprises EIKESVQTF (SEQ ID NO: 15). In another example, the one or more polypeptides comprises FASEAARVV (SEQ ID NO: 17). In another example embodiment, the one or more polypeptides comprises EEFEPSTQYEY (SEQ ID NO: 20). In another example embodiment, the one or more polypeptides comprises SEFSSLPSY (SEQ ID NO: 27). In another example embodiment, the one or more polypeptides comprises DEFVVVTV (SEQ ID NO: 11). In another example embodiment, the one or more polypeptides comprises LEDKAFQL (SEQ ID NO: 10). In another example embodiment, the one or more polypeptides comprises EILDITPCSF (SEQ ID NO: 33). In certain example embodiment, the C is cysteinylated. In another example, the one or more polypeptides comprises EILDITPCSFG (SEQ ID NO: 47). In one example embodiment, the C is cysteinylated. In another example, the one or more polypeptides comprises HADQLTPTW (SEQ ID NO: 35). In another example embodiment, the one or more polypeptides comprises KNIDGYFKIY (SEQ ID NO: 36). In another example embodiment, the one or more polypeptides comprises NATNVVIKV (SEQ ID NO: 37). In another example embodiment, the one or more polypeptides comprises QLTPTWRVY (SEQ ID NO: 38). In another example embodiment, the one or more polypeptides comprises VATSRTLSY (SEQ ID NO: 41). In another example embodiment, the one or more polypeptides comprises VGYLQPRTF (SEQ ID NO: 39). In another example embodiment, the one or more polypeptides comprises APHGHVMVEL (SEQ ID NO: 14). In one example embodiment, the M is oxidized. In another example embodiment, the one or more polypeptides comprises STSAFVETV (SEQ ID NO: 19). In another example embodiment, the one or more polypeptides comprises KRVDWTIEY (SEQ ID NO: 29). In another example embodiment, the one or more polypeptides comprises FGDDTVIEV (SEQ ID NO: 23). In another example embodiment, the one or more polypeptides comprises IRQEEVQEL (SEQ ID NO: 31). In another example embodiment, the one or more polypeptides comprises APRITFGGP (SEQ ID NO: 42). In another example embodiment, the one or more polypeptides comprises ELPDEFVVV (SEQ ID NO: 12). In another example embodiment, the one or more polypeptides comprises KAFQLTPIAV (SEQ ID NO: 13). In another example embodiment, the one or more polypeptides comprises SLEDKAFQL (SEQ ID NO: 7). In another example embodiment, the one or more polypeptides comprises GLITLSYHL (SEQ ID NO: 5). In another example embodiment, the one or more polypeptides comprises GPMVLRGLIT (SEQ ID NO: 6). In another example embodiment, the one or more polypeptides comprises MLLGSMLYM (SEQ ID NO: 4). In another example embodiment, the one or more polypeptides comprises YLNSTNVTI (SEQ ID NO: 24). In certain example embodiments, the one or more polypeptides comprises TAQNSVRVL (SEQ ID NO: 18). In one example embodiment, the one or more polypeptides comprises TTTIKPVTY (SEQ ID NO: 21). In one example embodiment, the one or more polypeptides comprises TVIEVQGY (SEQ ID NO: 22). In one example embodiment, the one or more polypeptides comprises METGGFSIDLP (SEQ ID NO: 43). In one example embodiment, the one or more polypeptides comprises LSNPVILTK (SEQ ID NO: 44). In one example embodiment, the one or more polypeptides comprises LATNNLVVM (SEQ ID NO: 16). In one example embodiment, the one or more polypeptides comprises YLFDESGEFKL (SEQ ID NO: 25). In one example embodiment, the one or more polypeptides comprises AGTDTTITV (SEQ ID NO: 26). In one example embodiment, the one or more polypeptides comprises SVVSKVVKV (SEQ ID NO: 30). In one example embodiment, the one or more polypeptides comprises ELPDEFVVTV (SEQ ID NO: 9). In one example embodiment, the one or more polypeptides comprises NLNESLIDL (SEQ ID NO: 40). In one example embodiment, the one or more polypeptides comprises LSASLSNFLSI (SEQ ID NO: 45). In one example embodiment, the one or more polypeptides comprises MPFQKPITL (SEQ ID NO: 46). In the embodiments disclsoed herein, one or more Ms may be oxidized and/or the Ns deaminated.

The polypeptides herein may also include those have homology with the exemplary polypeptides herein. For example, the polypeptides may include those have at least 50%, at least 55%, at least 60%, at least 65%, at least 70%, at least 75%, at least 80%, at least 85%, at least 90%, or at least 95%, at least 96%, at least 97%, at least 98%, or at least 99% sequence identity with the exemplary polypeptides. The terms "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

In some cases, the one or more polypeptides comprises a motif of $XN_1XXXXXXN_2$ (SEQ ID NO: 1), where $N_1$ is E, A, V, L, or P; $N_2$ is F, Y, L, or V; and X is any amino acid (the X amino acids in the motif can be the same or different). In some embodiments, the one or more peptides comprises a motif of $XN_1XXXXXXN_2$ (SEQ ID NO: 2), wherein in some embodiments $N_1$ is E, A, V, L, T, S, I, M, G, R, Y, K, D, Q, F, or P, wherein in some embodiments $N_2$ is F, Y, L, W, I, K, A, M, or V, and wherein X is any amino acid (each X can be independently selected from any amino acid and can be the same or different). In one example, the one or more polypeptides comprises a sequence of XEXXXXXXF (SEQ ID NO: 48). In another example, the one or more polypeptides comprises a sequence of XEXXXXXXY (SEQ ID NO: 49). In another example, the one or more polypeptides comprises a sequence of XEXXXXXXL (SEQ ID NO: 50). In another example, the one or more polypeptides comprises a sequence of XEXXXXXXV (SEQ ID NO: 51). In another example, the one or more polypeptides comprises a sequence of XEXXXXXXW (SEQ ID NO: 52). In another example, the one or more polypeptides comprises a sequence of XEXXXXXXI (SEQ ID NO: 53). In another example, the one or more polypeptides comprises a sequence of XEXXXXXXK (SEQ ID NO: 54). In another example, the one or more polypeptides comprises a sequence of XEXXXXXXA (SEQ ID NO: 55). In another example, the one or more polypeptides comprises a sequence of XEXXXXXXM (SEQ ID NO: 56). In another example, the one or more polypeptides comprises a sequence of XAXXXXXXF (SEQ ID NO: 57). In another example, the one or more polypeptides comprises a sequence of XAXXXXXXY (SEQ ID NO: 58). In another example, the one or more polypeptides comprises a sequence of XAXXXXXXL (SEQ ID NO: 59). In another example, the one or more polypeptides comprises a sequence of XAXXXXXXV (SEQ ID NO: 60). In another example, the one or more polypeptides comprises a sequence of XAXXXXXXW (SEQ ID NO: 61). In another example, the one or more polypeptides comprises a sequence of XAXXXXXXI (SEQ ID NO: 62). In another example, the one or more polypeptides comprises a sequence of XAXXXXXXK (SEQ ID NO: 63). In another example, the one or more polypeptides comprises a sequence of XAXXXXXXA (SEQ ID NO: 64). In another example, the one or more polypeptides comprises a sequence of XAXXXXXXM (SEQ ID NO: 65). In another example, the one or more polypeptides comprises a sequence of XVXXXXXXF (SEQ ID NO: 66). In another example, the one or more polypeptides comprises a sequence of XVXXXXXXY (SEQ ID NO: 67). In another example, the one or more polypeptides comprises a sequence of XVXXXXXXL (SEQ ID NO: 68). In another example, the one or more polypeptides comprises a sequence of XVXXXXXXV (SEQ ID NO: 69). In another example, the one or more polypeptides comprises a sequence of XVXXXXXXW (SEQ ID NO: 70). In another example, the one or more polypeptides comprises a sequence of XVXXXXXXI (SEQ ID NO: 71). In another example, the one or more polypeptides comprises a sequence of XVXXXXXXK (SEQ ID NO: 72). In another example, the one or more polypeptides comprises a sequence of XVXXXXXXA (SEQ ID NO: 73). In another example, the one or more polypeptides comprises a sequence of XVXXXXXXM (SEQ ID NO: 74). In another example, the one or more polypeptides comprises a sequence of XLXXXXXXF (SEQ ID NO: 75). In another example, the one or more polypeptides comprises a sequence of XLXXXXXXY (SEQ ID NO: 76). In another example, the one or more polypeptides comprises a sequence of XLXXXXXXL (SEQ ID NO: 77). In another example, the one or more polypeptides comprises a sequence of XLXXXXXXV (SEQ ID NO: 78). In another example, the one or more polypeptides comprises a sequence of XLXXXXXXW (SEQ ID NO: 79). In another example, the one or more polypeptides comprises a sequence of XLXXXXXXI (SEQ ID NO: 80). In another example, the one or more polypeptides comprises a sequence of XLXXXXXXK (SEQ ID NO: 81). In another example, the one or more polypeptides comprises a sequence of XLXXXXXXA (SEQ ID NO: 82). In another example, the one or more polypeptides comprises a sequence of XLXXXXXXM (SEQ ID NO: 83). In another example, the one or more polypeptides comprises a sequence of XPXXXXXXF (SEQ ID NO: 84). In another example, the one or more polypeptides comprises a sequence of XPXXXXXXY (SEQ ID NO: 85). In another example, the one or more polypeptides comprises a sequence of XPXXXXXXL (SEQ ID NO: 86). In another example, the one or more polypeptides comprises a sequence of XPXXXXXXV (SEQ ID NO: 87). In another example, the one or more polypeptides comprises a sequence of XPXXXXXXW (SEQ ID NO: 88). In another example, the one or more polypeptides comprises a sequence of XPXXXXXXI (SEQ ID NO: 89). In another example, the one or more polypeptides comprises a sequence of XPXXXXXXK (SEQ ID NO: 90). In another example, the one or more polypeptides comprises a sequence of XPXXXXXXA (SEQ ID NO: 91). In another example, the one or more polypeptides comprises a sequence of XPXXXXXXM (SEQ ID NO: 92).

In another example, the one or more polypeptides comprises a sequence of XTXXXXXXF (SEQ ID NO: 93). In another example, the one or more polypeptides comprises a sequence of XTXXXXXXY (SEQ ID NO: 94). In another example, the one or more polypeptides comprises a sequence of XTXXXXXXL (SEQ ID NO: 95). In another example, the one or more polypeptides comprises a sequence of XTXXXXXXV (SEQ ID NO: 96). In another example, the one or more polypeptides comprises a sequence of XTXXXXXXW (SEQ ID NO: 97). In another example, the one or more polypeptides comprises a sequence of XTXXXXXXI (SEQ ID NO: 98). In another example, the one or more polypeptides comprises a sequence of XTXXXXXXK (SEQ ID NO: 99). In another example, the one or more polypeptides comprises a sequence of XTXXXXXXA (SEQ ID NO: 100). In another example, the one or more polypeptides comprises a sequence of XTXXXXXXM (SEQ ID NO: 101).

In another example, the one or more polypeptides comprises a sequence of XSXXXXXXF (SEQ ID NO: 102). In another example, the one or more polypeptides comprises a sequence of XSXXXXXXY (SEQ ID NO: 103). In another example, the one or more polypeptides comprises a sequence of XSXXXXXXL (SEQ ID NO: 104). In another example, the one or more polypeptides comprises a sequence of XSXXXXXXV (SEQ ID NO: 105). In another example, the one or more polypeptides comprises a sequence of XSXXXXXXW (SEQ ID NO: 106). In another example, the one or more polypeptides comprises a sequence of XSXXXXXXI (SEQ ID NO: 107). In another example, the one or more polypeptides comprises a sequence of XSXXXXXXK (SEQ ID NO: 108). In another example, the one or more polypeptides comprises a sequence of XSXXXXXXA (SEQ ID NO: 109). In another example, the one or more polypeptides comprises a sequence of XSXXXXXXM (SEQ ID NO: 110).

In another example, the one or more polypeptides comprises a sequence of XIXXXXXXF (SEQ ID NO: 111). In another example, the one or more polypeptides comprises a sequence of XIXXXXXXY (SEQ ID NO: 112). In another example, the one or more polypeptides comprises a sequence of XIXXXXXXL (SEQ ID NO: 113). In another example, the one or more polypeptides comprises a sequence of XIXXXXXXV (SEQ ID NO: 114). In another example, the one or more polypeptides comprises a sequence of XIXXXXXXW (SEQ ID NO: 115). In another example, the one or more polypeptides comprises a sequence of XIXXXXXXI (SEQ ID NO: 116). In another example, the one or more polypeptides comprises a sequence of XIXXXXXXK (SEQ ID NO: 117). In another example, the one or more polypeptides comprises a sequence of XIXXXXXXA (SEQ ID NO: 118). In another example, the one or more polypeptides comprises a sequence of XIXXXXXXM (SEQ ID NO: 119).

In another example, the one or more polypeptides comprises a sequence of XMXXXXXXF (SEQ ID NO: 120). In another example, the one or more polypeptides comprises a sequence of XMXXXXXXY (SEQ ID NO: 121). In another example, the one or more polypeptides comprises a sequence of XMXXXXXXL (SEQ ID NO: 122). In another example, the one or more polypeptides comprises a sequence of XMXXXXXXV (SEQ ID NO: 123). In another example, the one or more polypeptides comprises a sequence of XMXXXXXXW (SEQ ID NO: 124). In another example, the one or more polypeptides comprises a sequence of XMXXXXXXI (SEQ ID NO: 125). In another example, the one or more polypeptides comprises a sequence of XMXXXXXXK (SEQ ID NO: 126). In another example, the one or more polypeptides comprises a sequence of XMXXXXXXA (SEQ ID NO: 127). In another example, the one or more polypeptides comprises a sequence of XMXXXXXXM (SEQ ID NO: 128).

In another example, the one or more polypeptides comprises a sequence of XGXXXXXXF (SEQ ID NO: 129). In another example, the one or more polypeptides comprises a sequence of XGXXXXXXY (SEQ ID NO: 130). In another example, the one or more polypeptides comprises a sequence of XGXXXXXXL (SEQ ID NO: 131). In another example, the one or more polypeptides comprises a sequence of XGXXXXXXV (SEQ ID NO: 132). In another example, the one or more polypeptides comprises a sequence of XGXXXXXXW (SEQ ID NO: 133). In another example, the one or more polypeptides comprises a sequence of XGXXXXXXI (SEQ ID NO: 134). In another example, the one or more polypeptides comprises a sequence of XGXXXXXXK (SEQ ID NO: 135). In another example, the one or more polypeptides comprises a sequence of XGXXXXXXA (SEQ ID NO: 136). In another example, the one or more polypeptides comprises a sequence of XGXXXXXXM (SEQ ID NO: 137).

In another example, the one or more polypeptides comprises a sequence of XRXXXXXXF (SEQ ID NO: 138). In another example, the one or more polypeptides comprises a sequence of XRXXXXXXY (SEQ ID NO: 139). In another example, the one or more polypeptides comprises a sequence of XRXXXXXXL (SEQ ID NO: 140). In another example, the one or more polypeptides comprises a sequence of XRXXXXXXV (SEQ ID NO: 141). In another example, the one or more polypeptides comprises a sequence of XRXXXXXXW (SEQ ID NO: 142). In another example, the one or more polypeptides comprises a sequence of XRXXXXXXI (SEQ ID NO: 143). In another example, the one or more polypeptides comprises a sequence of XRXXXXXXK (SEQ ID NO: 144). In another example, the one or more polypeptides comprises a sequence of XRXXXXXXA (SEQ ID NO: 145). In another example, the one or more polypeptides comprises a sequence of XRXXXXXXM (SEQ ID NO: 146).

In another example, the one or more polypeptides comprises a sequence of XYXXXXXXF (SEQ ID NO: 147). In another example, the one or more polypeptides comprises a sequence of XYXXXXXXY (SEQ ID NO: 148). In another example, the one or more polypeptides comprises a sequence of XYXXXXXXL (SEQ ID NO: 149). In another example, the one or more polypeptides comprises a sequence of XYXXXXXXV (SEQ ID NO: 150). In another example, the one or more polypeptides comprises a sequence of XYXXXXXXW (SEQ ID NO: 151). In another example, the one or more polypeptides comprises a sequence of XXXXXXXXI (SEQ ID NO: 152). In another example, the one or more polypeptides comprises a sequence of XYXXXXXXK (SEQ ID NO: 153). In another example, the one or more polypeptides comprises a sequence of XYXXXXXXA (SEQ ID NO: 154). In another example, the one or more polypeptides comprises a sequence of XYXXXXXXM (SEQ ID NO: 155).

In another example, the one or more polypeptides comprises a sequence of XKXXXXXXF (SEQ ID NO: 156). In another example, the one or more polypeptides comprises a sequence of XKXXXXXXY (SEQ ID NO: 157). In another example, the one or more polypeptides comprises a sequence of XKXXXXXXL (SEQ ID NO: 158). In another example, the one or more polypeptides comprises a sequence of XKXXXXXXV (SEQ ID NO: 159). In another example, the one or more polypeptides comprises a sequence of XKXXXXXXW (SEQ ID NO: 160). In another example, the one or more polypeptides comprises a sequence of XKXXXXXXI (SEQ ID NO: 161). In another example, the one or more polypeptides comprises a sequence of XKXXXXXXK (SEQ ID NO: 162). In another example, the one or more polypeptides comprises a sequence of XKXXXXXXA (SEQ ID NO: 163). In another example, the one or more polypeptides comprises a sequence of XKXXXXXXM (SEQ ID NO: 164).

In another example, the one or more polypeptides comprises a sequence of XDXXXXXXF (SEQ ID NO: 165). In another example, the one or more polypeptides comprises a sequence of XDXXXXXXY (SEQ ID NO: 166). In another example, the one or more polypeptides comprises a sequence of XDXXXXXXL (SEQ ID NO: 167). In another example, the one or more polypeptides comprises a sequence of XDXXXXXXV (SEQ ID NO: 168). In another example, the one or more polypeptides comprises a sequence of XDXXXXXXW (SEQ ID NO: 169). In another example, the one or more polypeptides comprises a sequence of XDXXXXXXI (SEQ ID NO: 170). In another example, the one or more polypeptides comprises a sequence of XDXXXXXXK (SEQ ID NO: 171). In another example, the one or more polypeptides comprises a sequence of XDXXXXXXA (SEQ ID NO: 172). In another example, the one or more polypeptides comprises a sequence of XDXXXXXXM (SEQ ID NO: 173).

In another example, the one or more polypeptides comprises a sequence of XQXXXXXXF (SEQ ID NO: 174). In another example, the one or more polypeptides comprises a sequence of XQXXXXXXY (SEQ ID NO: 175). In another example, the one or more polypeptides comprises a sequence of XQXXXXXXL (SEQ ID NO: 176). In another example, the one or more polypeptides comprises a sequence of XQXXXXXXV (SEQ ID NO: 177). In another example, the one or more polypeptides comprises a sequence of XQXXXXXXW (SEQ ID NO: 178). In another example, the one or more polypeptides comprises a sequence of XQXXXXXXI (SEQ ID NO: 179). In another example, the one or more polypeptides comprises a sequence of XQXXXXXXK (SEQ ID NO: 180). In another example, the one or more polypeptides comprises a sequence of XQXXXXXXA (SEQ ID NO: 181). In another example, the one or more polypeptides comprises a sequence of XQXXXXXXM (SEQ ID NO: 182).

In another example, the one or more polypeptides comprises a sequence of XFXXXXXXF (SEQ ID NO: 183). In another example, the one or more polypeptides comprises a sequence of XFXXXXXXY (SEQ ID NO: 184). In another example, the one or more polypeptides comprises a sequence of XFXXXXXXL (SEQ ID NO: 185). In another example, the one or more polypeptides comprises a sequence of XFXXXXXXV (SEQ ID NO: 186). In another example, the one or more polypeptides comprises a sequence of XFXXXXXXW (SEQ ID NO: 187). In another example, the one or more polypeptides comprises a sequence of XFXXXXXXI (SEQ ID NO: 188). In another example, the one or more polypeptides comprises a sequence of XFXXXXXXK (SEQ ID NO: 189). In another example, the one or more polypeptides comprises a sequence of XFXXXXXXA (SEQ ID NO: 190). In another example, the one or more polypeptides comprises a sequence of XFXXXXXXM (SEQ ID NO: 191).

In one example embodiment, the one or more polypeptides comprises a motif of $N_3N_1N_4N_5N_6N_7N_8N_9N_2$ (SEQ ID NO: 3), wherein $N_1$ is optionally E, A, V, L, T, S, I, M, G, R, Y, K, D, Q, F, or P, wherein $N_2$ is optionally F, Y, L, W, I, K, A, M, T, or V, wherein $N_3$ is optionally E, D, K, R, N, S, G, L, V, T, F, N, Y, M, or A, wherein $N_4$ is optionally I, V, A, K, R, F, H, L, D, T, S, Q, N, Y, P, or G, wherein $N_5$ is optionally E, D, G, S, P, K, N, A, Q, L, H, or A, wherein $N_6$ is optionally R, P, G, K, A, L, Y, W, F, T, E, S, or V, wherein $N_7$ is optionally I, L, V, Y, F, T, S, P, G, E, A, H, or V, wherein $N_8$ is optionally S, L, P, I, V, Q, H, E, A, K, R, Y, W, N or M, and wherein No is optionally S, G, E, A, T, K, Q, N, R, V, D, F, or L.

Modifications on Polypeptides

The polypeptides herein may comprise one or more modifications (e.g., post-translational modifications). In some cases, the polypeptides may comprise cysteinylated Cysteine. Examples of such modified polypeptide include EILDITPcSF (SEQ ID NO: 32) and EILDITPcSFG (SEQ ID NO: 34) where the underlined cysteine residues are cysteinylated. In certain cases, the polypeptides may comprise oxidized methionine. Examples of such modified polypeptides include APHGHVmVEL (SEQ ID NO: 192), GPmVLRGLIT (SEQ ID NO: 193), mLLGSMLYM (SEQ ID NO: 194), MLLGSmLYM (SEQ ID NO: 195), and MLLGSMLYm (SEQ ID NO: 196), where the underlined methionine residues are oxidized.

Other examples of modifications include ubiquitination, phosphorylation, sulfonation, glycosylation, acetylation, methylation, ADP-ribosylation, methionine oxidation, cysteine oxidation, cysteine lipidation, farnesylation, geranylation, pyroglutamation, and deamidation.

In some embodiments, the polypeptide comprises a motif (e.g., $XN_1XXXXXXN_2$ (SEQ ID NO: 1 or SEQ ID NO: 2) and/or $N_3N_1N_4N_5N_6N_7N_8N_9N_2$ (SEQ ID NO: 3)) as previously described and one or more (e.g., 1, 2, 3, 4, 5, 6, 7, 8, or 9) of the amino acids in the motif is/are each independently modified with an ubiquitination, phosphorylation, sulfonation, glycosylation, acetylation, methylation, ADP-ribosylation, methionine oxidation, cysteine oxidation, cysteine lipidation, farnesylation, geranylation, pyroglutamation, or deamidation.

Sizes of Polypeptides

The polypeptides may be any length that is reasonable for an epitope. For example, the polypeptides may have a size of from 5 to 30, e.g., from 5 to 25, from 5 to 20, from 5 to 15, from 5 to 10, from 6 to 10, from 7 to 9, or from 8 to 9 amino acids. For example, the polypeptides may have 5, 6, 7, 8, 9, 10, 11, 12, 13, 14, or 15 amino acids. In some embodiments, the optimal length of a polypeptide may be determined based the immunogenicity of the polypeptides of different lengths when introduced to a cell or subject.

Polynucleotides and Vectors

The present disclosure also includes one or more polynucleotides comprising coding sequences of the polypeptide(s) described herein. As used herein, a polynucleotide may be DNA, RNA, or a hybrid thereof, including without limitation, cDNA, mRNA, genomic DNA, mitochondrial DNA, sgRNA, siRNA, shRNA, miRNA, tRNA, lRNA, snRNA, lncRNA, and synthetic (such as chemically synthesized) DNA or RNA or hybrids thereof. In some examples, a nucleic acid is mRNA. The nucleic acid may be double-stranded or single-stranded. Where single-stranded, the nucleic acid may be the sense strand or the antisense strand. Nucleic acids can include natural nucleotides (such as A, T/U, C, and G), modified nucleotides, analogs of natural nucleotides, such as labeled nucleotides, or any combination thereof.

In certain embodiments, the polynucleotide sequence is recombinant DNA. In further embodiments, the polynucleotide sequence further comprises additional sequences as described elsewhere herein. In certain embodiments, the nucleic acid sequence is synthesized in vitro.

Synthetic mRNA

In some embodiments, the polynucleotide is mRNA, e.g., synthetic mRNA. The mRNA may comprise coding sequence(s) for one or more polypeptides herein. A synthetic mRNA may be an mRNA produced through an in vitro transcription reaction or through artificial (non-natural) chemical synthesis or through a combination thereof. In some embodiments, the synthetic mRNA further comprises a poly A tail, a Kozak sequence, a 3' untranslated region, a 5' untranslated region, or any combination thereof. Poly A tails in particular can be added to a synthetic RNA using a variety of art-recognized techniques, e.g., using poly A polymerase, using transcription directly from PCR products, or by ligating to the 3' end of a synthetic RNA with RNA ligase.

The mRNA may comprise one or more stabilizing elements that maintain or enhance the stabilities of mRNA, e.g., reducing or preventing degradation of the mRNA. Examples of stabilizing elements include untranslated regions (UTR) at their 5'-end (5'UTR) and/or at their 3'-end (3'UTR), in addition to other structural features, such as a 5'-cap structure or a 3'-poly(A) tail. The stabilizing elements may be a histone stem-loop, e.g., a histone stem loop added by a stem-loop binding protein (SLBP).

Vectors

The polynucleotides herein may be in a vector. In some cases, a vector comprises a polynucleotide, the polynucleotide comprising a sequence encoding a barcoding construct operably linked to a first promoter that is an antisense promoter, wherein the barcoding construct comprises a trans-splicing element and a barcode sequence.

The vector may be used for delivering the polynucleotide to cells and/or control the expression of the polynucleotide. A vector refers to a nucleic acid molecule capable of transporting another nucleic acid to which it has been linked. A vector may be a replicon, such as a plasmid, phage, or cosmid, into which another DNA segment may be inserted so as to bring about the replication of the inserted segment. Generally, a vector is capable of replication when associated with the proper control elements. Examples of vectors include nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. A vector may be a plasmid, e.g., a circular double stranded DNA loop into which additional DNA segments can be inserted, such as by standard molecular cloning techniques.

Certain vectors may be capable of directing the expression of genes to which they are operatively-linked. Such vectors are referred to herein as "expression vectors." Common expression vectors of utility in recombinant DNA techniques are often in the form of plasmids. A vector may be a recombinant expression vector that comprises a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. As used herein, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Regulatory Elements

A polynucleotide or vector herein may comprise one or more regulatory elements (or sequences encoding thereof), such as transcription control sequences, e.g., sequences which control the initiation, elongation and termination of transcription. The regulatory element(s) may be operably linked to coding sequences of the engineered proteins. The term "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

Exemplary regulatory elements include transcription control sequences, e.g., sequences that control transcription initiation, such as promoter, enhancer, operator and repressor sequences. In some cases, a regulatory element may be a transcription terminator or a sequence encoding thereof. A transcription terminator may comprise a section of nucleic acid sequence that marks the end of a gene or operon in genomic DNA during transcription. This sequence may mediate transcriptional termination by providing signals in the newly synthesized transcript RNA that trigger processes which release the transcript RNA from the transcriptional complex. A regulatory element may be an antisense sequence. In certain case, a regulatory element may be a sense sequence.

Promoters

In some cases, the promoter may be a constitutive promoter, e.g., U6 and H1 promoters, retroviral Rous sarcoma virus (RSV) LTR promoter, cytomegalovirus (CMV) promoter, SV40 promoter, dihydrofolate reductase promoter, β-actin promoter, phosphoglycerol kinase (PGK) promoter, ubiquitin C, U5 snRNA, U7 snRNA, tRNA promoters or EF1α promoter. In certain cases, the promoter may be a tissue-specific promoter may direct expression primarily in a desired tissue of interest, such as muscle, neuron, bone, skin, blood, specific organs (e.g., liver, pancreas), or particular cell types (e.g. lymphocytes). Examples of tissue-specific promoters include Ick, myogenin, or thyl promoters. In some embodiments, the promoter may direct expression in a temporal-dependent manner, such as in a cell-cycle dependent or developmental stage-dependent manner, which may or may not also be tissue or cell-type specific. In certain cases, the promoter may be an inducible promoter, e.g., can be activated by a chemical such as doxycycline.

Codon Optimization

In some embodiments, the polynucleotides herein may be codon optimized, e.g., for expression in a eukaryotic cells such as a mammalian cell or a plant cell. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. In certain embodiments, the polynucleotides are not codon optimized.

Codon optimization a canonical ORF may be guided by the information of internal out-of-frame ORFs of the canonical ORF, e.g., information of the sequences, positions, and expression products of internal out-of-frame ORFs, as well as their functions and activities of the expression products. For example, a canonical ORF of a polynucleotides may be codon optimized in a way that the internal out-of-frame ORF(s) of the canonical ORF is not interrupted, so that the expression of the internal out-of-frame ORFs is maintained. In certain cases, the codon optimization may be performed so that both the canonical ORF and the internal out-of-frame ORF(s) are optimized. In some cases, the present disclosure provides a method of designing an immunogenic composition, comprising: identifying immunogenic peptides derived from expression of out-of-frame ORFs; and codon optimizing nucleic-acid based vaccines directed to immunogenic peptides derived from in-frame ORFs such that expression of immunogenic peptides derived from out-of-frame ORFs is maintained.

Antigenic Components

The composition herein may further comprise one or more antigenic components. Antigenic components include components that specifically trigger the immune response against the antigen or antigens from which the antigenic components are derived. Examples of the antigenic components include whole virions (e.g., live attenuated or inactive forms), proteins (such as, but not limited to, envelope and capsid proteins), carbohydrates and lipids derived therefrom, polynucleotides encoding such proteins, as well as combinations thereof, and fragments of the same which are capable of eliciting an immune response in a host. Examples of the antigenic components also include non-replicating viral vector, replicating viral vector, proteins or peptides derived from one or more proteins of the virus, virus-like particles, DNA, and RNA molecules, e.g., DNA or RNA molecules encoding antigenic peptides. In one example, the antigenic components may be capable of stimulating production of an antibody targeting SARS-COV-2.

In some examples, the antigenic components are one or more components in a vaccine against SARS-COV-2, e.g., LNP-encapsulated mRNA vaccine encoding S protein (e.g., mRNA-1273), Adenovirus type 5 vector that expresses S protein (e.g., Ad5-nCOV), DNA plasmid encoding S protein delivered by electroporation (e.g., INO-4800), DCs modified with lentiviral vector expressing synthetic minigene based on domains of selected viral proteins (e.g., LV-SMENP-DC), aAPCs modified with lentiviral vector expressing synthetic minigene based on domains of selected viral proteins (e.g., Pathogenspecific aAPC). Other examples of the antigenic components include those described in Le T T et al., The COVID-19 vaccine development landscape, Nature Reviews Drug Discovery 19, 305-306 (2020), which is incorporated herein in its entirety. In some embodiments, the antigenic components antigenic polypeptides from a nucleocapsid phosphoprotein of SARS-COV-2, a spike glycoprotein of SARS-COV-2, or a combination thereof, or one or more polynucleotides encoding the one or more antigenic polypeptides.

Therapeutic Agents

In some embodiments, the compositions may further comprise one or more therapeutic agents such as anti-viral therapeutics. Such agents may be used together with the immunogenic composition herein for treating virus infection and related health problems. In some cases, the therapeutic agent(s) are drug(s) for treating SARS-COV-2 and related diseases. Examples of such therapeutic agents include nucleoside analogues (e.g., Remdesivir, Favipiravir, Ribavirin), HIV protease inhibitors (e.g., Kaletra (lopinavir/ritonavir)), agents targeting proinflammatory hypercytokinemia (e.g., Tocilizumab and leronlimab), IFNλ, Antiparasitics (e.g., Ivermectin), antimalarial drugs (e.g., Chloroquine and hydroxychloroquine), agents targeting cardioprotective derivatives (e.g., Colchicine), agents targeting angiotensin-converting enzyme 2 (ACE2), Nicotine, Vitamin D, and Spironolactone. Additional examples of therapeutic agents can be included in the composition include those described in Konstantinidou S K et al., Repurposing current therapeutic regimens against SARS-COV-2 (Review), Exp Ther Med. 2020 September; 20 (3): 1845-1855, which is incorporated herein in its entirety.

Pharmaceutical Formulations

In another aspect, the present disclosure provides pharmaceutical formulations comprising the compositions, or one or more components of the compositions. A pharmaceutical composition may further comprise one or more excipients, such as pharmaceutically acceptable carriers suitable for administration to cells or to a subject. In some examples, the pharmaceutical composition is a vaccine, which elicit protective immunity to a recipient.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof. Examples of buffering agents are e.g. citric acid, acetic acid, tartaric acid, lactic acid, hydrogenphosphoric acid, diethyl amine etc. Suitable examples of preservatives for use in compositions are parabenes, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives. The term "pharmaceutically acceptable" as used throughout this specification is consistent with the art and means compatible with the other ingredients of a pharmaceutical composition and not deleterious to the recipient thereof.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical compositions can be applied parenterally, rectally, orally or topically. For example, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. The compositions herein may be administered by the same route or may be administered by a different route. By means of example, and without limitation, cells may be administered parenterally, and other active components may be administered orally. In some cases, the composition or pharmaceutical composition may be intramuscular injection. In some cases, the composition or pharmaceutical composition may be intravascular injection.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further examples of suitably pharmaceutically acceptable carriers or additives include proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14:323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

The pharmaceutical compositions may comprise one or more pharmaceutically acceptable salts. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, pamoate, valerate, and the like which can be used as a dosage form for modifying the solubility or hydrolysis characteristics or can be used in sustained release or pro-drug formulations. It will be understood that, as used herein, references to specific agents (e.g., neuromedin U receptor agonists or antagonists), also include the pharmaceutically acceptable salts thereof.

The pharmaceutical composition may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

In some embodiments, the pharmaceutical compositions further comprise one or more adjuvants. Adjuvants may be molecules or compounds that have intrinsic immunomodulatory properties and, when administered in conjunction with an antigen, effectively potentiate the host antigen-specific immune responses compared to responses raised when antigen is given alone. Examples of adjuvants include aluminum hydroxide and aluminum phosphate, saponins e.g., QUIL-A® (commercially available from Brenntag Biosector A/S), QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion may be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks. Other examples of adjuvants include Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Aluminium salts (e.g. AdjuPhos), Adjuplex, and MF59, lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-I, IL-2, IL-4, IL-6, IL-8, IL-IO, and IL-12 or encoding nucleic acids thereof.

Various delivery systems are known and can be used to administer the pharmacological compositions including encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321:574 (1989) and a semi-permeable polymeric material (See, for example, Howard, et al., J. Neurosurg. 71:105 (1989)). Additionally, the controlled release system can be placed in proximity of the therapeutic target (e.g., a tumor or infected tissue), thus requiring only a fraction of the systemic dose. See, for example, Goodson, In: Medical Applications of Controlled Release, 1984. (CRC Press, Boca Raton, Fla.).

Cells and Organisms

In another aspect, the present disclosure provides cells and organisms comprising the compositions herein. The cells may be in tissue, organ, or isolated cells. Such cells may be of a unique type of cells or a group of different types of cells such as cultured cell lines, primary cells and proliferative cells. The cells may be prokaryotic cells, lower eukaryotic cells such as yeast, and other eukaryotic cells such as insect cells, plant and mammalian (e.g., human or non-human) cells as well as cells capable of producing the vector of the invention (e.g. 293, HER96, PERC.6 cells, Vero, HeLa, CEF, duck cell lines, etc.). The cells may include cells which can be or has been the recipient of the vector described herein as well as progeny of such cells. Host cells can be cultured in conventional fermentation bioreactors, flasks, and petri plates. Culturing can be carried out at a temperature, pH and oxygen content appropriate for a given cell. No attempts will be made here to describe in detail the various prokaryote and eukaryotic host cells and methods known for the production of the polypeptides and vectors herein.

METHODS OF TREATMENTS AND PROPHYLAXIS

In another aspect, the present disclosure provides methods of treating and/or preventing (e.g., immunizing) an infection (e.g., viral infection) in a subject, and/or disease and conditions related to the infection. Generally, the methods may comprise administering a pharmaceutically effective (e.g., therapeutically effective amount or prophylactically effective amount)) amount of the composition herein to a subject, e.g., a subject in need thereof. In some cases, the method comprise administering the composition(s), the polynucleotide(s), and/or the vector(s) herein to a subject. A pharmaceutically effective amount refers to an amount which can elicit a biological, medicinal, or immunological response in a tissue, system, or subject (e.g., animal or human) that can prevent or alleviate one or more of the local or systemic symptoms or features of a disease or condition being treated.

In certain examples, the methods may be used to induce a T cell response and/or antibody response to SARS-COV-2 in a subject. In some cases, the methods may comprise administering the polypeptides and antigenic agents, and/or anti-viral therapeutics, or polynucleotides encoding thereof to a subject (e.g., a subject in need thereof).

Methods of administrating to a subject include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment and prophylaxis; this may be achieved by, for example, local infusion during surgery, topical application, by injection, by means of a catheter, by means of a suppository, or by means of an implant.

The term “subject” or “patient” is intended to include mammalian organisms. Examples of subjects/patients include humans and non-human mammals, e.g., non-human primates, dogs, cows, horses, pigs, sheep, goats, cats, mice, rabbits, rats, and transgenic non-human animals. In specific embodiments of the invention, the subject is a human.

In some cases, the methods comprise administering to a subject the pharmaceutical compositions alone or in concert with other therapeutic agents at appropriate dosages defined by routine testing in order to obtain optimal efficacy while minimizing any potential toxicity. The dosage regimen utilizing a pharmaceutical composition may be selected in accordance with a variety of factors including type, species, age, weight, sex, medical condition of the patient; the severity of the condition to be treated; the route of administration; the renal and hepatic function of the patient; and the particular pharmaceutical composition employed.

Optimal precision in achieving concentrations of the therapeutic regimen within the range that yields maximum efficacy with minimal toxicity may require a regimen based on the kinetics of the pharmaceutical composition’s availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical composition and various therapeutic agents may be independently optimized and combined to achieve a synergistic result wherein the pathology is reduced more than it would be if either was used alone.

In particular, toxicity and therapeutic efficacy of the pharmaceutical composition may be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effect is the therapeutic index and it may be expressed as the ratio LD50/ED50. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the ED50 with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

The methods may comprise administering a booster agent in addition to the administration of the composition therein. A booster agent may be an extra administration of the composition herein or a different agent. A booster (or booster vaccine) may be given after an earlier administration of the composition. The time of administration between the initial administration of the composition and the booster may be at least 1 minute, at least 5 minutes, at least 10 minutes, at least 20 minutes, at least 30 minutes, at least 40 minutes, at least 50 minutes, at least 1 hour, at least 2 hours, at least 4 hours, at least 8 hours, at least 12 hours, at least 1 day, at least 1 week, at least 2 week, at least 3 week, at least 1 month, at least 2 months, at least 3 months, at least 4 months, at least 5 months, at least 6 months, at least 1 year, at least 5 years, at least 10 years, and any time period in-between.

Delivery to Cells and Organisms

The present disclosure also provides delivery systems for introducing the compositions herein to cells, tissues, organs, or organisms. A delivery system may comprise one or more delivery vehicles and/or cargos. Exemplary delivery systems and methods include those described in paragraphs to of Feng Zhang et al., (WO2016106236A1), and pages 1241-1251 and Table 1 of Lino C A et al., Delivering CRISPR: a review of the challenges and approaches, DRUG DELIVERY, 2018, VOL. 25, NO. 1, 1234-1257, which are incorporated by reference herein in their entireties.

Cargos

The delivery systems may comprise one or more cargos. A cargo may comprise one or more of the following: i) one or more polypeptides herein, ii) one or more polynucleotides encoding the polypeptide(s) or vectors comprising the polynucleotides; (iii) mRNA molecules encoding the one or more polypeptides; iv) cells comprising i), ii) and/or iii). In some examples, a cargo may comprise a plasmid encoding one or more engineered proteins herein.

Physical Delivery

In some embodiments, the cargos may be introduced to cells by physical delivery methods. Examples of physical methods include microinjection, electroporation, and hydrodynamic delivery. Both nucleic acid and proteins may be delivered using such methods. For example, the polypeptides and polynucleotides may be prepared in vitro, isolated, (refolded, purified if needed), and introduced to cells.

Microinjection

Microinjection of the cargo directly to cells can achieve high efficiency, e.g., above 90% or about 100%. In some embodiments, microinjection may be performed using a microscope and a needle (e.g., with 0.5-5.0 μm in diameter) to pierce a cell membrane and deliver the cargo directly to a target site within the cell. Microinjection may be used for in vitro and ex vivo delivery.

Polynucleotides and vectors comprising coding sequences for the polypeptides may be microinjected. In some cases, microinjection may be used i) to deliver DNA directly to a cell nucleus, and/or ii) to deliver mRNA (e.g., in vitro transcribed) to a cell nucleus or cytoplasm.

Microinjection may be used to generate genetically modified animals. For example, gene editing cargos may be injected into zygotes to allow for efficient germline modification. Such approach can yield normal embryos and full-term mouse pups harboring the desired modification(s).

Electroporation

In some embodiments, the cargos and/or delivery vehicles may be delivered by electroporation. Electroporation may use pulsed high-voltage electrical currents to transiently open nanometer-sized pores within the cellular membrane of cells suspended in buffer, allowing for components with hydrodynamic diameters of tens of nanometers to flow into the cell. In some cases, electroporation may be used on various cell types and efficiently transfer cargo into cells. Electroporation may be used for in vitro and ex vivo delivery.

Electroporation may also be used to deliver the cargo to into the nuclei of mammalian cells by applying specific voltage and reagents, e.g., by nucleofection. Such approaches include those described in Wu Y, et al. (2015). Cell Res 25:67-79; Ye L, et al. (2014). Proc Natl Acad Sci USA 111:9591-6; Choi P S, Meyerson M. (2014). Nat Commun 5:3728; Wang J, Quake S R. (2014). Proc Natl Acad Sci 111:13157-62. Electroporation may also be used to deliver the cargo in vivo, e.g., with methods described in Zuckermann M, et al. (2015). Nat Commun 6:7391.

Hydrodynamic Delivery

Hydrodynamic delivery may also be used for delivering the cargos, e.g., for in vivo delivery. In some examples, hydrodynamic delivery may be performed by rapidly pushing a large volume (8-10% body weight) solution containing the gene editing cargo into the bloodstream of a subject (e.g., an animal or human), e.g., for mice, via the tail vein. As blood is incompressible, the large bolus of liquid may result in an increase in hydrodynamic pressure that temporarily enhances permeability into endothelial and parenchymal cells, allowing for cargo not normally capable of crossing a cellular membrane to pass into cells. This approach may be used for delivering naked DNA plasmids and proteins. The delivered cargos may be enriched in liver, kidney, lung, muscle, and/or heart.

Transfection

The cargos, e.g., nucleic acids, may be introduced to cells by transfection methods for introducing nucleic acids into cells. Examples of transfection methods include calcium phosphate-mediated transfection, cationic transfection, liposome transfection, dendrimer transfection, heat shock transfection, magnetofection, lipofection, impalefection, optical transfection, proprietary agent-enhanced uptake of nucleic acid.

Delivery Vehicles

The delivery systems may comprise one or more delivery vehicles. The delivery vehicles may deliver the cargo into cells, tissues, organs, or organisms (e.g., animals or plants). The cargos may be packaged, carried, or otherwise associated with the delivery vehicles. The delivery vehicles may be selected based on the types of cargo to be delivered, and/or the delivery is in vitro and/or in vivo. Examples of delivery vehicles include vectors, viruses, non-viral vehicles, and other delivery reagents described herein.

The delivery vehicles in accordance with the present invention may a greatest dimension (e.g. diameter) of less than 100 microns (μm). In some embodiments, the delivery vehicles have a greatest dimension of less than 10 μm. In some embodiments, the delivery vehicles may have a greatest dimension of less than 2000 nanometers (nm). In some embodiments, the delivery vehicles may have a greatest dimension of less than 1000 nanometers (nm). In some embodiments, the delivery vehicles may have a greatest dimension (e.g., diameter) of less than 900 nm, less than 800 nm, less than 700 nm, less than 600 nm, less than 500 nm, less than 400 nm, less than 300 nm, less than 200 nm, less than 150 nm, or less than 100 nm, less than 50 nm. In some embodiments, the delivery vehicles may have a greatest dimension ranging between 25 nm and 200 nm.

In some embodiments, the delivery vehicles may be or comprise particles. For example, the delivery vehicle may be or comprise nanoparticles (e.g., particles with a greatest dimension (e.g., diameter) no greater than 1000 nm. The particles may be provided in different forms, e.g., as solid particles (e.g., metal such as silver, gold, iron, titanium), non-metal, lipid-based solids, polymers), suspensions of particles, or combinations thereof. Metal, dielectric, and semiconductor particles may be prepared, as well as hybrid structures (e.g., core-shell particles).

Viral Vectors

The cargos may be delivered by viruses. In some embodiments, viral vectors are used. A viral vector may comprise virally-derived DNA or RNA sequences for packaging into a virus (e.g., retroviruses, replication defective retroviruses, adenoviruses, replication defective adenoviruses, and adeno-associated viruses). Viral vectors also include polynucleotides carried by a virus for transfection into a host cell. Viruses and viral vectors may be used for in vitro, ex vivo, and/or in vivo deliveries.

Adeno Associated Virus (AAV)

The compositions herein may be delivered by adeno associated virus (AAV). AAV vectors may be used for such delivery. AAV, of the Dependovirus genus and Parvoviridae family, is a single stranded DNA virus. In some embodiments, AAV may provide a persistent source of the provided DNA, as AAV delivered genomic material can exist indefinitely in cells, e.g., either as exogenous DNA or, with some modification, be directly integrated into the host DNA. In some embodiments, AAV do not cause or relate with any diseases in humans. The virus itself is able to efficiently infect cells while provoking little to no innate or adaptive immune response or associated toxicity.

Examples of AAV that can be used herein include AAV-1, AAV-2, AAV-3, AAV-4, AAV-5, AAV-6, AAV-8, and AAV-9. The type of AAV may be selected with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium. Examples of cell types targeted by AAV are described in Grimm, D. et al, J. Virol. 82:5887-5911 (2008)). In some examples, AAV particles may be created in HEK 293 T cells. Once particles with specific tropism have been created, they are used to infect the target cell line much in the same way that native viral particles do. This may allow for persistent presence of engineered proteins in the infected cell type, and what makes this version of delivery particularly suited to cases where long-term expression is desirable. Examples of doses and formulations for AAV that can be used include those describe in U.S. Pat. Nos. 8,454,972 and 8,404,658.

Various strategies may be used for delivery the systems and compositions herein with AAVs. In some examples, coding sequences of engineered proteins may be packaged directly onto one DNA plasmid vector and delivered via one AAV particle. In some examples, AAVs may be used to deliver gRNAs into cells that have been previously engineered to express the engineered protein. In some examples, coding sequences of two or more engineered proteins may be made into two separate AAV particles, which are used for co-transfection of target cells.

Lentiviruses

The compositions herein may be delivered by lentiviruses. Lentiviral vectors may be used for such delivery. Lentiviruses are complex retroviruses that have the ability to infect and express their genes in both mitotic and post-mitotic cells.

Examples of lentiviruses include human immunodeficiency virus (HIV), which may use its envelope glycoproteins of other viruses to target a broad range of cell types; minimal non-primate lentiviral vectors based on the equine infectious anemia virus (EIAV), which may be used for ocular therapies. In certain embodiments, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2: 36ra43) may be used and/or adapted to the nucleic acid-targeting system herein.

Lentiviruses may be pseudo-typed with other viral proteins, such as the G protein of vesicular stomatitis virus. In doing so, the cellular tropism of the lentiviruses can be altered to be as broad or narrow as desired. In some cases, to improve safety, second- and third-generation lentiviral systems may split essential genes across three plasmids, which may reduce the likelihood of accidental reconstitution of viable viral particles within cells.

In some examples, leveraging the integration ability, lentiviruses may be used to create libraries of cells comprising various genetic modifications, e.g., for screening and/or studying genes and signaling pathways.

Adenoviruses

The systems and compositions herein may be delivered by adenoviruses. Adenoviral vectors may be used for such delivery. Adenoviruses include nonenveloped viruses with an icosahedral nucleocapsid containing a double stranded DNA genome. Adenoviruses may infect dividing and non-dividing cells.

Non-Viral Vehicles

The delivery vehicles may comprise non-viral vehicles. In general, methods and vehicles capable of delivering nucleic acids and/or proteins may be used for delivering the systems compositions herein. Examples of non-viral vehicles include lipid nanoparticles, cell-penetrating peptides (CPPs), DNA nanoclews, gold nanoparticles, streptolysin O, multifunctional envelope-type nanodevices (MENDs), lipid-coated mesoporous silica particles, and other inorganic nanoparticles.

Lipid Particles

The delivery vehicles may comprise lipid particles, e.g., lipid nanoparticles (LNPs) and liposomes.

Lipid Nanoparticles (LNPs)

LNPs may encapsulate nucleic acids within cationic lipid particles (e.g., liposomes), and may be delivered to cells with relative ease. In some examples, lipid nanoparticles do not contain any viral components, which helps minimize safety and immunogenicity concerns. Lipid particles may be used for in vitro, ex vivo, and in vivo deliveries. Lipid particles may be used for various scales of cell populations.

In some examples. LNPs may be used for delivering DNA molecules and/or RNA molecules. In certain cases, LNPs may be use for delivering RNP complexes.

Components in LNPs may comprise cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), R-3-[(ro-methoxy-poly(ethylene glycol) 2000) carbamoyl]-1,2-dimyristyloxlpropyl-3-amine (PEG-C-DOMG, and any combination thereof. Preparation of LNPs and encapsulation may be adapted from Rosin et al, Molecular Therapy, vol. 19, no. 12, pages 1286-220 December 2011).

Liposomes

In some embodiments, a lipid particle may be liposome. Liposomes are spherical vesicle structures composed of a uni- or multilamellar lipid bilayer surrounding internal aqueous compartments and a relatively impermeable outer lipophilic phospholipid bilayer. In some embodiments, liposomes are biocompatible, nontoxic, can deliver both hydrophilic and lipophilic drug molecules, protect their cargo from degradation by plasma enzymes, and transport their load across biological membranes and the blood brain barrier (BBB).

Liposomes can be made from several different types of lipids, e.g., phospholipids. A liposome may comprise natural phospholipids and lipids such as 1,2-distearoryl-sn-glycero-3-phosphatidyl choline (DSPC), sphingomyelin, egg phosphatidylcholines, monosialoganglioside, or any combination thereof.

Several other additives may be added to liposomes in order to modify their structure and properties. For instance, liposomes may further comprise cholesterol, sphingomyelin, and/or 1,2-dioleoyl-sn-glycero-3-phosphoethanolamine (DOPE), e.g., to increase stability and/or to prevent the leakage of the liposomal inner cargo.

Stable Nucleic-Acid-Lipid Particles (SNALPs)

In some embodiments, the lipid particles may be stable nucleic acid lipid particles (SNALPs). SNALPs may comprise an ionizable lipid (DLinDMA) (e.g., cationic at low pH), a neutral helper lipid, cholesterol, a diffusible polyethylene glycol (PEG)-lipid, or any combination thereof. In some examples, SNALPs may comprise synthetic cholesterol, dipalmitoylphosphatidylcholine, 3-N-[(w-methoxy polyethylene glycol) 2000) carbamoyl]-1,2-dimyrestyloxypropylamine, and cationic 1,2-dilinoleyloxy-3-N,Ndimethylaminopropane. In some examples, SNALPs may comprise synthetic cholesterol, 1,2-distearoyl-sn-glycero-3-phosphocholine, PEG-CDMA, and 1,2-dilinoleyloxy-3-(N;N-dimethyl) aminopropane (DLinDMA).

Other Lipids

The lipid particles may also comprise one or more other types of lipids, e.g., cationic lipids, such as amino lipid 2,2-dilinoleyl-4-dimethylaminoethyl-[1,3]-dioxolane (DLin-KC2-DMA), DLin-KC2-DMA4, C12-200 and colipids distearoylphosphatidylcholine, cholesterol, and PEG-DMG.

Lipoplexes/Polyplexes

In some embodiments, the delivery vehicles comprise lipoplexes and/or polyplexes. Lipoplexes may bind to negatively charged cell membrane and induce endocytosis into the cells. Examples of lipoplexes may be complexes comprising lipid(s) and non-lipid components. Examples of lipoplexes and polyplexes include FuGENE-6 reagent, a non-liposomal solution containing lipids and other components, zwitterionic amino lipids (ZALs), Ca2b (e.g., forming DNA/$Ca^{2+}$ microcomplexes), polyethylenimine (PEI) (e.g., branched PEI), and poly(L-lysine) (PLL).

Cell Penetrating Peptides

In some embodiments, the delivery vehicles comprise cell penetrating peptides (CPPs). CPPs are short peptides that facilitate cellular uptake of various molecular cargo (e.g., from nanosized particles to small chemical molecules and large fragments of DNA).

CPPs may be of different sizes, amino acid sequences, and charges. In some examples, CPPs can translocate the plasma membrane and facilitate the delivery of various molecular cargoes to the cytoplasm or an organelle. CPPs may be introduced into cells via different mechanisms, e.g., direct penetration in the membrane, endocytosis-mediated entry, and translocation through the formation of a transitory structure.

CPPs may have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. Another type of CPPs is the trans-activating transcriptional activator (Tat) from Human Immunodeficiency Virus 1 (HIV-1). Examples of CPPs include to Penetratin, Tat (48-60), Transportan, and (R-AhX-R4) (Ahx refers to aminohexanoyl), Kaposi fibroblast growth factor (FGF) signal peptide sequence, integrin β3 signal peptide sequence, polyarginine peptide Args sequence, Guanine rich-molecular transporters, and sweet arrow peptide. Examples of CPPs and related applications also include those described in U.S. Pat. No. 8,372,951.

CPPs can be used for in vitro and ex vivo work quite readily, and extensive optimization for each cargo and cell type is usually required. In some examples, CPPs may be covalently attached to the engineered protein directly, which is then complexed with the gRNA and delivered to cells. CPP may also be used to delivery RNPs.

CPPs may be used to deliver the compositions and systems to plants. In some examples, CPPs may be used to deliver the components to plant protoplasts, which are then regenerated to plant cells and further to plants.

DNA Nanoclews

In some embodiments, the delivery vehicles comprise DNA nanoclews. A DNA nanoclew refers to a sphere-like structure of DNA (e.g., with a shape of a ball of yarn). The nanoclew may be synthesized by rolling circle amplification with palindromic sequences that aide in the self-assembly of the structure. The sphere may then be loaded with a payload. An example of DNA nanoclew is described in Sun W et al, J Am Chem Soc. 2014 Oct. 22; 136 (42): 14722-5; and Sun W et al, Angew Chem Int Ed Engl. 2015 Oct. 5; 54 (41): 12029-33. A DNA nanoclew may be coated, e.g., coated with PEI to induce endosomal escape.

Gold Nanoparticles

In some embodiments, the delivery vehicles comprise gold nanoparticles (also referred to AuNPs or colloidal gold). Gold nanoparticles may form complex with cargos. Gold nanoparticles may be coated, e.g., coated in a silicate and an endosomal disruptive polymer, PAsp (DET). Examples of gold nanoparticles include AuraSense Therapeutics' Spherical Nucleic Acid (SNA™) constructs, and those described in Mout R, et al. (2017). ACS Nano 11:2452-8; Lee K, et al. (2017). Nat Biomed Eng 1:889-901.

iTOP

In some embodiments, the delivery vehicles comprise iTOP. iTOP refers to a combination of small molecules drives the highly efficient intracellular delivery of native proteins, independent of any transduction peptide. iTOP may be used for induced transduction by osmocytosis and propanebetaine, using NaCl-mediated hyperosmolality together with a transduction compound (propanebetaine) to trigger macropinocytotic uptake into cells of extracellular macromolecules. Examples of iTOP methods and reagents include those described in D'Astolfo D S, Pagliero R J, Pras A, et al. (2015). Cell 161:674-690.

Polymer-Based Particles

In some embodiments, the delivery vehicles may comprise polymer-based particles (e.g., nanoparticles). In some embodiments, the polymer-based particles may mimic a viral mechanism of membrane fusion. The polymer-based particles may be a synthetic copy of Influenza virus machinery and form transfection complexes with various types of nucleic acids ((siRNA, miRNA, plasmid DNA or shRNA, mRNA) that cells take up via the endocytosis pathway, a process that involves the formation of an acidic compartment. The low pH in late endosomes acts as a chemical switch that renders the particle surface hydrophobic and facilitates membrane crossing. Once in the cytosol, the particle releases its payload for cellular action. This Active Endosome Escape technology is safe and maximizes transfection efficiency as it is using a natural uptake pathway.

Streptolysin O (SLO)

The delivery vehicles may be streptolysin O (SLO). SLO is a toxin produced by Group A streptococci that works by creating pores in mammalian cell membranes. SLO may act in a reversible manner, which allows for the delivery of proteins (e.g., up to 100 kDa) to the cytosol of cells without compromising overall viability. Examples of SLO include those described in Sierig G, et al. (2003). Infect Immun 71:446-55; Walev I, et al. (2001). Proc Natl Acad Sci USA 98:3185-90; Teng K W, et al. (2017). Elife 6: e25460.

Multifunctional Envelope-Type Nanodevice (MEND)

The delivery vehicles may comprise multifunctional envelope-type nanodevice (MENDs). MENDs may comprise condensed plasmid DNA, a PLL core, and a lipid film shell. A MEND may further comprise cell-penetrating peptide (e.g., stearyl octaarginine). The cell penetrating peptide may be in the lipid shell. The lipid envelope may be modified with one or more functional components, e.g., one or more of: polyethylene glycol (e.g., to increase vascular circulation time), ligands for targeting of specific tissues/cells, additional cell-penetrating peptides (e.g., for greater cellular delivery), lipids to enhance endosomal escape, and nuclear delivery tags. In some examples, the MEND may be a tetra-lamellar MEND (T-MEND), which may target the cellular nucleus and mitochondria. In certain examples, a MEND may be a PEG-peptide-DOPE-conjugated MEND (PPD-MEND), which may target bladder cancer cells. Examples of MENDs include those described in Kogure K, et al. (2004). J Control Release 98:317-23; Nakamura T, et al. (2012). Acc Chem Res 45:1113-21.

Lipid-Coated Mesoporous Silica Particles

The delivery vehicles may comprise lipid-coated mesoporous silica particles. Lipid-coated mesoporous silica particles may comprise a mesoporous silica nanoparticle core and a lipid membrane shell. The silica core may have a large internal surface area, leading to high cargo loading capacities. In some embodiments, pore sizes, pore chemistry, and overall particle sizes may be modified for loading different types of cargos. The lipid coating of the particle may also be modified to maximize cargo loading, increase circulation times, and provide precise targeting and cargo release. Examples of lipid-coated mesoporous silica particles include those described in Du X, et al. (2014). Biomaterials 35:5580-90; Durfee P N, et al. (2016). ACS Nano 10:8325-45.

Inorganic Nanoparticles

The delivery vehicles may comprise inorganic nanoparticles. Examples of inorganic nanoparticles include carbon nanotubes (CNTs) (e.g., as described in Bates K and Kostarelos K. (2013). Adv Drug Deliv Rev 65:2023-33.), bare mesoporous silica nanoparticles (MSNPs) (e.g., as described in Luo G F, et al. (2014). Sci Rep 4:6064), and dense silica nanoparticles (SiNPs) (as described in Luo D and Saltzman W M. (2000). Nat Biotechnol 18:893-5).

Exosomes

The delivery vehicles may comprise exosomes. Exosomes include membrane bound extracellular vesicles, which can be used to contain and delivery various types of biomolecules, such as proteins, carbohydrates, lipids, and nucleic acids, and complexes thereof (e.g., RNPs). Examples of exosomes include those described in Schroeder A, et al., J Intern Med. 2010 January;267 (1): 9-21; El-Andaloussi S, et al., Nat Protoc. 2012 December; 7 (12): 2112-26; Uno Y, et al., Hum Gene Ther. 2011 June; 22 (6): 711-9; Zou W, et al., Hum Gene Ther. 2011 April; 22 (4): 465-75.

In some examples, the exosome may form a complex (e.g., by binding directly or indirectly) to one or more components of the cargo. In certain examples, a molecule of an exosome may be fused with first adapter protein and a component of the cargo may be fused with a second adapter protein. The first and the second adapter protein may specifically bind each other, thus associating the cargo with the exosome. Examples of such exosomes include those described in Ye Y, et al., Biomater Sci. 2020 Apr. 28. doi: 10.1039/d0bm00427 h.

ADDITIONAL EXEMPLARY APPLICATIONS

In another aspect, the present disclosure provides methods of determining an infection status of a subject. In some embodiments, the methods comprise contacting immune cells derived from the subject with the composition herein; and detecting cross-reactivity of the immune cells to the composition.

In some embodiments, the methods may be used for performing T cell assay. For example, the methods may determine T cells' response to the compositions such as the polypeptides. The response may be used to evaluate the infection or immunity status of the subject from which the T cells are derived from. In one example, T cells (e.g., CD8+ T cells) may be isolated from PBMCs and incubated with the compositions herein. Proliferation of T cells can be measured by 3H thymidine incorporation. Secretion of cytokines from the T cells may be measured, e.g., by ELISA.

In some embodiments, the information of HLA-I peptides from internal out-of-frame ORFs may be used to modify the sequence of canonical ORFs, e.g., to ensure the continuous synthesis and presentation of peptides from the optimized sequences.

METHOD OF IDENTIFYING IMMUNOGENIC POLYPEPTIDES

In another aspect, the present disclosure provides methods for screening and identifying the immunogenic polypeptides herein. In general, the methods comprise isolating complex(es) of MHC-I (e.g., HLA-I) and binding partners from cells infected by a pathogen such as a virus (e.g., SARS-COV-2), and characterizing (e.g., determining the sequences) of polypeptides in the isolated complex, and identifying polypeptides derived from one or more proteins of the virus. In some embodiments, the method can include identifying polypeptides derived from one or more open reading frames. In some embodiments, the open reading frames are annotated ORFs, alternative ORFs, canonical ORFs, and/or noncanonical ORFs. ORFs are discussed and described in greater detail elsewhere herein.

In certain examples, the methods of identifying immunogenic peptides comprising: a) lysing cells having a potential to express the immunogenic peptides of interest with a lysis buffer comprising a cell membrane disrupting detergent; b) enzymatic shearing of nucleic acids in the lysed cells; c) isolating HLA-I from the lysed cells, wherein the HLA-I is in complex with one or more polypeptides or proteins from the lysed cells; and d) determining sequences of the one or more polypeptides or proteins in complex with the HLA-I from (c).

The cells used in the method may be treated with one or more cell signaling molecules related to infection by the pathogen. In some cases, the cells may express (e.g., overexpress by an exogenous gene) one or more proteins regulating or mediating a virus infection. For example, the cells may express one or more receptors involved in a viral infection process, e.g., ACE-2 and TMPRSS2. In certain cases, the cells may be engineered to alter (e.g., increase or decrease) HLA presentation. For example, the cells may express (e.g., by one or more exogenous genes) one or more of CITA, proteasome subunits, TPA, POMP, or ubiquitin-proteasome genes.

In some embodiments, the methods comprise lysing the cells infected by the virus with a lysis buffer. The lysis buffer may be capable of breaking the cells while retaining intact complexes of HMC-I and its binding partners. The lysis buffer may comprise one or more membrane disrupting detergents. In one example, the membrane disrupting detergent is Triton-X. The concentration of the Triton-X in the lysis buffer may be from 0.1% to 5%, e.g., from 0.5% to 3%, from 1% to 2%, from 1.2% to 1.8%, or from 1.4% to 1.6%. In one example, the concentration of the Triton-X in the lysis buffer may be about 1%, about 1.1%, about 1.2%, about 1.3%, about 1.4%, about 1.5%, about 1.6%, about 1.7%, about 1.8%, about 1.9%, or about 2.0%.

In some embodiments, the methods comprise shearing nucleic acid (e.g., DNA) in the lysed cells. In some examples, the shearing is enzymatic shearing, e.g., no sonication is used. In such cases, the shearing may be performed using an enzyme, e.g., nuclease. The nuclease may be an endonuclease that degrades all forms of DNA and RNA (single stranded, double stranded, linear and circular) while having no proteolytic activity. The endonuclease may be derived from *Serratia marcescens* or a variant thereof. In one example, the endonuclease is Benzonase. A salt may be used together with the enzyme in shearing the nucleic acid. The salt may be a Magnesium salt, e.g., $MgCl_2$, $MgSO_4$, and magnesium acetate.

The methods may further comprise isolating MHC-I from the lysed cells. In an embodiment isolating the MHC-I comprises isolating the HLA-I from the lysed cells, wherein the HLA-I (or other MHC-I) is in complex with one or more polypeptides or proteins from the lysed cells. Such polypeptides and proteins may be derived the virus that infects the cells. The isolation may be performed using immunoprecipitation, e.g., using a reagent that bind to one or more components of MHC-1 or one or more molecules attached to MHC-1.

The methods may also comprise determining the sequences of the one or more polypeptides or proteins in complex with the MHC-I. In some embodiments, the sequences may be determined using mass spectrometry, e.g., liquid chromatography tandem mass spectrometry analysis.

In some embodiments, the methods may comprise characterizing the nucleic acids, e.g., RNA, in the infected. The results of the characterization may be used to determine the viral abundance in the cells. The determination may be performed using sequencing technologies such as shotgun sequencing, resequencing, de novo assembly, exome sequencing, DNA-Seq, Targeted DNA-Seq, Methyl-Seq, Targeted methyl-Seq, DNase-Seq, Sono-Seq, FAIRE-seq, MAINE-Seq, RNA-Seq, ChIP-Seq, RIP-Seq, CLIP-Seq, HITS-Seq, FRT-Seq, NET-Seq, Hi-C, Chia-PET, Ribo-Seq, TRAP, PARS, synthetic saturation mutagenesis, Immuno-Seq, Deep protein mutagenesis, PhIT-Seq, SMRT, and genome-wide chromatin interaction mapping. In some embodiments, the methods comprise performing RNA-Seq on the RNA in the infected cells.

The methods may further comprise identifying HLA alleles that bind the polypeptides identified in using an HLA I epitope binding predictor and selecting a subset of polypeptides that bind a defined percentage of HLA I alleles in a population. The binding predictor may be a machine learning-based method, e.g., the methods described in O'Donnell T J, et al., MHCflurry 2.0: Improved Pan-Allele Prediction of MHC Class I-Presented Peptides by Incorporating Antigen Processing, Cell Syst. 2020 Jul. 22; 11 (1): 42-48.e7; Poran A, et al., Sequence-based prediction of SARS-COV-2 vaccine targets using a mass spectrometry-based bioinformatics predictor identifies immunogenic T cell epitopes. Genome Med 12, 70 (2020); and Sarkizova, S., Klaeger, S., Le, P. M. et al. A large peptidome dataset improves HLA class I epitope prediction across most of the human population. *Nat Biotechnol* 38, 199-209 (2020). https://doi.org/10.1038/s41587-019-0322-9, which are each incorporated by reference herein in their entireties.

The immunogenic polypeptides may be selected based on sequencing data. For example, the methods may further comprise selecting immunogenic polypeptides demonstrating a relative abundance above a defined threshold as determine by analysis of the complete cellular transcriptome and/or proteome. In some cases, the expression level of genes may be determined (e.g., by computational methods based on the sequencing data) and the polypeptides may be ranked and selected from highly abundant genes (e.g., genes with high expression levels). Alternatively or additionally, ribosomal sequencing may be used (in some cases no RNA-seq data is used) to identify polypeptides that are being actively translated by the cell at one or more time points, and only those polypeptides that are actively translated are selected. The datasets from this approach are different from conventional mass-spectrometry search datasets in that they include out-of-frame ORFs, which may include internal out-of-frame ORFs.

mRNA Vaccines

In some embodiments, one or more polynucleotides encoding the one or more immunogenic polypeptides described herein are included in an mRNA vaccine composition. The mRNA vaccine composition can be administered to a subject in need thereof. In some embodiments, the vaccine is administered to a subject in an effective amount to induce an immune response in the subject.

Described herein are pharmaceutical compositions that include one or more isolated messenger ribonucleic (mRNA) polynucleotides encoding at least one SARS-COV-2 antigenic polypeptide or an immunogenic fragment thereof (e.g., an immunogenic fragment capable of inducing an immune response to the antigenic polypeptide), such as any of those polynucleotides described in greater detail elsewhere herein, where the isolated mRNA is formulated in a lipid nanoparticle. As used herein "antigenic polypeptide" encompasses immunogenic fragments of the antigenic polypeptide (an immunogenic fragment that is induces (or is capable of inducing) an immune response to a SARS-COV-2 variant. The mRNA encoding at least one SARS-COV-2 antigenic polypeptide or immunogenic fragment thereof can include an open reading frame that encodes the at least one SARS-COV-2 antigenic polypeptide or immunogenic fragment thereof. In some embodiments, the open reading frame encodes at least two, at least five, or at least ten SARS-CoV-2 antigenic polypeptides and/or immunogenic fragments thereof. In some embodiments, the open reading frame encodes at least 100 antigenic polypeptides. In some embodiments, the open reading frame encodes 2-100 SARS-COV-2 antigenic polypeptides and/or immunogenic fragments thereof.

In some embodiments, the pharmaceutical composition comprises a plurality of lipid nanoparticles comprising a cationic lipid, a neutral lipid, a cholesterol, and a PEG lipid, wherein the plurality of lipid nanoparticles optionally has a mean particle size of between 80 nm and 160 nm; and wherein the lipid nanoparticles comprise one or more polynucleotides encoding at least one SARS-COV-2 antigenic polypeptide or an immunogenic fragment thereof.

In some embodiments, the mRNA vaccine is multivalent. In some embodiments, the mRNA of the mRNA vaccine is codon-optimized. In some embodiments, a RNA (e.g., mRNA) vaccine further includes an adjuvant.

In some embodiments, the isolated mRNA is not self-replicating.

In some embodiment, the isolated mRNA comprises and/or encodes one or more 5'terminal cap (or cap structure), 3'terminal cap, 5'untranslated region, 3'untranslated region, a tailing region, or any combination thereof.

In some embodiments, the capping region of the isolated mRNA region may be from 1 to 10, e.g., 2-9, 3-8, 4-7, 1-5, 5-10, or at least 2, or 10 or fewer nucleotides in length. In some embodiments, the cap is absent.

In some embodiments, a 5'-cap structure is cap0, cap1, ARCA, inosine, N1-methyl-guanosine, 2'-fluoro-guanosine, 7-deaza-guanosine, 8-oxo-guanosine, 2-amino-guanosine, LNA-guanosine, or 2-azido-guanosine.

In some embodiments, the 5'terminal cap is 7 mG (5') ppp (5') NlmpNp, m7GpppG cap, Nr-methylguanine. In some embodiments, the 3'terminal cap is a 3'-O-methyl-m7GpppG.

In some embodiments, the 3'-UTR is an alpha-globin 3'-UTR. In some embodiments, the 5'-UTR comprises a Kozak sequence.

In some embodiments, the tailing sequence may range from absent to 500 nucleotides in length (e.g., at least 60, 70, 80, 90, 120, 140, 160, 180, 200, 250, 300, 350, 400, 450, or 500 nucleotides). In some embodiments, the tailing region is or includes a poly A tail. Where the tailing region is a polyA tail, the length may be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional. In some embodiments, the poly-A tail is at least 160 nucleotides in length.

In some embodiments, the at least one SARS-COV-2 antigenic polypeptide linked to or fused to a signal peptide. In some embodiments, the isolated mRNA encoding a SARS-Cov-2 antigenic polypeptide or immunogenic fragment thereof further includes a polynucleotide sequence encoding a signal peptide. In some embodiments, the signal peptide is selected from: a HuIgGk signal peptide (METPAQLLFLLLLWLPDTTG (SEQ ID NO: 197)); IgE heavy chain epsilon-1 signal peptide (MDWTWILFLVAAATRVHS (SEQ ID NO: 198)); Japanese encephalitis PRM signal sequence (MLGSNSGQRVVFTILLLLVAPAYS (SEQ ID NO: 199)), VSVg protein signal sequence (MKCLLYLAFLFIGVNCA (SEQ ID NO: 200)) and Japanese encephalitis JEV signal sequence (MWLVSLAIVTACAGA (SEQ ID NO: 201)). In some embodiments, the signal peptide is fused to the N-terminus of at least one SARS-COV-2 antigenic polypeptide. In some embodiments, a signal peptide is fused to the C-terminus of at least one SARS-COV-2 antigenic polypeptide.

In some embodiments, the polynucleotides of the mRNA vaccine composition are structurally modified and/or chemically modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

In some embodiments, the polynucleotide, e.g., an mRNA of an mRNA vaccine composition described herein comprises at least one chemical modification. In some embodiments, the polynucleotide, e.g., an mRNA of an mRNA vaccine composition does not comprise a chemical or structural modification.

In some embodiments, the at least one chemical modification is selected from pseudouridine, N1-methylpseudouridine, N1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, the chemical modification is in the 5-position of the uracil. In some embodiments, the chemical modification is a N1-methylpseudouridine. In some embodiments, the chemical modification is a N1-ethylpseudouridine.

In some embodiments, about 10%, 15%, 20%, 24%, 30%, 35%, 40%, 45%, 50%, 55%, 60%, 65%, 70%, 75%, 80%, 85%, 90%, 95%, to/or about 100% of the uracil in of the SARS-COV-2 antigenic polypeptide or immunogenic fragment thereof encoding polynucleotide, such in the open reading frame, have a chemical modification, In some embodiments, 100% of the uracil in the open reading frame of the SARS-COV-2 antigenic polypeptide or immunogenic fragment thereof encoding polynucleotide have a N1-methyl pseudouridine in the 5-position of the uracil.

In some embodiments, the mRNA polynucleotide includes a stabilization element. In some embodiments, the stabilization element is a histone stem-loop. In some embodiments, the stabilization element is a nucleic acid sequence having increased GC content relative to wild type sequence.

In one embodiment, the mRNA polynucleotide may include a sequence encoding a self-cleaving peptide. The self-cleaving peptide may be, but is not limited to, a 2A peptide. As a non-limiting example, the 2A peptide may have the protein sequence: GSGATNFSLLKQAGDVEENPGP (SEQ ID NO: 202), fragments or variants thereof. In one embodiment, the 2A peptide cleaves between the last glycine and last proline. As another non-limiting example, the polynucleotides of the present invention may include a polynucleotide sequence encoding the 2A peptide having the protein sequence GSGATNFSLLKQAGDVEENPGP fragments or variants thereof.

One such polynucleotide sequence encoding the 2A peptide is GGAAGCGGAGCTACTAACTTCAGCCTGCTGAAGCAGGCTGGAGACGTGGAG GAGAACCCTGGACCT (SEQ ID NO: 203). The polynucleotide sequence of the 2A peptide may be modified or codon optimized by the methods described herein and/or are known in the art.

In one embodiment, this sequence may be used to separate the coding region of two or more polypeptides of interest. As a non-limiting example, the sequence encoding the 2A peptide may be between a first coding region A and a second coding region B (A-2Apep-B). The presence of the 2 A peptide would result in the cleavage of one long protein into protein A, protein B and the 2A peptide. Protein A and protein B may be the same or different peptides or polypeptides of interest. In another embodiment, the 2A peptide may be used in the polynucleotides of the present invention to produce two, three, four, five, six, seven, eight, nine, ten or more proteins.

In some embodiments, the length of an mRNA included in the mRNA vaccine is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the length of an mRNA included in the mRNA vaccine includes from about 30 to about 100,000 nucleotides (e.g., from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

In some embodiments, the polynucleotides are linear. In yet another embodiment, the polynucleotides of the present invention that are circular are known as "circular polynucleotides" or "circP." As used herein, "circular polynucleotides" or "circP" means a single stranded circular polynucleotide which acts substantially like, and has the properties of, an R A. The term "circular" is also meant to encompass any secondary or tertiary configuration of the circP.

Other RNA modifications for mRNA vaccines and production of mRNA can be as described e.g., U.S. Pat. Nos. 8,278,036, 8,691,966, 8,748,089, 9,750,824, 10,232,055, 10,703,789, 10,702,600, 10,577,403, 10,442,756, 10,266,485, 10,064,959, 9,868,692, 10,064,959, 10,272,150; U.S. Publications, US20130197068, US20170043037, US20130261172, US20200030460, US20150038558, US20190274968, US20180303925, US20200276300; International Patent Application Publication Nos. WO/2018/081638A1, WO/2016/176330A1, which are incorporated herein by reference.

In some embodiments, the mRNA vaccine includes one or more additional mRNAs that encode a polypeptide adjuvant. In some embodiments, the mRNA vaccine includes one or more additional mRNAs that encode a non SARS-Cov-2 antigen, such as an antigen to another disease causing agent.

In some embodiments, the one or more additional mRNAs that encode a polypeptide adjuvant encode a flagellin polypeptide. In some embodiments, at least one flagellin polypeptide (e.g., encoded flagellin polypeptide) is an immunogenic flagellin fragment. In some embodiments at least one flagellin polypeptide has at least 80%, at least 85%, at least 90%, or at least 95% identity to a flagellin polypeptide having a sequence identified by any one of SEQ ID NO: 54-56 of U.S. Pat. No. 10,272,150.

In some embodiments, at least one flagellin polypeptide and at least one SARS-Cov2 and/or additional antigenic polypeptide are encoded by a single RNA (e.g., mRNA) polynucleotide. In other embodiments, at least one flagellin polypeptide and at least one SARS-Cov2 and/or additional antigenic polypeptide are each encoded by a different RNA polynucleotide.

The isolated mRNA(s) can be made in part or using only in vitro transcription. Methods of making polynucleotides by in vitro transcription are known in the art and are described in U.S. Provisional Patent Application Nos. 61/618,862, 61/681,645, 61/737,130, 61/618,866, 61/681,647, 61/737,134, 61/618,868, 61/681,648, 61/737,135, 61/618,873, 61/681,650, 61/737,147, 61/618,878, 61/681,654, 61/737,152, 61/618,885, 61/681,658, 61/737,155, 61/618,896, 61/668,157, 61/681,661, 61/737,160, 61/618,911, 61/681,667, 61/737,168, 61/618,922, 61/681,675, 61/737,174, 61/618,935, 61/681,687, 61/737,184, 61/618,945, 61/681,696, 61/737,191, 61/618,953, 61/681,704 61/737,203; International Publication Nos WO2013151666, WO2013151668, WO2013151663, WO2013151669, WO2013151670, WO2013151664, WO2013151665, WO2013151736, WO2013151672, WO2013151671 WO2013151667, and WO/2020/205793A1; the contents of each of which are herein incorporated by reference in their entireties.

Lipid Nanoparticles

The isolated mRNAs and orther polynucleotides of the mRNa vaccine can be formulated in a lipid nanoparticle. In some embodiments, the lipid nanoparticle is a cationic lipid nanoparticle.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, the cationic lipid is a biodegradable cationic lipid. In some embodiments, the biodegradable cationic lipid comprises an ester linkage. In some embodiments, the biodegradable cationic lipid comprises DLin-DMA with an internal ester, DLin-DMA with a terminal ester, DLin-MC3-DMA with an internal ester, or DLin-MC3-DMA with a terminal ester.

In some embodiments, a lipid nanoparticle comprises a cationic lipid, a PEG-modified lipid, a sterol and a non-cationic lipid. In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino) butanoyl)oxy) heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530). In some embodiments, the neutral lipid is 1,2-distearoyl-sn-glycero-3-phosphocholine (DSPC), the sterol is cholesterol, and the PEG-modified lipid is 1,2-dimyristoyl-racalycero-3-methoxypolyethylene glycol-2000 (PEG-DMG) or PEG-CDMA.

In some embodiments, the lipid nanoparticle is any nanoparticle described in U.S. Pat. No. 10,442,756, and/or comprises any compound described in U.S. Pat. No. 10,442,756, including but not limited to a nanoparticle according to any one of Formulas (IA) or (II) described therein.

In some embodiments, the lipid nanoparticle is any nanoparticle described in e.g., U.S. Pat. No. 10,266,485, and/or comprises any compound described in U.S. Pat. No. 10,266,485, including but not limited to a nanoparticle according to Formula (II) described therein.

In some embodiments, the lipid nanoparticle is a nanoparticle described in U.S. Pat. No. 9,868,692, and/or comprises a compound described in e.g., U.S. Pat. No. 9,868,692, including but not limited to a nanoparticle according to Formula (I), (IA), (II), (IIa), (IIb), (IIc), (IId), (IIe), In some embodiments, a lipid nanoparticle comprises compounds of Formula (I) and/or Formula (II) as described in U.S. patent Ser. No. 10/272,150.

In some embodiments, the mRNA vaccine is formulated in a lipid nanoparticle that comprises a compound selected from Compounds 3, 18, 20, 25, 26, 29, 30, 60, 108-112 and 122 of U.S. Pat. No. 10,272,150.

In some embodiments, at least 80% (e.g., 85%, 90%, 95%, 98%, 99%) of the uracil in the open reading frame have a chemical modification, optionally wherein the vaccine is formulated in a lipid nanoparticle (e.g., a lipid nanoparticle comprises a cationic lipid, a PEG-modified lipid, a sterol and a non-cationic lipid).

In some embodiments, the lipid nanoparticle has a mean diameter of 50-200 nm.

In some embodiments, a lipid nanoparticle comprises compounds of Formula (I) and/or Formula (II), as discussed below.

In some embodiments, a lipid nanoparticle comprises Compounds 3, 18, 20, 25, 26, 29, 30, 60, 108-112, or 122 as set forth in U.S. patent Ser. No. 10/272,150.

In some embodiments, the lipid nanoparticle has a polydispersity value of less than 0.4 (e.g., less than 0.3, 0.2 or 0.1).

In some embodiments, a plurality of lipid nanoparticles, such as when contained in a formulation, has a mean PDI of between 0.02 and 0.2.

In some embodiments, a plurality of lipid nanoparticles, such as when contained in a formulation comprising one or more polynucleotide(s), has a mean lipid to polynucleotide ratio (wt/wt) of between 10 and 20.

In some embodiments, the lipid nanoparticle has a net neutral charge at a neutral pH value.

Methods of mRNA Vaccination

The compositions described herein can be used to induce an antigen specific immune response to a SARS-Cov-2 variant.

In some embodiments, the methods of inducing an antigen specific immune response in a subject include administering to the subject any of the RNA (e.g., mRNA) vaccine as provided herein in an amount effective to produce an antigen-specific immune response.

In some embodiments, an antigen-specific immune response comprises a T cell response and/or a B cell response.

In some embodiments, a method of producing an antigen-specific immune response comprises administering to a subject a single dose (no booster dose) of a RNA (e.g., mRNA) vaccine of the present disclosure.

In some embodiments, the RNA (e.g., mRNA) vaccine is a combination vaccine comprising a combination of an mRNA vaccine described herein and at least one other mRNA vaccine. The at least one other mRNA vaccine can be against the same or a different virus or disease-causing agent.

In some embodiments, a method further comprises administering to the subject a second (booster) dose of a RNA (e.g., mRNA) vaccine. Additional doses of a RNA (e.g., mRNA) vaccine may be administered.

In some embodiments, the subject exhibits a seroconversion rate of at least 80% (e.g., at least 85%, at least 90%, or at least 95%) following the first dose or the second (booster) dose of the vaccine. Seroconversion is the time period during which a specific antibody develops and becomes detectable in the blood. After seroconversion has occurred, a virus can be detected in blood tests for the antibody. During an infection or immunization, antigens enter the blood, and the immune system begins to produce antibodies in response. Before seroconversion, the antigen itself may or may not be detectable, but antibodies are considered absent. During seroconversion, antibodies are present but not yet detectable. Any time after seroconversion, the antibodies can be detected in the blood, indicating a prior or current infection.

In some embodiments, a RNA (e.g., mRNA) vaccine described herein is administered to a subject by intradermal, subcutaneous, or intramuscular injection. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

In some embodiments, the anti-antigenic polypeptide antibody titer produced in the subject is increased by at least 1 log relative to a control. In some embodiments, the anti-antigenic polypeptide antibody titer produced in the subject is increased by 1-3 log relative to a control.

In some embodiments, the anti-antigenic polypeptide antibody titer produced in a subject is increased at least 2 times relative to a control. In some embodiments, the anti-antigenic polypeptide antibody titer produced in the subject is increased at least 5 times relative to a control. In some embodiments, the anti-antigenic polypeptide antibody titer produced in the subject is increased at least 10 times relative to a control. In some embodiments, the anti-antigenic polypeptide antibody titer produced in the subject is increased 2-10 times relative to a control.

In some embodiments, the control is an anti-antigenic polypeptide antibody titer produced in a subject who has not been administered a RNA (e.g., mRNA) vaccine of the present disclosure. In some embodiments, the control is an anti-antigenic polypeptide antibody titer produced in a subject who has been administered a live attenuated or inactivated vaccine against SARS-COV-2 or wherein the control is an anti-antigenic polypeptide antibody titer produced in a subject who has been administered a recombinant or purified SARS-COV-2 protein vaccine.

In some embodiments, the control is an anti-antigenic polypeptide antibody titer produced in a subject who has been administered a virus-like particle (VLP) vaccine comprising structural proteins of SARS-COV-2.

The RNA (e.g., mRNA) vaccine of the present disclosure can be administered to a subject in an effective amount (e.g., an amount effective to induce an immune response in the subject).

In some embodiments, the RNA (e.g., mRNA) vaccine is formulated in an effective amount to produce an antigen specific immune response in a subject.

In some embodiments, the effective amount is a total dose of 25 μg to 1000 μg, or 50 μg to 1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments, the efficacy (or effectiveness) of a RNA (e.g., mRNA) vaccine is greater than 60%.

Vaccine efficacy may be assessed using standard analyses (see, e.g., Weinberg et al., *J Infect Dis.* 2010 Jun. 1; 201 (11): 1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(ARU-ARV)/ARU\times 100;\text{ and}$$

$$\text{Efficacy}=(1-RR)\times 100.$$

Likewise, vaccine effectiveness may be assessed using standard analyses (see, e.g., Weinberg et al., *J Infect Dis.* 2010 Jun. 1; 201 (11): 1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, the efficacy (or effectiveness) of a RNA (e.g., mRNA) vaccine is at least 65%, at least 70%, at least 75%, at least 80%, at least 85%, or at least 90%.

In some embodiments, the vaccine immunizes the subject against one or more SARS-Cov-2 variants. Exemplary SARS-COV-2 variants are described elsewhere herein.

In some embodiments, the subject to which the mRNA vaccine of the present disclosure is administered is about 5 years old or younger. For example, the subject may be between the ages of about 1 year and about 5 years (e.g., about 1, 2, 3, 5 or 5 years), or between the ages of about 6 months and about 1 year (e.g., about 6, 7, 8, 9, 10, 11 or 12 months). In some embodiments, the subject is about 12 months or younger (e.g., 12, 11, 10, 9, 8, 7, 6, 5, 4, 3, 2 months or 1 month). In some embodiments, the subject is about 6 months or younger.

In some embodiments, the subject to which the mRNA vaccine of the present disclosure is administered was born full term (e.g., about 37-42 weeks). In some embodiments, the subject was born prematurely, for example, at about 36 weeks of gestation or earlier (e.g., about 36, 35, 34, 33, 32, 31, 30, 29, 28, 27, 26 or 25 weeks). For example, the subject may have been born at about 32 weeks of gestation or earlier. In some embodiments, the subject was born prematurely between about 32 weeks and about 36 weeks of gestation. In such subjects, a RNA (e.g., mRNA) vaccine may be administered later in life, for example, at the age of about 6 months to about 5 years, or older.

In some embodiments, the subject to which the mRNA vaccine of the present disclosure is administered the subject to which the mRNA vaccine of the present disclosure is administered is pregnant (e.g., in the first, second or third trimester) when administered an RNA (e.g., mRNA) vaccine.

In some embodiments, the subject to which the mRNA vaccine of the present disclosure is administered is a young adult between the ages of about 20 years and about 50 years (e.g., about 20, 25, 30, 35, 40, 45 or 50 years old).

In some embodiments, the subject to which the mRNA vaccine of the present disclosure is administered is an elderly subject about 60 years old, about 70 years old, or older (e.g., about 60, 65, 70, 75, 80, 85, 90, or about 100 or more years old).

In some embodiments, the subject to which the mRNA vaccine of the present disclosure is administered has a chronic pulmonary disease (e.g., chronic obstructive pulmonary disease (COPD) or asthma). Two forms of COPD include chronic bronchitis, which involves a long-term cough with mucus, and emphysema, which involves damage to the lungs over time. Thus, a subject administered a RNA (e.g., mRNA) vaccine may have chronic bronchitis or emphysema.

In some embodiments, the subject to which the mRNA vaccine of the present disclosure is administered is immunocompromised (has an impaired immune system, e.g., has an immune disorder or autoimmune disorder).

In some embodiments, the mRNA vaccine of the present disclosure is delivered to a subject at a dosage of between 10 μg/kg and 400 μg/kg of the nucleic acid vaccine is administered to the subject. In some embodiments the dosage of the RNA polynucleotide is 1-5 μg, 5-10 μg, 10-15μ, 15-20μ, 10-25μ, 20-25μ, 20-50μ, 30-50μ, 40-50μ, 40-60μ, 60-80μ, 60-100 μg, 50-100 μg, 80-120 μg, 40-120 μg, 40-150 μg, 50-150 μg, 50-200 μg, 80-200 μg, 100-200 μg, 120-250μ, 150-250μ, 180-280μ, 200-300μ, 50-300μ, 80-300μ, 100-300μ, 40-300μ g, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the subject can receive 1, 2, 3, 4, 5, 6, 7, or more doses. After the initial dose (given at day zero) the subject can receive one or more (e.g., 1, 2, 3, 4, 5, 6, 7, 8, 9, 10, or more additional doses, referred to in the art as "booster" doses. The booster doses can follow the initial dose at any suitable time interval such as within days, weeks, months, or even years. In some embodiments, multiple booster doses are needed close in time after the inital dose (such as within 1, 2, 3, or 4 weeks after the initial dose) followed by a larger gap in time (e.g., months or years before subsequent booster doses are needed). In some embodiments, a first dose of the mRNA vaccine is administered to the subject on day zero. In some embodiments, a second dose of the mRNA vaccine ais administered to the subject on day 14, 21, 28, 35, 42, 49, 56, 63, 70, 77, 84 or more days after the first dose. In some embodiments, a third dose of the mRNA vaccine ais administered to the subject on day 14, 21, 28, 35, 42, 49, 56, 63, 70, 77, 84 or more days after the first and/or second dose.

In some embodiments, the mRNA vaccine confers an antibody titer superior to the criterion for seroprotection for a SARS-COV-2 variant for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In some embodiments, a unit of use vaccine comprises between 10 μg and 400 μg of one or more RNA polynucleotides encoding the SARS-Cov-2 antigenic polypeptide(s) and/or immunogenic fragment(s) thereof and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a SARS-COV-2 variant in an individual or population of individuals comprising administering to said individual or population an mRNA vaccine described herein.

In some embodiments, the methods of vaccinating a subject comprising administering to the subject a single dosage of between 25 μg/kg and 400 μg/kg of an mRNA vaccine comprising one or more RNA polynucleotides encoding a SARS-COV-2 antigenic polypeptide and/or an immunogenic fragment thereof in an effective amount to vaccinate the subject.

In some embodiments, the mRNA vaccines comprising one or more RNA polynucleotides encoding a SARS-COV-2 antigenic polypeptide and/or an immunogenic fragment thereof, wherein the RNA comprises at least one chemical modification, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

In some embodiments, the mRNA vaccine comprises an LNP formulated RNA polynucleotide having an open reading frame comprising no nucleotide modifications (unmodified), the open reading frame one or more RNA polynucleotides encoding a SARS-COV-2 antigenic polypeptide and/or an immunogenic fragment thereof, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

In some embodiments, the mRNA vaccine comprises an LNP formulated RNA polynucleotide having an open reading frame comprising one or more modifications, the open reading frame one or more RNA polynucleotides encoding a SARS-COV-2 antigenic polypeptide and/or an immunogenic fragment thereof, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

In some embodiments, the method includes vaccinating a subject with a combination vaccine including at least two nucleic acid sequences encoding respiratory antigens, wherein at least one encodes a SARS-COV-2 antigen wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms.

In some embodiments, vaccines of the invention (e.g., LNP-encapsulated mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In some embodiments, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.)

In some embodiments, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

SARS-COV-2 Variants

The present disclosure relates to and/or involves SARS-COV-2. More particularly the disclosure describes, inter alia, SARS-COV-2 variant immunogenic polypeptides and encoding polynucleotides. As described herein are vaccines that include the SARS-COV-2 variant immunogenic polypeptides and/or encoding polynucleotides. Such vaccines can be effective against one or more SARS-COV-2 variants.

As used herein, the term "variant" refers to any virus having one or more mutations as compared to a known virus. A strain is a genetic variant or subtype of a virus. The terms 'strain', 'variant', and 'isolate' may be used interchangeably. In certain embodiments, a variant has developed a "specific group of mutations" that causes the variant to behave differently than that of the strain it originated from. While there are many thousands of variants of SARS-COV-2, (Koyama, Takahiko Koyama; Platt, Daniela; Parida, Laxmi (June 2020). "Variant analysis of SARS-COV-2 genomes". Bulletin of the World Health Organization. 98:495-504) there are also much larger groupings called clades. Several different clade nomenclatures for SARS-COV-2 have been proposed. As of December 2020, GISAID, referring to SARS-COV-2 as hCoV-19 identified seven clades (O, S, L, V, G, GH, and GR) (Alm E, Broberg E K, Connor T, et al. Geographical and temporal distribution of SARS-COV-2 clades in the WHO European Region, January to June 2020 [published correction appears in Euro Surveill. 2020 August; 25 (33):]. Euro Surveill. 2020; 25 (32): 2001410). Also as of December 2020, Nextstrain identified five (19A, 19B, 20A, 20B, and 20C) (Cited in Alm et al. 2020). Guan et al. identified five global clades (G614, S84, V251, 1378 and D392) (Guan Q, Sadykov M, Mfarrej S, et al. A genetic barcode of SARS-COV-2 for monitoring global distribution of different clades during the COVID-19 pandemic. Int J Infect Dis. 2020; 100:216-223). Rambaut et al. proposed the term "lineage" in a 2020 article in Nature Microbiology; as of December 2020, there have been five major lineages (A, B, B.1, B.1.1, and B.1.777) identified (Rambaut, A.; Holmes, E. C.; O'Toole, Á.; et al. "A dynamic nomenclature proposal for SARS-COV-2 lineages to assist genomic epidemiology". 5:1403-1407).

Genetic variants of SARS-COV-2 have been emerging and circulating around the world throughout the COVID-19 pandemic (see, e.g., The US Centers for Disease Control and Prevention; www.cdc.gov/coronavirus/2019-ncov/variants/variant-info.html). Exemplary, non-limiting variants applicable to the present disclosure include variants of SARS-COV-2, particularly those having substitutions of therapeutic concern. Table 10 shows exemplary, non-limiting genetic substitutions in SARS-COV-2 variants.

TABLE 10

| Spike Protein Substitution | Common Pango Lineages with Spike Protein Substitutions |
|---|---|
| L452R | A.2.5, B.1, B.1.429, B.1.427, B.1.617.1, B.1.526.1, B.1.617.2, C.36.3 |
| E484K | B.1.1.318, B.1.1.7, B.1.351, B.1.525, B.1.526, B.1.621, B.1.623, P.1, P.1.1, P.1.2, R.1 |
| K417N, E484K, N501Y | B.1.351, B.1.351.3 |
| K417T, E484K, N501Y | P.1, P.1.1, P.1.2 |

Phylogenetic Assignment of Named Global Outbreak (PANGO) Lineages is software tool developed by members of the Rambaut Lab. The associated web application was developed by the Centre for Genomic Pathogen Surveillance in South Cambridgeshire and is intended to implement the dynamic nomenclature of SARS-COV-2 lineages, known as the PANGO nomenclature. It is available at cov-lineages.org.

In some embodiments, the SARS-COV-2 variant is and/or includes: B.1.1.7, also known as Alpha (WHO) or UK variant, having the following spike protein substitutions: 69del, 70del, 144del, (E484K*), (S494P*), N501Y, A570D, D614G, P681H, T716I, S982A, and D1118H (K1191N*); B.1.351, also known as Beta (WHO) or South Africa variant, having the following spike protein substitutions: D80A, D215G, 241del, 242del, 243del, K417N, E484K, N501Y, D614G, and A701V; B.1.427, also known as Epsilon (WHO) or US California variant, having the following spike protein substitutions: L452R, and D614G; B.1.429, also known as Epsilon (WHO) or US California variant, having the following spike protein substitutions: S13I, W152C, L452R, and D614G; B.1.617.2, also known as Delta (WHO) or India variant, having the following spike protein substitutions: T19R, (G142D), 156del, 157del, R158G, L452R, T478K, D614G, P681R, and D95ON; and P.1, also known as Gamma (WHO) or Japan/Brazil variant, having the following spike protein substitutions: L18F, T20N, P26S, D138Y, R190S, K417T, E484K, N501Y, D614G, H655Y, and T1027I, or any combination thereof.

In some embodiments, the SARS-COV-2 variant is classified and/or otherwise identified as a Variant of Concern (VOC) by the World Health Organization and/or the U.S. Centers for Disease Control. A VOC is a variant for which there is evidence of an increase in transmissibility, more severe disease (e.g., increased hospitalizations or deaths), significant reduction in neutralization by antibodies generated during previous infection or vaccination, reduced effectiveness of treatments or vaccines, or diagnostic detection failures.

In some embodiments, the SARS-Cov-2 variant is classified and/or otherwise identified as a Variant of High Consequence (VHC) by the World Health Organization and/or the U.S. Centers for Disease Control. A variant of high consequence has clear evidence that prevention measures or medical countermeasures (MCMs) have significantly reduced effectiveness relative to previously circulating variants.

In some embodiments, the SARS-Cov-2 variant is classified and/or otherwise identified as a Variant of Interest (VOI) by the World Health Organization and/or the U.S. Centers for Disease Control. A VOI is a variant with specific genetic markers that have been associated with changes to receptor binding, reduced neutralization by antibodies generated against previous infection or vaccination, reduced efficacy of treatments, potential diagnostic impact, or predicted increase in transmissibility or disease severity.

In some embodiments, the SARS-Cov-2 variant is classified and/or is otherwise identified as a Variant of Note (VON). As used herein, VON refers to both "variants of concern" and "variants of note" as the two phrases are used and defined by Pangolin (cov-lineages.org) and provided in their available "VOC reports" available at cov-lineages.org.

In some embodiments the SARS-Cov-2 variant is a VOC. In some embodiments, the SARS-COV-2 variant is or includes an Alpha variant (e.g., Pango lineage B.1.1.7), a Beta variant (e.g., Pango lineage B.1.351, B.1.351.1, B.1.351.2, and/or B.1.351.3), a Delta variant (e.g., Pango lineage B.1.617.2, AY.1, AY.2, AY.3 and/or AY.3.1); a Gamma variant (e.g., Pango lineage P.1, P.1.1, P.1.2, P.1.4, P.1.6, and/or P.1.7), or any combination thereof.

In some embodiments the SARS-Cov-2 variant is a VOI. In some embodiments, the SARS-COV-2 variant is or includes an Eta variant (e.g., Pango lineage B.1.525 (Spike protein substitutions A67V, 69del, 70del, 144del, E484K, D614G, Q677H, F888L)); an Iota variant (e.g., Pango lineage B.1.526 (Spike protein substitutions L5F, (D80G*), T95I, (Y144-*), (F157S*), D253G, (L452R*), (S477N*), E484K, D614G, A701V, (T859N*), (D950H*), (Q957R*))); a Kappa variant (e.g., Pango lineage B.1.617.1 (Spike protein substitutions (T951), G142D, E154K, L452R, E484Q, D614G, P681R, Q1071H)); Pango lineage variant B.1.617.2 (Spike protein substitutions T19R, G142D, L452R, E484Q, D614G, P681R, D950N)), Lambda (e.g., Pango lineage C.37); or any combination thereof.

In some embodiments SARS-Cov-2 variant is a VON. In some embodiments, the SARS-Cov-2 variant is or includes Pango lineage variant P.1 (alias, B.1.1.28.1.) as described in Rambaut et al. 2020. Nat. Microbiol. 5:1403-1407) (spike protein substitutions: T20N, P26S, D138Y, R190S, K417T, E484K, N501Y, H655Y, TI027I)); an Alpha variant (e.g., Pango lineage B.1.1.7); a Beta variant (e.g., Pango lineage B.1.351, B.1.351.1, B.1.351.2, and/or B.1.351.3); Pango lineage variant B.1.617.2 (Spike protein substitutions T19R, G142D, L452R, E484Q, D614G, P681R, D950N)); an Eta variant (e.g., Pango lineage B.1.525); Pango lineage variant A.23.1 (as described in Bugembe et al. medRxiv. 2021. doi: https://doi.org/10.1101/2021.02.08.21251393) (spike protein substitutions: F157L, V367F, Q613H, P681R); or any combination thereof.

EXAMPLES

Example 1

Mapping the repertoire of severe acute respiratory syndrome coronavirus 2 (SARS-CoV-2) derived class I human leukocyte antigen (HLA-I) peptides can deepen our understanding of the viral footprint as seen by cytotoxic T cells. However, no datasets are currently available that characterize naturally processed and presented peptides in infected cells. Therefore, Applicant profiled the HLA-I immunopeptidomes of two human cell lines across multiple timepoints pre and post infection using mass spectrometry. The pre infection profile provided a baseline or reference point to determine protein enrichment or depletion due to infection. Applicant found HLA-I peptides that were derived from canonical ORFs, as well as internal out of frame ORFs in Spike and Nucleoprotein. Although viral proteins were highly expressed, the representation of viral HLA-I peptides was relatively low.-Finally, Applicant demonstrated that the peptides identified by MS are highly likely to bind to HLA-I alleles that provide population coverage of up to 80%. These biological insights and the list of naturally presented SARS-COV-2 HLA-I peptides will facilitate data-driven, informed selection of peptides for immune monitoring and vaccines.

In this example, Applicant presents the first examination of HLA-I immunopeptidome in two human cell-lines infected with SARS-COV-2 paired with RNA-seq and whole proteome analysis. Applicant identified viral HLA-I peptides derived from both canonical and internal out-of-frame ORFs and monitored their dynamics over multiple timepoints post infection. Using whole proteome measurements, Applicant show that SARS-COV-2 interfered with cellular pathways related to the proteosome that may result in lower presentation of viral peptides. This study provides a list of SARS-COV-2 HLA-I peptides that undergo endogenous processing and presentation that can inform future T cells assays in patients and contribute to the design of vaccines.

Untargeted Profiling of HLA-I Peptides in SARS-COV-2 Infected Cells

To decipher the repertoire of human and viral derived HLA-I peptides, Applicant immunoprecipitated HLA-I proteins from SARS-COV-2 infected A549 and HEK293T cells that were transduced to stably express ACE2 and TMPRSS2, and subjected HLA bound peptides to liquid chromatography tandem mass spectrometry analysis (LC-MS/MS) (FIG. 1A). A549 lung carcinoma cells were selected because of their biological relevance and prevalent usage in SARS-CoV-2 studies, while HEK293T cells were chosen because they endogenously express HLA-A*02:01, a high frequency HLA-I allele (EUR: 29.6%; AFA: 12.5%; API: 9.5%; HIS: 19.4%; USA: 24.2%, (Gragert et al. 2013)). The nine HLA-I alleles expressed by HEK293T and A549 cover 63.8% of the population (FIG. 1B), which gave confidence that the results were broadly applicable to a large patient population. Applicant encountered two experimental challenges that required adaptation of the commonly used HLA-I IP and virus inactivation protocols. First, to shear the DNA before immunoprecipitation, Applicant replaced the sonication step with the addition of Benzonase nuclease (Abelin et al. 2019). Second, to inactivate SARS-COV-2 while maintaining the HLA-peptide complex intact, Applicant incubated the samples with a lysis buffer containing 1.5% Triton-X instead of heating or chemically inactivating. Applicant confirmed viral inactivation by plaques assay. Additionally, Applicant performed whole proteome LC-MS/MS of the IP flow-through and RNA-seq to determine viral abundances in cells at both the protein and RNA levels and to gain an understanding of how SARS-COV-2 might be impacting cellular pathways. To investigate the kinetics of HLA-I presentation Applicant performed a time course experiment at 3 h, 6 h, 12 h, 18 h and 24 h post infection in A549 cells. To allow the detection of peptides from the complete translatome of SARS-COV-2, Applicant combined the 23 novel ORFs recently identified by Finkel et al. (Finkel et al. 2020) with the list of canonical ORFs and the human refseq database for LC-MS/MS data analysis (FIG. 1A).

In total, Applicant identified 5,837 and 6,372 HLA-bound 8-11mer peptides in uninfected and infected A549, and 4,281 and 1,336 unique peptides in HEK293T cells, respectively. Applicant found that length distributions do not differ between infected and uninfected cells and the majority of HLA-I peptides were 9-mers (FIG. 1C). To understand the effect of SARS-COV-2 infection on HLA-I presentation, Applicant compared the 9-mer peptide motifs observed in HEK293T and A549 cells to those in uninfected cells (FIG. 1D). There were no apparent changes in peptide motif between the two conditions, and Applicant observed the same amino acids in the expected anchor positions 2 and 9. Finally, Applicant inferred the most likely HLA-allele to which the identified peptides were bound using HLAthena predictions (Sarkizova et al. 2020). A549 expressed A*25:01/30:01, B*18:01/44:03 and C*12:03/16:01, HEK293T endogenously express A*02:01, B*07:02 and C*07:02 (determined by HLA allotyping). The majority of peptides presented by HLA-I were assigned to A*25:01 for A549 cells and A*02:01 for HEK293T (FIG. 1E), and infection with Sars-COV-2 does not seem to alter this distribution. Interestingly, a larger fraction (18-24%) of peptides were predicted to bind to multiple alleles including HLA-C alleles in the A549 cell line. HLA-C binding peptides are often deprioritized compared to HLA-A and HLA-B peptides in both epitope prediction and T cell assay studies, yet these data suggest they should be reconsidered for future analyses.

Mapping SARS-COV-2 HLA-I Peptides from Canonical ORFs

Figure 2A:
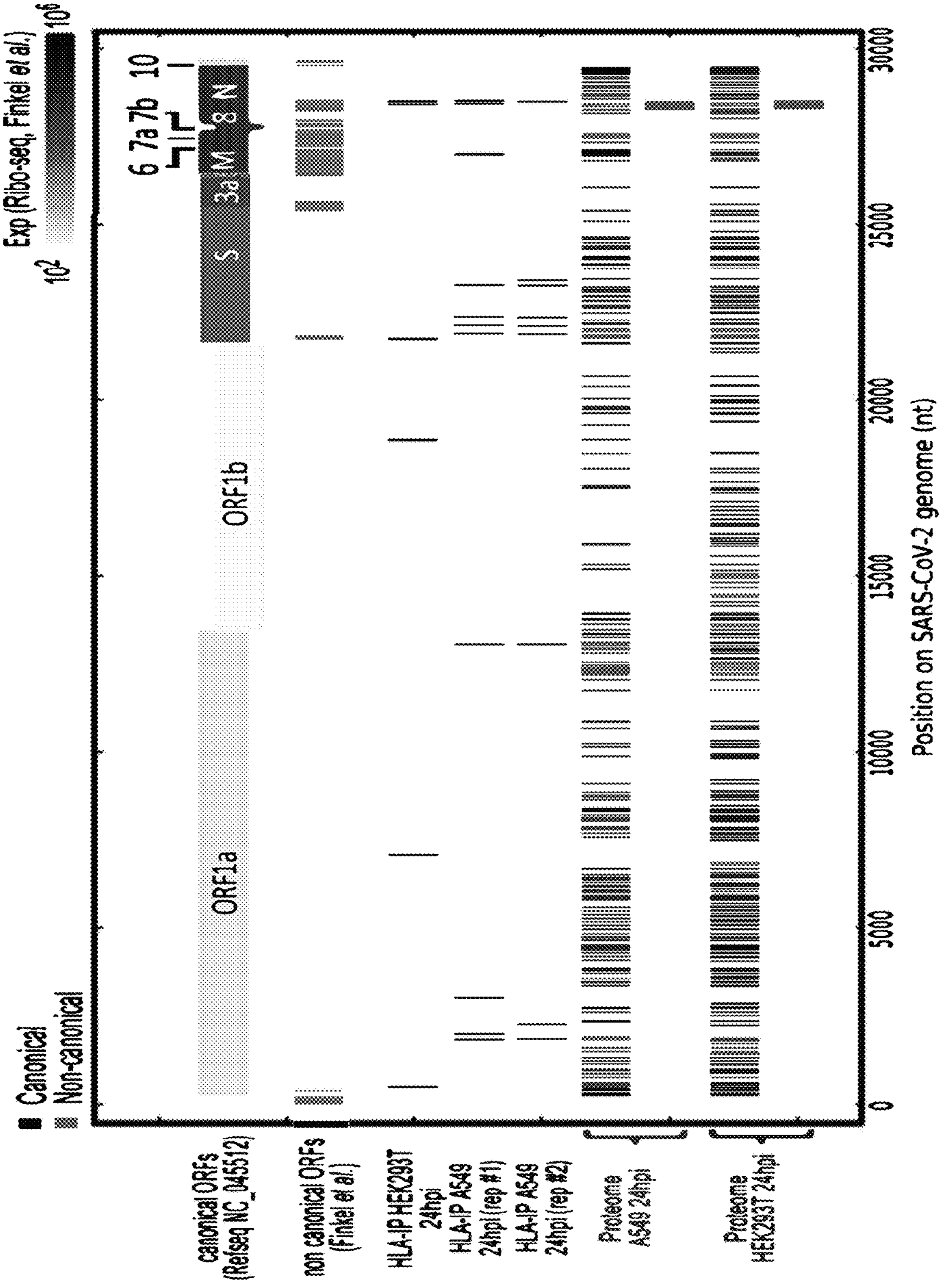
FIGS. 2A-2D-SARS-COV-2 HLA-I immunopeptidome and whole proteome.

Next, Applicant examined HLA-I peptides that are derived from SARS-COV-2 genome (FIG. 2A). Applicant identified 17 viral HLA-I peptides in A549 and 11 in HEK293T from source proteins expressed from canonical ORFs (according to refseq NC_045512.2 annotations): nsp1, nsp2, nsp3, nsp5 nsp8, nsp10, nsp14, ORF7a, nsp15, N, S and M proteins (Table 1). See also e.g., Table 2 in Example 2. Applicant also identified 9 viral peptides that were derived from out-of-frame ORFs in S and N proteins. See also e.g., Example 2. These HLA-I peptides were predicted as good binders by HLAthena to at least one of the expressed HLA alleles. KRVDWTIEY (SEQ ID NO: 29) from nsp14 and FASEAARVV (SEQ ID NO: 17) from nsp2 were also independently confirmed in biochemical binding assays (Covid19 Intavis_Immunitrack stability dataset 1). Additional binding data is shown in Example 2.

Figure 2B:
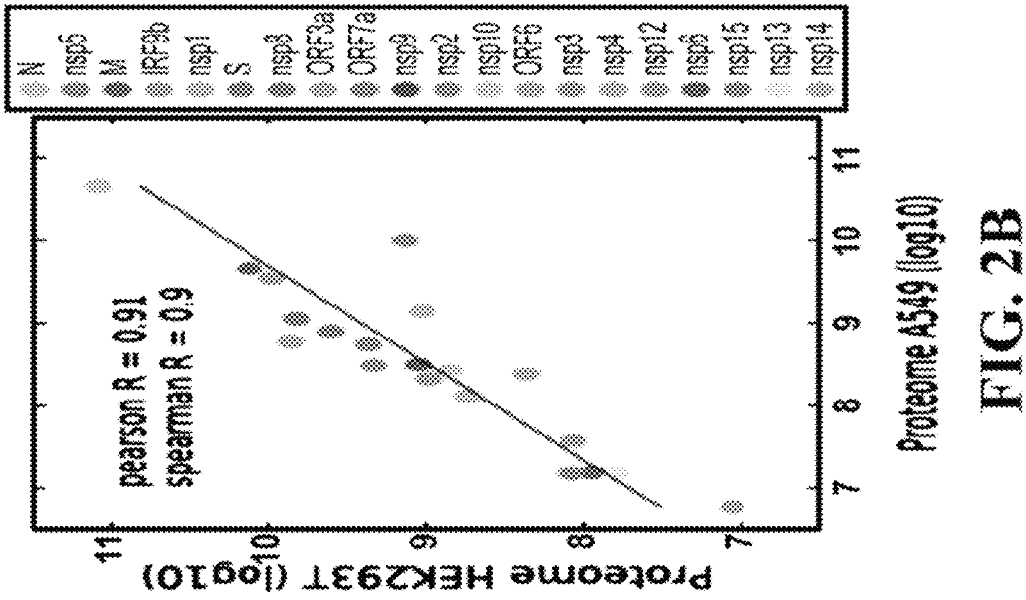
Figure 2C:
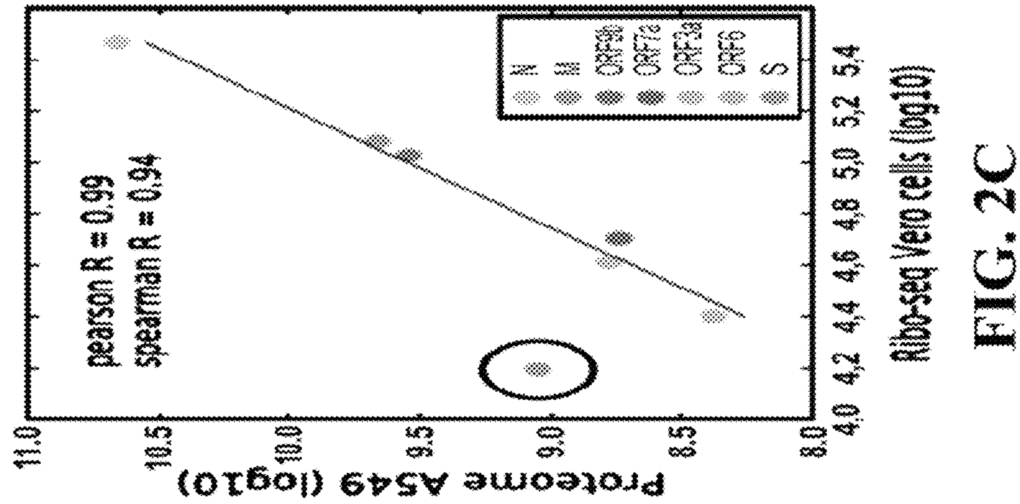
Figure 2D:
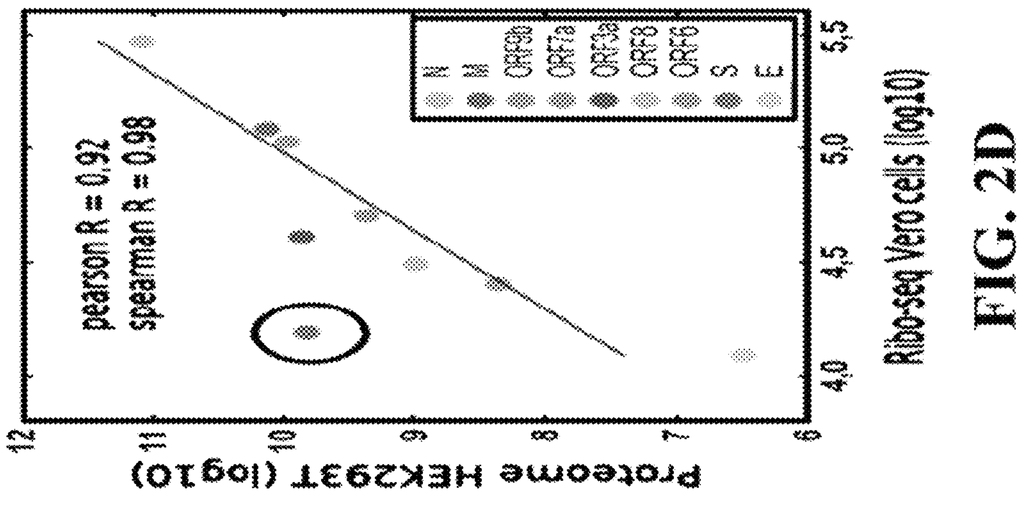

Surprisingly, Applicant did not detect HLA-I peptides from highly abundant SARS-CoV-2 proteins such as ORF3a, ORF8 and ORF6. To test if undetected HLA-I peptides could be explained by underrepresentation of tryptic peptides from these source protein, as some proteasome subunits have a tryptic-like specificity, Applicant examined the whole proteome mass-spectrometry data generated from the HLA-I IP cell lysates flowthrough (FIGS. 1A, 2A). Applicant found a strong correlation between viral protein expression in the proteome of the two cell lines (Pearson R=0.91 and Spearman R=0.9, FIG. 2B). Moreover, full proteome measurements correlated with recently published Ribo-seq translation measurements in infected Vero cells (Finkel et al. 2020) (Pearson R=0.99, Spearman R=0.94 for A549 and Pearson R=0.92, Spearman R=0.98 for HEK293T, FIGS. 2C,2D). Applicant did not uncover evidence to support a reduced tryptic coverage in SARS-COV-2 source proteins suggesting that the precursors for HLA-I peptides from these highly expressed viral proteins available in the infected cells. The S protein was revealed as an outlier in both cell lines in our analysis, as it had a higher expression in the proteome data compared to the Ribo-seq measurements, which suggested it may undergo positive post-translational regulation. Interestingly, although nsps were post-translationally cleaved from a single polyprotein, their expression levels are quite diverse. Moreover, while the translation of ORF1a, the source polyprotein of nsps 1-11, was 10-1000-fold lower than structural ORFs (Finkel et al. 2020), some nsps expression was within the range of the structural proteins (e.g., nsp1 and nsp8, FIG. 2B).

SARS-COV-2 HLA-I Peptides Derived from Internal Out of Frame ORFs in S and N

Figure 3B:
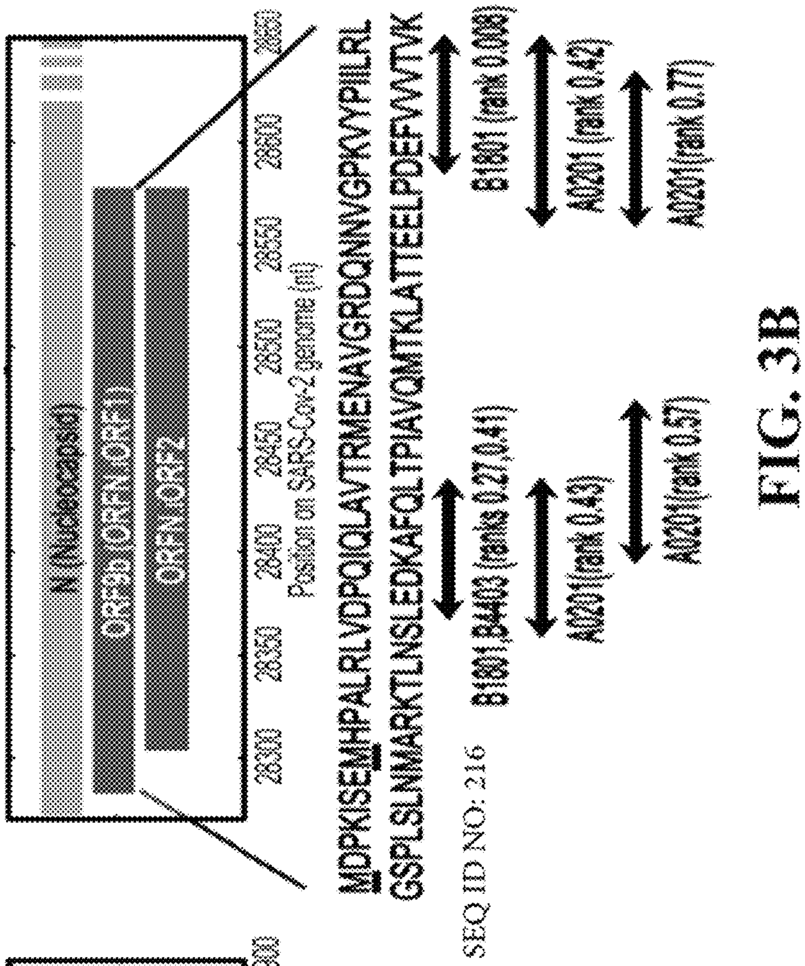
FIGS. 3A-3G-SARS-COV-2 HLA-I peptides from S.iORF1/2 and ORF9b.
Figure 3A:
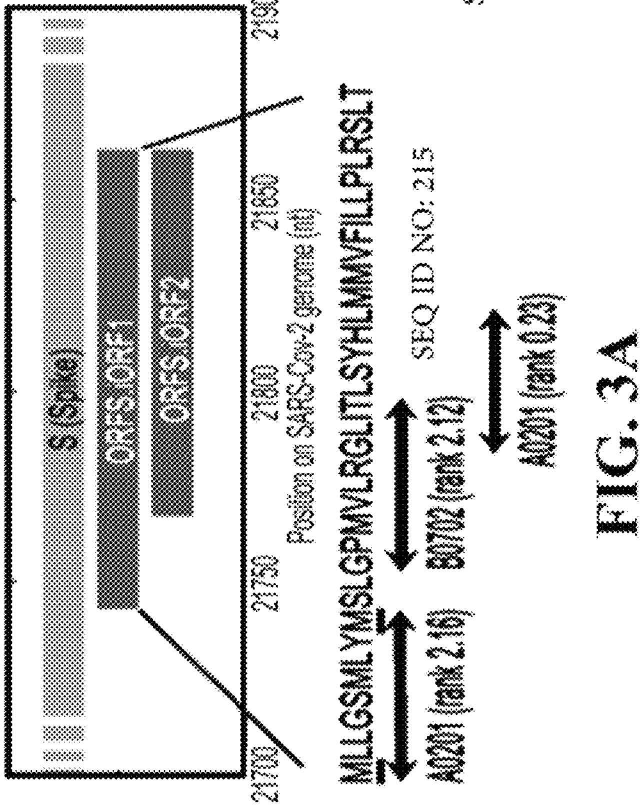

Two of the LC-MS/MS detected HLA-I peptides in HEK293T, GPMVLRGLIT (SEQ ID NO: 6) and GLITLSYHL (SEQ ID NO: 5), were processed from internal out of frame ORFs in the coding region of S (FIG. 3A). GLITLSYHL (SEQ ID NO: 5) was a strong binder to A*02:01 (rank 0.23), while GPMVLRGLIT (SEQ ID NO: 6) bound to B*07:02 (% %) suggesting the potential for widespread presentation of these HLA-I peptides expressed from internal out-of-frame ORFs in the population. In addition, four HLA-I peptides from ORF9b, an internal out-of-frame ORF in the coding region of the Nucleoprotein (N), were identified in A549 and HEK293T cells (FIG. 3B). These HLA-I peptides covered overlapping epitope sequences in both cell lines and contain the binding motifs that match the expressed HLA-I alleles. All four HLA-I peptides were predicted to be highly likely to bind to either A*02:01 in HEK293T cells (SLEDKAFQL (SEQ ID NO: 7) and ELPDEFVVVTV (SEQ ID NO: 8), rank 0.43 and 0.42, respectively) or B*18:01 in A549 cells (LEDKAFQL (SEQ ID NO: 10) and DEFVVVTV (SEQ ID NO: 11), rank 0.27 and 0.0008, respectively).

Figure 3C:
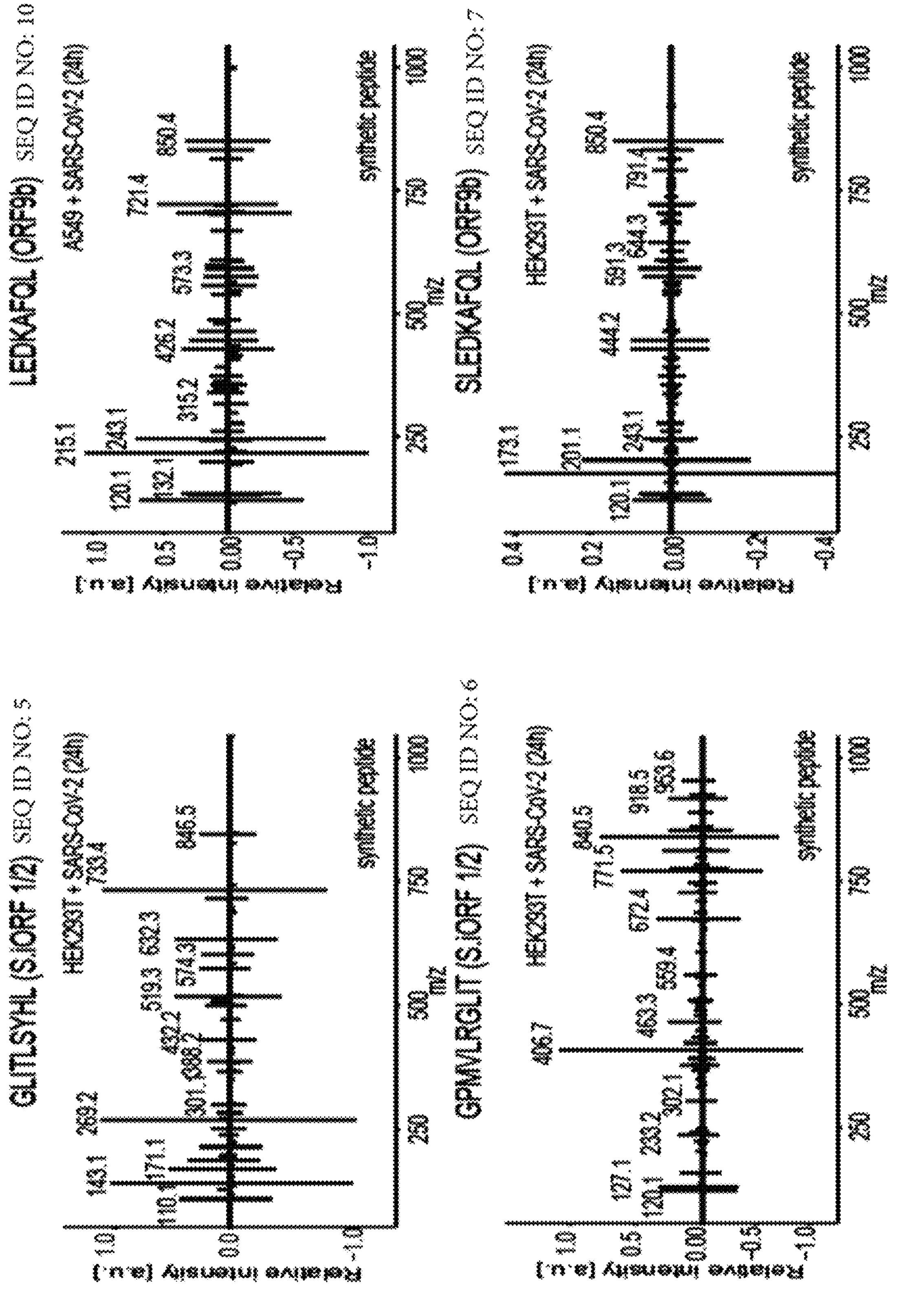

Validation of Detected Antigens Using Synthetic Peptides is Shown in FIG. 3C.

Figure 3D:
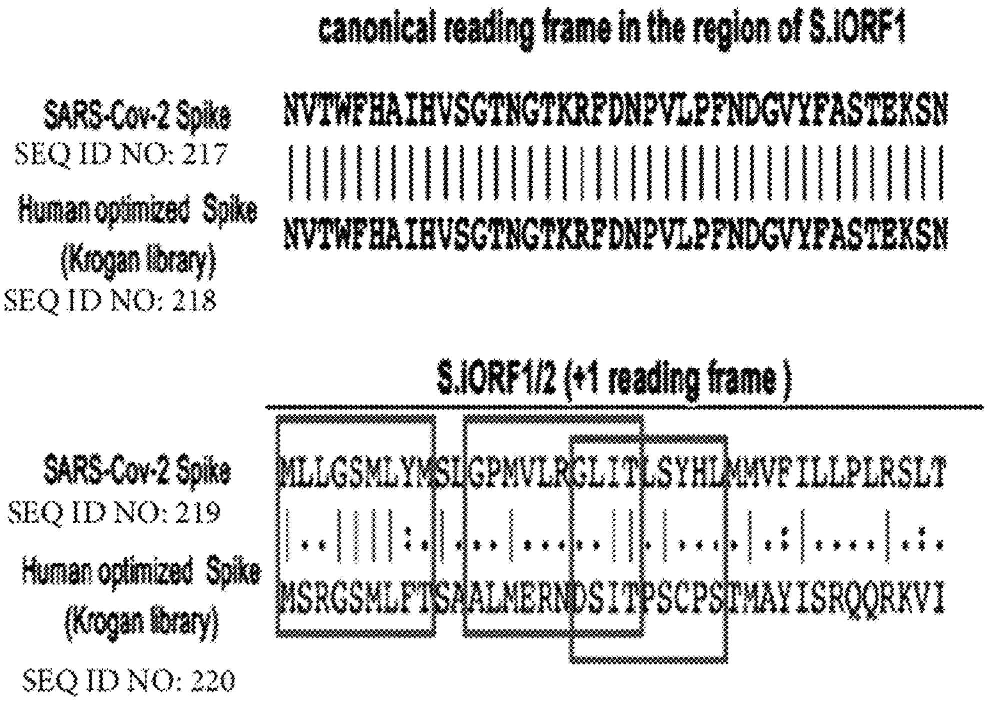

The Spike glycoprotein is the target of multiple SARS-COV-2 vaccines under development (Callaway 2020). Two of these vaccines are utilizing RNA-based delivery methods that often involve manipulating the native nucleotide sequence, such as codon optimization, to enhance expression. These techniques maintain the amino acids composition of the canonical ORF, yet may alter the sequence of proteins encoded in alternative reading frames. In the context of T cell immunity, it is crucial to understand the effect of optimizing RNA sequences of S on the endogenously processed and presented HLA-I peptides derived from the two internal out-of-frame S.iORF1/2. To evaluate the possible effects of codon optimization on HLA-I antigen presentation, Applicant examined the nucleotide sequence in the region encoding S.iORF1/2 in the human optimized S from the Krogan library (Gordon et al. 2020). As expected, there was no change in the main ORF, however, the aa sequence in the +1 frame, which encoded S.iORF1/2, was significantly different (FIG. 3D). Since the two methionines driving the translation of S.iORF1 and S.iORF2 are preserved, it was possible that these ORFs were expressed in the human optimized construct. However, the HLA-I peptides likely to be processed from the optimized S nucleotide sequence were not predicted to bind the same HLA-I alleles that Applicant identified in our experiment as they have reduced rank scores (2.12 to 38.2 and 0.23 to 91.1 for GPMVLRGLIT (SEQ ID NO: 6) and GLITLSYHL (SEQ ID NO: 5), respectively, FIG. 3D). These data suggest that RNA-based vaccine design may preclude the HLA-I presentation of SARS-COV-2 peptides that were derived from overlapping ORFs.

Figure 4A:
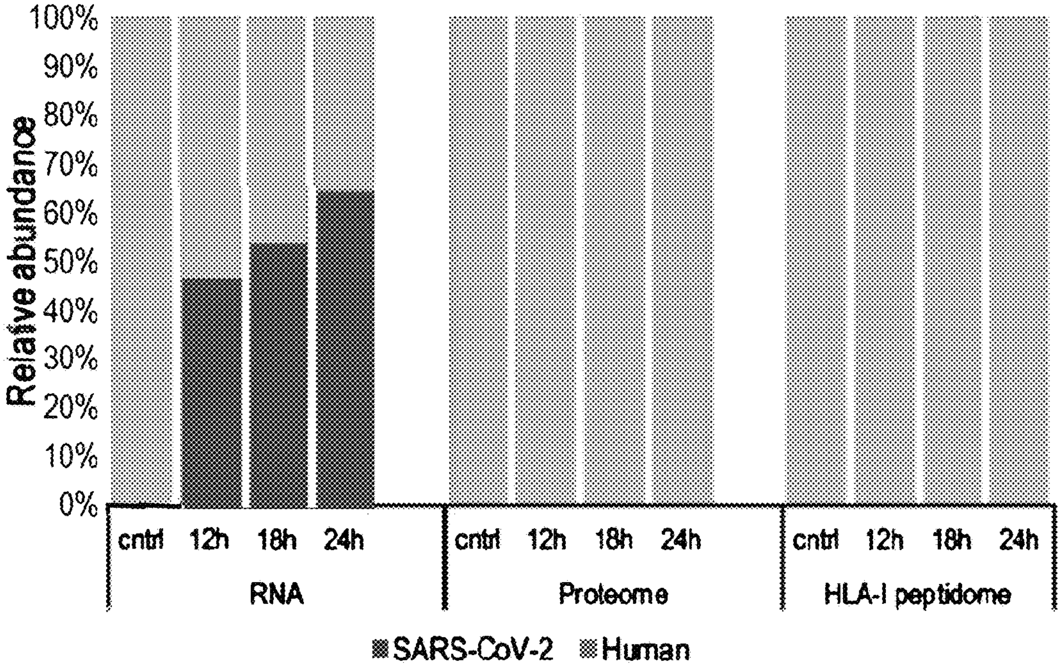
FIGS. 4A-4B-HLA-I peptide presentation dynamics of SARS-COV-2 infected cells.
Figure 4B:
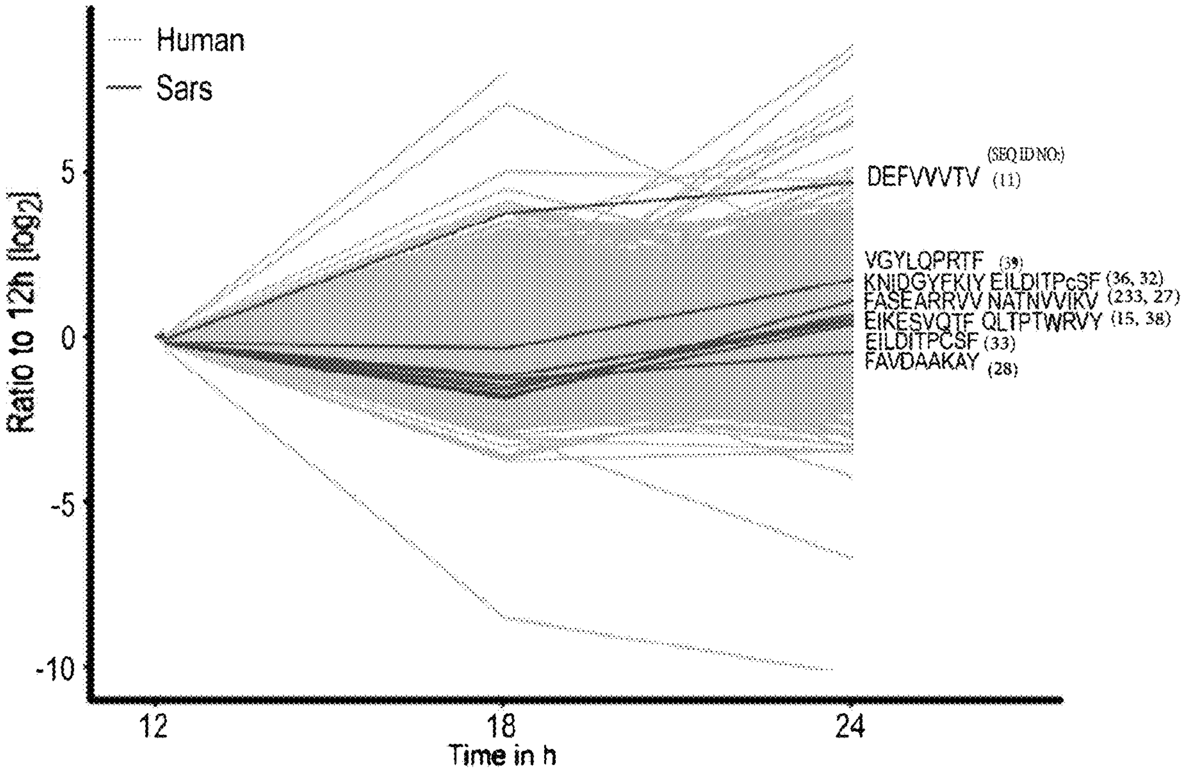

HLA-I Peptides Derived from SARS-COV-2 do not Change Over a Time Course of Infection To investigate the dynamics of HLA-I presentation during infection Applicant performed a time course experiment in which samples for immunopeptidomics, proteomics and RNA-seq were harvested 3, 6, 12, 18 and 24 hours post infection. Applicant chose these time points based on a recent study showing low abundance of SARS-COV-2 proteins prior to 10 hours post infection (Bojkova et al. 2020). RNA-seq measurements showed progressively high infection with 47%, 54% and 65% of the cell's transcriptome mapped to SARS-COV-2 genome after 12, 18 and 24 hours, respectively (FIG. 4A). Notably, only 0.004% of total protein intensity contributed from SARS-COV-2 after 24 hours in the whole proteome data. A similar trend was observed in the HLA-I immunopeptidome, in which viral peptides represent only 0.004% of the total intensity. Regardless of the relatively low total contribution in the proteome, seven viral HLA-I peptides were identified in a label free experiment of the 24 h time point with three peptides observed in all timepoints. HLA-I peptides discovered exclusively in the earliest 12 h time point were derived from S protein. To rule out the possibility of missing values due to the stochastic sampling of LC-MS/MS, we also utilized tandem mass tags (TMT). TMT enabled the detection of 11 viral antigens with coverage across all timepoints (FIG. 4B). Applicant observed that the abundance of HLA-I peptides increases slightly over time, with the exception of the Orf9b peptide, DEFVVVTV (SEQ ID NO: 11), that changes more than 2-fold over the course of 24 h. Similar trends were observed for self HLA-I peptides, with the majority of peptides not changing or slightly increasing at later timepoints. The stable expression of SARS-COV-2 HLA-I peptides over time is favorable for vaccine strategies that are attempting to target CD8+ T cells. Additional timecourse results are shown in Example 2.

Figure 5A:
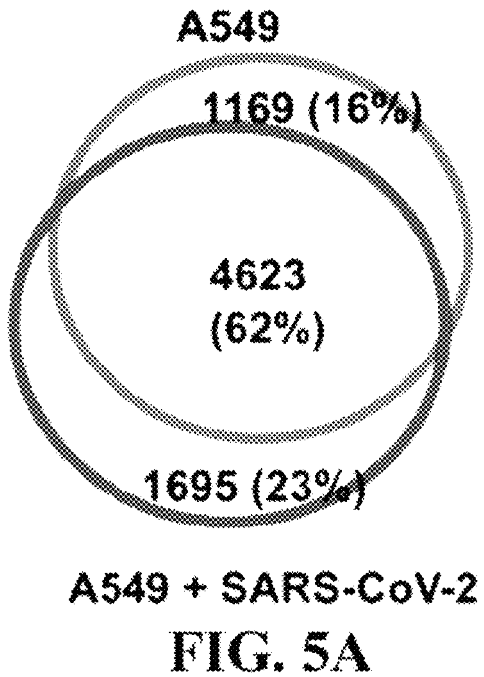
FIGS. 5A-5F-Changes in HLA-I peptide presentation caused by SARS-COV-2 infection.
Figure 5B:
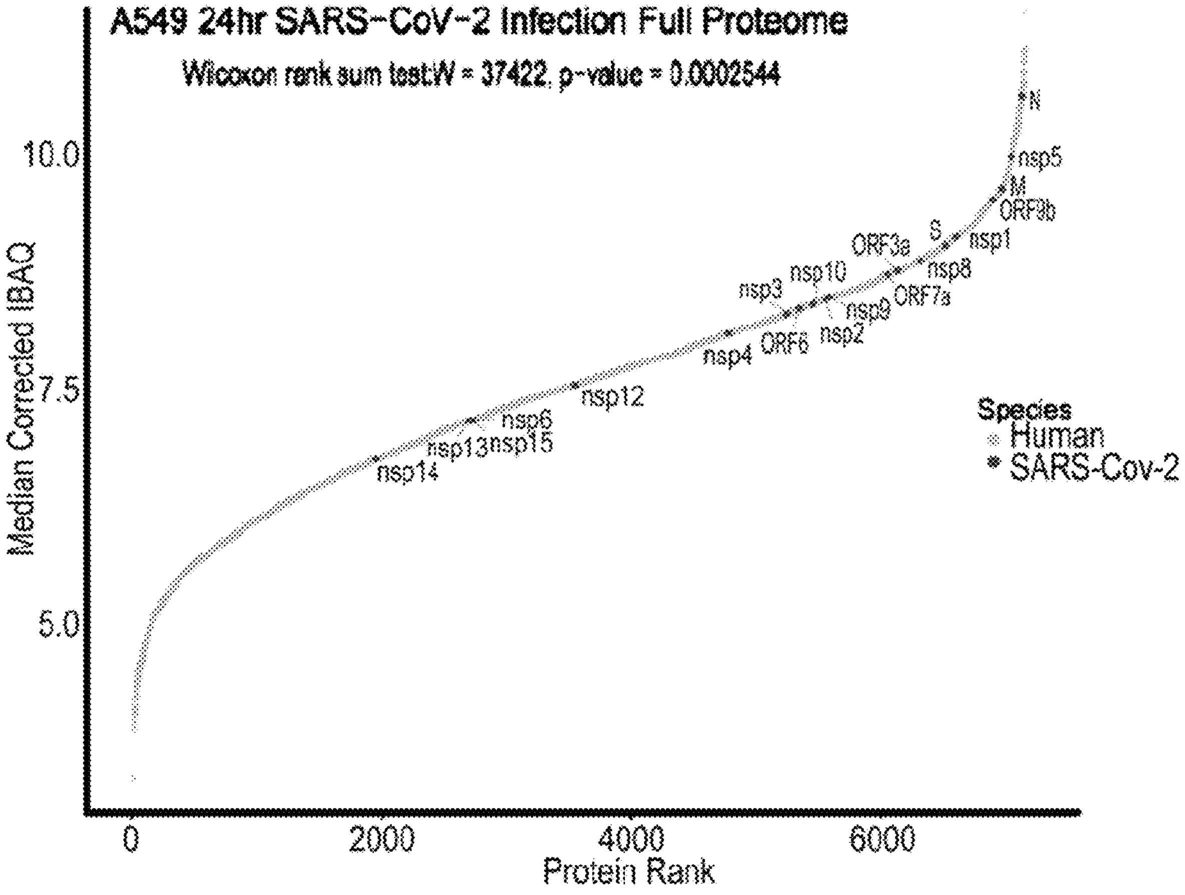
Figure 5C:
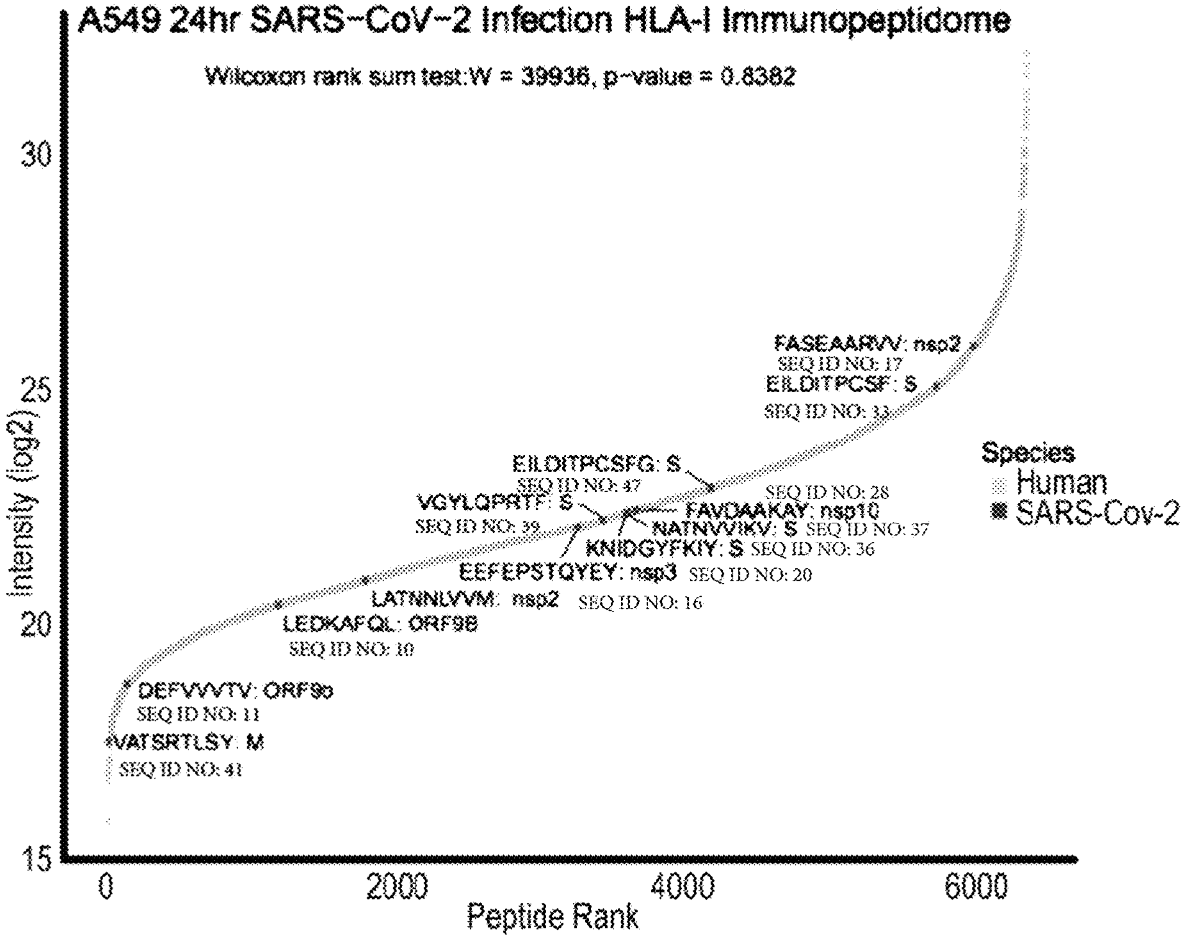
Figure 5D:
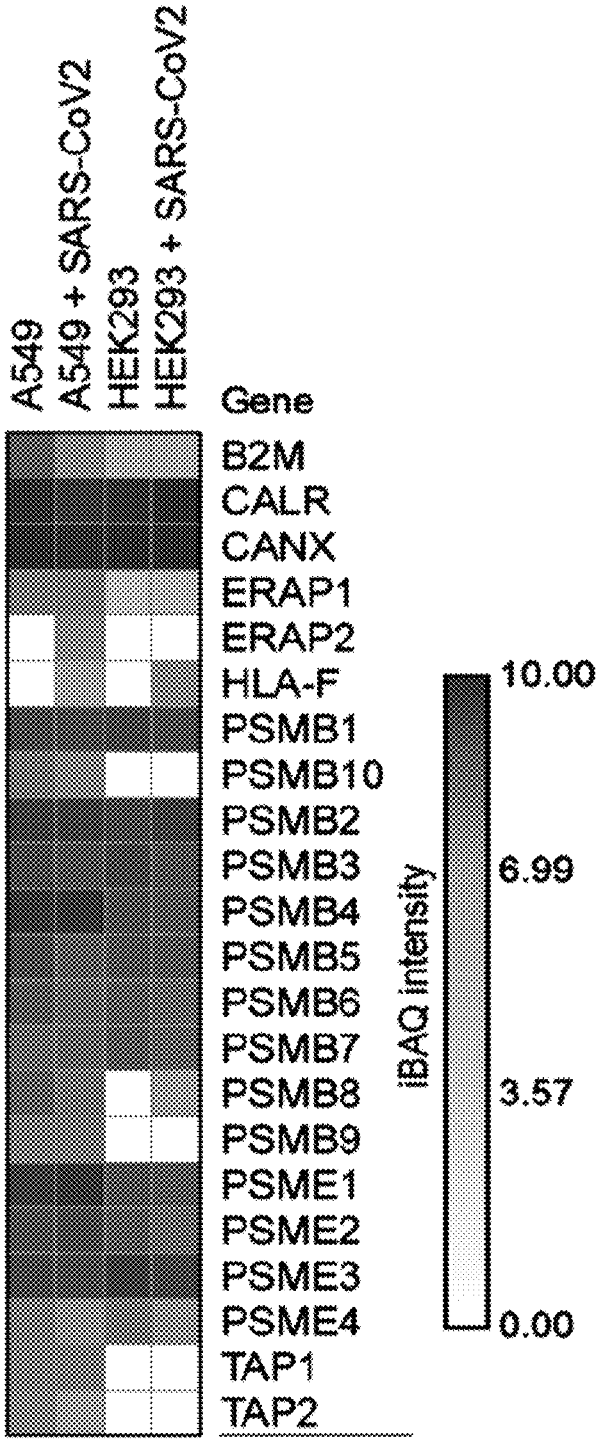
Figure 5E:
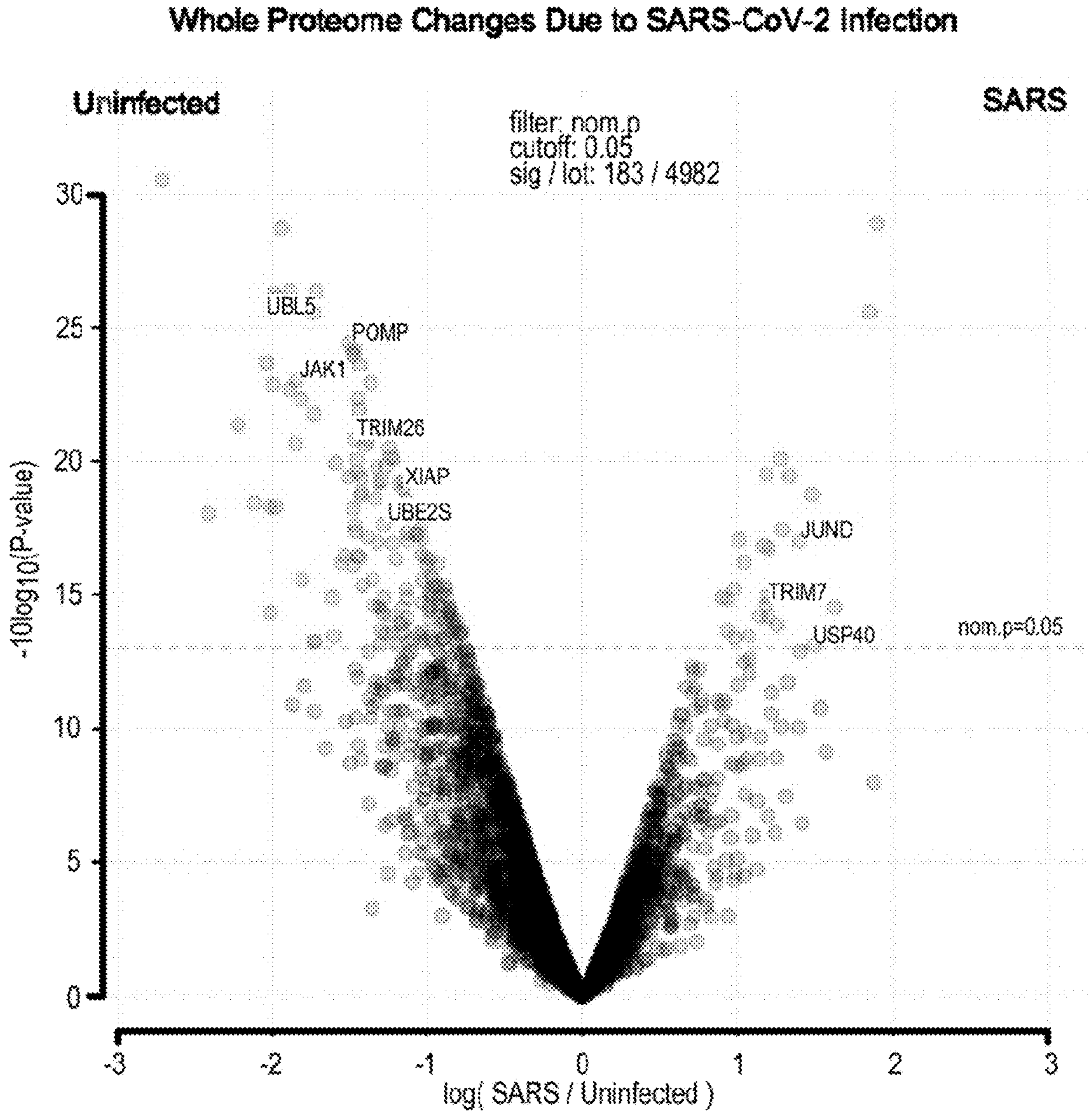
Figure 5F:
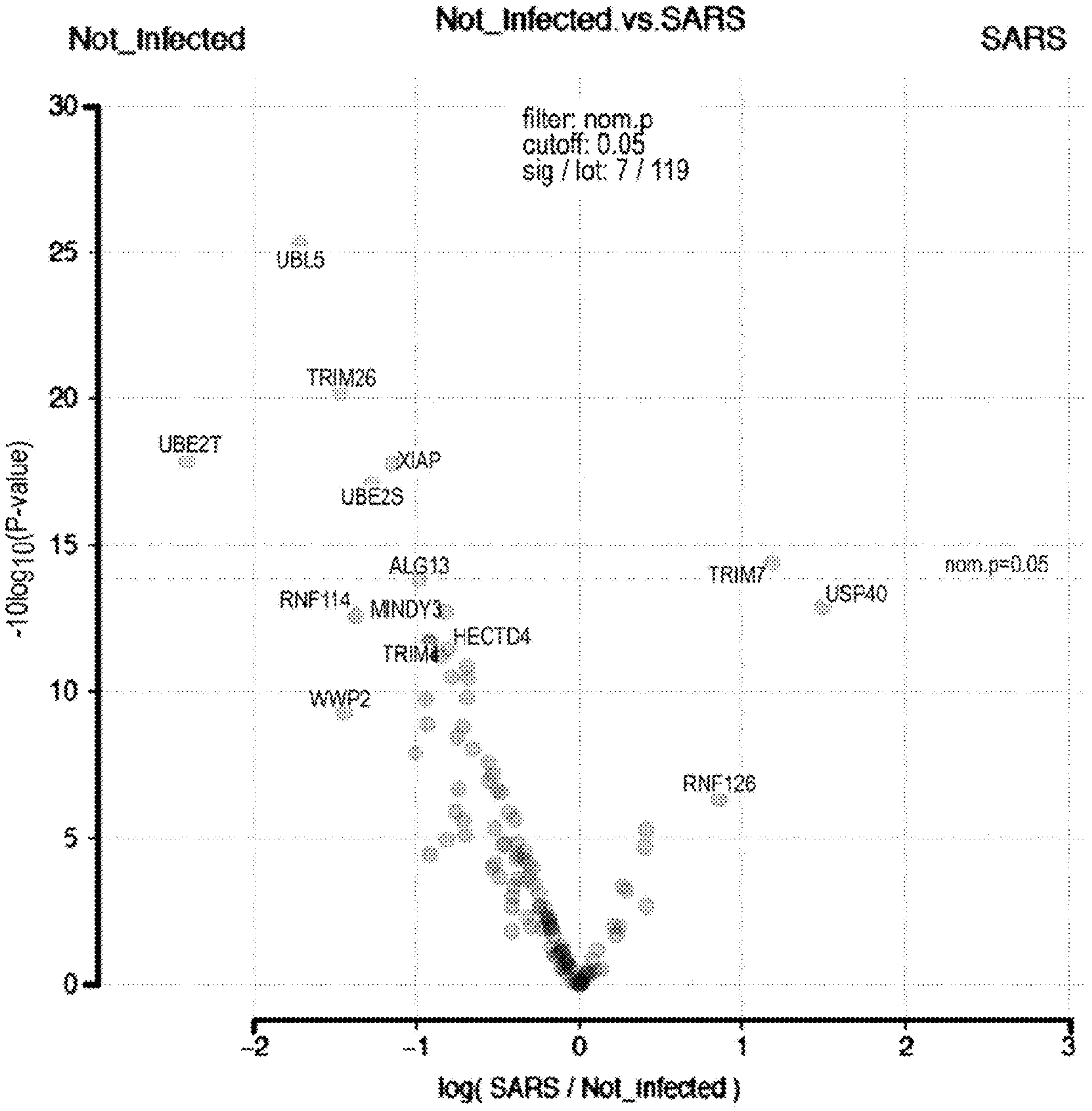

SARS-COV-2 Infection Interferes with Cellular Pathways that May Impact HLA-I Peptide Processing and Presentation The lack of detectable HLA-I peptides from highly expressed SARS-COV-2 proteins, such as N, as well as the results from the time course experiment encouraged Applicant to investigate the impact of SARS-COV-2 infection on the HLA-I presentation pathway. Applicant initially compared the overlap between HLA-I peptidomes of uninfected and 24 hr post infection cells and found 62% of these peptides were detected in both experiments (FIG. 5A). Interestingly, although viral proteins were highly expressed and exceed most of the cellular proteins (Wilcoxon rank-sum test, p<10-4 and p<10-6 for A549 and HEK293T cells, respectively, FIG. 5B and Supporting Fig. SXA), viral HLA-I peptides were not over represented (Wilcoxon ranksum test, p>0.8 and p>0.4 for A549 and HEK293T cells, respectively (FIG. 5C). Together, these two observations suggested that the virus may interfere with the antigen processing and presentation machinery to mask its presence in the cell. Therefore, Applicant interrogated the whole proteomics data on the post HLA-I IP cell lysate. Applicant evaluated canonical HLA-I presentation pathway proteins across both the uninfected and 24 hr post infection A549 and HEK293T full proteome samples (FIG. 5D), and observed no significant differences in proteins such as B2M, ERAP1/2, TAP1/2, and proteasome subunits. Applicant then compared all proteins detected across A549 and HEK293T experiments to determine if upstream antigen processing proteins might be affected (FIG. 5E). Applicant also determined that several ubiquitination pathway genes appear to be significantly altered in response to the SARS-COV-2 infection (FIG. 5F), including a depletion in TRIM26 and an enrichment in TRIM7, which was recently shown to bind to M (See Weingarten-Gabby et al. 2020. SARS-COV-2 infected cells present HLA-I peptides from canonical and out-of-frame ORFs. BioRxIV. doi: https://doi.org/10.1101/2020.10.02.324145, which is incorporated by reference as if expressed in its entirety herein). See also Example 2. Taken together, these data suggest that SARS-COV-2 may interfere with the HLA-I pathway through both POMP depletion and by altering ubiquitination enzymes to prevent highly expressed SARS proteins from being processed and presented.

Figure 6B:
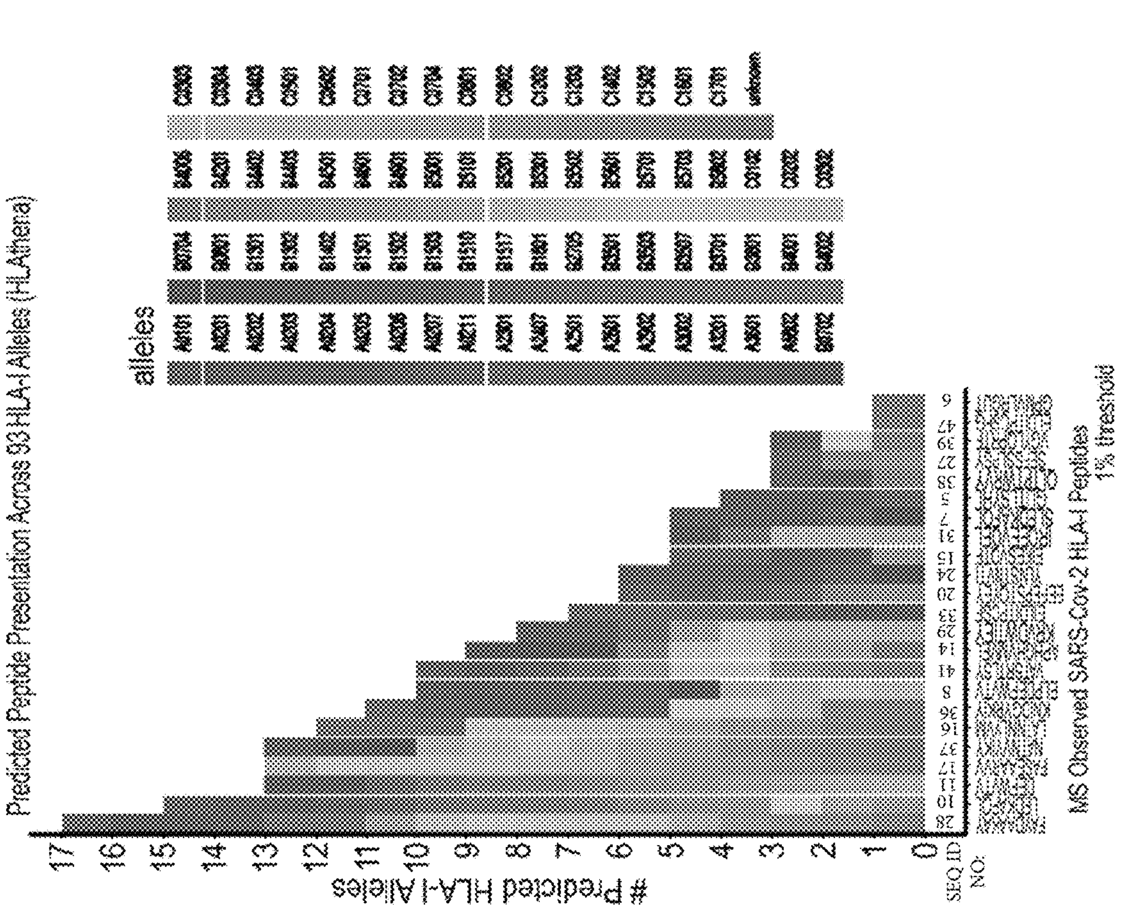
FIGS. 6A-6B-Epitope prediction of SARS-COV-2 derived HLA-I peptides by host cells.
Figure 6A:
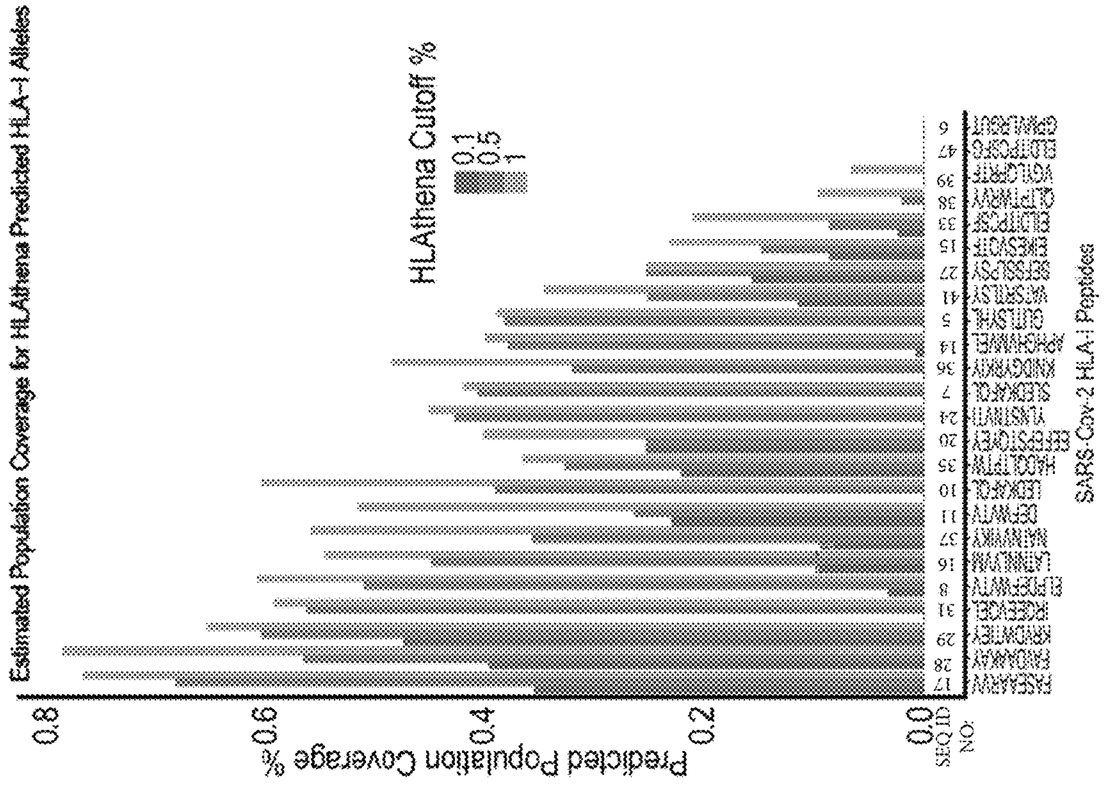

The SARS-COV-2 HLA-I Peptides Detected in this Study are Predicted to Bind 73 HLA-I Alleles To evaluate the accuracy of HLA-I epitope prediction methods, Applicant compared how well prediction algorithms did at ranking the SARS-COV-2 HLA-I peptides identified by LC-MS/MS. Applicant focused on two machine learning based prediction methods that were trained on monoallelic mass spectrometry data for this analysis (Sarkizova et al. 2020; Poran et al. 2020). HLAthena predictions at different rank cutoffs (top 0.1%, 0.5%, 1%) were assessed based on their ability to identify the observed SARS-COV-2 HLA-I peptides (FIG. 6A). From the 23 total HLA-I peptides, The most stringent cutoff, 0.1%, was able to capture 14 (61%) peptides, while 0.5% and 1% captured 20 (87%) and 21 (92%) respectively. Only the top 1% of predicted HLA-I peptides from canonical ORFs were reported for RECON predictions, and of those, 13 of 16 (81%) were identified. Using the top 1% cutoff datasets, we estimated the population coverage of the MS observed SARS-COV-2 HLA-I peptides ranges from ~7% to ~80% (median~38%) (FIG. 6B).

MS observed SARS-COV-2 HLA-I peptides were predicted to bind well to a set of 73 HLA-A,-B, and -C alleles by HLAthena and 57 by RECON. This difference is likely due to the fact that HLAthena supports 92 HLA-I alleles, while RECON supported 74 at the time of publication. These data demonstrated that HLA-I immunopeptidomics on only two cell lines combined with accurate epitope prediction tools can rapidly prioritize multiple CD8+ T cell epitopes with high population coverage for COVID19 immune monitoring and vaccine development as well as provide candidates to monitor in patients over time.

The study provided the first view of SARS-COV-2 peptides that are endogenously processed and presented on the HLA-I in infected cells. Remarkably, 6 of the 20 viral peptides detected in our study are derived from internal out of frame ORFs in SARS-COV-2 genome. This striking observation suggests that current studies on T cells from COVID19 patients, which traditionally focus on the canonical viral ORFs, exclude a set of host cell presented epitopes. The currently published peptide pools may be subject to false negative results. Therefore, unbiased approaches like LC-MS/MS based immunopeptidomics that identify naturally presented SARS-CoV-2 peptides can inform the design of future pools to allow a more accurate interpretation of T cell responses in COVID19 patients.

Applicant demonstrates that synthetic approaches aiming at enhancing the expression of canonical ORFs, some of which may be utilized in the current vaccine strategies, may eliminate the production of the HLA-I peptides derived from overlapping reading frames. This is important when considering the induction of memory T cells in response to SARS-COV-2 vaccines that overexpress the Spike ORF. Examination of the effects of sequence manipulation on the amino acids encoded from S.iORF1 and S.iORF2 may be performed with emphasis on the frame that produced the two HLA-I peptides that Applicant identified GPMVLRGLIT (SEQ ID NO: 6) and GLITLSYHL (SEQ ID NO: 5). In broader terms, many viral genomes have evolved to increase their coding capacity by utilizing overlapping ORFs and programed frameshifting. Thus, the findings emphasize the importance of combining unbiased approaches to detect the complete translatome and immunopeptidome of viruses to design vaccines that will optimize both antibodies and T cells responses.

The study provides a few evidences that SARS-COV-2 may interfere with the presentation of viral peptides. First, although cells are highly infected, with more than 60% of the transcriptome derived from the virus, only X of the 6,372 HLA-I peptides detected represent viral proteins. Moreover, while whole proteomics measurements show high abundance of viral proteins in comparison to host proteins, viral HLA-I peptides are not presented more frequently as would be expected. Second, SARS-COV-2 infection leads to significant decrease in the expression of POMP, an essential chaperone for the 20S proteasome assembly, and alters the expression of proteins in the ubiquitination pathway. By impacting proteasomal degradation SARS-COV-2 may reduce the precursors for downstream processing and HLA-I presentation. Third, although the nucleoprotein is the most abundant viral protein Applicant did not find HLA-I peptides that are derived from its sequence. This observation may represent a limitation of our method or that N-derived peptides are less likely to be presented on the 9 HLA-I alleles tested. However, a recent study that tested the reactivity of CD8+ T cells in COVID19 patients found more reactive T cells for Spike (26%), M (22%), and nsp6 (15%) than for N (12%) (Grifoni et al. 2020) suggesting that N is presented less efficiently than other viral proteins with lower expression levels.

Although our study provides experimental measurements for only nine HLA alleles (three in HEK293T cells and six in A549 cells), Applicant show that these alleles cover a desired percentage of the populations. Two of the alleles, A0201 and B0702, are considered among the most abundant alleles and thus, are prioritized by other researchers for in-vitro and in-vivo studies (Grifoni et al. 2020; Ferretti et al.), allowing a direct comparison between our results and other efforts.

METHODS

Cells

Human embryonic kidney HEK293TT cells, human lung A549 cells, and Agrican green monkey kidney Vero E6 cells were maintained at 37° C. and 5% $CO_2$ in DMEM containing 10% FBS. Applicant generated HEK293TT and A549 cells stably expressing human ACE2 and TMPRSS2 by transducing them with lentivirus particles carrying these two cDNAs followed by selection with 1 μg/ml concentration of puromycin and blasticidin. Allotypes of A549 and HEK293T cells.

SARS-COV-2 Virus Stock

The 2019-nCOV/USA-WA1/2020 isolate (NCBI accession number: MN985325) of SARS-COV-2 was obtained from the Centers for Disease Control and Prevention and BEI Resources. To generate the virus master stock, Applicant infected Vero E6 cells with this isolate for 1 h at 37° C., removed the virus inoculum, rinsed the cell monolayer with 1×PBS, and added DMEM supplemented with 2% FBS. Three days later, when the cytopathic effect of the virus became visible, Applicant harvested the culture medium, passed through a 0.2u filter, and stored it at −80° C. To generate the virus working stock, Applicant infected Vero E6 cells with the master stock at a multiplicity of infection (MOI) of 0.1 plaque forming units (PFU)/cell and harvested the culture medium three days later using the same protocol as for the master stock.

Plaque Assay

The plaque assay was performed on Vero E6 cells. Briefly, Applicant seeded the cells into a 12-well plate at a density of $2.5\times10^5$ cells per well, and the next day, infected them with serial 10-fold dilutions of the virus for 1 h at 37° C. Applicant then added 1 ml per well of the overlay medium containing 2×DMEM (Gibco: #12800017) supplemented with 4% FBS and mixed at a 1:1 ratio with 1.2% Avicel (DuPont; RC-581) to obtain the final concentrations of 2% and 0.6% for FBS and Avicel, respectively. Three days later, Applicant removed the overlay medium, rinsed the cell monolayer with 1×PBS and fixed the cells with 4% paraformaldehyde for 30 minutes at room temperature. 0.1% crystal violet was used to visualize the plaques.

RNA-Seq

A549/HEK293TT cells were seeded on 6-well plates (one well per condition). After 11-24 hr, cells were infected with SARS-COV-2 with multiplicity of infection (MOI) of 3. At 12, 18 and 24 hrs post infection cells were lysed using Trizol (Thermo, 15596026). Total RNA was isolated using standard phenol chloroform precipitation. Standard Illumina TruSeq Stranded mRNA (LT) was performed using 500 ng of total RNA input (illumina, FC-122-2101). Oligo-dT beads were used to capture polyA tails of mRNA followed by fragmentation and priming of captured mRNA (8 minutes at 94C). Immediately first strand cDNA synthesis was performed. Second strand cDNA synthesis was performed using second strand marking master and DNA polymerase 1 and RNase H. cDNA was adenylated at the 3' ends followed immediately by RNA end ligation single-index adapters (AR001-AR012). Library amplification was performed for 15 cycles under standard illumina library PCR conditions. Library quantitation was performed using Agilent 2200 TapeStation D1000 ScreenTape (Agilent, 5067-5582). RNA sequencing was performed on the NextSeq 550 System using a NextSeq V2.5 High Output 75 cycle kit (illumina, 20024906).

Immunoprecipitation of HLA-I Complex

A549/HEK293T cells engineered to express SARS-COV-2 entry factors were seeded into nine 15 cm dishes (three dishes per time point) at a density of 15 million cells per dish for A549 cells and 20 million cells per dish for HEK293T cells. The next day, the cells were infected with SARS-COV-2 at a multiplicity of infection (MOI) of 3. To synchronize infection, the virus was bound to target cells in a small volume of opti-MEM on ice for one hour, followed by addition of DMEM/2% FBS and switching to 37° C. At 12, 18, and 24 h post-infection, the cells from three dishes were scraped into 3 ml/dish of cold lysis buffer (20 mM Tris, pH 8.0, 100 mM NaCl, 6 mM $MgCl_2$, 1 mM EDTA, 60 mM Octyl β-d-glucopyranoside, 0.2 mM Iodoacetamide, 1.5% Triton X-100, 50×Complete Protease Inhibitor Tablet-EDTA free and PMSF) obtaining a total of 9 ml lysate. This lysate was split into 6 eppendorf tubes, with each tube receiving 1.5 ml volume, and incubated on ice for 15 min with 1 ul of Benzonase (Thomas Scientific, E1014-25KU) to degrade nucleic acid. The lysates were then centrifuged at 4,000 rpm for 22 min at 4° C. and the supernatants were transferred to another set of six eppendorf tubes containing a mixture of pre-washed beads (Millipore Sigma, GE17-0886-01) and 50 ul of an MHC class I antibody (W6/32) (Santa Cruz Biotechnology, sc-32235). The immune complexes were captured on the beads by incubating on a rotor at 4° C. for 3 hr. The unbound lysates were kept for whole proteomics analysis while the beads were washed to remove non-specifically bound material. In total, nine washing steps were performed; one wash with 1 mL of cold lysis wash buffer (20 mM Tris, pH 8.0, 100 mM NaCl, 6 mM $MgCl_2$, 1 mM EDTA, 60 mM Octyl β-d-glucopyranoside, 0.2 mM Iodoacetamide, 1.5% Triton X-100), four washes with 1 mL of cold complete wash buffer (20 mM Tris, pH 8.0, 100 mM NaCl, 1 mM EDTA, 60 mM Octyl β-d-glucopyranoside, 0.2 mM Iodoacetamide), and four washes with 20 mM Tris pH 8.0 buffer. Dry beads were stored in −80 c until mass-spectrometry analysis was performed.

HLA Peptidomics LC-MS/MS Data Generation

HLA peptides were eluted and desalted from beads as described previously (Sarkizova et al. 2020). After the primary elution step, HLA peptides were reconstituted in 3% ACN/5% FA and subjected to microscaled basic reverse phase separation. Briefly, peptides were loaded on Stage-tips with 2 punches of SDB-XC material (Empore 3M) and eluted in three fractions with increasing the amount of ACN (5%, 10% and 30% in 0.1% $NH_4OH$). For the time course experiment, one third of each sample was also labelled with TMT6 (Thermo Fisher Scientific, 12 h: 126, 18 h: 128, 24 h: 130), combined and desalted on C18, eluting with increasing amount of ACN (10%, 15% and 50%) in 5 mM Ammonium Formate. Peptides were reconstituted in 3% ACN/5% FA prior to loading on the analytical column (packed in-house, 75 μm New Objective, C18 Reprosil Dr Maisch). MS/MS were acquired on a Thermo Orbitrap Exploris 480 equipped with FAIMS (Thermo Fisher Scientific) in data dependent acquisition. FAIMS CVs were set to −50 and −70 with a cycle time of 1.5s per FAIMS experiment. MS2 filltime was set to 100 ms, collision energy was 29CE or 32CE for TMT respectively. The TMT labelled sample was also acquired without FAIMS using the same parameters.

Whole Proteome LC-MS/MS Data Generation 200 uL aliquot of HLA IP supernatants were reduced for 30 minutes with 5 mM DTT (Pierce DTT: A39255) and alkylated with 10 mM IAA (Sigma IAA: A3221-10VL) for 45 minutes both at 25° C. on a shaker (1000 rpm). Protein precipitation using methanol/chloroform was then performed. Briefly, methanol was added at a volume of 4× that of HLA IP supernant aliquot. This was followed by a 1× volume of chloroform and 3× volume of water. The sample was mixed by vortexing and incubated at −20° C. for 1.5 hours. Samples were then centrifuged at 14,000 rpm for 10 minutes and the upper liquid layer was removed leaving a protein pellet. The pellet was rinsed with 3× volume of methanol, vortexed lightly and centrifuged at 14,000 rpm for 10 minutes. Supernatant was removed and discarded without disturbing the pellet. Pellets were resuspended in 100 mM triethylammonium bicarbonate (pH 8.5) (TEAB). Samples were digested with LysC (1:50) for 2 hours on a shaker (1000 rpm) at 25° C., followed by trypsin (1:50) overnight. Samples were acidified by 1% formic acid final concentration and dried. Samples were reconstituted to 1 ug/uL using 3% ACN/5% FA for LC-MS/MS analysis.

Peptidomics and Proteomics Mass-Spectrometry Data Interpretation

MS/MS spectra were searched with Spectrum Mill (v 7.3 pre-release) against a RefSeq-based sequence database containing 41,457 proteins mapped to the human reference genome (hg38) obtained via the UCSC Table Browser (genome.ucsc.edu/cgi-bin/hgTables) on Jun. 29, 2018, with the addition of 13 proteins encoded in the human mitochondrial genome, 264 common laboratory contaminant proteins, 553 human internal out-of-frame small open reading frames, 28 SARS-Cov2 proteins obtained from RefSeq derived from the original Wuhan-Hu-1 China isolate NC_045512.2 (https://www.ncbi.nlm.nih.gov/nuccore/1798174254) [Wu; 2020], and 23 novel unannotated virus ORFs whose translation is supported by Riboseq (Finkel et al. 2020) for a total of 42,337 proteins. Amongst the 28 annotated SARS-Cov2 proteins Applicant opted to omit the full length polyproteins ORF1a and ORF1ab, to simplify peptide-to-protein assignment, and instead represented ORF1ab as the mature 16 individual non-structural proteins that result from proteolytic processing of the 1a and 1ab polyproteins. Applicant further added the D614G variant of the SARS-Cov2 Spike protein that is commonly observed in European and American virus isolates.

Statistical Analysis

Data analysis was performed using R Studio, Python and Excel.

TABLE 1

| Sequence | Post translational modifications | Length | Protein | Cell line | Experiment 24 h (R1) | Experiment timecourse 12 h |
|---|---|---|---|---|---|---|
| FAVDAAKAY (SEQ ID NO: 28) | | 9 | nsp10 | A549 | x | |
| EIKESVQTF (SEQ ID NO: 15) | | 9 | nsp2 | A549 | | |
| FASEAARVV (SEQ ID NO: 17) | | 9 | nsp2 | A549 | x | |
| LATNNLVVM (SEQ ID NO: 16) | | 9 | nsp2 | A549 | x | |
| EEFEPSTQYEY (SEQ ID NO: 20) | | 11 | nsp3 | A549 | x | |
| SEFSSLPSY (SEQ ID NO: 27) | | 9 | nsp8 | A549 | | |
| DEFVVVTV (SEQ ID NO: 11) | | 8 | ORF9b protein | A549 | x | |
| LEDKAFQL (SEQ ID NO: 10) | | 8 | ORF9b protein | A549 | x | |
| EILDITPcSF (SEQ ID NO: 32) | cysteinylated Cys | 10 | S | A549 | x | x |
| EILDITPCSF (SEQ ID NO: 33) | | 10 | S | A549 | | |
| EILDITPcSFG (SEQ ID NO: 34) | cysteinylated Cys | 11 | S | A549 | x | x |
| HADQLTPTW (SEQ ID NO: 35) | | 9 | S | A549 | x | x |
| KNIDGYFKIY (SEQ ID NO: 36) | | 10 | S | A549 | x | x |
| NATNVVIKV (SEQ ID NO: 37) | | 9 | S | A549 | x | |
| QLTPTWRVY (SEQ ID NO: 38) | | 9 | S | A549 | | |
| VATSRTLSY (SEQ ID NO: 41) | | 9 | M | A549 | x | |
| VGYLQPRTF (SEQ ID NO: 39) | | 9 | S | A549 | x | |

TABLE 1-continued

| | | | | | | |
|---|---|---|---|---|---|---|
| APHGHVmVEL (SEQ ID NO: 192) | oxidized M | 10 | nsp1 | HEK293 | x | |
| STSAFVETV (SEQ ID NO: 19) | | 9 | nsp2 | HEK293 | | |
| KRVDWTIEY (SEQ ID NO: 29) | | 9 | nsp14 | HEK293 | x | |
| FGDDTVIEV (SEQ ID NO: 23) | | 9 | nsp3 | HEK293 | | |
| IRQEEVQEL (SEQ ID NO: 31) | | 9 | ORF7a | HEK293 | x (reset) | |
| APRITFGGP (SEQ ID NO: 42) | | 9 | N | HEK293 | | x |
| ELPDEFVVV (SEQ ID NO: 12) | | 9 | ORF9b protein | HEK293 | | x |
| ELPDEFVVVTV (SEQ ID NO: 8) | | 11 | ORF9b protein | HEK293 | x | |
| KAFQLTPIAV (SEQ ID NO: 13) | | 10 | ORF9b protein | HEK293 | | |
| SLEDKAFQL (SEQ ID NO: 7) | | 9 | ORF9b protein | HEK293 | x | x |
| GLITLSYHL (SEQ ID NO: 5) | | 9 | ORFS.iORF1\|ORFS.iORF2 | HEK293 | x | |
| GPmVLRGLIT (SEQ ID NO: 193) | oxidized M | 10 | ORFS.iORF1\|ORFS.iORF2 | HEK293 | x | x |
| MLLGSMLYM (SEQ ID NO: 204) | oxidized M | 9 | ORFS.iORF1\| | HEK293 | x | |
| YLnSTnVTI (SEQ ID NO: 205) | deamidated N | 9 | nsp3 | HEK293 | x | |

| Sequence | Experiment timecourse 18 h | Experiment timecourse 24 h (R2) | timecourse TMT FAIMS | timecourse TMT no FAIMS | most likely HLA Allele (HLAthena) | rank HLAthena |
|---|---|---|---|---|---|---|
| FAVDAAKAY (SEQ ID NO: 28) | | x | x | | C1203, C1601 | 0.003 |
| EIKESVQTF (SEQ ID NO: 15) | | | x | | A2501 | 0.018 |
| FASEAARVV (SEQ ID NO: 17) | x | x | x | | C1601 | 0.05 |
| LATNNLVVM (SEQ ID NO: 16) | | | | | C1203, C1601 | 0.08 |
| EEFEPSTQYEY (SEQ ID NO: 20) | | | | | B1801, B4403 | 0.02 |
| SEFSSLPSY (SEQ ID NO: 27) | | | x | | B1801, B4403 | 0.025 |
| DEFVVVTV (SEQ ID NO: 11) | | | x | x | B1801 | 0.008 |
| LEDKAFQL (SEQ ID NO: 10) | | | | | B1801, B4403 | 0.27 |
| EILDITPcSF (SEQ ID NO: 32) | x | x | x | | A2501 | 0.1 |
| EILDITPCSF (SEQ ID NO: 33) | | | x | | A2501 | 0.1 |
| EILDITPcSFG (SEQ ID NO: 34) | | x | | | A2501 | 4.52 |

TABLE 1-continued

| | | | | | | |
|---|---|---|---|---|---|---|
| HADQLTPTW (SEQ ID NO: 35) | x | | x | | A2501 | 1.52 |
| KNIDGYFKIY (SEQ ID NO: 36) | x | x | | x | B1801 | 0.87 |
| NATNVVIKV (SEQ ID NO: 37) | | | x | x | C1203, C1601 | 0.018 |
| QLTPTWRVY (SEQ ID NO: 38) | | | x | x | C1601 | 0.77 |
| VATSRTLSY (SEQ ID NO: 41) | | | | | C1601 | 0.0007 |
| VGYLQPRTF (SEQ ID NO: 39) | x | x | x | x | C1601 | 0.63 |
| APHGHVmVEL (SEQ ID NO: 192) | | | | | B0702 | 0.11 |
| STSAFVETV (SEQ ID NO: 19) | | | x | | A0201 | 1.31 |
| KRVDWTIEY (SEQ ID NO: 29) | | | | | C0702 | 0.02 |
| FGDDTVIEV (SEQ ID NO: 23) | | | x | | A0201 | 0.53 |
| IRQEEVQEL (SEQ ID NO: 31) | | | x | | C0702 | 0.13 |
| APRITFGGP (SEQ ID NO: 42) | x | | | | B0702 | 3.05 |
| ELPDEFVVV (SEQ ID NO: 12) | x | x | x | | A0201 | 0.77 |
| ELPDEFVVVTV (SEQ ID NO: 8) | x | | | | A0201 | 0.42 |
| KAFQLTPIAV (SEQ ID NO: 13) | | | x | | A0201 | 0.57 |
| SLEDKAFQL (SEQ ID NO: 7) | x | x | x | | A0201 | 0.43 |
| GLITLSYHL (SEQ ID NO: 5) | | | | | A0201 | 0.23 |
| GPmVLRGLIT (SEQ ID NO: 193) | x | x | | x(M native) | B0702 | 2.12 |
| MLLGSMLYM (SEQ ID NO: 204) | | | | | A0201 | 2.16 |
| YLnSTnVTI (SEQ ID NO: 205) | | | | | A0201 | 0.14 |

Example 2

As researchers work to continue the development of effective vaccines and therapeutics for Severe Acute Respiratory Syndrome Coronavirus 2 (SARS-COV-2), the virus causing the ongoing Coronavirus Disease 19 (COVID-19) pandemic (Lu et al., 2020), it is critical to decipher how infected host cells interact with the immune system. Previous insights from SARS-COV and MERS-COV, as well as emerging evidence from SARS-COV-2, imply that T cell responses play an essential role in SARS-COV-2 immunity and viral clearance (Altmann and Boyton, 2020; Grifoni et al., 2020a; Le Bert et al., 2020; Moderbacher et al., 2020; Sekine et al., 2020). Growing concerns about emerging viral variants and potential resistance to antibody defenses spurred renewed discussions about other immune responses and, in particular, cytotoxic T cell responses (Ledford, 2021). When viruses infect cells, their proteins are processed and presented on the host cell surface by class I human leukocyte antigen (HLA-I). Circulating cytotoxic T cells recognize the presented foreign antigens and initiate an immune response, resulting in the clearance of infected cells. Investigating the repertoire of SARS-COV-2 derived HLA-I peptides will enable identification of viral signatures responsible for activation of cytotoxic T cells.

The vast majority of studies that have interrogated the interaction between T cells and SARS-COV-2 antigens to date utilized overlapping peptide tiling approaches and/or bioinformatic predictions of HLA-I binding affinity (Campbell et al., 2020; Ferretti et al., 2020; Grifoni et al., 2020b;

Nguyen et al., 2020; Poran et al., 2020; Tarke et al., 2020). While HLA-I prediction is undoubtedly a useful tool to identify putative antigens, it has limitations. First, antigen processing and presentation is a multi-step biological pathway, that includes translation of source proteins, degradation by the proteasome, peptide cleavage by aminopeptidases, peptide translocation into the endoplasmic reticulum (ER) by transporter associated with antigen presentation (TAP) and finally, HLA-I binding (Neefjes et al., 2011). Although many computational predictors now account for some of these steps, the average positive predictive values achieved across HLA alleles is still about 64% (Sarkizova et al., 2020). Second, prediction models do not account for ways in which viruses may manipulate cellular processes upon infection, which can affect antigen presentation. For example, viruses can attenuate translation of host proteins, downregulate the proteasome machinery, and interfere with HLA-I expression (Hansen and Bouvier, 2009; Sonenberg and Hinnebusch, 2009). These changes shape the collection of viral and human-derived HLA-I peptides presented to the immune system. Third, prediction models do not capture the dynamics of viral protein expression during the course of infection. Kinetics studies in vaccinia and Influenza viruses have shown that HLA-I presentation of viral epitopes can peak at 3.5-9.5 hours post infection (Croft et al., 2013; Wu et al., 2019). Moreover, translation inhibition of host genes by many viruses can suppress MHC class I presentation later in infection. Thus, proteins that are expressed earlier in the virus life cycle may contribute more to the repertoire of viral epitopes. In light of these limitations, experimental measurements of naturally presented peptides can vastly contribute to our understanding of SARS-COV-2 T cells immune response.

Mass spectrometry based HLA-I immunopeptidomics provides a direct and untargeted method to discover endogenously presented peptides and to learn rules that govern antigen processing and presentation (Abelin et al., 2017; Bassani-Sternberg and Gfeller, 2016; Chong et al., 2018; Sarkizova et al., 2020). This technology has facilitated the detection of virus-derived HLA-I peptides for West Nile virus, vaccinia virus, human immunodeficiency virus (HIV), human cytomegalovirus (HCMV) and measles virus (Croft et al., 2013; Erhard et al., 2018; McMurtrey et al., 2008; Rucevic et al., 2016; Schellens et al., 2015; Ternette et al., 2016). These infectious disease studies revealed new antigens, characterized the kinetics of presented peptides during infection, and identified the sequences that activate T cell responses.

Analysis of mass spectrometry-derived data relies upon selecting a set of viral ORFs to interrogate, and has largely focused on canonical ORFs. Over the past decade, genome-wide profiling of translated sequences has revealed a striking number of non-canonical ORFs in mammalian and viral genomes (Finkel et al., 2020a; Ingolia et al., 2009, 2011; Stern-Ginossar et al., 2012). While the function of most of these non-canonical ORFs remains unknown, it is becoming clear that the translated polypeptides, including from short ORFs, serve as fruitful substrates for the antigen presentation machinery in viral infection, uninfected cells and cancer (Chen et al., 2020b; Hickman et al., 2018; Ingolia et al., 2014; Maness et al., 2010; Ouspenskaia et al., 2020; Ruiz Cuevas et al., 2021; Starck and Shastri, 2016; Yang et al., 2016). Importantly, a recent study identified 23 novel ORFs in the genome of SARS-COV-2, some of which have higher expression levels than the canonical viral ORFs (Finkel et al., 2020b). Whether these non-canonical ORFs give rise to HLA-I bound peptides remains unknown.

This Example at least presents examination of HLA-I immunopeptidome in two SARS-CoV-2-infected human cell lines, and complement this analysis with RNA-seq, global proteomics measurements and biochemical binding assays. Viral HLA-I peptides were identified that are derived from both canonical and non-canonical ORFs and monitor the dynamics of viral protein expression and peptides presentation over multiple timepoints post infection. It is shown that peptides derived from out-of-frame ORFs elicit T cell responses in immunized HLA-A2 transgenic mice and COVID-19 patients using ELISpot and multiplexed barcoded tetramer assays combined with single cell sequencing. These assays uncovered overall higher reactivity to the non-canonical HLA-I peptides than canonical, with one peptide presenting greater responses than some of the strongest T cell epitopes reported to date. Using whole proteome measurements, it is shown that the time of viral protein expression correlates with HLA-I presentation and immunogenicity and that SARS-COV-2 interferes with the cellular proteasomal pathway, potentially resulting in lower presentation of viral peptides. Computational predictions suggest that the detected HLA-I peptides can be presented by additional HLA-I alleles in the population beyond the nine alleles tested in our study. These findings can inform future immune monitoring assays in patients and aid in the design of efficacious vaccines. See also Weingarten-Gabbay et al., 2021. Cell. 184:3962-3980 (2021) and supplementary data, which is incorporated by reference herein as if expressed in its entirety herein.

Results

Profiling HLA-I Peptides in SARS-COV-2 Infected Cells by Mass Spectrometry

To interrogate the repertoire of human and viral HLA-I peptides, we immunoprecipitated (IP) HLA-I proteins from SARS-COV-2-infected human lung A549 cells and human kidney HEK293T cells that were transduced to stably express ACE2 and TMPRSS2, two known viral entry factors. Then their HLA bound peptides were analyzed by liquid chromatography tandem mass spectrometry (LC-MS/MS) (FIG. 1A). The whole proteome of the IP flowthrough was also analyzed by LC-MS/MS and RNA-seq was performed to examine the effect of SARS-COV-2 on human gene expression. To investigate the kinetics of HLA-I presentation, a time course experiment was performed at 3, 6, 12, 18 and 24 hours post infection (hpi) in both cell lines. To allow for the detection of peptides from the complete translatome of SARS-COV-2, the 23 novel ORFs recently identified by Finkel et al. (Finkel et al., 2020b) was combined with the list of canonical ORFs and the human RefSeq database for LC-MS/MS data analysis (FIG. 1A).

Figure 12A:
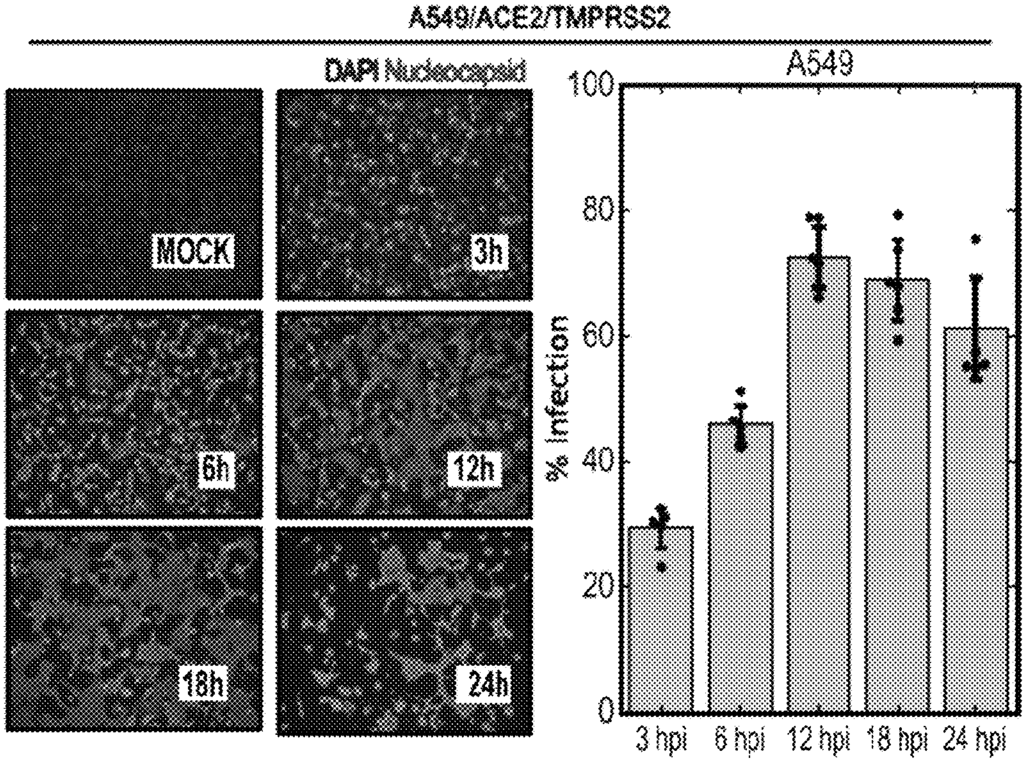
FIGS. 12A-12B-SARS-COV-2 infection of HEK293T/ACE2/TMPRSS2 and A549/ACE2/TMPRSS2. A549 (FIG. 12A) and HEK293T (FIG. 12B) cells expressing ACE2 and TMPRSS2 were infected with SARS-COV-2 at MOI of 3 for 3, 6, 12, 18, and 24 hours. Fixed cells were incubated with a fluorescence antibody to the nucleocapsid and DAPI stain was used to label the nuclei. Immunofluorescent images were taken using an EVOS microscope with 10× lens and infection rates were calculated with ImageJ.
Figure 12B:
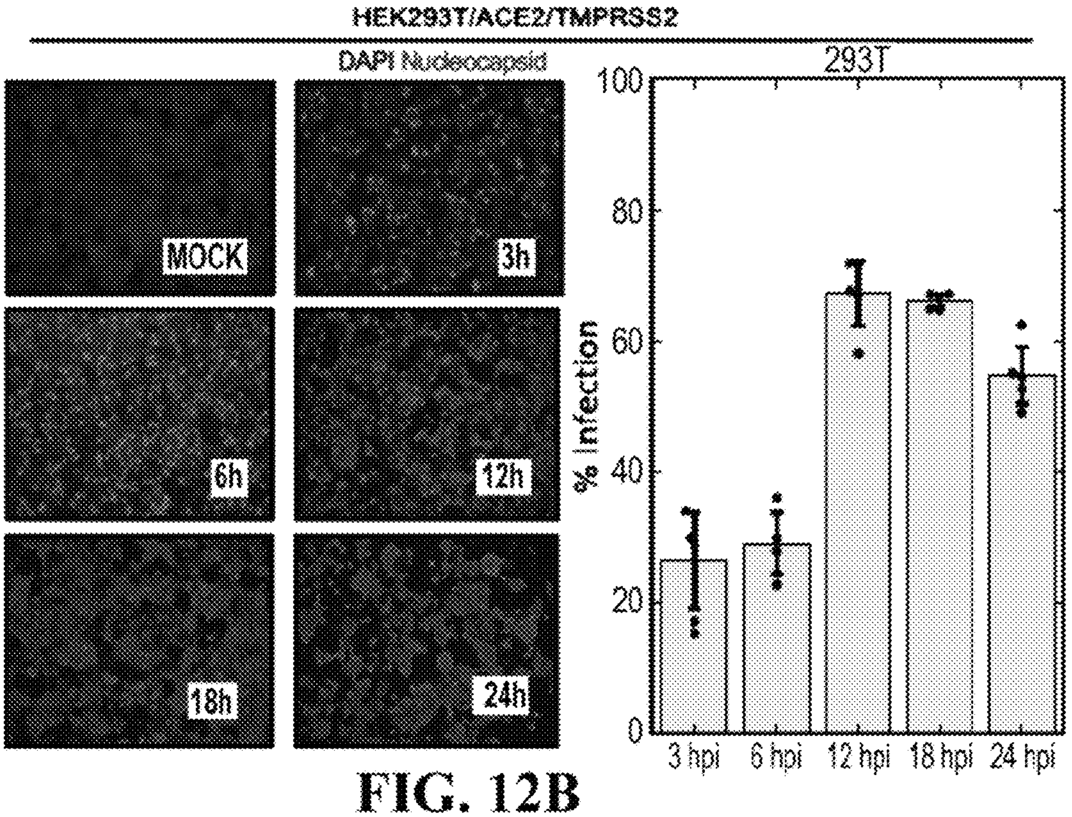

A focus on achieving both biological relevance and HLA-I allelic coverage of the human population was implemented in choosing cell types for this study. A549 are lung carcinoma cells representing the key biological target of SARS-COV-2, and thus commonly used in COVID-19 studies. HEK293T cells endogenously express HLA-A*02:01 and B*07:02, two high frequency HLA-I alleles (AFA: 12.5%, API: 9.5%, HIS: 19.4%, EUR: 29.6%, USA: 24.2% for A*02:01; and AFA: 7.3%, API: 2.6%, HIS: 5.4%, EUR: 14.0%, USA: 10.8% for B*07:02 (Gragert et al., 2013; Poran et al., 2020)). While HEK293T cells do not represent cells from the respiratory system, it was shown that SARS-COV-2 has renal tropism (Puelles et al., 2020) and can directly infect human kidney organoids (Monteil et al., 2020). Together, the nine HLA-I alleles expressed by HEK293T and A549 cells cover at least one allele in 63.8% of the human population (FIG. 1B, Methods). Using immunofluorescence staining of the nucleocapsid protein we evaluate that about 70% of the transduced cells were infected at the peak infection time (FIGS. 12A-12B).

Figure 13A:
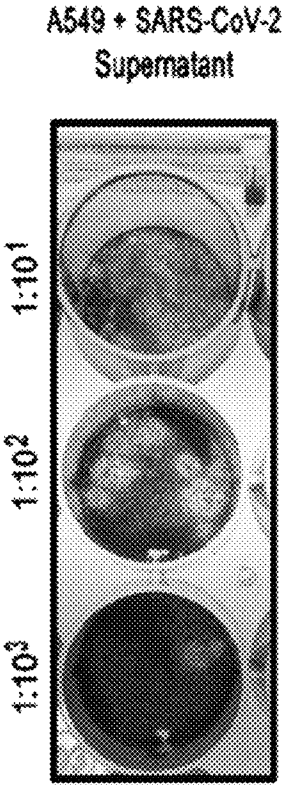
FIGS. 13A-13C-SARS-COV-2 inactivation for HLA-IP experiments. A549 cells were infected with SARS-COV-2 at MOI of 3 for 24 hours and virus inactivation was determined by plaque assay. 10-fold serial dilutions were prepared in Opti-MEM and used to infect Vero cells in a 24-wells plate.
Figure 13B:
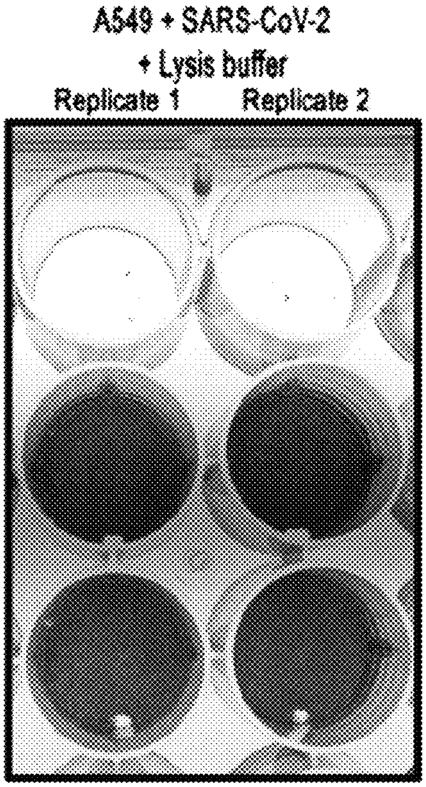
Figure 13C:
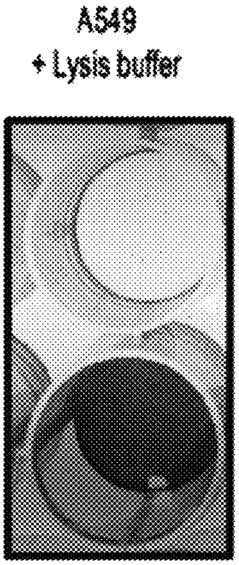

Immunopeptidome analysis of high-containment pathogens is technically challenging and requires implementation of protocols that achieve complete virus inactivation while maintaining the integrity of the HLA-peptide complex. Therefore, the protocol was revised to accommodate the needs and restrictions associated with working in a biosafety level 3 (BSL3) laboratory. First, Benzonase nuclease was used instead of sonication to shear the genomic DNA before immunoprecipitation (Abelin et al., 2019). Second, the virus was inactivated using a lysis buffer containing 1.5% Triton-X, thereby obviating the need to boil or chemically process the cell lysates. The preliminary investigation showed that these experimental conditions achieved complete virus inactivation (FIGS. 13A-13C).

Figure 14A:
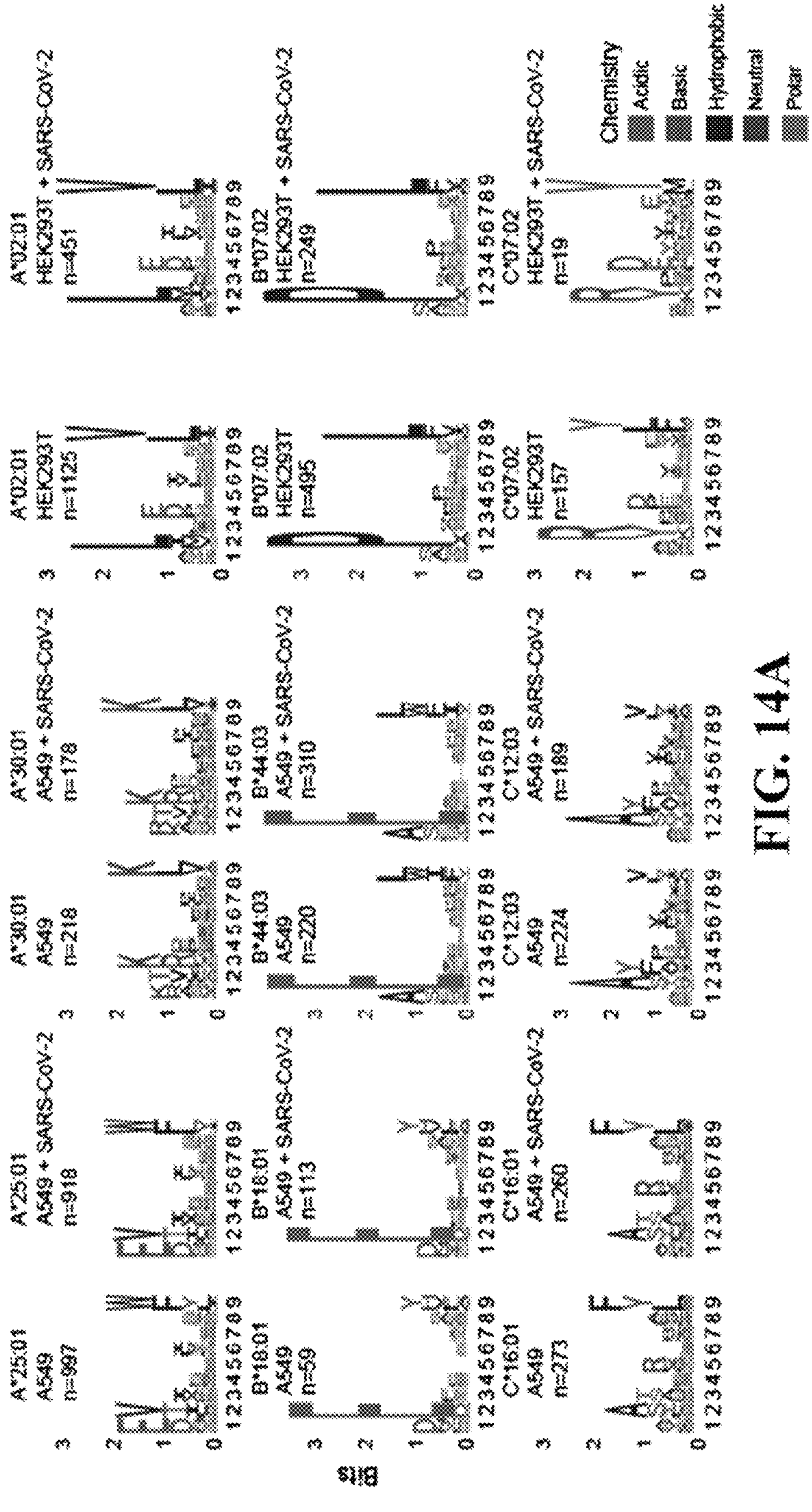
FIGS. 14A-14E-Peptide logos and allele assignment for all experiments.
Figure 14B:
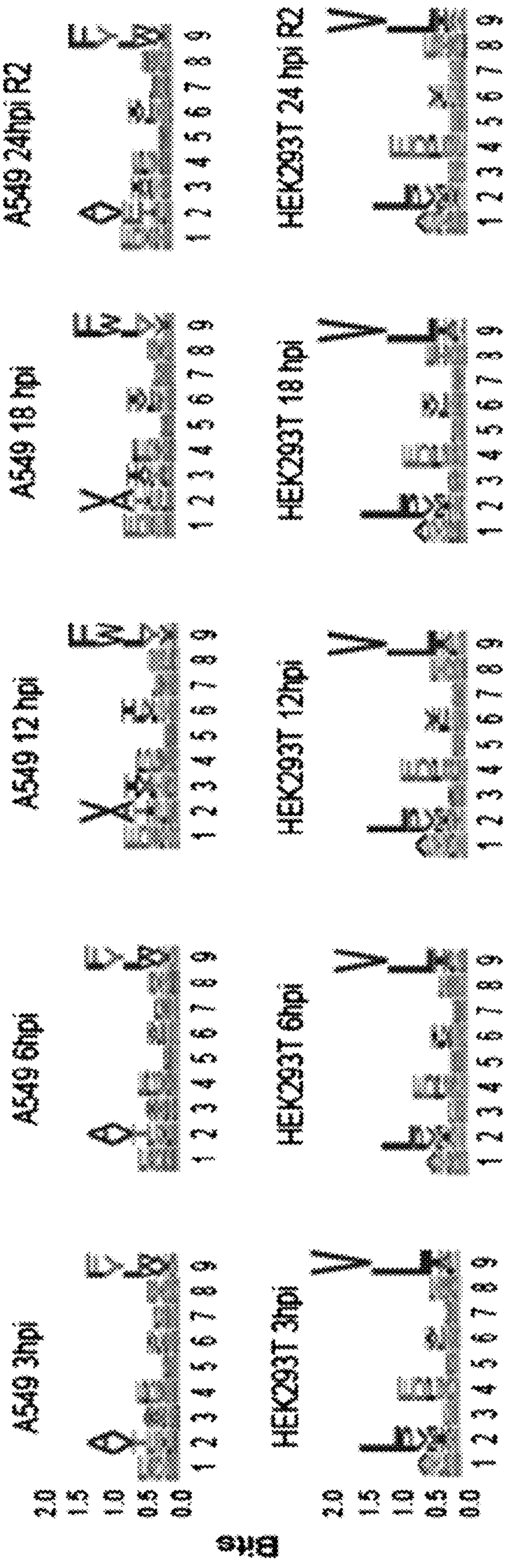

The technical performance of these assays was validated by examining the overall characteristics of presented HLA peptides. 5,837 and 6,372 HLA-bound 8-11mer peptides were identified in uninfected and infected (24 hpi) A549 cells, and 4,281 and 1,336 unique peptides in HEK293T cells, respectively (data not shown). The reduction in the total number of peptides after infection in HEK293T cells is most likely due to cell death (about 50% of cells 24hpi). As expected, it was found that the peptide length distribution was not influenced by the virus infection, and the majority of HLA-I peptides were 9-mers (FIG. 1C). Next, binding motif analyses were performed and the amino acid composition of all 9-mer peptides was compared between uninfected and infected cells at the cellular level and individual HLA alleles (FIG. 1D and FIGS. 14A and 14B). Major differences were not identified in peptide motifs following infection and observed the same amino acids at the main anchor positions 2 and 9 in line with the expected binding motifs of the alleles expressed in the two cell lines. Table 3 shows the allele coverage in the experimental cell lines.

TABLE 3

| population | allele | frequency % | coverage % |
|---|---|---|---|
| World | A0201 | 15.28 | 28.23 |
| World | A2501 | 0.45 | 0.90 |
| World | A3001 | 2.51 | 4.95 |
| World | B0702 | 4.11 | 8.04 |
| World | B1801 | 2.30 | 4.55 |
| World | B4403 | 4.47 | 8.75 |
| World | C0702 | 13.10 | 24.49 |
| World | C1203 | 1.96 | 3.88 |
| World | C1601 | 2.42 | 4.78 |
| EUR | A0201 | 29.60 | 50.44 |
| EUR | A2501 | 1.93 | 3.81 |
| EUR | A3001 | 1.34 | 2.66 |
| EUR | B0702 | 13.99 | 26.02 |
| EUR | B1801 | 4.62 | 9.03 |
| EUR | B4403 | 4.96 | 9.68 |
| EUR | C0702 | 15.01 | 27.76 |
| EUR | C1203 | 4.89 | 9.54 |
| EUR | C1601 | 3.54 | 6.95 |
| AFA | A0201 | 12.46 | 23.36 |
| AFA | A2501 | 0.50 | 1.00 |
| AFA | A3001 | 6.91 | 13.33 |
| AFA | B0702 | 7.30 | 14.07 |
| AFA | B1801 | 3.57 | 7.01 |
| AFA | B4403 | 5.37 | 10.46 |
| AFA | C0702 | 6.97 | 13.45 |
| AFA | C1203 | 1.78 | 3.53 |
| AFA | C1601 | 9.79 | 18.62 |
| API | A0201 | 9.46 | 18.02 |
| API | A2501 | 0.06 | 0.11 |
| API | A3001 | 2.06 | 4.08 |
| API | B0702 | 2.63 | 5.19 |
| API | B1801 | 1.16 | 2.31 |
| API | B4403 | 4.24 | 8.31 |
| API | C0702 | 14.56 | 27.00 |
| API | C1203 | 2.74 | 5.40 |
| API | C1601 | 0.17 | 0.34 |
| HIS | A0201 | 19.40 | 35.04 |
| HIS | A2501 | 0.88 | 1.75 |
| HIS | A3001 | 2.11 | 4.17 |
| HIS | B0702 | 5.45 | 10.61 |
| HIS | B1801 | 3.95 | 7.75 |
| HIS | B4403 | 6.08 | 11.79 |
| HIS | C0702 | 11.28 | 21.29 |
| HIS | C1203 | 4.13 | 8.08 |
| HIS | C1601 | 5.05 | 9.85 |
| USA | A0201 | 24.16 | 42.48 |
| USA | A2501 | 1.42 | 2.83 |
| USA | A3001 | 2.27 | 4.48 |
| USA | B0702 | 10.82 | 20.48 |
| USA | B1801 | 4.13 | 8.08 |
| USA | B4403 | 5.16 | 10.06 |
| USA | C0702 | 13.25 | 24.75 |
| USA | C1203 | 4.20 | 8.22 |
| USA | C1601 | 4.41 | 8.62 |

As previously described HLA-I peptidomics were performed (data not shown). Peptide identifications from HLA-I immunoprecipitation experiments in A549 and HEK293T cells+/− SARS-COV-2 after filtering for contaminants and length 8-11 were performed as previously noted (data not shown). For TMT time course experiments, peptides were filtered for quantitative values and TMT ratios to the 24 h time point were median normalized.

Figure 1E:
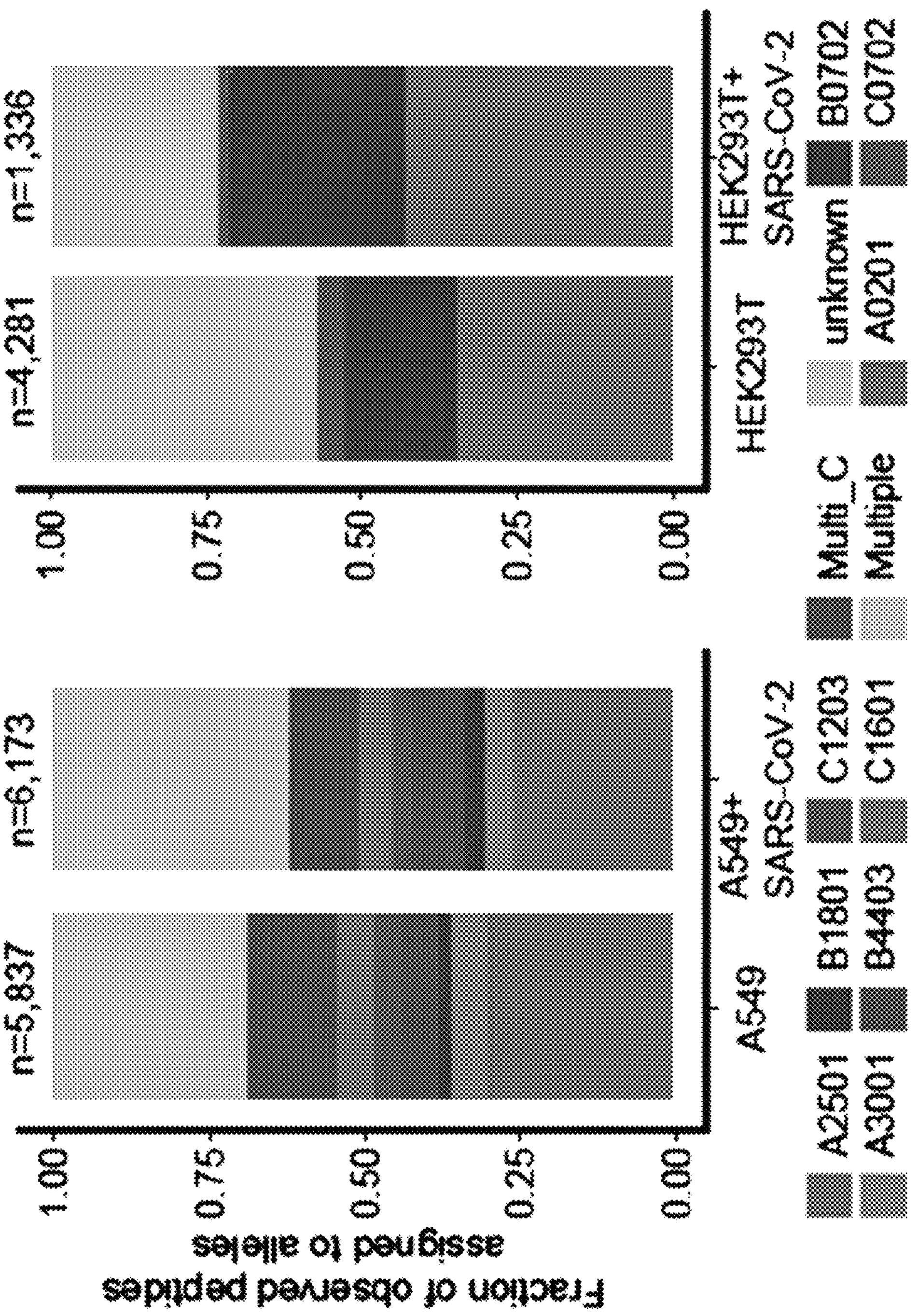
Figure 14C:
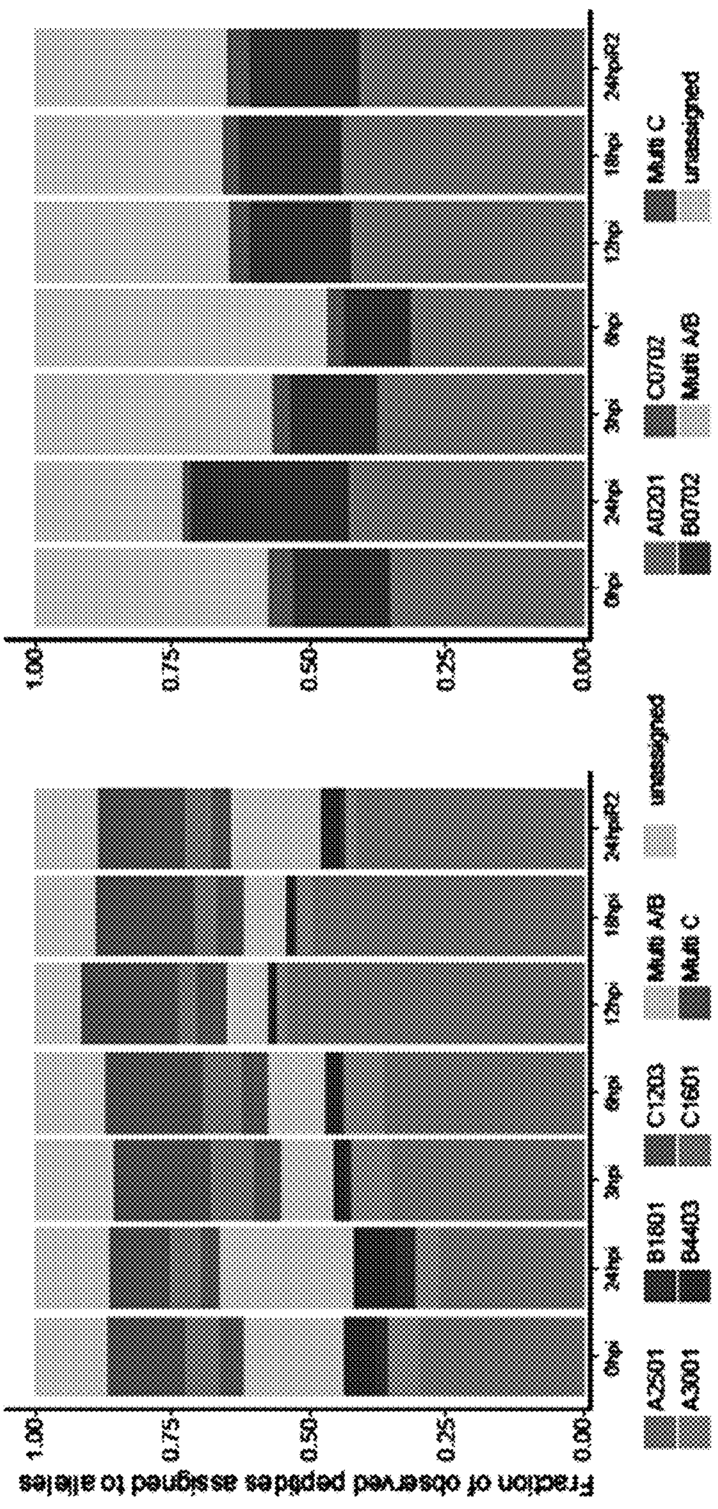

To evaluate if the LC-MS/MS-detected peptides are indeed predicted to bind to the expressed HLA-I alleles, the most likely allele to which each peptide binds was inferred using HLAthena predictions (Sarkizova et al., 2020). A549 cells express A*25:01/30:01, B*18:01/44:03 and C*12:03/16:01, while HEK293T cells express A*02:01, B*07:02 and C*07:02 (determined by HLA allotyping). At a stringent cutoff of predicted percentile rank <=0.5, 87% of A549 and 73% of HEK293T identified peptides post infection were assigned to at least one of the alleles in the corresponding cell line (FIG. 1E, and FIG. 14C). The majority of presented peptides were assigned to A*25:01 and A*02:01 for A549 and HEK293T cells, respectively; infection with SARS-COV-2 did not alter this distribution.

Figure 14D:
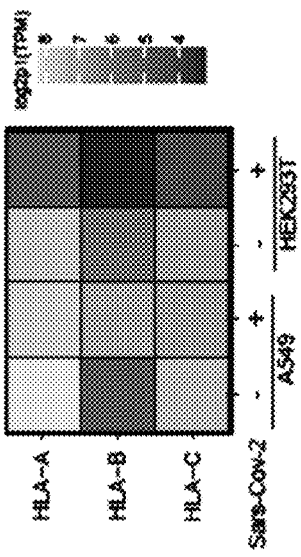

The observed differences in relative HLA alleles representation could stem from the expression levels of individual alleles and/or the range of peptides each allele can bind. The lack of allele-specific antibodies prevents direct protein level measurements of each individual HLA allele. Similarly, high transcript homology between individual HLA alleles only allows for relative expression quantification between the three HLA loci, HLA-A,-B and -C. Examining our RNA-seq measurements, a higher level of HLA-A expression was found compared to HLA-B and -C in both uninfected cell lines (FIG. 14D). After infection, a shift towards HLA-B-presented peptides (fold changes 1.44 and 1.25 for A549 and HEK293T, respectively) and a corresponding increase in HLA-B expression for A549 (fold change=1.48) was observed, which agrees with previous reports of HLA-B upregulation upon activation of the IFNγ response (Girdlestone, 1995; Javitt et al., 2019). Elevated HLA-B expression was not observed in HEK293T post infection.

Figure 14E:
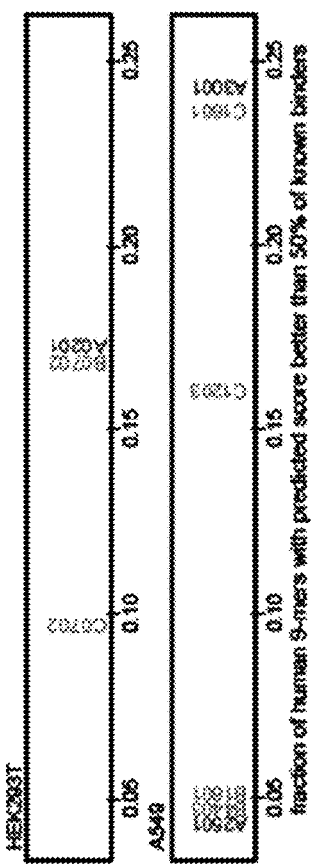

To estimate the contribution of the range of peptides each allele can bind to the obtained surface representations, we scored all human-derived 9-mer peptides for each allele (FIG. 14E). This analysis suggests that A*02:01 is more permissive than C*07:02 and, to a small extend B*07:02, which likely further contributes to the larger fraction of A*02:01 peptides observed for HEK293T. Similarly, the limited range of peptides that A549 HLA-B alleles accommodate likely contributes to the lower frequency of HLA-B peptides detected in A549. While A*25:01 is predicted to accommodate a narrower range of peptides compared to A*30:01, we detect ~7-fold more A*25:01 than A*30:01 peptides, possibly suggesting higher A*25:01 expression compared to A*30:01. Overall, these analyses suggest that the relative representation of HLA alleles on the cell surface is influenced by both the expression level as well as the permissiveness of the binding motif of each allele.

Detecting HLA-I peptides across SARS-COV-2 genome

Next, HLA-I peptides were examined that are derived from the SARS-COV-2 genome (FIG. 7A and Table 2). 28 peptides were identified from canonical proteins (nsp1, nsp2, nsp3, nsp5, nsp8, nsp10, nsp14, nsp15, S, M, ORF7a and N; according to RefSeq NC_045512.2). Strikingly, 9 peptides were derived from out-of-frame ORFs in S and N (described in detail below). Searching the data against in-silico 6 frames translation of SARS-COV-2 proteome, four matching peptides were found, however, manual inspection of ribosome profiling data (Finkel et al., 2020b) did not support translated ORFs in these regions. In addition to the use of a stringent FDR cut-off of 1.5% for automated interpretation of peptide spectrum matches from our LC-MS/MS data, SARS-COV-2-derived peptide identifications were designated high, medium, or low confidence using synthetic peptides measurements (for 24 epitopes) and by manually inspecting the spectra (see Methods). Most of the HLA-I peptides were detected in more than one experiment and predicted as good binders by HLAthena to at least one of the expressed HLA alleles.

Table 2 shows HLA-I bound peptide sequences from SARS-COV-2 proteins identified in both A549 and HEK293T cells. Cysteines were detected in their carbamidomethylated or cysteinylated modification state, methionines were oxidized. “x” denotes identification in individual experiments, “T” in TMT experiments, “-” indicates that the peptide was detected but did not pass FDR correction in that sample, confidence level in identification was evaluated based on Spectrum Mill Score, after manual inspection of MS/MS spectra and comparison to synthetic peptide spectra for available peptides (Y=validated by synthetic peptide, N/A=synthetic peptide not available). For binding prediction using HLAthena, residues were considered unmodified, columns show the most likely HLA allele a peptide is bound to in the respective cell line as well as the percentile binding rank.

TABLE 2

SARS-CoV-2 HLA-I peptides

| Cell line | Sequence | Length | Protein | Exp. 24 h (R1) | 3 h | 6 h | 12 h | 18 h | 24 h (R2) | # exp observed in | Syn. Peptide | Spectrum Mill Score | Confidence level | HLA Allele (HLA-thena) | rank (HLA-thena) | Binding in vitro ($IC_{50}$, [nM]*) |
|---|---|---|---|---|---|---|---|---|---|---|---|---|---|---|---|---|
| A549 | FAVDAAKAY (SEQ ID NO: 28) | 9 | nsp10 | x | T | x/T | T | T | x/T | 5 | Y | 17.03 | High | C1203, C1601 | 0.0027 | N/A |
| | EIKESVQTF (SEQ ID NO: 15) | 9 | nsp2 | | T | T | T | T | T | 2 | Y | 8.83 | High | A2501 | 0.0184 | N/A |
| | FASEAARVV (SEQ ID NO: 17) | 9 | nsp2 | x | x/T | x/T | T | x/T | x/T | 7 | Y | 13.87 | High | C1601 | 0.0049 | N/A |
| | LATNNLVVM (SEQ ID NO: 16) | 9 | nsp2 | x | | | | | | 1 | N/A | 5.26 | Medium/LOW | C1203, C1601 | 0.0848 | N/A |
| | TAQNSVRVL (SEQ ID NO: 18) | 9 | nsp2 | | T | T | | | T | 1 | N/A | 8.08 | High | C1203, C1601 | 0.1829 | N/A |
| | EEFEPSTQYEY (SEQ ID NO: 20) | 11 | nsp3 | x | | | | | | 1 | Y | 13.67 | High | B1801, B4403 | 0.0194 | N/A |
| | TTTIKPVTY (SEQ ID NO: 21) | 9 | nsp3 | | | x | | | | 1 | N/A | 10.04 | High | C1601 | 0.0869 | N/A |
| | TVIEVQGY (SEQ ID NO: 22) | 8 | nsp3 | | T | T | | | T | 1 | N/A | 7.82 | High | A2501 | 0.0528 | N/A |
| | SEFSSLPSY (SEQ ID NO: 27) | 9 | nsp8 | | | | T | T | T | 1 | Y | 6.85 | High | B1801, B4403 | 0.0246 | 0.37 |
| | DEFVVVTV (SEQ ID NO: 11) | 8 | ORF9b | x | T | T | T | T | T | 3 | Y | 5.5 | High | B1801 | 0.0083 | <0.5 |
| | LEDKAFQL (SEQ ID NO: 10) | 8 | ORF9b | x | | | | | | 1 | Y | 6.97 | High | B1801, B4403 | 0.2739 | 35 |
| | EILDITPCSF (SEQ ID NO: 33) | 10 | S | x | | x | x/T | x/T | x/T | 6 | N/A | 15.03 | High | A2501 | 0.0955 | N/A |
| | EILDITPCSFG (SEQ ID NO: 47) | 11 | S | x | | | x | | x | 3 | N/A | 9.83 | High | A2501 | 4.5204 | N/A |
| | HADQLTPTW* (SEQ ID NO: 35) | 9 | S | x | x | x | x/T | x/T | T | 6 | Y | 15.03 | Medium, also in neg. control | A2501 | 1.5199 | N/A |

TABLE 2 -continued

SARS-CoV-2 HLA-I peptides

| Cell line | Sequence | Length | Protein | Exp. 24 h (R1) | 3 h | 6 h | 12 h | 18 h | 24 h (R2) | # exp Observed in | Syn. Peptide | Spectrum Mill Score | Confidence level | HLA Allele (HLA-thena) | rank (HLA-thena) | Binding in vitro ($IC_{50}$, [nM]*) |
|---|---|---|---|---|---|---|---|---|---|---|---|---|---|---|---|---|
| | KNIDGYFKIY (SEQ ID NO: 36) | 10 | S | x | T | T | x | x | x | 5 | Y | 16.92 | High | B1801 | 0.8731 | >70000 |
| | NATNVVIKV (SEQ ID NO: 37) | 9 | S | x | T | x/T | T | T | T | 4 | Y | 10.1 | High | C1203, C1601 | 0.0180 | N/A |
| | QLTPTWRVY (SEQ ID NO: 38) | 9 | S | | | | T | T | T | 3 | Y | 7.97 | High | C1601 | 0.7696 | N/A |
| | VGYLQPRTF (SEQ ID NO: 39) | 9 | S | x | | x | T | x/T | x/T | 5 | Y | 11.81 | High | C1601 | 0.6251 | N/A |
| | VATSRTLSY (SEQ ID NO: 41) | 9 | M | x | T | T | | | T | 2 | N/A | 7.64 | Medium | C1601 | 0.0007 | N/A |
| | METGGFSIDLP (SEQ ID NO: 43) | 11 | F3 R196 | x | | | | | | 1 | N/A | 5.49 | Medium | B1801 | 3.2422 | N/A |
| | LSNPVILTK (SEQ ID NO: 44) | 9 | F2 R32 | | T | T | | | T | 1 | N/A | 5.83 | Medium | A3001 | 1.6274 | N/A |
| HEK293T | APHGHVMVEL (SEQ ID NO: 14) | 10 | nsp1 | x | T | T | | | T | 2 | Y | 14.36 | High | B0702 | 0.1099 | 6.1 |
| | STSAFVETV (SEQ ID NO: 19) | 9 | nsp2 | | T | T | T | T | T | 2 | N/A | 11.55 | High | A0201 | 1.3088 | N/A |
| | KRVDWTIEY (SEQ ID NO: 29) | 9 | nsp14 | x | T | T | | | T | 2 | Y | 13.86 | High | C0702 | 0.0180 | N/A |
| | FGDDTVIEV (SEQ ID NO: 23) | 9 | nsp3 | — | T | T | T | T | T | 2 | Y | 10.68 | High | A0201 | 0.5348 | 3.8 |
| | YLNSTNVTI (SEQ ID NO: 24) | 9 | nsp3 | x | | | | | | 1 | Y | 7.31 | Medium | A0201 | 0.1354 | 12 |
| | YLFDESGEFKL (SEQ ID NO: 25) | 11 | nsp3 | | T | T | | | T | 1 | N/A | 4.94 | Medium | A0201 | 0.0052 | N/A |
| | AGTDTTITV (SEQ ID NO: 26) | 9 | nsp5 | | T | T | | | T | 1 | N/A | 5.48 | Medium (not valid with 6 frame search) | A0201 | 3.4456 | N/A |

TABLE 2 -continued

SARS-CoV-2 HLA-I peptides

| | | | | | | | | | | | | | | | |
|---|---|---|---|---|---|---|---|---|---|---|---|---|---|---|---|
| SVVSKVVKV (SEQ ID NO: 30) | 9 | nsp15 | | T | T | | | T | 1 | N/A | 6.81 | Medium | A0201 | 0.1482 | N/A |
| IRQEEVQEL (SEQ ID NO: 31) | 9 | ORF7a | — | T | x/T | T | T | T | 3 | Y | 16.01 | High | C0702 | 0.1322 | N/A |
| APRITFGGP (SEQ ID NO: 42) | 9 | N | | | x | x | x | — | 3 | Y | 15.03 | High | B0702 | 3.0563 | N/A |
| ELPDEFVVV (SEQ ID NO: 12) | 9 | ORF9b | | | x | x/T | x/T | x/T | 5 | Y | 9.01 | High | A0201 | 0.7673 | 460 |
| ELPDEFVVVTV (SEQ ID NO: 8) | 11 | ORF9b | | | | | x | | 1 | Y | 5 | High | A0201 | 0.4190 | 1.6 |
| KAFQLTPIAV (SEQ ID NO: 13) | 10 | ORF9b | | T | T | T | T | T | 2 | N/A | 6.46 | High | A0201 | 0.5696 | 7.8 |
| SLEDKAFQL (SEQ ID NO: 7) | 9 | ORF9b | x | T | x/T | x/T | x/T | x/T | 7 | Y | 14.5 | High | A0201 | 0.4349 | 20 |
| NLNESLIDL (SEQ ID NO: 40) | 9 | S | | T | T | | | T | 1 | N/A | 7.75 | High | A0201 | 0.8444 | N/A |
| GLITLSYHL (SEQ ID NO: 5) | 9 | S.iORF1/2 | x | | | | | | 1 | Y | 11.09 | High | A0201 | 0.2323 | <0.5 |
| GPMVLRGLIT (SEQ ID NO: 6) | 10 | S.iORF1/2 | x | | x | x/T | x/T | x/T | 6 | Y | 15.37 | High | B0702 | 2.1237 | 168 |
| MLLGSMLYM (SEQ ID NO: 4) | 9 | S.iORF1 | x | | | | | | 3 | Y | 11.22 | High | A0201 | 2.1581 | <0.5 |
| LSASLSNFLSI (SEQ ID NO: 45) | 11 | F6 R325 | x | x | | | | | 2 | N/A | 10.63 | Medium, also in neg. control | A0201 | 5.9332 | N/A |
| MPFQKPITL (SEQ ID NO: 46) | 9 | F3 R683 | x | | | | | | 1 | N/A | 14.2 | High | B0702 | 0.0269 | N/A |

*For in-vitro binding assay, IC50 <500 nM indicates binding.

**HADQLTPTW (SEQ ID NO: 35) swas observed in non-infected A549 cells

Figure 7A:
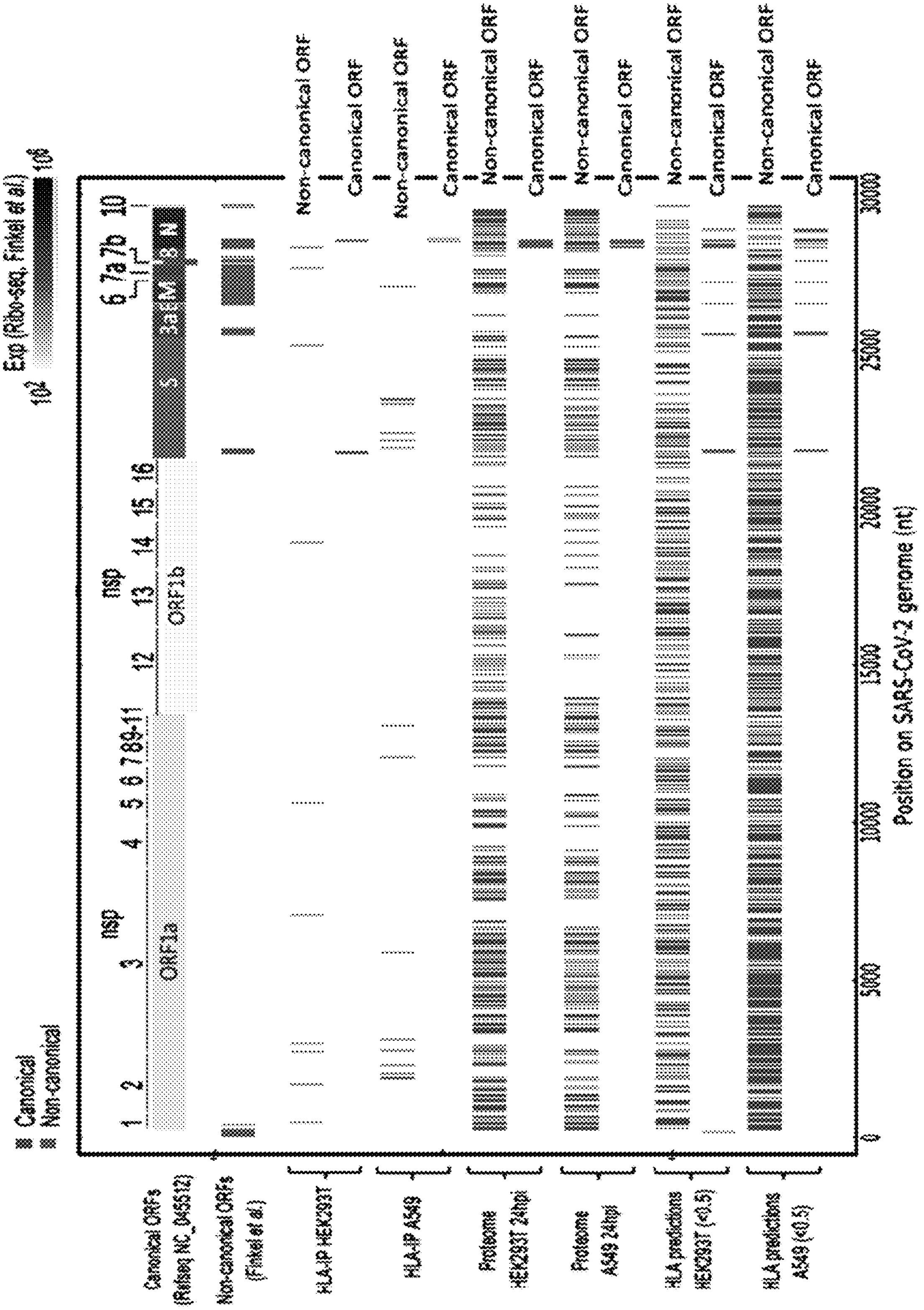
FIGS. 7A-7H-SARS-COV-2 HLA-I immunopeptidome and whole proteome.
Figure 7B:
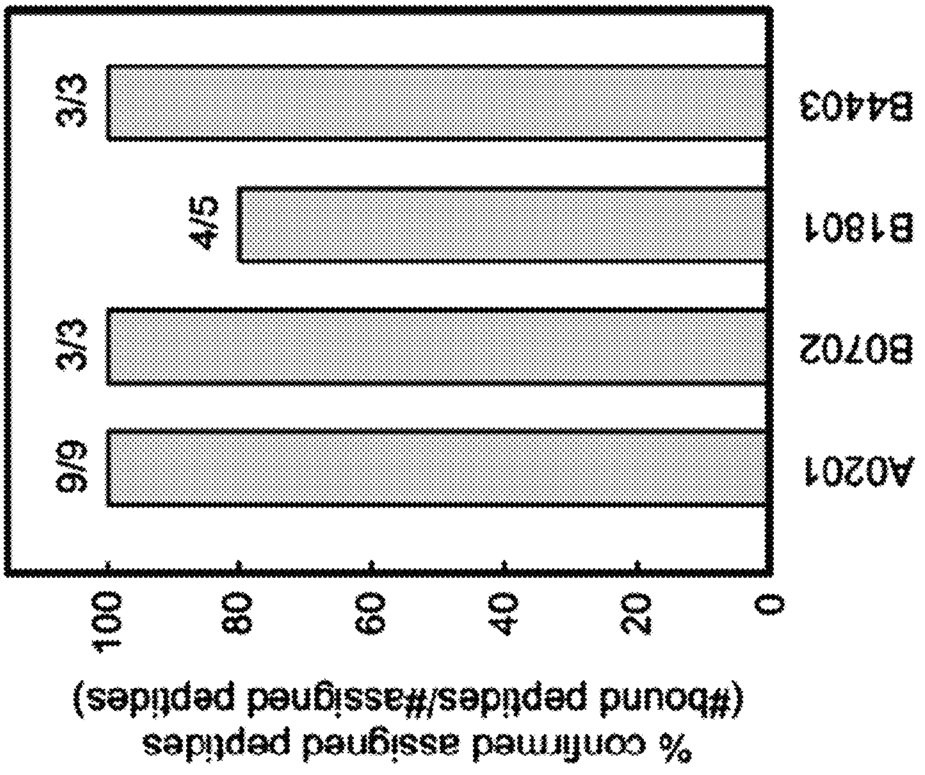

To evaluate the binding affinity of the detected peptides to the predicted HLA alleles in the cell lines (Table 2) in-vitro binding assays with synthetic peptides and purified MHC complexes matching four of the HLA alleles expressed in A549 and HEK293T cells was performed (A*02:01, B*07:02, B*18:01 and B*44:03). Binding ($IC_{50}$<500 nM) was confirmed for 19 of the 20 HLA-I peptides assigned to these alleles (FIG. 7B and Table 4). In addition, FASEAARVV (SEQ ID NO: 17) from nsp2, IRQEEVQEL (SEQ ID NO: 31) from ORF7a, KRVDWTIEY (SEQ ID NO: 29) from nsp14, and YLNSTNVTI (SEQ ID NO: 24) from nsp3 were also independently confirmed in previously generated biochemical binding assays (Covid19 Intavis_Immunitrack stability dataset 1, https://www.immunitrack.com/free-corona-virus-report-for-download/). One peptide, HADQLTPTW (SEQ ID NO: 35), was also detected in non-infected A549 cells and thus, we removed it from all subsequent mass spectrometry analyses. Table 4 shows Binding affinities of 30 synthetic HLA-I peptides and nine purified MHC complexes matching four HLA alleles expressed in A549 and HEK293T cells (A*02:01, B*07:02, B*18:01 and B*44:03) and five alleles for which we predicted presentation based on HLAthena (A*01:01, A*26:01, B*15:01, B*44:02 and B*51:01). Affinity scores were computed for each allele based on the concentration of synthetic peptide required to inhibit the binding of a high affinity radiolabeled ligand by 50% ($IC_{50}$). $IC_{50}$<500 nM is considered positive binding (highlighted by bold font); +++ indicates $IC_{50}$<0.5 nM (below detection levels); A dash line indicates $IC_{50}$>70000 nM.

TABLE 4

In-vitro binding measurements of HLA-I peptides and purified MHC complexes.

| Peptide ID | LJI ID | ORF type | Sequence | Organism | Protein | Len | Assigned HLA | HLAthena prediction (Rank) |
|---|---|---|---|---|---|---|---|---|
| Peptide 1 | 7283.0001 | canonical | APHGHVMVEL (SEQ ID NO: 14) | SARS-CoV-2 | nsp1 | 10 | B0702 | 0.11 |
| Peptide 2 | 7283.0002 | canonical | IRQEEVQEL (SEQ ID NO: 31) | SARS-CoV-2 | ORF7a | 9 | C0702 | 0.13 |
| Peptide 3 | 7283.0003 | non-canonical | SLEDKAFQL (SEQ ID NO: 7) | SARS-CoV-2 | ORF9b | 9 | A0201 | 0.43 |
| Peptide 4 | 7283.0004 | non-canonical | GPMVLRGLIT (SEQ ID NO: 6) | SARS-CoV-2 | ORFS. iORF1/2 | 10 | B0702 | 2.12 |
| Peptide 5 | 7283.0005 | non-canonical | GLITLSYHL (SEQ ID NO: 5) | SARS-CoV-2 | ORFS. iORF1/2 | 9 | A0201 | 0.23 |
| Peptide 6 | 7283.0006 | non-canonical | ELPDEFVVVTV (SEQ ID NO: 8) | SARS-CoV-2 | ORF9b | 11 | A0201 | 0.42 |
| Peptide 7 | 7283.0007 | canonical | KRVDWTIEY (SEQ ID NO: 29) | SARS-CoV-2 | nsp14 | 9 | C0702 | 0.02 |
| Peptide 8 | 7283.0008 | canonical | FAVDAAKAY (SEQ ID NO: 28) | SARS-CoV-2 | nsp10 | 9 | C1203, C1601 | 0.00 |
| Peptide 9 | 7283.0009 | canonical | FASEAARVV (SEQ ID NO: 17) | SARS-CoV-2 | nsp2 | 9 | C1601 | 0.00 |
| Peptide 10 | 7283.0010 | canonical | EEFEPSTQYEY (SEQ ID NO: 20) | SARS-CoV-2 | nsp3 | 11 | B1801, B4403 | 0.02 |
| Peptide 12 | 7283.0012 | non-canonical | LEDKAFQL (SEQ ID NO: 10) | SARS-CoV-2 | ORF9b | 8 | B1801, B4403 | 0.27 |
| Peptide 13 | 7283.0013 | canonical | HADQLTPTW (SEQ ID NO: 35) | SARS-CoV-2 | S | 9 | A2501 | 1.52 |
| Peptide 14 | 7283.0014 | canonical | EILDITPCSFG (SEQ ID NO: 47) | SARS-CoV-2 | S | 11 | A2501 | 4.52 |
| Peptide 15 | 7283.0015 | canonical | EILDITPCSF (SEQ ID NO: 33) | SARS-CoV-2 | S | 10 | A2501 | 0.10 |
| Peptide 16 | 7283.0016 | canonical | KNIDGYFKIY (SEQ ID NO: 36) | SARS-CoV-2 | S | 10 | B1801 | 0.87 |
| Peptide 17 | 7283.0017 | canonical | EIKESVQTF (SEQ ID NO: 15) | SARS-CoV-2 | nsp2 | 9 | A2501 | 0.02 |
| Peptide 18 | 7283.0018 | canonical | SEFSSLPSY (SEQ ID NO: 27) | SARS-CoV-2 | nsp8 | 9 | B1801, B4403 | 0.02 |
| Peptide 19 | 7283.0019 | non-canonical | DEFVVVTV (SEQ ID NO: 11) | SARS-CoV-2 | ORF9b | 8 | B1801 | 0.01 |

TABLE 4-continued

In-vitro binding measurements of HLA-I peptides and purified MHC complexes.

| Peptide 20 | 7283.0020 | canonical | NATNVVIKV (SEQ ID NO: 37) | SARS-CoV-2 | S | 9 | C1203, C1601 | 0.02 |
| Peptide 21 | 7283.0021 | canonical | VGYLQPRTF (SEQ ID NO: 39) | SARS-CoV-2 | S | 9 | C1601 | 0.63 |
| Peptide 22 | 7283.0022 | canonical | QLTPTWRVY (SEQ ID NO: 38) | SARS-CoV-2 | S | 9 | C1601 | 0.77 |
| Peptide 23 | 7283.0023 | non-canonical | MLLGSMLYM (SEQ ID NO: 4) | SARS-CoV-2 | ORFS.iORF1 | 9 | A0201 | 2.16 |
| Peptide 24 | 7283.0024 | canonical | YLNSTNVTI (SEQ ID NO: 24) | SARS-CoV-2 | nsp3 | 9 | A0201 | 0.14 |
| Peptide 25 | 7283.0025 | canonical | VATSRTLSY (SEQ ID NO: 41) | SARS-CoV-2 | M | 9 | C1601 | 0.00 |
| Peptide 26 | 7283.0026 | canonical | LATNNLVVM (SEQ ID NO: 16) | SARS-CoV-2 | nsp2 | 9 | C1203, C1601 | 0.08 |
| Peptide 27 | 7283.0027 | canonical | STSAFVETV (SEQ ID NO: 19) | SARS-CoV-2 | nsp2 | 9 | A0201 | 1.31 |
| Peptide 28 | 7283.0028 | canonical | FGDDTVIEV (SEQ ID NO: 23) | SARS-CoV-2 | nsp3 | 9 | A0201 | 0.53 |
| Peptide 29 | 7283.0029 | canonical | APRITFGGP (SEQ ID NO: 42) | SARS-CoV-2 | N | 9 | B0702 | 3.06 |
| Peptide 30 | 7283.0030 | non-canonical | ELPDEFVVV (SEQ ID NO: 12) | SARS-CoV-2 | ORF9b | 9 | A0201 | 0.77 |
| Peptide 31 | 7283.0031 | non-canonical | KAFQLTPIAV (SEQ ID NO: 13) | SARS-CoV-2 | ORF9b | 10 | A0201 | 0.57 |

| Peptide ID | HLA-A*01:01 | HLA-A*02:01 | HLA-A*26:01 | HLA-B*07:02 | HLA-B*15:01 | HLA-B*18:01 | HLA-B*44:02 | HLA-B*44:03 | HLA-B*51:01 |
|---|---|---|---|---|---|---|---|---|---|
| Peptide 1 | — | — | — | **6.1** | — | — | — | — | — |
| Peptide 2 | — | — | — | — | — | — | — | — | — |
| Peptide 3 | — | **20** | — | — | 1585 | — | — | — | — |
| Peptide 4 | — | 2002 | 884 | **168** | 8552 | — | — | — | — |
| Peptide 5 | — | +++ | 40310 | 14300 | 1500 | — | 25960 | 24304 | — |
| Peptide 6 | — | **1.6** | 72 | — | 35095 | 1133 | — | — | — |
| Peptide 7 | — | — | — | — | 356 | — | — | — | 22730 |
| Peptide 8 | — | — | 6.7 | — | 2.7 | 35856 | — | — | — |
| Peptide 9 | — | 495 | 734 | 8546 | 2546 | 49532 | — | — | 207 |
| Peptide 10 | — | — | 18805 | — | 78 | **1.1** | 50 | **0.41** | — |
| Peptide 12 | — | 3891 | — | — | 14707 | **35** | 35395 | **208** | — |
| Peptide 13 | — | — | — | — | 13435 | 3353 | 5258 | 1802 | — |
| Peptide 14 | — | 7908 | 732 | — | 44304 | 22862 | — | — | — |
| Peptide 15 | — | 9089 | **2.6** | — | 454 | 17434 | 18268 | 10811 | — |
| Peptide 16 | — | 11813 | — | — | 1449 | — | — | — | — |
| Peptide 17 | — | — | 7.8 | — | 4934 | — | 37214 | — | — |
| Peptide 18 | 39796 | — | 875 | — | 6.9 | **0.37** | 16 | **8.2** | — |
| Peptide 19 | — | 13022 | 9548 | 52825 | 2054 | +++ | 2795 | 1283 | 12791 |
| Peptide 20 | — | 1165 | 43443 | — | — | — | — | 8106 | 536 |

TABLE 4 -continued

| In-vitro binding measurements of HLA-I peptides and purified MHC complexes. | | | | | | | | | |
|---|---|---|---|---|---|---|---|---|---|
| Peptide 21 | — | — | — | — | 777 | 707 | — | — | 2393 |
| Peptide 22 | — | — | — | — | **11** | — | — | — | — |
| Peptide 23 | — | **+++** | 45517 | — | **1.1** | — | 18915 | — | 7872 |
| Peptide 24 | — | **12** | — | 7933 | **1.2** | — | — | 49631 | 3621 |
| Peptide 25 | 18751 | — | 11838 | — | **267** | — | — | — | — |
| Peptide 26 | — | — | — | **55** | **315** | — | 40182 | 46503 | 32710 |
| Peptide 27 | 12684 | **26** | 12065 | 8863 | 10440 | — | — | — | — |
| Peptide 28 | — | **3.8** | — | — | 2382 | — | — | — | 45711 |
| Peptide 29 | — | 893 | — | **59** | — | — | — | — | — |
| Peptide 30 | — | **460** | 6860 | — | — | — | — | — | — |
| Peptide 31 | — | **7.8** | — | 8598 | 1203 | 3872 | — | 16437 | 38654 |

Figure 7C:
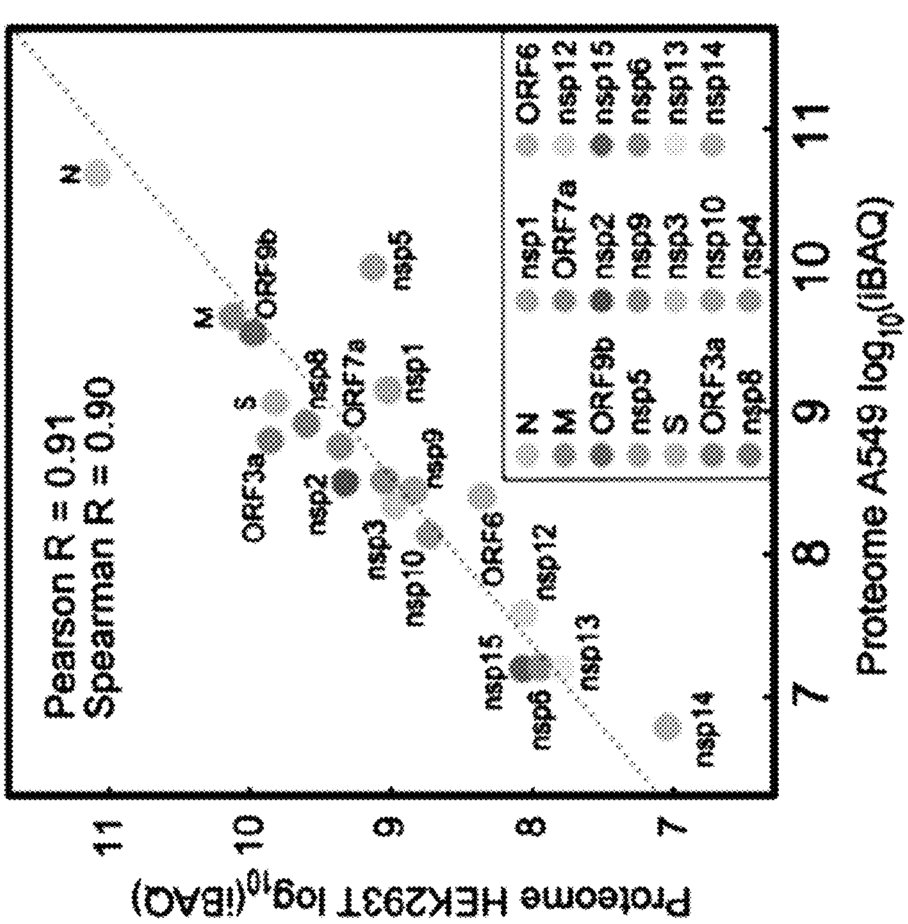
Figure 7D:
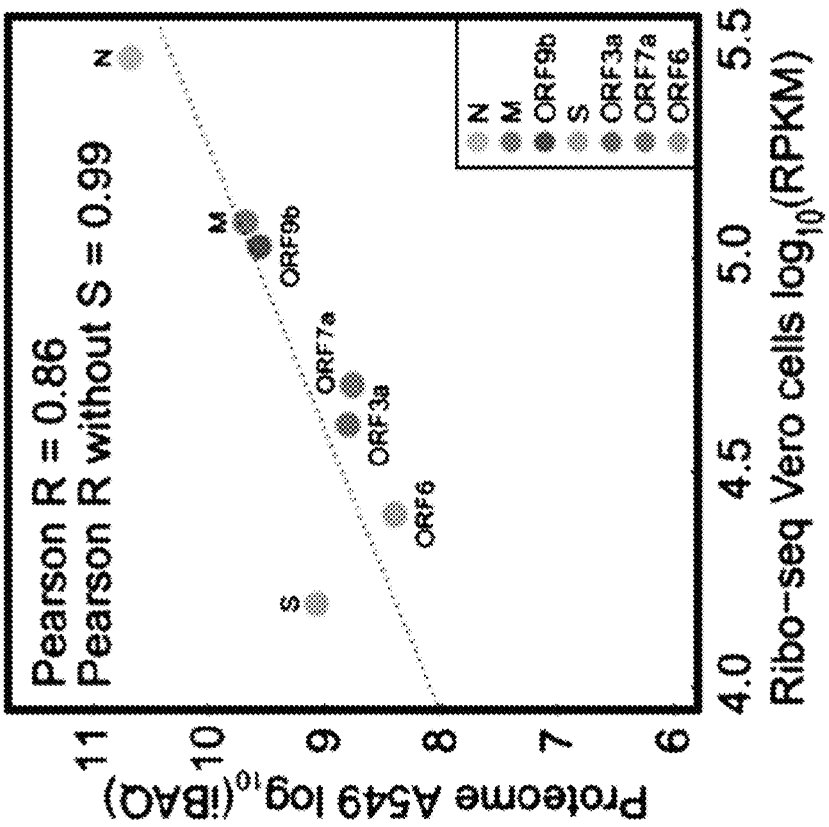
Figure 7E:
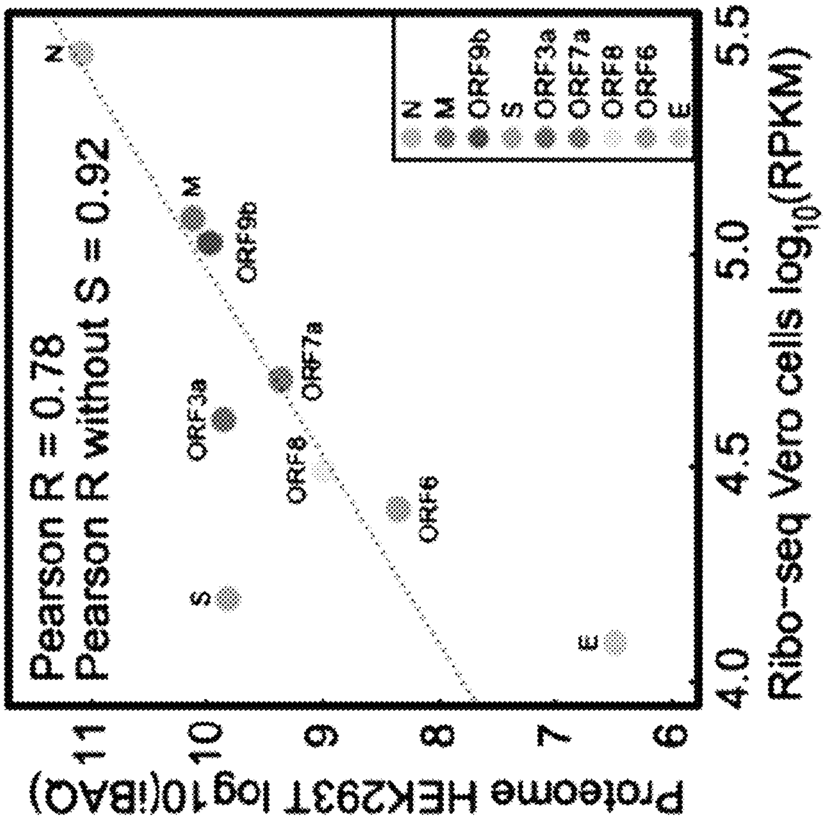

A dash indicates $IC_{50}$ >70000 nM.
Binding <500 nM highlighted by bold font.
+++ indicates $IC_{50}$ <0.5 nM.
Underlined indicates an assigned allele Surprisingly, only one HLA-I peptide with an atypical HLA-B*07:02 binding motif was detected from N, a SARS-COV-2 protein expected to be highly abundant based on previous RNA-seq and Ribo-seq studies (Finkel et al., 2020b; Kim et al., 2020). To test if this low representation could be explained by lower expression of N in our experiment, the whole proteome mass spectrometry data generated from the flowthrough of the HLA-IP was examined. A strong correlation was found between the abundance of viral proteins in the proteome of the two cell lines in our study (Pearson R=0.91, FIG. 7C), and with recently published Ribo-seq translation measurements in infected Vero cells (Finkel et al., 2020b) (Pearson R=0.86 and R=0.78 for A549 and HEK293T, respectively; FIGS. 7D and 7E and Table 5A). The N protein remained the most abundant viral protein in both cell lines.

Figure 7F:
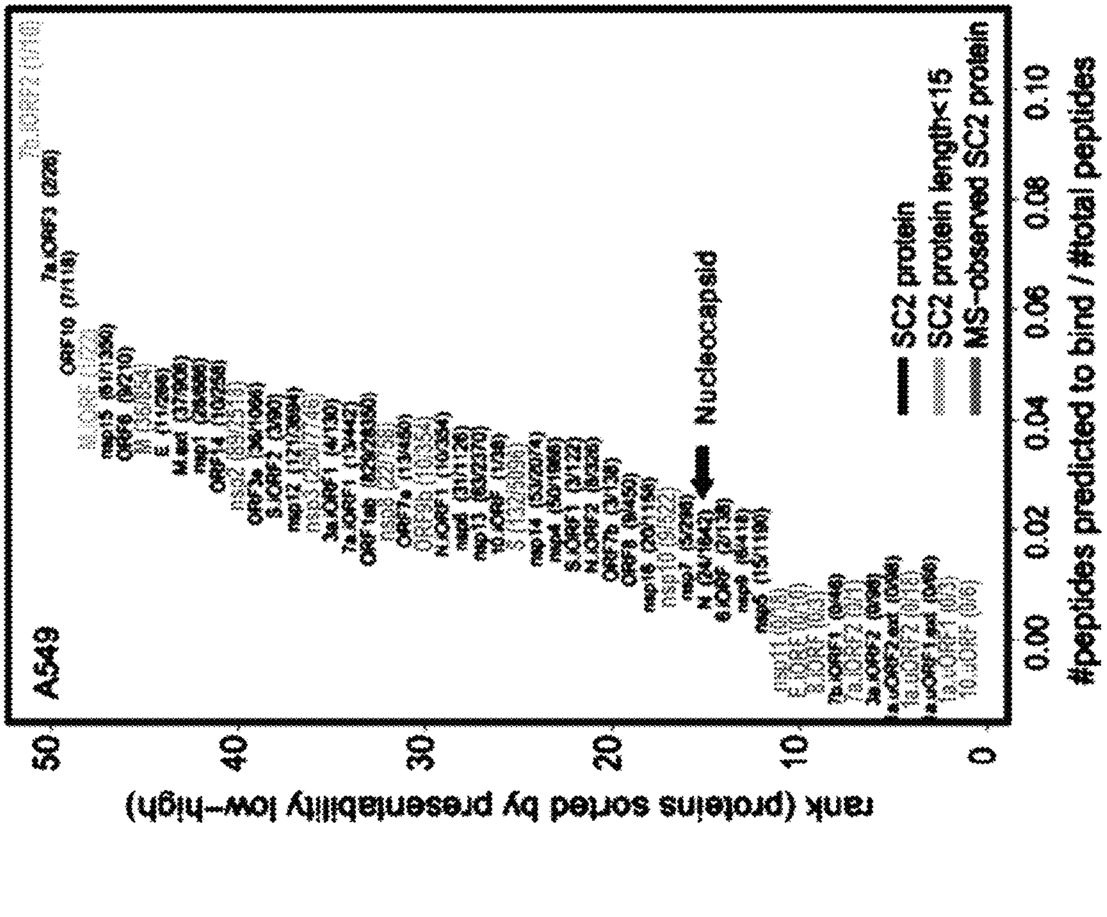
Figure 7G:
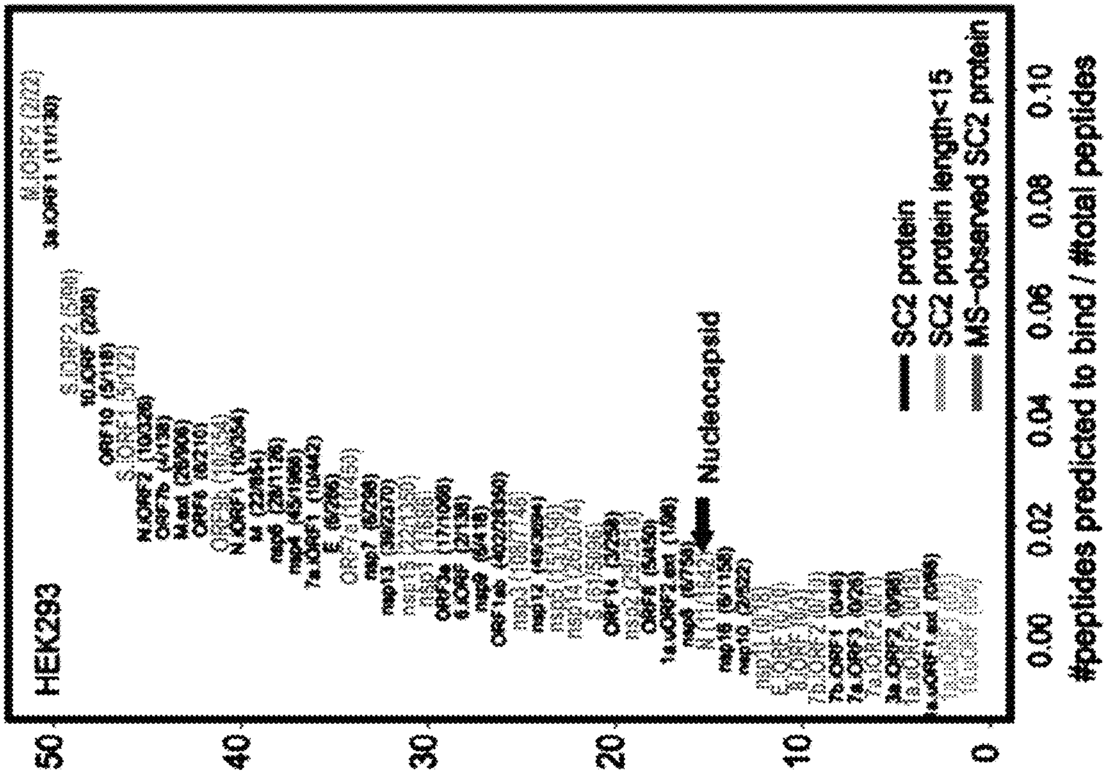
Figure 7H:
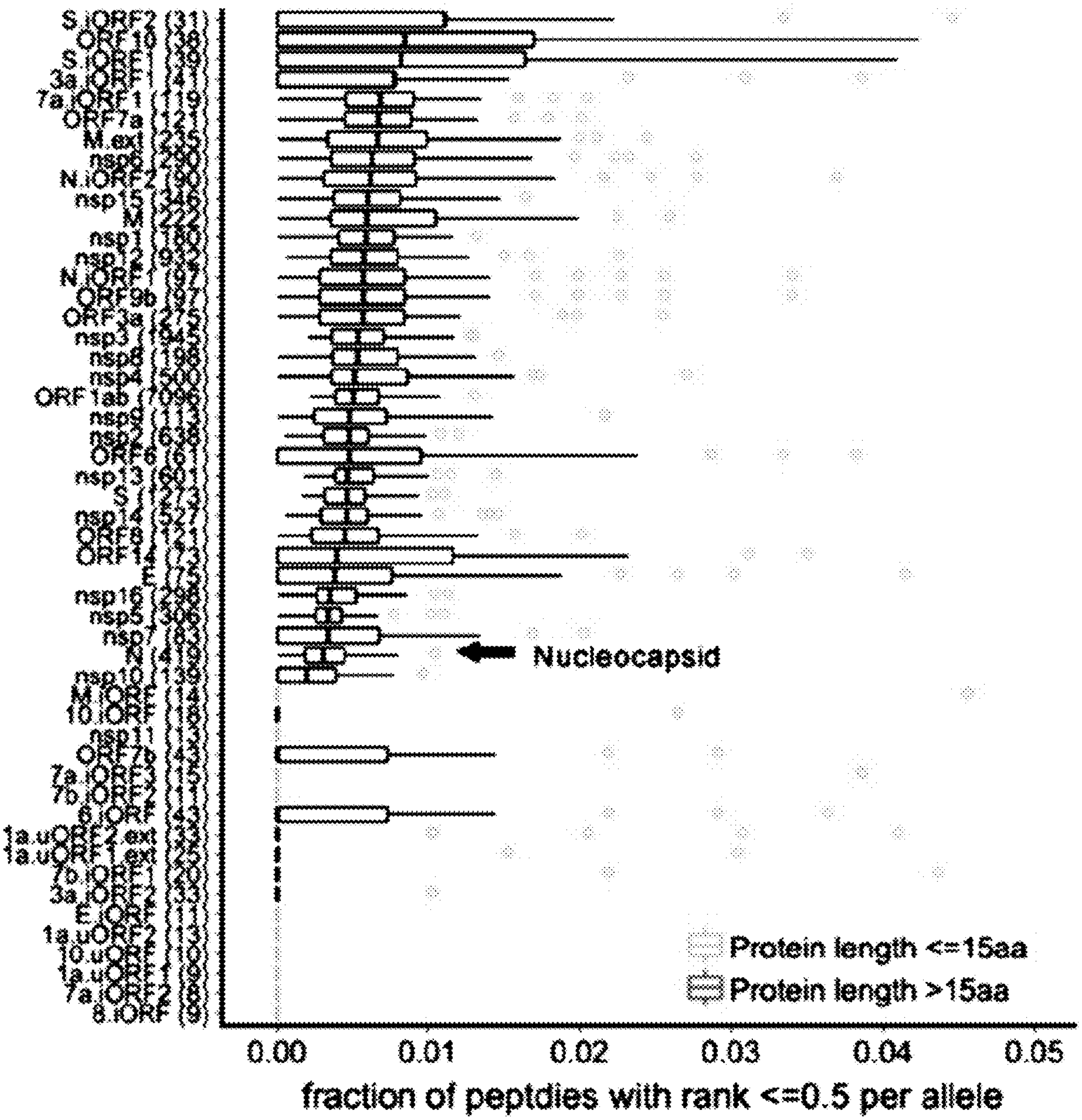

Without being bound by theory, another potential explanation for reduced HLA-I presentation of N derived peptides was hypothesized, namely that the protein harbors fewer peptides compatible with the HLA binding motifs. To test if the low presentation of peptides from N stems from intrinsic properties of the protein sequence, we computed for each SARS-COV-2 ORF the ratio between the number of peptides that are predicted to be presented by at least one of the HLA-I alleles in each cell line and the number of total 8-11mers. Notably, N harbors less presentable peptides than most SARS-COV-2 proteins in both cell lines (FIGS. 7F-7G and Table 5B). The analysis was then expanded to 92 HLA-I alleles with high population coverage and with immunopeptidome-trained predictors (Sarkizova et al., 2020) (FIG. 7H and Table 5B). This analysis implied that N is among the least presentable canonical proteins of SARS-COV-2, exceeded only by nsp10, nsp11 and ORF7b. Nonetheless, an nsp10 derived HLA-I peptide was detected in A549 cells (FIG. 7A). Together, these results hint that N might be less presented than expected by its high expression levels in infected cells (about 10-fold greater than the next most abundant viral protein, FIG. 7C).

Tables 5A-5B show SARS-COV-2 protein abundance and presentability. Table 5A shows SARS-COV-2 protein expression values as determined by whole proteome measurements in A549 and HEK293T cells and Ribo-Seq translation measurements that were previously published for Vero cells (Finkel et al., 2020b)). iBAQ-intensity-based absolute quantification. Table 5B shows HLA-I presentability estimates of SARS-COV-2 ORFs based on HLAthena predictions.

TABLE 5A

| SARS-CoV-2 protein abundance. | | | |
|---|---|---|---|
| SARS-CoV-2 Protein* | Proteome A549 log10(iBAQ) | Proteome HEK293T log10(iBAQ) | Ribo-seq Finkel et. al. (chx mean RPKM) |
| N | 10.6838 | 11.0857 | 293655.1145 |
| M | 9.6832 | 10.1197 | 121179.8465 |
| ORF9b | 9.5643 | 9.974 | 106480.3716 |
| nsp5 | 10.0264 | 9.1273 | NaN |
| S | 9.0701 | 9.8182 | 15648.6866 |
| ORF3a | 8.8004 | 9.8546 | 40845.54295 |
| nsp8 | 8.9184 | 9.5997 | NaN |
| nsp1 | 9.1659 | 9.0199 | NaN |
| ORF7a | 8.7613 | 9.3614 | 50612.85941 |
| ORF8 | NaN | 8.9932 | 31104.73178 |
| nsp2 | 8.5059 | 9.3273 | NaN |
| nsp9 | 8.5188 | 9.044 | NaN |
| nsp3 | 8.3431 | 8.9745 | NaN |
| nsp10 | 8.4466 | 8.8422 | NaN |
| nsp4 | 8.1335 | 8.7269 | NaN |
| ORF6 | 8.4021 | 8.3568 | 25280.79667 |
| nsp12 | 7.5873 | 8.0576 | NaN |
| nsp15 | 7.1958 | 8.069 | NaN |
| nsp6 | 7.2054 | 7.9413 | NaN |
| nsp16 | NaN | 7.5285 | NaN |
| nsp13 | 7.1948 | 7.7905 | NaN |
| nsp7 | NaN | 7.039 | NaN |
| nsp14 | 6.7825 | 7.0481 | NaN |
| E | NaN | 6.4898 | 12351.48544 |

TABLE 5B

| SARS-CoV-2 presentability estimates. | | | | | |
|---|---|---|---|---|---|
| name | lenAA | total number of peptides (8-11mers) | number of pepties predicted to bind | fraction of peptides predicted to bind | rank (low-high) |
| A549 | | | | | |
| 10.uORF | 10 | 6 | 0 | 0.0000 | 1 |
| 1a.uORF1 | 9 | 3 | 0 | 0.0000 | 2 |
| 1a.uORF1.ext | 25 | 66 | 0 | 0.0000 | 3 |
| 1a.uORF2 | 13 | 18 | 0 | 0.0000 | 4 |
| 1a.uORF2.ext | 33 | 98 | 0 | 0.0000 | 5 |
| 3a.iORF2 | 33 | 98 | 0 | 0.0000 | 6 |
| 7a.iORF2 | 8 | 1 | 0 | 0.0000 | 7 |
| 7b.iORF1 | 20 | 46 | 0 | 0.0000 | 8 |
| 8.iORF | 9 | 3 | 0 | 0.0000 | 9 |
| E.iORF | 11 | 10 | 0 | 0.0000 | 10 |
| nsp11 | 13 | 18 | 0 | 0.0000 | 11 |
| nsp5 | 306 | 1190 | 15 | 0.0126 | 12 |
| nsp9 | 113 | 418 | 6 | 0.0144 | 13 |
| 6.iORF | 43 | 138 | 2 | 0.0145 | 14 |
| N | 419 | 1642 | 24 | 0.0146 | 15 |
| nsp7 | 83 | 298 | 5 | 0.0168 | 16 |
| nsp10 | 139 | 522 | 9 | 0.0172 | 17 |
| nsp16 | 298 | 1158 | 20 | 0.0173 | 18 |
| ORF8 | 121 | 450 | 9 | 0.0200 | 19 |
| ORF7b | 43 | 138 | 3 | 0.0217 | 20 |
| N.iORF2 | 90 | 326 | 8 | 0.0245 | 21 |
| S.iORF1 | 39 | 122 | 3 | 0.0246 | 22 |
| nsp4 | 500 | 1966 | 50 | 0.0254 | 23 |
| nsp14 | 527 | 2074 | 53 | 0.0256 | 24 |
| S | 1273 | 5096 | 132 | 0.0259 | 25 |
| 10.iORF | 18 | 38 | 1 | 0.0263 | 26 |
| nsp13 | 601 | 2370 | 63 | 0.0266 | 27 |
| nsp6 | 290 | 1126 | 31 | 0.0275 | 28 |
| N.iORF1 | 97 | 354 | 10 | 0.0282 | 29 |
| ORF9b | 97 | 354 | 10 | 0.0282 | 30 |
| ORF7a | 121 | 450 | 13 | 0.0289 | 31 |
| nsp8 | 198 | 758 | 22 | 0.0290 | 32 |
| ORF1ab | 7096 | 28350 | 829 | 0.0292 | 33 |
| 7a.iORF1 | 119 | 442 | 13 | 0.0294 | 34 |
| 3a.iORF1 | 41 | 130 | 4 | 0.0308 | 35 |
| nsp3 | 1945 | 7746 | 250 | 0.0323 | 36 |
| nsp12 | 932 | 3694 | 121 | 0.0328 | 37 |
| S.iORF2 | 31 | 90 | 3 | 0.0333 | 38 |
| ORF3a | 275 | 1066 | 36 | 0.0338 | 39 |
| nsp2 | 638 | 2518 | 89 | 0.0353 | 40 |
| ORF14 | 73 | 258 | 10 | 0.0388 | 41 |
| nsp1 | 180 | 686 | 28 | 0.0408 | 42 |
| M.ext | 235 | 906 | 37 | 0.0408 | 43 |
| E | 75 | 266 | 11 | 0.0414 | 44 |
| M | 222 | 854 | 36 | 0.0422 | 45 |
| ORF6 | 61 | 210 | 9 | 0.0429 | 46 |
| nsp15 | 346 | 1350 | 61 | 0.0452 | 47 |
| M.iORF | 14 | 22 | 1 | 0.0455 | 48 |
| ORF10 | 38 | 118 | 7 | 0.0593 | 49 |
| 7a.iORF3 | 15 | 26 | 2 | 0.0769 | 50 |
| 7b.iORF2 | 11 | 10 | 1 | 0.1000 | 51 |
| HEK293T | | | | | |
| 10.uORF | 10 | 6 | 0 | 0.0000 | 1 |
| 1a.uORF1 | 9 | 3 | 0 | 0.0000 | 2 |
| 1a.uORF1.ext | 25 | 66 | 0 | 0.0000 | 3 |
| 1a.uORF2 | 13 | 18 | 0 | 0.0000 | 4 |
| 3a.iORF2 | 33 | 98 | 0 | 0.0000 | 5 |
| 7a.iORF2 | 8 | 1 | 0 | 0.0000 | 6 |
| 7a.iORF3 | 15 | 26 | 0 | 0.0000 | 7 |
| 7b.iORF1 | 20 | 46 | 0 | 0.0000 | 8 |
| 7b.iORF2 | 11 | 10 | 0 | 0.0000 | 9 |
| 8.iORF | 9 | 3 | 0 | 0.0000 | 10 |
| E.iORF | 11 | 10 | 0 | 0.0000 | 11 |
| nsp11 | 13 | 18 | 0 | 0.0000 | 12 |
| nsp10 | 139 | 522 | 2 | 0.0038 | 13 |
| nsp16 | 298 | 1158 | 6 | 0.0052 | 14 |
| N | 419 | 1642 | 11 | 0.0067 | 15 |
| nsp8 | 198 | 758 | 6 | 0.0079 | 16 |
| 1a.uORF2.ext | 33 | 98 | 1 | 0.0102 | 17 |
| ORF8 | 121 | 450 | 5 | 0.0111 | 18 |

TABLE 5B-continued

| SARS-CoV-2 presentability estimates. | | | | | |
|---|---|---|---|---|---|
| nsp2 | 638 | 2518 | 29 | 0.0115 | 19 |
| ORF14 | 73 | 258 | 3 | 0.0116 | 20 |
| S | 1273 | 5096 | 61 | 0.0120 | 21 |
| nsp14 | 527 | 2074 | 26 | 0.0125 | 22 |
| nsp5 | 306 | 1190 | 15 | 0.0126 | 23 |
| nsp12 | 932 | 3694 | 49 | 0.0133 | 24 |
| nsp3 | 1945 | 7746 | 108 | 0.0139 | 25 |
| ORF1ab | 7096 | 28350 | 402 | 0.0142 | 26 |
| nsp9 | 113 | 418 | 6 | 0.0144 | 27 |
| 6.iORF | 43 | 138 | 2 | 0.0145 | 28 |
| ORF3a | 275 | 1066 | 17 | 0.0159 | 29 |
| nsp1 | 180 | 686 | 11 | 0.0160 | 30 |
| nsp15 | 346 | 1350 | 22 | 0.0163 | 31 |
| nsp13 | 601 | 2370 | 39 | 0.0165 | 32 |
| nsp7 | 83 | 298 | 6 | 0.0201 | 33 |
| ORF7a | 121 | 450 | 10 | 0.0222 | 34 |
| E | 75 | 266 | 6 | 0.0226 | 35 |
| 7a.iORF1 | 119 | 442 | 10 | 0.0226 | 36 |
| nsp4 | 500 | 1966 | 45 | 0.0229 | 37 |
| nsp6 | 290 | 1126 | 28 | 0.0249 | 38 |
| M | 222 | 854 | 22 | 0.0258 | 39 |
| N.iORF1 | 97 | 354 | 10 | 0.0282 | 40 |
| ORF9b | 97 | 354 | 10 | 0.0282 | 41 |
| ORF6 | 61 | 210 | 6 | 0.0286 | 42 |
| M.ext | 235 | 906 | 26 | 0.0287 | 43 |
| ORF7b | 43 | 138 | 4 | 0.0290 | 44 |
| N.iORF2 | 90 | 326 | 10 | 0.0307 | 45 |
| S.iORF1 | 39 | 122 | 5 | 0.0410 | 46 |
| ORF10 | 38 | 118 | 5 | 0.0424 | 47 |
| 10.iORF | 18 | 38 | 2 | 0.0526 | 48 |
| S.iORF2 | 31 | 90 | 5 | 0.0556 | 49 |
| 3a.iORF1 | 41 | 130 | 11 | 0.0846 | 50 |
| M.iORF | 14 | 22 | 2 | 0.0909 | 51 |

| 92 HLA alleles | | | | |
|---|---|---|---|---|
| name | lenAA | fraction of pepties predicted to bind (mean alleles) | fraction of pepties predicted to bind (median alleles) | rank (low-high) |
| 10.uORF | 10 | 0.0000 | 0.0000 | 1 |
| 1a.uORF1 | 9 | 0.0000 | 0.0000 | 2 |
| 7a.iORF2 | 8 | 0.0000 | 0.0000 | 3 |
| 8.iORF | 9 | 0.0000 | 0.0000 | 4 |
| 1a.uORF2 | 13 | 0.0006 | 0.0000 | 5 |
| E.iORF | 11 | 0.0011 | 0.0000 | 6 |
| 3a.iORF2 | 33 | 0.0011 | 0.0000 | 7 |
| 7b.iORF1 | 20 | 0.0014 | 0.0000 | 8 |
| 1a.uORF1.ext | 25 | 0.0018 | 0.0000 | 9 |
| 1a.uORF2.ext | 33 | 0.0035 | 0.0000 | 10 |
| 6.iORF | 43 | 0.0054 | 0.0000 | 11 |
| 7a.iORF3 | 15 | 0.0054 | 0.0000 | 12 |
| 7b.iORF2 | 11 | 0.0054 | 0.0000 | 13 |
| ORF7b | 43 | 0.0065 | 0.0000 | 14 |
| nsp11 | 13 | 0.0066 | 0.0000 | 15 |
| 10.iORF | 18 | 0.0072 | 0.0000 | 16 |
| M.iORF | 14 | 0.0128 | 0.0000 | 17 |
| nsp10 | 139 | 0.0026 | 0.0019 | 18 |
| N | 419 | 0.0034 | 0.0030 | 19 |
| nsp7 | 83 | 0.0037 | 0.0034 | 20 |
| nsp5 | 306 | 0.0035 | 0.0034 | 21 |
| nsp16 | 298 | 0.0039 | 0.0035 | 22 |
| E | 75 | 0.0069 | 0.0038 | 23 |
| ORF14 | 73 | 0.0062 | 0.0039 | 24 |
| ORF8 | 121 | 0.0048 | 0.0044 | 25 |
| nsp14 | 527 | 0.0049 | 0.0046 | 26 |
| S | 1273 | 0.0048 | 0.0046 | 27 |
| nsp13 | 601 | 0.0053 | 0.0046 | 28 |
| ORF6 | 61 | 0.0079 | 0.0048 | 29 |
| nsp2 | 638 | 0.0048 | 0.0048 | 30 |
| nsp9 | 113 | 0.0052 | 0.0048 | 31 |
| ORF1ab | 7096 | 0.0054 | 0.0050 | 32 |
| nsp4 | 500 | 0.0064 | 0.0051 | 33 |
| nsp8 | 198 | 0.0056 | 0.0053 | 34 |
| nsp3 | 1945 | 0.0057 | 0.0053 | 35 |
| ORF3a | 275 | 0.0066 | 0.0056 | 36 |

TABLE 5B-continued

| SARS-CoV-2 presentability estimates. | | | | |
|---|---|---|---|---|
| N.iORF1 | 97 | 0.0073 | 0.0056 | 37 |
| ORF9b | 97 | 0.0073 | 0.0056 | 38 |
| nsp12 | 932 | 0.0063 | 0.0057 | 39 |
| nsp1 | 180 | 0.0058 | 0.0058 | 40 |
| M | 222 | 0.0076 | 0.0059 | 41 |
| nsp15 | 346 | 0.0062 | 0.0059 | 42 |
| N.iORF2 | 90 | 0.0071 | 0.0061 | 43 |
| nsp6 | 290 | 0.0071 | 0.0062 | 44 |
| M.ext | 235 | 0.0076 | 0.0066 | 45 |
| ORF7a | 121 | 0.0065 | 0.0067 | 46 |
| 7a.iORF1 | 119 | 0.0066 | 0.0068 | 47 |
| 3a.iORF1 | 41 | 0.0094 | 0.0077 | 48 |
| S.iORF1 | 39 | 0.0080 | 0.0082 | 49 |
| ORF10 | 38 | 0.0129 | 0.0085 | 50 |
| S.iORF2 | 31 | 0.0098 | 0.0111 | 51 |

The deep coverage of the viral proteins in whole proteome analysis (24 proteins) allowed us to uncover a number of other interesting insights. While the translation of ORF1a and lab, the source polyproteins of nsps 1-16, is 10-1000 fold lower than structural ORFs (Finkel et al., 2020b), it was found that the abundance of some non-structural proteins was comparable to that of structural proteins (e.g., nsp1 and nsp8, FIG. 7C). Interestingly, although nsps 1-11 are post-translationally cleaved from the same polyproteins, their expression levels were quite variable (FIG. 7C). This finding is consistent with two additional proteomics studies of SARS-COV-2 infected cells utilizing different detergents in their lysis buffers (Schmidt et al., 2020; Stukalov et al., 2020), suggesting that the observed differences in expression are not due to detergent solubility. Moreover, nsps 12-15, which are post-translationally cleaved from polyprotein lab downstream to the frameshift signal, are indeed expressed at lower levels, as expected. Another interesting observation is that the S protein appeared as an outlier in both cell lines with higher expression in the proteome data compared to the Ribo-seq measurements, which suggests it may undergo positive post-translational regulation (FIGS. 7D-7E, computed Pearson R when omitting S was increased from 0.86 to 0.99 and 0.78 to 0.92 in A549 and HEK293T cells, respectively).

Kinetics of SARS-COV-2 Protein Expression and HLA-I Peptides Presentation

To investigate the dynamics of HLA-I presentation during infection, HLA-I immunopeptidome analysis in A549 and HEK293T cells was performed at 3, 6, 12, 18 and 24hpi. To compare the abundance of HLA-I peptides across all five time points we utilized isobaric chemical labeling with tandem mass tags (TMT) for precise relative quantification and to reduce missing values due to stochastic sampling by LC-MS/MS. Due to technical reasons, the infection time course analysis was split into two batches. The first batch contained time points 3, 6, and 24 hpi, while the second batch 12, 18, and 24 hpi. Since the 24hpi time point was common to both batches, it was used to normalize peptides from each run.

Figure 8A:
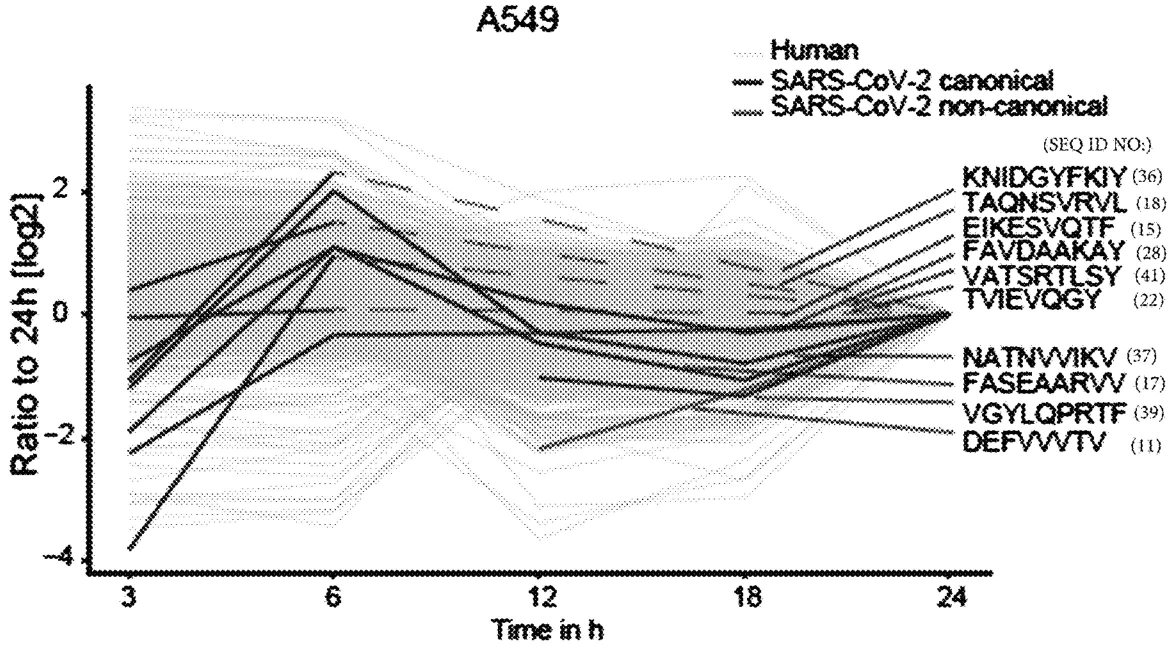
FIGS. 8A-8E—HLA-I peptides dynamics in SARS-COV-2 infected cells.
Figure 8B:
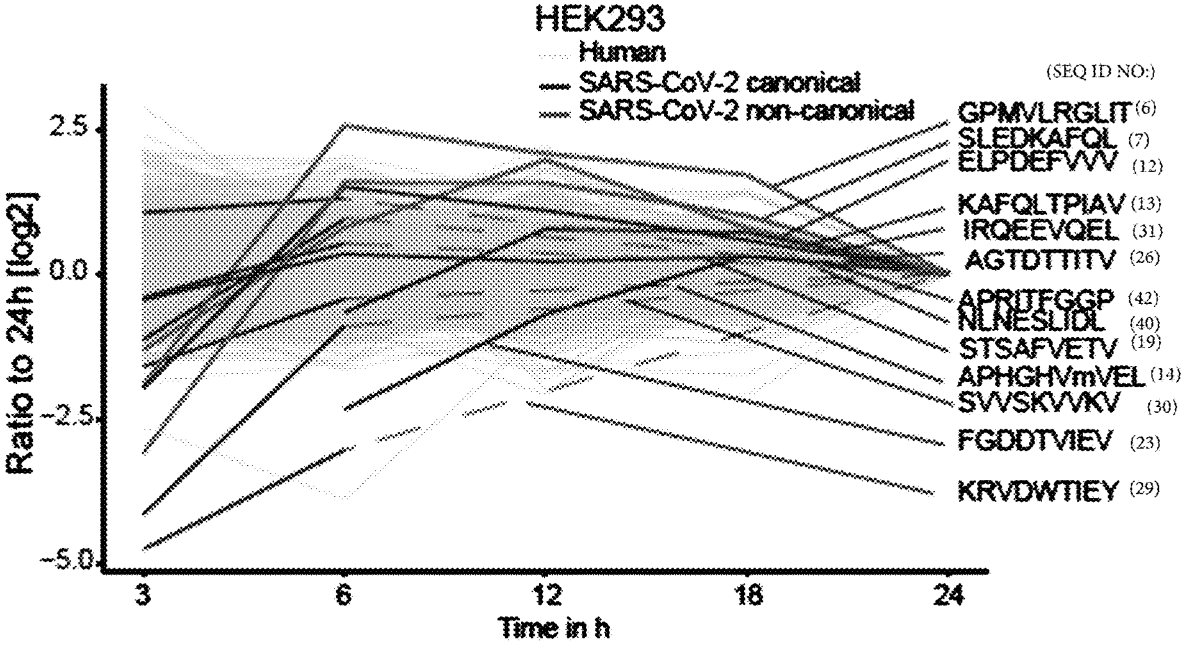

Labeling with TMT enabled the detection of 10 viral HLA-I peptides in A549 cells; four peptides were quantified across all timepoints, two were only detected in the 12|18|24 h plex, and four were only detected in the 3|6|24 h plex (see e.g., FIG. 8A and Table 3). It is likely that peptides that were detected only in the 3|6|24 h plex were also presented on HLA-I at 12 and 18hpi, however, due to separate cell culture experiments, varying instrument sensitivity and stochastic peak picking, they were not detected in the 12|18|24 h plex. Although their dynamics at 12 and 18hpi (denoted as dashed lines in FIG. 8A) cannot be inferred, three of the four peptides were presented at lower abundance at 24 in comparison to the 6hpi time point. Together with the four peptides that were observed across all time points, HLA-I presentation of viral peptides peaked at 6hpi, similarly to previous reports in vaccinia virus (Croft et al., 2013) and influenza virus (Wu et al., 2019). While some human-derived HLA-I peptides changed over time as well, the majority was fairly stable.

A similar pattern of achieving maximal viral peptides presentation in earlier time points in HEK293T cells was observed as well. Overall, 13 peptides from SARS-COV-2 were detected in TMT labeled immunopeptidome experiments, with the caveat of observing some peptides only in the 3|6|24 h plex as described above (FIG. 8B and Table 3). Examining the dynamics of HLA-I peptides observed across all time points and in the 3|6|24 h plex, it was found that similarly to A549, the abundance of some HLA-I peptides peaked at 6hpi, however, it was also observed maximal presentation at 12, 18 and 24hpi for others. Notably, peptides from non-canonical ORFs were among the most abundant peptides over time (GPMVLRGLIT (SEQ ID NO: 6) from S.iORF1/2, SLEDKAFQL (SEQ ID NO: 7) and ELPDEFVVV (SEQ ID NO: 12) from ORF9b).

Figure 8D:
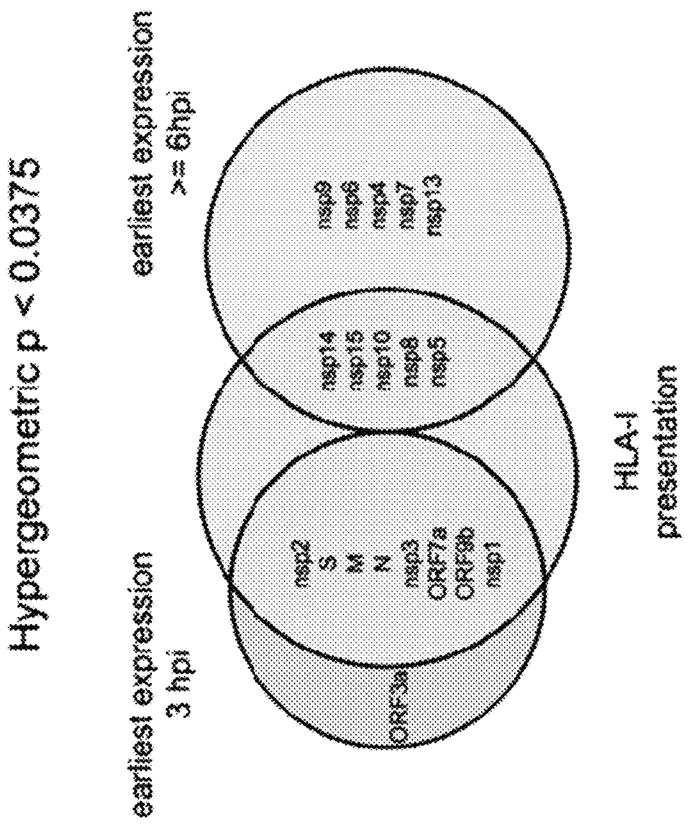
Figure 8C:
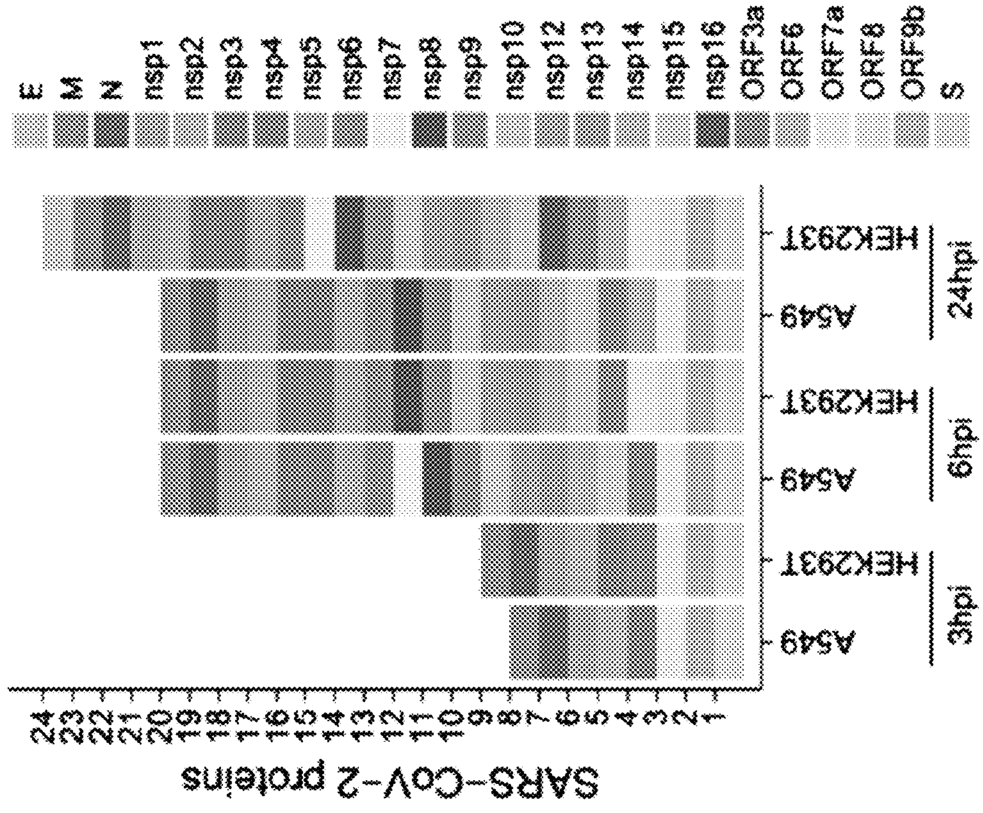
Figure 8E:
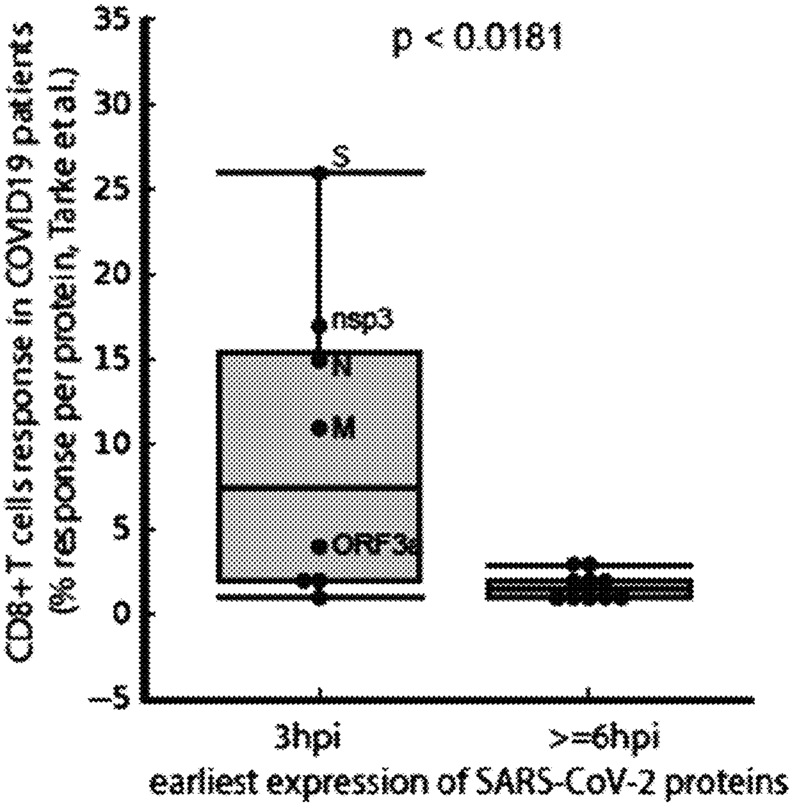

To examine the relationship between HLA peptide presentation and the time of viral protein expression, fractionated whole proteome mass spectrometry analysis was additionally performed across 3, 6, and 24hpi timepoints from the same cell lysates. While the majority of viral proteins were expressed in cells at 6hpi, only eight and nine proteins were detected at 3hpi in A549 and HEK293T cells, respectively (FIG. 8C). These proteins include S, N, M, ORF7a, ORF3a, nsp1, nsp2, and nsp3 as well as the out-of-frame ORF ORF9b. It was found that viral proteins detected as early as 3hpi contributed to HLA-I presentation more than viral proteins expressed at 6hpi or later as all proteins except ORF3a gave rise to HLA-I peptides (Hypergeometric p-value for enrichment of 3hpi expressed proteins in the pool of HLA-I presented proteins $p<0.0375$, FIG. 8D). Moreover, proteins that were detected early in our whole proteome analysis elicited stronger CD8+ T cell responses in COVID-19 convalescent patients recently measured by another study (Tarke et al., 2020) (Wilcoxon rank-sum $p<0.0181$, FIG. 8E). This observation may hint at a potential explanation to a surprising finding that nsp3 is among the four most immunogenic proteins of SARS-COV-2 in COVID-19 patients (Tarke et al., 2020). While nsp3 is not expressed at high levels, it's early expression in infected cells may contribute to presentation of nsp3-derived HLA-I peptides. Together, these findings suggest that the timing of viral protein expression is a key determinant of SARS-COV-2 antigen presentation and consecutive T cell activation.

Figure 9A:
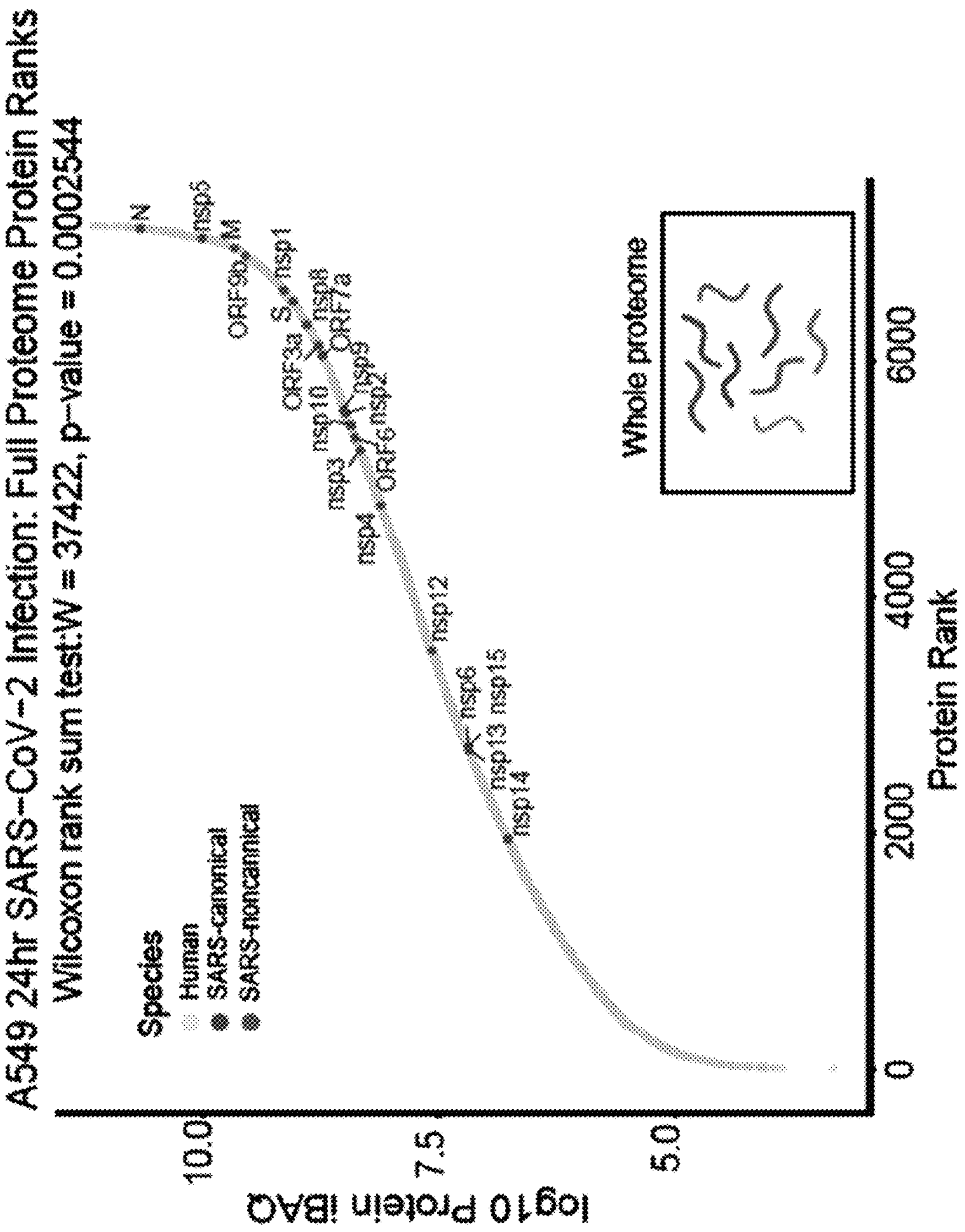
FIGS. 9A-9F—The effect of SARS-COV-2 infection on antigen presentation in host cells.
Figure 9B:
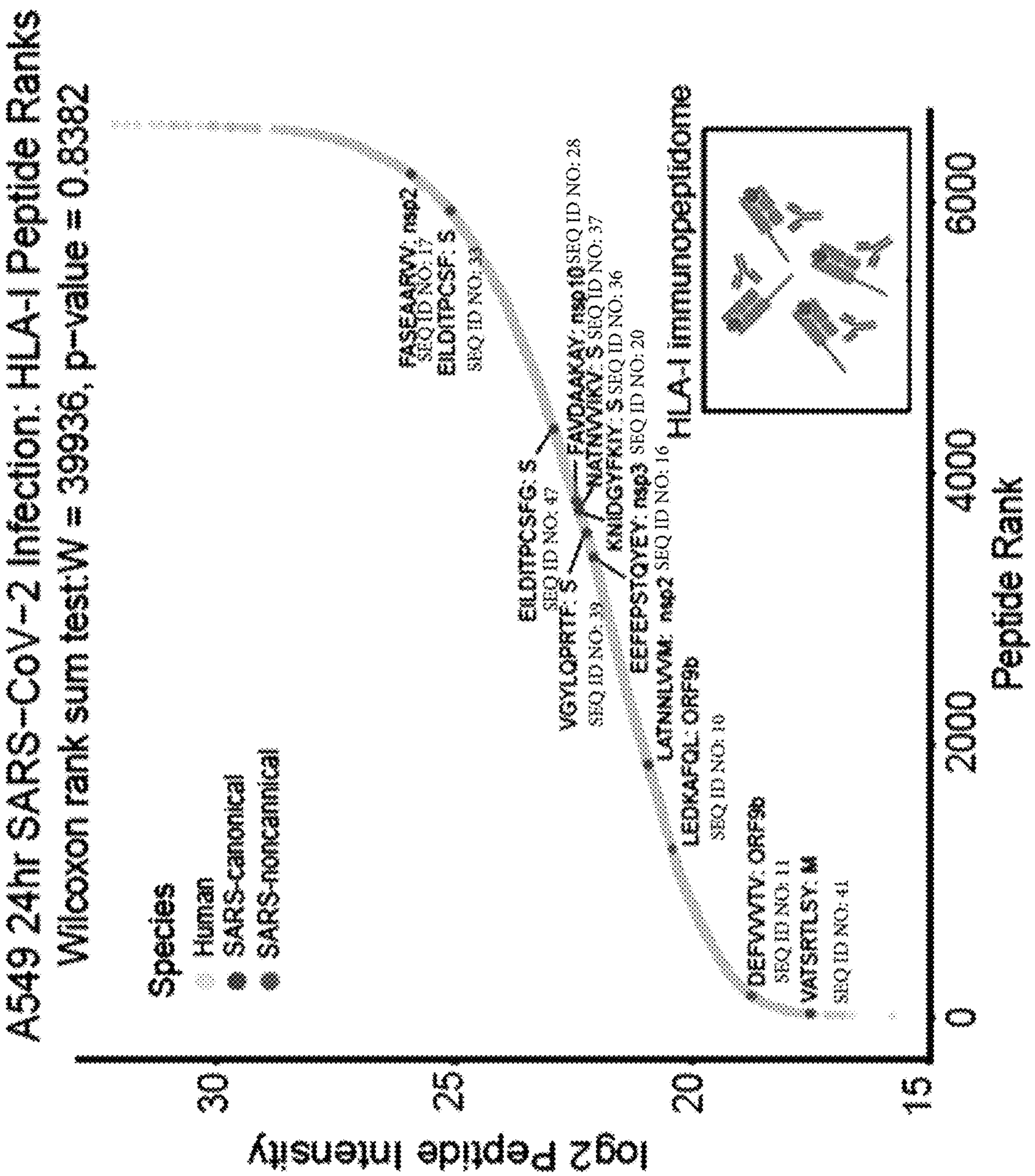
Figures 15A, 15B:
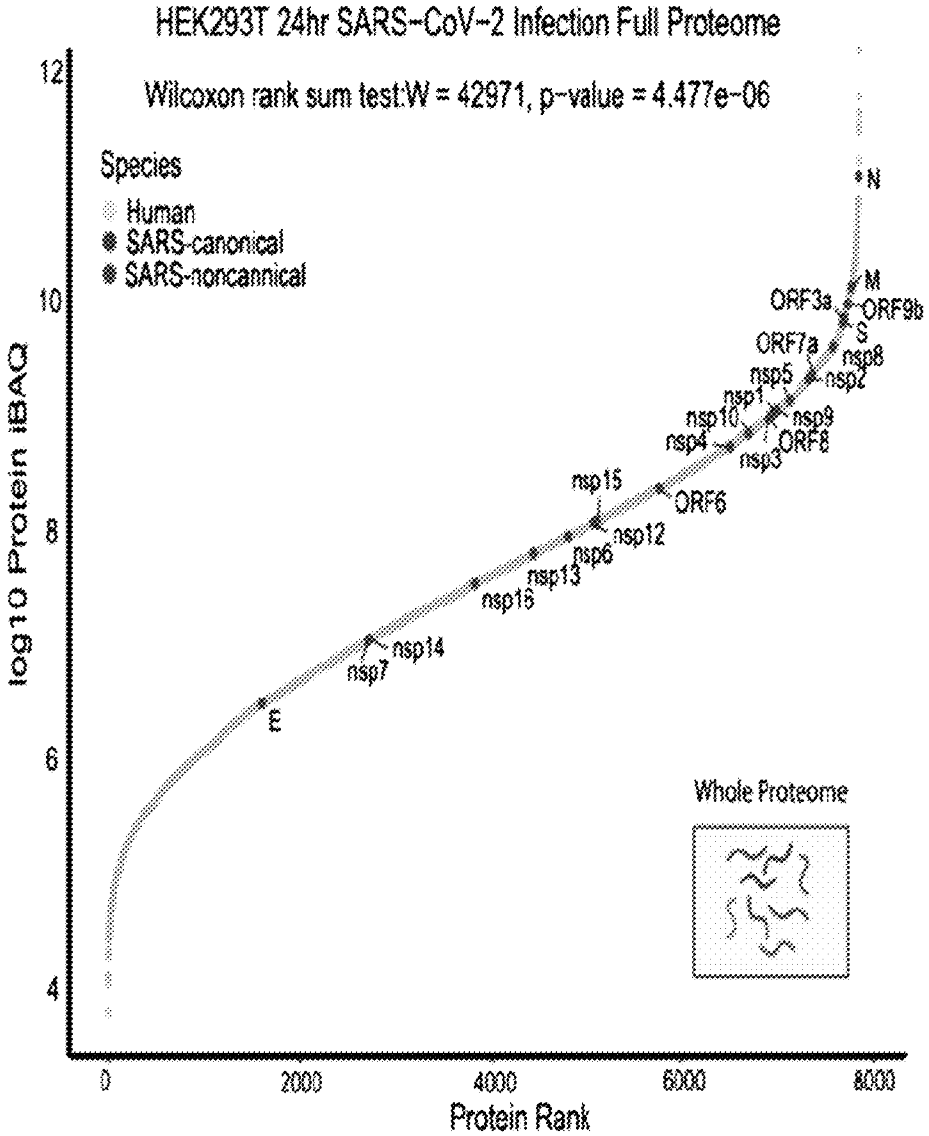
FIGS. 15A-15E—SARS-COV-2 peptides abundance and antigen presentation pathway proteins in infected cells.
Figure 15C:
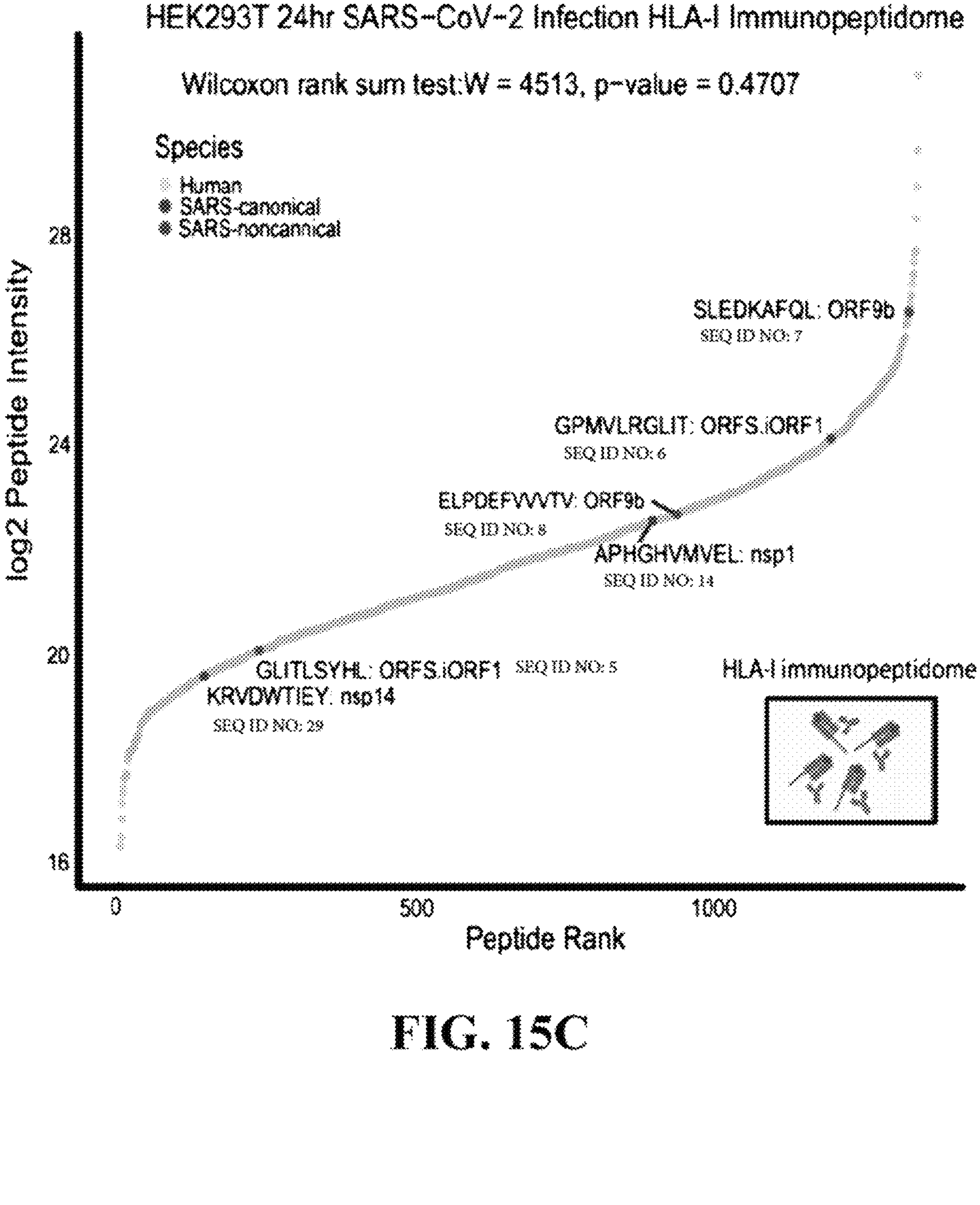

SARS-COV-2 Infection Interferes with Cellular Pathways that May Impact HLA-I Peptide Processing and Presentation To investigate how the levels of viral source proteins impact their ability to be processed and presented, we evaluated both the total abundance of viral proteins relative to host proteins and the rank of individual SARS-COV-2 proteins compared to human proteins. Although the overall viral abundance in the host proteome 24hpi is relatively low (HEK293T-2.6%; A549-3%, FIG. 15A), individual viral proteins are highly expressed and exceed most of the cellular human proteins (Wilcoxon rank-sum test, $p<10-4$ and $p<10-6$ for A549 and HEK293T cells, respectively, FIGS. 15A-15C and Tables 6A-6B and data not shown). In contrast to the high expression of their source proteins, the intensity of viral HLA-I peptides is similar to peptides from the host proteome, indicating that viral peptides are not preferentially presented in infected cells (Wilcoxon rank-sum test, p>0.8 and p>0.4 for A549 and HEK293T cells, respectively, FIGS. 9A-9B, FIGS. 15B-15C, and Tables 5A-5B). Moreover, as recently shown for influenza virus (Wu et al., 2019), we found that the intensity of the viral HLA-I peptides do not directly correlate with their source protein abundances. For example, although ORF9b is the fourth highest ranked viral protein in A549, the two HLA-I peptides derived from it are ranked toward the bottom of SARS-CoV-2 HLA-I peptides (FIGS. 9A-9B).

Tables 6A-6B show data associated with whole proteome analyses of A549 and HEK293T cells+/− SARS-COV-2 at 0, 3, 6, and 24hpi. Table 6A contains the protein groups used to plot the results from the two sample t-test results (FIGS. 9E-9F). These annotations are a combination of manual curation and combination of KEGG and GO annotations of genes from proteasomal, antigen processing, ubiquitination pathway, IFN signaling, and SARS genes. t-test results from uninfected vs. 3,6, and 24 hpi were obtained (data not shown). Table 6B contains all proteins that are statistically enriched or depleted in response to SARS-COV-2 infection in HEK293T and A549 cells. Whole proteome data from the Spectrum Mill database search from uninfected, 3,6, and 24hpi fractionated whole proteome samples was obtained (data not shown). MaxQuant LFQ results reported by this study (data not shown) were used for comparison in FIGS. 9F and 15E.

TABLE 6A

Shows the protein groups used to plot the results from the two sample t-test results (FIGS. 9E and 9F). These annotations are a combination of manual curation, KEGG, and GO annotations of genes from proteasomal pathway, antigen processing, ubiquitination pathway, IFN signaling, and SARS-CoV-2 genes.

| pathway | geneSymbol | proteinName |
|---|---|---|
| SARS | E | E |
| SARS | M | M |
| SARS | N | N |
| SARS | S | S |
| SARS | ORF3a | ORF3a |
| SARS | ORF6 | ORF6 |
| SARS | ORF7a | ORF7a |
| SARS | ORF8 | ORF8 |
| SARS | ORF9b | ORF9b |
| SARS | nsp1 | nsp1 |
| SARS | nsp2 | nsp2 |
| SARS | nsp3 | nsp3 |
| SARS | nsp4 | nsp4 |
| SARS | nsp5 | nsp5 |
| SARS | nsp6 | nsp6 |
| SARS | nsp7 | nsp7 |
| SARS | nsp8 | nsp8 |
| SARS | nsp9 | nsp9 |
| SARS | nsp10 | nsp10 |
| SARS | nsp12 | nsp12 |
| SARS | nsp13 | nsp13 |
| SARS | nsp14 | nsp14 |
| SARS | nsp15 | nsp15 |
| SARS | nsp16 | nsp16 |
| Ub | USP54 | inactive ubiquitin carboxyl-terminal hydrolase 54 isoform 2 GN = USP54 |
| Ub | USP34 | ubiquitin carboxyl-terminal hydrolase 34 GN = USP34 |
| Ub | USP53 | inactive ubiquitin carboxyl-terminal hydrolase 53 GN = USP53 |
| Ub | USP43 | ubiquitin carboxyl-terminal hydrolase 43 isoform 2 GN = USP43 |
| Ub | MYCBP2 | E3 ubiquitin-protein ligase MYCBP2 GN = MYCBP2 |
| Ub | HERC1 | probable E3 ubiquitin-protein ligase HERC1 GN = HERC1 |
| Ub | WWP1 | NEDD4-like E3 ubiquitin-protein ligase WWP1 GN = WWP1 |
| Ub | MARCH7 | E3 ubiquitin-protein ligase MARCH7 isoform a GN = MARCH7 |
| Ub | DTX3L | E3 ubiquitin-protein ligase DTX3L GN = DTX3L |
| Ub | UBE3B | ubiquitin-protein ligase E3B isoform 1 GN = UBE3B |
| Ub | USP9Y | probable ubiquitin carboxyl-terminal hydrolase FAF-Y GN = USP9Y |
| Ub | USP32 | ubiquitin carboxyl-terminal hydrolase 32 GN = USP32 |
| Ub | WWP2 | NEDD4-like E3 ubiquitin-protein ligase WWP2 isoform 4 GN = WWP2 |
| Ub | ATG10 | ubiquitin-like-conjugating enzyme ATG10 GN = ATG10 |
| Ub | HECTD4 | probable E3 ubiquitin-protein ligase HECTD4 GN = HECTD4 |
| Ub | SH3RF1 | E3 ubiquitin-protein ligase SH3RF1 GN = SH3RF1 |
| Ub | USP30 | ubiquitin carboxyl-terminal hydrolase 30 isoform 2 GN = USP30 |
| Ub | HERC2 | E3 ubiquitin-protein ligase HERC2 GN = HERC2 |
| Ub | COP1 | E3 ubiquitin-protein ligase COP1 isoform b GN = COP1 |
| Ub | RNFT1 | E3 ubiquitin-protein ligase RNFT1 GN = RNFT1 |
| Ub | UBE2E2 | ubiquitin-conjugating enzyme E2 E2 GN = UBE2E2 |
| Ub | RNF19A | E3 ubiquitin-protein ligase RNF19A GN = RNF19A |
| Ub | USP38 | ubiquitin carboxyl-terminal hydrolase 38 isoform 2 GN = USP38 |
| Ub | USP31 | ubiquitin carboxyl-terminal hydrolase 31 GN = USP31 |
| Ub | SMURF2 | E3 ubiquitin-protein ligase SMURF2 GN = SMURF2 |
| Ub | CHFR | E3 ubiquitin-protein ligase CHFR isoform 1 GN = CHFR |
| Ub | FANCL | E3 ubiquitin-protein ligase FANCL isoform 1 GN = FANCL |
| Ub | TRIM32 | E3 ubiquitin-protein ligase TRIM32 GN = TRIM32 |
| Ub | BAP1 | ubiquitin carboxyl-terminal hydrolase BAP1 GN = BAP1 |
| Ub | DTX2 | probable E3 ubiquitin-protein ligase DTX2 isoform a GN = DTX2 |
| Ub | CYLD | ubiquitin carboxyl-terminal hydrolase CYLD isoform 2 GN = CYLD |

TABLE 6A-continued

Shows the protein groups used to plot the results from the two sample t-test results (FIGS. 9E and 9F). These annotations are a combination of manual curation, KEGG, and GO annotations of genes from proteasomal pathway, antigen processing, ubiquitination pathway, IFN signaling, and SARS-CoV-2 genes.

| pathway | geneSymbol | proteinName |
|---|---|---|
| Ub | HACE1 | E3 ubiquitin-protein ligase HACE1 isoform b GN = HACE1 |
| Ub | RNF169 | E3 ubiquitin-protein ligase RNF169 GN = RNF169 |
| Ub | PDZRN3 | E3 ubiquitin-protein ligase PDZRN3 isoform 2 GN = PDZRN3 |
| Ub | USP27X | ubiquitin carboxyl-terminal hydrolase 27 GN = USP27X |
| Ub | ZNRF2 | E3 ubiquitin-protein ligase ZNRF2 GN = ZNRF2 |
| Ub | USP42 | ubiquitin carboxyl-terminal hydrolase 42 GN = USP42 |
| Ub | JADE2 | E3 ubiquitin-protein ligase Jade-2 isoform 1 GN = JADE2 |
| Ub | NEDD4L | E3 ubiquitin-protein ligase NEDD4-like isoform 1 GN = NEDD4L |
| Ub | TRIM37 | E3 ubiquitin-protein ligase TRIM37 isoform a GN = TRIM37 |
| Ub | TOPORS | E3 ubiquitin-protein ligase Topors isoform 1 GN = TOPORS |
| Ub | TRAF7 | E3 ubiquitin-protein ligase TRAF7 GN = TRAF7 |
| Ub | RNF111 | E3 ubiquitin-protein ligase Arkadia isoform 1 GN = RNF111 |
| Ub | RNF138 | E3 ubiquitin-protein ligase RNF138 isoform 1 GN = RNF138 |
| Ub | TRIM13 | E3 ubiquitin-protein ligase TRIM13 isoform 2 GN = TRIM13 |
| Ub | RNF26 | E3 ubiquitin-protein ligase RNF26 GN = RNF26 |
| Ub | TRIM69 | #N/A |
| Ub | USP4 | ubiquitin carboxyl-terminal hydrolase 4 isoform a GN = USP4 |
| Ub | MARCH9 | E3 ubiquitin-protein ligase MARCH9 precursor GN = MARCH9 |
| Ub | RLIM | E3 ubiquitin-protein ligase RLIM GN = RLIM |
| Ub | UBR3 | E3 ubiquitin-protein ligase UBR3 GN = UBR3 |
| Ub | SMURF1 | E3 ubiquitin-protein ligase SMURF1 isoform 3 GN = SMURF1 |
| Ub | HERPUD1 | homocysteine-responsive endoplasmic reticulum-resident ubiquitin-like domain member 1 protein isoform 2 GN = HERPUD1 |
| Ub | SHPRH | E3 ubiquitin-protein ligase SHPRH isoform a GN = SHPRH |
| Ub | MKRN1 | E3 ubiquitin-protein ligase makorin-1 isoform 1 GN = MKRN1 |
| Ub | RBBP6 | E3 ubiquitin-protein ligase RBBP6 isoform 1 GN = RBBP6 |
| Ub | RNF146 | E3 ubiquitin-protein ligase RNF146 isoform a GN = RNF146 |
| Ub | DZIP3 | E3 ubiquitin-protein ligase DZIP3 GN = DZIP3 |
| Ub | TRIM21 | E3 ubiquitin-protein ligase TRIM21 GN = TRIM21 |
| Ub | UBE3D | E3 ubiquitin-protein ligase E3D isoform 1 GN = UBE3D |
| Ub | HERC6 | probable E3 ubiquitin-protein ligase HERC6 isoform 2 GN = HERC6 |
| Ub | RFWD3 | E3 ubiquitin-protein ligase RFWD3 GN = RFWD3 |
| Ub | TRIM56 | E3 ubiquitin-protein ligase TRIM56 GN = TRIM56 |
| Ub | RNF168 | E3 ubiquitin-protein ligase RNF168 GN = RNF168 |
| Ub | USP8 | ubiquitin carboxyl-terminal hydrolase 8 isoform a GN = USP8 |
| Ub | RNF216 | E3 ubiquitin-protein ligase RNF216 isoform a GN = RNF216 |
| Ub | MIB1 | E3 ubiquitin-protein ligase MIB1 GN = MIB1 |
| Ub | CBLB | E3 ubiquitin-protein ligase CBL-B isoform a GN = CBLB |
| Ub | USP20 | ubiquitin carboxyl-terminal hydrolase 20 GN = USP20 |
| Ub | AMFR | E3 ubiquitin-protein ligase AMFR isoform c GN = AMFR |
| Ub | UBAP2L | ubiquitin-associated protein 2-like isoform a GN = UBAP2L |
| Ub | RNF123 | E3 ubiquitin-protein ligase RNF123 GN = RNF123 |
| Ub | RNF170 | E3 ubiquitin-protein ligase RNF170 isoform a GN = RNF170 |
| Ub | USP16 | ubiquitin carboxyl-terminal hydrolase 16 isoform b GN = USP16 |
| Ub | TTC3 | E3 ubiquitin-protein ligase TTC3 isoform 3 GN = TTC3 |
| Ub | USP28 | ubiquitin carboxyl-terminal hydrolase 28 isoform b GN = USP28 |
| Ub | RNF34 | E3 ubiquitin-protein ligase RNF34 isoform 2 GN = RNF34 |
| Ub | RNF31 | E3 ubiquitin-protein ligase RNF31 isoform 1 GN = RNF31 |
| Ub | RNF4 | E3 ubiquitin-protein ligase RNF4 isoform 1 GN = RNF4 |
| Ub | MID2 | probable E3 ubiquitin-protein ligase MID2 isoform 1 GN = MID2 |
| Ub | NEDD4 | E3 ubiquitin-protein ligase NEDD4 isoform 1 GN = NEDD4 |
| Ub | PJA2 | E3 ubiquitin-protein ligase Praja-2 GN = PJA2 |
| Ub | UBR1 | E3 ubiquitin-protein ligase UBR1 GN = UBR1 |
| Ub | UBR2 | E3 ubiquitin-protein ligase UBR2 isoform 3 GN = UBR2 |
| Ub | DESI2 | deubiquitinase DESI2 isoform 1 GN = DESI2 |
| Ub | RNF220 | E3 ubiquitin-protein ligase RNF220 isoform 1 GN = RNF220 |
| Ub | LNX1 | E3 ubiquitin-protein ligase LNX isoform a GN = LNX1 |
| Ub | TRIM33 | E3 ubiquitin-protein ligase TRIM33 isoform alpha GN = TRIM33 |
| Ub | ZRANB1 | ubiquitin thioesterase ZRANB1 GN = ZRANB1 |
| Ub | RAD18 | E3 ubiquitin-protein ligase RAD18 GN = RAD18 |
| Ub | TRIM38 | E3 ubiquitin-protein ligase TRIM38 GN = TRIM38 |
| Ub | OTULINL | inactive ubiquitin thioesterase FAM105A GN = OTULINL |
| Ub | UBE2J1 | ubiquitin-conjugating enzyme E2 JI GN = UBE2J1 |
| Ub | RNF213 | E3 ubiquitin-protein ligase RNF213 isoform 3 GN = RNF213 |
| Ub | RNF135 | E3 ubiquitin-protein ligase RNF135 isoform 1 GN = RNF135 |
| Ub | MIB2 | E3 ubiquitin-protein ligase MIB2 isoform 2 GN = MIB2 |
| Ub | USP1 | ubiquitin carboxyl-terminal hydrolase 1 GN = USP1 |
| Ub | RNF149 | E3 ubiquitin-protein ligase RNF149 precursor GN = RNF149 |
| Ub | RNF14 | E3 ubiquitin-protein ligase RNF14 isoform 1 GN = RNF14 |
| Ub | MYSM1 | histone H2A deubiquitinase MYSM1 GN = MYSM1 |
| Ub | CDC34 | ubiquitin-conjugating enzyme E2 R1 GN = CDC34 |
| Ub | UNKL | putative E3 ubiquitin-protein ligase UNKL isoform 1 GN = UNKL |
| Ub | UEVLD | ubiquitin-conjugating enzyme E2 variant 3 isoform a GN = UEVLD |
| Ub | PJA1 | E3 ubiquitin-protein ligase Praja-1 isoform b GN = PJA1 |

TABLE 6A-continued

Shows the protein groups used to plot the results from the two sample t-test results (FIGS. 9E and 9F). These annotations are a combination of manual curation, KEGG, and GO annotations of genes from proteasomal pathway, antigen processing, ubiquitination pathway, IFN signaling, and SARS-CoV-2 genes.

| pathway | geneSymbol | proteinName |
|---|---|---|
| Ub | USP40 | ubiquitin carboxyl-terminal hydrolase 40 GN = USP40 |
| Ub | SIAH1 | E3 ubiquitin-proteinligase SIAH1 isoform b GN = SIAH1 |
| Ub | HECW1 | E3 ubiquitin-protein ligase HECW1 isoform b GN = HECW1 |
| Ub | TRIM22 | E3 ubiquitin-protein ligase TRIM22 isoform 2 GN = TRIM22 |
| Ub | RNF126 | E3 ubiquitin-protein ligase RNF126 GN = RNF126 |
| Ub | USP37 | ubiquitin carboxyl-terminal hydrolase 37 GN = USP37 |
| Ub | ZNRF1 | E3 ubiquitin-protein ligase ZNRF1 GN = ZNRF1 |
| Ub | RNF13 | E3 ubiquitin-protein ligase RNF13 isoform 1 GN = RNF13 |
| Ub | TRIM63 | E3 ubiquitin-protein ligase TRIM63 GN = TRIM63 |
| Ub | USP33 | ubiquitin carboxyl-terminal hydrolase 33 isoform 1 GN = USP33 |
| Ub | HERC4 | probable E3 ubiquitin-protein ligase HERC4 isoform c GN = HERC4 |
| Ub | USP11 | ubiquitin carboxyl-terminal hydrolase 11 GN = USP11 |
| Ub | USP24 | ubiquitin carboxyl-terminal hydrolase 24 GN = USP24 |
| Ub | TRIM4 | E3 ubiquitin-protein ligase TRIM4 isoform alpha GN = TRIM4 |
| Ub | RNF41 | E3 ubiquitin-protein ligase NRDP1 isoform 1 GN = RNF41 |
| Ub | RNF5 | E3 ubiquitin-protein ligase RNF5 GN = RNF5 |
| Ub | YOD1 | ubiquitin thioesterase OTU1 isoform 2 GN = YOD1 |
| Ub | MEX3C | RNA-binding E3 ubiquitin-protein ligase MEX3C GN = MEX3C |
| Ub | LRSAM1 | E3 ubiquitin-protein ligase LRSAM1 isoform 1 GN = LRSAM1 |
| Ub | USP19 | ubiquitin carboxyl-terminal hydrolase 19 isoform 1 GN = USP19 |
| Ub | NEURL1B | E3 ubiquitin-protein ligase NEURL1B isoform hNEUR2-deltaNHR1 GN = NEURL1B |
| Ub | USP22 | ubiquitin carboxyl-terminal hydrolase 22 GN = USP22 |
| Ub | USP46 | ubiquitin carboxyl-terminal hydrolase 46 isoform 2 GN = USP46 |
| Ub | TRIM68 | E3 ubiquitin-protein ligase TRIM68 isoform 1 GN = TRIM68 |
| Ub | UBTD2 | ubiquitin domain-containing protein 2 GN = UBTD2 |
| Ub | MINDY3 | ubiquitin carboxyl-terminal hydrolase MINDY-3 isoform a GN = MINDY3 |
| Ub | UBAC1 | ubiquitin-associated domain-containing protein 1 GN = UBAC1 |
| Ub | RNF25 | E3 ubiquitin-protein ligase RNF25 GN = RNF25 |
| Ub | XIAP | E3 ubiquitin-protein ligase XIAP GN = XIAP |
| Ub | ZFP91 | E3 ubiquitin-protein ligase ZFP91 isoform 2 GN = ZFP91 |
| Ub | MUL1 | mitochondrial ubiquitin ligase activator of NFKB 1 GN = MUL1 |
| Ub | TRIM9 | E3 ubiquitin-protein ligase TRIM9 isoform 1 GN = TRIM9 |
| Ub | TRIM11 | E3 ubiquitin-protein ligase TRIM11 GN = TRIM11 |
| Ub | UBE2E1 | ubiquitin-conjugating enzyme E2 E1 isoform 3 GN = UBE2E1 |
| Ub | RNF187 | E3 ubiquitin-protein ligase RNF187 GN = RNF187 |
| Ub | PELI2 | E3 ubiquitin-protein ligase pellino homolog 2 GN = PELI2 |
| Ub | USP44 | ubiquitin carboxyl-terminal hydrolase 44 GN = USP44 |
| Ub | CBLL1 | E3 ubiquitin-protein ligase Hakai isoform 2 GN = CBLL1 |
| Ub | UHRF2 | E3 ubiquitin-protein ligase UHRF2 GN = UHRF2 |
| Ub | RNF114 | E3 ubiquitin-protein ligase RNF114 GN = RNF114 |
| Ub | RNF115 | E3 ubiquitin-protein ligase RNF115 GN = RNF115 |
| Ub | SYVN1 | E3 ubiquitin-protein ligase synoyiolin isoform a precursor GN = SYVN1 |
| Ub | USP3 | ubiquitin carboxyl-terminal hydrolase 3 isoform 1 GN = USP3 |
| Ub | UBE4B | ubiquitin conjugation factor E4 B isoform 1 GN = UBE4B |
| Ub | RNF130 | E3 ubiquitin-protein ligase RNF130 isoform 2 precursor GN = RNF130 |
| Ub | USP12 | ubiquitin carboxyl-terminal hydrolase 12 GN = USP12 |
| Ub | ARIH2 | E3 ubiquitin-protein ligase ARIH2 isoform a GN = ARIH2 |
| Ub | MINDY4 | probable ubiquitin carboxyl-terminal hydrolase MINDY-4 GN = MINDY4 |
| Ub | VCPIP1 | deubiquitinating protein VCIP135 GN = VCPIP1 |
| Ub | ALG13 | putative bifunctional UDP-N-acetylglucosamine transferase and deubiquitinase ALG13 isoform 1 GN = ALG13 |
| Ub | MGRN1 | E3 ubiquitin-protein ligase MGRN1 isoform 3 GN = MGRN1 |
| Ub | UBE4A | ubiquitin conjugation factor E4 A isoform 2 GN = UBE4A |
| Ub | UBL5 | ubiquitin-like protein 5 GN = UBL5 |
| Ub | ATG12 | ubiquitin-like protein ATG12 isoform 1 GN = ATG12 |
| Ub | AREL1 | apoptosis-resistant E3 ubiquitin protein ligase 1 GN = AREL1 |
| Ub | TRIML2 | probable E3 ubiquitin-protein ligase TRIML2 isoform 1 GN = TRIML2 |
| Ub | TRIP12 | E3 ubiquitin-protein ligase TRIP12 isoform a GN = TRIP12 |
| Ub | USP6 | ubiquitin carboxyl-terminal hydrolase 6 GN = USP6 |
| Ub | MARCH6 | E3 ubiquitin-protein ligase MARCH6 isoform 1 GN = MARCH6 |
| Ub | HECTD1 | E3 ubiquitin-protein ligase HECTD1 GN = HECTD1 |
| Ub | TMUB2 | transmembrane and ubiquitin-like domain-containing protein 2 isoform b GN = TMUB2 |
| Ub | USP13 | ubiquitin carboxyl-terminal hydrolase 13 GN = USP13 |
| Ub | UBR5 | E3 ubiquitin-protein ligase UBR5 isoform 2 GN = UBR5 |
| Ub | RBX1 | E3 ubiquitin-protein ligase RBX1 GN = RBX1 |
| Ub | USP29 | ubiquitin carboxyl-terminal hydrolase 29 GN = USP29 |
| Ub | LTN1 | E3 ubiquitin-protein ligase listerin isoform 2 GN = LTN1 |
| Ub | HECW2 | E3 ubiquitin-protein ligase HECW2 isoform 1 GN = HECW2 |
| Ub | KCMF1 | E3 ubiquitin-protein ligase KCMF1 GN = KCMF1 |
| Ub | TRIM7 | E3 ubiquitin-protein ligase TRIM7 isoform 1 GN = TRIM7 |
| Ub | TRIM50 | E3 ubiquitin-protein ligase TRIM50 isoform b GN = TRIM50 |
| Ub | UBE2J2 | ubiquitin-conjugating enzyme E2 J2 isoform 2 GN = UBE2J2 |
| Ub | DTX3 | probable E3 ubiquitin-protein ligase DTX3 isoform b GN = DTX3 |
| Ub | ATG7 | ubiquitin-like modifier-activating enzyme ATG7 isoform b GN = ATG7 |

TABLE 6A-continued

Shows the protein groups used to plot the results from the two sample t-test results (FIGS. 9E and 9F). These annotations are a combination of manual curation, KEGG, and GO annotations of genes from proteasomal pathway, antigen processing, ubiquitination pathway, IFN signaling, and SARS-CoV-2 genes.

| pathway | geneSymbol | proteinName |
|---|---|---|
| Ub | SIAH2 | E3 ubiquitin-protein ligase SIAH2 GN = SIAH2 |
| Ub | UBL7 | ubiquitin-like protein 7 isoform a GN = UBL7 |
| Ub | UBE2B | ubiquitin-conjugating enzyme E2 B GN = UBE2B |
| Ub | BRCC3 | lys-63-specific deubiquitinase BRCC36 isoform 2 GN = BRCC3 |
| Ub | HERPUD2 | homocysteine-responsive endoplasmic reticulum-resident ubiquitin-like domain member 2 protein GN = HERPUD2 |
| Ub | MID1 | E3 ubiquitin-protein ligase Midline-1 isoform 1 GN = MID1 |
| Ub | USP47 | ubiquitin carboxyl-terminal hydrolase 47 isoform a GN = USP47 |
| Ub | RNF8 | E3 ubiquitin-protein ligase RNF8 isoform 1 GN = RNF8 |
| Ub | USP25 | ubiquitin carboxyl-terminal hydrolase 25 isoform USP25m GN = USP25 |
| Ub | UBB | polyubiquitin-B precursor GN = UBB |
| Ub | USP26 | ubiquitin carboxyl-terminal hydrolase 26 GN = USP26 |
| Ub | CBL | E3 ubiquitin-protein ligase CBL GN = CBL |
| Ub | UBE2Q1 | ubiquitin-conjugating enzyme E2 Q1 GN = UBE2Q1 |
| Ub | RFFL | E3 ubiquitin-protein ligase rififylin GN = RFFL |
| Ub | UBAP1 | ubiquitin-associated protein 1 isoform 2 GN = UBAP1 |
| Ub | UBE2W | ubiquitin-conjugating enzyme E2 W isoform 1 GN = UBE2W |
| Ub | OTUD6B | deubiquitinase OTUD6B isoform 2 GN = OTUD6B |
| Ub | OTUB2 | ubiquitin thioesterase OTUB2 GN = OTUB2 |
| Ub | UHRF1 | E3 ubiquitin-protein ligase UHRF1 isoform 1 GN = UHRF1 |
| Ub | ZNF598 | E3 ubiquitin-protein ligase ZNF598 GN = ZNF598 |
| Ub | ITCH | E3 ubiquitin-protein ligase Itchy homolog isoform 1 GN = ITCH |
| Ub | ATG3 | ubiquitin-like-conjugating enzyme ATG3 isoform 2 GN = ATG3 |
| Ub | UBE2Q2 | ubiquitin-conjugating enzyme E2 Q2 isoform 3 GN = UBE2Q2 |
| Ub | UBE3C | ubiquitin-protein ligase E3C GN = UBE3C |
| Ub | RING1 | E3 ubiquitin-protein ligase RING1 GN = RING1 |
| Ub | USP48 | ubiquitin carboxyl-terminal hydrolase 48 isoform f GN = USP48 |
| Ub | RNF167 | E3 ubiquitin-protein ligase RNF167 isoform a precursor GN = RNF167 |
| Ub | RNF139 | E3 ubiquitin-protein ligase RNF139 GN = RNF139 |
| Ub | UBAP2 | ubiquitin-associated protein 2 isoform 1 GN = UBAP2 |
| Ub | RNF40 | E3 ubiquitin-protein ligase BRE1B isoform 2 GN = RNF40 |
| Ub | UBL3 | ubiquitin-like protein 3 precursor GN = UBL3 |
| Ub | MSL2 | E3 ubiquitin-protein ligase MSL2 isoform 2 GN = MSL2 |
| Ub | HECTD3 | E3 ubiquitin-protein ligase HECTD3 GN = HECTD3 |
| Ub | USP14 | ubiquitin carboxyl-terminal hydrolase 14 isoform b GN = USP14 |
| Ub | MKRN2 | probable E3 ubiquitin-protein ligase makorin-2 isoform 1 GN = MKRN2 |
| Ub | OTULIN | ubiquitin thioesterase otulin GN = OTULIN |
| Ub | UBE2C | ubiquitin-conjugating enzyme E2 C isoform 1 GN = UBE2C |
| Ub | TRIM23 | E3 ubiquitin-protein ligase TRIM23 isoform alpha GN = TRIM23 |
| Ub | UBE2S | ubiquitin-conjugating enzyme E2 S GN = UBE2S |
| Ub | RNF2 | E3 ubiquitin-protein ligase RING2 GN = RNF2 |
| Ub | PELI1 | E3 ubiquitin-protein ligase pellino homolog 1 GN = PELI1 |
| Ub | PPP1R11 | E3 ubiquitin-protein ligase PPP1R11 GN = PPP1R11 |
| Ub | ZSWIM2 | E3 ubiquitin-protein ligase ZSWIM2 GN = ZSWIM2 |
| Ub | UBR7 | putative E3 ubiquitin-protein ligase UBR7 GN = UBR7 |
| Ub | UBTD1 | ubiquitin domain-containing protein 1 GN = UBTD1 |
| Ub | TMUB1 | transmembrane and ubiquitin-like domain-containing protein 1 GN = TMUB1 |
| Ub | RNF185 | E3 ubiquitin-protein ligase RNF185 isoform 1 GN = RNF185 |
| Ub | UBAC2 | ubiquitin-associated domain-containing protein 2 isoform 1 precursor GN = UBAC2 |
| Ub | UBA5 | ubiquitin-like modifier-activating enzyme 5 isoform 2 GN = UBA5 |
| Ub | MARCH5 | E3 ubiquitin-protein ligase MARCH5 GN = MARCH5 |
| Ub | UBE3A | ubiquitin-protein ligase E3A isoform 2 GN = UBE3A |
| Ub | UBE2L6 | ubiquitin/ISG15-conjugating enzyme E2 L6 isoform 1 GN = UBE2L6 |
| Ub | TRIM25 | E3 ubiquitin/ISG15 ligase TRIM25 GN = TRIM25 |
| Ub | ARIH1 | E3 ubiquitin-protein ligase ARIH1 GN = ARIH1 |
| Ub | UBASH3B | ubiquitin-associated and SH3 domain-containing protein B isoform 1 GN = UBASH3B |
| Ub | UBR4 | E3 ubiquitin-protein ligase UBR4 GN = UBR4 |
| Ub | RNF20 | E3 ubiquitin-protein ligase BRE1A GN = RNF20 |
| Ub | USP10 | ubiquitin carboxyl-terminal hydrolase 10 isoform 1 GN = USP10 |
| Ub | UBE2Z | ubiquitin-conjugating enzyme E2 Z GN = UBE2Z |
| Ub | UBE2R2 | ubiquitin-conjugating enzyme E2 R2 GN = UBE2R2 |
| Ub | RNF181 | E3 ubiquitin-protein ligase RNF181 GN = RNF181 |
| Ub | UBE2D1 | ubiquitin-conjugating enzyme E2 D1 isoform 2 GN = UBE2D1 |
| Ub | URM1 | ubiquitin-related modifier 1 isoform b GN = URM1 |
| Ub | UBFD1 | ubiquitin domain-containing protein UBFD1 GN = UBFD1 |
| Ub | MINDY4B | inactive ubiquitin carboxyl-terminal hydrolase MINDY-4B GN = MINDY4B |
| Ub | UBE2G1 | ubiquitin-conjugating enzyme E2 G1 GN = UBE2G1 |
| Ub | ADRM1 | proteasomal ubiquitin receptor ADRM1 isoform 1 GN = ADRM1 |
| Ub | HUWE1 | E3 ubiquitin-protein ligase HUWE1 GN = HUWE1 |
| Ub | UBLCP1 | ubiquitin-like domain-containing CTD phosphatase 1 GN = UBLCP1 |
| Ub | USP15 | ubiquitin carboxyl-terminal hydrolase 15 isoform 1 GN = USP15 |
| Ub | USP9X | probable ubiquitin carboxyl-terminal hydrolase FAF-X isoform 3 GN = USP9X |
| Ub | UBE2A | ubiquitin-conjugating enzyme E2 A isoform 4 GN = UBE2A |
| Ub | UBL4A | ubiquitin-like protein 4A GN = UBL4A |

TABLE 6A-continued

Shows the protein groups used to plot the results from the two sample t-test results (FIGS. 9E and 9F). These annotations are a combination of manual curation, KEGG, and GO annotations of genes from proteasomal pathway, antigen processing, ubiquitination pathway, IFN signaling, and SARS-CoV-2 genes.

| pathway | geneSymbol | proteinName |
|---|---|---|
| Ub | UBE2V2 | ubiquitin-conjugating enzyme E2 variant 2 GN = UBE2V2 |
| Ub | UBE2O | (E3-independent) E2 ubiquitin-conjugating enzyme GN = UBE2O |
| Ub | UBA6 | ubiquitin-like modifier-activating enzyme 6 GN = UBA6 |
| Ub | UCHL3 | ubiquitin carboxyl-terminal hydrolase isozyme L3 isoform 2 GN = UCHL3 |
| Ub | UBE2E3 | ubiquitin-conjugating enzyme E2 E3 GN = UBE2E3 |
| Ub | USP7 | ubiquitin carboxyl-terminal hydrolase 7 isoform 1 GN = USP7 |
| Ub | RNF6 | E3 ubiquitin-protein ligase RNF6 isoform 1 GN = RNF6 |
| Ub | STUB1 | E3 ubiquitin-protein ligase CHIP isoform a GN = STUB1 |
| Ub | UBE2H | ubiquitin-conjugating enzyme E2 H isoform 1 GN = UBE2H |
| Ub | UFD1 | ubiquitin recognition factor in ER-associated degradation protein 1 isoform A GN = UFD1 |
| Ub | UBE2T | ubiquitin-conjugating enzyme E2 T isoform 1 GN = UBE2T |
| Ub | UCHL5 | ubiquitin carboxyl-terminal hydrolase isozyme L5 isoform 6 GN = UCHL5 |
| Ub | UFC1 | ubiquitin-fold modifier-conjugating enzyme 1 GN = UFC1 |
| Ub | UBE2G2 | ubiquitin-conjugating enzyme E2 G2 isoform 1 GN = UBE2G2 |
| Ub | UFM1 | ubiquitin-fold modifier 1 isoform 1 precursor GN = UFM1 |
| Ub | USP5 | ubiquitin carboxyl-terminal hydrolase 5 isoform 1 GN = USP5 |
| Ub | ISG15 | ubiquitin-like protein ISG15 GN = ISG15 |
| Ub | UBE2K | ubiquitin-conjugating enzyme E2 K isoform 1 GN = UBE2K |
| Ub | OTUB1 | ubiquitin thioesterase OTUB1 GN = OTUB1 |
| Ub | UBE2D2 | ubiquitin-conjugating enzyme E2 D2 isoform 1 GN = UBE2D2 |
| Ub | UBE2D3 | ubiquitin-conjugating enzyme E2 D3 isoform 1 GN = UBE2D3 |
| Ub | UBE2V1 | ubiquitin-conjugating enzyme E2 variant 1 isoform d GN = UBE2V1 |
| Ub | UBE2L3 | ubiquitin-conjugating enzyme E2 L3 isoform 4 GN = UBE2L3 |
| Ub | UBA1 | ubiquitin-like modifier-activating enzyme 1 GN = UBA1 |
| Ub | UBE2N | ubiquitin-conjugating enzyme E2 N GN = UBE2N |
| Ub | UCHL1 | ubiquitin carboxyl-terminal hydrolase isozyme L1 GN = UCHL1 |
| Proteasome | POMP | proteasome maturation protein GN = POMP |
| Proteasome | PSMA4 | proteasome subunit alpha type-4 isoform 1 GN = PSMA4 |
| Proteasome | PSME4 | proteasome activator complex subunit 4 GN = PSME4 |
| Proteasome | PSMA1 | proteasome subunit alpha type-1 isoform 2 GN = PSMA1 |
| Proteasome | PSMD13 | 26S proteasome non-ATPase regulatory subunit 13 isoform 1 GN = PSMD13 |
| Proteasome | PSMC6 | 26S proteasome regulatory subunit 10B GN = PSMC6 |
| Proteasome | PSMB6 | proteasome subunit beta type-6 isoform 1 precursor GN = PSMB6 |
| Proteasome | PSMA5 | proteasome subunit alpha type-5 isoform 1 GN = PSMA5 |
| Proteasome | PSMB3 | proteasome subunit beta type-3 GN = PSMB3 |
| Proteasome | PSMA6 | proteasome subunit alpha type-6 isoform a GN = PSMA6 |
| Proteasome | PSMB5 | proteasome subunit beta type-5 isoform 3 GN = PSMB5 |
| Proteasome | PSMD12 | 26S proteasome non-ATPase regulatory subunit 12 isoform 1 GN = PSMD12 |
| Proteasome | PSMA3 | proteasome subunit alpha type-3 isoform 1 GN = PSMA3 |
| Proteasome | PSMC5 | 26S proteasome regulatory subunit 8 isoform 2 GN = PSMC5 |
| Proteasome | PSMB1 | proteasome subunit beta type-1 GN = PSMB1 |
| Proteasome | PSMC4 | 26S proteasome regulatory subunit 6B isoform 1 GN = PSMC4 |
| Proteasome | PSMG2 | proteasome assembly chaperone 2 isoform 1 GN = PSMG2 |
| Proteasome | PSMD6 | 26S proteasome non-ATPase regulatory subunit 6 isoform 1 GN = PSMD6 |
| Proteasome | PSMD3 | 26S proteasome non-ATPase regulatory subunit 3 GN = PSMD3 |
| Proteasome | PSMD14 | 26S proteasome non-ATPase regulatory subunit 14 GN = PSMD14 |
| Proteasome | PSMD2 | 26S proteasome non-ATPase regulatory subunit 2 isoform 1 GN = PSMD2 |
| Proteasome | PSMD1 | 26S proteasome non-ATPase regulatory subunit 1 isoform 1 GN = PSMD1 |
| Proteasome | PSMC1 | 26S proteasome regulatory subunit 4 isoform a GN = PSMC1 |
| Proteasome | PSMF1 | proteasome inhibitor PI31 subunit isoform 4 GN = PSMF1 |
| Proteasome | PSME3 | proteasome activator complex subunit 3 isoform 1 GN = PSME3 |
| Proteasome | PSMG3 | proteasome assembly chaperone 3 GN = PSMG3 |
| Proteasome | PSMG4 | proteasome assembly chaperone 4 isoform b GN = PSMG4 |
| Proteasome | PSMD8 | 26S proteasome non-ATPase regulatory subunit 8 GN = PSMD8 |
| Proteasome | PSMD9 | 26S proteasome non-ATPase regulatory subunit 9 isoform 1 GN = PSMD9 |
| Proteasome | PSMA2 | proteasome subunit alpha type-2 GN = PSMA2 |
| Proteasome | PSMD4 | 26S proteasome non-ATPase regulatory subunit 4 isoform 1 GN = PSMD4 |
| Proteasome | PSMD10 | 26S proteasome non-ATPase regulatory subunit 10 isoform 1 GN = PSMD10 |
| Proteasome | PSMC2 | 26S proteasome regulatory subunit 7 isoform 1 GN = PSMC2 |
| Proteasome | PSMB7 | proteasome subunit beta type-7 precursor GN = PSMB7 |
| Proteasome | PSMB2 | proteasome subunit beta type-2 isoform 1 GN = PSMB2 |
| Proteasome | PSMG1 | proteasome assembly chaperone 1 isoform 3 GN = PSMG1 |
| Proteasome | PSMD7 | 26S proteasome non-ATPase regulatory subunit 7 GN = PSMD7 |
| Proteasome | PSME2 | proteasome activator complex subunit 2 GN = PSME2 |
| Proteasome | PSMA7 | proteasome subunit alpha type-7 GN = PSMA7 |
| Proteasome | PSMB4 | proteasome subunit beta type-4 GN = PSMB4 |
| Proteasome | PSME1 | proteasome activator complex subunit 1 isoform 1 GN = PSME1 |
| Proteasome | PSMB10 | proteasome subunit beta type-10 precursor GN = PSMB10 |
| Proteasome | PSMC3 | 26S proteasome regulatory subunit 6A GN = PSMC3 |
| Proteasome | PSMB8 | proteasome subunit beta type-8 isoform E1 precursor GN = PSMB8 |
| Proteasome | PSMD11 | 26S proteasome non-ATPase regulatory subunit 11 GN = PSMD11 |
| Proteasome | PSMD5 | 26S proteasome non-ATPase regulatory subunit 5 isoform 1 GN = PSMD5 |
| Proteasome | PSMB9 | proteasome subunit beta type-9 precursor GN = PSMB9 |
| Proteasome | PSMA8 | proteasome subunit alpha-type 8 isoform 2 GN = PSMA8 |

TABLE 6A-continued

Shows the protein groups used to plot the results from the two sample t-test results (FIGS. 9E and 9F). These annotations are a combination of manual curation, KEGG, and GO annotations of genes from proteasomal pathway, antigen processing, ubiquitination pathway, IFN signaling, and SARS-CoV-2 genes.

| pathway | geneSymbol | proteinName |
|---|---|---|
| IFN | ADAR | adenosine deaminase, RNA-specific |
| IFN | CACTIN | cactin, spliceosome C complex subunit |
| IFN | CDC37 | cell division cycle 37 |
| IFN | CNOT7 | CCR4-NOT transcription complex, subunit 7 |
| IFN | DCST1 | DC-STAMP domain containing 1 |
| IFN | FADD | Fas (TNFRSF6)-associated via death domain |
| IFN | GM45717 | predicted gene 45717 |
| IFN | HSP84-2 | heat shock protein, 2 |
| IFN | IFITM1 | interferon induced transmembrane protein 1 |
| IFN | IFITM2 | interferon induced transmembrane protein 2 |
| IFN | IFITM3 | interferon induced transmembrane protein 3 |
| IFN | IFITM6 | interferon induced transmembrane protein 6 |
| IFN | IFITM7 | interferon induced transmembrane protein 7 |
| IFN | IFNA1 | interferon alpha 1 |
| IFN | IFNAR1 | interferon (alpha and beta) receptor 1 |
| IFN | IFNAR2 | interferon (alpha and beta) receptor 2 |
| IFN | IFNB1 | interferon beta 1, fibroblast |
| IFN | IKBKE | inhibitor of kappaB kinase epsilon |
| IFN | IRAK1 | interleukin-1 receptor-associated kinase 1 |
| IFN | IRF3 | interferon regulatory factor 3 |
| IFN | IRF7 | interferon regulatory factor 7 |
| IFN | LSM14A | LSM14A mRNA processing body assembly factor |
| IFN | MAVS | mitochondrial antiviral signaling protein |
| IFN | METTL3 | methyltransferase like 3 |
| IFN | MMP12 | matrix metallopeptidase 12 |
| IFN | MUL1 | mitochondrial ubiquitin ligase activator of NFKB 1 |
| IFN | MYD88 | myeloid differentiation primary response gene 88 |
| IFN | NLRC5 | NLR family, CARD domain containing 5 |
| IFN | OAS2 | 2'-5' oligoadenylate synthetase 2 |
| IFN | PTPN2 | protein tyrosine phosphatase, non-receptor type 2 |
| IFN | SAMHD1 | SAM domain and HD domain, 1 |
| IFN | STAT1 | signal transducer and activator of transcription 1 |
| IFN | STAT2 | signal transducer and activator of transcription 2 |
| IFN | TBK1 | TANK-binding kinase 1 |
| IFN | TREX1 | three prime repair exonuclease 1 |
| IFN | TRIM6 | tripartite motif-containing 6 |
| IFN | TTLL12 | tubulin tyrosine ligase-like family, member 12 |
| IFN | UBE2K | ubiquitin-conjugating enzyme E2K |
| IFN | WNT5A | wingless-type MMTV integration site family, member 5A |
| IFN | YTHDF2 | YTH N6-methyladenosine RNA binding protein 2 |
| IFN | YTHDF3 | YTH N6-methyladenosine RNA binding protein 3 |
| IFN | ZBP1 | Z-DNA binding protein 1 |
| IFN | TYK2 | non-receptor tyrosine-protein kinase TYK2 GN = TYK2 |
| IFN | JAK1 | tyrosine-protein kinase JAK1 isoform 1 GN = JAK1 |
| Ag processing | POMP | proteasome maturation protein GN = POMP |
| Ag processing | PSMA4 | proteasome subunit alpha type-4 isoform 1 GN = PSMA4 |
| Ag processing | THBS1 | thrombospondin-1 precursor GN = THBS1 |
| Ag processing | PSME4 | proteasome activator complex subunit 4 GN = PSME4 |
| Ag processing | AP3B1 | AP-3 complex subunit beta-1 isoform 2 GN = AP3B1 |
| Ag processing | AP3D1 | AP-3 complex subunit delta-1 isoform 3 GN = AP3D1 |
| Ag processing | PSMA1 | proteasome subunit alpha type-1 isoform 2 GN = PSMA1 |
| Ag processing | PSMD13 | 26S proteasome non-ATPase regulatory subunit 13 isoform 1 GN = PSMD13 |
| Ag processing | PSMC6 | 26S proteasome regulatory subunit 10B GN = PSMC6 |
| Ag processing | PSMB6 | proteasome subunit beta type-6 isoform 1 precursor GN = PSMB6 |
| Ag processing | PSMA5 | proteasome subunit alpha type-5 isoform 1 GN = PSMA5 |
| Ag processing | PSMB3 | proteasome subunit beta type-3 GN = PSMB3 |
| Ag processing | PSMA6 | proteasome subunit alpha type-6 isoform a GN = PSMA6 |
| Ag processing | PSMB5 | proteasome subunit beta type-5 isoform 3 GN = PSMB5 |
| Ag processing | PSMD12 | 26S proteasome non-ATPase regulatory subunit 12 isoform 1 GN = PSMD12 |
| Ag processing | PSMA3 | proteasome subunit alpha type-3 isoform 1 GN = PSMA3 |
| Ag processing | PSMC5 | 26S proteasome regulatory subunit 8 isoform 2 GN = PSMC5 |
| Ag processing | PSMB1 | proteasome subunit beta type-1 GN = PSMB1 |
| Ag processing | PSMC4 | 26S proteasome regulatory subunit 6B isoform 1 GN = PSMC4 |
| Ag processing | RAB10 | ras-related protein Rab-10 GN = RAB10 |
| Ag processing | TRAF6 | TNF receptor-associated factor 6 GN = TRAF6 |
| Ag processing | PSMG2 | proteasome assembly chaperone 2 isoform 1 GN = PSMG2 |
| Ag processing | YTHDF1 | YTH domain-containing family protein 1 GN = YTHDF1 |
| Ag processing | ATG5 | autophagy protein 5 isoform a GN = ATG5 |
| Ag processing | PSMD6 | 26S proteasome non-ATPase regulatory subunit 6 isoform 1 GN = PSMD6 |
| Ag processing | PSMD3 | 26S proteasome non-ATPase regulatory subunit 3 GN = PSMD3 |
| Ag processing | PSMD14 | 26S proteasome non-ATPase regulatory subunit 14 GN = PSMD14 |
| Ag processing | PSMD2 | 26S proteasome non-ATPase regulatory subunit 2 isoform 1 GN = PSMD2 |
| Ag processing | PSMD1 | 26S proteasome non-ATPase regulatory subunit 1 isoform 1 GN = PSMD1 |
| Ag processing | BAG6 | large proline-rich protein BAG6 isoform b GN = BAG6 |

TABLE 6A-continued

Shows the protein groups used to plot the results from the two sample t-test results (FIGS. 9E and 9F). These annotations are a combination of manual curation, KEGG, and GO annotations of genes from proteasomal pathway, antigen processing, ubiquitination pathway, IFN signaling, and SARS-CoV-2 genes.

| pathway | geneSymbol | proteinName |
|---|---|---|
| Ag processing | PSMC1 | 26S proteasome regulatory subunit 4 isoform a GN = PSMC1 |
| Ag processing | PSMF1 | proteasome inhibitor PI31 subunit isoform 4 GN = PSMF1 |
| Ag processing | RAB8B | ras-related protein Rab-8B GN = RAB8B |
| Ag processing | IDE | insulin-degrading enzyme isoform 3 GN = IDE |
| Ag processing | PSME3 | proteasome activator complex subunit 3 isoform 1 GN = PSME3 |
| Ag processing | B2M | beta-2-microglobulin precursor GN = B2M |
| Ag processing | PSMG3 | proteasome assembly chaperone 3 GN = PSMG3 |
| Ag processing | RAB35 | ras-related protein Rab-35 isoform 2 GN = RAB35 |
| Ag processing | PSMG4 | proteasome assembly chaperone 4 isoform b GN = PSMG4 |
| Ag processing | WASHC1 | WASH complex subunit 1 GN = WASHC1 |
| Ag processing | IFI30 | gamma-interferon-inducible lysosomal thiol reductase preproprotein GN = IFI30 |
| Ag processing | RAB27A | ras-related protein Rab-27A GN = RAB27A |
| Ag processing | TREX1 | three-prime repair exonuclease 1 isoform c GN = TREX1 |
| Ag processing | FLT3 | receptor-type tyrosine-protein kinase FLT3 precursor GN = FLT3 |
| Ag processing | WDFY4 | WD repeat- and FYVE domain-containing protein 4 GN = WDFY4 |
| Ag processing | MFSD6 | major facilitator superfamily domain-containing protein 6 GN = MFSD6 |
| Ag processing | PSMD8 | 26S proteasome non-ATPase regulatory subunit 8 GN = PSMD8 |
| Ag processing | PSMD9 | 26S proteasome non-ATPase regulatory subunit 9 isoform 1 GN = PSMD9 |
| Ag processing | PSMA2 | proteasome subunit alpha type-2 GN = PSMA2 |
| Ag processing | RAB5B | ras-related protein Rab-5B isoform 1 GN = RAB5B |
| Ag processing | RAB6A | ras-related protein Rab-6A isoform b GN = RAB6A |
| Ag processing | CALR | calreticulin precursor GN = CALR |
| Ag processing | RAB4A | ras-related protein Rab-4A isoform 1 GN = RAB4A |
| Ag processing | GBA | glucosylceramidase isoform 1 precursor GN = GBA |
| Ag processing | PSMD4 | 26S proteasome non-ATPase regulatory subunit 4 isoform 1 GN = PSMD4 |
| Ag processing | CTSL | cathepsin L1 isoform 1 preproprotein GN = CTSL |
| Ag processing | PSMD10 | 26S proteasome non-ATPase regulatory subunit 10 isoform 1 GN = PSMD10 |
| Ag processing | RAB34 | ras-related protein Rab-34 isoform 5 GN = RAB34 |
| Ag processing | PIKFYVE | 1-phosphatidylinositol 3-phosphate 5-kinase isoform 2 GN = PIKFYVE |
| Ag processing | PSMC2 | 26S proteasome regulatory subunit 7 isoform 1 GN = PSMC2 |
| Ag processing | PSMB7 | proteasome subunit beta type-7 precursor GN = PSMB7 |
| Ag processing | PSMB2 | proteasome subunit beta type-2 isoform 1 GN = PSMB2 |
| Ag processing | HFE | hereditary hemochromatosis protein isoform 1 precursor GN = HFE |
| Ag processing | PSAP | prosaposin isoform b preproprotein GN = PSAP |
| Ag processing | PSMG1 | proteasome assembly chaperone 1 isoform 3 GN = PSMG1 |
| Ag processing | PSMD7 | 26S proteasome non-ATPase regulatory subunit 7 GN = PSMD7 |
| Ag processing | PSME2 | proteasome activator complex subunit 2 GN = PSME2 |
| Ag processing | RAB32 | ras-related protein Rab-32 GN = RAB32 |
| Ag processing | RELB | transcription factor RelB GN = RELB |
| Ag processing | PSMA7 | proteasome subunit alpha type-7 GN = PSMA7 |
| Ag processing | PSMB4 | proteasome subunit beta type-4 GN = PSMB4 |
| Ag processing | UNC93B1 | protein unc-93 homolog B1 GN = UNC93B1 |
| Ag processing | ERAP1 | endoplasmic reticulum aminopeptidase 1 isoform b precursor GN = ERAP1 |
| Ag processing | RFTN1 | raftlin GN = RFTN1 |
| Ag processing | TAP2 | antigen peptide transporter 2 isoform 1 GN = TAP2 |
| Ag processing | PSME1 | proteasome activator complex subunit 1 isoform 1 GN = PSME1 |
| Ag processing | RAB3B | ras-related protein Rab-3B GN = RAB3B |
| Ag processing | PSMB10 | proteasome subunit beta type-10 precursor GN = PSMB10 |
| Ag processing | PSMC3 | 26S proteasome regulatory subunit 6A GN = PSMC3 |
| Ag processing | PSMB8 | proteasome subunit beta type-8 isoform E1 precursor GN = PSMB8 |
| Ag processing | TAPBP | tapasin isoform 1 precursor GN = TAPBP |
| Ag processing | ICAM1 | intercellular adhesion molecule 1 precursor GN = ICAM1 |
| Ag processing | PSMD11 | 26S proteasome non-ATPase regulatory subunit 11 GN = PSMD11 |
| Ag processing | PSMD5 | 26S proteasome non-ATPase regulatory subunit 5 isoform 1 GN = PSMD5 |
| Ag processing | PYCARD | apoptosis-associated speck-like protein containing a CARD isoform b GN = PYCARD |
| Ag processing | PSMB9 | proteasome subunit beta type-9 precursor GN = PSMB9 |
| Ag processing | CD68 | macrosialin isoform B precursor GN = CD68 |
| Ag processing | PSMA8 | proteasome subunit alpha-type 8 isoform 2 GN = PSMA8 |
| Ag processing | EXT1 | exostosin-1 GN = EXT1 |
| Ag processing | PTPN22 | tyrosine-protein phosphatase non-receptor type 22 isoform 3 GN = PTPN22 |
| Ag processing | TAP1 | antigen peptide transporter 1 isoform 1 GN = TAP1 |

TABLE 6B

Contains all proteins that are statistically enriched or depleted in response to SARS-CoV-2 infection in HEK293T and A549 cells.

| idx | Gene Symbol | pathway | proteinName | A549_FX | HEK_FX | SARS_A549_24 hr_FX |
|---|---|---|---|---|---|---|
| 3 | ORF9b | SARS | ORF9b | 4.28 | 4.28 | 9.5643 |
| 9 | ORF7a | SARS | ORF7a | 4.28 | 4.28 | 8.7613 |
| 1 | N | SARS | N | 4.28 | 4.28 | 10.6838 |
| 12 | nsp3 | SARS | nsp3 | 4.28 | 4.28 | 8.3431 |
| 5 | S | SARS | S | 4.28 | 4.28 | 9.0701 |
| 19 | nsp6 | SARS | nsp6 | 4.28 | 4.28 | 7.2054 |
| 13 | nsp10 | SARS | nsp10 | 4.28 | 4.28 | 8.4466 |
| 7 | nsp8 | SARS | nsp8 | 4.28 | 4.28 | 8.9184 |
| 6 | ORF3a | SARS | ORF3a | 4.28 | 4.28 | 8.8004 |
| 2 | M | SARS | M | 4.28 | 4.28 | 9.6832 |
| 10 | nsp2 | SARS | nsp2 | 4.28 | 4.28 | 8.5059 |
| 18 | TMED7-TICAM2 | NA | NA | 5.16 | 5.16 | 8.54542 |
| 14 | nsp4 | SARS | nsp4 | 4.28 | 4.28 | 8.1335 |
| 4 | nsp5 | SARS | nsp5 | 4.28 | 4.28 | 10.0264 |
| 8 | nsp1 | SARS | nsp1 | 4.28 | 4.28 | 9.1659 |
| 54 | GIMAP7 | NA | NA | 5.16 | 5.16 | 7.62864 |
| 17 | nsp15 | SARS | nsp15 | 4.28 | 4.28 | 7.1958 |
| 11 | nsp9 | SARS | nsp9 | 4.28 | 4.28 | 8.5188 |
| 20 | nsp13 | SARS | nsp13 | 4.28 | 4.28 | 7.1948 |
| 93 | NUDT8 | NA | NA | 5.16 | 5.16 | 7.16627 |
| 40 | nsp14 | SARS | nsp14 | 4.28 | 4.28 | 6.7825 |
| 33 | GANAB | NA | NA | 6.40767 | 7.38633 | 9.34854 |
| 63 | SH3RF2 | NA | NA | 5.16 | 5.16 | 7.92254 |
| 16 | nsp12 | SARS | nsp12 | 4.28 | 4.28 | 7.5873 |
| 78 | MGAT5B | NA | NA | 7.519 | 7.05306 | 5.16 |
| 87 | SVIP | NA | NA | 6.74615 | 7.59067 | 5.16 |
| 26 | MVB12B | NA | NA | 5.75177 | 5.16 | 8.84397 |
| 35 | SLC25A46 | NA | NA | 7.55481 | 8.19694 | 5.16 |
| 138 | XYLB | NA | NA | 6.87526 | 6.62833 | 5.16 |
| 105 | EBNA1BP2 | NA | NA | 6.12302 | 6.27173 | 8.07528 |
| 141 | YAE1 | NA | NA | 6.76423 | 6.64661 | 5.16 |
| 131 | UBE2F | NA | NA | 6.74764 | 6.88127 | 5.16 |
| 30 | ING2 | NA | NA | 7.5142 | 8.33903 | 5.16 |
| 142 | MUL1 | Ub, IFN | mitochondrial ubiquitin ligase activator of NFKB 1 GN = MUL1 | 6.71511 | 6.69387 | 5.16 |
| 43 | EIF2B4 | NA | NA | 6.01614 | 5.10804 | 7.95948 |
| 102 | EXT2 | NA | NA | 6.97758 | 7.4194 | 5.16 |
| 23 | MAD2L1BP | NA | NA | 8.54711 | 7.93329 | 5.16 |
| 107 | KATNB1 | NA | NA | 6.94954 | 7.11242 | 5.16 |
| 21 | ZWINT | NA | NA | 8.29518 | 8.44072 | 5.16 |
| 127 | NEU1 | NA | NA | 6.84234 | 6.87992 | 5.16 |
| 135 | TCF12 | NA | NA | 6.9272 | 6.65123 | 5.16 |
| 146 | C16orf70 | NA | NA | 6.80018 | 6.72174 | 5.29567 |
| 100 | AVL9 | NA | NA | 7.43897 | 6.94893 | 5.16 |
| 36 | SPTAN1 | NA | NA | 5.65059 | 5.77428 | 8.24482 |
| 66 | C14orf119 | NA | NA | 7.07427 | 7.81061 | 5.16 |
| 104 | WDR62 | NA | NA | 7.08504 | 7.04618 | 5.41753 |
| 68 | RTL8C | NA | NA | 7.48605 | 7.31528 | 5.16 |
| 44 | GPN3 | NA | NA | 8.4572 | 7.98076 | 5.16 |
| 133 | PEX1 | NA | NA | 6.95938 | 6.63995 | 5.14707 |
| 32 | TMBIM6 | NA | NA | 7.81904 | 7.96583 | 5.16 |
| 97 | HUS1 | NA | NA | 7.37247 | 6.84606 | 5.16 |
| 74 | AMD1 | NA | NA | 7.30171 | 7.34951 | 5.16 |
| 108 | PTOV1 | NA | NA | 7.14977 | 6.9081 | 5.16 |
| 42 | CCDC91 | NA | NA | 7.89089 | 7.62144 | 5.16 |
| 122 | C3orf38 | NA | NA | 7.0453 | 6.74119 | 5.16 |
| 76 | PTPRF | NA | NA | 7.41808 | 7.0392 | 4.98268 |
| 95 | TYK2 | IFN | non-receptor tyrosine-protein kinase TYK2 GN = TYK2 | 7.09359 | 7.14549 | 5.16 |
| 124 | ARMC9 | NA | NA | 7.258 | 6.83061 | 5.46937 |
| 51 | FIG. 4 | NA | NA | 7.56528 | 7.58935 | 5.16 |
| 77 | KLHL11 | NA | NA | 7.05323 | 7.53313 | 5.16 |
| 58 | ZBTB8OS | NA | NA | 7.39991 | 7.65077 | 5.16 |
| 121 | KLHL22 | NA | NA | 6.93243 | 6.87114 | 5.16 |
| 113 | TAB2 | NA | NA | 6.71441 | 7.22894 | 5.16 |
| 116 | LONP2 | NA | NA | 7.12323 | 6.78131 | 5.16 |

TABLE 6B-continued

Contains all proteins that are statistically enriched or depleted in response to SARS-CoV-2 infection in HEK293T and A549 cells.

| | | | | | | |
|---|---|---|---|---|---|---|
| 119 | UBXN8 | NA | NA | 6.8597 | 6.98755 | 5.16 |
| 86 | BRD9 | NA | NA | 7.11857 | 7.25535 | 5.16 |
| 34 | MACO1 | NA | NA | 7.54435 | 8.30111 | 5.12563 |
| 31 | FTL | NA | NA | 8.82175 | 8.35704 | 6.5396 |
| 114 | URGCP | NA | NA | 7.31647 | 7.19259 | 5.70264 |
| 92 | VPS37C | NA | NA | 7.33683 | 6.9488 | 5.16 |
| 111 | SETBP1 | NA | NA | 5.1801 | 5.01025 | 7.19503 |
| 136 | RAD51AP1 | NA | NA | 6.75252 | 6.81837 | 5.16 |
| 139 | KIAA0355 | NA | NA | 6.74581 | 6.75013 | 5.16 |
| 123 | HMG20B | NA | NA | 7.04417 | 6.73725 | 5.16 |
| 46 | SDHC | NA | NA | 8.37315 | 7.41094 | 5.16 |
| 137 | FOPNL | NA | NA | 6.91681 | 6.63052 | 5.16 |
| 45 | MED29 | NA | NA | 7.76151 | 7.94996 | 5.16 |
| 83 | TIMM17A | NA | NA | 7.76757 | 7.34974 | 5.86391 |
| 70 | RIOK2 | NA | NA | 7.50851 | 7.72971 | 5.64839 |
| 27 | DMAC1 | NA | NA | 8.54856 | 7.64707 | 5.16 |
| 60 | CENPK | NA | NA | 7.5826 | 7.44812 | 5.16 |
| 144 | TRAPPC6A | NA | NA | 6.61008 | 6.75869 | 5.16 |
| 59 | CDC42EP1 | NA | NA | 7.0509 | 7.9949 | 5.16 |
| 98 | SFR1 | NA | NA | 7.20178 | 7.01025 | 5.16 |
| 89 | FIGNL1 | NA | NA | 7.22883 | 7.0968 | 5.16 |
| 69 | DVL3 | NA | NA | 7.77744 | 6.97683 | 5.16 |
| 38 | RRAGA | NA | NA | 7.75504 | 7.90821 | 5.16 |
| 57 | GNL3L | NA | NA | 7.20961 | 7.8753 | 5.16 |
| 52 | UBE2B | Ub | ubiquitin-conjugating enzyme E2 B GN = UBE2B | 7.42988 | 7.70339 | 5.16 |
| 49 | PIAS4 | NA | NA | 7.4824 | 7.74274 | 5.16 |
| 29 | CRCP | NA | NA | 7.94801 | 7.90778 | 5.16 |
| 67 | LIN9 | NA | NA | 7.13339 | 7.89814 | 5.16 |
| 64 | BOLA1 | NA | NA | 6.99592 | 7.9552 | 5.16 |
| 120 | MLF2 | NA | NA | 8.10982 | 8.3972 | 6.65391 |
| 25 | RNF181 | Ub | E3 ubiquitin-protein ligase RNF181 GN = RNF181 | 8.0121 | 8.40212 | 5.16 |
| 61 | IQGAP3 | NA | NA | 7.97856 | 7.39418 | 5.54585 |
| 28 | CUEDC2 | NA | NA | 7.41344 | 8.56386 | 5.16 |
| 39 | ETNK1 | NA | NA | 7.64392 | 7.9914 | 5.16 |
| 115 | C6orf106 | NA | NA | 6.7847 | 7.16608 | 5.16 |
| 53 | CEP170 | NA | NA | 4.92607 | 5.76297 | 8.05556 |
| 65 | AURKA | NA | NA | 7.32702 | 7.57264 | 5.16 |
| 84 | CALCOCO2 | NA | NA | 7.67372 | 7.62207 | 5.16 |
| 130 | EEF2K | NA | NA | 6.9691 | 6.66576 | 5.16 |
| 47 | ITM2B | NA | NA | 7.30316 | 8.02715 | 5.16 |
| 125 | UBL5 | Ub | ubiquitin-like protein 5 GN = UBL5 | 8.78481 | 8.85015 | 6.93942 |
| 109 | TRIM11 | Ub | E3 ubiquitin-protein ligase TRIM11 GN = TRIM11 | 6.74419 | 7.29307 | 5.16 |
| 132 | TADA1 | NA | NA | 6.76131 | 6.85322 | 5.16 |
| 112 | NEK3 | NA | NA | 7.29447 | 6.70288 | 5.16 |
| 90 | IFT74 | NA | NA | 8.31087 | 7.68155 | 6.00069 |
| 99 | KCTD10 | NA | NA | 7.32018 | 6.86261 | 5.16 |
| 110 | LAPTM4A | NA | NA | 7.13413 | 6.88988 | 5.16 |
| 55 | MID1IP1 | NA | NA | 7.78343 | 7.9223 | 5.76805 |
| 101 | TOP3B | NA | NA | 7.14499 | 6.75397 | 4.93357 |
| 41 | CDC20 | NA | NA | 7.76224 | 7.77715 | 5.16 |
| 106 | GRN | NA | NA | 7.17075 | 6.9081 | 5.16 |
| 73 | IMPA2 | NA | NA | 7.74867 | 6.96118 | 5.16 |
| 24 | YPEL5 | NA | NA | 7.78453 | 8.64819 | 5.16 |
| 118 | CENPF | NA | NA | 6.69278 | 7.17093 | 5.16 |
| 79 | TLE1 | NA | NA | 7.44871 | 6.93207 | 5.04912 |
| 50 | RPAIN | NA | NA | 8.18159 | 7.02867 | 5.16 |
| 140 | CCNL1 | NA | NA | 6.89724 | 6.89486 | 5.45966 |
| 145 | POMP | Proteasome, Ag processing | proteasome maturation protein GN = POMP | 8.16835 | 8.31727 | 6.76333 |
| 85 | CD99L2 | NA | NA | 8.04581 | 7.29337 | 5.86984 |
| 94 | GMEB1 | NA | NA | 6.98918 | 7.60008 | 5.30172 |
| 128 | RPS6KA5 | NA | NA | 7.1207 | 7.08826 | 5.16 |

TABLE 6B-continued

Contains all proteins that are statistically enriched or depleted in response to SARS-CoV-2 infection in HEK293T and A549 cells.

| | | | | | | |
|---|---|---|---|---|---|---|
| 71 | CDCA3 | NA | NA | 7.66563 | 7.08352 | 5.16 |
| 96 | SYNRG | NA | NA | 7.45806 | 7.72754 | 5.58526 |
| 129 | MYO19 | NA | NA | 7.17972 | 6.73838 | 5.16 |
| 62 | RXRA | NA | NA | 7.23969 | 7.72759 | 5.16 |
| 117 | IFNGR1 | NA | NA | 7.12329 | 6.93428 | 5.16 |
| 82 | SLBP | NA | NA | 6.93503 | 7.49038 | 5.16 |
| 126 | RNF31 | Ub | E3 ubiquitin-protein ligase RNF31 isoform 1 GN = RNF31 | 6.98847 | 6.77776 | 5.16 |
| 81 | TEX30 | NA | NA | 6.82746 | 7.61317 | 5.16 |
| 72 | MAPK7 | NA | NA | 7.85756 | 6.88112 | 5.16 |
| 56 | ZNHIT3 | NA | NA | 7.30996 | 7.77534 | 5.16 |
| 103 | UBN2 | NA | NA | 6.93992 | 6.61416 | 5.16 |
| 91 | KIF20A | NA | NA | 6.86353 | 7.43857 | 5.16 |
| 22 | MRFAP1 | NA | NA | 8.05253 | 8.67615 | 5.16 |
| 48 | SLC7A6OS | NA | NA | 7.17862 | 8.06937 | 5.16 |
| 143 | C1orf112 | NA | NA | 6.69761 | 6.67634 | 5.16 |
| 37 | C12orf73 | NA | NA | 7.60597 | 8.0614 | 5.16 |
| 75 | TTC33 | NA | NA | 6.87851 | 7.7657 | 5.16 |
| 134 | PNPLA2 | NA | NA | 6.72195 | 6.86733 | 5.16 |
| 80 | PLIN2 | NA | NA | 7.11868 | 7.3591 | 5.16 |
| 88 | TMEM259 | NA | NA | 7.33459 | 6.99736 | 5.16 |
| 15 | ORF6 | SARS | ORF6 | 4.28 | 4.28 | 8.4021 |

| idx | SARS_HEK_24 hr_FX | SARS_A549_3 hr_FX | SARS_A549_6 hr_FX | SARS_HEK_3 hr_FX |
|---|---|---|---|---|
| 3 | 9.974 | 7.7619 | 9.7518 | 8.2347 |
| 9 | 9.3614 | 7.8576 | 9.026 | 8.21 |
| 1 | 11.0857 | 8.4207 | 10.1475 | 8.5226 |
| 12 | 8.9745 | 6.5329 | 8.2957 | 6.6888 |
| 5 | 9.8182 | 7.132 | 8.9502 | 7.8297 |
| 19 | 7.9413 | 4.28 | 7.9956 | 4.28 |
| 13 | 8.8422 | 4.28 | 8.0162 | 4.28 |
| 7 | 9.5997 | 4.28 | 8.3172 | 4.28 |
| 6 | 9.8546 | 4.28 | 8.9582 | 7.0803 |
| 2 | 10.1197 | 8.0095 | 9.5256 | 8.2954 |
| 10 | 9.3273 | 6.2344 | 8.5069 | 7.1763 |
| 18 | 8.41237 | 8.4908 | 8.46291 | 8.01737 |
| 14 | 8.7269 | 4.28 | 7.871 | 4.28 |
| 4 | 9.1273 | 4.28 | 8.1879 | 4.28 |
| 8 | 9.0199 | 7.9017 | 8.7855 | 7.974 |
| 54 | 7.4872 | 7.8167 | 8.05416 | 7.86664 |
| 17 | 8.069 | 4.28 | 6.9448 | 4.28 |
| 11 | 9.044 | 4.28 | 8.3779 | 4.28 |
| 20 | 7.7905 | 4.28 | 7.0469 | 4.28 |
| 93 | 7.10296 | 6.46379 | 6.67147 | 6.84178 |
| 40 | 7.0481 | 4.28 | 7.4141 | 4.28 |
| 33 | 9.89027 | 9.29014 | 9.28527 | 5.07174 |
| 63 | 7.03238 | 6.6657 | 7.04541 | 6.28304 |
| 16 | 8.0576 | 4.28 | 7.2983 | 4.28 |
| 78 | 5.16 | 5.75431 | 5.52849 | 5.86011 |
| 87 | 5.16 | 8.55887 | 8.77036 | 8.73779 |
| 26 | 8.06909 | 7.11249 | 6.72851 | 7.01864 |
| 35 | 5.16 | 7.18105 | 6.77896 | 5.44795 |
| 138 | 5.16 | 7.82298 | 7.51855 | 7.78536 |
| 105 | 8.09854 | 8.09173 | 6.96962 | 7.23812 |
| 141 | 5.16 | 7.24663 | 7.79748 | 7.034 |
| 131 | 5.16 | 6.37219 | 7.49327 | 7.4547 |
| 30 | 5.16 | 8.19978 | 6.66523 | 6.96095 |
| 142 | 5.16 | 7.25154 | 7.643 | 7.49712 |
| 43 | 8.25074 | 6.54145 | 6.61855 | 6.53524 |
| 102 | 5.43347 | 6.74931 | 8.74039 | 7.81074 |
| 23 | 5.16 | 7.08912 | 6.70975 | 7.78395 |
| 107 | 5.16 | 6.84901 | 7.78051 | 7.61291 |
| 21 | 5.16 | 7.84206 | 7.71975 | 8.33723 |
| 127 | 5.16 | 7.16292 | 7.35769 | 7.12794 |
| 135 | 5.16 | 7.68537 | 7.51116 | 6.99238 |
| 146 | 5.26189 | 7.35785 | 7.73712 | 7.77801 |
| 100 | 5.41852 | 7.93224 | 8.07353 | 8.49115 |
| 36 | 8.56811 | 8.30083 | 8.28258 | 6.75884 |
| 66 | 5.16 | 7.52051 | 8.38432 | 7.14093 |
| 104 | 4.92771 | 7.38777 | 7.59556 | 7.49095 |
| 68 | 5.16 | 7.72375 | 7.96595 | 7.49081 |
| 44 | 6.23405 | 7.75491 | 7.54675 | 7.76987 |

TABLE 6B-continued

Contains all proteins that are statistically enriched or depleted in response to SARS-CoV-2 infection in HEK293T and A549 cells.

| | | | | |
|---|---|---|---|---|
| 133 | 5.16 | 6.9799 | 7.36114 | 7.55908 |
| 32 | 5.16 | 7.72375 | 7.26867 | 7.88457 |
| 97 | 5.16 | 7.28291 | 7.81611 | 7.78092 |
| 74 | 5.16 | 7.77604 | 7.65638 | 7.15227 |
| 108 | 5.16 | 7.41427 | 7.4156 | 7.33241 |
| 42 | 5.16 | 7.52105 | 7.49415 | 7.07952 |
| 122 | 5.16 | 7.24292 | 7.14754 | 7.27069 |
| 76 | 5.16 | 7.15747 | 7.58327 | 7.48285 |
| 95 | 5.16 | 7.11834 | 6.94201 | 7.13422 |
| 124 | 5.16 | 7.39864 | 7.72342 | 7.9135 |
| 51 | 5.16 | 7.29575 | 7.40309 | 7.41812 |
| 77 | 5.16 | 7.47717 | 7.87891 | 7.42077 |
| 58 | 5.16 | 6.22643 | 7.90247 | 7.69377 |
| 121 | 5.16 | 7.08985 | 7.13418 | 7.38691 |
| 113 | 5.11472 | 7.24663 | 7.32736 | 7.65838 |
| 116 | 5.16 | 7.15767 | 7.77896 | 7.44783 |
| 119 | 5.16 | 6.77148 | 7.22265 | 7.38298 |
| 86 | 5.16 | 6.41609 | 6.55887 | 7.34178 |
| 34 | 5.28537 | 7.1419 | 7.78259 | 7.03052 |
| 31 | 5.16 | 8.52746 | 8.49736 | 8.28325 |
| 114 | 5.16 | 7.62706 | 7.52034 | 7.71466 |
| 92 | 5.16 | 8.41776 | 7.47365 | 7.98381 |
| 111 | 6.68234 | 6.28163 | 5.16 | 5.33824 |
| 136 | 5.16 | 6.2438 | 6.7662 | 7.96705 |
| 139 | 5.16 | 7.2596 | 7.22118 | 7.40605 |
| 123 | 5.16 | 6.68525 | 6.36561 | 7.34591 |
| 46 | 5.6117 | 8.21331 | 8.25432 | 8.26587 |
| 137 | 5.16 | 7.06307 | 7.22605 | 6.88167 |
| 45 | 5.51835 | 8.11134 | 8.11424 | 8.19285 |
| 83 | 5.16 | 8.17914 | 7.93139 | 8.03134 |
| 70 | 5.16 | 8.5916 | 7.96872 | 7.78793 |
| 27 | 5.16 | 8.34773 | 8.7192 | 8.01276 |
| 60 | 5.16 | 5.80503 | 6.57427 | 7.04488 |
| 144 | 5.16 | 6.90607 | 8.17405 | 7.8821 |
| 59 | 5.16 | 7.42518 | 7.8373 | 8.08735 |
| 98 | 5.16 | 7.37988 | 7.43059 | 7.45117 |
| 89 | 5.16 | 6.88263 | 7.35313 | 7.60983 |
| 69 | 5.16 | 6.72812 | 7.00081 | 7.03179 |
| 38 | 5.16 | 8.01037 | 7.87126 | 8.33111 |
| 57 | 5.16 | 8.38355 | 7.79629 | 7.82204 |
| 52 | 5.16 | 6.97388 | 7.77151 | 7.14093 |
| 49 | 5.16 | 6.46118 | 6.38976 | 7.35863 |
| 29 | 5.16 | 7.64981 | 7.47698 | 8.08195 |
| 67 | 5.35157 | 7.01174 | 6.4358 | 8.38263 |
| 64 | 5.16 | 7.48725 | 7.99517 | 8.15259 |
| 120 | 6.36538 | 8.14725 | 8.05666 | 8.70237 |
| 25 | 5.16 | 8.15034 | 7.76963 | 8.25805 |
| 61 | 5.16 | 8.01736 | 7.79253 | 7.0528 |
| 28 | 5.16 | 7.70835 | 7.24554 | 8.35019 |
| 39 | 5.16 | 7.90929 | 7.77544 | 7.97743 |
| 115 | 5.16 | 6.51208 | 5.99221 | 6.99924 |
| 53 | 7.43861 | 4.7726 | 5.99071 | 8.14707 |
| 65 | 5.16 | 7.82004 | 7.489 | 7.69515 |
| 84 | 6.04521 | 7.77927 | 8.3382 | 8.03017 |
| 130 | 5.16 | 6.9456 | 7.54435 | 6.95225 |
| 47 | 5.16 | 7.6524 | 7.38865 | 7.34836 |
| 125 | 7.23961 | 8.49527 | 8.55569 | 8.82196 |
| 109 | 5.16 | 8.16366 | 6.90278 | 7.77713 |
| 132 | 5.16 | 6.65891 | 6.78995 | 9.93266 |
| 112 | 5.16 | 6.99427 | 6.45317 | 7.23296 |
| 90 | 6.00061 | 8.02551 | 8.00924 | 8.3038 |
| 99 | 5.16 | 7.29115 | 7.67027 | 7.51277 |
| 110 | 5.16 | 7.53333 | 7.1401 | 7.20661 |
| 55 | 5.16 | 7.93359 | 8.12318 | 8.22865 |
| 101 | 5.16 | 7.79708 | 8.03998 | 7.23446 |
| 41 | 5.16 | 7.72187 | 7.86533 | 7.74447 |
| 106 | 5.16 | 7.19323 | 7.54099 | 7.71434 |
| 73 | 5.16 | 7.51862 | 7.2699 | 6.60568 |
| 24 | 5.16 | 7.92457 | 7.93113 | 7.84238 |
| 118 | 5.16 | 6.57522 | 6.51365 | 7.82379 |
| 79 | 5.16 | 7.59103 | 7.57903 | 7.65298 |
| 50 | 5.16 | 7.68954 | 7.50168 | 7.47768 |
| 140 | 5.16 | 7.73672 | 6.97206 | 7.80098 |
| 145 | 6.68661 | 8.33825 | 8.24425 | 8.33503 |
| 85 | 5.37899 | 7.70355 | 7.53695 | 7.92961 |
| 94 | 5.3431 | 7.73351 | 7.13209 | 8.1745 |
| 128 | 5.66016 | 5.16 | 6.20969 | 7.4791 |

TABLE 6B-continued

Contains all proteins that are statistically enriched or depleted in response to SARS-CoV-2 infection in HEK293T and A549 cells.

| | | | | |
|---|---|---|---|---|
| 71 | 5.16 | 7.49018 | 7.00924 | 7.66809 |
| 96 | 5.69696 | 7.59423 | 7.81276 | 7.16194 |
| 129 | 5.38122 | 8.10697 | 7.90176 | 7.1399 |
| 62 | 5.16 | 8.18831 | 8.07815 | 8.15881 |
| 117 | 5.33836 | 6.88193 | 6.73345 | 7.05199 |
| 82 | 5.16 | 7.66857 | 7.31854 | 8.08294 |
| 126 | 5.16 | 7.52182 | 7.29324 | 6.61604 |
| 81 | 5.16 | 6.66657 | 7.07235 | 7.7925 |
| 72 | 5.16 | 7.4676 | 7.38458 | 7.65686 |
| 56 | 5.16 | 7.16216 | 7.52061 | 7.39339 |
| 103 | 4.59498 | 6.80099 | 6.4046 | 7.23625 |
| 91 | 5.16 | 6.87794 | 6.91559 | 7.63308 |
| 22 | 5.16 | 7.87641 | 8.00521 | 8.23033 |
| 48 | 5.16 | 7.19145 | 7.20439 | 8.14093 |
| 143 | 5.16 | 7.29632 | 6.2582 | 7.47493 |
| 37 | 5.16 | 7.61178 | 7.81828 | 7.61285 |
| 75 | 5.16 | 7.13466 | 7.22773 | 8.15115 |
| 134 | 5.16 | 7.33173 | 7.44523 | 7.054 |
| 80 | 5.16 | 8.05181 | 8.07823 | 7.26142 |
| 88 | 5.16 | 7.66685 | 7.05429 | 7.2248 |
| 15 | 8.3568 | 4.28 | 4.28 | 4.28 |

| idx | SARS_HEK_6 hr_FX | mean_diff_0_24 | pval_0_24 | pval_0_3 | pval_0_6 | A549_0_24_diff |
|---|---|---|---|---|---|---|
| 3 | 9.6775 | 5.48915 | 0.00039 | 0.00099 | 1.84E−05 | 5.2843 |
| 9 | 8.9534 | 4.78135 | 0.00134 | 0.0005 | 2.61E−05 | 4.4813 |
| 1 | 10.0138 | 6.60475 | 0.00024 | 0.000057 | 0.000028 | 6.4038 |
| 12 | 8.3519 | 4.3788 | 0.00187 | 0.0004 | 3.38E−05 | 4.0631 |
| 5 | 8.8341 | 5.16415 | 0.00188 | 0.00367 | 4.18E−05 | 4.7901 |
| 19 | 7.9345 | 3.29335 | 0.00529 | 1 | 4.44E−05 | 2.9254 |
| 13 | 8.1218 | 4.3644 | 0.00062 | 1 | 6.21E−05 | 4.1666 |
| 7 | 8.1666 | 4.97905 | 0.00164 | 1 | 8.71E−05 | 4.6384 |
| 6 | 9.1856 | 5.0475 | 0.0045 | 0.34962 | 0.00011 | 4.5204 |
| 2 | 9.2693 | 5.62145 | 0.00042 | 2.98E−04 | 1.17E−04 | 5.4032 |
| 10 | 8.2433 | 4.6366 | 0.00305 | 0.01516 | 0.00022 | 4.2259 |
| 18 | 8.24881 | 3.31889 | 0.00047 | 0.00052 | 0.00026 | 3.38542 |
| 14 | 8.1342 | 4.1502 | 0.00183 | 1 | 0.00028 | 3.8535 |
| 4 | 7.89 | 5.29685 | 0.00275 | 1 | 0.00035 | 5.7464 |
| 8 | 8.3846 | 4.8129 | 4.76E−05 | 6.60E−05 | 0.00049 | 4.8859 |
| 54 | 7.54605 | 2.39792 | 0.00169 | 0.00039 | 0.00108 | 2.46864 |
| 17 | 6.5905 | 3.3524 | 0.00759 | 1 | 0.00148 | 2.9158 |
| 11 | 7.7798 | 4.5014 | 0.00113 | 1 | 0.00173 | 4.2388 |
| 20 | 6.5635 | 3.21265 | 0.00341 | 1 | 0.00292 | 2.9148 |
| 93 | 7.00709 | 1.97462 | 0.00344 | 0.00568 | 0.0035 | 2.00627 |
| 40 | 6.7485 | 2.6353 | 0.00081 | 1 | 0.00483 | 2.5025 |
| 33 | 9.29154 | 2.72241 | 0.00536 | 0.86669 | 0.00561 | 2.94087 |
| 63 | 6.47133 | 2.31746 | 0.00621 | 0.00889 | 0.00769 | 2.76254 |
| 16 | 6.5321 | 3.54245 | 0.00154 | 1 | 0.0079 | 3.3073 |
| 78 | 5.98703 | −2.12603 | 0.00391 | 0.00755 | 0.01105 | −2.359 |
| 87 | 8.62251 | −2.00841 | 0.00953 | 0.0203 | 0.01851 | −1.58615 |
| 26 | 6.54647 | 3.00065 | 0.0028 | 0.0078 | 0.02316 | 3.09221 |
| 35 | 6.3287 | −2.71587 | 0.00211 | 0.09464 | 0.02445 | −2.39481 |
| 138 | 7.65708 | −1.5918 | 0.00854 | 0.01411 | 0.03147 | −1.71526 |
| 105 | 7.67799 | 1.88953 | 0.00422 | 0.021 | 0.03438 | 1.95226 |
| 141 | 9.19319 | −1.54542 | 0.00866 | 0.1536 | 0.03507 | −1.60423 |
| 131 | 7.65633 | −1.65446 | 0.00683 | 0.83916 | 0.03713 | −1.58764 |
| 30 | 6.84333 | −2.76661 | 0.00281 | 0.58691 | 0.04011 | −2.3542 |
| 142 | 7.28888 | −1.54449 | 0.00845 | 0.05502 | 0.04706 | −1.55511 |
| 43 | 6.91204 | 2.54302 | 0.00499 | 0.07409 | 0.04707 | 1.94334 |
| 102 | 7.95033 | −1.90175 | 0.00645 | 0.87224 | 0.04864 | −1.81758 |
| 23 | 7.45019 | −3.0802 | 0.00122 | 0.12191 | 0.05285 | −3.38711 |
| 107 | 7.62128 | −1.87098 | 0.00442 | 0.61255 | 0.05435 | −1.78954 |
| 21 | 7.72843 | −3.20795 | 0.00054 | 0.40121 | 0.05501 | −3.13518 |
| 127 | 7.69714 | −1.70113 | 0.00596 | 0.28561 | 0.06599 | −1.68234 |
| 135 | 7.35687 | −1.62921 | 0.00809 | 0.19814 | 0.06886 | −1.7672 |
| 146 | 7.1552 | −1.48218 | 0.00992 | 0.04545 | 0.09728 | −1.50451 |
| 100 | 7.70156 | −1.90469 | 0.0068 | 0.04726 | 0.09961 | −2.27897 |
| 36 | 6.3439 | 2.69402 | 0.00132 | 0.04198 | 0.10056 | 2.59423 |
| 66 | 8.07913 | −2.28244 | 0.00487 | 0.78222 | 0.10283 | −1.91427 |
| 104 | 7.50885 | −1.89299 | 0.00627 | 0.18567 | 0.10725 | −1.66751 |
| 68 | 7.83048 | −2.24067 | 0.00224 | 0.45905 | 0.113 | −2.32605 |
| 44 | 7.7319 | −2.52195 | 0.00789 | 0.18913 | 0.12439 | −3.2972 |
| 133 | 7.25595 | −1.64613 | 0.00818 | 0.23163 | 0.12522 | −1.81231 |
| 32 | 7.52662 | −2.73244 | 0.00102 | 0.73424 | 0.12604 | −2.65904 |
| 97 | 7.602 | −1.94927 | 0.00596 | 0.29377 | 0.12728 | −2.21247 |
| 74 | 7.92551 | −2.16561 | 0.00241 | 0.68971 | 0.13952 | −2.14171 |
| 108 | 7.56441 | −1.86893 | 0.00473 | 0.23786 | 0.14406 | −1.98977 |

TABLE 6B-continued

Contains all proteins that are statistically enriched or depleted in response to SARS-CoV-2 infection in HEK293T and A549 cells.

| | | | | | | |
|---|---|---|---|---|---|---|
| 42 | 6.69104 | −2.59616 | 0.00139 | 0.20071 | 0.1623 | −2.73089 |
| 122 | 7.66878 | −1.73324 | 0.00667 | 0.22839 | 0.18327 | −1.8853 |
| 76 | 7.76926 | −2.1573 | 0.00344 | 0.76974 | 0.18335 | −2.43541 |
| 95 | 5.47957 | −1.95954 | 0.00353 | 0.97804 | 0.19492 | −1.93359 |
| 124 | 7.33596 | −1.72962 | 0.0092 | 0.14316 | 0.19653 | −1.78863 |
| 51 | 6.57176 | −2.41732 | 0.00157 | 0.39992 | 0.19819 | −2.40528 |
| 77 | 7.613 | −2.13318 | 0.00395 | 0.6181 | 0.21366 | −1.89323 |
| 58 | 7.88101 | −2.36534 | 0.00195 | 0.39078 | 0.21518 | −2.23991 |
| 121 | 7.39037 | −1.74179 | 0.00549 | 0.2579 | 0.22366 | −1.77243 |
| 113 | 7.46763 | −1.83432 | 0.00732 | 0.22212 | 0.23221 | −1.55441 |
| 116 | 7.1176 | −1.79227 | 0.00617 | 0.28204 | 0.23756 | −1.96323 |
| 119 | 7.27895 | −1.76363 | 0.00539 | 0.65864 | 0.23915 | −1.6997 |
| 86 | 7.02317 | −2.02696 | 0.00322 | 0.49436 | 0.24559 | −1.95857 |
| 34 | 6.3686 | −2.71723 | 0.00272 | 0.08311 | 0.25054 | −2.41872 |
| 31 | 7.31638 | −2.73959 | 0.00973 | 0.57056 | 0.25866 | −2.28215 |
| 114 | 7.60961 | −1.82321 | 0.00799 | 0.15445 | 0.26156 | −1.61384 |
| 92 | 7.51802 | −1.98281 | 0.00452 | 0.02911 | 0.26361 | −2.17683 |
| 111 | 6.08023 | 1.84351 | 0.00747 | 0.1635 | 0.27263 | 2.01493 |
| 136 | 8.64234 | −1.62544 | 0.00708 | 0.65618 | 0.27361 | −1.59252 |
| 139 | 6.92019 | −1.58797 | 0.00764 | 0.07011 | 0.27576 | −1.58581 |
| 123 | 6.69987 | −1.73071 | 0.00672 | 0.73915 | 0.27665 | −1.88417 |
| 46 | 8.6353 | −2.5062 | 0.00652 | 0.45315 | 0.28061 | −3.21315 |
| 137 | 6.98696 | −1.61367 | 0.00846 | 0.48804 | 0.28244 | −1.75681 |
| 45 | 8.19115 | −2.51656 | 0.00187 | 0.2878 | 0.28809 | −2.60151 |
| 83 | 7.82481 | −2.0467 | 0.00849 | 0.12503 | 0.31679 | −1.90366 |
| 70 | 7.83872 | −2.21492 | 0.00377 | 0.20903 | 0.31696 | −1.86012 |
| 27 | 8.42544 | −2.93782 | 0.00261 | 0.85304 | 0.31809 | −3.38856 |
| 60 | 7.51657 | −2.35536 | 0.00181 | 0.10035 | 0.32329 | −2.4226 |
| 144 | 6.59721 | −1.52438 | 0.00925 | 0.17262 | 0.32346 | −1.45008 |
| 59 | 8.12815 | −2.3629 | 0.00642 | 0.65036 | 0.34351 | −1.8909 |
| 98 | 7.30478 | −1.94601 | 0.00389 | 0.26992 | 0.34633 | −2.04178 |
| 89 | 7.46963 | −2.00282 | 0.00336 | 0.82464 | 0.35779 | −2.06883 |
| 69 | 6.98042 | −2.21713 | 0.00614 | 0.26888 | 0.35809 | −2.61744 |
| 38 | 8.42111 | −2.67162 | 0.00112 | 0.26843 | 0.36881 | −2.59504 |
| 57 | 7.95308 | −2.38246 | 0.00363 | 0.22635 | 0.38367 | −2.04961 |
| 52 | 7.83942 | −2.40663 | 0.00187 | 0.12102 | 0.39761 | −2.26988 |
| 49 | 7.78754 | −2.45257 | 0.00172 | 0.16331 | 0.40846 | −2.3224 |
| 29 | 7.87723 | −2.76789 | 0.00093 | 0.83442 | 0.41066 | −2.78801 |
| 67 | 7.60404 | −2.25998 | 0.00559 | 0.78224 | 0.42542 | −1.97339 |
| 64 | 7.70635 | −2.31556 | 0.00712 | 0.51448 | 0.43426 | −1.83592 |
| 120 | 8.0252 | −1.74387 | 0.00744 | 0.62351 | 0.44865 | −1.45591 |
| 25 | 8.14127 | −3.04711 | 0.00087 | 0.99196 | 0.45266 | −2.8521 |
| 61 | 6.81905 | −2.33345 | 0.00419 | 0.76311 | 0.46698 | −2.43271 |
| 28 | 7.88126 | −2.82865 | 0.00495 | 0.94256 | 0.46884 | −2.25344 |
| 39 | 7.3824 | −2.65766 | 0.0014 | 0.65745 | 0.46993 | −2.48392 |
| 115 | 7.1764 | −1.81539 | 0.0062 | 0.53139 | 0.48504 | −1.6247 |
| 53 | 5.37879 | 2.40256 | 0.00727 | 0.43407 | 0.48508 | 3.12949 |
| 65 | 7.83129 | −2.28983 | 0.0022 | 0.28742 | 0.4897 | −2.16702 |
| 84 | 7.51565 | −2.04529 | 0.00968 | 0.35891 | 0.50203 | −2.51372 |
| 130 | 6.68323 | −1.65743 | 0.00783 | 0.6325 | 0.50469 | −1.8091 |
| 47 | 7.44525 | −2.50516 | 0.00336 | 0.67563 | 0.51836 | −2.14316 |
| 125 | 8.74074 | −1.72796 | 0.00676 | 0.57327 | 0.52126 | −1.84538 |
| 109 | 7.73745 | −1.85863 | 0.00736 | 0.04866 | 0.52269 | −1.58419 |
| 132 | 7.2048 | −1.64727 | 0.00681 | 0.28751 | 0.53086 | −1.60131 |
| 112 | 7.04391 | −1.83868 | 0.00823 | 0.74199 | 0.54826 | −2.13447 |
| 90 | 7.52235 | −1.99556 | 0.00654 | 0.64534 | 0.56743 | −2.31018 |
| 99 | 6.98042 | −1.93139 | 0.00552 | 0.35186 | 0.5709 | −2.16018 |
| 110 | 7.18186 | −1.85201 | 0.00491 | 0.26146 | 0.5792 | −1.97413 |
| 55 | 7.88276 | −2.38884 | 0.00332 | 0.42701 | 0.58253 | −2.01539 |
| 101 | 6.55107 | −1.90269 | 0.00578 | 0.17147 | 0.59874 | −2.21142 |
| 41 | 7.9282 | −2.6097 | 0.00117 | 0.88119 | 0.61188 | −2.60224 |
| 106 | 6.908 | −1.87943 | 0.00473 | 0.25662 | 0.61468 | −2.01075 |
| 73 | 7.05922 | −2.19493 | 0.00621 | 0.58534 | 0.63899 | −2.58867 |
| 24 | 8.10775 | −3.05636 | 0.00208 | 0.44145 | 0.64431 | −2.62453 |
| 118 | 7.93496 | −1.77186 | 0.0078 | 0.64411 | 0.64764 | −1.53278 |
| 79 | 7.10484 | −2.08583 | 0.00466 | 0.22168 | 0.68206 | −2.39959 |
| 50 | 8.16462 | −2.44513 | 0.00846 | 0.96658 | 0.69256 | −3.02159 |
| 140 | 6.59333 | −1.58622 | 0.00913 | 0.02074 | 0.69422 | −1.43757 |
| 145 | 8.04436 | −1.51784 | 0.0095 | 0.71074 | 0.71062 | −1.40502 |
| 85 | 7.52585 | −2.04518 | 0.00989 | 0.70833 | 0.71896 | −2.17597 |
| 94 | 7.74847 | −1.97222 | 0.00662 | 0.14055 | 0.72831 | −1.68746 |
| 128 | 7.59721 | −1.6944 | 0.00949 | 0.41972 | 0.73565 | −1.9607 |
| 71 | 7.48901 | −2.21457 | 0.00409 | 0.5557 | 0.74386 | −2.50563 |
| 96 | 7.14444 | −1.95169 | 0.00424 | 0.50672 | 0.75982 | −1.8728 |
| 129 | 6.38016 | −1.68844 | 0.0095 | 0.21468 | 0.78416 | −2.01972 |
| 62 | 6.53133 | −2.32364 | 0.0029 | 0.07827 | 0.79173 | −2.07969 |
| 117 | 7.17231 | −1.77961 | 0.00577 | 0.81473 | 0.80531 | −1.96329 |

TABLE 6B-continued

Contains all proteins that are statistically enriched or depleted in response to SARS-CoV-2 infection in HEK293T and A549 cells.

| | | | | | | |
|---|---|---|---|---|---|---|
| 82 | 7.26776 | −2.0527 | 0.00518 | 0.12545 | 0.80604 | −1.77503 |
| 126 | 6.23887 | −1.72311 | 0.00621 | 0.67237 | 0.80925 | −1.82847 |
| 81 | 7.19609 | −2.06032 | 0.00779 | 0.98739 | 0.82729 | −1.66746 |
| 72 | 7.16584 | −2.20934 | 0.00871 | 0.67524 | 0.83771 | −2.69756 |
| 56 | 7.4581 | −2.38265 | 0.00254 | 0.42337 | 0.86144 | −2.14996 |
| 103 | 7.03349 | −1.89955 | 0.00815 | 0.4697 | 0.8748 | −1.77992 |
| 91 | 7.27621 | −1.99105 | 0.00599 | 0.81303 | 0.8781 | −1.70353 |
| 22 | 8.86045 | −3.20434 | 0.00107 | 0.42127 | 0.88606 | −2.89253 |
| 48 | 7.92114 | −2.46399 | 0.00496 | 0.93977 | 0.90375 | −2.01862 |
| 143 | 7.02991 | −1.52697 | 0.0088 | 0.04478 | 0.91159 | −1.53761 |
| 37 | 7.82338 | −2.67369 | 0.0016 | 0.47774 | 0.96598 | −2.44597 |
| 75 | 7.43884 | −2.16211 | 0.00794 | 0.58494 | 0.97923 | −1.71851 |
| 134 | 6.16708 | −1.63464 | 0.00718 | 0.19672 | 0.98344 | −1.56195 |
| 80 | 6.41487 | −2.07889 | 0.00317 | 0.3316 | 0.99122 | −1.95868 |
| 88 | 7.27749 | −2.00598 | 0.00404 | 0.41209 | 0.99976 | −2.17459 |
| 15 | 4.28 | 4.09945 | 7.74E−06 | 1 | 1 | 4.1221 |

| idx | A549_0_24_dir | A549_0_3_diff | A549_0_3_dir | A549_3_6_diff |
|---|---|---|---|---|
| 3 | 1 | 3.4819 | 1 | 1.9899 |
| 9 | 1 | 3.5776 | 1 | 1.1684 |
| 1 | 1 | 4.1407 | 1 | 1.7268 |
| 12 | 1 | 2.2529 | 1 | 1.7628 |
| 5 | 1 | 2.852 | 1 | 1.8182 |
| 19 | 1 | 0 | 0 | 3.7156 |
| 13 | 1 | 0 | 0 | 3.7362 |
| 7 | 1 | 0 | 0 | 4.0372 |
| 6 | 1 | 0 | 0 | 4.6782 |
| 2 | 1 | 3.7295 | 1 | 1.5161 |
| 10 | 1 | 1.9544 | 1 | 2.2725 |
| 18 | 1 | 3.3308 | 1 | −0.02789 |
| 14 | 1 | 0 | 0 | 3.591 |
| 4 | 1 | 0 | 0 | 3.9079 |
| 8 | 1 | 3.6217 | 1 | 0.8838 |
| 54 | 1 | 2.6567 | 1 | 0.23746 |
| 17 | 1 | 0 | 0 | 2.6648 |
| 11 | 1 | 0 | 0 | 4.0979 |
| 20 | 1 | 0 | 0 | 2.7669 |
| 93 | 1 | 1.30379 | 1 | 0.20768 |
| 40 | 1 | 0 | 0 | 3.1341 |
| 33 | 1 | 2.88247 | 1 | −0.00487 |
| 63 | 1 | 1.5057 | 1 | 0.37971 |
| 16 | 1 | 0 | 0 | 3.0183 |
| 78 | −1 | −1.76469 | −1 | −0.22582 |
| 87 | −1 | 1.81272 | 1 | 0.21149 |
| 26 | 1 | 1.36072 | 1 | −0.38397 |
| 35 | −1 | −0.37376 | −1 | −0.4021 |
| 138 | −1 | 0.94772 | 1 | −0.30443 |
| 105 | 1 | 1.96872 | 1 | −1.12211 |
| 141 | −1 | 0.4824 | 1 | 0.55085 |
| 131 | −1 | −0.37545 | −1 | 1.12108 |
| 30 | −1 | 0.68558 | 1 | −1.53455 |
| 142 | −1 | 0.53643 | 1 | 0.39146 |
| 43 | 1 | 0.52531 | 1 | 0.0771 |
| 102 | −1 | −0.22827 | −1 | 1.99109 |
| 23 | −1 | −1.45799 | −1 | −0.37937 |
| 107 | −1 | −0.10053 | −1 | 0.9315 |
| 21 | −1 | −0.45311 | −1 | −0.12231 |
| 127 | −1 | 0.32057 | 1 | 0.19478 |
| 135 | −1 | 0.75817 | 1 | −0.17421 |
| 146 | −1 | 0.55767 | 1 | 0.37927 |
| 100 | −1 | 0.49327 | 1 | 0.14129 |
| 36 | 1 | 2.65024 | 1 | −0.01825 |
| 66 | −1 | 0.44624 | 1 | 0.86381 |
| 104 | −1 | 0.30273 | 1 | 0.2078 |
| 68 | −1 | 0.2377 | 1 | 0.2422 |
| 44 | −1 | −0.70229 | −1 | −0.20816 |
| 133 | −1 | 0.02051 | 0 | 0.38124 |
| 32 | −1 | −0.09529 | 0 | −0.45509 |
| 97 | −1 | −0.08956 | 0 | 0.5332 |
| 74 | −1 | 0.47433 | 1 | −0.11966 |
| 108 | −1 | 0.2645 | 1 | 0.00133 |
| 42 | −1 | −0.36984 | −1 | −0.0269 |
| 122 | −1 | 0.19762 | 1 | −0.09537 |
| 76 | −1 | −0.26062 | −1 | 0.4258 |
| 95 | −1 | 0.02474 | 0 | −0.17633 |
| 124 | −1 | 0.14064 | 1 | 0.32479 |

TABLE 6B-continued

Contains all proteins that are statistically enriched or depleted in response to SARS-CoV-2 infection in HEK293T and A549 cells.

| | | | | |
|---|---|---|---|---|
| 51 | −1 | −0.26953 | −1 | 0.10734 |
| 77 | −1 | 0.42393 | 1 | 0.40174 |
| 58 | −1 | −1.17348 | −1 | 1.67605 |
| 121 | −1 | 0.15741 | 1 | 0.04433 |
| 113 | −1 | 0.53222 | 1 | 0.08073 |
| 116 | −1 | 0.03444 | 0 | 0.62129 |
| 119 | −1 | −0.08822 | 0 | 0.45117 |
| 86 | −1 | −0.70248 | −1 | 0.14278 |
| 34 | −1 | −0.40245 | −1 | 0.64069 |
| 31 | −1 | −0.29429 | −1 | −0.0301 |
| 114 | −1 | 0.31059 | 1 | −0.10672 |
| 92 | −1 | 1.08094 | 1 | −0.94411 |
| 111 | 1 | 1.10152 | 1 | −1.12163 |
| 136 | −1 | −0.50871 | −1 | 0.5224 |
| 139 | −1 | 0.51379 | 1 | −0.03842 |
| 123 | −1 | −0.35892 | −1 | −0.31964 |
| 46 | −1 | −0.15984 | −1 | 0.04101 |
| 137 | −1 | 0.14626 | 1 | 0.16297 |
| 45 | −1 | 0.34982 | 1 | 0.0029 |
| 83 | −1 | 0.41157 | 1 | −0.24774 |
| 70 | −1 | 1.08309 | 1 | −0.62287 |
| 27 | −1 | −0.20083 | −1 | 0.37147 |
| 60 | −1 | −1.77757 | −1 | 0.76924 |
| 144 | −1 | 0.29598 | 1 | 1.26798 |
| 59 | −1 | 0.37428 | 1 | 0.41212 |
| 98 | −1 | 0.1781 | 1 | 0.05071 |
| 89 | −1 | −0.3462 | −1 | 0.47051 |
| 69 | −1 | −1.04932 | −1 | 0.27269 |
| 38 | −1 | 0.25534 | 1 | −0.13912 |
| 57 | −1 | 1.17394 | 1 | −0.58726 |
| 52 | −1 | −0.456 | −1 | 0.79764 |
| 49 | −1 | −1.02122 | −1 | −0.07142 |
| 29 | −1 | −0.29821 | −1 | −0.17282 |
| 67 | −1 | −0.12165 | −1 | −0.57594 |
| 64 | −1 | 0.49133 | 1 | 0.50793 |
| 120 | −1 | 0.03743 | 0 | −0.09058 |
| 25 | −1 | 0.13824 | 1 | −0.38071 |
| 61 | −1 | 0.0388 | 0 | −0.22483 |
| 28 | −1 | 0.29491 | 1 | −0.46281 |
| 39 | −1 | 0.26537 | 1 | −0.13385 |
| 115 | −1 | −0.27262 | −1 | −0.51987 |
| 53 | 1 | −0.15347 | −1 | 1.21811 |
| 65 | −1 | 0.49302 | 1 | −0.33103 |
| 84 | −1 | 0.10555 | 1 | 0.55893 |
| 130 | −1 | −0.0235 | 0 | 0.59875 |
| 47 | −1 | 0.34924 | 1 | −0.26374 |
| 125 | −1 | −0.28953 | −1 | 0.06041 |
| 109 | −1 | 1.41947 | 1 | −1.26087 |
| 132 | −1 | −0.1024 | −1 | 0.13104 |
| 112 | −1 | −0.3002 | −1 | −0.5411 |
| 90 | −1 | −0.28536 | −1 | −0.01628 |
| 99 | −1 | −0.02902 | 0 | 0.37911 |
| 110 | −1 | 0.3992 | 1 | −0.39323 |
| 55 | −1 | 0.15016 | 1 | 0.18959 |
| 101 | −1 | 0.65209 | 1 | 0.2429 |
| 41 | −1 | −0.04038 | 0 | 0.14346 |
| 106 | −1 | 0.02248 | 0 | 0.34776 |
| 73 | −1 | −0.23005 | −1 | −0.24872 |
| 24 | −1 | 0.14004 | 1 | 0.00655 |
| 118 | −1 | −0.11757 | −1 | −0.06157 |
| 79 | −1 | 0.14232 | 1 | −0.01201 |
| 50 | −1 | −0.49205 | −1 | −0.18786 |
| 140 | −1 | 0.83948 | 1 | −0.76466 |
| 145 | −1 | 0.16989 | 1 | −0.094 |
| 85 | −1 | −0.34226 | −1 | −0.1666 |
| 94 | −1 | 0.74433 | 1 | −0.60143 |
| 128 | −1 | −1.9607 | −1 | 1.04969 |
| 71 | −1 | −0.17544 | −1 | −0.48094 |
| 96 | −1 | 0.13616 | 1 | 0.21854 |
| 129 | −1 | 0.92725 | 1 | −0.20521 |
| 62 | −1 | 0.94862 | 1 | −0.11016 |
| 117 | −1 | −0.24136 | −1 | −0.14849 |
| 82 | −1 | 0.73355 | 1 | −0.35003 |
| 126 | −1 | 0.53335 | 1 | −0.22859 |
| 81 | −1 | −0.16089 | −1 | 0.40578 |
| 72 | −1 | −0.38996 | −1 | −0.08303 |
| 56 | −1 | −0.14781 | −1 | 0.35845 |

TABLE 6B-continued

Contains all proteins that are statistically enriched or depleted in response to SARS-CoV-2 infection in HEK293T and A549 cells.

| | | | | |
|---|---|---|---|---|
| 103 | −1 | −0.13893 | −1 | −0.39639 |
| 91 | −1 | 0.01441 | 0 | 0.03765 |
| 22 | −1 | −0.17612 | −1 | 0.1288 |
| 48 | −1 | 0.01284 | 0 | 0.01294 |
| 143 | −1 | 0.59872 | 1 | −1.03812 |
| 37 | −1 | 0.00581 | 0 | 0.2065 |
| 75 | −1 | 0.25615 | 1 | 0.09308 |
| 134 | −1 | 0.60978 | 1 | 0.11351 |
| 80 | −1 | 0.93313 | 1 | 0.02641 |
| 88 | −1 | 0.33225 | 1 | −0.61256 |
| 15 | 1 | 0 | 0 | 0 |

| idx | A549_3_6_dir | A549_6_24_diff | A549_6_24_dir | HEK_0_24_diff | HEK_0_24_dir |
|---|---|---|---|---|---|
| 3 | 1 | −0.1875 | −1 | 5.694 | 1 |
| 9 | 1 | −0.2647 | −1 | 5.0814 | 1 |
| 1 | 1 | 0.5363 | 1 | 6.8057 | 1 |
| 12 | 1 | 0.0474 | 0 | 4.6945 | 1 |
| 5 | 1 | 0.1199 | 1 | 5.5382 | 1 |
| 19 | 1 | −0.7902 | −1 | 3.6613 | 1 |
| 13 | 1 | 0.4304 | 1 | 4.5622 | 1 |
| 7 | 1 | 0.6012 | 1 | 5.3197 | 1 |
| 6 | 1 | −0.1578 | −1 | 5.5746 | 1 |
| 2 | 1 | 0.1576 | 1 | 5.8397 | 1 |
| 10 | 1 | −0.001 | 0 | 5.0473 | 1 |
| 18 | 0 | 0.0825 | 0 | 3.25237 | 1 |
| 14 | 1 | 0.2625 | 1 | 4.4469 | 1 |
| 4 | 1 | 1.8385 | 1 | 4.8473 | 1 |
| 8 | 1 | 0.3804 | 1 | 4.7399 | 1 |
| 54 | 1 | −0.42553 | −1 | 2.3272 | 1 |
| 17 | 1 | 0.251 | 1 | 3.789 | 1 |
| 11 | 1 | 0.1409 | 1 | 4.764 | 1 |
| 20 | 1 | 0.1479 | 1 | 3.5105 | 1 |
| 93 | 1 | 0.4948 | 1 | 1.94296 | 1 |
| 40 | 1 | −0.6316 | −1 | 2.7681 | 1 |
| 33 | 0 | 0.06328 | 0 | 2.50394 | 1 |
| 63 | 1 | 0.87714 | 1 | 1.87238 | 1 |
| 16 | 1 | 0.289 | 1 | 3.7776 | 1 |
| 78 | −1 | −0.36849 | −1 | −1.89306 | −1 |
| 87 | 1 | −3.61036 | −1 | −2.43067 | −1 |
| 26 | −1 | 2.11546 | 1 | 2.90909 | 1 |
| 35 | −1 | −1.61896 | −1 | −3.03694 | −1 |
| 138 | −1 | −2.35855 | −1 | −1.46833 | −1 |
| 105 | −1 | 1.10566 | 1 | 1.8268 | 1 |
| 141 | 1 | −2.63748 | −1 | −1.48661 | −1 |
| 131 | 1 | −2.33327 | −1 | −1.72127 | −1 |
| 30 | −1 | −1.50523 | −1 | −3.17903 | −1 |
| 142 | 1 | −2.483 | −1 | −1.53387 | −1 |
| 43 | 0 | 1.34094 | 1 | 3.1427 | 1 |
| 102 | 1 | −3.58039 | −1 | −1.98593 | −1 |
| 23 | −1 | −1.54975 | −1 | −2.77329 | −1 |
| 107 | 1 | −2.62051 | −1 | −1.95242 | −1 |
| 21 | −1 | −2.55975 | −1 | −3.28072 | −1 |
| 127 | 1 | −2.19769 | −1 | −1.71992 | −1 |
| 135 | −1 | −2.35116 | −1 | −1.49123 | −1 |
| 146 | 1 | −2.44145 | −1 | −1.45985 | −1 |
| 100 | 1 | −2.91353 | −1 | −1.53041 | −1 |
| 36 | 0 | −0.03776 | 0 | 2.79382 | 1 |
| 66 | 1 | −3.22432 | −1 | −2.65061 | −1 |
| 104 | 1 | −2.17803 | −1 | −2.11847 | −1 |
| 68 | 1 | −2.80595 | −1 | −2.15528 | −1 |
| 44 | −1 | −2.38675 | −1 | −1.74671 | −1 |
| 133 | 1 | −2.21406 | −1 | −1.47995 | −1 |
| 32 | −1 | −2.10867 | −1 | −2.80583 | −1 |
| 97 | 1 | −2.65611 | −1 | −1.68606 | −1 |
| 74 | −1 | −2.49638 | −1 | −2.18951 | −1 |
| 108 | 0 | −2.2556 | −1 | −1.7481 | −1 |
| 42 | 0 | −2.33415 | −1 | −2.46144 | −1 |
| 122 | 0 | −1.98754 | −1 | −1.58119 | −1 |
| 76 | 1 | −2.60059 | −1 | −1.8792 | −1 |
| 95 | −1 | −1.78201 | −1 | −1.98549 | −1 |
| 124 | 1 | −2.25405 | −1 | −1.67061 | −1 |
| 51 | 1 | −2.24309 | −1 | −2.42935 | −1 |
| 77 | 1 | −2.71891 | −1 | −2.37313 | −1 |
| 58 | 1 | −2.74247 | −1 | −2.49077 | −1 |
| 121 | 0 | −1.97418 | −1 | −1.71114 | −1 |
| 113 | 0 | −2.16736 | −1 | −2.11422 | −1 |

TABLE 6B-continued

Contains all proteins that are statistically enriched or depleted in response to SARS-CoV-2 infection in HEK293T and A549 cells.

| | | | | | |
|---|---|---|---|---|---|
| 116 | 1 | −2.61896 | −1 | −1.62131 | −1 |
| 119 | 1 | −2.06265 | −1 | −1.82755 | −1 |
| 86 | 1 | −1.39887 | −1 | −2.09535 | −1 |
| 34 | 1 | −2.65696 | −1 | −3.01574 | −1 |
| 31 | 0 | −1.95776 | −1 | −3.19704 | −1 |
| 114 | −1 | −1.8177 | −1 | −2.03259 | −1 |
| 92 | −1 | −2.31365 | −1 | −1.7888 | −1 |
| 111 | −1 | 2.03503 | 1 | 1.67209 | 1 |
| 136 | 1 | −1.6062 | −1 | −1.65837 | −1 |
| 139 | 0 | −2.06118 | −1 | −1.59013 | −1 |
| 123 | −1 | −1.20561 | −1 | −1.57725 | −1 |
| 46 | 0 | −3.09432 | −1 | −1.79924 | −1 |
| 137 | 1 | −2.06605 | −1 | −1.47052 | −1 |
| 45 | 0 | −2.95424 | −1 | −2.43161 | −1 |
| 83 | −1 | −2.06748 | −1 | −2.18974 | −1 |
| 70 | −1 | −2.32033 | −1 | −2.56971 | −1 |
| 27 | 1 | −3.5592 | −1 | −2.48707 | −1 |
| 60 | 1 | −1.41427 | −1 | −2.28812 | −1 |
| 144 | 1 | −3.01405 | −1 | −1.59869 | −1 |
| 59 | 1 | −2.6773 | −1 | −2.8349 | −1 |
| 98 | 0 | −2.27059 | −1 | −1.85025 | −1 |
| 89 | 1 | −2.19313 | −1 | −1.9368 | −1 |
| 69 | 1 | −1.84081 | −1 | −1.81683 | −1 |
| 38 | −1 | −2.71126 | −1 | −2.74821 | −1 |
| 57 | −1 | −2.63629 | −1 | −2.7153 | −1 |
| 52 | 1 | −2.61151 | −1 | −2.54339 | −1 |
| 49 | 0 | −1.22976 | −1 | −2.58274 | −1 |
| 29 | −1 | −2.31698 | −1 | −2.74778 | −1 |
| 67 | −1 | −1.2758 | −1 | −2.54657 | −1 |
| 64 | 1 | −2.83517 | −1 | −2.7952 | −1 |
| 120 | 0 | −1.40276 | −1 | −2.03182 | −1 |
| 25 | −1 | −2.60963 | −1 | −3.24212 | −1 |
| 61 | −1 | −2.24668 | −1 | −2.23418 | −1 |
| 28 | −1 | −2.08554 | −1 | −3.40386 | −1 |
| 39 | −1 | −2.61544 | −1 | −2.8314 | −1 |
| 115 | −1 | −0.83221 | −1 | −2.00608 | −1 |
| 53 | 1 | 2.06484 | 1 | 1.67564 | 1 |
| 65 | −1 | −2.329 | −1 | −2.41264 | −1 |
| 84 | 1 | −3.1782 | −1 | −1.57686 | −1 |
| 130 | 1 | −2.38435 | −1 | −1.50576 | −1 |
| 47 | −1 | −2.22865 | −1 | −2.86715 | −1 |
| 125 | 0 | −1.61626 | −1 | −1.61054 | −1 |
| 109 | −1 | −1.74278 | −1 | −2.13307 | −1 |
| 132 | 1 | −1.62995 | −1 | −1.69322 | −1 |
| 112 | −1 | −1.29317 | −1 | −1.54288 | −1 |
| 90 | 0 | −2.00854 | −1 | −1.68094 | −1 |
| 99 | 1 | −2.51027 | −1 | −1.70261 | −1 |
| 110 | −1 | −1.9801 | −1 | −1.72988 | −1 |
| 55 | 1 | −2.35514 | −1 | −2.7623 | −1 |
| 101 | 1 | −3.10641 | −1 | −1.59397 | −1 |
| 41 | 1 | −2.70533 | −1 | −2.61715 | −1 |
| 106 | 1 | −2.38099 | −1 | −1.7481 | −1 |
| 73 | −1 | −2.1099 | −1 | −1.80118 | −1 |
| 24 | 0 | −2.77113 | −1 | −3.48819 | −1 |
| 118 | 0 | −1.35365 | −1 | −2.01093 | −1 |
| 79 | 0 | −2.5299 | −1 | −1.77207 | −1 |
| 50 | −1 | −2.34168 | −1 | −1.86867 | −1 |
| 140 | −1 | −1.51239 | −1 | −1.73486 | −1 |
| 145 | 0 | −1.48092 | −1 | −1.63066 | −1 |
| 85 | −1 | −1.66711 | −1 | −1.91438 | −1 |
| 94 | −1 | −1.83036 | −1 | −2.25698 | −1 |
| 128 | 1 | −1.04969 | −1 | −1.4281 | −1 |
| 71 | −1 | −1.84924 | −1 | −1.92352 | −1 |
| 96 | 1 | −2.2275 | −1 | −2.03058 | −1 |
| 129 | −1 | −2.74176 | −1 | −1.35716 | −1 |
| 62 | −1 | −2.91815 | −1 | −2.56759 | −1 |
| 117 | −1 | −1.57345 | −1 | −1.59592 | −1 |
| 82 | −1 | −2.15854 | −1 | −2.33038 | −1 |
| 126 | −1 | −2.13324 | −1 | −1.61776 | −1 |
| 81 | 1 | −1.91235 | −1 | −2.45317 | −1 |
| 72 | 0 | −2.22458 | −1 | −1.72112 | −1 |
| 56 | 1 | −2.36061 | −1 | −2.61534 | −1 |
| 103 | −1 | −1.2446 | −1 | −2.01918 | −1 |
| 91 | 0 | −1.75559 | −1 | −2.27857 | −1 |
| 22 | 1 | −2.84521 | −1 | −3.51615 | −1 |
| 48 | 0 | −2.04439 | −1 | −2.90937 | −1 |
| 143 | −1 | −1.0982 | −1 | −1.51634 | −1 |

TABLE 6B-continued

Contains all proteins that are statistically enriched or depleted in response to SARS-CoV-2 infection in HEK293T and A549 cells.

| | | | | | |
|---|---|---|---|---|---|
| 37 | 1 | −2.65828 | −1 | −2.9014 | −1 |
| 75 | 0 | −2.06773 | −1 | −2.6057 | −1 |
| 134 | 1 | −2.28523 | −1 | −1.70733 | −1 |
| 80 | 0 | −2.91823 | −1 | −2.1991 | −1 |
| 88 | −1 | −1.89429 | −1 | −1.83736 | −1 |
| 15 | 0 | 4.1221 | 1 | 4.0768 | 1 |

| idx | HEK_0_3_diff | HEK_0_3_dir | HEK_3_6_diff | HEK_3_6_dir | HEK_6_24_diff |
|---|---|---|---|---|---|
| 3 | 3.9547 | 1 | 1.4428 | 1 | 0.2965 |
| 9 | 3.93 | 1 | 0.7434 | 1 | 0.408 |
| 1 | 4.2426 | 1 | 1.4912 | 1 | 1.0719 |
| 12 | 2.4088 | 1 | 1.6631 | 1 | 0.6226 |
| 5 | 3.5497 | 1 | 1.0044 | 1 | 0.9841 |
| 19 | 0 | 0 | 3.6545 | 1 | 0.0068 |
| 13 | 0 | 0 | 3.8418 | 1 | 0.7204 |
| 7 | 0 | 0 | 3.8866 | 1 | 1.4331 |
| 6 | 2.8003 | 1 | 2.1053 | 1 | 0.669 |
| 2 | 4.0154 | 1 | 0.9739 | 1 | 0.8504 |
| 10 | 2.8963 | 1 | 1.067 | 1 | 1.084 |
| 18 | 2.85737 | 1 | 0.23144 | 1 | 0.16357 |
| 14 | 0 | 0 | 3.8542 | 1 | 0.5927 |
| 4 | 0 | 0 | 3.61 | 1 | 1.2373 |
| 8 | 3.694 | 1 | 0.4106 | 1 | 0.6353 |
| 54 | 2.70664 | 1 | −0.32058 | −1 | −0.05885 |
| 17 | 0 | 0 | 2.3105 | 1 | 1.4785 |
| 11 | 0 | 0 | 3.4998 | 1 | 1.2642 |
| 20 | 0 | 0 | 2.2835 | 1 | 1.227 |
| 93 | 1.68178 | 1 | 0.16531 | 1 | 0.09588 |
| 40 | 0 | 0 | 2.4685 | 1 | 0.2996 |
| 33 | −2.31459 | −1 | 4.21981 | 1 | 0.59873 |
| 63 | 1.12304 | 1 | 0.18829 | 1 | 0.56105 |
| 16 | 0 | 0 | 2.2521 | 1 | 1.5255 |
| 78 | −1.19296 | −1 | 0.12692 | 1 | −0.82703 |
| 87 | 1.14712 | 1 | −0.11528 | −1 | −3.46251 |
| 26 | 1.85864 | 1 | −0.47217 | −1 | 1.52262 |
| 35 | −2.74898 | −1 | 0.88075 | 1 | −1.1687 |
| 138 | 1.15703 | 1 | −0.12828 | −1 | −2.49708 |
| 105 | 0.96638 | 1 | 0.43987 | 1 | 0.42055 |
| 141 | 0.38739 | 1 | 2.15919 | 1 | −4.03319 |
| 131 | 0.57343 | 1 | 0.20163 | 1 | −2.49633 |
| 30 | −1.37808 | −1 | −0.11761 | −1 | −1.68333 |
| 142 | 0.80324 | 1 | −0.20824 | −1 | −2.12888 |
| 43 | 1.4272 | 1 | 0.3768 | 1 | 1.3387 |
| 102 | 0.39134 | 1 | 0.13959 | 1 | −2.51686 |
| 23 | −0.14934 | −1 | −0.33377 | −1 | −2.29019 |
| 107 | 0.50049 | 1 | 0.00837 | 0 | −2.46128 |
| 21 | −0.10349 | −1 | −0.6088 | −1 | −2.56843 |
| 127 | 0.24802 | 1 | 0.5692 | 1 | −2.53714 |
| 135 | 0.34116 | 1 | 0.36449 | 1 | −2.19687 |
| 146 | 1.05627 | 1 | −0.62281 | −1 | −1.89331 |
| 100 | 1.54223 | 1 | −0.7896 | −1 | −2.28304 |
| 36 | 0.98455 | 1 | −0.41493 | −1 | 2.2242 |
| 66 | −0.66968 | −1 | 0.93819 | 1 | −2.91913 |
| 104 | 0.44477 | 1 | 0.0179 | 0 | −2.58114 |
| 68 | 0.17553 | 1 | 0.33967 | 1 | −2.67048 |
| 44 | −0.21088 | −1 | −0.03797 | 0 | −1.49785 |
| 133 | 0.91913 | 1 | −0.30313 | −1 | −2.09595 |
| 32 | −0.08126 | 0 | −0.35795 | −1 | −2.36662 |
| 97 | 0.93486 | 1 | −0.17892 | −1 | −2.442 |
| 74 | −0.19724 | −1 | 0.77324 | 1 | −2.76551 |
| 108 | 0.42431 | 1 | 0.232 | 1 | −2.40441 |
| 42 | −0.54192 | −1 | −0.38848 | −1 | −1.53104 |
| 122 | 0.5295 | 1 | 0.39809 | 1 | −2.50878 |
| 76 | 0.44365 | 1 | 0.28641 | 1 | −2.60926 |
| 95 | −0.01127 | 0 | −1.65466 | −1 | −0.31957 |
| 124 | 1.08288 | 1 | −0.57754 | −1 | −2.17596 |
| 51 | −0.17124 | −1 | −0.84636 | −1 | −1.41176 |
| 77 | −0.11236 | −1 | 0.19223 | 1 | −2.453 |
| 58 | 0.043 | 0 | 0.18723 | 1 | −2.72101 |
| 121 | 0.51577 | 1 | 0.00346 | 0 | −2.23037 |
| 113 | 0.42944 | 1 | −0.19076 | −1 | −2.35291 |
| 116 | 0.66652 | 1 | −0.33024 | −1 | −1.9576 |
| 119 | 0.39543 | 1 | −0.10404 | −1 | −2.11895 |
| 86 | 0.08643 | 0 | −0.31861 | −1 | −1.86317 |
| 34 | −1.27059 | −1 | −0.66192 | −1 | −1.08323 |
| 31 | −0.07379 | 0 | −0.96687 | −1 | −2.15638 |

TABLE 6B-continued

Contains all proteins that are statistically enriched or depleted in response to SARS-CoV-2 infection in HEK293T and A549 cells.

| | | | | | |
|---|---|---|---|---|---|
| 114 | 0.52207 | 1 | −0.10505 | −1 | −2.44961 |
| 92 | 1.03501 | 1 | −0.46578 | −1 | −2.35802 |
| 111 | 0.32799 | 1 | 0.74199 | 1 | 0.60211 |
| 136 | 1.14869 | 1 | 0.67529 | 1 | −3.48234 |
| 139 | 0.65592 | 1 | −0.48586 | −1 | −1.76019 |
| 123 | 0.60866 | 1 | −0.64605 | −1 | −1.53987 |
| 46 | 0.85493 | 1 | 0.36942 | 1 | −3.0236 |
| 137 | 0.25115 | 1 | 0.10529 | 1 | −1.82696 |
| 45 | 0.24289 | 1 | −0.0017 | 0 | −2.6728 |
| 83 | 0.6816 | 1 | −0.20654 | −1 | −2.66481 |
| 70 | 0.05822 | 0 | 0.05078 | 0 | −2.67872 |
| 27 | 0.36569 | 1 | 0.41267 | 1 | −3.26544 |
| 60 | −0.40324 | −1 | 0.47169 | 1 | −2.35657 |
| 144 | 1.12341 | 1 | −1.28489 | −1 | −1.43721 |
| 59 | 0.09245 | 0 | 0.0408 | 0 | −2.96815 |
| 98 | 0.44092 | 1 | −0.14639 | −1 | −2.14478 |
| 89 | 0.51303 | 1 | −0.1402 | −1 | −2.30963 |
| 69 | 0.05496 | 0 | −0.05137 | 0 | −1.82042 |
| 38 | 0.4229 | 1 | 0.09 | 0 | −3.26111 |
| 57 | −0.05326 | 0 | 0.13104 | 1 | −2.79308 |
| 52 | −0.56246 | −1 | 0.69848 | 1 | −2.67942 |
| 49 | −0.38412 | −1 | 0.42891 | 1 | −2.62754 |
| 29 | 0.17418 | 1 | −0.20473 | −1 | −2.71723 |
| 67 | 0.48448 | 1 | −0.77858 | −1 | −2.25247 |
| 64 | 0.19739 | 1 | −0.44624 | −1 | −2.54635 |
| 120 | 0.30518 | 1 | −0.67717 | −1 | −1.65983 |
| 25 | −0.14407 | −1 | −0.11677 | −1 | −2.98127 |
| 61 | −0.34138 | −1 | −0.23374 | −1 | −1.65905 |
| 28 | −0.21367 | −1 | −0.46893 | −1 | −2.72126 |
| 39 | −0.01397 | 0 | −0.59503 | −1 | −2.2224 |
| 115 | −0.16684 | −1 | 0.17717 | 1 | −2.0164 |
| 53 | 2.3841 | 1 | −2.76828 | −1 | 2.05982 |
| 65 | 0.12251 | 1 | 0.13614 | 1 | −2.67129 |
| 84 | 4.08E−01 | 1 | −0.51452 | −1 | −1.47044 |
| 130 | 0.2865 | 1 | −0.26903 | −1 | −1.52323 |
| 47 | −0.67879 | −1 | 0.09688 | 0 | −2.28525 |
| 125 | −0.02819 | 0 | −0.08122 | 0 | −1.50113 |
| 109 | 0.48406 | 1 | −0.03968 | 0 | −2.57745 |
| 132 | 3.07943 | 1 | −2.72786 | −1 | −2.0448 |
| 112 | 0.53008 | 1 | −0.18905 | −1 | −1.88391 |
| 90 | 0.62225 | 1 | −0.78146 | −1 | −1.52174 |
| 99 | 0.65016 | 1 | −0.53235 | −1 | −1.82042 |
| 110 | 0.31673 | 1 | −0.02475 | 0 | −2.02186 |
| 55 | 0.30635 | 1 | −0.34588 | −1 | −2.72276 |
| 101 | 0.48049 | 1 | −0.68339 | −1 | −1.39107 |
| 41 | −0.03269 | 0 | 0.18373 | 1 | −2.7682 |
| 106 | 0.80624 | 1 | −0.80634 | −1 | −1.748 |
| 73 | −0.3555 | −1 | 0.45354 | 1 | −1.89922 |
| 24 | −0.80581 | −1 | 0.26537 | 1 | −2.94775 |
| 118 | 0.65286 | 1 | 0.11117 | 1 | −2.77496 |
| 79 | 0.72091 | 1 | −0.54814 | −1 | −1.94484 |
| 50 | 0.449 | 1 | 0.68695 | 1 | −3.00462 |
| 140 | 0.90613 | 1 | −1.20766 | −1 | −1.43333 |
| 145 | 0.01776 | 0 | −0.29066 | −1 | −1.35775 |
| 85 | 0.63624 | 1 | −0.40376 | −1 | −2.14686 |
| 94 | 0.57442 | 1 | −0.42603 | −1 | −2.40537 |
| 128 | 0.39085 | 1 | 0.1181 | 1 | −1.93705 |
| 71 | 0.58457 | 1 | −0.17907 | −1 | −2.32901 |
| 96 | −0.5656 | −1 | −0.0175 | 0 | −1.44748 |
| 129 | 0.40152 | 1 | −0.75974 | −1 | −0.99894 |
| 62 | 0.43121 | 1 | −1.62748 | −1 | −1.37133 |
| 117 | 0.11772 | 1 | 0.12032 | 1 | −1.83395 |
| 82 | 0.59256 | 1 | −0.81518 | −1 | −2.10776 |
| 126 | −0.16172 | −1 | −0.37717 | −1 | −1.07887 |
| 81 | 0.17933 | 1 | −0.59641 | −1 | −2.03609 |
| 72 | 0.77574 | 1 | −0.49102 | −1 | −2.00584 |
| 56 | −0.38195 | −1 | 0.06471 | 0 | −2.2981 |
| 103 | 0.62209 | 1 | −0.20276 | −1 | −2.43851 |
| 91 | 0.1945 | 1 | −0.35686 | −1 | −2.11621 |
| 22 | −0.44581 | −1 | 0.63011 | 1 | −3.70045 |
| 48 | 0.07156 | 0 | −0.21979 | −1 | −2.76114 |
| 143 | 0.79859 | 1 | −0.44502 | −1 | −1.86991 |
| 37 | −0.44855 | −1 | 0.21052 | 1 | −2.66338 |

TABLE 6B-continued

Contains all proteins that are statistically enriched or depleted in response to SARS-CoV-2 infection in HEK293T and A549 cells.

| | | | | | |
|---|---|---|---|---|---|
| 75 | 0.38545 | 1 | −0.71231 | −1 | −2.27884 |
| 134 | 0.18667 | 1 | −0.88692 | −1 | −1.00708 |
| 80 | −0.09769 | 0 | −0.84655 | −1 | −1.25487 |
| 88 | 0.22744 | 1 | 0.05269 | 0 | −2.11749 |
| 15 | 0 | 0 | 0 | 0 | 4.0768 |

| idx | HEK_6_24_dir | dir_FX_count_0 | dir_FX_count_p1 | dir_FX_count_n1 |
|---|---|---|---|---|
| 3 | 1 | 0 | 7 | 1 |
| 9 | 1 | 0 | 7 | 1 |
| 1 | 1 | 0 | 8 | 0 |
| 12 | 1 | 1 | 7 | 0 |
| 5 | 1 | 0 | 8 | 0 |
| 19 | 0 | 3 | 4 | 1 |
| 13 | 1 | 2 | 6 | 0 |
| 7 | 1 | 2 | 6 | 0 |
| 6 | 1 | 1 | 6 | 1 |
| 2 | 1 | 0 | 8 | 0 |
| 10 | 1 | 1 | 7 | 0 |
| 18 | 1 | 2 | 6 | 0 |
| 14 | 1 | 2 | 6 | 0 |
| 4 | 1 | 2 | 6 | 0 |
| 8 | 1 | 0 | 8 | 0 |
| 54 | 0 | 1 | 5 | 2 |
| 17 | 1 | 2 | 6 | 0 |
| 11 | 1 | 2 | 6 | 0 |
| 20 | 1 | 2 | 6 | 0 |
| 93 | 0 | 1 | 7 | 0 |
| 40 | 1 | 2 | 5 | 1 |
| 33 | 1 | 2 | 5 | 1 |
| 63 | 1 | 0 | 8 | 0 |
| 16 | 1 | 2 | 6 | 0 |
| 78 | −1 | 0 | 1 | 7 |
| 87 | −1 | 0 | 3 | 5 |
| 26 | 1 | 0 | 6 | 2 |
| 35 | −1 | 0 | 1 | 7 |
| 138 | −1 | 0 | 2 | 6 |
| 105 | 1 | 0 | 7 | 1 |
| 141 | −1 | 0 | 4 | 4 |
| 131 | −1 | 0 | 3 | 5 |
| 30 | −1 | 0 | 1 | 7 |
| 142 | −1 | 0 | 3 | 5 |
| 43 | 1 | 1 | 7 | 0 |
| 102 | −1 | 0 | 3 | 5 |
| 23 | −1 | 0 | 0 | 8 |
| 107 | −1 | 1 | 2 | 5 |
| 21 | −1 | 0 | 0 | 8 |
| 127 | −1 | 0 | 4 | 4 |
| 135 | −1 | 0 | 3 | 5 |
| 146 | −1 | 0 | 3 | 5 |
| 100 | −1 | 0 | 3 | 5 |
| 36 | 1 | 2 | 5 | 1 |
| 66 | −1 | 0 | 3 | 5 |
| 104 | −1 | 1 | 3 | 4 |
| 68 | −1 | 0 | 4 | 4 |
| 44 | −1 | 1 | 0 | 7 |
| 133 | −1 | 1 | 2 | 5 |
| 32 | −1 | 2 | 0 | 6 |
| 97 | −1 | 1 | 2 | 5 |
| 74 | −1 | 0 | 2 | 6 |
| 108 | −1 | 1 | 3 | 4 |
| 42 | −1 | 1 | 0 | 7 |
| 122 | −1 | 1 | 3 | 4 |
| 76 | −1 | 0 | 3 | 5 |
| 95 | −1 | 2 | 0 | 6 |
| 124 | −1 | 0 | 3 | 5 |
| 51 | −1 | 0 | 1 | 7 |
| 77 | −1 | 0 | 3 | 5 |
| 58 | −1 | 1 | 2 | 5 |
| 121 | −1 | 2 | 2 | 4 |
| 113 | −1 | 1 | 2 | 5 |
| 116 | −1 | 1 | 2 | 5 |
| 119 | −1 | 1 | 2 | 5 |
| 86 | −1 | 1 | 1 | 6 |
| 34 | −1 | 0 | 1 | 7 |
| 31 | −1 | 2 | 0 | 6 |
| 114 | −1 | 0 | 2 | 6 |

TABLE 6B-continued

Contains all proteins that are statistically enriched or depleted in response to SARS-CoV-2 infection in HEK293T and A549 cells.

| | | | | |
|---|---|---|---|---|
| 92 | −1 | 0 | 2 | 6 |
| 111 | 1 | 0 | 7 | 1 |
| 136 | −1 | 0 | 3 | 5 |
| 139 | −1 | 1 | 2 | 5 |
| 123 | −1 | 0 | 1 | 7 |
| 46 | −1 | 1 | 2 | 5 |
| 137 | −1 | 0 | 4 | 4 |
| 45 | −1 | 2 | 2 | 4 |
| 83 | −1 | 0 | 2 | 6 |
| 70 | −1 | 2 | 1 | 5 |
| 27 | −1 | 0 | 3 | 5 |
| 60 | −1 | 0 | 2 | 6 |
| 144 | −1 | 0 | 3 | 5 |
| 59 | −1 | 2 | 2 | 4 |
| 98 | −1 | 1 | 2 | 5 |
| 89 | −1 | 0 | 2 | 6 |
| 69 | −1 | 2 | 1 | 5 |
| 38 | −1 | 1 | 2 | 5 |
| 57 | −1 | 1 | 2 | 5 |
| 52 | −1 | 0 | 2 | 6 |
| 49 | −1 | 1 | 1 | 6 |
| 29 | −1 | 0 | 1 | 7 |
| 67 | −1 | 0 | 1 | 7 |
| 64 | −1 | 0 | 3 | 5 |
| 120 | −1 | 2 | 1 | 5 |
| 25 | −1 | 0 | 1 | 7 |
| 61 | −1 | 1 | 0 | 7 |
| 28 | −1 | 0 | 1 | 7 |
| 39 | −1 | 1 | 1 | 6 |
| 115 | −1 | 0 | 1 | 7 |
| 53 | 1 | 0 | 6 | 2 |
| 65 | −1 | 0 | 3 | 5 |
| 84 | −1 | 0 | 3 | 5 |
| 130 | −1 | 1 | 2 | 5 |
| 47 | −1 | 1 | 1 | 6 |
| 125 | −1 | 3 | 0 | 5 |
| 109 | −1 | 1 | 2 | 5 |
| 132 | −1 | 0 | 2 | 6 |
| 112 | −1 | 0 | 1 | 7 |
| 90 | −1 | 1 | 1 | 6 |
| 99 | −1 | 1 | 2 | 5 |
| 110 | −1 | 1 | 2 | 5 |
| 55 | −1 | 0 | 3 | 5 |
| 101 | −1 | 0 | 3 | 5 |
| 41 | −1 | 2 | 2 | 4 |
| 106 | −1 | 1 | 2 | 5 |
| 73 | −1 | 0 | 1 | 7 |
| 24 | −1 | 1 | 2 | 5 |
| 118 | −1 | 1 | 2 | 5 |
| 79 | −1 | 1 | 2 | 5 |
| 50 | −1 | 0 | 2 | 6 |
| 140 | −1 | 0 | 2 | 6 |
| 145 | −1 | 2 | 1 | 5 |
| 85 | −1 | 0 | 1 | 7 |
| 94 | −1 | 0 | 2 | 6 |
| 128 | −1 | 0 | 3 | 5 |
| 71 | −1 | 0 | 1 | 7 |
| 96 | −1 | 1 | 2 | 5 |
| 129 | −1 | 0 | 2 | 6 |
| 62 | −1 | 0 | 2 | 6 |
| 117 | −1 | 0 | 2 | 6 |
| 82 | −1 | 0 | 2 | 6 |
| 126 | −1 | 0 | 1 | 7 |
| 81 | −1 | 0 | 2 | 6 |
| 72 | −1 | 1 | 1 | 6 |
| 56 | −1 | 1 | 1 | 6 |
| 103 | −1 | 0 | 1 | 7 |
| 91 | −1 | 2 | 1 | 5 |
| 22 | −1 | 0 | 2 | 6 |
| 48 | −1 | 3 | 0 | 5 |
| 143 | −1 | 0 | 2 | 6 |
| 37 | −1 | 1 | 2 | 5 |
| 75 | −1 | 1 | 2 | 5 |
| 134 | −1 | 0 | 3 | 5 |

TABLE 6B-continued

| Contains all proteins that are statistically enriched or depleted in response to SARS-CoV-2 infection in HEK293T and A549 cells. | | | | |
|---|---|---|---|---|
| 80 | −1 | 2 | 1 | 5 |
| 88 | −1 | 1 | 2 | 5 |
| 15 | 1 | 4 | 4 | 0 |

To assess if there are global changes in HLA-I antigen presentation due to SARS-COV-2 infection, the overlap between HLA-I peptidomes of uninfected and 24hpi A549 cells was compared. A degree of overlap of these peptides was found detected in both experiments (62%, FIG. 9C) was similar to what is seen in biological replicates of the same sample (Abelin et al., 2017; Demmers et al., 2019; Sarkizova et al., 2020). The high overlap of host HLA-I peptides in infected and uninfected cells and the relatively low HLA-I peptides representation from viral proteins that are expressed 6hpi or later (FIG. 8D) prompted interrogation of the whole proteome data for evidence of viral interference with the antigen presentation and protein degradation pathways. Because the whole proteome from the cell lysate post HLA immunopurification was analyzed, the levels of HLA-A,-B and -C could not be evaluated. However, all other host proteins should remain intact and enable proteomic analyses of host responses to infection.

Figure 9D:
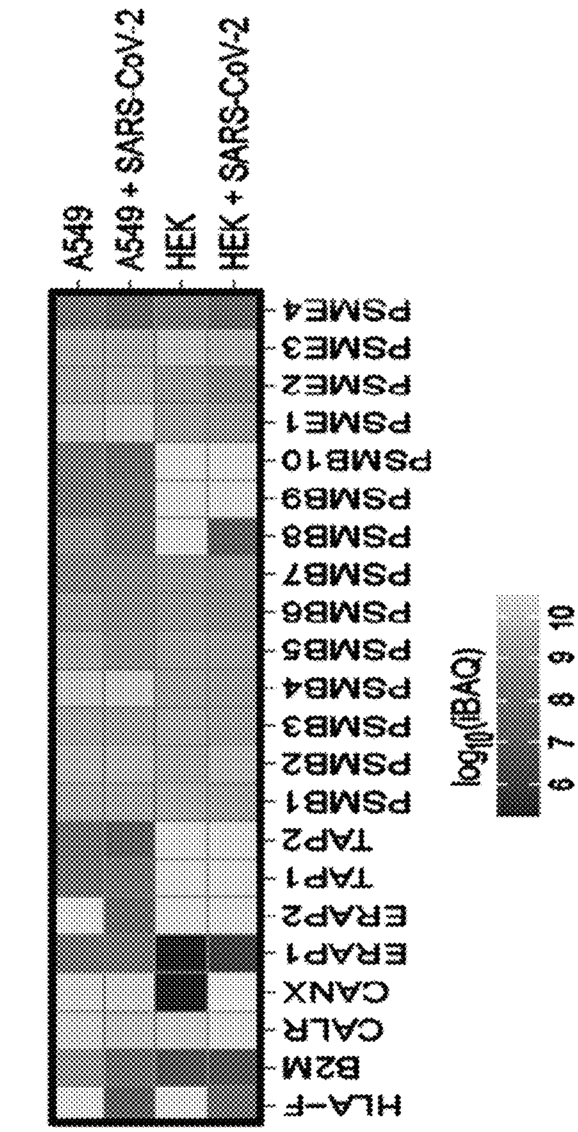
Figure 9C:
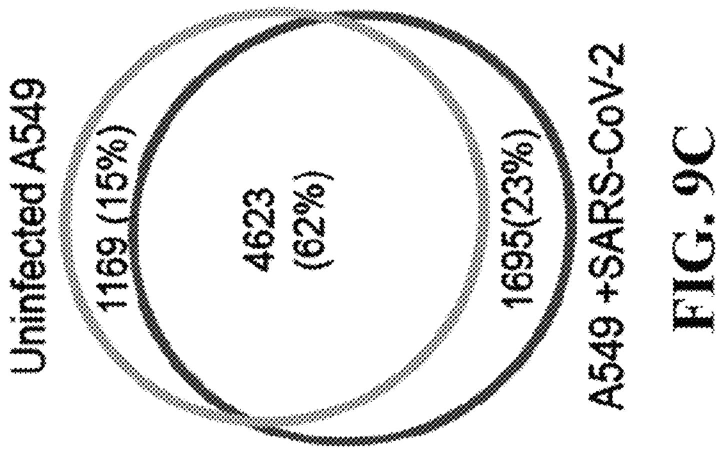
Figure 9F:
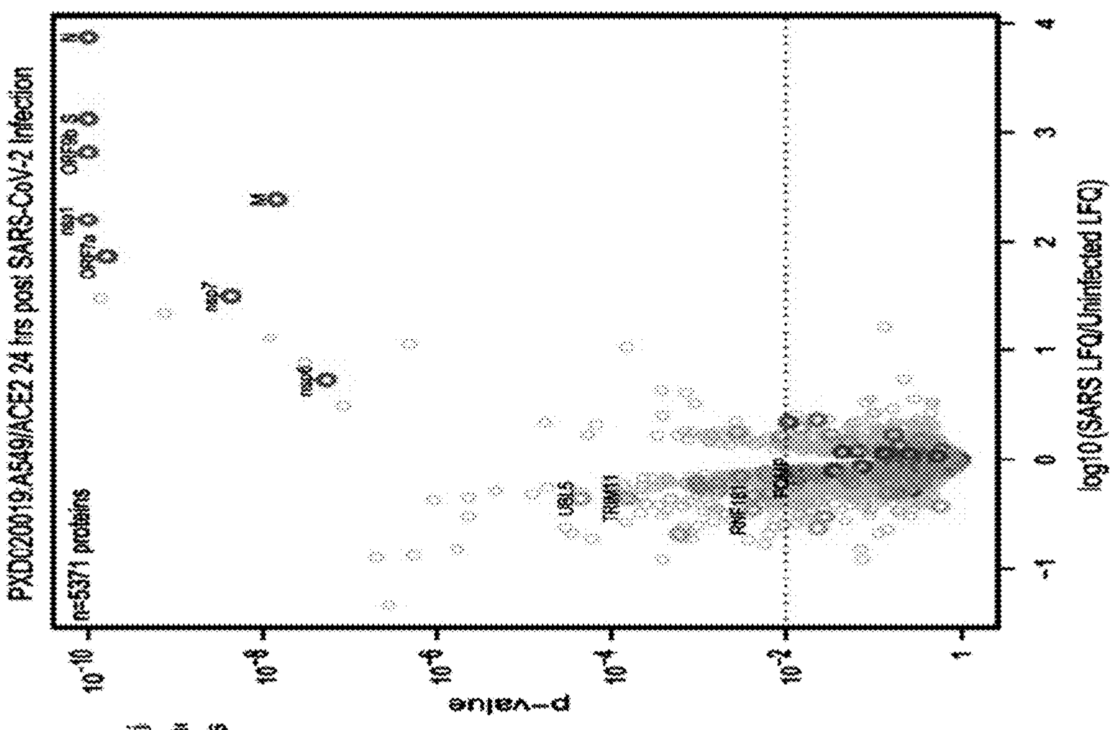
Figure 9E:
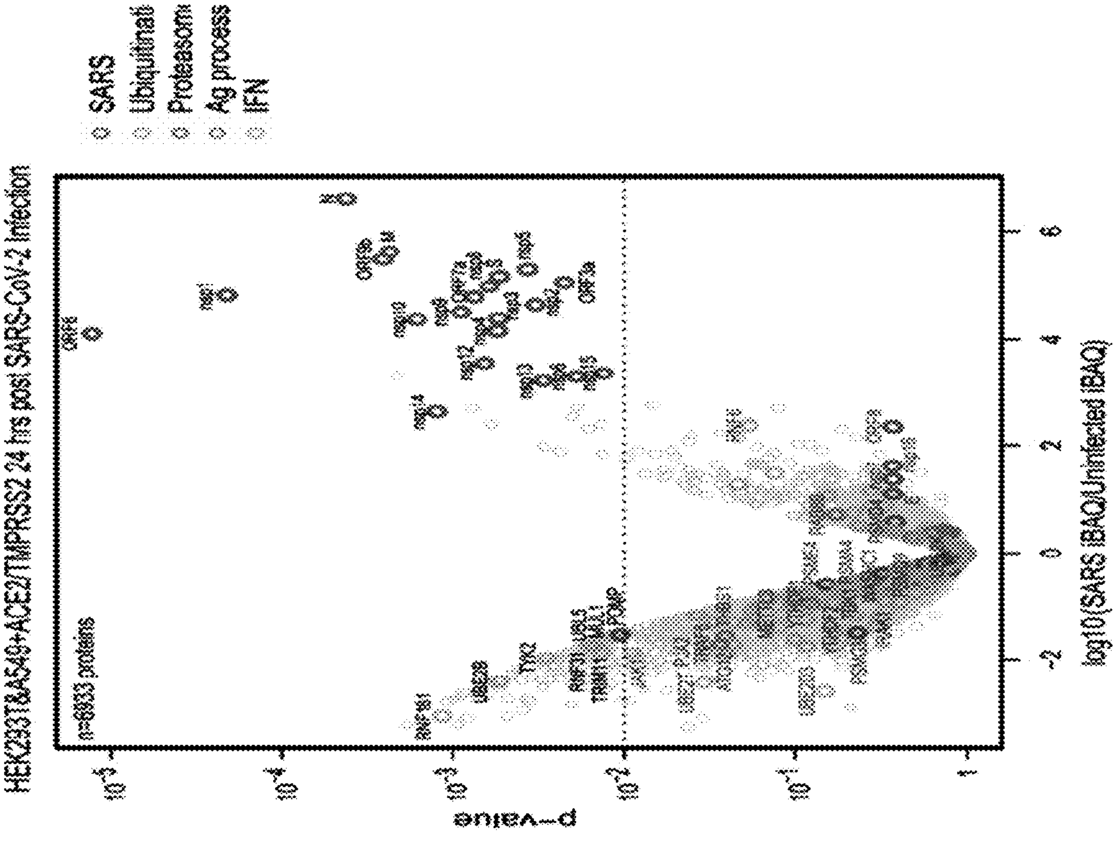
Figure 15D:
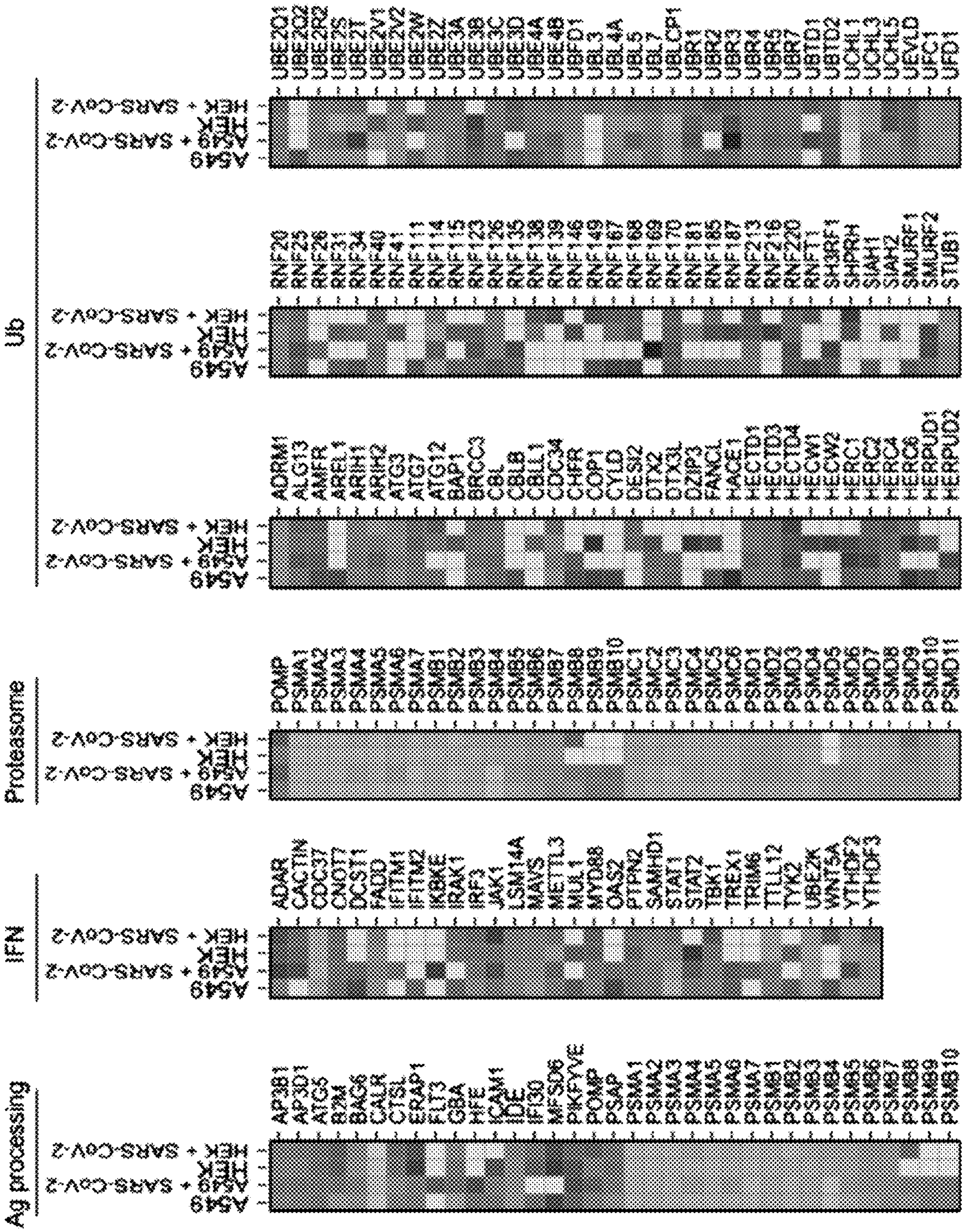
Figure 15D:
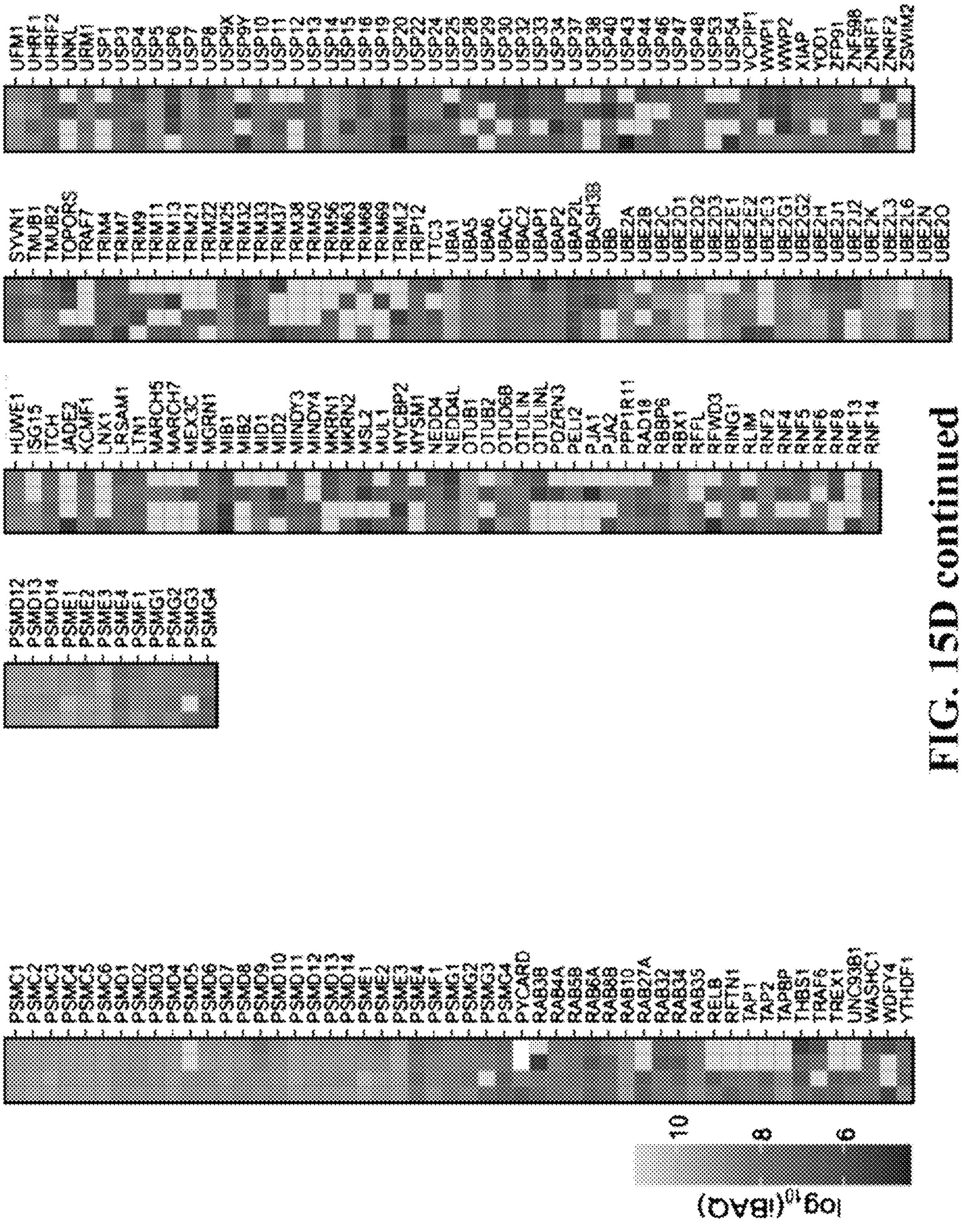
Figure 15E:
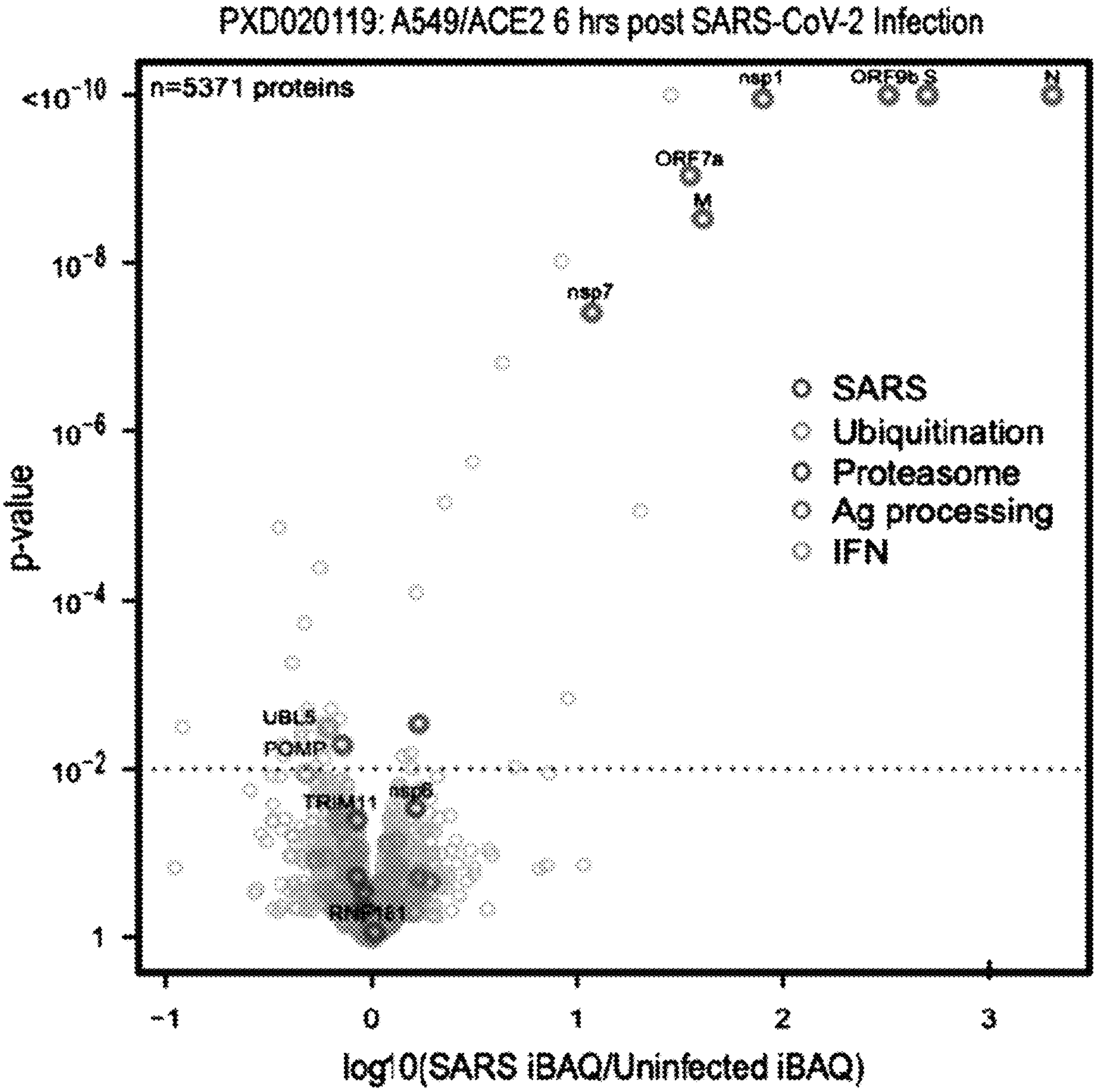

Initially, the canonical HLA-I presentation pathway proteins was evaluated across both the uninfected and 24hpi A549 and HEK293T cells in the fractionated proteome data that contained about 7,000 quantified proteins (FIG. 9D, FIG. 15D, and Tables 6A-6B and data not shown). Although some antigen processing proteins had cell type specific expression patterns, no significant differences in these proteins was observed, such as B2M, ERAP1/2, TAP1/2, and proteasome subunits upon SARS-COV-2 infection. Of note, HLA-F, which has been shown to not be sensitive to the W6/32 antibody used for the HLA IP (Wainwright et al., 2000), and thus should not be depleted from the lysate prior whole proteome analysis, showed increased expression upon infection. HLA-F has recently been recognized as an immune regulatory molecule that interacts with KIR3DS1 on NK cells during viral infection (Lunemann et al., 2018).

Next, all proteins detected in uninfected and 24 hpi A549 and HEK293T were compared to determine if proteins involved in ubiquitination, proteasomal function, antigen processing and IFN signaling were altered (FIG. 9E, Tables 6A-6B, and data not shown). A general depletion of ubiquitination pathway proteins was observed, with several significantly altered in response to SARS-COV-2 infection (FIG. 9E and Table 6A-6B), including depletion of RNF181, UBE2B, and TRIM11. POMP (proteasome maturation protein), a chaperone critical for the assembly of 20S proteasomes and immunoproteasomes, was the most significantly depleted proteasomal protein in both infected cell lines ($p<0.0095$). POMP has recently been reported to impact ORF9c stability, which has been implicated in suppressing the antiviral response in cells (Dominguez Andres et al., 2020). As reported across multiple cell lines infected with SARS-COV-2 (Chen et al., 2020a), the tyrosine kinase, JAK1, critical for IFN signaling, was depleted in both A549 and HEK293T cells upon SARS-COV-2 infection (FIG. 9E). The observed depletion of POMP and ubiquitination pathway proteins was confirmed in an independent proteome study (PXD020019, (Stukalov et al. 2020)) that profiled uninfected and infected A549/ACE2 cells 6hpi (FIG. 15E) and 24hpi (FIG. 9F). Taken together, these data suggest that SARS-COV-2 may interfere with IFN signaling proteins and the HLA-I pathway through both POMP depletion and by altering ubiquitination pathway proteins, that in turn, may prevent abundant SARS proteins expressed later in infection from being effectively processed and presented.

SARS-COV-2 HLA-I Peptides are Derived from Internal Out-of-Frame ORFs in S and N Remarkably, nine HLA-I peptides processed from internal out-of-frame ORFs present in the coding region of S and N were detected. In the S.iORF1/2 proteins, three HLA-I peptides were detected: GPMVLRGLIT (SEQ ID NO: 6), GLITLSYHL (SEQ ID NO: 5) and MLLGSMLYM (SEQ ID NO: 4) in HEK293T cells, all of which are predicted to bind HLA alleles in this cell line FIG. 3A. GLITLSYHL (SEQ ID NO: 5) is predicted to bind strongly to A*02:01 (rank 0.23), and GPMVLRGLIT (SEQ ID NO: 6) and MLLGSMLYM (SEQ ID NO: 4) are predicted to bind weakly to B*07:02 and A*02:01 (rank 2.12 and 2.16, respectively), In addition, six HLA-I peptides from ORF9b were detected, an internal out-of-frame ORF in the coding region of N, in A549 and HEK293T cells (FIG. 3B). These HLA-I peptides cover overlapping protein sequences in both cell lines and contain binding motifs compatible with the expressed HLA-I alleles. All six HLA-I peptides were predicted to be highly likely to bind to either A*02:01 in HEK293T cells (SLEDKAFQL (SEQ ID NO: 7), KAFQLTPIAV (SEQ ID NO: 13), ELPDEFVVV (SEQ ID NO: 12), and ELPDEFVVVTV (SEQ ID NO: 8), rank 0.43, 0.57, 0.77 and 0.42, respectively) or B*18:01 in A549 cells (LEDKAFQL (SEQ ID NO: 10) and DEFVVVTV (SEQ ID NO: 11), rank 0.27 and 0.0008, respectively). To validate the amino acid sequences of these non-canonical peptides, the tandem mass spectra of synthetic peptides were compared to the experimental spectra and observed high correlation between fragment ions and retention times (+/−2 minutes, FIG. 3C).

Figure 3E:
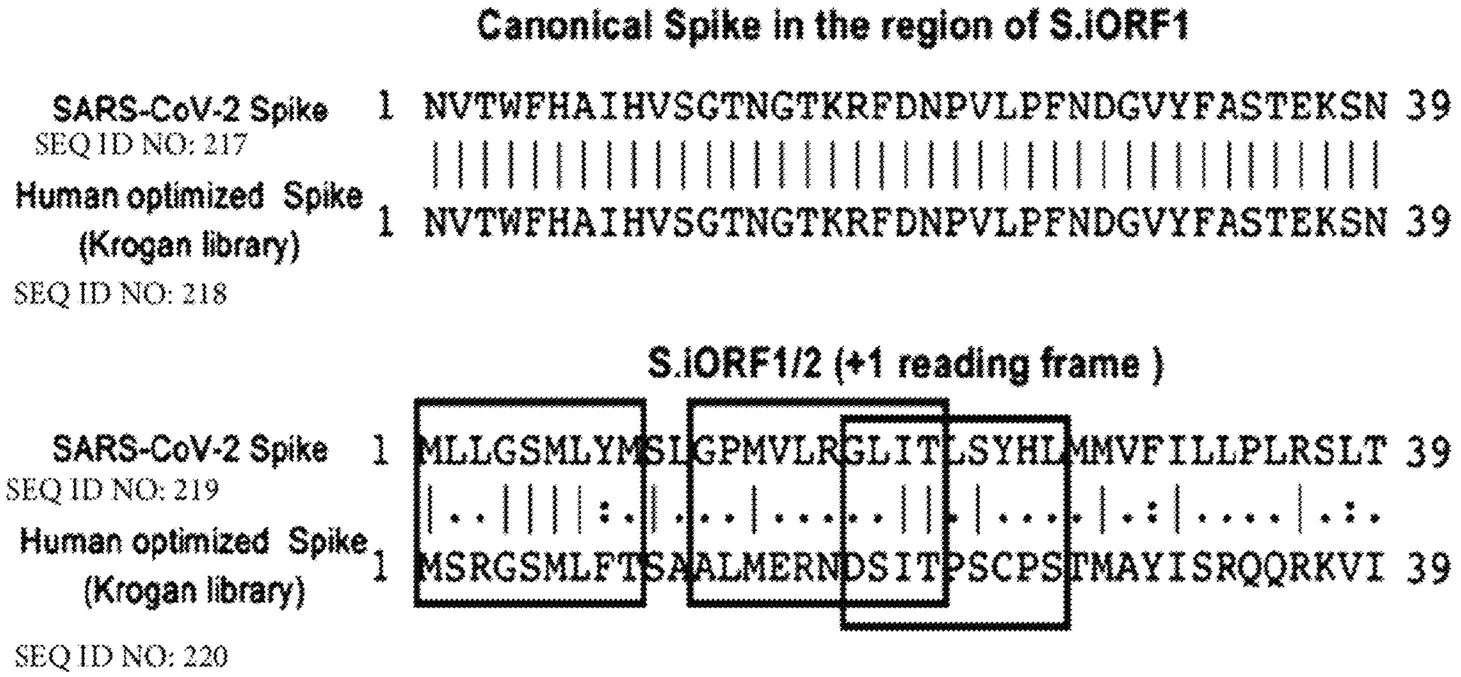
Figure 3G:
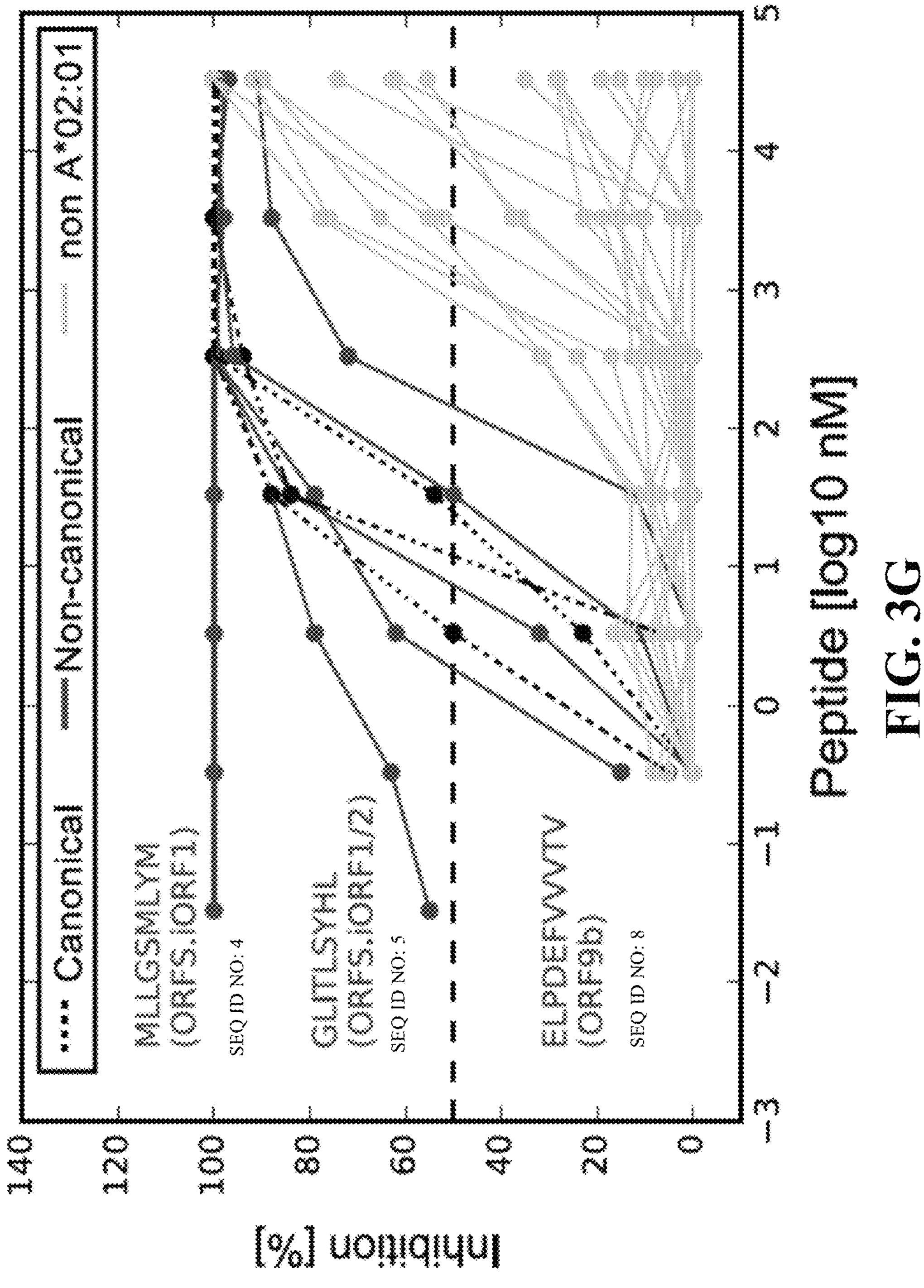

Six of the peptides from out-of-frame ORFs were predicted to bind HLA-A*02:01 in HEK293T cells, suggesting the potential for widespread presentation of these non-canonical HLA-I peptides in the population. To confirm presentation by HLA-A*02:01 in-vitro binding assays were performed in the presence of a high affinity radiolabeled A*02:01 ligand (FIG. 3E and Table 4). All six peptides were confirmed to bind to HLA-A*02:01 ($IC_{50}$<500 nM). (FIG. 3G, Table 4)) Interestingly, the three peptides with highest affinity among all tested HLA-I peptides were originated from out-of-frame ORFs, two from S.iORF1/2 (MLLGSMLYM (SEQ ID NO: 4) and GLITLSYHL (SEQ ID NO: 5), $IC_{50}$<0.5 nM) and one from ORF9b (ELPDEFVVVTV (SEQ ID NO: 8), $IC_{50}$=1.6 nM).

In the context of T cell immunity and vaccine development, it is crucial to understand the effect of optimizing RNA sequences on the endogenously processed and presented HLA-I peptides derived from internal out-of-frame ORFs. Exogenous expression of viral proteins in vaccines often involve manipulating the native nucleotide sequence, e.g., via codon optimization, to enhance expression. These techniques maintain the amino acids sequence of the canonical ORF, yet may alter the sequence of proteins encoded in alternative reading frames. In addition to the two current mRNA vaccines targeting the S glycoprotein (Callaway, 2020; Jackson et al., 2020; Mulligan et al., 2020) the nucleocapsid is also considered for vaccine development (Dutta et al., 2020; Zhu et al., 2004). It was thus aimed to investigate the effect of optimizing the RNA sequence of S and N on the endogenously processed and presented HLA-I peptides derived from S.iORF1/2 and ORF9b, respectively.

Figure 3F:
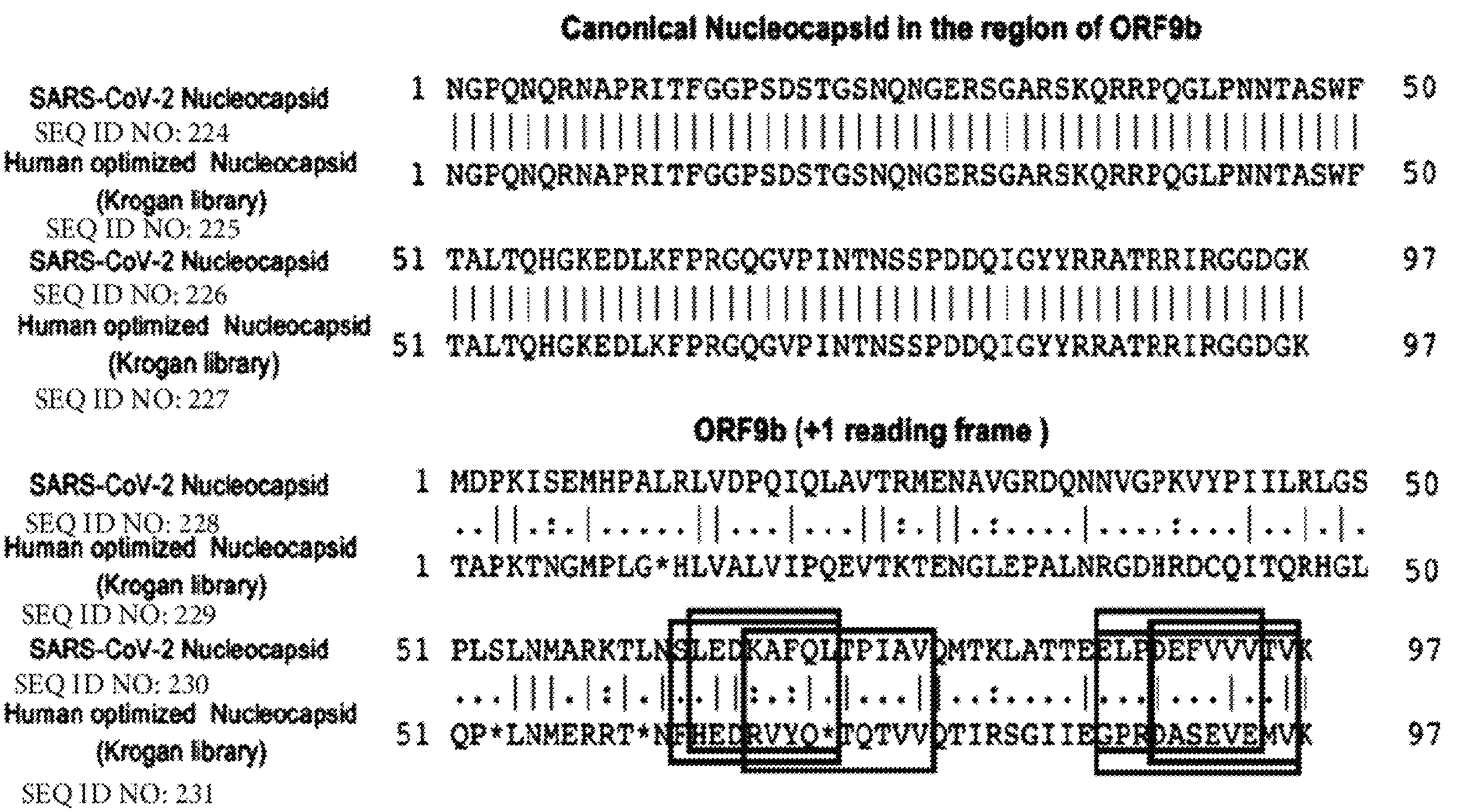

The native viral sequence was compared to synthetic S and N from a SARS-COV-2 human optimized ORFs library (Gordon et al., 2020) in the regions encoding the two internal out-of-frame ORFs. As expected, there was no change in the main ORFs, however, the amino acid sequence in the +1 frame, which encodes S.iORF1/2 and ORF9b, is significantly different (FIGS. 3D and 3F). In the case of S.iORF1, it is possible that this ORF is expressed in the human optimized construct, since the methionine driving its translation is preserved, however, the sequence of potential HLA-I peptides would be different (FIG. 3E). In the case of ORF9b, the start codon was mutated, few stop codons were introduced along the ORF, and the sequence of potential HLA-I peptides themselves was altered (FIG. 3F). These data suggest that human codon optimization of the main ORF may preclude the HLA-I presentation of peptides encoded from alternative ORFs.

Out-of-Frame HLA-I Peptides Elicit T Cell Responses in Humanized HLA-A2 Mice and COVID-19 Patients To evaluate the immunogenicity of the HLA-A*02:01 peptides detected by mass spectrometry, three assays probing the T cell responses in a humanized mouse model, COVID-19 patients, and unexposed humans were conducted. First, five transgenic HLA-A2 mice were immunized with a pool of nine HLA-A*02:01 peptides for 10 days and tested the T cell responses to individual peptides using INFγ ELISpot assay. A positive response was observed to three non-canonical peptides from out-of-frame ORFs, two from S.iORF1/2 (GLITLSYHL (SEQ ID NO: 5) and MLLGSMLYM (SEQ ID NO: 4)) and one from ORF9b (ELPDEFVVVTV (SEQ ID NO: 8)), as well as a canonical peptide from nsp3 (YLNSTNVTI (SEQ ID NO: 24)) FIGS. 10A-10B. T cell responses to these four peptides exceeded by >3-fold the responses to a peptide from the Gag protein of HIV, used as a negative control.

Figure 10B:
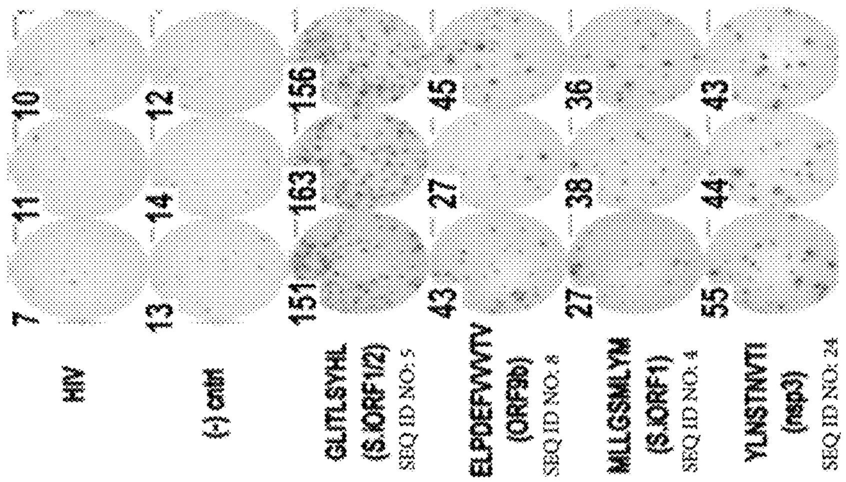
FIGS. 10A-10G-T cell responses to SARS-COV-2 HLA-I peptides.
Figure 10A:
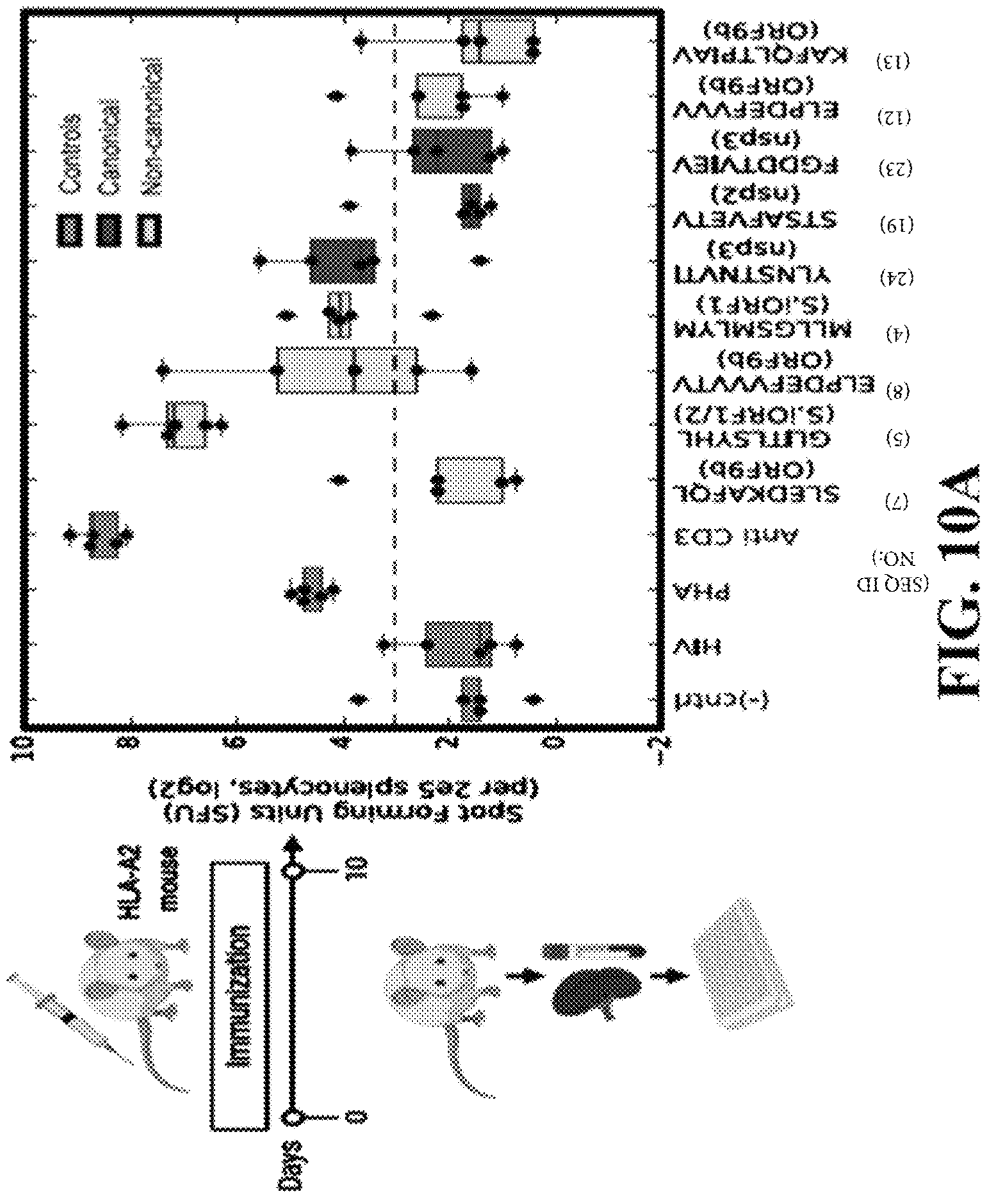
Figure 10D:
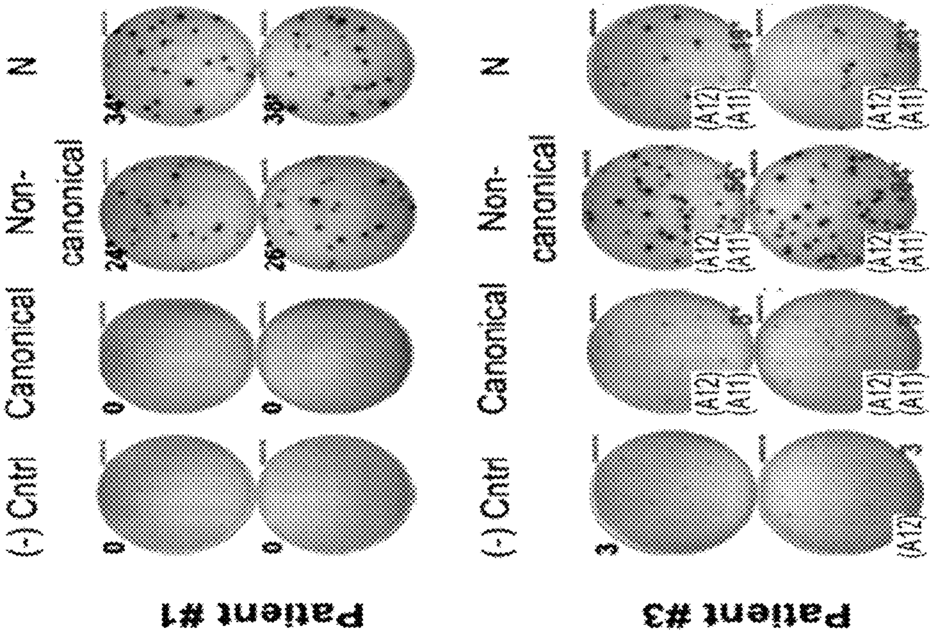
Figure 10C:
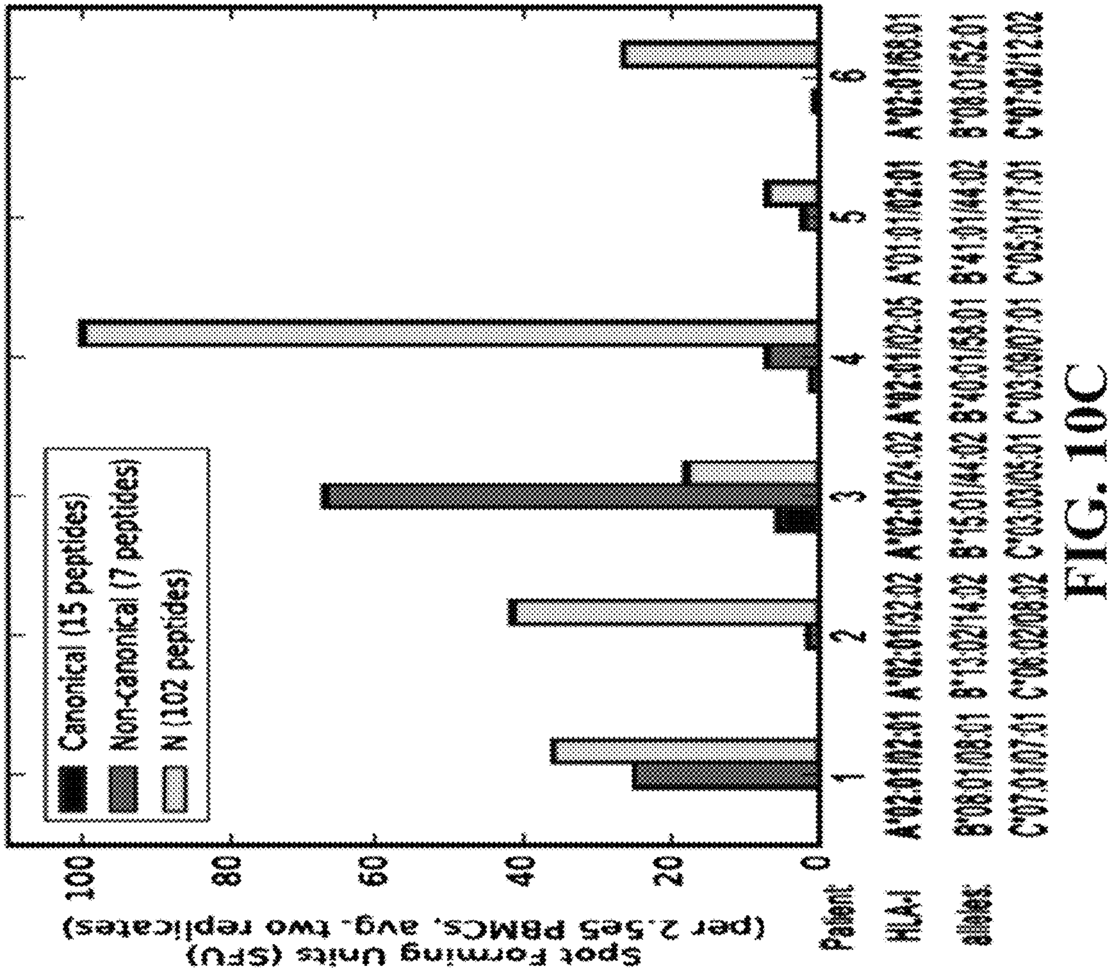

Next, the immunogenicity of the HLA-I peptides in the context of COVID-19 disease was investigated. ELISpot assays were performed with PBMCs from six convalescent patients expressing HLA-A*02:01 and monitored IFNγ secretion in response to a pool of 15 HLA-I peptides from canonical ORFs and 7 peptides from the out-of-frame ORFs (3 from S.iORF1/2 and 4 from ORF9b, Table 7). As a positive control, the T cells responses were compared to a pool of 102 peptides tiling the nucleocapsid (NC) protein measured in the same patients as part of another study (Gallagher et al. in preparation). Positive responses to the non-canonical pool in two of the six samples was observed (FIGS. 10C-10D). Notably, in one patient the T cell responses to the non-canonical pool exceeded the responses to the NC pool, although the number of tested peptides is 14-fold lower (7 vs. 102 peptides in the non-canonical and the NC pools, respectively).

Table 7 shows a list of HLA-I peptides tested in the two pools of canonical and non-canonical ORFs.

TABLE 7

| Peptide pool | Peptide sequence | Peptide length | SARS-Cov-2 protein | Cell Line |
|---|---|---|---|---|
| 1-cannonical | APHGHVMVEL (SEQ ID NO: 14) | 10 | nsp1 | A549 |
| 1-cannonical | EEFEPSTQYEY (SEQ ID NO: 20) | 11 | nsp3 | A549 |
| 1-cannonical | EIKESVQTF (SEQ ID NO: 15) | 9 | nsp2 | A549 |
| 1-cannonical | EILDITPCSF (SEQ ID NO: 33) | 10 | S | A549 |
| 1-cannonical | EILDITPCSFG (SEQ ID NO: 47) | 11 | S | A549 |
| 1-cannonical | FASEAARVV (SEQ ID NO: 17) | 9 | nsp2 | A549 |
| 1-cannonical | FAVDAAKAY (SEQ ID NO: 28) | 9 | nsp10 | A549 |
| 1-cannonical | IRQEEVQEL (SEQ ID NO: 31) | 9 | ORF7a | A549 |
| 1-cannonical | KNIDGYFKIY (SEQ ID NO: 36) | 10 | S | HEK293T |
| 1-cannonical | KRVDWTIEY (SEQ ID NO: 29) | 9 | nsp14 | HEK293T |
| 1-cannonical | NATNVVIKV (SEQ ID NO: 37) | 9 | S | HEK293T |
| 1-cannonical | QLTPTWRVY (SEQ ID NO: 38) | 9 | S | HEK293T |

TABLE 7-continued

| Peptide pool | Peptide sequence | Peptide length | SARS-Cov-2 protein | Cell Line |
|---|---|---|---|---|
| 1-cannonical | SEFSSLPSY (SEQ ID NO: 27) | 9 | nsp8 | HEK293T |
| 1-cannonical | VGYLQPRTF (SEQ ID NO: 39) | 9 | S | HEK293T |
| 1-cannonical | YLNSTNVTI (SEQ ID NO: 24) | 9 | nsp3 | HEK293T |
| 2-non-cannonical | DEFVVVTV (SEQ ID NO: 11) | 8 | ORF9b | A549 |
| 2-non-cannonical | ELPDEFVVVTV (SEQ ID NO: 8) | 11 | ORF9b | A549 |
| 2-non-cannonical | GLITLSYHL (SEQ ID NO: 5) | 9 | ORFS. iORF1/2 | A549 |
| 2-non-cannonical | GPMVLRGLIT (SEQ ID NO: 6) | 10 | ORFS. iORF1/2 | A549 |
| 2-non-cannonical | LEDKAFQL (SEQ ID NO: 10) | 8 | ORF9b | HEK293T |
| 2-non-cannonical | MLLGSMLYM (SEQ ID NO: 4) | 9 | ORFS. iORF1/2 | HEK293T |
| 2-non-cannonical | SLEDKAFQL (SEQ ID NO: 7) | 9 | ORF9b | HEK293T |

Figure 10E:
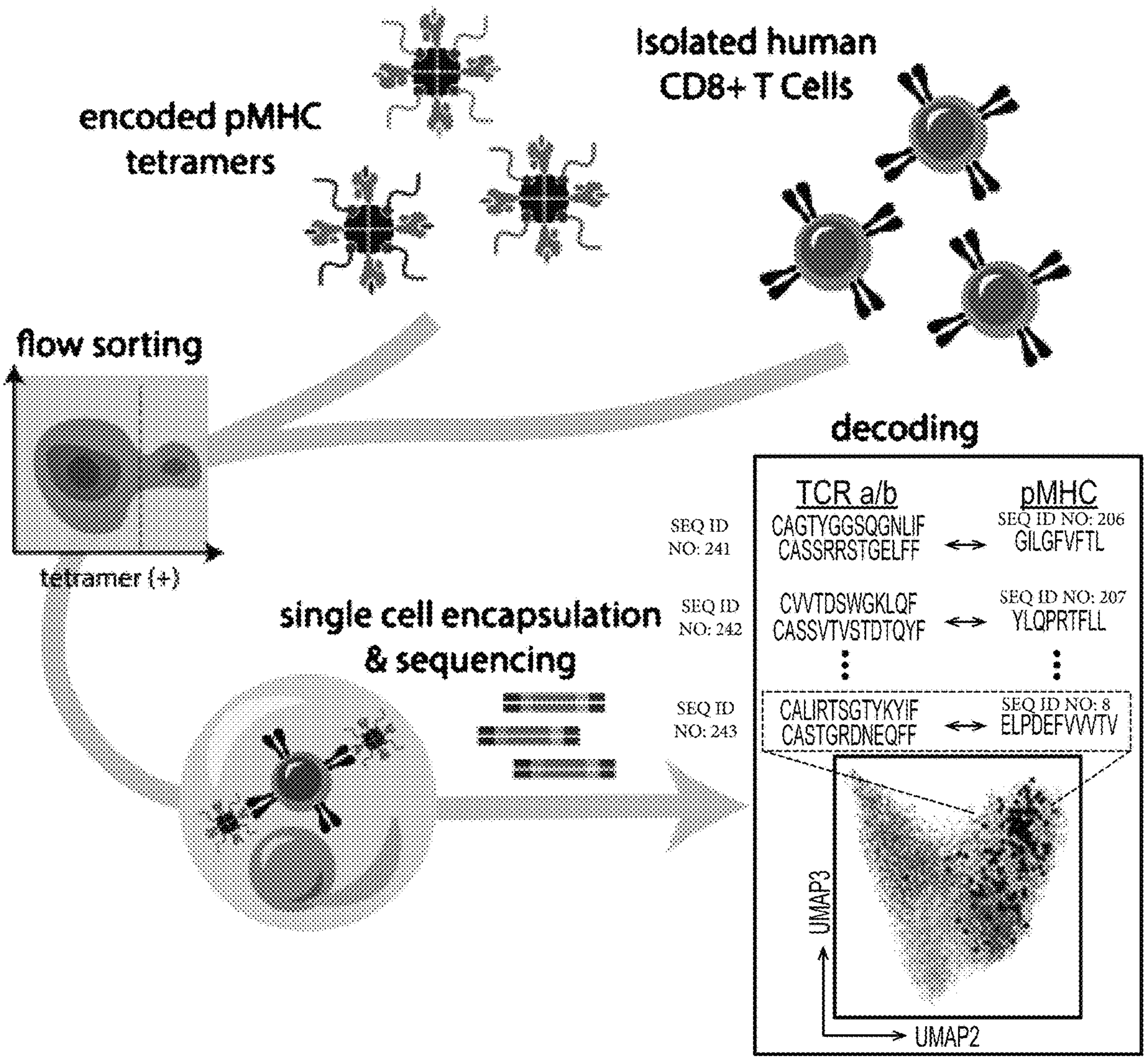

To delineate the T cell responses against individual HLA-I peptides in humans, a novel multiplexed technology combining barcoded tetramer assay and single-cell sequencing in collaboration with Repertoire Immune Medicines was utilized. DNA-encoded pMHCs and single-cell sequencing was used to detect and characterize epitope-reactive CD8+ T cells in convalescent COVID-19 patients and unexposed subjects (FIG. 10E). Briefly, we produced a library of barcoded HLA-A*02:01 tetramers with 30 HLA-I peptides discovered in the study was produced with, 10 that bind HLA-A*02:01 and 20 that do not according to the affinity measurements demonstrated herein (Table 4). As positive controls, we included an HLA-A*02:01 epitope from Influenza A virus (GILGFVFTL (SEQ ID NO: 206)) and three commonly recognized HLA-A*02:01 epitopes from SARS-COV-2 (YLQPRTFLL (SEQ ID NO: 207), KLWAQCVQL (SEQ ID NO: 208), LLYDANYFL (SEQ ID NO: 209) (Ferretti et al., 2020)). Enriched CD8+ cells from each sample were stained with the tetramer library, and tetramer-positive T cells were sorted by flow cytometry followed by single-cell sequencing. Using this method, we obtained information on: (i) the number of CD8+ T cells reacting to each peptide in each sample; (ii) the sequences of the T cell receptors (TCRs, paired a/b chains) recognizing each peptide; and (iii) gene expression profile of individual reacting CD8+ T cell.

Figure 10F:
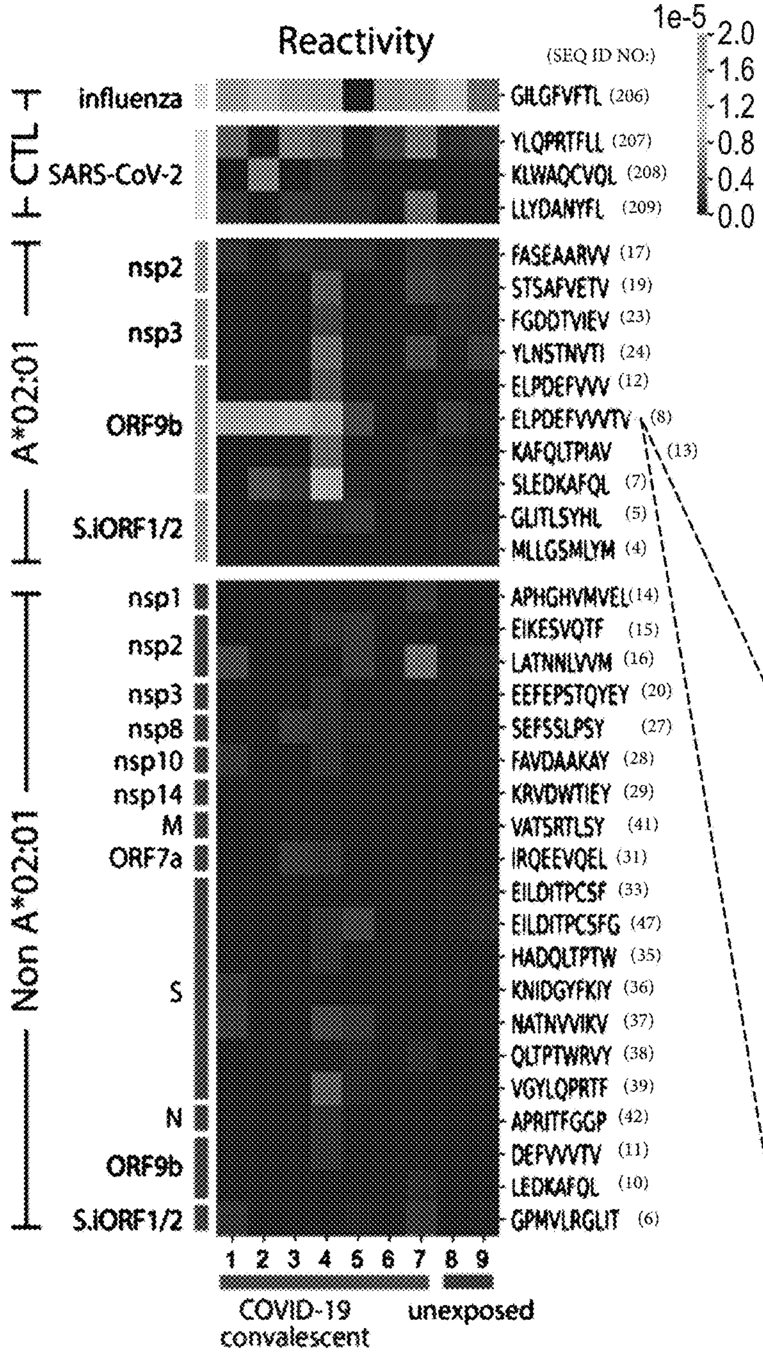

Testing nine HLA-A*02:01 samples (seven COVID-19 convalescent and two unexposed) reactivity to our positive controls as well as to non-canonical HLA-I peptides was observed. The previously reported A*02:01 epitopes from influenza and SARS-COV-2 all elicited expected responses, albeit relatively weak responses to KLWAQCVQL (SEQ ID NO: 208) (FIG. 10F and Table 8A). Moreover, HLA-I peptides that bind A*02:01 elicited stronger CD8+ responses than peptides that were detected on other HLA alleles (Wilcoxon rank-sum p<10-6, FIG. 16A). Two non-canonical peptides from ORF9b, ELPDEFVVVTV (SEQ ID NO: 8) and SLEDKAFQL (SEQ ID NO: 7), were in the top five reactive peptides (ranked according to the number of T cell clones in convalescent samples, Table 8B). Strikingly, ELPDEFVVVTV (SEQ ID NO: 8) invoked the strongest CD8+ response among all tested HLA-I peptides, with the frequency of detected T cells similar to that observed for the influenza epitope and above those for the three well-described SARS-COV-2 epitopes. One of these epitopes, YLQPRTFLL (SEQ ID NO: 207), was considered the most reactive SARS-COV-2 epitope in a few independent studies (Ferretti et al., 2020; Habel et al., 2020; Shomuradova et al., 2020) and is the subject for commercial monomer and tetramer assays offered by multiple companies.

Figure 10G:
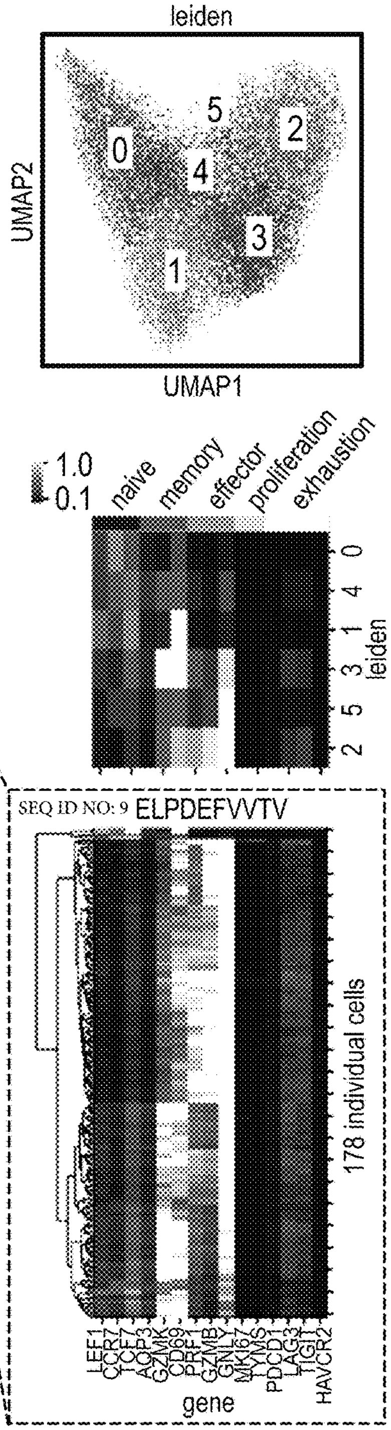
Figure 16B:
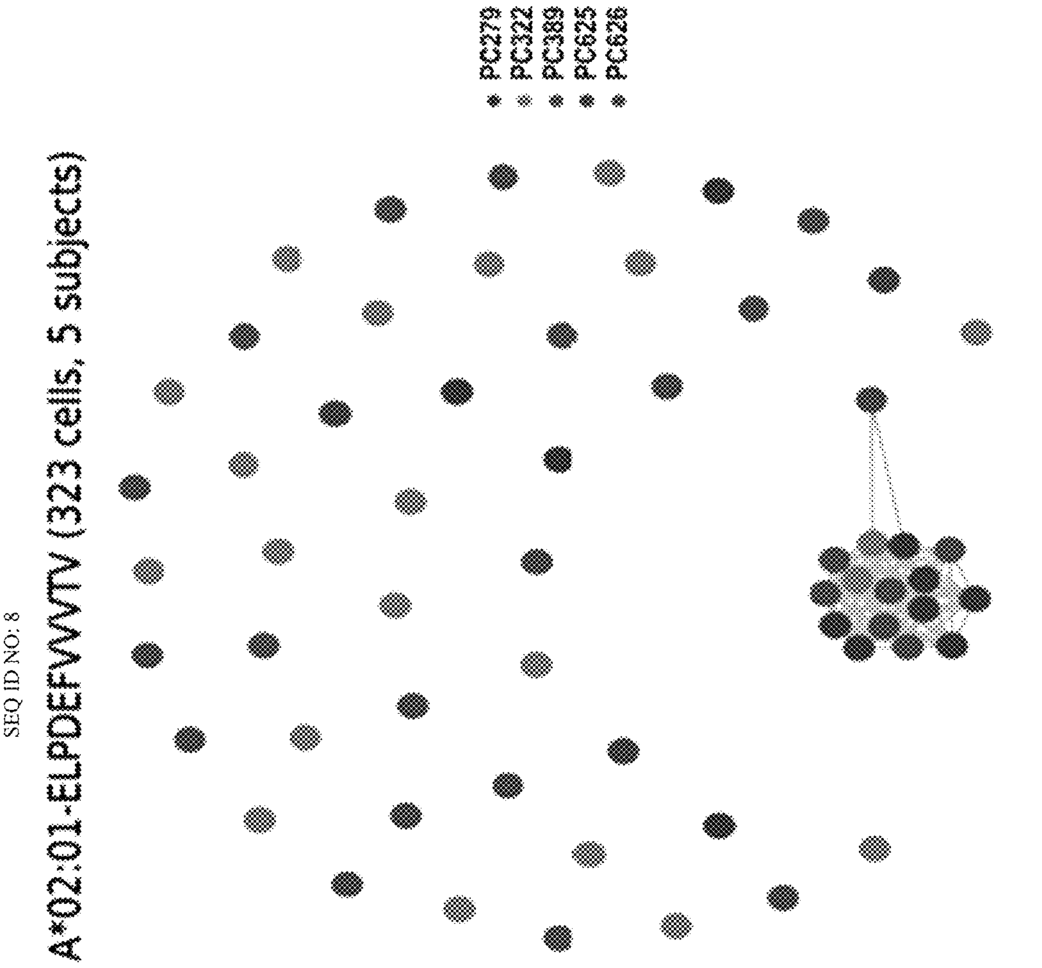
FIGS. 16A-16D-CD8+ responses to HLA-I peptides in HLA-A*02:01 COVID-19 patients and TCR homology in ELPDEFVVVTV (SEQ ID NO: 8) reacting T cells.
Figure 16A:
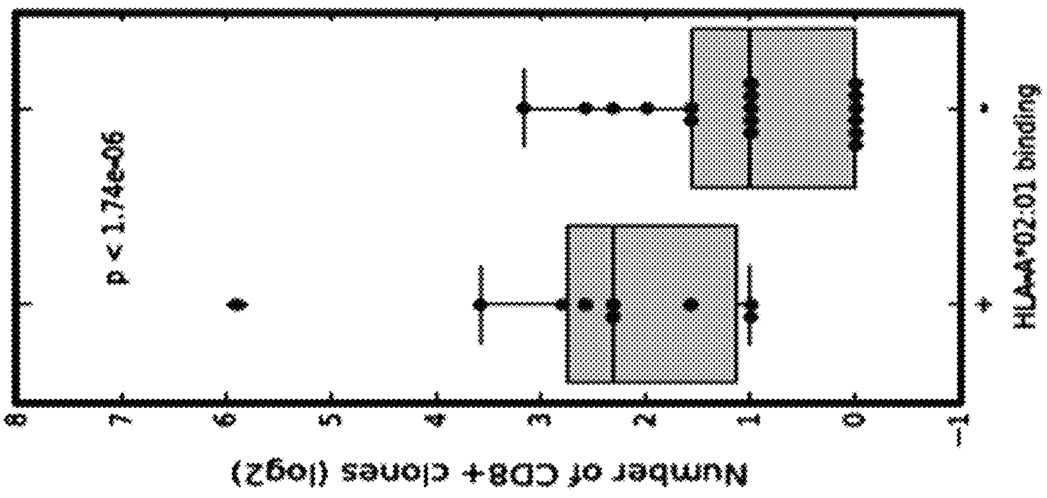
Figure 16C:
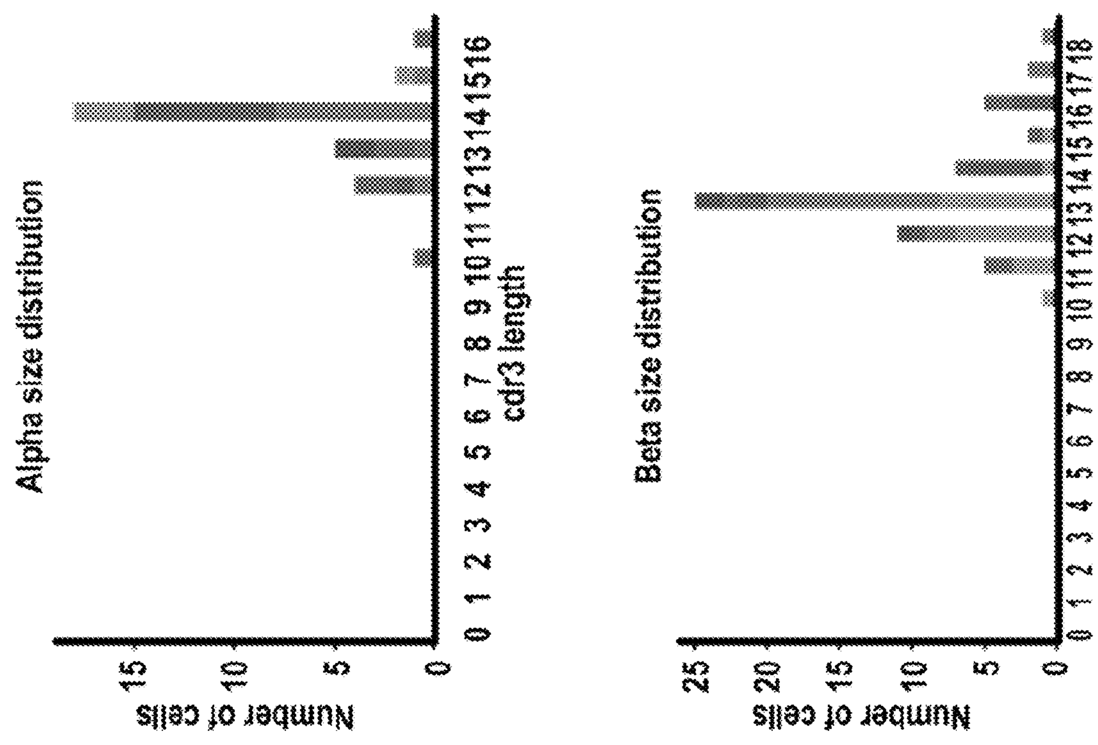
Figure 16D:

Examining the gene expression profile and the TCR sequence of the reacting T cells provides additional supporting evidence for the functional relevance of the ELPDEFVVVTV (SEQ ID NO: 8) epitope during the course of COVID-19. To characterize the cell state, single-cell transcriptomics analysis was visualized via uniform manifold approximation and projection (UMAP) (FIG. 10G). Most cells reactive to ELPDEFVVVTV (SEQ ID NO: 8) showed high expression of effector markers and moderate to high expression of memory markers according to a recent COVID-19 CD8+ subpopulation profiling (Su et al., 2020). This functional state is consistent with clusters 2 and 3 in the UMAP analysis (see ELPDEFVVVTV (SEQ ID NO: 8)-specific T cell in UMAP in FIG. 10E). In addition, when the sequences of the TCRs in CD8+ reacting to ELPDEFVVVTV (SEQ ID NO: 8) were examined a homologous CDR3 motif across different patients was found (FIGS. 16B-16D).

Figure 17A:
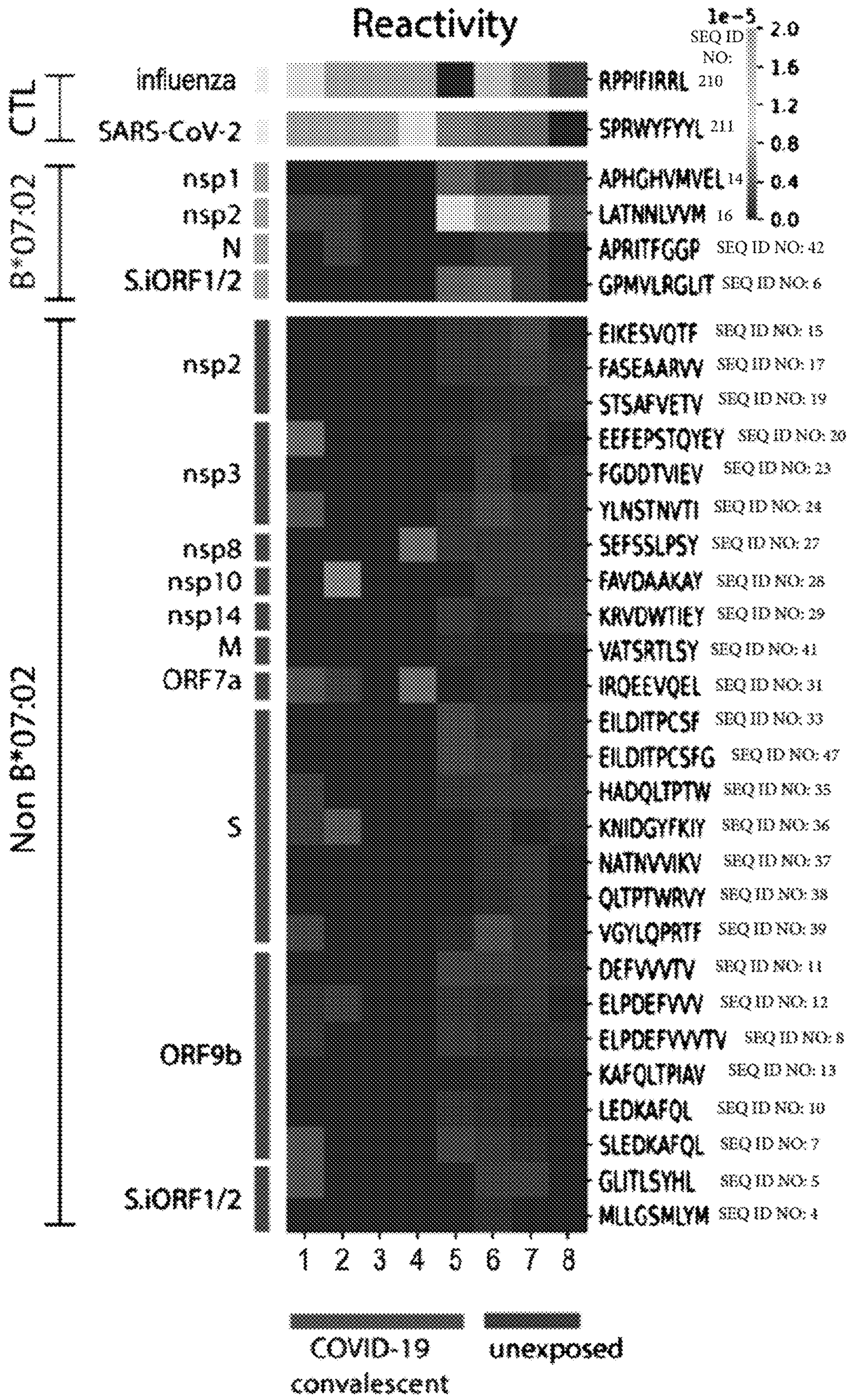
FIGS. 17A-17B-CD8+ T cells responses to HLA-I peptides in HLA-B*07:02 COVID-19 patients.
Figure 17B:
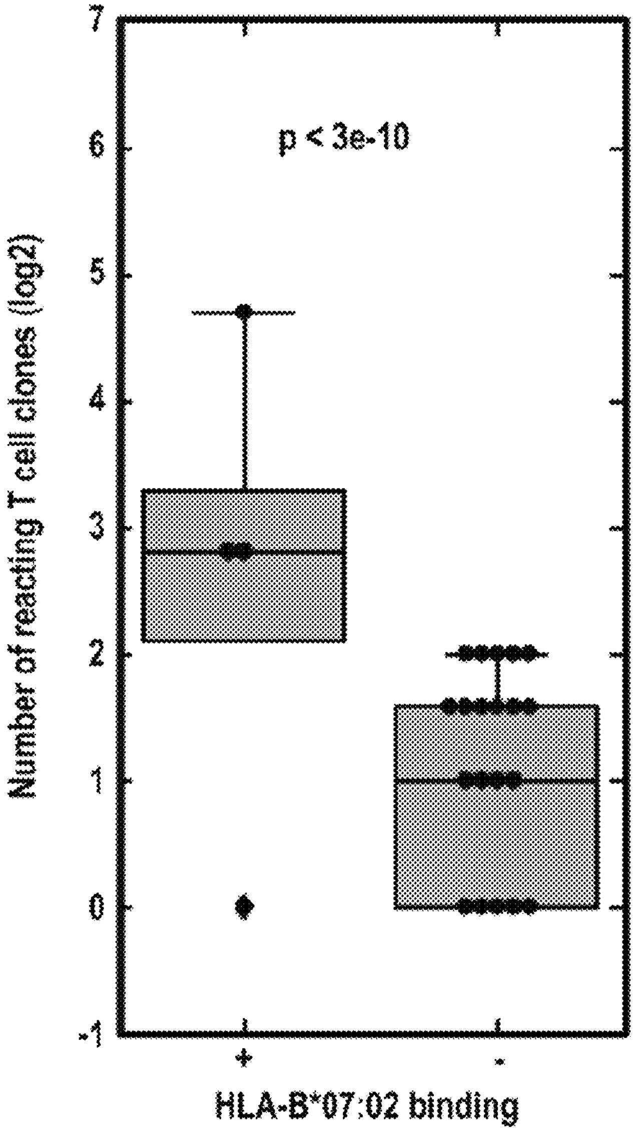
Figure 18A:
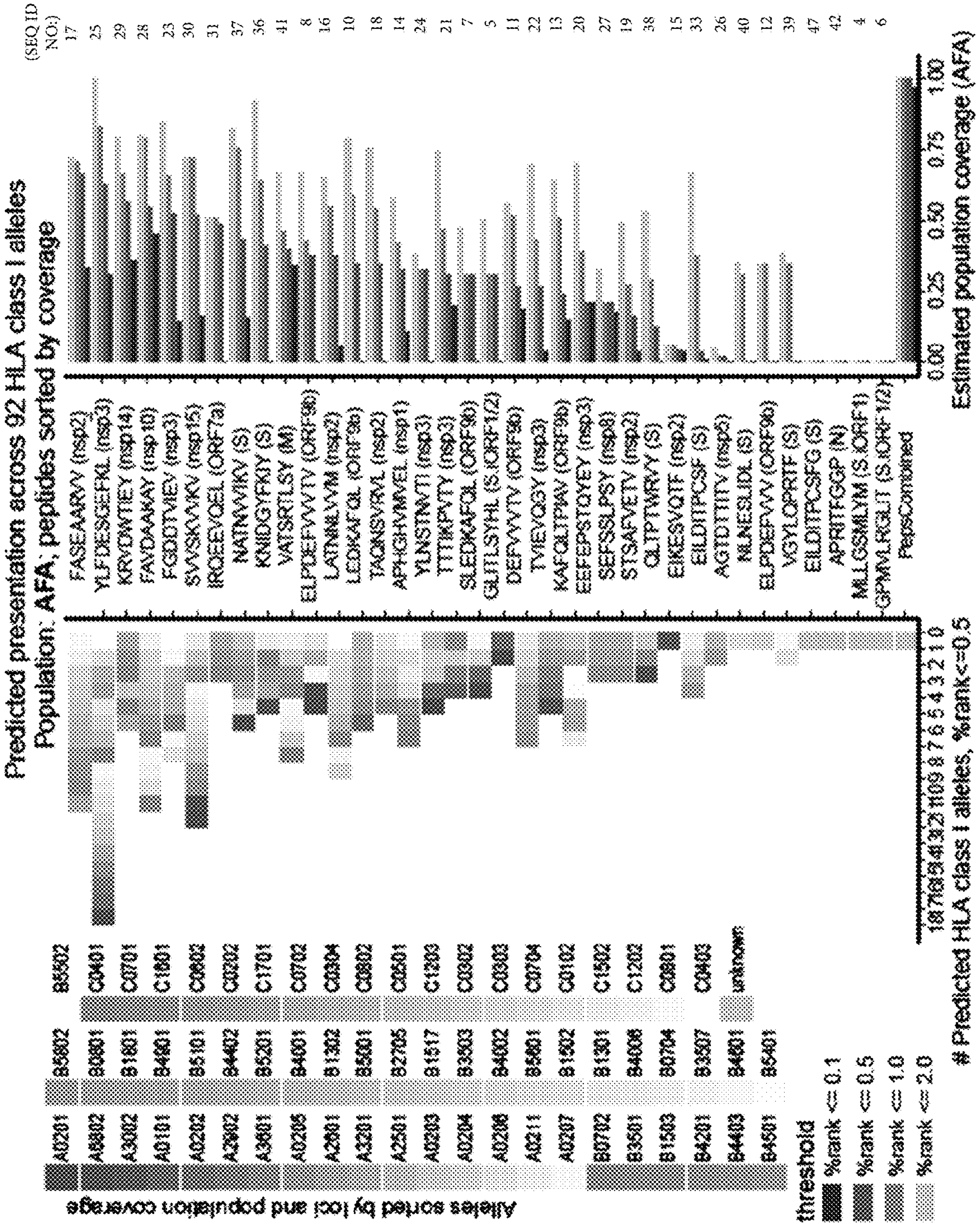
FIGS. 18A-18E. Population coverage estimates of MS-identified SARS-COV-2 HLA-I peptides. Similar to FIGS. 10A-10G, HLAthena predictions for 92 HLA-I alleles using percentile rank cutoff values of 0.1, 0.5, 1, and 2% were used to show the number of alleles and estimated coverage for each LC-MS/MS-observed SARS-COV-2 peptides across (FIG. 18A (SEQ ID NO: 4-8, 10-31, 33, 36-42, 47)) AFA, (FIG. 18B (SEQ ID NO: 4-8, 10-31, 33, 36-42, 47)) API, (FIG. 18C (SEQ ID NO: 4-8, 10-31, 33, 36-42, 47)) EUR, (FIG. 18D (SEQ ID NO: 4-8, 10-31, 33, 36-42, 47)) HIS, and (FIG. 18E (SEQ ID NO: 4-8, 10-31, 33, 36-42, 47)) USA populations. Alleles are colored and ordered according to loci and the corresponding population frequency (high to low color intensity). Peptides are ordered according to their estimated coverage at % rank cutoff of 0.5.
Figure 18B:
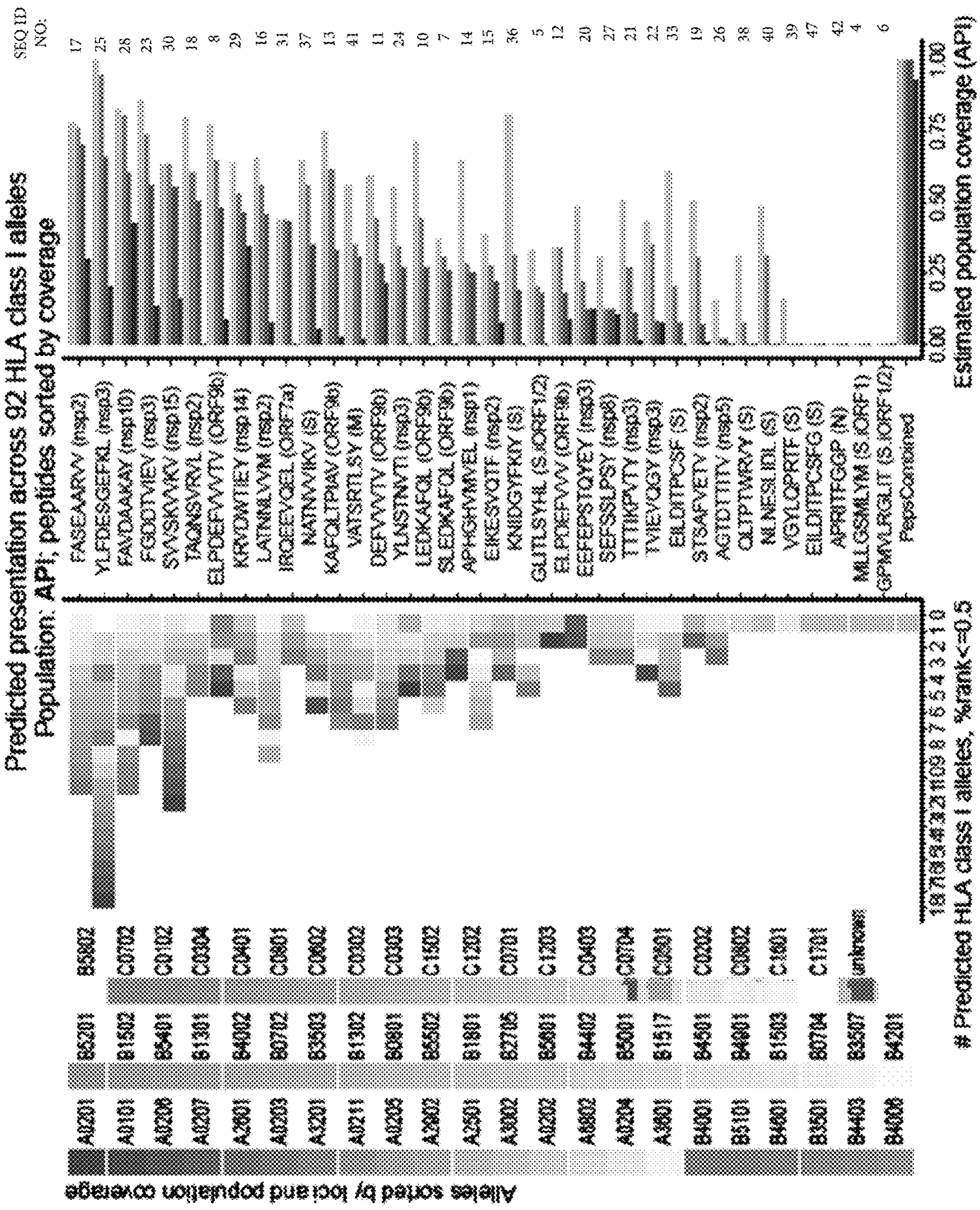
Figure 18C:
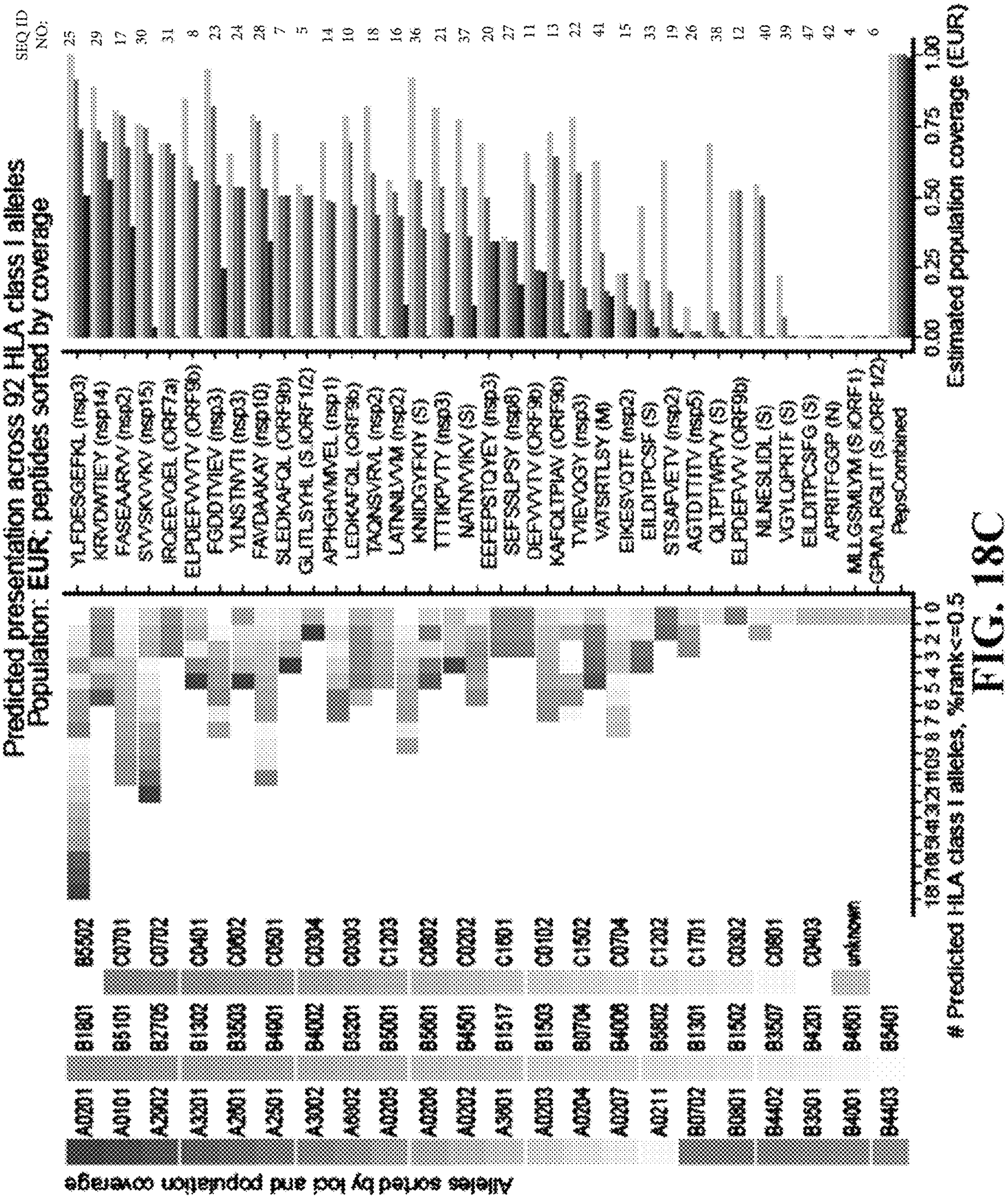
Figure 18D:
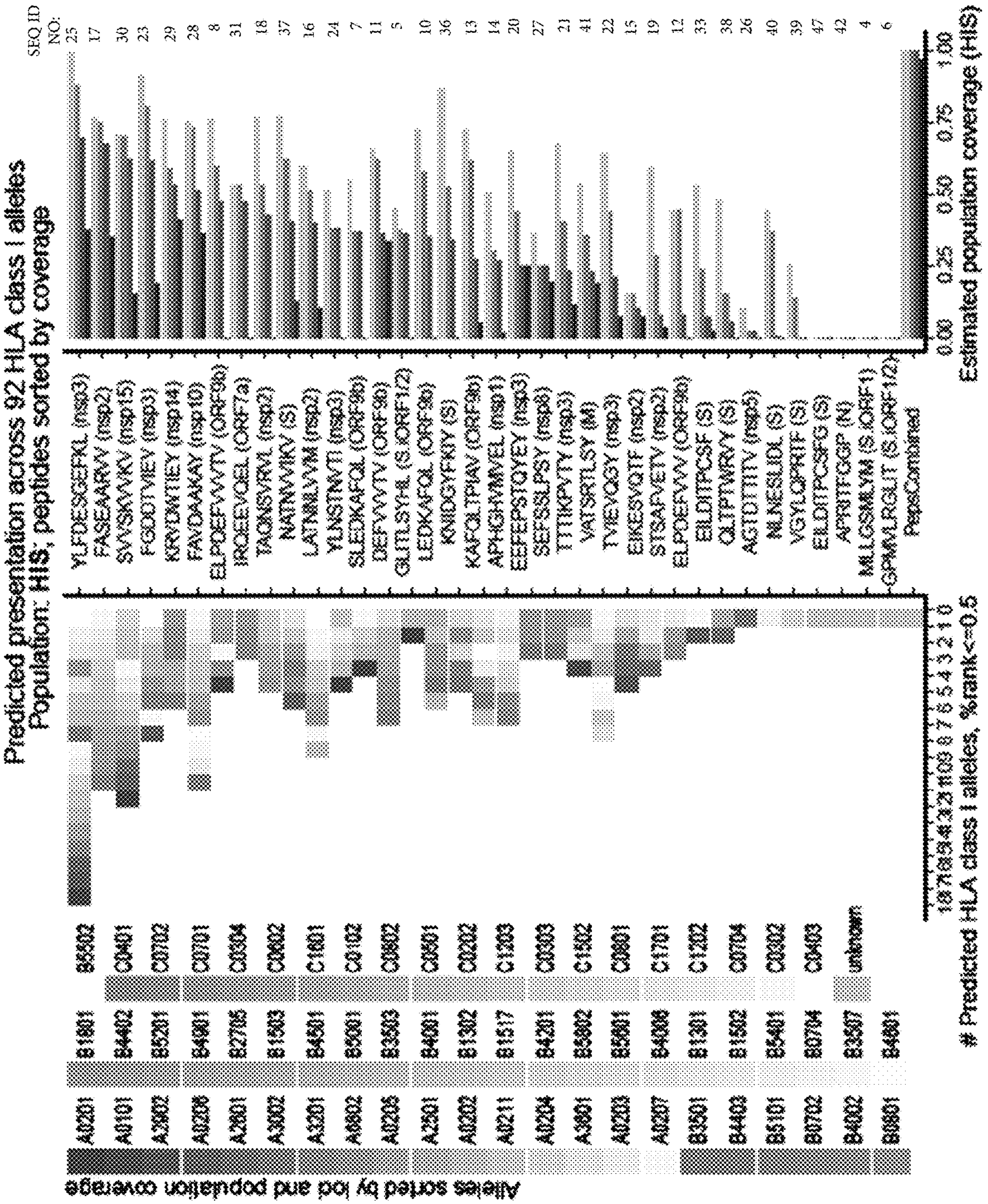
Figure 18E:
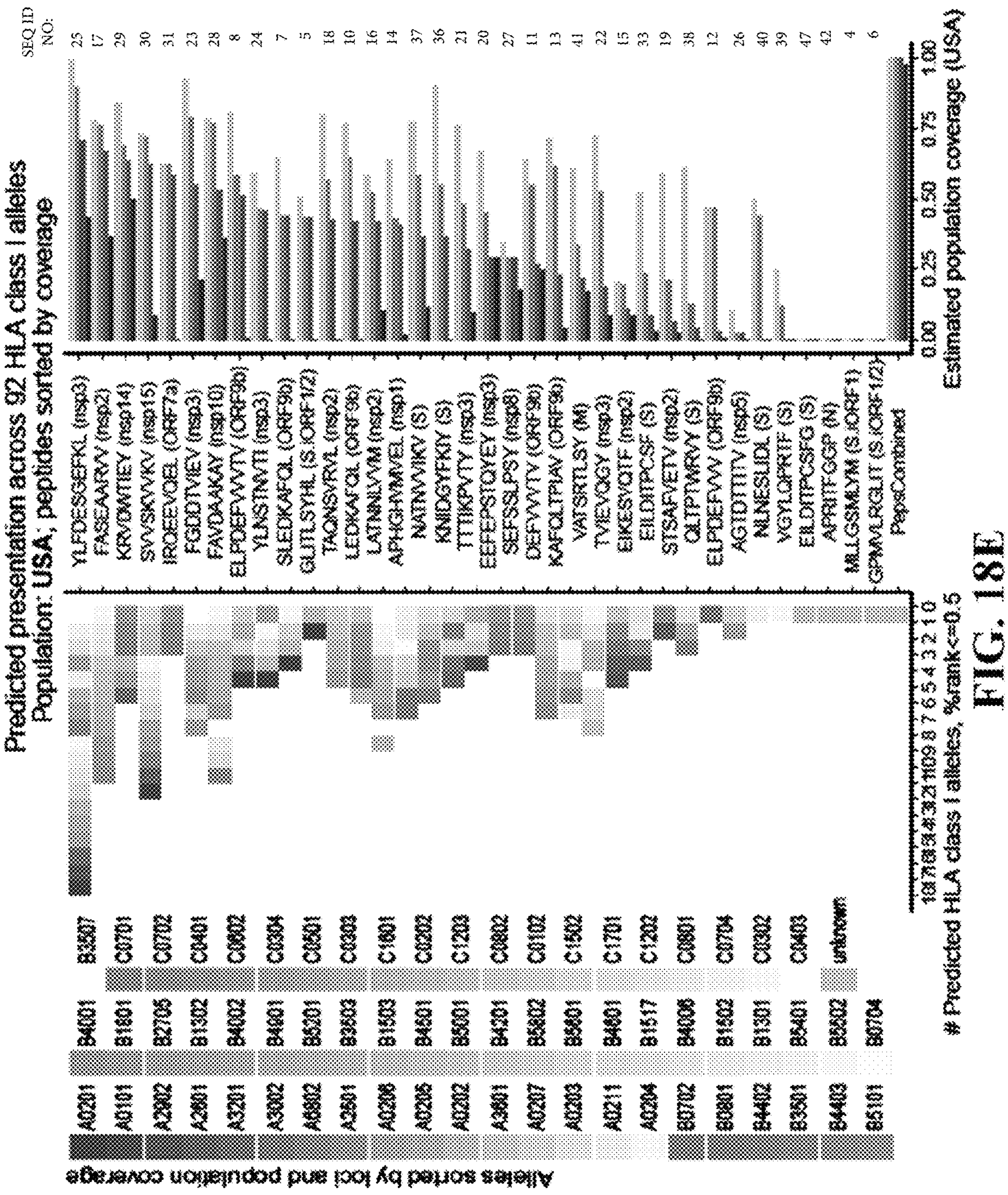

While the T cell data provides strong evidence for CD8+ responses to peptides from ORF9b in COVID-19 patients, significant responses to HLA-I peptides from S.iORF1/2, GLITLSYHL (SEQ ID NO: 5) and MLLGSMLYM (SEQ ID NO: 4) were not detected in the seven tested COVID-19 samples. To evaluate the immunogenicity of the third HLA-I peptide from S.iORF1/2, GPMVLRGLIT (SEQ ID NO: 6), an additional barcoded tetramer assay with PBMCs from COVID-19 patients expressing HLA-B*07:02 and a B*07:02 tetramer library was performed. As controls, B*07:02 epitopes from EBV (RPPIFIRRL (SEQ ID NO: 210)) and SARS-CoV-2 (SPRWYFYYL (SEQ ID NO: 211)) were included. As expected, positive reactivity to the two control peptides as well as overall greater CD8+ responses to HLA-I peptides that bind B*07:02 than peptides that do not (Wilcoxon rank-sum p<10-10, FIGS. 17A-17B and Table 8B) was observed. However, no significant responses to GPMVLRGLIT (SEQ ID NO: 6) in patients was observed, although this peptide was detected multiple times in the mass spectrometry experiments (Table 3). It is possible that our assay was not sensitive enough to capture T cell responses to the three non-canonical peptides from S.iORF1/2 since we also observe weak responses to KLWAQCVQL (SEQ ID NO: 208), a commonly recognized A*02:01 epitope in COVID-19 patients (Ferretti et al., 2020; Takagi and Matsui, 2020) with similar reactivity to GLITLSYHL (SEQ ID NO: 5) from S.iORF1/2.

Tables 8A-8B show (Table 8A) A table of tested peptides in a multiplexed tetramer assay and the summary statistics of the T cell responses in seven convalescent COVID-19 patients and two unexposed subjects expressing HLA-A*02:01. clonotype—the total number of unique reacting T cell clones in positive samples based on the CDR3 region of the T cell receptor; nCells—the total number of reacting T cells in positive samples; subjects—the number of patients in which positive T cells were obtained. Peptides were ranked according to the number of detected reacting T cell clones. GILGFVFTL (SEQ ID NO: 206) from Influenza virus and YLQPRTFLL (SEQ ID NO: 207), KLWAQCVQL (SEQ ID NO: 208), LLYDANYFL (SEQ ID NO: 209) from SARS-COV-2 served as positive controls. (Table 8B) Similar to (Table 8A) but for B*07:02 tetramer library. Summary statistics of the T cell responses in five convalescent COVID-19 patients and three unexposed subjects expressing HLA-B*07:02. RPPIFIRRL (SEQ ID NO: 210) from EBV and SPRWYFYYL (SEQ ID NO: 211) from SARS-COV-2 served as positive controls.

TABLE 8A

| | Bind_ | | COVID-19 convalescent (n subjects = 7) | | | Unexposed (n subjects = 2) | | |
|---|---|---|---|---|---|---|---|---|
| | A0201 | Protein | clonotypes | nCells | subjects | clonotypes | nCells | subjects |
| GILGFVFTL (SEQ ID NO: 206) | not tested | Matrix protein 1, Influenza A02:01(+) cntrl | 150 | 825 | 7 | 42 | 80 | 2 |
| ELPDEFVVVTV (SEQ ID NO: 8) | Yes | ORF9b | 60 | 323 | 5 | 6 | 6 | 2 |
| YLQPRTFLL (SEQ ID NO: 207) | not tested | S, SARS-CoV-2 A02:01(+) cntrl | 20 | 25 | 5 | 7 | 7 | 2 |
| LLYDANYFL (SEQ ID NO: 209) | not tested | ORF3a, SARS-CoV-2 A02:01(+) cntrl | 13 | 13 | 5 | 2 | 2 | 2 |
| SLEDKAFQL (SEQ ID NO: 7) | Yes | ORF9b | 12 | 12 | 5 | 5 | 5 | 2 |
| LATNNLVVM (SEQ ID NO: 16) | No | nsp2 | 9 | 14 | 3 | 4 | 4 | 2 |
| YLNSTNVTI (SEQ ID NO: 24) | Yes | nsp3 | 7 | 8 | 3 | 7 | 7 | 2 |
| FASEAARVV (SEQ ID NO: 17) | Yes | nsp2 | 6 | 8 | 5 | 5 | 5 | 2 |
| NATNVVIKV (SEQ ID NO: 37) | No | S | 6 | 8 | 3 | 1 | 1 | 1 |
| STSAFVETV (SEQ ID NO: 19) | Yes | nsp2 | 5 | 6 | 2 | 5 | 7 | 2 |
| KAFQLTPIAV (SEQ ID NO: 13) | Yes | ORF9b | 5 | 5 | 2 | 1 | 1 | 1 |
| GPMVLRGLIT (SEQ ID NO: 6) | No | ORFS.iORF1/2 | 5 | 5 | 3 | 1 | 1 | 1 |
| VGYLQPRTF (SEQ ID NO: 39) | No | S | 4 | 4 | 2 | 1 | 1 | 1 |
| EILDITPCSFG (SEQ ID NO: 47) | No | S | 3 | 5 | 2 | 4 | 4 | 2 |
| ELPDEFVVV (SEQ ID NO: 12) | Yes | ORF9b | 3 | 3 | 1 | 0 | 0 | 0 |
| SEFSSLPSY (SEQ ID NO: 27) | No | nsp8 | 3 | 3 | 3 | 0 | 0 | 0 |

TABLE 8A-continued

| | Bind_ A0201 | Protein | COVID-19 convalescent (n subjects = 7) clonotypes | nCells | subjects | Unexposed (n subjects = 2) clonotypes | nCells | subjects |
|---|---|---|---|---|---|---|---|---|
| KLWAQCVQL (SEQ ID NO: 208) | not tested | nsp7, SARS-CoV-2 A02:01(+) cntrl | 3 | 3 | 2 | 1 | 1 | 1 |
| EIKESVQTF (SEQ ID NO: 15) | No | nsp2 | 2 | 4 | 2 | 0 | 0 | 0 |
| IRQEEVQEL (SEQ ID NO: 31) | No | ORF7a | 2 | 2 | 2 | 1 | 1 | 1 |
| QLTPTWRVY (SEQ ID NO: 38) | No | S | 2 | 2 | 2 | 0 | 0 | 0 |
| FAVDAAKAY (SEQ ID NO: 28) | No | nsp10 | 2 | 3 | 2 | 1 | 1 | 1 |
| GLITLSYHL (SEQ ID NO: 5) | Yes | ORFS.iORF1/2 | 2 | 4 | 2 | 2 | 2 | 2 |
| FGDDTVIEV (SEQ ID NO: 23) | Yes | nsp3 | 2 | 2 | 1 | 4 | 4 | 2 |
| KNIDGYFKIY (SEQ ID NO: 36) | No | S | 2 | 2 | 1 | 1 | 1 | 1 |
| APHGHVMVEL (SEQ ID NO: 14) | No | nsp1 | 1 | 2 | 1 | 0 | 0 | 0 |
| APRITFGGP (SEQ ID NO: 42) | No | N | 1 | 1 | 1 | 0 | 0 | 0 |
| HADQLTPTW (SEQ ID NO: 35) | No | S | 1 | 1 | 1 | 0 | 0 | 0 |
| LEDKAFQL (SEQ ID NO: 10) | No | ORF9b | 1 | 1 | 1 | 0 | 0 | 0 |
| EEFEPSTQYEY (SEQ ID NO: 20) | No | nsp3 | 1 | 1 | 1 | 1 | 1 | 1 |
| DEFVVVTV (SEQ ID NO: 11) | No | ORF9b | 1 | 1 | 1 | 0 | 0 | 0 |
| KRVDWTIEY (SEQ ID NO: 29) | No | nsp14 | 0 | 0 | 0 | 0 | 0 | 0 |
| EILDITPCSF (SEQ ID NO: 33) | No | S | 0 | 0 | 0 | 3 | 3 | 2 |
| MLLGSMLYM (SEQ ID NO: 4) | Yes | ORFS.iORF1 | 0 | 0 | 0 | 4 | 4 | 2 |
| VATSRTLSY (SEQ ID NO: 41) | No | M | 0 | 0 | 0 | 0 | 0 | 0 |
| RPPIFIRRL (SEQ ID NO: 210) | not tested | Nuclear antigen 3, EBV B07:02(+) cntrl | 0 | 0 | 0 | 0 | 0 | 0 |
| SPRWYFYYL (SEQ ID NO: 211) | not tested | N, SARS-CoV-2 B07:02(+) cntrl | 0 | 0 | 0 | 0 | 0 | 0 |

TABLE 8B

| | Bind_ B0702 | Protein | COVID-19 convalescent (n subjects = 5) | | | Unexposed (n subjects = 3) | | |
|---|---|---|---|---|---|---|---|---|
| | | | clonotypes (conv) | nCells (conv) | subjects (conv) | clonotypes (unex) | nCells (unex) | subjects (unex) |
| SPRWYFYYL (SEQ ID NO: 211) | not tested | N, SARS-CoV-2 B07:02(+) cntrl | 136 | 320 | 5 | 45 | 49 | 3 |
| RPPIFIRRL (SEQ ID NO: 210) | not tested | Nuclear antigen 3, EBV B07:02(+) cntrl | 37 | 200 | 5 | 58 | 162 | 3 |
| LATNNLVVM (SEQ ID NO: 16) | Yes | nsp2 | 26 | 35 | 3 | 275 | 279 | 3 |
| APHGHVMVEL (SEQ ID NO: 14) | Yes | nsp1 | 7 | 9 | 1 | 19 | 19 | 3 |
| GPMVLRGLIT (SEQ ID NO: 6) | Yes | ORFS.iORF1/2 | 7 | 9 | 1 | 31 | 31 | 2 |
| SEFSSLPSY (SEQ ID NO: 27) | No | nsp8 | 4 | 4 | 2 | 10 | 10 | 3 |
| SLEDKAFQL (SEQ ID NO: 7) | No | ORF9b | 4 | 6 | 2 | 9 | 9 | 2 |
| YLNSTNVTI (SEQ ID NO: 24) | No | nsp3 | 4 | 4 | 2 | 17 | 17 | 3 |
| EILDITPCSFG (SEQ ID NO: 47) | No | S | 4 | 5 | 1 | 13 | 13 | 3 |
| EILDITPCSF (SEQ ID NO: 33) | No | S | 4 | 5 | 1 | 9 | 9 | 3 |
| KRVDWTIEY (SEQ ID NO: 29) | No | nsp14 | 3 | 3 | 1 | 9 | 9 | 3 |
| ELPDEFVVV (SEQ ID NO: 12) | No | ORF9b | 3 | 4 | 3 | 5 | 5 | 2 |
| HADQLTPTW (SEQ ID NO: 35) | No | S | 3 | 3 | 2 | 12 | 12 | 3 |
| IRQEEVQEL (SEQ ID NO: 31) | No | ORF7a | 3 | 4 | 3 | 3 | 3 | 1 |
| VGYLQPRTF (SEQ ID NO: 39) | No | S | 3 | 3 | 2 | 18 | 18 | 2 |
| ELPDEFVVVTV (SEQ ID NO: 8) | No | ORF9b | 3 | 4 | 2 | 6 | 7 | 3 |
| DEFVVVTV (SEQ ID NO: 11) | No | ORF9b | 2 | 4 | 1 | 13 | 13 | 3 |
| KNIDGYFKIY (SEQ ID NO: 36) | No | S | 2 | 3 | 2 | 6 | 6 | 2 |
| EEFEPSTQYEY (SEQ ID NO: 20) | No | nsp3 | 2 | 4 | 2 | 8 | 8 | 2 |
| FAVDAAKAY (SEQ ID NO: 28) | No | nsp10 | 2 | 4 | 1 | 13 | 13 | 3 |
| EIKESVQTF (SEQ ID NO: 15) | No | nsp2 | 1 | 2 | 1 | 6 | 6 | 2 |
| LEDKAFQL (SEQ ID NO: 10) | No | ORF9b | 1 | 2 | 1 | 3 | 3 | 1 |
| VATSRTLSY (SEQ ID NO: 41) | No | M | 1 | 1 | 1 | 1 | 1 | 1 |
| APRITFGGP (SEQ ID NO: 42) | Yes | N | 1 | 1 | 1 | 8 | 9 | 2 |

TABLE 8B-continued

| | Bind_ B0702 | Protein | COVID-19 convalescent (n subjects = 5) clonotypes (conv) | nCells (conv) | subjects (conv) | Unexposed (n subjects = 3) clonotypes (unex) | nCells (unex) | subjects (unex) |
|---|---|---|---|---|---|---|---|---|
| FASEAARVV (SEQ ID NO: 17) | No | nsp2 | 1 | 2 | 1 | 10 | 10 | 3 |
| GILGFVFTL (SEQ ID NO: 206) | not tested | Matrix protein 1, Influenza A02:01(+) cntrl | 1 | 1 | 1 | 14 | 14 | 3 |
| KLWAQCVQL (SEQ ID NO: 208) | not tested | nsp7, SARS-CoV-2 A02:01(+) cntrl | 1 | 1 | 1 | 3 | 3 | 1 |
| GLITLSYHL (SEQ ID NO: 5) | No | ORFS.iORF1/2 | 1 | 2 | 1 | 9 | 9 | 2 |
| NATNVVIKV (SEQ ID NO: 37) | No | S | 0 | 0 | 0 | 8 | 8 | 2 |
| QLTPTWRVY (SEQ ID NO: 38) | No | S | 0 | 0 | 0 | 6 | 6 | 2 |
| MLLGSMLYM (SEQ ID NO: 4) | No | ORFS.iORF1 | 0 | 0 | 0 | 2 | 2 | 1 |
| STSAFVETV (SEQ ID NO: 19) | No | nsp2 | 0 | 0 | 0 | 8 | 8 | 3 |
| FGDDTVIEV (SEQ ID NO: 23) | No | nsp3 | 0 | 0 | 0 | 5 | 5 | 2 |
| KAFQLTPIAV (SEQ ID NO: 13) | No | ORF9b | 0 | 0 | 0 | 2 | 2 | 1 |
| LLYDANYFL (SEQ ID NO: 209) | not tested | ORF3a, SARS-CoV-2 A02:01(+) cntrl | 0 | 0 | 0 | 0 | 0 | 0 |
| YLQPRTFLL (SEQ ID NO: 207) | not tested | S, SARS-CoV-2 A02:01(+) cntrl | 0 | 0 | 0 | 2 | 2 | 2 |

LC-MS/MS-Identified SARS-COV-2 Peptides can be Presented by Additional HLA Alleles in the Population Increasingly accurate HLA-I presentation prediction tools are routinely applied to the full transcriptome or proteome of an organism to computationally nominate presentable epitopes. However, these tools are trained on data that is agnostic to virus-specific processes that may interfere with the presentation pathway. Thus, the sensitivity and specificity of in silico predictions for any particular virus are insufficiently characterized. To assess how well computational tools would recover the HLA-I peptides that we identified by LC-MS/MS, HLAthena (predictor trained exclusively on endogenous HLA epitopes) (Abelin et al., 2017; Sarkizova et al., 2020) was used to retrospectively predict all 8-11mer peptides tiling known SARS-COV-2 proteins against the complement of HLA-I alleles expressed by A549 and HEK293T (FIG. 11A and Table 9A). Of the 36 MS-identified peptides, 23 had a predicted percentile rank <0.5 and 31 had percentile rank <2. The single A549 peptides with % rank >1, EILDITPCSFG (SEQ ID NO: 47), was also observed in a shorter form, EILDITPCSF (SEQ ID NO: 33), with a much more favorable prediction (% rank-0.095), suggesting that a phenylalanine C-terminal anchor is preferable and thus the 11mer could be bound with an overhang. Similarly, GPMVLRGLIT (SEQ ID NO: 6) was more favorably predicted as a 9-mer, GPMVLRGLI (SEQ ID NO: 212), although the short version was not detected.

Within a total of 39,875 SARS-COV-2 8-11mers, 14 out of 18 A549 peptides and 11 out of 18 HEK293T peptides had percentile rank scores within the top 1000 viral peptides (top 1.5% and 1.7% for A549 and HEK293T, respectively). To account for variability in viral protein expression levels, this analysis was also performed within the source protein of each peptide. It was found that 16 out of 36 peptides scored within the top 10 epitopes amongst all 8-11mers that the source protein can give rise to, and 21 scored within the top 20. Overall, predicted ranks were higher for A549 compared to HEK293T, which could partially be due to the larger number of viable cells and deeper peptidome we obtained for A549. These observations suggest that while an in silico epitope prediction scheme that nominates the top 10-20 peptides of each viral protein would recover ~50% (16-29 of 36) of observed epitopes with very high priority, this short list would still only encompass ~5-10% true LC-MS/MS positives.

Next, the HLA allele coverage achieved was estimated by the observed endogenously processed and presented viral epitopes amongst AFA, API, EUR, HIS, USA, and World populations at different rank cutoffs (top 0.1%, 0.5%, 1% and 2%) based on HLAthena predictions across 92 HLA-A,-B, and -C alleles (FIG. 11B, FIGS. 18A-18E, and Tables 9B and 9C). At the second most stringent cutoff, % rank <=0.5, 31 of the 36 individual peptides were predicted to bind at least one allele (range: 1-21, median: 4.9, mean: 4.5) with 3-69% (median: 30%, mean: 31%) world coverage. Combined together, the MS-identified peptide pool was estimated to cover at least one HLA-A,-B, or-C allele for 99% of the population with at least one peptide.

TABLE 9A

| | | | | | | | | | | | | | |
|---|---|---|---|---|---|---|---|---|---|---|---|---|---|
| | HLA Predictions | | | | | | | | | | | | |
| | | | | | | HLAthena | | | | | | | |
| | peptide | pep length | viral protein | # experiments detected | best predicted rank (MSi) | best predicted allele (MSi) | rank within all viral peptides | percentile rank within all viral proteins | rank within protein | # of peptides in protein | % rank with in protein | number of alleles with prank <=2 | all alleles with prank <=2 |
| A549 | VATSRTLSY (SEQ ID NO: 41) | 9 | M | 2 | 0.0007 | C1601 | 2 | 0.0050 | 1 | 854 | 0.1171 | 2 | C1203, C1601 |
| | FAVDAAKAY (SEQ ID NO: 28) | 9 | nsp10 | 5 | 0.0027 | C1601 | 8 | 0.0201 | 1 | 522 | 0.1916 | 3 | A2501, C1203, C1601 |
| | FASEAARVV (SEQ ID NO: 17) | 9 | nsp2 | 7<br>1 | 0.0049 | C1601 | 18 | 0.045 | 2 | 2518 | 0.0794 | 2 | C1203, C1601 |
| | DEFVVVTV (SEQ ID NO: 11) | 8 | ORF9b | 3 | 0.0083 | B1801 | 24 | 0.0602 | 2 | 354 | 0.5650 | 2 | B1801, B4403 |
| | NATNVVIKV (SEQ ID NO: 37) | 9 | S | 4 | 0.0180 | C1203 | 45 | 0.1129 | 5 | 5096 | 0.0981 | 2 | C1203, C1601 |
| | EIKESVQTF (SEQ ID NO: 15) | 9 | nsp2 | 2 | 0.0184 | A2501 | 47 | 0.1179 | 3 | 2518 | 0.1191 | 1 | A2501 |
| | EEFEPSTQYEY (SEQ ID NO: 20) | 11 | nsp3 | 1 | 0.0194 | B1801 | 49 | 0.1229 | 18 | 7746 | 0.2324 | 3 | A2501, B1801, B4403 |
| | SEFSSLPSY (SEQ ID NO: 27) | 9 | nsp8 | 1 | 0.0246 | B1801 | 59 | 0.1480 | 1 | 758 | 0.1319 | 2 | B1801, B4403 |
| | TVIEVQGY (SEQ ID NO: 22) | 8 | nsp3 | 1 | 0.0582 | A2501 | 128 | 0.3210 | 34 | 7746 | 0.4389 | 1 | A2501 |
| | LATNNLVVM (SEQ ID NO: 16) | 9 | nsp2 | 1 | 0.0848 | C1203 | 189 | 0.4740 | 18 | 2518 | 0.7149 | 2 | C1203, C1601 |
| | TTTIKPVTY (SEQ ID NO: 21) | 9 | nsp3 | 1 | 0.0869 | C1601 | 196 | 0.4915 | 51 | 7746 | 0.6584 | 4 | A2501, B1801, C1203, C1601 |
| | EILDITPCSF (SEQ ID NO: 33) | 10 | S | 6 | 0.0955 | A2501 | 210 | 0.5266 | 32 | 5096 | 0.6279 | 2 | A2501, B1801 |
| | TAQNSVRVL (SEQ ID NO: 18) | 9 | nsp2 | 1 | 0.1829 | C1601 | 398 | 0.9981 | 41 | 2518 | 1.6283 | 2 | C1203, C1601 |
| | LEDKAFQL (SEQ ID NO: 10) | 8 | ORF9b | 1 | 0.2740 | B1801 | 613 | 1.5373 | 6 | 354 | 1.6949 | 2 | B1801, B4403 |

TABLE 9A -continued

| | | | | | | | | | | | | | |
|---|---|---|---|---|---|---|---|---|---|---|---|---|---|
| HLA Predictions | | | | | | | | | | | | | |
| | VGYLQPRTF (SEQ ID NO: 39) | 9 | S | 5 | 0.6251 | C1601 | 1473 | 3.6940 | 185 | 5096 | 3.6303 | 1 | C1601 |
| | QLTPTWRVY (SEQ ID NO: 38) | 9 | S | 3 | 0.7696 | C1601 | 1835 | 4.6019 | 238 | 5096 | 4.6703 | 3 | A2501, C1203, C1601 |
| | KNIDGYFKIY (SEQ ID NO: 36) | 10 | S | 5 | 0.8731 | B1801 | 2074 | 5.2013 | 265 | 5096 | 5.2002 | 4 | B1801, B4403, C1203, C1601 |
| | EILDITPCSFG (SEQ ID NO: 47) | 11 | S | 3 | 4.5200 | A2501 | 10633 | 26.6658 | 1274 | 5096 | 25.0000 | 0 | unknown |
| HEK293 | YLFDESGEFKL (SEQ ID NO: 25) | 11 | nsp3 | 1 | 0.0052 | A0201 | 6 | 0.0150 | 1 | 7746 | 0.0129 | 2 | A0201, C0702 |
| | KRVDWTIEY (SEQ ID NO: 29) | 9 | nsp14 | 2 | 0.0180 | C0702 | 13 | 0.0326 | 1 | 2074 | 0.0482 | 1 | C0702 |
| | APHGHVMVEL (SEQ ID NO: 14) | 10 | nsp1 | 2 | 0.1099 | B0702 | 95 | 0.2382 | 3 | 686 | 0.4373 | 1 | B0702 |
| | IRQEEVQEL (SEQ ID NO: 31) | 9 | ORF7a | 3 | 0.1322 | C0702 | 122 | 0.3060 | 3 | 450 | 0.6667 | 1 | C0702 |
| | YLNSTNVTI (SEQ ID NO: 24) | 9 | nsp3 | 1 | 0.1354 | A0201 | 126 | 0.3160 | 24 | 7746 | 0.3098 | 1 | A0201 |
| | SVVSKVVKV (SEQ ID NO: 30) | 9 | nsp15 | 1 | 0.1482 | A0201 | 145 | 0.3636 | 5 | 1350 | 0.3704 | 1 | A0201 |
| | GLITLSYHL (SEQ ID NO: 5) | 9 | S.iORF1/2 | 1 | 0.2323 | A0201 | 245 | 0.6144 | 3 | 90 | 3.3333 | 1 | A0201 |
| | ELPDEFVVVTV (SEQ ID NO: 8) | 11 | ORF9b | 1 | 0.4190 | A0201 | 489 | 1.2263 | 9 | 354 | 2.5424 | 1 | A0201 |
| | SLEDKAFQL (SEQ ID NO: 7) | 9 | ORF9b | 7 | 0.4349 | A0201 | 512 | 1.2840 | 10 | 354 | 2.8249 | 1 | A0201 |
| | FGDDTVIEV (SEQ ID NO: 23) | 9 | nsp3 | 2 | 0.5348 | A0201 | 629 | 1.5774 | 114 | 7746 | 1.4717 | 1 | A0201 |
| | KAFQLTPIAV (SEQ ID NO: 13) | 10 | ORF9b | 2 | 0.5696 | A0201 | 682 | 1.7103 | 12 | 354 | 3.3898 | 1 | A0201 |
| | ELPDEFVVV (SEQ ID NO: 12) | 9 | ORF9b | 5 | 0.7673 | A0201 | 1006 | 2.5229 | 18 | 354 | 5.0847 | 1 | A0201 |
| | NLNESLIDL (SEQ ID NO: 40) | 9 | S | 1 | 0.8444 | A0201 | 1131 | 2.8364 | 140 | 5090 | 2.7473 | 1 | A0201 |

TABLE 9A -continued

HLA Predictions

| | | | | | | | | | | | | | |
|---|---|---|---|---|---|---|---|---|---|---|---|---|---|
| | STSAFVETV (SEQ ID NO: 19) | 9 | nsp2 | 2 | 1.3088 | A0201 | 1866 | 4.6796 | 84 | 2518 | 3.3360 | 1 | A0201 |
| | GPMVLRGLIT (SEQ ID NO: 6) | 10 | S.iORF1/2 | 6 | 2.1237 | B0702 | 3184 | 7.9850 | 18 | 90 | 20.0000 | 0 | unknown |
| | MLLGSMLYM (SEQ ID NO: 4) | 9 | S.iORF1 | 3 | 2.1581 | A0201 | 3238 | 8.1204 | 23 | 122 | 18.8525 | 0 | unknown |
| | APRITFGGP (SEQ ID NO: 42) | 9 | N | 3 | 3.0563 | B0702 | 4781 | 11.9900 | 151 | 1642 | 9.1961 | 0 | unknown |
| | AGTDTTITV (SEQ ID NO: 26) | 9 | nsp5 | 1 | 3.4456 | A0201 | 5467 | 13.7103 | 129 | 1190 | 10.8403 | 0 | unknown |

| | | | | | | NetMHC.EL | | | | | | |
|---|---|---|---|---|---|---|---|---|---|---|---|---|
| | peptide | pep length | viral protein | # experiments detected | best predicted rank | best predicted allele | rank within all viral peptides | percentile rank within all viral proteins | rank with in protein | % rank within protein | number of alleles with prank <=2 | all alleles with prank <= 2 |
| A549 | VATSRTLSY (SEQ ID NO: 41) | 9 | M | 2 | 0.2747 | C1203 | 319 | 0.8000 | 5 | 0.5855 | 3 | A2501, C1203, C1601 |
| | FAVDAAKAY (SEQ ID NO: 28) | 9 | nsp10 | 5 | 0.0388 | A2501 | 51 | 0.1279 | 1 | 0.1916 | 4 | A2501, B1801, C1203, C1601 |
| | FASEAARVV (SEQ ID NO: 17) | 9 | nsp2 | 7 | 0.4669 | C1203 | 537 | 1.3467 | 37 | 1.4694 | 2 | C1203, C1601 |
| | DEFVVVTV (SEQ ID NO: 11) | 8 | ORF9b | 3 | 0.3051 | B1801 | 358 | 0.8978 | 5 | 1.4124 | 1 | B1801 |
| | NATNVVIKV (SEQ ID NO: 37) | 9 | S | 4 | 4.4224 | C1203 | 3870 | 9.7053 | 482 | 9.4584 | 0 | unknown |
| | EIKESVQTF (SEQ ID NO: 15) | 9 | nsp2 | 2 | 0.0116 | A2501 | 18 | 0.0451 | 2 | 0.0794 | 1 | A2501 |
| | EEFEPSTQYEY (SEQ ID NO: 20) | 11 | nsp3 | 1 | 0.0604 | B1801 | 76 | 0.1906 | 21 | 0.2711 | 2 | B1801, B4403 |
| | SEFSSLPSY (SEQ ID NO: 27) | 9 | nsp8 | 1 | 0.0049 | B1801 | 6 | 0.0150 | 1 | 0.1319 | 3 | A2501, B1801, B4403 |
| | TVIEVQGY (SEQ ID NO: 22) | 8 | nsp3 | 1 | 0.6897 | A2501 | 764 | 1.9160 | 193 | 2.4916 | 1 | A2501 |

TABLE 9A -continued

| HLA Predictions | | | | | | | | | | | | |
|---|---|---|---|---|---|---|---|---|---|---|---|---|
| | LATNNLVVM (SEQ ID NO: 16) | 9 | nsp2 | 1 | 0.8716 | C1203 | 932 | 2.3373 | 72 | 2.8594 | 2 | C1203, C1601 |
| | TTTIKPVTY (SEQ ID NO: 21) | 9 | nsp3 | 1 | 0.5000 | A2501 | 571 | 1.4320 | 139 | 1.7945 | 1 | A2501 |
| | EILDITPCSF (SEQ ID NO: 33) | 10 | S | 6 | 0.2582 | A2501 | 303 | 0.7599 | 35 | 0.6868 | 1 | A2501 |
| | TAQNSVRVL (SEQ ID NO: 18) | 9 | nsp2 | 1 | 0.6833 | C1601 | 756 | 1.8959 | 56 | 2.2240 | 2 | C1203, C1601 |
| | LEDKAFQL (SEQ ID NO: 10) | 8 | ORF9b | 1 | 2.3170 | B1801 | 2268 | 5.6878 | 21 | 5.9322 | 0 | unknown |
| | VGYLQPRTF (SEQ ID NO: 39) | 9 | S | 5 | 0.3630 | C1610 | 409 | 1.0257 | 51 | 1.0008 | 2 | C1203, C1601 |
| | QLTPTWRVY (SEQ ID NO: 38) | 9 | S | 3 | 1.9329 | A2501 | 1915 | 4.8025 | 239 | 4.6900 | 1 | A2501 |
| | KNIDGYFKIY (SEQ ID NO: 36) | 10 | S | 5 | 4.5554 | B4403 | 3961 | 9.9335 | 493 | 9.6743 | 0 | unknown |
| | EILDITPCSFG (SEQ ID NO: 47) | 11 | S | 3 | 24.2039 | A2501 | 16524 | 41.4395 | 2066 | 40.5416 | 0 | unknown |
| HEK293 | YLFDESGEFKL (SEQ ID NO: 25) | 11 | nsp3 | 1 | 0.0721 | A0201 | 27 | 0.0677 | 5 | 0.0645 | 1 | A0201 |
| | KRVDWTIEY (SEQ ID NO: 29) | 9 | nsp14 | 2 | 0.0798 | C0702 | 29 | 0.0727 | 3 | 0.1446 | 1 | C0702 |
| | APHGHVMVEL (SEQ ID NO: 14) | 10 | nsp1 | 2 | 0.1336 | B0702 | 61 | 0.1530 | 2 | 0.2915 | 1 | B0702 |
| | IRQEEVQEL (SEQ ID NO: 31) | 9 | ORF7a | 3 | 0.2608 | C0702 | 126 | 0.3160 | 1 | 0.2222 | 1 | C0702 |
| | YLNSTNVTI (SEQ ID NO: 24) | 9 | nsp3 | 1 | 0.1219 | A0201 | 57 | 0.1429 | 9 | 0.1162 | 1 | A0201 |
| | SVVSKVVKV (SEQ ID NO: 30) | 9 | nsp15 | 1 | 0.7246 | A0201 | 410 | 1.0282 | 15 | 1.1111 | 1 | A0201 |
| | GLITLSYHL (SEQ ID NO: 5) | 9 | S.iORF1/2 | 1 | 0.1875 | A0201 | 88 | 0.2207 | 1 | 1.1111 | 1 | A0201 |
| | ELPDEFVVVTV (SEQ ID NO: 8) | 11 | ORF9b | 1 | 4.4149 | A0201 | 2917 | 7.3154 | 36 | 10.1695 | 0 | unknown |

TABLE 9A -continued

| HLA Predictions | | | | | | | | | | | |
|---|---|---|---|---|---|---|---|---|---|---|---|
| SLEDKAFQL (SEQ ID NO: 7) | 9 | ORF9b | 7 | 0.2732 | A0201 | 135 | 0.3386 | 5 | 1.4124 | 1 | A0201 |
| FGDDTVIEV (SEQ ID NO: 23) | 9 | nsp3 | 2 | 0.8750 | A0201 | 504 | 1.2639 | 89 | 1.1490 | 1 | A0201 |
| KAFQLTPIAV (SEQ ID NO: 13) | 10 | ORF9b | 2 | 5.8640 | A0201 | 3877 | 9.7229 | 57 | 16.1017 | 0 | unknown |
| ELPDEFVVV (SEQ ID NO: 12) | 9 | ORF9b | 5 | 1.4838 | A0201 | 915 | 2.2947 | 17 | 4.8023 | 1 | A0201 |
| NLNESLIDL (SEQ ID NO: 40) | 9 | S | 1 | 0.5256 | A0201 | 272 | 0.6821 | 22 | 0.4317 | 1 | A0201 |
| STSAFVETV (SEQ ID NO: 19) | 9 | nsp2 | 2 | 1.3131 | A0201 | 804 | 2.0163 | 38 | 1.5091 | 1 | A0201 |
| GPMVLRGLIT (SEQ ID NO: 6) | 10 | S.iORF1/2 | 6 | 5.0765 | B0702 | 3370 | 8.4514 | 22 | 24.4444 | 0 | unknown |
| MLLGSMLYM (SEQ ID NO: 4) | 9 | S.iORF1 | 3 | 0.5413 | A0201 | 287 | 0.7197 | 4 | 3.2787 | 1 | A0201 |
| APRITFGGP (SEQ ID NO: 42) | 9 | N | 3 | 2.8837 | B0702 | 1897 | 4.7574 | 55 | 3.3496 | 0 | unknown |
| AGTDTTITV (SEQ ID NO: 26) | 9 | nsp5 | 1 | 6.0434 | A0201 | 4023 | 10.0890 | 116 | 9.7479 | 0 | unknown |

TABLE 9B

| Allele Frequencies | | | | | | | |
|---|---|---|---|---|---|---|---|
| allele | locus | World | EUR | AFA | API | HIS | USA |
| A0101 | A | 0.04843 | 0.17181 | 0.04742 | 0.05082 | 0.06702 | 0.1285958 |
| A0201 | A | 0.15284 | 0.29604 | 0.12458 | 0.09458 | 0.19403 | 0.2415828 |
| A0202 | A | 0.00803 | 0.00083 | 0.04201 | 0.00028 | 0.00678 | 0.0073167 |
| A0203 | A | 0.0151 | 0 | 0.00021 | 0.03162 | 0.00025 | 0.0022221 |
| A0204 | A | 0.00295 | 0 | 0.00021 | 0 | 0.00276 | 0.0005137 |
| A0205 | A | 0.00849 | 0.00801 | 0.01872 | 0.00339 | 0.01481 | 0.0103171 |
| A0206 | A | 0.03469 | 0.00197 | 0.00021 | 0.04828 | 0.03916 | 0.0114304 |
| A0207 | A | 0.02127 | 0 | 0 | 0.04376 | 0 | 0.0029757 |
| A0211 | A | 0.00316 | 0 | 0.00021 | 0.01158 | 0.00326 | 0.0013891 |
| A0301 | A | 0.04272 | 0.14347 | 0.08132 | 0.02597 | 0.07907 | 0.1158797 |
| A1101 | A | 0.11661 | 0.05642 | 0.01581 | 0.17899 | 0.04618 | 0.0575514 |
| A1102 | A | 0.00698 | 0.00006 | 0 | 0.01525 | 0 | 0.0010744 |
| A2301 | A | 0.02335 | 0.01684 | 0.10774 | 0.00226 | 0.0369 | 0.0314688 |
| A2402 | A | 0.18816 | 0.08686 | 0.02205 | 0.18238 | 0.12324 | 0.0911385 |
| A2407 | A | 0.0046 | 0.00006 | 0.00083 | 0.01779 | 0.0005 | 0.0014455 |
| A2501 | A | 0.00451 | 0.01925 | 0.00499 | 0.00056 | 0.00879 | 0.0142415 |
| A2601 | A | 0.03354 | 0.02948 | 0.01414 | 0.03896 | 0.02887 | 0.0279771 |
| A2902 | A | 0.01626 | 0.03279 | 0.0364 | 0.00141 | 0.04167 | 0.0326992 |
| A3001 | A | 0.02505 | 0.01341 | 0.06905 | 0.02061 | 0.02108 | 0.0226496 |
| A3002 | A | 0.01489 | 0.00921 | 0.06219 | 0.00056 | 0.02811 | 0.0189945 |
| A3101 | A | 0.04093 | 0.02351 | 0.0104 | 0.03247 | 0.04794 | 0.0266753 |
| A3201 | A | 0.01434 | 0.03133 | 0.01414 | 0.01299 | 0.02711 | 0.0270539 |
| A3301 | A | 0.01153 | 0.00991 | 0.02121 | 0.00113 | 0.01958 | 0.0125178 |
| A3303 | A | 0.04081 | 0.00133 | 0.04451 | 0.0943 | 0.01305 | 0.0154576 |
| A3401 | A | 0.01618 | 0 | 0.00042 | 0.01581 | 0.00025 | 0.0011749 |
| A3402 | A | 0.00535 | 0.00044 | 0.03349 | 0.00028 | 0.00326 | 0.0053211 |
| A3601 | A | 0.00391 | 0.00006 | 0.02413 | 0 | 0.00276 | 0.0037324 |
| A6601 | A | 0.00573 | 0.00261 | 0.01477 | 0.00028 | 0.00552 | 0.004581 |
| A6801 | A | 0.02299 | 0.02503 | 0.03681 | 0.01863 | 0.04694 | 0.0300177 |
| A6802 | A | 0.01323 | 0.00845 | 0.0651 | 0.00028 | 0.0246 | 0.0182713 |
| A7401 | A | 0.00779 | 0.00006 | 0.0522 | 0.00113 | 0.00753 | 0.0083821 |
| B0702 | B | 0.04105 | 0.13987 | 0.07303 | 0.02632 | 0.05453 | 0.108239 |
| B0704 | B | 0.03122 | 0.00044 | 0 | 0 | 0 | 0.0002741 |
| B0801 | B | 0.0296 | 0.12525 | 0.03838 | 0.01641 | 0.04452 | 0.0920867 |
| B1301 | B | 0.0257 | 0 | 0.00041 | 0.03254 | 0.00075 | 0.0023993 |
| B1302 | B | 0.01418 | 0.02644 | 0.00954 | 0.0232 | 0.01201 | 0.0214323 |
| B1402 | B | 0.01234 | 0.03095 | 0.02199 | 0.00113 | 0.04102 | 0.0295029 |
| B1501 | B | 0.03431 | 0.06654 | 0.00975 | 0.0348 | 0.02876 | 0.0501793 |
| B1502 | B | 0.01319 | 0 | 0.00083 | 0.03565 | 0.00025 | 0.0025786 |
| B1503 | B | 0.01184 | 0.00089 | 0.06245 | 0.00028 | 0.01601 | 0.0116971 |
| B1510 | B | 0.00612 | 0.00013 | 0.03029 | 0.00085 | 0.00475 | 0.0050034 |
| B1517 | B | 0.00294 | 0.00273 | 0.00602 | 0.00453 | 0.0065 | 0.0039535 |
| B1801 | B | 0.02299 | 0.0462 | 0.03568 | 0.0116 | 0.03952 | 0.0412724 |
| B2705 | B | 0.01236 | 0.03254 | 0.00664 | 0.00849 | 0.01676 | 0.0246826 |
| B3501 | B | 0.05466 | 0.05713 | 0.06494 | 0.04273 | 0.06353 | 0.0583159 |
| B3503 | B | 0.0093 | 0.01563 | 0.00353 | 0.02405 | 0.01376 | 0.0142641 |
| B3507 | B | 0.01281 | 0 | 0 | 0 | 0 | 0 |
| B3701 | B | 0.02498 | 0.01347 | 0.00539 | 0.01471 | 0.00575 | 0.011121 |
| B3801 | B | 0.00789 | 0.0218 | 0.00166 | 0.00453 | 0.01926 | 0.0175 |
| B3802 | B | 0.00928 | 0 | 0 | 0.0365 | 0 | 0.002482 |
| B4001 | B | 0.0512 | 0.05643 | 0.01328 | 0.0798 | 0.01351 | 0.0447263 |
| B4002 | B | 0.04175 | 0.00991 | 0.00353 | 0.03056 | 0.04852 | 0.017261 |
| B4006 | B | 0.01799 | 0.00006 | 0.00021 | 0.03707 | 0.00275 | 0.0030701 |
| B4201 | B | 0.01045 | 0 | 0.05456 | 0 | 0.00625 | 0.0083565 |
| B4402 | B | 0.02162 | 0.09011 | 0.02116 | 0.00764 | 0.03327 | 0.0653279 |
| B4403 | B | 0.04473 | 0.04963 | 0.05373 | 0.04244 | 0.06078 | 0.0516488 |
| B4501 | B | 0.00995 | 0.00426 | 0.04502 | 0.00226 | 0.01526 | 0.0114811 |
| B4601 | B | 0.02358 | 0 | 0 | 0.06112 | 0 | 0.0041562 |
| B4901 | B | 0.00881 | 0.01341 | 0.02822 | 0.00113 | 0.02351 | 0.0163223 |
| B5001 | B | 0.00933 | 0.00807 | 0.00934 | 0.00736 | 0.01451 | 0.0093241 |
| B5101 | B | 0.05222 | 0.04544 | 0.02178 | 0.06282 | 0.05778 | 0.0456469 |
| B5201 | B | 0.02331 | 0.0096 | 0.01432 | 0.03679 | 0.02676 | 0.0150968 |
| B5301 | B | 0.01622 | 0.00324 | 0.11245 | 0.00085 | 0.01551 | 0.0197619 |
| B5401 | B | 0.01386 | 0 | 0 | 0.03282 | 0.00025 | 0.0022758 |
| B5501 | B | 0.00624 | 0.01729 | 0.00415 | 0.00538 | 0.01051 | 0.0135392 |
| B5502 | B | 0.01 | 0 | 0 | 0.01585 | 0 | 0.0010778 |
| B5601 | B | 0.01416 | 0.00496 | 0.00228 | 0.00792 | 0.0035 | 0.0045479 |
| B5701 | B | 0.01018 | 0.03832 | 0.00477 | 0.02066 | 0.01176 | 0.0279824 |
| B5703 | B | 0.00468 | 0.00032 | 0.03382 | 0 | 0.00675 | 0.0058854 |
| B5801 | B | 0.02891 | 0.0047 | 0.03506 | 0.05772 | 0.01451 | 0.0140698 |
| B5802 | B | 0.00836 | 0.00006 | 0.04108 | 0 | 0.0045 | 0.006293 |
| C0102 | C | 0.08481 | 0.02922 | 0.0085 | 0.13375 | 0.04927 | 0.0371011 |
| C0202 | C | 0.02805 | 0.03729 | 0.08461 | 0.00395 | 0.04227 | 0.0421929 |
| C0302 | C | 0.02461 | 0.00146 | 0.01369 | 0.05643 | 0.00625 | 0.0076676 |
| C0303 | C | 0.0558 | 0.05457 | 0.01182 | 0.05023 | 0.03402 | 0.0449723 |
| C0304 | C | 0.09132 | 0.08215 | 0.0533 | 0.08352 | 0.06978 | 0.076229 |

TABLE 9B-continued

| Allele Frequencies | | | | | | | |
|---|---|---|---|---|---|---|---|
| allele | locus | World | EUR | AFA | API | HIS | USA |
| C0401 | C | 0.11177 | 0.10534 | 0.18457 | 0.0807 | 0.16508 | 0.1247163 |
| C0403 | C | 0.01942 | 0 | 0.00041 | 0.01467 | 0.00025 | 0.0010961 |
| C0501 | C | 0.02614 | 0.09136 | 0.03526 | 0.00847 | 0.04652 | 0.0703703 |
| C0602 | C | 0.0616 | 0.09301 | 0.08855 | 0.06518 | 0.05878 | 0.0844999 |
| C0701 | C | 0.06887 | 0.16658 | 0.12401 | 0.03894 | 0.10355 | 0.1411454 |
| C0702 | C | 0.13101 | 0.15006 | 0.06968 | 0.1456 | 0.11281 | 0.1325102 |
| C0704 | C | 0.01467 | 0.01118 | 0.00871 | 0.01016 | 0.0095 | 0.0104865 |
| C0801 | C | 0.04522 | 0.00006 | 0.00124 | 0.07985 | 0.02826 | 0.0106059 |
| C0802 | C | 0.02017 | 0.03875 | 0.03733 | 0.00395 | 0.04927 | 0.0380463 |
| C1202 | C | 0.03191 | 0.00934 | 0.00145 | 0.04486 | 0.01301 | 0.0113519 |
| C1203 | C | 0.01959 | 0.04892 | 0.01783 | 0.02737 | 0.04127 | 0.0419732 |
| C1402 | C | 0.02539 | 0.0115 | 0.01265 | 0.04797 | 0.01326 | 0.0144427 |
| C1403 | C | 0.01471 | 0.00013 | 0.0027 | 0.01383 | 0.0005 | 0.0014685 |
| C1502 | C | 0.03362 | 0.01861 | 0.00539 | 0.04966 | 0.03052 | 0.0210593 |
| C1601 | C | 0.0242 | 0.03539 | 0.09788 | 0.00169 | 0.05053 | 0.0440742 |
| C1701 | C | 0.0188 | 0.00667 | 0.07362 | 0.00141 | 0.02251 | 0.0180045 |

TABLE 9C

| | Estimated Population Coverage | | | | | | | | | | | | | | | |
|---|---|---|---|---|---|---|---|---|---|---|---|---|---|---|---|---|
| | Peptide | thr0.1_assign_alleles | thr0.1_num_alleles | thr0.1_coverage | thr0.2_assign_alleles | thr0.2_num_alleles | thr0.2_coverage | thr0.3_assign_alleles | thr0.3_num_alleles | thr0.3_coverage | thr0.4_assign_alleles | thr0.4_num_alleles | thr0.4_coverage | thr0.5_assign_alleles | thr0.5_num_alleles | thr0.5_coverage |
| A549 | DEFVVVTV (SEQ ID NO: 11) | B1801, B4002, B4901, B5001, B5101 | 5 | 0.2519 | B1801, B4002, B4901, B5001, B5101 | 5 | 0.2519 | B1801, B4002, B4006, B4901, B5001, B5101 | 6 | 0.2827 | B1801, B4002, B4006, B4501, B4901, B5001, B5101 | 7 | 0.2995 | B1801, B4002, B4006, B4501, B4901, B5001, B5101 | 7 | 0.2995 |
| | LEDKAFQL (SEQ ID NO: 10) | unknown | 0 | 0.0000 | unknown | 0 | 0.0000 | B1801, B4001 | 2 | 0.1429 | B1801, B4001, C0802 | 3 | 0.1771 | A0202, B1801, B4001, B4402, B4403, C0802 | 6 | 0.3022 |
| | TVIEVQGY (SEQ ID NO: 22) | A2501, A2601 | 2 | 0.0747 | A2501, A2601 | 2 | 0.0747 | A2501, A2601, A3601 | 3 | 0.0822 | A2501, A2601, A3601 | 3 | 0.0822 | A2501, A2601, A2902, A3002, A3601 | 5 | 0.1409 |
| | EIKESVQTF (SEQ ID NO: 15) | A2501, A2601 | 2 | 0.0747 | A2501, A2601 | 2 | 0.0747 | A2501, A2601 | 2 | 0.0747 | A2501, A2601, B1502 | 3 | 0.0989 | A2501, A2601, B1502, C1202 | 4 | 0.1555 |
| | FASEAARVV (SEQ ID NO: 17) | C0303, C0304, C1203, C1601 | 4 | 0.3454 | C0302, C0303, C0304, C0602, C1203, C1601 | 6 | 0.4774 | C0202, C0302, C0303, C0304, C0602, C1202, C1203, C1601 | 8 | 0.5605 | C0202, C0302, C0303, C0304, C0602, C0801, C1202, C1203, C1601 | 9 | 0.6184 | B5101, C0202, C0302, C0303, C0304, C0602. C0801, C0802, C1202, C1203, C1601 | 11 | 0.6793 |
| | FAVDAAKAY | B3501. B3507, B4601, C0202, | 8 | 0.4234 | B3501, B3507, B4601, C0202, | 10 | 0.5663 | B1502. B3501, B3507, B4601, | 11 | 0.5788 | B1502, B3501, B3507, B4601, | 11 | 0.5788 | B1502, B3501, B3507, B4601, | 11 | 0.5788 |

TABLE 9C-continued

| Estimated Population Coverage | | | | | | | | | | | | | | | |
|---|---|---|---|---|---|---|---|---|---|---|---|---|---|---|---|
| (SEQ ID NO: 28) | C0302, C0303, C1202, C1601 | | | C0302, C0303, C0304, C1202, C1203, C1601 | | | C0202. C0302, C0303, C0304, C1202, C1203, C1601 | | | C0202, C0302. C0303, C0304, C1202, C1203, C1601 | | | C0202, C0302, C0303, C0304, C1202, C1203, C1601 | | |
| LATNNLVVM (SEQ ID NO: 16) | C0704, C1203 | 2 | 0.0673 | B3503, C0302, C0704, C1203, C1601 | 5 | 0.1748 | B3503, B3507, C0302, C0304, C0704, C1203, C1601 | 7 | 0.3482 | B3503, B3507, C0302, C0303, C0304, C0704, C1203, C1601 | 8 | 0.4333 | B3503, B3507, C0302, C0303, C0304, C0403, C0704, C1203, C1601 | 9 | 0.4615 |
| NATNVVIKV (SEQ ID NO: 37) | A6802, C1203 | 2 | 0.0641 | A6802, C1203 | 2 | 0.0641 | A0206, A6802, C1203 | 3 | 0.1287 | A0206, A6802, B5101, C0602, C1203 | 5 | 0.3126 | A0206, A6802, B5101, C0602, C1203, C1701 | 6 | 0.3404 |
| QLTPTWRVY (SEQ ID NO: 38) | unknown | 0 | 0.0000 | unknown | 0 | 0.0000 | unknown | 0 | 0.0000 | unknown | 0 | 0.0000 | A3002 | 1 | 0.0296 |
| SEFSSLPSY (SEQ ID NO: 27) | B1801, B4403 | 2 | 0.1309 | B1801, B4402, B4403 | 3 | 0.1707 | B1801, B4402, B4403 | 3 | 0.1707 | B1801, B4402, B4403 | 3 | 0.1707 | B1801, B4402, B4403 | 3 | 0.1707 |
| TAQNSVRVL (SEQ ID NO: 18) | unknown | 0 | 0.0000 | C1601 | 1 | 0.0478 | C1203, C1601 | 2 | 0.0857 | C1203, C1601 | 2 | 0.0857 | C0102, C0303, C0304, C1203, C1601 | 5 | 0.4754 |

TABLE 9C-continued

| Estimated Population Coverage | | | | | | | | | | | | | | | |
|---|---|---|---|---|---|---|---|---|---|---|---|---|---|---|---|
| TTTIKPVTY (SEQ ID NO: 21) | B1517, C1601 | 2 | 0.0534 | B1517, C1601 | 2 | 0.0534 | A3601, B1517, C1601 | 3 | 0.0608 | A0101, A3601, B1517, C1601 | 4 | 0.1499 | A0101, A3601, B1517, C1601 | 4 | 0.1499 |
| VATSRTLSY (SEQ ID NO: 41) | B1517, C0202, C1601 | 3 | 0.1070 | B1517, C0202, C0302, C1202, C1601 | 5 | 0.2104 | B1517, B4601, C0202, C0302, C1202, C1601 | 6 | 0.2473 | B1517, B3507, B4601, C0202, C0302, C1202, C1601 | 7 | 0.2670 | A3601, B1517, B3507, B4601, C0202, C0302, C1202, C1601 | 8 | 0.2727 |
| VGYLQPRTF (SEQ ID NO: 39) | unknown | 0 | 0.0000 | unknown | 0 | 0.0000 | unknown | 0 | 0.0000 | unknown | 0 | 0.0000 | unknown | 0 | 0.0000 |
| EILDITPCSF (SEQ ID NO: 33) | A2501 | 1 | 0.0090 | A2501 | 1 | 0.0090 | A2501 | 1 | 0.0090 | A2501 | 1 | 0.0090 | A2501, A2601 | 2 | 0.0747 |
| KNIDGYFKIY (SEQ ID NO: 36) | unknown | 0 | 0.0000 | A3002, C1502 | 2 | 0.0937 | A3002, C1502 | 2 | 0.0937 | A3002, B5802, C0701, C1502 | 4 | 0.2313 | A3002, A3201, B5802, C0701, C1502 | 5 | 0.2535 |
| EEFEPSTQYEY | B1801, B4402, B4403 | 3 | 0.1707 | B1801, B4402, B4403 | 3 | 0.1707 | B1801, B4402, B4403 | 3 | 0.1707 | B1801, B4402, B4403 | 3 | 0.1707 | B1801, B4402, B4403 | 3 | 0.1707 |

TABLE 9C-continued

| | | Estimated Population Coverage | | | | | | | | | | | | | |
|---|---|---|---|---|---|---|---|---|---|---|---|---|---|---|---|
| | (SEQ ID NO: 20) | | | | | | | | | | | | | | |
| | EIL DIT PCS FG (SEQ ID NO: 47) | unknown | 0 | 0.0000 | unknown | 0 | 0.0000 | unknown | 0 | 0.0000 | unknown | 0 | 0.0000 | unknown | 0 | 0.0000 |
| HEK293 | AG TDT TIT V (SEQ ID NO: 26 | unknown | 0 | 0.0000 | unknown | 0 | 0.0000 | unknown | 0 | 0.0000 | unknown | 0 | 0.0000 | C0704 | 1 | 0.0291 |
| | APR ITF GGP (SEQ ID NO: 42) | unknown | 0 | 0.0000 | unknown | 0 | 0.0000 | unknown | 0 | 0.0000 | unknown | 0 | 0.0000 | unknown | 0 | 0.0000 |
| | ELP DEF VV V (SEQ ID NO: 12 | A0207 | 1 | 0.0421 | A0206, A0207 | 2 | 0.1088 | A0206, A0207 | 2 | 0.1088 | A0206, A0207 | 2 | 0.1088 | A0206, A0207 | 2 | 0.1088 |
| | FGD DT VIE V (SEQ ID NO: 23) | A0207, C0403, C0501, C0802 | 4 | 0.1639 | A0207, C0401, C0403, C0501, C0801, C0802 | 6 | 0.4213 | A0206, A0207, C0401, C0403, C0501, C0801, C0802 | 7 | 0.4616 | A0206, A0207, C0401, C0403, C0501, C0801, C0802 | 7 | 0.4616 | A0206, A0207, C0304, C0401, C0403, C0501, C0801, C0802 | 8 | 0.5806 |

TABLE 9C-continued

| Estimated Population Coverage | | | | | | | | | | | | | | | |
|---|---|---|---|---|---|---|---|---|---|---|---|---|---|---|---|
| GLITLSYHL (SEQ ID NO: 5) | unknown | 0 | 0.0000 | unknown | 0 | 0.0000 | A0201, A0202 | 2 | 0.2959 | A0201, A0202 | 2 | 0.2959 | A0201, A0202 | 2 | 0.2959 |
| IRQEEVQEL (SEQ ID NO: 31) | unknown | 0 | 0.0000 | C0702 | 1 | 0.2449 | C0701, C0702 | 2 | 0.3598 | C0602, C0701, C0702 | 3 | 0.4546 | C0602, C0701, C0702 | 3 | 0.4546 |
| KRVDWTIEY (SEQ ID NO: 29) | B2705, C0701, C0702 | 3 | 0.3755 | B2705, C0602, C0701, C0702 | 4 | 0.4680 | B1503, B2705, C0602, C0701, C0702 | 5 | 0.4807 | A3201, B1503, B2705, C0602, C0701, C0702 | 6 | 0.4955 | A3201, B1503, B2705, C0602, C0701, C0702 | 6 | 0.4955 |
| MLLGSMLYM (SEQ ID NO: 4) | unknown | 0 | 0.0000 | unknown | 0 | 0.0000 | unknown | 0 | 0.0000 | unknown | 0 | 0.0000 | unknown | 0 | 0.0000 |
| NLNESLIDL (SEQ ID NO: 40) | unknown | 0 | 0.0000 | unknown | 0 | 0.0000 | unknown | 0 | 0.0000 | A0204 | 1 | 0.0059 | A0204 | 1 | 0.0059 |
| SLEDKAFQL | unknown | 0 | 0.0000 | A0207 | 1 | 0.0421 | A0207 | 1 | 0.0421 | A0204, A0207 | 2 | 0.0479 | A0201, A0202, A0204, A0207 | 4 | 0.3359 |

TABLE 9C-continued

Estimated Population Coverage

| | | | | | | | | | | | | | | | |
|---|---|---|---|---|---|---|---|---|---|---|---|---|---|---|---|
| (SEQ ID NO: 7) | | | | | | | | | | | | | | | |
| STSAFVETV (SEQ ID NO: 19) | A0205 | 1 | 0.0169 | A0205, A6802 | 2 | 0.0430 | A0205, A6802 | 2 | 0.0430 | A0205, A6802 | 2 | 0.0430 | A0203, A0205, A6802 | 3 | 0.0723 |
| SVVSKYVKV (SEQ ID NO: 30) | A0203, A0205, A0206, A6802 | 4 | 0.1379 | A0201, A0203, A0205, A0206, A2601, A6802 | 6 | 0.4493 | A0201, A0203, A0205, A0206, A0207, A0211, A2601, A6802, C0202 | 9 | 0.5134 | A0201, A0203, A0204, A0205, A0206, A0207, A0211, A2601, A6802, C0202, C1502 | 11 | 0.5502 | A0201, A0203, A0204, A0205, A0206, A0207, A0211, A2601, A6802, C0202, C1203, C1502 | 12 | 0.5688 |
| YLNSTNVTI (SEQ ID NO: 24) | unknown | 0 | 0.0000 | A0201, A0203 | 2 | 0.3077 | A0201, A0202, A0203 | 3 | 0.3210 | A0201, A0202, A0203, A0204 | 4 | 0.3258 | A0201, A0202, A0203, A0204, B1302 | 5 | 0.3448 |
| APHGHVMVEL (SEQ ID NO: 14) | B4201 | 1 | 0.0208 | B0702, B0704, B0801, B4201 | 4 | 0.2120 | B0702, B0704, B0801, B4201, C0704 | 5 | 0.2350 | B0702, B0704, B0801, B4201, C0704, C0801 | 6 | 0.3036 | B0702, B0704, B0801, B4201, B5601, C0704, C0801 | 7 | 0.3256 |
| GPMVLRGLIT | unknown | 0 | 0.0000 | unknown | 0 | 0.0000 | unknown | 0 | 0.0000 | unknown | 0 | 0.0000 | unknown | 0 | 0.0000 |

TABLE 9C-continued

| Estimated Population Coverage | | | | | | | | | | | | | | | |
|---|---|---|---|---|---|---|---|---|---|---|---|---|---|---|---|
| (SEQ ID NO: 6) | | | | | | | | | | | | | | | |
| KAF QLT PIA V (SEQ ID NO: 13) | A0211, C1701 | 2 | 0.0433 | A0211, B5401, C1701 | 3 | 0.0697 | A0211, B5101, B5401, B5502, C1701, G0104 | 6 | 0.1834 | A0211, B5101, B5401, B5502, C1203, C1701, G0104 | 7 | 0.2156 | A0211, B5101, B5201, B5401, B5502, C1203, C1701, G0104 | 8 | 0.2547 |
| ELP DEF VV VT V (SEQ ID NO: 8) | A0207 | 1 | 0.0421 | A0207 | 1 | 0.0421 | A0207, B5201 | 2 | 0.0862 | A0207, B5201, C0102 | 3 | 0.2346 | A0201, A0207, A6802, B5201, C0102 | 5 | 0.4723 |
| YLF DES GEF KL (SEQ ID NO: 25) | A0201, A0202, A0204, A0211 | 4 | 0.3061 | A0201, A0202, A0203, A0204, A0205, A0206, A0207, A0211, A2902, C1701, G0101, G0103, G0104 | 13 | 0.4768 | A0201, A0202, A0203, A0204, A0205, A0206, A0207, A0211, A2902, B1301, B3503, C1701, G0101, G0103, G0104 | 15 | 0.5127 | A0201, A0202, A0203, A0204, A0205, A0206, A0207, A0211, A2902, A3201, B1301, B3501, B3503, C0304, C0403, C1701, G0101, G0103, G0104 | 19 | 0.6719 | A0201, A0202, A0203, A0204, A0205, A0206, A0207, A0211, A2902, A3201, B1301, B1302, B3501, B3503, C0304, C0403, C0704, C1701, G0101, G0103, G0104 | 21 | 0.6927 |
| Peps Com bined | B1801, B4002, B4901, B5001, B5101, unknown, A2 501,A2 601,A2 | 38 | 0.9585 | B1801, B4002, B4901, B5001, B5101, unknown, A2 501,A2 601,A2 | 52 | 0.9958 | B1801, B4002, B4006, B4901, B5001, B5101, B1801, B4001, A2501, | 60 | 0.9978 | B1801, B4002, B4006, B4501, B4901, B5001, B5101, B1801, B4001, | 65 | 0.9996 | B1801, B4002, B4006, B4501, B4901, B5001, B5101, A0202, B1801, | 67 | 0.9996 |

TABLE 9C-continued

| Estimated Population Coverage | | | | |
|---|---|---|---|---|
| 501,A2 | 501,A2 | A2601, | C0802, | B4001, |
| 601,C0 | 601,C0 | A3601, | A2501, | B4402, |
| 303,C0 | 302,C0 | A2501, | A2601, | B4403, |
| 304,C1 | 303,C0 | A2601, | A3601, | C0802, |
| 203,C1 | 304,C0 | C0202, | A2501, | A2501, |
| 601,B3 | 602,C1 | C0302, | A2601, | A2601, |
| 501,B3 | 203,C1 | C0303, | B1502, | A2902, |
| 507,B4 | 601,B3 | C0304, | C0202, | A3002, |
| 601,C0 | 501,B3 | C0602, | C0302, | A3601, |
| 202,C0 | 507,B4 | C1202, | C0304, | A2601, |
| 303,C1 | 202,C0 | C1601, | C0602, | B1502, |
| 202,C1 | 302,C0 | B1502, | C0801, | C1202, |
| 601,C0 | 303,C0 | B3501, | C1202, | B5101, |
| 704,C1 | 304,C1 | B3507, | C1203, | C0202, |
| 203,A6 | 202,C1 | B4601, | C1601, | C0302, |
| 802,C1 | 203,C1 | C0202, | B1502, | C0303, |
| 203,un | 601,B3 | C0302, | B3501, | C0304, |
| known, | 503,C0 | C0303, | B3507, | C0602, |
| B1801, | 302,C0 | C0304, | B4601, | C0801, |
| B4403, | 704,C1 | C1202, | C0202, | C0802, |
| unkno | 203,C1 | C1203, | C0302, | C1202, |
| wn,B1 | 601,A6 | C1601, | C0303, | C1203, |
| 517,C1 | 802,C1 | B3503, | C0304, | C1601, |
| 601,B1 | 203,un | B3507, | C1202, | B1502, |
| 517,C0 | known, | C0302, | C1203, | B3501, |
| 202,C1 | B1801, | C0304, | C1601, | B3507, |
| 601,un | B4402, | C0704, | B3503, | B4601, |
| known, | B4403, | C1203, | B3507, | C0202, |
| A2501, | C1601, | C1601, | C0302, | C0302, |
| unkno | B1517, | A0206, | C0303, | C0303, |
| wn,B1 | C1601, | A6802, | C0304, | C0304, |
| 801,B4 | B1517, | C1203, | C0704, | C1202, |
| 402,B4 | C0202, | unkno | C1203, | C1203, |
| 403,un | C0302, | wn,B18 | C1601, | C1601, |
| known, | C1202, | 01,B44 | A0206, | B3503, |
| unkno | C1601, | 02,B44 | A6802, | B3507, |
| wn,unk | unkno | 03,C12 | B5101, | C0302, |
| nown, | wn,A2 | 03,C16 | C0602, | C0303, |
| A0207, | 501,A3 | 01,A36 | C1203, | C0304, |
| A0207, | 002,C1 | 01,B15 | unknow | C0403, |
| C0403, | 502,B1 | 17,C16 | n,B180 | C0704, |
| C0501, | 801,B4 | 01,B15 | 1,B440 | C1203, |
| C0802, | 402,B4 | 17,B46 | 2,B440 | C1601, |
| unkno | 403,un | 01,C02 | 3,C120 | A0206, |
| wn,unk | known, | 02,C03 | 3,C160 | A6802, |
| nown, | unkno | 02,C12 | 1,A010 | B5101, |
| B2705, | wn,unk | 02,C16 | 1,A360 | C0602, |
| C0701, | nown, | 01,unk | 1,B151 | C1203, |
| C0702, | A0206, | nown, | 7,C160 | C1701, |
| unkno | A0207, | A2501, | 1,B151 | A3002, |
| wn,unk | A0207, | A3002, | 7,B350 | B1801, |

TABLE 9C-continued

| Estimated Population Coverage | | | | |
|---|---|---|---|---|
| nown,u | C0401, | C1502, | 7,B460 | B4402, |
| nknow | C0403, | B1801, | 1,C020 | B4403, |
| n,A020 | C0501, | B4402, | 2,C030 | C0102, |
| 5,A020 | C0801, | B4403, | 2,C120 | C0303, |
| 3,A020 | C0802, | unkno | 2,C160 | C0304, |
| 5,A020 | unkno | wn,unk | 1,unkno | C1203, |
| 6,A680 | wn,C07 | nown,u | wn,A25 | C1601, |
| 2,unkn | 02,B27 | nknow | 01,A30 | A0101, |
| own,B | 05,C06 | n,A020 | 02,B58 | A3601, |
| 4201,u | 02,C07 | 6,A020 | 02,C07 | B1517, |
| nknow | 01,C07 | 7,A020 | 01,C15 | C1601, |
| n,A021 | 02,unk | 6,A020 | 02,B18 | A3601, |
| 1,C170 | nown,u | 7,C040 | 01,B44 | B1517, |
| 1,A020 | nknow | 1,C040 | 02,B44 | B3507, |
| 7,A020 | n,A020 | 3,C050 | 03,unkn | B4601, |
| 1,A020 | 7,A020 | 1,C080 | own,un | C0202, |
| 2,A020 | 5,A680 | 1,C080 | known, | C0302, |
| 4,A021 | 2,A020 | 2,A020 | unknow | C1202, |
| 1 | 1,A020 | 1,A020 | n,A020 | C1601, |
| | 3,A020 | 2,C070 | 6,A020 | unkno |
| | 5,A020 | 1,C070 | 7,A020 | wn,A2 |
| | 6,A260 | 2,B150 | 6,A020 | 501,A2 |
| | 1,A680 | 3,B270 | 7,C040 | 601,A3 |
| | 2,A020 | 5,C060 | 1,C040 | 002,A3 |
| | 1,A020 | 2,C070 | 3,C050 | 802,C0 |
| | 2,B070 | 2,unkn | 1,C080 | 701,C1 |
| | 4,B080 | own,un | 2,A020 | 502,B1 |
| | 1,B420 | known, | 1,A020 | 801,B4 |
| | 1,unkn | A0207, | 2,C060 | 402,B4 |
| | own,A | A0205, | 2,C070 | 403,un |
| | 0211,B | A6802, | 1,C070 | known, |
| | 5401,C | A0201, | 2,A320 | C0704, |
| | 1701,A | A0203, | 1,B150 | unkno |
| | 0207,A | A0205, | 3,B270 | wn,A0 |
| | 0201,A | A0206, | 5,C060 | 206,A0 |
| | 0202,A | A0207, | 2,C070 | 207,A0 |
| | 0203,A | A0211, | 1,C070 | 206,A0 |
| | 0204,A | A2601, | 2,unkno | 207,C0 |
| | 0205,A | A6802, | wn,A02 | 304,C0 |
| | 0206,A | C0202, | 04,A02 | 401,C0 |
| | 0207,A | A0201, | 04,A02 | 403,C0 |
| | 0211,A | A0202, | 07,A02 | 501,C0 |
| | 2902,C | A0203, | 05,A68 | 801,C0 |
| | 1701,G | B0702, | 02,A02 | 802,A0 |
| | 0101,G | B0704, | 01,A02 | 201,A0 |
| | 0103,G | B0801, | 03,A02 | 202,C0 |
| | 0104 | B4201, | 04,A02 | 602,C0 |
| | | C0704, | 05,A02 | 701,C0 |
| | | unkno | 06,A02 | 702,A3 |
| | | wn,A0 | 07,A02 | 201,B1 |
| | | 211,B5 | 11,A26 | 503,B2 |

TABLE 9C-continued

| Estimated Population Coverage | | |
|---|---|---|
| 101,B5 | 01,A68 | 705,C0 |
| 401,B5 | 02,C02 | 602,C0 |
| 502,C1 | 02,C15 | 701,C0 |
| 701,G0 | 02,A02 | 702,un |
| 104,A0 | 01,A02 | known, |
| 207,B5 | 02,A02 | A0204, |
| 201,A0 | 03,A02 | A0201, |
| 201,A0 | 04,B07 | A0202, |
| 202,A0 | 02,B07 | A0204, |
| 203,A0 | 04,B08 | A0207, |
| 204,A0 | 01,B42 | A0203, |
| 205,A0 | 01,C07 | A0205, |
| 206,A0 | 04,C08 | A6802, |
| 207,A0 | 01,unkn | A0201, |
| 211,A2 | own,A0 | A0203, |
| 902,B1 | 211,B5 | A0204, |
| 301,B3 | 101,B5 | A0205, |
| 503,C1 | 401,B5 | A0206, |
| 701,G0 | 502,C1 | A0207, |
| 101,G0 | 203,C1 | A0211, |
| 103,G0 | 701,G0 | A2601, |
| 104 | 104,A0 | A6802, |
| | 207,B5 | C0202, |
| | 201,C0 | C1203, |
| | 102,A0 | C1502, |
| | 201,A0 | A0201, |
| | 202,A0 | A0202, |
| | 203,A0 | A0203, |
| | 204,A0 | A0204, |
| | 205,A0 | B1302, |
| | 206,A0 | B0702, |
| | 207,A0 | B0704, |
| | 211,A2 | B0801, |
| | 902,A3 | B4201, |
| | 201,B1 | B5601, |
| | 301,B3 | C0704, |
| | 501,B3 | C0801, |
| | 503,C0 | unkno |
| | 304,C0 | wn,A0 |
| | 403,C1 | 211,B5 |
| | 701,G0 | 101,B5 |
| | 101,G0 | 201,B5 |
| | 103,G0 | 401,B5 |
| | 104 | 502,C1 |
| | | 203,C1 |
| | | 701,G0 |
| | | 104,A0 |
| | | 201,A0 |
| | | 207,A6 |
| | | 802,B5 |
| | | 201,C0 |

TABLE 9C-continued

Estimated Population Coverage

| | | | | | | | | | | | | | | | |
|---|---|---|---|---|---|---|---|---|---|---|---|---|---|---|---|
| | | | | | | | | | | | | | 102,A0 201,A0 202,A0 203,A0 204,A0 205,A0 206,A0 207,A0 211,A2 902,A3 201,B1 301,B1 302,B3 501,B3 503,C0 304,C0 403,C0 704,C1 701,G0 101,G0 103,G0 104 | | |
| | Peptide | thr0.6_ assign_ alleles | thr0.6_ num_ alleles | thr0.6_ cover- age | thr0.7_ assign_ alleles | thr0.7_ num_ alleles | thr0.7_ cover- age | thr0.8_ assign_ alleles | thr0.8_ num_ alleles | thr0.8_ cover- age | thr0.9_ assign_ alleles | thr0.9_ num_ alleles | thr0.9_ cover- age | thr1_ assign_ alleles | thr1_ num_ alleles | thr1_ cover- age |
| A549 | DEFVVVTV (SEQ ID NO: 11) | B1801, B3701, B4002, B4006, B4403, B4501, B4901, B5001, B5101 | 9 | 0.4113 | B1402, B1801, B3701, B4002, B4006, B4403, B4501, B4901, B5001, B5101 | 10 | 0.4301 | B1402,B1801,B3701,B4002,B4006,B4402,B4403,B4501,B4901,B5001,B5101 | 11 | 0.4623 | A6802, B1402, B1801, B3701, B4002, B4006, B4402, B4403, B4501, B4901, B5001, B5101 | 12 | 0.4764 | A6802, B1402, B1801, B3701, B4002, B4006, B4402, B4403, B4501, B4901, B5001, B5101, B5201 | 13 | 0.5092 |
| | LEDKAFQL (SEQ ID NO: 10) | A0202, B1801, B3801, B4001, B4402, B4403, C0802 | 7 | 0.3149 | A0202, A3601, B1510, B1801, B3503, B3801, B4001, B4002, B4402, B4403, C0802 | 11 | 0.4085 | A0202,A3601,B1510,B1801,B3503,B3801,B4001,B4002,B4402,B4403,B4501,B5703,C0802 | 13 | 0.4301 | A0101, A0202, A3601, B1510, B1801, B3503, B3801, B4001, B4002, B4402, B4403, | 14 | 0.4846 | A0101, A0202, A3601, B1510, B1801, B3503, B3801, B4001, B4002, B4402, B4403, | 15 | 0.4999 |

TABLE 9C-continued

| Estimated Population Coverage | | | | | | | | | | | | | | | |
|---|---|---|---|---|---|---|---|---|---|---|---|---|---|---|---|
| | | | | | | | | | | B4501, B5703, C0802 | | | B4501, B5703, C0704, C0802 | | |
| TVIEVQGY (SEQ ID NO: 22) | A0101, A2501, A2601, A2902, A3002, A3601 | 6 | 0.2283 | A0101, A2501, A2601, A2902, A3002, A3601, B1502 | 7 | 0.2485 | A0101,A2501,A2601,A2902,A3002,A3601,B1502,B3501 | 8 | 0.3295 | A0101, A2501, A2601, A2902, A3002, A3601, B1501, B1502, B3501 | 9 | 0.3779 | A0101, A2501, A2601, A2902, A3002, A3601, B1501, B1502, B3501 | 9 | 0.3779 |
| EIKESVQTF (SEQ ID NO: 15) | A2501, A2601, B1502, C1202 | 4 | 0.1555 | A2501, A2601, B1502, C1202 | 4 | 0.1555 | A2501,A2601,B1502,C1202 | 4 | 0.1555 | A2501, A2601, B1501, B1502, C1202 | 5 | 0.2132 | A2501, A2601, B1501, B1502, C1202 | 5 | 0.2132 |
| FASEARVV (SEQ ID NO: 17) | B5101, C0202, C0302, C0303, C0304, C0602, C0801, C0802, C1202, C1203, C1601 | 11 | 0.6793 | B5101, C0202, C0302, C0303, C0304, C0602, C0801, C0802, C1202, C1203, C1601 | 11 | 0.6793 | B5101,C0202,C0302,C0303, C0304,C0602,C0801,C0802, C1202,C1203,C1601 | 11 | 0.6793 | B5101, C0202, C0302, C0303, C0304, C0602, C0801, C0802, C1202, C1203, C1502, C1601 | 12 | 0.7143 | B5101, C0202, C0302, C0303, C0304, C0501, C0602, C0801, C0802, C1202, C1203, C1502, C1601 | 13 | 0.7402 |
| FAVDAAKAY (SEQ ID NO: 28) | B1501, B1502, B3501, B3507, B4601, C0202, C0302, C0303, C0304, C1202, C1203, C1601 | 12 | 0.6105 | B1501, B1502, B1503, B3501, B3507, B4601, B5301, C0202, C0302, C0303, C0304, C0702, C1202, C1203, C1601 | 15 | 0.7553 | A2902.B1501,B1502,B1503,B3501,B3507,B4601,B5301,C0202,C0302,C0303,C0304,C0702,C1202,C1203,C1601 | 16 | 0.7632 | A2902, B1501, B1502, B1503, B3501, B3507, B4601, B5301, C0202, C0302, C0303, C0304, C0702, C1202, C1203, C1601 | 16 | 0.7632 | A2902, B1501, B1502, B1503, B3501, B3507, B4601, B5301, C0202, C0302, C0303, C0304, C0702, C1202, C1203, C1402, C1601 | 17 | 0.7831 |

TABLE 9C-continued

| Estimated Population Coverage | | | | | | | | | | | | | | | |
|---|---|---|---|---|---|---|---|---|---|---|---|---|---|---|---|
| LATNNLVVM (SEQ ID NO: 16) | B3503, B3507, C0302, C0303, C0304, C0403, C0704, C1203, C1601, C1701 | 10 | 0.4882 | B3501, B3503, B3507, C0302, C0303, C0304, C0403, C0704, C1203, C1601, C1701 | 11 | 0.5438 | B3501,B3503,B3507,C0302, C0303,C0304,C0403,C0704, C1202,C1203,C1601,C1701 | 12 | 0.5827 | B3501, B3503, B3507, C0302, C0303, C0304, C0403, C0704, C1202, C1203, C1601, C1701 | 12 | 0.5827 | B3501, B3503, B3507, C0302, C0303, C0304, C0403, C0704, C1202, C1203, C1601, C1701 | 12 | 0.5827 |
| NATNVVIKV (SEQ ID NO: 37) | A0206, A6802, B5101, C0602, C1203, C1701 | 6 | 0.3404 | A0206, A6802, B5101, C0602, C1203, C1701 | 6 | 0.3404 | A0206,A6802,B5101,C0602,C1203,C1601,C1701 | 7 | 0.3754 | A0206, A6802, B1302, B5101, C0202, C0602, C0801, C1203, C1601, C1701 | 10 | 0.4911 | A0206, A6802, B1302, B5101, B5301, C0202, C0602, C0704, C0801, C1203, C1502, C1601, C1701 | 13 | 0.5660 |
| QLTPTWRVY (SEQ ID NO: 38) | A3002 | 1 | 0.0296 | A3002 | 1 | 0.0296 | A3002,B1502,C1601 | 3 | 0.1002 | A3002, B1502, C1601 | 3 | 0.1002 | A3002, B1502, C1601 | 3 | 0.1002 |
| SEFSSLPSY (SEQ ID NO: 27) | B1801, B4402, B4403 | 3 | 0.1707 | B1801, B4402, B4403 | 3 | 0.1707 | B1801,B4402,B4403 | 3 | 0.1707 | B1801, B4402, B4403 | 3 | 0.1707 | B1801, B4402, B4403 | 3 | 0.1707 |
| TAQNSVRVL (SEQ ID NO: 18) | B0704, C0102, C0303, C0304, C0602, C1203, C1601 | 7 | 0.5878 | B0704, B4201, C0102, C0303, C0304, C0602, C1203, C1601 | 8 | 0.5967 | B0704,B4201,C0102,C0303, C0304,C0602,C1203,C1601 | 8 | 0.5967 | B0704, B4201, C0102, C0303, C0304, C0602, C1203, C1601 | 8 | 0.5967 | B0704, B4201, C0102, C0303, C0304, C0602, C0704, C1203, C1601 | 9 | 0.6143 |

TABLE 9C-continued

| Estimated Population Coverage | | | | | | | | | | | | | | | |
|---|---|---|---|---|---|---|---|---|---|---|---|---|---|---|---|
| TTTIKPVTY (SEQ ID NO: 21) | A0101, A3601, B1502, B1517, C1601 | 5 | 0.1722 | A0101, A3601, B1502, B1517, B1801, C1601 | 6 | 0.2105 | A0101,A3601,B1502,B1517,B1801,C1601 | 6 | 0.2105 | A0101, A3002, A3601, B1502, B1517, B1801, B5701, C1203, C1601 | 9 | 0.2810 | A0101, A3002, A3601, B1502, B1517, B1801, B5701, C1203, C1601 | 9 | 0.2810 |
| VATSRTLSY (SEQ ID NO: 41) | A2902, A3601, B1517, B3507, B4601, C0202, C0302, C1202, C1203, C1601 | 10 | 0.3268 | A2902, A3601, B1517, B3507, B4601, C0202, C0302, C1202, C1203, C1601 | 10 | 0.3268 | A2902,A3601,B1517,B3507,B4601,C0202,C0302,C1202,C1203,C1601 | 10 | 0.3268 | A2902, A3601, B1517, B3507, B4601, C0202, C0302, C1202, C1203, C1601 | 10 | 0.3268 | A2902, A3601, B1517, B3507, B4601, C0202, C0302, C1202, C1203, C1601 | 10 | 0.3268 |
| VGYLQPRTF (SEQ ID NO: 39) | B1503 | 1 | 0.0235 | B1503, C1601 | 2 | 0.0702 | B1503,B5802,C1601 | 3 | 0.0859 | B1503, B5802, C1601 | 3 | 0.0859 | B1503, B5802, C1601 | 3 | 0.0859 |
| EILDITPCSF (SEQ ID NO: 33) | A2501, A2601 | 2 | 0.0747 | A2301, A2501, A2601 | 3 | 0.1190 | A2301,A2501,A2601,A6802 | 4 | 0.1437 | A2301, A2407, A2501, A2601, A3201, A6802 | 6 | 0.1784 | A2301, A2407, A2501, A2601, A3201, A6802, B1502, G0104 | 8 | 0.1999 |
| KNIDGYFKIY (SEQ ID NO: 36) | A3002, A3201, B1503, B1517, B5802, C0701, C1502 | 7 | 0.2756 | A3002, A3201, B1503, B1517, B5802, C0701, C1502 | 7 | 0.2756 | A3002,A3201,B1503,B1517,B5701,B5802,C0701,C1502 | 8 | 0.2906 | A2601, A3002, A3201, B1503, B1517, B1801, B5701, B5802, C0701, C1502 | 10 | 0.3699 | A2601, A3002, A3201, B1503, B1517, B1801, B5701, B5802, C0701, C1502, C1601 | 11 | 0.4034 |

TABLE 9C-continued

| | | Estimated Population Coverage | | | | | | | | | | | | | | |
|---|---|---|---|---|---|---|---|---|---|---|---|---|---|---|---|---|
| | EEF EPS TQ YE Y (SEQ ID NO: 20) | B1801, B4402, B4403 | 3 | 0.1707 | B1801, B4402, B4403 | 3 | 0.1707 | A3201,B 1801,B35 01,B4402 ,B4403 | 5 | 0.2881 | A3201, B1801, B3501, B4402, B4403 | 5 | 0.2881 | A2902, A3201, B1801, B3501, B4402, B4403 | 6 | 0.3114 |
| | EIL DIT PCS FG (SEQ ID NO: 47) | unknown | 0 | 0.0000 | unknown | 0 | 0.0000 | unknown | 0 | 0.0000 | unknown | 0 | 0.0000 | unknown | 0 | 0.0000 |
| HEK293 | AG TDT TIT V (SEQ ID NO: 26) | C0704 | 1 | 0.0291 | C0704 | 1 | 0.0291 | C0704 | 1 | 0.0291 | C0704 | 1 | 0.0291 | C0704 | 1 | 0.0291 |
| | APR ITF GGP (SEQ ID NO: 42) | unknown | 0 | 0.0000 | unknown | 0 | 0.0000 | unknown | 0 | 0.0000 | unknown | 0 | 0.0000 | unknown | 0 | 0.0000 |
| | ELP DEF VV V (SEQ ID NO: 12) | A0206, A0207, A6802 | 3 | 0.1336 | A0206, A0207, A6802 | 3 | 0.1336 | A0201,A 0206,A02 07,A6802 ,G0104 | 5 | 0.3948 | A0201, A0206, A0207, A6802, G0104 | 5 | 0.3948 | A0201, A0206, A0207, A6802, G0104 | 5 | 0.3948 |
| | FGD DT VIE V | A0201, A0206, A0207, C0304, | 9 | 0.7054 | A0201, A0206, A0207, C0304, | 9 | 0.7054 | A0201,A 0206,A02 07,C0303 ,C0304,C | 11 | 0.7772 | A0201, A0206, A0207, C0303, | 11 | 0.7772 | A0201, A0206, A0207, C0303, | 11 | 0.7772 |

TABLE 9C-continued

Estimated Population Coverage

| | | | | | | | | | | | | | | | |
|---|---|---|---|---|---|---|---|---|---|---|---|---|---|---|---|
| (SEQ ID NO: 23) | C0401, C0403, C0501, C0801, C0802 | | | C0401, C0403, C0501, C0801, C0802 | | | 0401,C04 03,C0501 ,C0801,C 0802,C15 02 | | | C0304, C0401, C0403, C0501, C0801, C0802, C1502 | | | C0304, C0401, C0403, C0501, C0801, C0802, C1502 | | |
| GLITLSYHL (SEQ ID NO: 5) | A0201, A0202 | 2 | 0.2959 | A0201, A0202 | 2 | 0.2959 | A0201,A 0202,A02 04 | 3 | 0.3008 | A0201, A0202, A0204 | 3 | 0.3008 | A0201, A0202, A0204, A0211 | 4 | 0.3061 |
| IRQEEVQEL (SEQ ID NO: 31) | C0602, C0701, C0702 | 3 | 0.4546 | C0602, C0701, C0702 | 3 | 0.4546 | C0602,C0 701,C070 2 | 3 | 0.4546 | C0602, C0701, C0702 | 3 | 0.4546 | B1402, B3801, C0602, C0701, C0702 | 5 | 0.4764 |
| KRVDWTIEY (SEQ ID NO: 29) | A3201, B1503, B2705, C0602, C0701, C0702 | 6 | 0.4955 | A3201, B1503, B2705, C0602, C0701, C0702 | 6 | 0.4955 | A3201,B 1503,B27 05,B4601 ,C0202,C 0602,C07 01,C0702 | 8 | 0.5553 | A3201, B1503, B2705, B4601, C0202, C0602, C0701, C0702 | 8 | 0.5553 | A3201, B1503, B2705, B4601, C0202, C0602, C0701, C0702 | 8 | 0.5553 |
| MLLGSMLYM (SEQ ID NO: 4) | unknown | 0 | 0.0000 | unknown | 0 | 0.0000 | unknown | 0 | 0.0000 | unknown | 0 | 0.0000 | unknown | 0 | 0.0000 |
| NLNESLIDL (SEQ ID NO: 40) | A0204 | 1 | 0.0059 | A0202, A0203, A0204 | 3 | 0.0515 | A0202,A 0203,A02 04 | 3 | 0.0515 | A0201, A0202, A0203, A0204 | 4 | 0.3258 | A0201, A0202, A0203, A0204, A0207 | 5 | 0.3603 |
| SLEDK | A0201, A0202, | 4 | 0.3359 | A0201, A0202, | 4 | 0.3359 | A0201,A 0202,A02 | 4 | 0.3359 | A0201, A0202, | 5 | 0.3696 | A0201, A0202, | 6 | 0.3696 |

TABLE 9C-continued

Estimated Population Coverage

| | | | | | | | | | | | | | | | |
|---|---|---|---|---|---|---|---|---|---|---|---|---|---|---|---|
| AFQL (SEQ ID NO: 7) | A0204, A0207 | | | A0204, A0207 | | | 04,A0207 | | | A0204, A0207, B1301 | | | A0204, A0207, B1301, G0103 | | |
| STSAFVETV (SEQ ID NO: 19) | A0202, A0203, A0205, A6802, C1502 | 5 | 0.1480 | A0202, A0203, A0205, A0206, A6802, C1502 | 6 | 0.2088 | A0202,A0203,A0205,A0206,A6802,C1502 | 6 | 0.2088 | A0202, A0203, A0205, A0206, A6802, C1203, C1502 | 7 | 0.2405 | A0202, A0203, A0205, A0206, A0211, A6802, C1203, C1502 | 8 | 0.2457 |
| SVVSKYVKV (SEQ ID NO: 30) | A0201, A0203, A0204, A0205, A0206, A0207, A0211, A2601, A6802, C0202, C1203, C1502 | 12 | 0.5688 | A0201, A0203, A0204, A0205, A0206, A0207, A0211, A2601, A6802, C0202, C1203, C1502 | 12 | 0.5688 | A0201,A0202,A0203,A0204,A0205,A0206,A0207,A0211,A2601,A6802,B1302,C0202,C1203,C1502,C1701 | 15 | 0.6069 | A0201, A0202, A0203, A0204, A0205, A0206, A0207, A0211, A2601, A6802, B1302, C0202, C0602, C1203, C1502, C1701 | 16 | 0.6589 | A0201, A0202, A0203, A0204, A0205, A0206, A0207, A0211, A2601, A6802, B1302, C0202, C0602, C1203, C1502, C1701 | 16 | 0.6589 |
| YLNSTNVTI (SEQ ID NO: 24) | A0201, A0202, A0203, A0204, A0207, B1302 | 6 | 0.3783 | A0201, A0202, A0203, A0204, A0207, B1302 | 6 | 0.3783 | A0201,A0202,A0203,A0204,A0207,B1302 | 6 | 0.3783 | A0201, A0202, A0203, A0204, A0207, B1302 | 6 | 0.3783 | A0201, A0202, A0203, A0204, A0207, B1302 | 6 | 0.3783 |
| APHGHVMVEL | B0702, B0704, B0801, B4201, | 8 | 0.3523 | B0702, B0704, B0801, B4201, | 8 | 0.3523 | B0702,B0704,B0801,B4201,B5601,C0 | 8 | 0.3523 | B0702, B0704, B0801, B4201, | 9 | 0.3671 | B0702, B0704, B0801, B4201, | 9 | 0.3671 |

TABLE 9C-continued

| Estimated Population Coverage | | | | | | | | | | | | | | | |
|---|---|---|---|---|---|---|---|---|---|---|---|---|---|---|---|
| (SEQ ID NO: 14) | B5601, C0704, C0801, C1701 | | | B5601, C0704, C0801, C1701 | | | 704,C080 1,C1701 | | | B5502, B5601, C0704, C0801, C1701 | | | B5502, B5601, C0704, C0801, C1701 | | |
| GP MV LRG LIT (SEQ ID NO: 6) | unknown | 0 | 0.0000 | unknown | 0 | 0.0000 | unknown | 0 | 0.0000 | unknown | 0 | 0.0000 | unknown | 0 | 0.0000 |
| KAF QLT PIA V (SEQ ID NO: 13) | A0201, A0211, A6802, B5101, B5201, B5401, B5502, C1203, C1701, G0104 | 10 | 0.4824 | A0201, A0211, A6802, B5101, B5201, B5401, B5502, C1203, C1701, G0104 | 10 | 0.4824 | A0201,A 0203,A02 11,A6802 ,B5101,B 5201,B54 01,B5502 ,B5601,C 1203,C17 01,G0104 | 12 | 0.5166 | A0201, A0203, A0211, A6802, B5101, B5201, B5401, B5502, B5601, C1203, C1701, G0101, G0104 | 13 | 0.5166 | A0201, A0203, A0204, A0206, A0211, A6802, B1302, B4006, B5101, B5201, B5401, B5502, B5601, C1203, C1701, G0101, G0104 | 17 | 0.5915 |
| ELP DEF VV VT V (SEQ ID NO: 8) | A0201, A0207, A6802, B5101, B5201, C0102 | 6 | 0.5273 | A0201, A0203, A0207, A6802, B5101, B5201, C0102 | 7 | 0.5447 | A0201,A 0203,A02 06,A0207 ,A6802,B 5101,B52 01,C0102 ,C0403 | 9 | 0.6009 | A0201, A0203, A0205, A0206, A0207, A6802, B5101, B5201, C0102, C0403 | 10 | 0.6097 | A0201, A0203, A0205, A0206, A0207, A6802, B5101, B5201, C0102, C0403 | 10 | 0.6097 |
| YLF DES GEF KL (SEQ ID NO: 25) | A0201, A0202, A0203, A0204, A0205, A0206, A0207, A0211, A2902, A3201, B1301, | 22 | 0.7506 | A0201, A0202, A0203, A0204, A0205, A0206, A0207, A0211, A2902, A3201, B1301, | 26 | 0.8326 | A0201,A 0202,A02 03,A0204 ,A0205,A 0206,A02 07,A0211 ,A2902,A 3201,B13 01,B1302 ,B1517,B 3501,B35 | 28 | 0.8646 | A0201, A0202, A0203, A0204, A0205, A0206, A0207, A0211, A2902, A3201, B1301, | 29 | 0.8953 | A0201, A0202, A0203, A0204, A0205, A0206, A0207, A0211, A2902, A3201, B1301, | 31 | 0.9189 |

TABLE 9C-continued

| Estimated Population Coverage | | | | | | | | | | | | | | | |
|---|---|---|---|---|---|---|---|---|---|---|---|---|---|---|---|
| | B1302, B3501, B3503, C0102, C0304, C0403, C0704, C1701, G0101, G0103, G0104 | | | B1302, B3501, B3503, C0102, C0302, C0303, C0304, C0403, C0704, C1402, C1502, C1701, G0101, G0103, G0104 | | | 03,C0102,C0302,C0303,C0304,C0403,C0602,C0704,C1402,C1502,C1701,G0101,G0103,G0104 | | | B1302, B1517, B3501, B3503, C0102, C0302, C0303, C0304, C0403, C0602, C0701, C0704, C1402, C1502, C1701, G0101, G0103, G0104 | | | B1302, B1517, B3501, B3503, C0102, C0302, C0303, C0304, C0403, C0602, C0701, C0704, C0801, C1402, C1403, C1502, C1701, G0101, G0103, G0104 | | |
| Peps Comb-ined | B1801, B3701, B4002, B4006, B4403, B4501, B4901, B5001, B5101, A0202, B1801, B3801, B4001, B4402, B4403, C0802, A0101, A2501, A2601, A2902, A3002, A3601, A2501, A2601, B1502, C1202, B5101, C0202, C0302, C0303, C0304, | 70 | 0.9998 | B1402, B1801, B3701, B4002, B4006, B4403, B4501, B4901, B5001, B5101, A0202, A3601, B1510, B1801, B3503, B3801, B4001, B4002, B4402, B4403, C0802, A0101, A2501, A2601, A2902, A3002, A3601, B1502, A2501, A2601, B1502, | 75 | 0.9999 | B1402,B1801,B3701,B4002,B4006,B4402,B4403,B4501,B4901,B5001,B5101,A0202,A3601,B1510,B1801,B3503,B3801,B4001,B4002,B4402,B4403,B4501,B5703,C0802,A0101,A2501,A2601,A2902,A3002,A3601,B1502,B3501,A2501,A2601,B1502,C1202,B5101,C0202,C0302,C0303,C0304,C | 77 | 0.9999 | A6802, B1402, B1801, B3701, B4002, B4006, B4402, B4403, B4501, B4901, B5001, B5101, A0101, A0202, A3601, B1510, B1801, B3503, B3801, B4001, B4002, B4402, B4403, B4501, B5703, C0802, A0101, A2501, A2601, A2902, A3002, | 78 | 0.9999 | A6802, B1402, B1801, B3701, B4002, B4006, B4402, B4403, B4501, B4901, B5001, B5101, B5201, A0101, A0202, A3601, B1510, B1801, B3503, B3801, B4001, B4002, B4402, B4403, B4501, B5703, C0704, C0802, A0101, A2501, A2601, | 79 | 1.0000 |

TABLE 9C-continued

| Estimated Population Coverage | | | | |
|---|---|---|---|---|
| C0602, | C1202, | 0602,C08 | A3601, | A2902, |
| C0801, | B5101, | 01,C0802 | B1501, | A3002, |
| C0802, | C0202, | ,C1202,C | B1502, | A3601, |
| C1202, | C0302, | 1203,C16 | B3501, | B1501, |
| C1203, | C0303, | 01,A2902 | A2501, | B1502, |
| C1601, | C0304, | ,B1501,B | A2601, | B3501, |
| B1501, | C0602, | 1502,B15 | B1501, | A2501, |
| B1502, | C0801, | 03,B3501 | B1502, | A2601, |
| B3501, | C0802, | ,B3507,B | C1202, | B1501, |
| B3507, | C1202, | 4601,B53 | B5101, | B1502, |
| B4601, | C1203, | 01,C0202 | C0202, | C1202, |
| C0202, | C1601, | ,C0302,C | C0302, | B5101, |
| C0302, | B1501, | 0303,C03 | C0303, | C0202, |
| C0303, | B1502, | 04,C0702 | C0304, | C0302, |
| C0304, | B1503, | ,C1202,C | C0602, | C0303, |
| C1202, | B3501, | 1203,C16 | C0801, | C0304, |
| C1203, | B3507, | 01,B3501 | C0802, | C0501, |
| C1601, | B4601, | ,B3503,B | C1202, | C0602, |
| B3503, | B5301, | 3507,C03 | C1203, | C0801, |
| B3507, | C0202, | 02,C0303 | C1502, | C0802, |
| C0302, | C0302, | ,C0304,C | C1601, | C1202, |
| C0303, | C0303, | 0403,C07 | A2902, | C1203, |
| C0304, | C0304, | 04,C1202 | B1501, | C1502, |
| C0403, | C0702, | ,C1203,C | B1502, | C1601, |
| C0704, | C1202, | 1601,C17 | B1503, | A2902, |
| C1203, | C1203, | 01,A0206 | B3501, | B1501, |
| C1601, | C1601, | ,A6802,B | B3507, | B1502, |
| C1701, | B3501, | 5101,C06 | B4601, | B1503, |
| A0206, | B3503, | 02,C1203 | B5301, | B3501, |
| A6802, | B3507, | ,C1601,C | C0202, | B3507, |
| B5101, | C0302, | 1701,A30 | C0302, | B4601, |
| C0602, | C0303, | 02,B1502 | C0303, | B5301, |
| C1203, | C0304, | ,C1601,B | C0304, | C0202, |
| C1701, | C0403, | 1801,B44 | C0702, | C0302, |
| A3002, | C0704, | 02,B4403 | C1202, | C0303, |
| B1801, | C1203, | ,B0704,B | C1203, | C0304, |
| B4402, | C1601, | 4201,C01 | C1601, | C0702, |
| B4403, | C1701, | 02,C0303 | B3501, | C1202, |
| B0704, | A0206, | ,C0304,C | B3503, | C1203, |
| C0102, | A6802, | 0602,C12 | B3507, | C1402, |
| C0303, | B5101, | 03,C1601 | C0302, | C1601, |
| C0304, | C0602, | ,A0101,A | C0303, | B3501, |
| C0602, | C1203, | 3601,B15 | C0304, | B3503, |
| C1203, | C1701, | 02,B1517 | C0403, | B3507, |
| C1601, | A3002, | ,B1801,C | C0704, | C0302, |
| A0101, | B1801, | 1601,A29 | C1202, | C0303, |
| A3601, | B4402, | 02,A3601 | C1203, | C0304, |
| B1502, | B4403, | ,B1517,B | C1601, | C0403, |
| B1517, | B0704, | 3507,B46 | C1701, | C0704, |
| C1601, | B4201, | 01,C0202 | A0206, | C1202, |
| A2902, | C0102, | ,C0302,C | A6802, | C1203, |

TABLE 9C-continued

| Estimated Population Coverage | | | | |
|---|---|---|---|---|
| A3601, | C0303, | 1202,C12 | B1302, | C1601, |
| B1517, | C0304, | 03,C1601 | B5101, | C1701, |
| B3507, | C0602, | ,B1503,B | C0202, | A0206, |
| B4601, | C1203, | 5802,C16 | C0602, | A6802, |
| C0202, | C1601, | 01,A2301 | C0801, | B1302, |
| C0302, | A0101, | ,A2501,A | C1203, | B5101, |
| C1202, | A3601, | 2601,A68 | C1601, | B5301, |
| C1203, | B1502, | 02,A3002 | C1701, | C0202, |
| C1601, | B1517, | ,A3201,B | A3002, | C0602, |
| B1503, | B1801, | 1503,B15 | B1502, | C0704, |
| A2501, | C1601, | 17,B5701 | C1601, | C0801, |
| A2601, | A2902, | ,B5802,C | B1801, | C1203, |
| A3002, | A3601, | 0701,C15 | B4402, | C1502, |
| A3201, | B1517, | 02,A3201 | B4403, | C1601, |
| B1503, | B3507, | ,B1801,B | B0704, | C1701, |
| B1517, | B4601, | 3501,B44 | B4201, | A3002, |
| B5802, | C0202, | 02,B4403 | C0102, | B1502, |
| C0701, | C0302, | ,unknown | C0303, | C1601, |
| C1502, | C1202, | ,C0704,u | C0304, | B1801, |
| B1801, | C1203, | nknown, | C0602, | B4402, |
| B4402, | C1601, | A0201,A | C1203, | B4403, |
| B4403, | B1503, | 0206,A02 | C1601, | B0704, |
| unkno | C1601, | 07,A6802 | A0101, | B4201, |
| wn,C0 | A2301, | ,G0104,A | A3002, | C0102, |
| 704,un | A2501, | 0201,A02 | A3601, | C0303, |
| known, | A2601, | 06,A0207 | B1502, | C0304, |
| A0206, | A3002, | ,C0303,C | B1517, | C0602, |
| A0207, | A3201, | 0304,C04 | B1801, | C0704, |
| A6802, | B1503, | 01,C0403 | B5701, | C1203, |
| A0201, | B1517, | ,C0501,C | C1203, | C1601, |
| A0206, | B5802, | 0801,C08 | C1601, | A0101, |
| A0207, | C0701, | 02,C1502 | A2902, | A3002, |
| C0304, | C1502, | ,A0201,A | A3601, | A3601, |
| C0401, | B1801, | 0202,A02 | B1517, | B1502, |
| C0403, | B4402, | 04,C0602 | B3507, | B1517, |
| C0501, | B4403, | ,C0701,C | B4601, | B1801, |
| C0801, | unkno | 0702,A32 | C0202, | B5701, |
| C0802, | wn,C07 | 01,B1503 | C0302, | C1203, |
| A0201, | 04,unk | ,B2705,B | C1202, | C1601, |
| A0202, | flown, | 4601,C02 | C1203, | A2902, |
| C0602, | A0206, | 02,C0602 | C1601, | A3601, |
| C0701, | A0207, | ,C0701,C | B1503, | B1517, |
| C0702, | A6802, | 0702,unk | B5802, | B3507, |
| A3201, | A0201, | nown,A0 | C1601, | B4601, |
| B1503, | A0206, | 202,A020 | A2301, | C0202, |
| B2705, | A0207, | 3,A0204, | A2407, | C0302, |
| C0602, | C0304, | A0201,A | A2501, | C1202, |
| C0701, | C0401, | 0202,A02 | A2601, | C1203, |
| C0702, | C0403, | 04,A0207 | A3201, | C1601, |
| unkno | C0501, | ,A0202,A | A6802, | B1503, |
| wn,A0 | C0801, | 0203,A02 | A2601, | B5802, |

TABLE 9C-continued

| Estimated Population Coverage | | | | |
|---|---|---|---|---|
| 204,A0 | C0802, | 05,A0206 | A3002, | C1601, |
| 201,A0 | A0201, | ,A6802,C | A3201, | A2301, |
| 202,A0 | A0202, | 1502,A02 | B1503, | A2407, |
| 204,A0 | C0602, | 01,A0202 | B1517, | A2501, |
| 207,A0 | C0701, | ,A0203,A | B1801, | A2601, |
| 202,A0 | C0702, | 0204,A02 | B5701, | A3201, |
| 203,A0 | A3201, | 05,A0206 | B5802, | A6802, |
| 205,A6 | B1503, | ,A0207,A | C0701, | B1502, |
| 802,C1 | B2705, | 0211,A26 | C1502, | G0104, |
| 502,A0 | C0602, | 01,A6802 | A3201, | A2601, |
| 201,A0 | C0701, | ,B1302,C | B1801, | A3002, |
| 203,A0 | C0702, | 0202,C12 | B3501, | A3201, |
| 204,A0 | unkno | 03,C1502 | B4402, | B1503, |
| 205,A0 | wn,A0 | ,C1701,A | B4403, | B1517, |
| 206,A0 | 202,A0 | 0201,A02 | unknow | B1801, |
| 207,A0 | 203,A0 | 02,A0203 | n,C070 | B5701, |
| 211,A2 | 204,A0 | ,A0204,A | 4,unkno | B5802, |
| 601,A6 | 201,A0 | 0207,B13 | wn,A02 | C0701, |
| 802,C0 | 202,A0 | 02,B0702 | 01,A02 | C1502, |
| 202,C1 | 204,A0 | ,B0704,B | 06,A02 | C1601, |
| 203,C1 | 207,A0 | 0801,B42 | 07,A68 | A2902, |
| 502,A0 | 202,A0 | 01,B5601 | 02,G01 | A3201, |
| 201,A0 | 203,A0 | ,C0704,C | 04,A02 | B1801, |
| 202,A0 | 205,A0 | 0801,C17 | 01,A02 | B3501, |
| 203,A0 | 206,A6 | 01,unkno | 06,A02 | B4402, |
| 204,A0 | 802,C1 | wn,A020 | 07,C03 | B4403, |
| 207,B1 | 502,A0 | 1,A0203, | 03,C03 | unkno |
| 302,B0 | 201,A0 | A0211,A | 04,C04 | wn,C07 |
| 702,B0 | 203,A0 | 6802,B51 | 01,C04 | 04,unk |
| 704,B0 | 204,A0 | 01,B5201 | 03,C05 | nown, |
| 801,B4 | 205,A0 | ,B5401,B | 01,C08 | A0201, |
| 201,B5 | 206,A0 | 5502,B56 | 01,C08 | A0206, |
| 601,C0 | 207,A0 | 01,C1203 | 02,C15 | A0207, |
| 704,C0 | 211,A2 | ,C1701,G | 02,A02 | A6802, |
| 801,C1 | 601,A6 | 0104,A02 | 01,A02 | G0104, |
| 701,un | 802,C0 | 01,A0203 | 02,A02 | A0201, |
| known, | 202,C1 | ,A0206,A | 04,C06 | A0206, |
| A0201, | 203,C1 | 0207,A68 | 02,C07 | A0207, |
| A0211, | 502,A0 | 02,B5101 | 01,C07 | C0303, |
| A6802, | 201,A0 | ,B5201,C | 02,A32 | C0304, |
| B5101, | 202,A0 | 0102,C04 | 01,B15 | C0401, |
| B5201, | 203,A0 | 03,A0201 | 03,B27 | C0403, |
| B5401, | 204,A0 | ,A0202,A | 05,B46 | C0501, |
| B5502, | 207,B1 | 0203,A02 | 01,C02 | C0801, |
| C1203, | 302,B0 | 04,A0205 | 02,C06 | C0802, |
| C1701, | 702,B0 | ,A0206,A | 02,C07 | C1502, |
| G0104, | 704,B0 | 0207,A02 | 01,C07 | A0201, |
| A0201, | 801,B4 | 11,A2902 | 02,unkn | A0202, |
| A0207, | 201,B5 | ,A3201,B | own,A0 | A0204, |
| A6802, | 601,C0 | 1301,B13 | 201,A0 | A0211, |
| B5101, | 704,C0 | 02,B1517 | 202,A0 | B1402, |

TABLE 9C-continued

| Estimated Population Coverage | | | | |
|---|---|---|---|---|
| B5201, | 801,C1 | ,B3501,B | 203,A0 | B3801, |
| C0102, | 701,un | 3503,C01 | 204,A0 | C0602, |
| A0201, | known, | 02,C0302 | 201,A0 | C0701, |
| A0202, | A0201, | ,C0303,C | 202,A0 | C0702, |
| A0203, | A0211, | 0304,C04 | 204,A0 | A3201, |
| A0204, | A6802, | 03,C0602 | 207,B1 | B1503, |
| A0205, | B5101, | ,C0704,C | 301,A0 | B2705, |
| A0206, | B5201, | 1402,C15 | 202,A0 | B4601, |
| A0207, | B5401, | 02,C1701 | 203,A0 | C0202, |
| A0211, | B5502, | ,G0101,G | 205,A0 | C0602, |
| A2902, | C1203, | 0103,G01 | 206,A6 | C0701, |
| A3201, | C1701, | 04 | 802,C1 | C0702, |
| B1301, | G0104, | | 203,C1 | unkno |
| B1302, | A0201, | | 502,A0 | wn,A0 |
| B3501, | A0203, | | 201,A0 | 201,A0 |
| B3503, | A0207, | | 202,A0 | 202,A0 |
| C0102, | A6802, | | 203,A0 | 203,A0 |
| C0304, | B5101, | | 204,A0 | 204,A0 |
| C0403, | B5201, | | 205,A0 | 207,A0 |
| C0704, | C0102, | | 206,A0 | 201,A0 |
| C1701, | A0201, | | 207,A0 | 202,A0 |
| G0101, | A0202, | | 211,A2 | 204,A0 |
| G0103, | A0203, | | 601,A6 | 207,B1 |
| G0104 | A0204, | | 802,B1 | 301,G0 |
| | A0205, | | 302,C0 | 103,A0 |
| | A0206, | | 202,C0 | 202,A0 |
| | A0207, | | 602,C1 | 203,A0 |
| | A0211, | | 203,C1 | 205,A0 |
| | A2902, | | 502,C1 | 206,A0 |
| | A3201, | | 701,A0 | 211,A6 |
| | B1301, | | 201,A0 | 802,C1 |
| | B1302, | | 202,A0 | 203,C1 |
| | B3501, | | 203,A0 | 502,A0 |
| | B3503, | | 204,A0 | 201,A0 |
| | C0102, | | 207,B1 | 202,A0 |
| | C0302, | | 302,B0 | 203,A0 |
| | C0303, | | 702,B0 | 204,A0 |
| | C0304, | | 704,B0 | 205,A0 |
| | C0403, | | 801,B4 | 206,A0 |
| | C0704, | | 201,B5 | 207,A0 |
| | C1402, | | 502,B5 | 211,A2 |
| | C1502, | | 601,C0 | 601,A6 |
| | C1701, | | 704,C0 | 802,B1 |
| | G0101, | | 801,C1 | 302,C0 |
| | G0103, | | 701,unk | 202,C0 |
| | G0104 | | nown,A | 602,C1 |
| | | | 0201,A | 203,C1 |
| | | | 0203,A | 502,C1 |
| | | | 0211,A | 701,A0 |
| | | | 6802,B | 201,A0 |
| | | | 5101,B | 202,A0 |

TABLE 9C-continued

| Estimated Population Coverage | | |
|---|---|---|
| | 5201,B | 203,A0 |
| | 5401,B | 204,A0 |
| | 5502,B | 207,B1 |
| | 5601,C | 302,B0 |
| | 1203,C | 702,B0 |
| | 1701,G | 704,B0 |
| | 0101,G | 801,B4 |
| | 0104,A | 201,B5 |
| | 0201,A | 502,B5 |
| | 0203,A | 601,C0 |
| | 0205,A | 704,C0 |
| | 0206,A | 801,C1 |
| | 0207,A | 701.un |
| | 6802,B | known, |
| | 5101,B | A0201, |
| | 5201,C | A0203, |
| | 0102,C | A0204, |
| | 0403,A | A0206, |
| | 0201,A | A0211, |
| | 0202,A | A6802, |
| | 0203,A | B1302, |
| | 0204,A | B4006, |
| | 0205,A | B5101, |
| | 0206,A | B5201, |
| | 0207,A | B5401, |
| | 0211,A | B5502, |
| | 2902,A | B5601, |
| | 3201,B | C1203, |
| | 1301,B | C1701, |
| | 1302,B | G0101, |
| | 1517,B | G0104, |
| | 3501,B | A0201, |
| | 3503,C | A0203, |
| | 0102,C | A0205, |
| | 0302,C | A0206, |
| | 0303,C | A0207, |
| | 0304,C | A6802, |
| | 0403,C | B5101, |
| | 0602,C | B5201, |
| | 0701,C | C0102, |
| | 0704,C | C0403, |
| | 1402,C | A0201, |
| | 1502,C | A0202, |
| | 1701,G | A0203, |
| | 0101,G | A0204, |
| | 0103,G | A0205, |
| | 0104 | A0206, |
| | | A0207, |
| | | A0211, |
| | | A2902, |
| | | A3201, |

TABLE 9C-continued

Estimated Population Coverage

| | Peptide | thr0.6_assign_alleles | thr0.6_num_alleles | thr0.6_coverage | thr0.7_assign_alleles | thr0.7_num_alleles | thr0.7_coverage | thr0.8_assign_alleles | thr0.8_num_alleles | thr0.8_coverage | thr0.9_assign_alleles | thr0.9_num_alleles | thr0.9_coverage | thr1_assign_alleles | thr1_num_alleles | thr1_coverage |
|---|---|---|---|---|---|---|---|---|---|---|---|---|---|---|---|---|
| | | | | | | | | | | | | | | B1301, B1302, B1517, B3501, B3503, C0102, C0302, C0303, C0304, C0403, C0602, C0701, C0704, C0801, C1402, C1403, C1502, C1701, G0101, G0103, G0104 | | |
| A549 | DEFVVVTV (SEQ ID NO: 11) | B1801, B3701, B4002, B4006, B4403, B4501, B4901, B5001, B5101 | 9 | 0.4113 | B1402, B1801, B3701, B4002, B4006, B4403, B4501, B4901, B5001, B5101 | 10 | 0.4301 | B1402,B1801,B3701,B4002,B4006,B4402,B4403,B4501,B4901,B5001,B5101 | 11 | 0.4623 | A6802, B1402, B1801, B3701, B4002, B4006, B4402, B4403, B4501, B4901, B5001, B5101 | 12 | 0.4764 | A6802, B1402, B1801, B3701, B4002, B4006, B4402, B4403, B4501, B4901, B5001, B5101, B5201 | 13 | 0.5092 |
| | LEDKAFQL (SEQ ID NO: 10) | A0202, B1801, B3801, B4001, B4402, B4403, C0802 | 7 | 0.3149 | A0202, A3601, B1510, B1801, B3503, B3801, B4001, B4002, B4402, B4403, C0802 | 11 | 0.4085 | A0202,A3601,B1510,B1801,B3503,B3801,B4001,B4002,B4402,B4403,B4501,B5703,C0802 | 13 | 0.4301 | A0101, A0202, A3601, B1510, B1801, B3503, B3801, B4001, B4002, B4402, B4403, B4501, | 14 | 0.4846 | A0101, A0202, A3601, B1510, B1801, B3503, B3801, B4001, B4002, B4402, B4403, B4501, | 15 | 0.4999 |

TABLE 9C-continued

Estimated Population Coverage

| | | | | | | | | | | | | | | | |
|---|---|---|---|---|---|---|---|---|---|---|---|---|---|---|---|
| | | | | | | | | | | B5703, C0802 | | | B5703, C0704, C0802 | | |
| TVIEVQGY (SEQ ID NO: 22) | A0101, A2501, A2601, A2902, A3002, A3601 | 6 | 0.2283 | A0101, A2501, A2601, A2902, A3002, A3601, B1502 | 7 | 0.2485 | A0101,A2501,A2601,A2902,A3002,A3601,B1502,B3501 | 8 | 0.3295 | A0101, A2501, A2601, A2902, A3002, A3601, B1501, B1502, B3501 | 9 | 0.3779 | A0101, A2501, A2601, A2902, A3002, A3601, B1501, B1502, B3501 | 9 | 0.3779 |
| EIKESVQTF (SEQ ID NO: 15) | A2501, A2601, B1502, C1202 | 4 | 0.1555 | A2501, A2601, B1502, C1202 | 4 | 0.1555 | A2501,A2601,B1502,C1202 | 4 | 0.1555 | A2501, A2601, B1501, B1502, C1202 | 5 | 0.2132 | A2501, A2601, B1501, B1502, C1202 | 5 | 0.2132 |
| FASEAARVV (SEQ ID NO: 17) | B5101, C0202, C0302, C0303, C0304, C0602, C0801, C0802, C1202, C1203, C1601 | 11 | 0.6793 | B5101, C0202, C0302, C0303, C0304, C0602, C0801, C0802, C1202, C1203, C1601 | 11 | 0.6793 | B5101,C0202,C0302,C0303,C0304,C0602,C0801,C0802,C1202,C1203,C1601 | 11 | 0.6793 | B5101, C0202, C0302, C0303, C0304, C0602, C0801, C0802, C1202, C1203, C1502, C1601 | 12 | 0.7143 | B5101, C0202, C0302, C0303, C0304, C0501, C0602, C0801, C0802, C1202, C1203, C1502, C1601 | 13 | 0.7402 |
| FAVDAAKAY (SEQ ID NO: 28) | B1501, B1502, B3501, B3507, B4601, C0202, C0302, C0303, C0304, C1202, C1203, C1601 | 12 | 0.6105 | B1501, B1502, B1503, B3501, B3507, B4601, B5301, C0202, C0302, C0303, C0304, C0702, C1202, C1203, C1601 | 15 | 0.7553 | A2902,B1501,B1502,B1503,B3501,B3507,B4601,B5301,C0202,C0302,C0303,C0304,C0702,C1202,C1203,C1601 | 16 | 0.7632 | A2902, B1501, B1502, B1503, B3501, B3507, B4601, B5301, C0202, C0302, C0303, C0304, C0702, C1202, C1203, C1601 | 16 | 0.7632 | A2902, B1501, B1502, B1503, B3501, B3507, B4601, B5301, C0202, C0302, C0303, C0304, C0702, C1202, C1203, C1402, C1601 | 17 | 0.7831 |
| LATNN | B3503, B3507, | 10 | 0.4882 | B3501, B3503, | 11 | 0.5438 | B3501,B3503,B350 | 12 | 0.5827 | B3501, B3503, | 12 | 0.5827 | B3501, B3503, | 12 | 0.5827 |

TABLE 9C-continued

| Estimated Population Coverage | | | | | | | | | | | | | | | |
|---|---|---|---|---|---|---|---|---|---|---|---|---|---|---|---|
| LVVM (SEQ ID NO: 16) | C0302, C0303, C0304, C0403, C0704, C1203, C1601, C1701 | | | B3507, C0302, C0303, C0304, C0403, C0704, C1203, C1601, C1701 | | | 7,C0302,C0303,C0304,C0403,C0704,C1202,C1203,C1601,C1701 | | | B3507, C0302, C0303, C0304, C0403, C0704, C1202, C1203, C1601, C1701 | | | B3507, C0302, C0303, C0304, C0403, C0704, C1202, C1203, C1601, C1701 | | |
| NATNVVIKV (SEQ ID NO: 37) | A0206, A6802, B5101, C0602, C1203, C1701 | 6 | 0.3404 | A0206, A6802, B5101, C0602, C1203, C1701 | 6 | 0.3404 | A0206,A6802,B5101,C0602,C1203,C1601,C1701 | 7 | 0.3754 | A0206, A6802, B1302, B5101, C0202, C0602, C0801, C1203, C1601, C1701 | 10 | 0.4911 | A0206, A6802, B1302, B5101, B5301, C0202, C0602, C0704, C0801, C1203, C1502, C1601, C1701 | 13 | 0.5660 |
| QLTPTWRVY (SEQ ID NO: 38) | A3002 | 1 | 0.0296 | A3002 | 1 | 0.0296 | A3002,B1502,C1601 | 3 | 0.1002 | A3002, B1502, C1601 | 3 | 0.1002 | A3002, B1502, C1601 | 3 | 0.1002 |
| SEFSSLPSY (SEQ ID NO: 27) | B1801, B4402, B4403 | 3 | 0.1707 | B1801, B4402, B4403 | 3 | 0.1707 | B1801,B4402,B4403 | 3 | 0.1707 | B1801, B4402, B4403 | 3 | 0.1707 | B1801, B4402, B4403 | 3 | 0.1707 |
| TAQNSVRVL (SEQ ID NO: 18) | B0704, C0102, C0303, C0304, C0602, C1203, C1601 | 7 | 0.5878 | B0704, B4201, C0102, C0303, C0304, C0602, C1203, C1601 | 8 | 0.5967 | B0704,B4201,C0102,C0303,C0304,C0602,C1203,C1601 | 8 | 0.5967 | B0704, B4201, C0102, C0303, C0304, C0602, C1203, C1601 | 8 | 0.5967 | B0704, B4201, C0102, C0303, C0304, C0602, C0704, C1203, C1601 | 9 | 0.6143 |
| TTTIKPVTY | A0101, A3601, B1502, B1517, | 5 | 0.1722 | A0101, A3601, B1502, B1517, | 6 | 0.2105 | A0101,A3601,B1502,B1517,B1801,C | 6 | 0.2105 | A0101, A3002, A3601, B1502, | 9 | 0.2810 | A0101, A3002, A3601, B1502, | 9 | 0.2810 |

TABLE 9C-continued

| Estimated Population Coverage | | | | | | | | | | | | | | | |
|---|---|---|---|---|---|---|---|---|---|---|---|---|---|---|---|
| (SEQ ID NO: 21) | C1601 | | | B1801, C1601 | | | 1601 | | | B1517, B1801, B5701, C1203, C1601 | | | B1517, B1801, B5701, C1203, C1601 | | |
| VATSRTLSY (SEQ ID NO: 41) | A2902, A3601, B1517, B3507, B4601, C0202, C0302, C1202, C1203, C1601 | 10 | 0.3268 | A2902, A3601, B1517, B3507, B4601, C0202, C0302, C1202, C1203, C1601 | 10 | 0.3268 | A2902,A3601,B1517,B3507,B4601,C0202,C0302,C1202,C1203,C1601 | 10 | 0.3268 | A2902, A3601, B1517, B3507, B4601, C0202, C0302, C1202, C1203, C1601 | 10 | 0.3268 | A2902, A3601, B1517, B3507, B4601, C0202, C0302, C1202, C1203, C1601 | 10 | 0.3268 |
| VGYLQPRTF (SEQ ID NO: 39) | B1503 | 1 | 0.0235 | B1503, C1601 | 2 | 0.0702 | B1503,B5802,C1601 | 3 | 0.859 | B1503, B5802, C1601 | 3 | 0.0859 | B1503, B5802, C1601 | 3 | 0.0859 |
| EILDITPCSF (SEQ ID NO: 33) | A2501, A2601 | 2 | 0.0747 | A2301, A2501, A2601 | 3 | 0.1190 | A2301,A2501,A2601,A6802 | 4 | 0.1437 | A2301, A2407, A2501, A2601, A3201, A6802 | 6 | 0.1784 | A2301, A2407, A2501, A2601, A3201, A6802, B1502, G0104 | 8 | 0.1999 |
| KNIDGYFKIY (SEQ ID NO: 36) | A3002, A3201, B1503, B1517, B5802, C0701, C1502 | 7 | 0.2756 | A3002, A3201, B1503, B1517, B5802, C0701, C1502 | 7 | 0.2756 | A3002,A3201,B1503,B1517,B5701,B5802,C0701,C1502 | 8 | 0.2906 | A2601, A3002, A3201, B1503, B1517, B1801, B5701, B5802, C0701, C1502 | 10 | 0.3699 | A2601, A3002, A3201, B1503, B1517, B1801, B5701, B5802, C0701, C1502, C1601 | 11 | 0.4034 |

TABLE 9C-continued

| | | Estimated Population Coverage | | | | | | | | | | | | | |
|---|---|---|---|---|---|---|---|---|---|---|---|---|---|---|---|
| | EEFEPSTQYEY (SEQ ID NO: 20) | B1801, B4402, B4403 | 3 | 0.1707 | B1801, B4402, B4403 | 3 | 0.1707 | A3201,B1801,B3501,B4402,B4403 | 5 | 0.2881 | A3201, B1801, B3501, B4402, B4403 | 5 | 0.2881 | A2902, A3201, B1801, B3501, B4402, B4403 | 6 | 0.3114 |
| | EILDITPCSFG (SEQ ID NO: 47) | unknown | 0 | 0.0000 | unknown | 0 | 0.0000 | unknownn | 0 | 0.0000 | unknown | 0 | 0.0000 | unknown | 0 | 0.0000 |
| HEK293 | AGTDTTITV (SEQ ID NO: 26) | C0704 | 1 | 0.0291 | C0704 | 1 | 0.0291 | C0704 | 1 | 0.0291 | C0704 | 1 | 0.0291 | C0704 | 1 | 0.0291 |
| | APRITFGGP (SEQ ID NO: 42) | unknown | 0 | 0.0000 | unknown | 0 | 0.0000 | unknown | 0 | 0.0000 | unknown | 0 | 0.0000 | unknown | 0 | 0.0000 |
| | ELPDEFVVV (SEQ ID NO: 12) | A0206, A0207, A6802 | 3 | 0.1336 | A0206, A0207, A6802 | 3 | 0.1336 | A0201,A0206,A0207,A6802,G0104 | 5 | 0.3948 | A0201, A0206, A0207, A6802, G0104 | 5 | 0.3948 | A0201, A0206, A0207, A6802, G0104 | 5 | 0.3948 |
| | FGDDTVIEV | A0201, A0206, A0207, C0304, | 9 | 0.7054 | A0201, A0206, A0207, C0304, | 9 | 0.7054 | A0201,A0206,A0207,C0303,C0304,C | 11 | 0.7772 | A0201, A0206, A0207, C0303, | 11 | 0.7772 | A0201, A0206, A0207, C0303, | 11 | 0.7772 |

TABLE 9C-continued

| | Estimated Population Coverage | | | | | | | | | | | | | | |
|---|---|---|---|---|---|---|---|---|---|---|---|---|---|---|---|
| (SEQ ID NO: 23) | C0401, C0403, C0501, C0801, C0802 | | | C0401, C0403, C0501, C0801, C0802 | | | 0401,C0403,C0501,C0801,C0802,C1502 | | | C0304, C0401, C0403, C0501, C0801, C0802, C1502 | | | C0304, C0401, C0403, C0501, C0801, C0802, C1502 | | |
| GLITLSYHL (SEQ ID NO: 5) | A0201, A0202 | 2 | 0.2959 | A0201, A0202 | 2 | 0.2959 | A0201,A0202,A0204 | 3 | 0.3008 | A0201, A0202, A0204 | 3 | 0.3008 | A0201, A0202, A0204, A0211 | 4 | 0.3061 |
| IRQEEVQEL (SEQ ID NO: 31) | C0602, C0701, C0702 | 3 | 0.4546 | C0602, C0701, C0702 | 3 | 0.4546 | C0602,C0701,C0702 | 3 | 0.4546 | C0602, C0701, C0702 | 3 | 0.4546 | B1402, B3801, C0602, C0701, C0702 | 5 | 0.4764 |
| KRVDWTIEY (SEQ ID NO: 29) | A3201, B1503, B2705, C0602, C0701, C0702 | 6 | 0.4955 | A3201, B1503, B2705, C0602, C0701, C0702 | 6 | 0.4955 | A3201,B1503,B2705,B4601,C0202,C0602,C0701,C0702 | 8 | 0.5553 | A3201, B1503, B2705, B4601, C0202, C0602, C0701, C0702 | 8 | 0.5553 | A3201, B1503, B2705, B4601, C0202, C0602, C0701, C0702 | 8 | 0.5553 |
| MLLGSMLYM (SEQ ID NO: 4) | unknown | 0 | 0.0000 | unknown | 0 | 0.0000 | unknown | 0 | 0.0000 | unknown | 0 | 0.0000 | unknown | 0 | 0.0000 |
| NLNESLIDL (SEQ ID NO: 40) | A0204 | 1 | 0.0059 | A0202, A0203, A0204 | 3 | 0.0515 | A0202,A0203,A0204 | 3 | 0.0515 | A0201, A0202, A0203, A0204 | 4 | 0.3258 | A0201, A0202, A0203, A0204, A0207 | 5 | 0.3603 |

TABLE 9C-continued

| Estimated Population Coverage | | | | | | | | | | | | | | | |
|---|---|---|---|---|---|---|---|---|---|---|---|---|---|---|---|
| SLEDKAFQL (SEQ ID NO: 7) | A0201, A0202, A0204, A0207 | 4 | 0.3359 | A0201, A0202, A0204, A0207 | 4 | 0.3359 | A0201,A0202,A0204,A0207 | 4 | 0.3359 | A0201, A0202, A0204, A0207, B1301 | 5 | 0.3696 | A0201, A0202, A0204, A0207, B1301, G0103 | 6 | 0.3696 |
| STSAFVETV (SEQ ID NO: 19) | A0202, A0203, A0205, A6802, C1502 | 5 | 0.1480 | A0202, A0203, A0205, A0206, A6802, C1502 | 6 | 0.2088 | A0202,A0203,A0205,A0206,A6802,C1502 | 6 | 0.2088 | A0202, A0203, A0205, A0206, A6802, C1203, C1502 | 7 | 0.2405 | A0202, A0203, A0205, A0206, A0211, A6802, C1203, C1502 | 8 | 0.2457 |
| SVVSKYVKV (SEQ ID NO: 30) | A0201, A0203, A0204, A0205, A0206, A0207, A0211, A2601, A6802, C0202, C1203, C1502 | 12 | 0.5688 | A0201, A0203, A0204, A0205, A0206, A0207, A0211, A2601, A6802, C0202, C1203, C1502 | 12 | 0.5688 | A0201,A0202,A0203,A0204,A0205,A0206,A0207,A0211,A2601,A6802,B1302,C0202,C1203,C1502,C1701 | 15 | 0.6069 | A0201, A0202, A0203, A0204, A0205, A0206, A0207, A0211, A2601, A6802, B1302, C0202, C0602, C1203, C1502, C1701 | 16 | 0.6589 | A0201, A0202, A0203, A0204, A0205, A0206, A0207, A0211, A2601, A6802, B1302, C0202, C0602, C1203, C1502, C1701 | 16 | 0.6589 |
| YLNSTNVTI (SEQ ID NO: 24) | A0201, A0202, A0203, A0204, A0207, B1302 | 6 | 0.3783 | A0201, A0202, A0203, A0204, A0207, B1302 | 6 | 0.3783 | A0201,A0202,A0203,A0204,A0207,B1302 | 6 | 0.3783 | A0201, A0202, A0203, A0204, A0207, B1302 | 6 | 0.3783 | A0201, A0202, A0203, A0204, A0207, B1302 | 6 | 0.3783 |
| APHGHVMVEL | B0702, B0704, B0801, B4201, | 8 | 0.3523 | B0702, B0704, B0801, B4201, | 8 | 0.3523 | B0702,B0704,B0801,B4201,B5601,C0 | 8 | 0.3523 | B0702, B0704, B0801, B4201, | 9 | 0.3671 | B0702, B0704, B0801, B4201, | 9 | 0.3671 |

TABLE 9C-continued

Estimated Population Coverage

| | | | | | | | | | | | | | | | |
|---|---|---|---|---|---|---|---|---|---|---|---|---|---|---|---|
| (SEQ ID NO: 14) | B5601, C0704, C0801, C1701 | | | B5601, C0704, C0801, C1701 | | | 704,C0801,C1701 | | | B5502, B5601, C0704, C0801, C1701 | | | B5502, B5601, C0704, C0801, C1701 | | |
| GPMVLRGLIT (SEQ ID NO: 6) | unknown | 0 | 0.0000 | unknown | 0 | 0.0000 | unknown | 0 | 0.0000 | unknown | 0 | 0.0000 | unknown | 0 | 0.0000 |
| KAFQLTPIAV (SEQ ID NO: 13) | A0201, A0211, A6802, B5101, B5201, B5401, B5502, C1203, C1701, G0104 | 10 | 0.4824 | A0201, A0211, A6802, B5101, B5201, B5401, B5502, C1203, C1701, G0104 | 10 | 0.4824 | A0201,A0203,A0211,A6802,B5101,B5201,B5401,B5502,B5601,C1203,C1701,G0104 | 12 | 0.5166 | A0201, A0203, A0211, A6802, B5101, B5201, B5401, B5502, B5601, C1203, C1701, G0101, G0104 | 13 | 0.5166 | A0201, A0203, A0204, A0206, A0211, A6802, B1302, B4006, B5101, B5201, B5401, B5502, B5601, C1203, C1701, G0101, G0104 | 17 | 0.5915 |
| ELPDEFVVVTV (SEQ ID NO: 8) | A0201, A0207, A6802, B5101, B5201, C0102 | 6 | 0.5273 | A0201, A0203, A0207, A6802, B5101, B5201, C0102 | 7 | 0.5447 | A0201,A0203,A0206,A0207,A6802,B5101,B5201,C0102,C0403 | 9 | 0.6009 | A0201, A0203, A0205, A0206, A0207, A6802, B5101, B5201, C0102, C0403 | 10 | 0.6097 | A0201, A0203, A0205, A0206, A0207, A6802, B5101, B5201, C0102, C0403 | 10 | 0.6097 |
| YLFDESGEFKL (SEQ ID NO: 25) | A0201, A0202, A0203, A0204, A0205, A0206, A0207, A0211, A2902, A3201, B1301, | 22 | 0.7506 | A0201, A0202, A0203, A0204, A0205, A0206, A0207, A0211, A2902, A3201, B1301, | 26 | 0.8326 | A0201,A0202,A0203,A0204,A0205,A0206,A0207,A0211,A2902,A3201,B1301,B1302,B1517,B3501,B35 | 28 | 0.8646 | A0201, A0202, A0203, A0204, A0205, A0206, A0207, A0211, A2902, A3201, B1301, | 29 | 0.8953 | A0201, A0202, A0203, A0204, A0205, A0206, A0207, A0211, A2902, A3201, B1301, | 31 | 0.9189 |

TABLE 9C-continued

| Estimated Population Coverage | | | | | | | | | | | | | | | |
|---|---|---|---|---|---|---|---|---|---|---|---|---|---|---|---|
| | B1302,<br>B3501,<br>B3503,<br>C0102,<br>C0304,<br>C0403,<br>C0704,<br>C1701,<br>G0101,<br>G0103,<br>G0104 | | | B1302,<br>B3501,<br>B3503,<br>C0102,<br>C0302,<br>C0303,<br>C0304,<br>C0403,<br>C0704,<br>C1402,<br>C1502,<br>C1701,<br>G0101,<br>G0103,<br>G0104 | | | 03,C0102<br>,C0302,C<br>0303,C03<br>04,C0403<br>,C0602,C<br>0704,C14<br>02,C1502<br>,C1701,G<br>0101,G01<br>03,G0104 | | | B1302,<br>B1517,<br>B3501,<br>B3503,<br>C0102,<br>C0302,<br>C0303,<br>C0304,<br>C0403,<br>C0602,<br>C0701,<br>C0704,<br>C1402,<br>C1502,<br>C1701,<br>G0101,<br>G0103,<br>G0104 | | | B1302,<br>B1517,<br>B3501,<br>B3503,<br>C0102,<br>C0302,<br>C0303,<br>C0304,<br>C0403,<br>C0602,<br>C0701,<br>C0704,<br>C0801,<br>C1402,<br>C1403,<br>C1502,<br>C1701,<br>G0101,<br>G0103,<br>G0104 | | |
| Peps Comb-ined | B1801,<br>B3701,<br>B4002,<br>B4006,<br>B4403,<br>B4501,<br>B4901,<br>B5001,<br>B5101,<br>A0202,<br>B1801,<br>B3801,<br>B4001,<br>B4402,<br>B4403,<br>C0802,<br>A0101,<br>A2501,<br>A2601,<br>A2902,<br>A3002,<br>A3601,<br>A2501,<br>A2601,<br>B1502,<br>C1202,<br>B5101,<br>C0202,<br>C0302,<br>C0303,<br>C0304, | 70 | 0.9998 | B1402,<br>B1801,<br>B3701,<br>B4002,<br>B4006,<br>B4403,<br>B4501,<br>B4901,<br>B5001,<br>B5101,<br>A0202,<br>A3601,<br>B1510,<br>B1801,<br>B3503,<br>B3801,<br>B4001,<br>B4002,<br>B4402,<br>B4403,<br>C0802,<br>A0101,<br>A2501,<br>A2601,<br>A2902,<br>A3002,<br>A3601,<br>B1502,<br>A2501,<br>A2601,<br>B1502, | 75 | 0.9999 | B1402,B1<br>801,B370<br>1,B4002,<br>B4006,B4<br>402,B440<br>3,B4501,<br>B4901,B5<br>001,B510<br>1,A0202,<br>A3601,B<br>1510,B18<br>01,B3503<br>,B3801,B<br>4001,B40<br>02,B4402<br>,B4403,B<br>4501,B57<br>03,C0802<br>,A0101,A<br>2501,A26<br>01,A2902<br>,A3002,A<br>3601,B15<br>02,B3501<br>,A2501,A<br>2601,B15<br>02,C1202<br>,B5101,C<br>0202,C03<br>02,C0303<br>,C0304,C | 77 | 0.999 | A6802,<br>B1402,<br>B1801,<br>B3701,<br>B4002,<br>B4006,<br>B4402,<br>B4403,<br>B4501,<br>B4901,<br>B5001,<br>B5101,<br>A0101,<br>A0202,<br>A3601,<br>B1510,<br>B1801,<br>B3503,<br>B3801,<br>B4001,<br>B4002,<br>B4402,<br>B4403,<br>B4501,<br>B5703,<br>C0802,<br>A0101,<br>A2501,<br>A2601,<br>A2902,<br>A3002, | 78 | 0.9999 | A6802,<br>B1402,<br>B1801,<br>B3701,<br>B4002,<br>B4006,<br>B4402,<br>B4403,<br>B4501,<br>B4901,<br>B5001,<br>B5101,<br>B5201,<br>A0101,<br>A0202,<br>A3601,<br>B1510,<br>B1801,<br>B3503,<br>B3801,<br>B4001,<br>B4002,<br>B4402,<br>B4403,<br>B4501,<br>B5703,<br>C0704,<br>C0802,<br>A0101,<br>A2501,<br>A2601, | 79 | 1.0000 |

TABLE 9C-continued

| Estimated Population Coverage | | | | |
|---|---|---|---|---|
| C0602, | C1202, | 0602,C08 | A3601, | A2902, |
| C0801, | B5101, | 01,C0802 | B1501, | A3002, |
| C0802, | C0202, | ,C1202,C | B1502, | A3601, |
| C1202, | C0302, | 1203,C16 | B3501, | B1501, |
| C1203, | C0303, | 01,A2902 | A2501, | B1502, |
| C1601, | C0304, | ,B1501,B | A2601, | B3501, |
| B1501, | C0602, | 1502,B15 | B1501, | A2501, |
| B1502, | C0801, | 03,B3501 | B1502, | A2601, |
| B3501, | C0802, | ,B3507,B | C1202, | B1501, |
| B3507, | C1202, | 4601,B53 | B5101, | B1502, |
| B4601, | C1203, | 01,C0202 | C0202, | C1202, |
| C0202, | C1601, | ,C0302,C | C0302, | B5101, |
| C0302, | B1501, | 0303,C03 | C0303, | C0202, |
| C0303, | B1502, | 04,C0702 | C0304, | C0302, |
| C0304, | B1503, | ,C1202,C | C0602, | C0303, |
| C1202, | B3501, | 1203,C16 | C0801, | C0304, |
| C1203, | B3507, | 01,B3501 | C0802, | C0501, |
| C1601, | B4601, | ,B3503,B | C1202, | C0602, |
| B3503, | B5301, | 3507,C03 | C1203, | C0801, |
| B3507, | C0202, | 02,C0303 | C1502, | C0802, |
| C0302, | C0302, | ,C0304,C | C1601, | C1202, |
| C0303, | C0303, | 0403,C07 | A2902, | C1203, |
| C0304, | C0304, | 04,C1202 | B1501, | C1502, |
| C0403, | C0702, | ,C1203,C | B1502, | C1601, |
| C0704, | C1202, | 1601,C17 | B1503, | A2902, |
| C1203, | C1203, | 01,A0206 | B3501, | B1501, |
| C1601, | C1601, | ,A6802,B | B3507, | B1502, |
| C1701, | B3501, | 5101,C06 | B4601, | B1503, |
| A0206, | B3503, | 02,C1203 | B5301, | B3501, |
| A6802, | B3507, | ,C1601,C | C0202, | B3507, |
| B5101, | C0302, | 1701,A30 | C0302, | B4601, |
| C0602, | C0303, | 02,B1502 | C0303, | B5301, |
| C1203, | C0304, | ,C1601,B | C0304, | C0202, |
| C1701, | C0403, | 1801,B44 | C0702, | C0302, |
| A3002, | C0704, | 02,B4403 | C1202, | C0303, |
| B1801, | C1203, | ,B0704,B | C1203, | C0304, |
| B4402, | C1601, | 4201,C01 | C1601, | C0702, |
| B4403, | C1701, | 02,C0303 | B3501, | C1202, |
| B0704, | A0206, | ,C0304,C | B3503, | C1203, |
| C0102, | A6802, | 0602,C12 | B3507, | C1402, |
| C0303, | B5101, | 03,C1601 | C0302, | C1601, |
| C0304, | C0602, | ,A0101,A | C0303, | B3501, |
| C0602, | C1203, | 3601,B15 | C0304, | B3503, |
| C1203, | C1701, | 02,B1517 | C0403, | B3507, |
| C1601, | A3002, | ,B1801,C | C0704, | C0302, |
| A0101, | B1801, | 1601,A29 | C1202, | C0303, |
| A3601, | B4402, | 02,A3601 | C1203, | C0304, |
| B1502, | B4403, | ,B1517,B | C1601, | C0403, |
| B1517, | B0704, | 3507,B46 | C1701, | C0704, |
| C1601, | B4201, | 01,C0202 | A0206, | C1202, |
| A2902, | C0102, | ,C0302,C | A6802, | C1203, |

TABLE 9C-continued

| Estimated Population Coverage | | | | |
|---|---|---|---|---|
| A3601, | C0303, | 1202,C12 | B1302, | C1601, |
| B1517, | C0304, | 03,C1601 | B5101, | C1701, |
| B3507, | C0602, | ,B1503,B | C0202, | A0206, |
| B4601, | C1203, | 5802,C16 | C0602, | A6802, |
| C0202, | C1601, | 01,A2301 | C0801, | B1302, |
| C0302, | A0101, | ,A2501,A | C1203, | B5101, |
| C1202, | A3601, | 2601,A68 | C1601, | B5301, |
| C1203, | B1502, | 02,A3002 | C1701, | C0202, |
| C1601, | B1517, | ,A3201,B | A3002, | C0602, |
| B1503, | B1801, | 1503,B15 | B1502, | C0704, |
| A2501, | C1601, | 17,B5701 | C1601, | C0801, |
| A2601, | A2902, | ,B5802,C | B1801, | C1203, |
| A3002, | A3601, | 0701,C15 | B4402, | C1502, |
| A3201, | B1517, | 02,A3201 | B4403, | C1601, |
| B1503, | B3507, | ,B1801,B | B0704, | C1701, |
| B1517, | B4601, | 3501,B44 | B4201, | A3002, |
| B5802, | C0202, | 02,B4403 | C0102, | B1502, |
| C0701, | C0302, | ,unknown | C0303, | C1601, |
| C1502, | C1202, | ,C0704,u | C0304, | B1801, |
| B1801, | C1203, | nknown, | C0602, | B4402, |
| B4402, | C1601, | A0201,A | C1203, | B4403, |
| B4403, | B1503, | 0206,A02 | C1601, | B0704, |
| unkno | C1601, | 07,A6802 | A0101, | B4201, |
| wn,C0 | A2301, | ,G0104,A | A3002, | C0102, |
| 704,un | A2501, | 0201,A02 | A3601, | C0303, |
| known, | A2601, | 06,A0207 | B1502, | C0304, |
| A0206, | A3002, | ,C0303,C | B1517, | C0602, |
| A0207, | A3201, | 0304,C04 | B1801, | C0704, |
| A6802, | B1503, | 01,C0403 | B5701, | C1203, |
| A0201, | B1517, | ,C0501,C | C1203, | C1601, |
| A0206, | B5802, | 0801,C08 | C1601, | A0101, |
| A0207, | C0701, | 02,C1502 | A2902, | A3002, |
| C0304, | C1502, | ,A0201,A | A3601, | A3601, |
| C0401, | B1801, | 0202,A02 | B1517, | B1502, |
| C0403, | B4402, | 04,C0602 | B3507, | B1517, |
| C0501, | B4403, | ,C0701,C | B4601, | B1801, |
| C0801, | unkno | 0702,A32 | C0202, | B5701, |
| C0802, | wn,C07 | 01,B1503 | C0302, | C1203, |
| A0201, | 04,unk | ,B2705,B | C1202, | C1601, |
| A0202, | nown, | 4601,C02 | C1203, | A2902, |
| C0602, | A0206, | 02,C0602 | C1601, | A3601, |
| C0701, | A0207, | ,C0701,C | B1503, | B1517, |
| C0702, | A6802, | 0702,unk | B5802, | B3507, |
| A3201, | A0201, | nown,A0 | C1601, | B4601, |
| B1503, | A0206, | 202,A020 | A2301, | C0202, |
| B2705, | A0207, | 3,A0204, | A2407, | C0302, |
| C0602, | C0304, | A0201,A | A2501, | C1202, |
| C0701, | C0401, | 0202,A02 | A2601, | C1203, |
| C0702, | C0403, | 04,A0207 | A3201, | C1601, |
| unkno | C0501, | ,A0202,A | A6802, | B1503, |
| wn,A0 | C0801, | 0203,A02 | A2601, | B5802, |

TABLE 9C-continued

| Estimated Population Coverage | | | | |
|---|---|---|---|---|
| 204,A0 | C0802, | 05,A0206 | A3002, | C1601, |
| 201,A0 | A0201, | ,A6802,C | A3201, | A2301, |
| 202,A0 | A0202, | 1502,A02 | B1503, | A2407, |
| 204,A0 | C0602, | 01,A0202 | B1517, | A2501, |
| 207,A0 | C0701, | ,A0203,A | B1801, | A2601, |
| 202,A0 | C0702, | 0204,A02 | B5701, | A3201, |
| 203,A0 | A3201, | 05,A0206 | B5802, | A6802, |
| 205,A6 | B1503, | ,A0207,A | C0701, | B1502, |
| 802,C1 | B2705, | 0211,A26 | C1502, | G0104, |
| 502,A0 | C0602, | 01,A6802 | A3201, | A2601, |
| 201,A0 | C0701, | ,B1302,C | B1801, | A3002, |
| 203,A0 | C0702, | 0202,C12 | B3501, | A3201, |
| 204,A0 | unkno | 03,C1502 | B4402, | B1503, |
| 205,A0 | wn,A0 | ,C1701,A | B4403, | B1517, |
| 206,A0 | 202,A0 | 0201,A02 | unknow | B1801, |
| 207,A0 | 203,A0 | 02,A0203 | n,C070 | B5701, |
| 211,A2 | 204,A0 | ,A0204,A | 4,unkno | B5802, |
| 601,A6 | 201,A0 | 0207,B13 | wn,A02 | C0701, |
| 802,C0 | 202,A0 | 02,B0702 | 01,A02 | C1502, |
| 202,C1 | 204,A0 | ,B0704,B | 06,A02 | C1601, |
| 203,C1 | 207,A0 | 0801,B42 | 07,A68 | A2902, |
| 502,A0 | 202,A0 | 01,B5601 | 02,G01 | A3201, |
| 201,A0 | 203,A0 | ,C0704,C | 04,A02 | B1801, |
| 202,A0 | 205,A0 | 0801,C17 | 01,A02 | B3501, |
| 203,A0 | 206,A6 | 01,unkno | 06,A02 | B4402, |
| 204,A0 | 802,C1 | wn,A020 | 07,C03 | B4403, |
| 207,B1 | 502,A0 | 1,A0203, | 03,C03 | unkno |
| 302,B0 | 201,A0 | A0211,A | 04,C04 | wn,C07 |
| 702,B0 | 203,A0 | 6802,B51 | 01,C04 | 04,unk |
| 704,B0 | 204,A0 | 01,B5201 | 03,C05 | nown, |
| 801,B4 | 205,A0 | ,B5401,B | 01,C08 | A0201, |
| 201,B5 | 206,A0 | 5502,B56 | 01,C08 | A0206, |
| 601,C0 | 207,A0 | 01,C1203 | 02,C15 | A0207, |
| 704,C0 | 211,A2 | ,C1701,G | 02,A02 | A6802, |
| 801,C1 | 601,A6 | 0104,A02 | 01,A02 | G0104, |
| 701,un | 802,C0 | 01,A0203 | 02,A02 | A0201, |
| known, | 202,C1 | ,A0206,A | 04,C06 | A0206, |
| A0201, | 203,C1 | 0207,A68 | 02,C07 | A0207, |
| A0211, | 502,A0 | 02,B5101 | 01,C07 | C0303, |
| A6802, | 201,A0 | ,B5201,C | 02,A32 | C0304, |
| B5101, | 202,A0 | 0102,C04 | 01,B15 | C0401, |
| B5201, | 203,A0 | 03,A0201 | 03,B27 | C0403, |
| B5401, | 204,A0 | ,A0202,A | 05,B46 | C0501, |
| B5502, | 207,B1 | 0203,A02 | 01,C02 | C0801, |
| C1203, | 302,B0 | 04,A0205 | 02,C06 | C0802, |
| C1701, | 702,B0 | ,A0206,A | 02,C07 | C1502, |
| G0104, | 704,B0 | 0207,A02 | 01,C07 | A0201, |
| A0201, | 801,B4 | 11,A2902 | 02,unkn | A0202, |
| A0207, | 201,B5 | ,A3201,B | own,A0 | A0204, |
| A6802, | 601,C0 | 1301,B13 | 201,A0 | A0211, |
| B5101, | 704,C0 | 02,B1517 | 202,A0 | B1402, |

TABLE 9C-continued

| Estimated Population Coverage | | | | |
|---|---|---|---|---|
| B5201, | 801,C1 | ,B3501,B | 203,A0 | B3801, |
| C0102, | 701,un | 3503,C01 | 204,A0 | C0602, |
| A0201, | known, | 02,C0302 | 201,A0 | C0701, |
| A0202, | A0201, | ,C0303,C | 202,A0 | C0702, |
| A0203, | A0211, | 0304,C04 | 204,A0 | A3201, |
| A0204, | A6802, | 03,C0602 | 207,B1 | B1503, |
| A0205, | B5101, | ,C0704,C | 301,A0 | B2705, |
| A0206, | B5201, | 1402,C15 | 202,A0 | B4601, |
| A0207, | B5401, | 02,C1701 | 203,A0 | C0202, |
| A0211, | B5502, | ,G0101,G | 205,A0 | C0602, |
| A2902, | C1203, | 0103,G01 | 206,A6 | C0701, |
| A3201, | C1701, | 04 | 802,C1 | C0702, |
| B1301, | G0104, | | 203,C1 | unkno |
| B1302, | A0201, | | 502,A0 | wn,A0 |
| B3501, | A0203, | | 201,A0 | 201,A0 |
| B3503, | A0207, | | 202,A0 | 202,A0 |
| C0102, | A6802, | | 203,A0 | 203,A0 |
| C0304, | B5101, | | 204,A0 | 204,A0 |
| C0403, | B5201, | | 205,A0 | 207,A0 |
| C0704, | C0102, | | 206,A0 | 201,A0 |
| C1701, | A0201, | | 207,A0 | 202,A0 |
| G0101, | A0202, | | 211,A2 | 204,A0 |
| G0103, | A0203, | | 601,A6 | 207,B1 |
| G0104 | A0204, | | 802,B1 | 301,G0 |
| | A0205, | | 302,C0 | 103,A0 |
| | A0206, | | 202,C0 | 202,A0 |
| | A0207, | | 602,C1 | 203,A0 |
| | A0211, | | 203,C1 | 205,A0 |
| | A2902, | | 502,C1 | 206,A0 |
| | A3201, | | 701,A0 | 211,A6 |
| | B1301, | | 201,A0 | 802,C1 |
| | B1302, | | 202,A0 | 203,C1 |
| | B3501, | | 203,A0 | 502,A0 |
| | B3503, | | 204,A0 | 201,A0 |
| | C0102, | | 207,B1 | 202,A0 |
| | C0302, | | 302,B0 | 203,A0 |
| | C0303, | | 702,B0 | 204,A0 |
| | C0304, | | 704,B0 | 205,A0 |
| | C0403, | | 801,B4 | 206,A0 |
| | C0704, | | 201,B5 | 207,A0 |
| | C1402, | | 502,B5 | 211,A2 |
| | C1502, | | 601,C0 | 601,A6 |
| | C1701, | | 704,C0 | 802,B1 |
| | G0101, | | 801,C1 | 302,C0 |
| | G0103, | | 701,unk | 202,C0 |
| | G0104 | | nown,A | 602,C1 |
| | | | 0201,A | 203,C1 |
| | | | 0203,A | 502,C1 |
| | | | 0211,A | 701,A0 |
| | | | 6802,B | 201,A0 |
| | | | 5101,B | 202,A0 |

TABLE 9C-continued

| Estimated Population Coverage | | |
|---|---|---|
| | 5201,B | 203,A0 |
| | 5401,B | 204,A0 |
| | 5502,B | 207,B1 |
| | 5601,C | 302,B0 |
| | 1203,C | 702,B0 |
| | 1701,G | 704,B0 |
| | 0101,G | 801,B4 |
| | 0104,A | 201,B5 |
| | 0201,A | 502,B5 |
| | 0203,A | 601,C0 |
| | 0205,A | 704,C0 |
| | 0206,A | 801,C1 |
| | 0207,A | 701.un |
| | 6802,B | known, |
| | 5101,B | A0201, |
| | 5201,C | A0203, |
| | 0102,C | A0204, |
| | 0403,A | A0206, |
| | 0201,A | A0211, |
| | 0202,A | A6802, |
| | 0203,A | B1302, |
| | 0204,A | B4006, |
| | 0205,A | B5101, |
| | 0206,A | B5201, |
| | 0207,A | B5401, |
| | 0211,A | B5502, |
| | 2902,A | B5601, |
| | 3201,B | C1203, |
| | 1301,B | C1701, |
| | 1302,B | G0101, |
| | 1517,B | G0104, |
| | 3501,B | A0201, |
| | 3503,C | A0203, |
| | 0102,C | A0205, |
| | 0302,C | A0206, |
| | 0303,C | A0207, |
| | 0304,C | A6802, |
| | 0403,C | B5101, |
| | 0602,C | B5201, |
| | 0701,C | C0102, |
| | 0704,C | C0403, |
| | 1402,C | A0201, |
| | 1502,C | A0202, |
| | 1701,G | A0203, |
| | 0101,G | A0205, |
| | 0103,G | A0206, |
| | 0104 | A0207, |
| | | A0211, |
| | | A2902, |
| | | A3201, |
| | | B1301, |

TABLE 9C-continued

Estimated Population Coverage

| | Pep-tide | thr1.1_assign_alleles | thr1.1_num alleles | thr1.1_cover-age | thr1.2_assign_alleles | thr1.2_num_alleles | thr1.2_cover-age | thr1.3_assign_alleles | thr1.3_num_alleles | thr1.3_cover-age | thr1.4_assign_alleles | thr1.4_num_alleles | thr1.4_cover-age | thr1.5_assign_alleles | thr1.5_num_alleles | thr1.5_cover-age |
|---|---|---|---|---|---|---|---|---|---|---|---|---|---|---|---|---|
| | | | | | | | | | | | | | | B1302, B1517, B3501, B3503, C0102, C0302, C0303, C0304, C0403, C0602, C0701, C0704, C0801, C1402, C1403, C1502, C1701, G0101, G0103, G0104 | | |
| A549 | DEF VV VT V (SEQ ID NO: 11) | A6802, B1402, B1801, B3701, B4002, B4006, B4402, B4403, B4501, B4901, B5001, B5101, B5201 | 13 | 0.5092 | A6802, B1402, B1801, B3701, B4002, B4006, B4402, B4403, B4501, B4901, B5001, B5101, B5101, | 13 | 0.5092 | A6802,B 1402,B18 01,B3701 ,B4002,B 4006,B44 02,B4403 ,B4501,B 4901,B50 01,B5101 ,B5201 B5001, B5001, B5201, | 13 | 0.5092 | A6802, B1402, B1801, B3701, B4002, B4006, B4402, B4403, B4501, B4901, B4901, B5201 | 13 | 0.5092 | A6802, B1402, B1801, B3701, B4001, B4002, B4006, B4402, B4403, B4501, B5101, B5201 C0704 | 15 | 0.5897 |
| | LED KAF QL (SEQ ID NO: 10) | A0101, A0202, A3601, B1510, B1801, B3503, B3801, B4001, B4002, B4402, B4403, B4501, B5703, | 15 | 0.4999 | A0101, A0202, A3601, B1510, B1801, B3503, B3801, B4001, B4002, B4402, B4403, B4501, B5703, | 15 | 0.4999 | A0101,A 0202,A36 01,B1510 ,B1801,B 3503,B38 01,B4001 ,B4002,B 4402,B44 03,B4501 ,B5001,B 5703,C07 04,C0802 | 16 | 0.5118 | A0101, A0202, A3601, B1510, B1517, B1801, B3503, B3801, B4001, B4002, B4402, B4403, B4501, | 17 | 0.5155 | A0101, A0202, A3601, B1510, B1517, B1801, B3503, B3801, B4001, B4002, B4402, B4403, B4501, | 17 | 0.5155 |

TABLE 9C-continued

| Estimated Population Coverage | | | | | | | | | | | | | | | |
|---|---|---|---|---|---|---|---|---|---|---|---|---|---|---|---|
| | C0704, C0802 | | | C0704, C0802 | | | | | | B5001, B5703, C0704, C0802 | | | B5001, B5703, C0704, C0802 | | |
| TVI EV QG Y (SEQ ID NO: 22) | A0101, A2501, A2601, A2902, A3002, A3601, B1501, B1502, B3501 | 9 | 0.3779 | A0101, A2501, A2601, A2902, A3002, A3601, B1501, B1502, B3501 | 9 | 0.3779 | A0101,A2501,A2601,A2902,A3002,A3201,A3601,B1501,B1502,B3501 | 10 | 0.3981 | A0101, A0301, A2501, A2601, A2902, A3002, A3201, A3601, B1501, B1502, B3501 | 11 | 0.4561 | A0101, A0301, A2501, A2601, A2902, A3002, A3201, A3601, B1501, B1502, B3501, B5301 | 12 | 0.4756 |
| EIK ESV QTF (SEQ ID NO: 15) | A2501, A2601, B1501, B1502, C1202 | 5 | 0.2132 | A2501, A2601, A3401, B1501, B1502, C1202 | 6 | 0.2394 | A2501,A2601,A3401,B1501,B1502,C1202 | 6 | 0.2394 | A2501, A2601, A3401, B1501, B1502, C1202 | 6 | 0.2394 | A2501, A2601, A3401, B1501, B1502, B4601, C1202 | 7 | 0.2766 |
| FAS EA AR VV (SEQ ID NO: 17) | B5101, C0202, C0302, C0303, C0304, C0501, C0602, C0801, C0802, C1202, C1203, C1502, C1601 | 13 | 0.7402 | B5101, C0202, C0302, C0303, C0304, C0501, C0602, C0801, C0802, C1202, C1203, C1502, C1601 | 13 | 0.7402 | B5101,C0202,C0302,C0303,C0304,C0501,C0602,C0801,C0802,C1202,C1203,C1502,C1601 | 13 | 0.7402 | B5101, C0202, C0302, C0303, C0304, C0501, C0602, C0704, C0801, C0802, C1202, C1203, C1502, C1601 | 14 | 0.7542 | B5101, C0202, C0302, C0303, C0304, C0501, C0602, C0704, C0801, C0802, C1202, C1203, C1502, C1601 | 14 | 0.7542 |
| FAV DA AK AY (SEQ ID NO: 28) | A2501, A2902, B1501, B1502, B1503, B3501, B3507, B4601, B5301, C0202, C0302, C0303, C0304, C0702, | 18 | 0.7850 | A2501, A2902, B1501, B1502, B1503, B3501, B3507, B4601, B5301, C0202, C0302, C0303, C0304, C0702, | 18 | 0.7850 | A2501,A2902,B1501,B1502,B1503,B3501,B3507,B4601,B5301,C0202,C0302,C0303,C0304,C0702,C1202,C1203,C1402,C1601 | 18 | 0.7850 | A2501, A2902, B1501, B1502, B1503, B3501, B3507, B4601, B5301, C0202, C0302, C0303, C0304, C0702, | 18 | 0.7850 | A2501, A2902, B1501, B1502, B1503, B3501, B3507, B4601, B5301, C0202, C0302, C0303, C0304, C0702, | 19 | 0.7960 |

TABLE 9C-continued

Estimated Population Coverage

| | | | | | | | | | | | | | | | |
|---|---|---|---|---|---|---|---|---|---|---|---|---|---|---|---|
| | C1202, C1203, C1402, C1601 | | | C1202, C1203, C1402, C1601 | | | | | | C1202, C1203, C1402, C1601 | | | C1202, C1203, C1402, C1403, C1601 | | |
| LATNNLVVM (SEQ ID NO: 16) | B3501, B3503, B3507, C0302, C0303, C0304, C0403, C0704, C1202, C1203, C1601, C1701 | 12 | 0.5827 | B3501, B3503, B3507, C0202, C0302, C0303, C0304, C0403, C0704, C1202, C1203, C1601, C1701 | 13 | 0.6155 | B3501,B3503,B3507,C0202,C0302,C0303,C0304,C0403,C0704,C0801,C1202,C1203,C1601,C1701 | 14 | 0.6655 | B3501, B3503, B3507, C0202, C0302, C0303, C0304, C0403, C0704, C0801, C1202, C1203, C1601, C1701 | 14 | 0.6655 | B3501, B3503, B3507, C0202, C0302, C0303, C0304, C0403, C0704, C0801, C1202, C1203, C1601, C1701 | 14 | 0.6655 |
| NATNVVIKV (SEQ ID NO: 37) | A0201, A0206, A6802, B1302, B5101, B5301, C0202, C0602, C0704, C0801, C1203, C1502, C1601, C1701 | 14 | 0.6942 | A0201, A0206, A6802, B1302, B5101, B5301, C0202, C0602, C0704, C0801, C1203, C1502, C1601, C1701 | 14 | 0.6942 | A0201,A0205,A0206,A6802,B1302,B5101,B5301,C0202,C0602,C0704,C0801,C1203,C1502,C1601,C1701 | 15 | 0.7006 | A0201, A0205, A0206, A6802, B1302, B5101, B5301, C0202, C0602, C0704, C0801, C1203, C1502, C1601, C1701 | 15 | 0.7006 | A0201, A0205, A0206, A6802, B1302, B5101, B5301, C0202, C0602, C0704, C0801, C1203, C1502, C1601, C1701 | 15 | 0.7006 |
| QLTPTWRVY (SEQ ID NO: 38) | A3002, B1502, C1601 | 3 | 0.1002 | A0101, A3002, B1502, C1601 | 4 | 0.1865 | A0101,A3002,B1502,C1601 | 4 | 0.1865 | A0101, A3002, B1502, C1601 | 4 | 0.1865 | A0101, A3002, B1501, B1502, C1203, C1601 | 6 | 0.2722 |
| SEFSSLPSY (SEQ ID NO: 27) | B1503, B1801, B4402, B4403 | 4 | 0.1921 | B1503, B1801, B4402, B4403 | 4 | 0.1921 | B1503,B1801,B4002,B4402,B4403 | 5 | 0.2654 | B1503, B1801, B4002, B4402, B4403 | 5 | 0.2654 | B1503, B1801, B4002, B4006, B4402, B4403 | 6 | 0.2959 |
| TAQNS | B0704, B3503, | 10 | 0.6218 | B0704, B3503, | 10 | 0.6218 | B0704,B3503,B420 | 10 | 0.6218 | B0704, B3503, | 14 | 0.7542 | B0704, B3503, | 14 | 0.7542 |

TABLE 9C-continued

| Estimated Population Coverage | | | | | | | | | | | | | | | |
|---|---|---|---|---|---|---|---|---|---|---|---|---|---|---|---|
| VR VL (SEQ ID NO: 18) | B4201, C0102, C0303, C0304, C0602, C0704, C1203, C1601 | | | B4201, C0102, C0303, C0304, C0602, C0704, C1203, C1601 | | | 1,C0102, C0303,C0 304,C060 2,C0704, C1203,C1 601 | | | B4201, B5802, C0102, C0303, C0304, C0602, C0701, C0704, C0802, C1202, C1203, C1601 | | | B4201, B5802, C0102, C0303, C0304, C0602, C0701, C0704, C0802, C1202, C1203, C1601 | | |
| TTT IKP VT Y (SEQ ID NO: 21) | A0101, A0301, A3002, A3601, B1502, B1517, B1801, B5701, C1202, C1203, C1601 | 11 | 0.3883 | A0101, A0301, A3002, A3601, B1502, B1517, B1801, B5701, C1202, C1203, C1601 | 11 | 0.3883 | A0101,A 0301,A30 02,A3601 ,B1502,B 1517,B18 01,B5701 ,C1202,C 1203,C16 01 | 11 | 0.3883 | A0101, A0301, A2902, A3002, A3601, B1502, B1517, B1801, B5701, B5703, C1202, C1203, C1601 | 13 | 0.4162 | A0101, A0301, A2902, A3002, A3601, B1502, B1517, B1801, B5701, B5703, C0202, C1202, C1203, C1601 | 14 | 0.4511 |
| VA TSR TLS Y (SEQ ID NO: 41) | A2902, A3601, B1517, B3507, B4601, C0202, C0302, C1202, C1203, C1601 | 10 | 0.3268 | A2902, A3601, B1517, B3507, B4601, C0202, C0302, C1202, C1203, C1601 | 10 | 0.3268 | A2902,A 3601,B15 17,B3507 ,B4601,C 202,C03 02,C1202 ,C1203,C 1601 | 10 | 0.3268 | A2902, A3601, B1517, B3507, B4601, C0202, C0302, C1202, C1203, C1601 | 10 | 0.3268 | A0101, A2902, A3601, B1501, B1517, B3507, B4601, C0202, C0302, C1202, C1203, C1601 | 12 | 0.4344 |
| VG YL QPR TF (SEQ ID NO: 39) | B1503, B5802, C1601 | 3 | 0.0859 | B1503, B5802, C1601 | 3 | 0.0859 | B1503,B5 701,B580 2,C1601 | 4 | 0.1408 | B1503, B5701, B5802, C1601 | 4 | 0.1048 | B1503, B5701, B5802, C1601 | 4 | 0.1048 |

TABLE 9C-continued

| Estimated Population Coverage | | | | | | | | | | | | | | | |
|---|---|---|---|---|---|---|---|---|---|---|---|---|---|---|---|
| EIL DIT PCS F (SEQ ID NO: 33) | A0211, A2301, A2407, A2501, A2601, A3201, A6802, B1502, C1402, G0104 | 10 | 0.2453 | A0211, A2301, A2407, A2501, A2601, A3201, A6802, B1502, C1402, G0104 | 10 | 0.2453 | A0211,A 2301,A24 07,A2501 ,A2601,A 3201,A34 02,A6802 ,B1502,B 3507,B46 01,C1402 G0104 | 13 | 0.3082 | A0211, A2301, A2407, A2501, A2601, A3201, A3402, A6802, B1502, B1801, B3507, B4601, C0202, C1202, C1402, G0104 | 16 | 0.4198 | A0211, A2301, A2407, A2501, A2601, A2902, A3201, A3402, A6802, B1502, B1801, B3507, B4601, C0202, C1202, C1402, G0101, G0104 | 18 | 0.4407 |
| KNI DG YFK IY (SEQ ID NO: 36) | A2601, A3002, A3201, B1503, B1517, B1801, B4403, B4601, B5701, B5802, C0701, C0704, C1502, C1601 | 14 | 0.5037 | A2601, A3002, A3201, A3601, B1503, B1517, B1801, B4403, B4601, B5701, B5802, C0701, C0704, C1502, C1601 | 15 | 0.5079 | A2601,A 3002,A32 01,A3601 ,B1503,B 1517,B18 01,B4403 ,B4601,B 5701,B58 02,C0701 ,C0702,C 0704,C15 02,C1601 ,C1701 | 17 | 0.6646 | A2601, A3002, A3201, A3601, B1503, B1517, B1801, B4403, B4601, B5701, B5802, C0701, C0702, C0704, C1502, C1601, C1701 | 17 | 0.6646 | A2601, A3002, A3201, A3601, B1503, B1517, B1801, B4403, B4601, B5701, B5802, C0701, C0702, C0704, C1502, C1601, C1701 | 17 | 0.6646 |
| EEF EPS TQ YE Y (SEQ ID NO: 20) | A2902, A3201, B1801, B3501, B4402, B4403, C1402 | 7 | 0.3459 | A2601, A2902, A3201, B1501, B1801, B3501, B3507, B4402, B4403, | 10 | 0.4557 | A2601,A 2902,A32 01,B1501 ,B1801,B 3501,B35 07,B4402 ,B4403,C 1402 | 10 | 0.4557 | A2501, A2601, A2902, A3201, B1501, B1801, B3501, B3507, B4402, | 12 | 0.4771 | A2501, A2601, A2902, A3201, B1501, B1801, B3501, B3507, B4402, | 14 | 0.5404 |

TABLE 9C-continued

| Estimated Population Coverage | | | | | | | | | | | | | | | | |
|---|---|---|---|---|---|---|---|---|---|---|---|---|---|---|---|---|
| | EIL DIT PCS FG (SEQ ID NO: 47) | unknown | 0 | 0.0000 | C1402 C1402, C1202, unknown | 0 | 0.0000 | unknown | 0 | 0.0000 | B4403, C0202, C1402, unknown | 0 | 0.0000 | B4403, C1403 C1403 unknown | 0 | 0.0000 |
| HEK293 | AG TDT TIT V (SEQ ID NO: 26) | C0704 | 1 | 0.0291 | C0704 | 1 | 0.0291 | C0704 | 1 | 0.0291 | C0704 | 1 | 0.0291 | C0704 | 1 | 0.0291 |
| | APR ITF GGP (SEQ ID NO: 42) | unknown | 0 | 0.0000 | unknown | 0 | 0.0000 | unknown | 0 | 0.0000 | unknown | 0 | 0.0000 | unkno wn | 0 | 0.0000 |
| | ELP DEF VV V (SEQ ID NO: 12) | A0201, A0206, A0207, A6802, G0104 | 5 | 0.3948 | A0201, A0206, A0207, A6802, G0104 | 5 | 0.3948 | A0201,A 0206,A02 07,A6802 ,G0101,G 0104 | 6 | 0.3948 | A0201, A0206, A0207, A6802, G0101, G0103, G0104 | 7 | 0.3948 | A0201, A0206, A0207, A6802, G0101, G0103, G0104 | 7 | 0.3948 |
| | FGD DT VIE V (SEQ ID NO: 23) | A0201, A0206, A0207, C0303, C0304, C0401, C0403, C0501, C0801, C0802, C1502 | 11 | 0.7772 | A0101, A0201, A0206, A0207, C0303, C0304, C0401, C0403, C0501, C0704, C0801, C0802, C1502 | 13 | 0.8132 | A0101,A 0201,A02 06,A0207 ,C0303,C 0304,C04 01,C0403 ,C0501,C 0704,C08 01,C0802 ,C1502 | 13 | 0.8123 | A0101, A0201, A0206, A0207, C0303, C0304, C0401, C0403, C0501, C0704, C0801, C0802, C1502 | 13 | 0.8132 | A0101, A0201, A0206, A0207, C0303, C0304, C0401, C0403, C0501, C0704, C0801, C0802, C1502 | 13 | 0.8132 |

TABLE 9C-continued

| Estimated Population Coverage | | | | | | | | | | | | | | | |
|---|---|---|---|---|---|---|---|---|---|---|---|---|---|---|---|
| GLITLSYHL (SEQ ID NO: 5) | A0201, A0202, A0204, A0211 | 4 | 0.3061 | A0201, A0202, A0204, A0211 | 4 | 0.3061 | A0201,A0202,A0204,A0205,A0211 | 5 | 0.3202 | A0201, A0202, A0204, A0205, A0211, A2301 | 6 | 0.3581 | A0201, A0202, A0204, A0205, A0211, A2301 | 6 | 0.3581 |
| IRQEEVQEL (SEQ ID NO: 31) | B1402, B3801, C0602, C0701, C0702 | 5 | 0.4764 | B1402, B3801, C0602, C0701, C0702 | 5 | 0.4764 | B1402,B3801,C0602,C0701, C0702 | 5 | 0.4764 | B1402, B3801, C0602, C0701, C0702 | 5 | 0.4764 | B1402, B3801, C0602, C0701, C0702 | 5 | 0.4764 |
| KRVDWTIEY (SEQ ID NO: 29) | A2902, A3201, B1503, B2705, B4601, C0202, C0602, C0701, C0702 | 9 | 0.5699 | A2902, A3201, B1503, B2705, B4601, C0202, C0602, C0701, C0702 | 9 | 0.5699 | A2902,A3002,A3201,B1503,B2705,B4601,C0202,C0602,C0701,C0702 | 10 | 0.5830 | A2902, A3002, A3201, B1503, B2705, B4601, C0202, C0602, C0701, C0702 | 10 | 0.5830 | A2902, A3002, A3201, B1503, B2705, B4601, B5701, C0202, C0602, C0701, C0702 | 11 | 0.5919 |
| MLLGSMLYM (SEQ ID NO: 4) | unknown | 0 | 0.0000 | unknown | 0 | 0.0000 | unknown | 0 | 0.0000 | unknown | 0 | 0.0000 | unknown | 0 | 0.0000 |
| NLNESLIDL (SEQ ID NO: 40) | A0201, A0202, A0203, A0204, A0207 | 5 | 0.3603 | A0201, A0202, A0203, A0204, A0207 | 5 | 0.3603 | A0201,A0202,A0203,A0204,A0207 | 5 | 0.3603 | A0201, A0202, A0203, A0204, A0207 | 5 | 0.3603 | A0201, A0202, A0203, A0204, A0207 | 5 | 0.3603 |
| SLEDKAFQL (SEQ ID NO: 7) | A0201, A0202, A0204, A0207, B1301, G0103, G0104 | 7 | 0.3696 | A0201, A0202, A0204, A0207, B1301, G0103, G0104 | 7 | 0.3696 | A0201,A0202,A0204,A0207,B1301,C0501,G0103,G0104 | 8 | 0.4021 | A0201, A0202, A0204, A0207, B1301, C0501, G0103, G0104 | 8 | 0.4021 | A0201, A0202, A0204, A0207, B1301, C0501, C0802, G0103, G0104 | 9 | 0.4267 |

TABLE 9C-continued

| | Estimated Population Coverage | | | | | | | | | | | | | | |
|---|---|---|---|---|---|---|---|---|---|---|---|---|---|---|---|
| STS AFV ETV (SEQ ID NO: 19) | A0202, A0203, A0205, A0206, A0211, A6802, C1203, C1502 | 8 | 0.2457 | A0202, A0203, A0205, A0206, A0211, A6802, C1203, C1502 | 8 | 0.2457 | A0202,A 0203,A02 04,A0205 ,A0206,A 0211,A68 02,C1203 ,C1502 | 9 | 0.2506 | A0201, A0202, A0203, A0204, A0205, A0206, A0211, A6802, C1203, C1502 | 10 | 0.4802 | A0201, A0202, A0203, A0204, A0205, A0206, A0211, A6802, C1203, C1502 | 10 | 0.4802 |
| SVV SKY VK V (SEQ ID NO: 30) | A0201, A0202, A0203, A0204, A0205, A0206, A0207, A0211, A2601, A6802, B1302, C0202, C0602, C1203, C1502, C1701 | 16 | 0.6589 | A0201, A0202, A0203, A0204, A0205, A0206, A0207, A0211, A2501, A2601, A6802, B1302, C0202, C0602, C1203, C1502, C1701 | 17 | 0.6632 | A0201,A 0202,A02 03,A0204 ,A0205,A 0206,A02 07,A0211 ,A2501,A 2601,A68 02,B1302 ,C0202,C 0602,C12 03,C1502 ,C1701 | 17 | 0.6632 | A0201, A0202, A0203, A0204, A0205, A0206, A0207, A0211, A2501, A2601, A6802, B1302, C0202, C0602, C1203, C1502, C1701 | 17 | 0.6632 | A0201, A0202, A0203, A0204, A0205, A0206, A0207, A0211, A2501, A2601, A6802, B1302, C0202, C0602, C1203, C1502, C1701 | 17 | 0.6632 |
| YL NST NV TI (SEQ ID NO: 24) | A0201, A0202, A0203, A0204, A0207, B1302 | 6 | 0.3783 | A0201, A0202, A0203, A0204, A0207, B1302 | 6 | 0.3783 | A0201,A 0202,A02 03,A0204 ,A0207,B 1302,B38 01 | 7 | 0.3882 | A0201, A0202, A0203, A0204, A0207, B1301, B1302, B3801, C0501 | 9 | 0.4499 | A0201, A0202, A0203, A0204, A0207, B1301, B1302, B3801, C0501 | 9 | 0.4499 |
| APH GH VM VEL (SEQ ID NO: 14) | B0702, B0704, B0801, B4201, B5501, B5502, B5601, C0704, C0801, C1701 | 10 | 0.3762 | B0702, B0704, B0801, B3503, B3507, B4201, B5501, B5502, B5601, C0704, C0801, C1701 | 12 | 0.4079 | B0702,B0 704,B080 1,B3503, B3507,B4 201,B550 1,B5502, B5601,C0 403,C070 4,C0801, C1701 | 13 | 0.4326 | B0702, B0704, B0801, B3503, B3507, B4201, B5501, B5502, B5601, C0403, C0704, C0801, C1701 | 13 | 0.4326 | B0702, B0704, B0801, B3503, B3507, B4201, B5501, B5502, B5601, C0403, C0704, C0801, C1701 | 13 | 0.4326 |

TABLE 9C-continued

| | Estimated Population Coverage | | | | | | | | | | | | | | |
|---|---|---|---|---|---|---|---|---|---|---|---|---|---|---|---|
| GP MV LRG LIT (SEQ ID NO: 6) | unknown | 0 | 0.0000 | unknown | 0 | 0.0000 | unknown | 0 | 0.0000 | unknown | 0 | 0.0000 | unknown | 0 | 0.0000 |
| KAF QLT PIA V (SEQ ID NO: 13) | A0201, A0202, A0203, A0204, A0205, A0206, A0211, A6802, B1302, B4006, B5101, B5201, B5401, B5502, B5601, C0704, C1203, C1701, G0101, G0104 | 20 | 0.6205 | A0201, A0202, A0203, A0204, A0205, A0206, A0211, A6802, B1302, B4006, B5101, B5201, B5401, B5502, B5601, C0704, C1203, C1701, G0101, G0104 | 20 | 0.6205 | A0201,A0202,A0203,A0204,A0205,A0206,A0211,A6802,B1302,B4006,B5101,B5201,B5401,B5502,B5601,C0704,C1203,C1701,G0101,G0104 | 20 | 0.6205 | A0201, A0202, A0203, A0204, A0205, A0206, A0211, A6802, B1302, B4006, B5101, B5201, B5401, B5501, B5502, B5601, C0704, C1203, C1701, G0101, G0104 | 21 | 0.6260 | A0201, A0202, A0203, A0204, A0205, A0206, A0211, A6802, B1302, B4006, B5101, B5201, B5401, B5501, B5502, B5601, C0704, C1203, C1701, G0101, G0104 | 21 | 0.6260 |
| ELP DEF VV VT V (SEQ ID NO: 8) | A0201, A0203, A0205, A0206, A0207, A2601, A6802, B5101, B5201, C0102, C0403, C0602 | 12 | 0.6910 | A0201, A0203, A0205, A0206, A0207, A2601, A6802, B5101, B5201, C0102, C0403, C0602, C0704 | 13 | 0.7018 | A0201,A0203,A0205,A0206,A0207,A2601,A6802,B5101,B5201,C0102,C0403,C0602,C0704,G0101,G0103,G0104 | 16 | 0.7018 | A0201, A0203, A0205, A0206, A0207, A2601, A6802, B5101, B5201, C0102, C0403, C0602, C0704, G0101, G0103, G0104 | 16 | 0.7018 | A0201, A0203, A0205, A0206, A0207, A2601, A6802, B5101, B5201, C0102, C0403, C0602, C0704, G0101, G0103, G0104 | 16 | 0.7018 |

TABLE 9C-continued

| Estimated Population Coverage | | | | | | | | | | | | | | | |
|---|---|---|---|---|---|---|---|---|---|---|---|---|---|---|---|
| YLF DES GEF KL (SEQ ID NO: 25) | A0201, A0202, A0203, A0204, A0205, A0206, A0207, A0211, A2902, A3201, B0801, B1301, B1302, B1510, B1517, B3501, B3503, B3801, C0102, C0302, C0303, C0304, C0403, C0602, C0701, C0702, C0704, C0801, C1402, C1403, C1502, C1601, C1701, G0101, G0103, G0104 | 36 | 0.9692 | A0201, A0202, A0203, A0204, A0205, A0206, A0207, A0211, A2902, A3201, B0801, B1301, B1302, B1510, B1517, B3501, B3503, B3507, B3801, C0102, C0302, C0303, C0304, C0401, C0403, C0501, C0602, C0701, C0702, C0704, C0801, C1402, C1403, C1502, C1601, C1701, G0101, G0103, G0104 | 39 | 0.9920 | A0201,A0202,A0203,A0204,A0205,A0206,A0207,A0211,A2902,A3201,B0801,B1301,B1302,B1510,B1517,B3501,B3503,B3507,B3801,C0102,C0302,C0303,C0304,C0401,C0403,C0501,C0602,C0701,C0702,C0704,C0801,C1402,C1403,C1502,C1601,C1701,G0101,G0103,G0104 | 39 | 0.9920 | A0201, A0202, A0203, A0204, A0205, A0206, A0207, A0211, A2407, A2902, A3201, B0801, B1301, B1302, B1502, B1510, B1517, B3501, B3503, B3507, B3801, B4601, C0102, C0302, C0303, C0304, C0401, C0403, C0501, C0602, C0701, C0702, C0704, C0801, C1402, C1403, C1502, C1601, C1701, G0101, G0103, G0104 | 42 | 0.9928 | A0201, A0202, A0203, A0204, A0205, A0206, A0207, A0211, A2407, A2902, A3201, B0801, B1301, B1302, B1502, B1510, B1517, B3501, B3503, B3507, B3801, B4601, B5201, B5301, C0102, C0302, C0303, C0304, C0401, C0403, C0501, C0602, C0701, C0702, C0704, C0801, C1402, C1403, C1502, C1601, C1701, G0101, G0103, G0104 | 44 | 0.9935 |
| Peps Comb-ined | A6802, B1402, B1801, B3701, B4002, B4006, B4402, | 81 | 1.0000 | A6802, B1402, B1801, B3701, B4002, B4006, B4402, | 82 | 1.0000 | A6802,B1402,B1801,B3701,B4002,B4006,B4402,B4403,B4501,B | 83 | 1.0000 | A6802, B1402, B1801, B3701, B4002, B4006, B4402, | 83 | 1.0000 | A6802, B1402, B1801, B3701, B4001, B4002, B4006, | 83 | 1.0000 |

TABLE 9C-continued

| Estimated Population Coverage | | | | |
|---|---|---|---|---|
| B4403, | B4403, | 4901,B50 | B4403, | B4402, |
| B4501, | B4501, | 01,B5101 | B4501, | B4403, |
| B4901, | B4901, | ,B5201,A | B4901, | B4501, |
| B5001, | B5001, | 0101,A02 | B5001, | B4901, |
| B5101, | B5101, | 02,A3601 | B5101, | B5001, |
| B5201, | B5201, | ,B1510,B | B5201, | B5101, |
| A0101, | A0101, | 1801,B35 | A0101, | B5201, |
| A0202, | A0202, | 03,B3801 | A0202, | C0704, |
| A3601, | A3601, | ,B4001,B | A3601, | A0101, |
| B1510, | B1510, | 4002,B44 | B1510, | A0202, |
| B1801, | B1801, | 02,B4403 | B1517, | A3601, |
| B3503, | B3503, | ,B4501,B | B1801, | B1510, |
| B3801, | B3801, | 5001,B57 | B3503, | B1517, |
| B4001, | B4001, | 03,C0704 | B3801, | B1801, |
| B4002, | B4002, | ,C0802,A | B4001, | B3503, |
| B4402, | B4402, | 0101,A25 | B4002, | B3801, |
| B4403, | B4403, | 01,A2601 | B4402, | B4001, |
| B4501, | B4501, | ,A2902,A | B4403, | B4002, |
| B5703, | B5703, | 3002,A32 | B4501, | B4402, |
| C0704, | C0704, | 01,A3601 | B5001, | B4403, |
| C0802, | C0802, | ,B1501,B | B5703, | B4501, |
| A0101, | A0101, | 1502,B35 | C0704, | B5001, |
| A2501, | A2501, | 01,A2501 | C0802, | B5703, |
| A2601, | A2601, | ,A2601,A | A0101, | C0704, |
| A2902, | A2902, | 3401,B15 | A0301, | C0802, |
| A3002, | A3002, | 01,B1502 | A2501, | A0101, |
| A3601, | A3601, | ,C1202,B | A2601, | A0301, |
| B1501, | B1501, | 5101,C02 | A2902, | A2501, |
| B1502, | B1502, | 02,C0302 | A3002, | A2601, |
| B3501, | B3501, | ,C0303,C | A3201, | A2902, |
| A2501, | A2501, | 0304,C05 | A3601, | A3002, |
| A2601, | A2601, | 01,C0602 | B1501, | A3201, |
| B1501, | A3401, | ,C0801,C | B1502, | A3601, |
| B1502, | B1501, | 0802,C12 | B3501, | B1501, |
| C1202, | B1502, | 02,C1203 | A2501, | B1502, |
| B5101, | C1202, | ,C1502,C | A2601, | B3501, |
| C0202, | B5101, | 1601,A25 | A3401, | B5301, |
| C0302, | C0202, | 01,A2902 | B1501, | A2501, |
| C0303, | C0302, | ,B1501,B | B1502, | A2601, |
| C0304, | C0303, | 1502,B15 | C1202, | A3401, |
| C0501, | C0304, | 03,B3501 | B5101, | B1501, |
| C0602, | C0501, | ,B3507,B | C0202, | B1502, |
| C0801, | C0602, | 4601,B53 | C0302, | B4601, |
| C0802, | C0801, | 01,C0202 | C0303, | C1202, |
| C1202, | C0802, | ,C0302,C | C0304, | B5101, |
| C1203, | C1202, | 0303,C03 | C0501, | C0202, |
| C1502, | C1203, | 04,C0702 | C0602, | C0302, |
| C1601, | C1502, | ,C1202,C | C0704, | C0303, |
| A2501, | C1601, | 1203,C14 | C0801, | C0304, |
| A2902, | A2501, | 02,C1601 | C0802, | C0501, |
| B1501, | A2902, | ,B3501,B | C1202, | C0602, |

TABLE 9C-continued

| Estimated Population Coverage | | | | |
|---|---|---|---|---|
| B1502, | B1501, | 3503,B35 | C1203, | C0704, |
| B1503, | B1502, | 07,C0202 | C1502, | C0801, |
| B3501, | B1503, | ,C0302,C | C1601, | C0802, |
| B3507, | B3501, | 0303,C03 | A2501, | C1202, |
| B4601, | B3507, | 04,C0403 | A2902, | C1203, |
| B5301, | B4601, | ,C0704,C | B1501, | C1502, |
| C0202, | B5301, | 0801,C12 | B1502, | C1601, |
| C0302, | C0202, | 02,C1203 | B1503, | A2501, |
| C0303, | C0302, | ,C1601,C | B3501, | A2902, |
| C0304, | C0303, | 1701,A02 | B3507, | B1501, |
| C0702, | C0304, | 01,A0205 | B4601, | B1502, |
| C1202, | C0702, | ,A0206,A | B5301, | B1503, |
| C1203, | C1202, | 6802,B13 | C0202, | B3501, |
| C1402, | C1203, | 02,B5101 | C0302, | B3507, |
| C1601, | C1402, | ,B5301,C | C0303, | B4601, |
| B3501, | C1601, | 0202,C06 | C0304, | B5301, |
| B3503, | B3501, | 02,C0704 | C0702, | C0202, |
| B3507, | B3503, | ,C0801,C | C1202, | C0302, |
| C0302, | B3507, | 1203,C15 | C1203, | C0303, |
| C0303, | C0202, | 02,C1601 | C1402, | C0304, |
| C0304, | C0302, | ,C1701,A | C1601, | C0702, |
| C0403, | C0303, | 0101,A30 | B3501, | C1202, |
| C0704, | C0304, | 02,B1502 | B3503, | C1203, |
| C1202, | C0403, | ,C1601,B | B3507, | C1402, |
| C1203, | C0704, | 1503,B18 | C0202, | C1403, |
| C1601, | C1202, | 01,B4002 | C0302, | C1601, |
| C1701, | C1203, | ,B4402,B | C0303, | B3501, |
| A0201, | C1601, | 4403,B07 | C0304, | B3503, |
| A0206, | C1701, | 04,B3503 | C0403, | B3507, |
| A6802, | A0201, | ,B4201,C | C0704, | C0202, |
| B1302, | A0206, | 0102,C03 | C0801, | C0302, |
| B5101, | A6802, | 03,C0304 | C1202, | C0303, |
| B5301, | B1302, | ,C0602,C | C1203, | C0304, |
| C0202, | B5101, | 0704,C12 | C1601, | C0403, |
| C0602, | B5301, | 03,C1601 | C1701, | C0704, |
| C0704, | C0202, | ,A0101,A | A0201, | C0801, |
| C0801, | C0602, | 0301,A30 | A0205, | C1202, |
| C1203, | C0704, | 02,A3601 | A0206, | C1203, |
| C1502, | C0801, | ,B1502,B | A6802, | C1601, |
| C1601, | C1203, | 1517,B18 | B1302, | C1701, |
| C1701, | C1502, | 01,B5701 | B5101, | A0201, |
| A3002, | C1601, | ,C1202,C | B5301, | A0205, |
| B1502, | C1701, | 1203,C16 | C0202, | A0206, |
| C1601, | A0101, | 01,A2902 | C0602, | A6802, |
| B1503, | A3002, | ,A3601,B | C0704, | B1302, |
| B1801, | B1502, | 1517,B35 | C0801, | B5101, |
| B4402, | C1601, | 07,B4601 | C1203, | B5301, |
| B4403, | B1503, | ,C0202,C | C1502, | C0202, |
| B0704, | B1801, | 0302,C12 | C1601, | C0602, |
| B3503, | B4402, | 02,C1203 | C1701, | C0704, |
| B4201, | B4403, | ,C1601,B | A0101, | C0801, |

TABLE 9C-continued

| Estimated Population Coverage | | | | |
|---|---|---|---|---|
| C0102, | B0704, | 1503,B57 | A3002, | C1203, |
| C0303, | B3503, | 01,B5802 | B1502, | C1502, |
| C0304, | B4201, | ,C1601,A | C1601, | C1601, |
| C0602, | C0102, | 0211,A23 | B1503, | C1701, |
| C0704, | C0303, | 01,A2407 | B1801, | A0101, |
| C1203, | C0304, | ,A2501,A | B4002, | A3002, |
| C1601, | C0602, | 2601,A32 | B4402, | B1501, |
| A0101, | C0704, | 01,A3402 | B4403, | B1502, |
| A0301, | C1203, | ,A6802,B | B0704, | C1203, |
| A3002, | C1601, | 1502,B35 | B3503, | C1601, |
| A3601, | A0101, | 07,B4601 | B4201, | B1503, |
| B1502, | A0301, | ,C1402,G | B5802, | B1801, |
| B1517, | A3002, | 0104,A26 | C0102, | B4002, |
| B1801, | A3601, | 01,A3002 | C0303, | B4006, |
| B5701, | B1502, | ,A3201,A | C0304, | B4402, |
| C1202, | B1517, | 3601,B15 | C0602, | B4403, |
| C1203, | B1801, | 03,B1517 | C0701, | B0704, |
| C1601, | B5701, | ,B1801,B | C0704, | B3503, |
| A2902, | C1202, | 4403,B46 | C0802, | B4201, |
| A3601, | C1203, | 01,B5701 | C1202, | B5802, |
| B1517, | C1601, | ,B5802,C | C1203, | C0102, |
| B3507, | A2902, | 0701,C07 | C1601, | C0303, |
| B4601, | A3601, | 02,C0704 | A0101, | C0304, |
| C0202, | B1517, | ,C1502,C | A0301, | C0602, |
| C0302, | B3507, | 1601,C17 | A2902, | C0701, |
| C1202, | B4601, | 01,A2601 | A3002, | C0704, |
| C1203, | C0202, | ,A2902,A | A3601, | C0802, |
| C1601, | C0302, | 3201,B15 | B1502, | C1202, |
| B1503, | C1202, | 01,B1801 | B1517, | C1203, |
| B5802, | C1203, | ,B3501,B | B1801, | C1601, |
| C1601, | C1601, | 3507,B44 | B5701, | A0101, |
| A0211, | B1503, | 02,B4403 | B5703, | A0301, |
| A2301, | B5802, | ,C1402,u | C1202, | A2902, |
| A2407, | C1601, | nknown, | C1203, | A3002, |
| A2501, | A0211, | C0704,un | C1601, | A3601, |
| A2601, | A2301, | known,A | A2902, | B1502, |
| A3201, | A2407, | 0201,A02 | A3601, | B1517, |
| A6802, | A2501, | 06,A0207 | B1517, | B1801, |
| B1502, | A2601, | ,A6802,G | B3507, | B5701, |
| C1402, | A3201, | 0101,G01 | B4601, | B5703, |
| G0104, | A6802, | 04,A0101 | C0202, | C0202, |
| A2601, | B1502, | ,A0201,A | C0302, | C1202, |
| A3002, | C1402, | 0206,A02 | C1202, | C1203, |
| A3201, | G0104, | 07,C0303 | C1203, | C1601, |
| B1503, | A2601, | ,C0304,C | C1601, | A0101, |
| B1517, | A3002, | 0401,C04 | B1503, | A2902, |
| B1801, | A3201, | 03,C0501 | B5701, | A3601, |
| B4403, | A3601, | ,C0704,C | B5802, | B1501, |
| B4601, | B1503, | 0801,C08 | C1601, | B1517, |
| B5701, | B1517, | 02,C1502 | A0211, | B3507, |
| B5802, | B1801, | ,A0201,A | A2301, | B4601, |

TABLE 9C-continued

| Estimated Population Coverage | | | | |
|---|---|---|---|---|
| C0701, | B4403, | 0202,A02 | A2407, | C0202, |
| C0704, | B4601, | 04,A0205 | A2501, | C0302, |
| C1502, | B5701, | ,A0211,B | A2601, | C1202, |
| C1601, | B5802, | 1402,B38 | A3201, | C1203, |
| A2902, | C0701, | 01,C0602 | A3402, | C1601, |
| A3201, | C0704, | ,C0701,C | A6802, | B1503, |
| B1801, | C1502, | 0702,A29 | B1502, | B5701, |
| B3501, | C1601, | 02,A3002 | B1801, | B5802, |
| B4402, | A2601, | ,A3201,B | B3507, | C1601, |
| B4403, | A2902, | 1503,B27 | B4601, | A0211, |
| C1402, | A3201, | 05,B4601 | C0202, | A2301, |
| unkno | B1501, | ,C0202,C | C1202, | A2407, |
| wn,C0 | B1801, | 0602,C07 | C1402, | A2501, |
| 704,un | B3501, | 01,C0702 | G0104, | A2601, |
| known, | B3507, | ,unknown | A2601, | A2902, |
| A0201, | B4402, | ,A0201,A | A3002, | A3201, |
| A0206, | B4403, | 0202,A02 | A3201, | A3402, |
| A0207, | C1402, | 03,A0204 | A3601, | A6802, |
| A6802, | unkno | ,A0207,A | B1503, | B1502, |
| G0104, | wn,C07 | 0201,A02 | B1517, | B1801, |
| A0201, | 04,unk | 02,A0204 | B1801, | B3507, |
| A0206, | flown, | ,A0207,B | B4403, | B4601, |
| A0207, | A0201, | 1301,C05 | B4601, | C0202, |
| C0303, | A0206, | 01,G0103 | B5701, | C1202, |
| C0304, | A0207, | ,G0104,A | B5802, | C1402, |
| C0401, | A6802, | 0202,A02 | C0701, | G0101, |
| C0403, | G0104, | 03,A0204 | C0702, | G0104, |
| C0501, | A0101, | ,A0205,A | C0704, | A2601, |
| C0801, | A0201, | 0206,A02 | C1502, | A3002, |
| C0802, | A0206, | 11,A6802 | C1601, | A3201, |
| C1502, | A0207, | ,C1203,C | C1701, | A3601, |
| A0201, | C0303, | 1502,A02 | A2501, | B1503, |
| A0202, | C0304, | 01,A0202 | A2601, | B1517, |
| A0204, | C0401, | ,A0203,A | A2902, | B1801, |
| A0211, | C0403, | 0204,A02 | A3201, | B4403, |
| B1402, | C0501, | 05,A0206 | B1501, | B4601, |
| B3801, | C0704, | ,A0207,A | B1801, | B5701, |
| C0602, | C0801, | 0211,A25 | B3501, | B5802, |
| C0701, | C0802, | 01,A2601 | B3507, | C0701, |
| C0702, | C1502, | ,A6802,B | B4402, | C0702, |
| A2902, | A0201, | 1302,C02 | B4403, | C0704, |
| A3201, | A0202, | 02,C0602 | C1402, | C1502, |
| B1503, | A0204, | ,C1203,C | C1403, | C1601, |
| B2705, | A0211, | 1502,C17 | unknow | C1701, |
| B4601, | B1402, | 01,A0201 | n,C070 | A2501, |
| C0202, | B3801, | ,A0202,A | 4,unkno | A2601, |
| C0602, | C0602, | 0203,A02 | wn,A02 | A2902, |
| C0701, | C0701, | 04,A0207 | 01,A02 | A3201, |
| C0702, | C0702, | ,B1302,B | 06,A02 | B1501, |
| unkno | A2902, | 3801,B07 | 07,A68 | B1801, |
| wn,A0 | A3201, | 02,B0704 | 02,G01 | B3501, |

TABLE 9C-continued

| Estimated Population Coverage | | | | |
|---|---|---|---|---|
| 201,A0 | B1503, | ,B0801,B | 01,G01 | B3507, |
| 202,A0 | B2705, | 3503,B35 | 03,G01 | B4402, |
| 203,A0 | B4601, | 07,B4201 | 04,A01 | B4403, |
| 204,A0 | C0202, | ,B5501,B | 01,A02 | C0202, |
| 207,A0 | C0602, | 5502,B56 | 01,A02 | C1202, |
| 201,A0 | C0701, | 01,C0403 | 06,A02 | C1402, |
| 202,A0 | C0702, | ,C0704,C | 07,C03 | C1403, |
| 204,A0 | unkno | 0801,C17 | 03,C03 | unkno |
| 207,B1 | wn,A0 | 01,unkno | 04,C04 | wn,C07 |
| 301,G0 | 201,A0 | wn,A020 | 01,C04 | 04,unk |
| 103,G0 | 202,A0 | 1,A0202, | 03,C05 | nown, |
| 104,A0 | 203,A0 | A0203,A | 01,C07 | A0201, |
| 202,A0 | 204,A0 | 0204,A02 | 04,C08 | A0206, |
| 203,A0 | 207,A0 | 05,A0206 | 01,C08 | A0207, |
| 205,A0 | 201,A0 | ,A0211,A | 02,C15 | A6802, |
| 206,A0 | 202,A0 | 6802,B13 | 02,A02 | G0101, |
| 211,A6 | 204,A0 | 02,B4006 | 01,A02 | G0103, |
| 802,C1 | 207,B1 | ,B5101,B | 02,A02 | G0104, |
| 203,C1 | 301,G0 | 5201,B54 | 04,A02 | A0101, |
| 502,A0 | 103,G0 | 01,B5502 | 05,A02 | A0201, |
| 201,A0 | 104,A0 | ,B5601,C | 11,A23 | A0206, |
| 202,A0 | 202,A0 | 0704,C12 | 01,B14 | A0207, |
| 203,A0 | 203,A0 | 03,C1701 | 02,B38 | C0303, |
| 204,A0 | 205,A0 | ,G0101,G | 01,C06 | C0304, |
| 205,A0 | 206,A0 | 0104,A02 | 02,C07 | C0401, |
| 206,A0 | 211,A6 | 01,A0203 | 01,C07 | C0403, |
| 207,A0 | 802,C1 | ,A0205,A | 02,A29 | C0501, |
| 211,A2 | 203,C1 | 0206,A02 | 02,A30 | C0704, |
| 601,A6 | 502,A0 | 07,A2601 | 02,A32 | C0801, |
| 802,B1 | 201,A0 | ,A6802,B | 01,B15 | C0802, |
| 302,C0 | 202,A0 | 5101,B52 | 03,B27 | C1502, |
| 202,C0 | 203,A0 | 01,C0102 | 05,B46 | A0201, |
| 602,C1 | 204,A0 | ,C0403,C | 01,C02 | A0202, |
| 203,C1 | 205,A0 | 0602,C07 | 02,C06 | A0204, |
| 502,C1 | 206,A0 | 04,G0101 | 02,C07 | A0205, |
| 701,A0 | 207,A0 | ,G0103,G | 01,C07 | A0211, |
| 201,A0 | 211,A2 | 0104,A02 | 02,unkn | A2301, |
| 202,A0 | 501,A2 | 01,A0202 | own,A0 | B1402, |
| 203,A0 | 601,A6 | ,A0203,A | 201,A0 | B3801, |
| 204,A0 | 802,B1 | 0204,A02 | 202,A0 | C0602, |
| 207,B1 | 302,C0 | 05,A0206 | 203,A0 | C0701, |
| 302,B0 | 202,C0 | ,A0207,A | 204,A0 | C0702, |
| 702,B0 | 602,C1 | 0211,A29 | 207,A0 | A2902, |
| 704,B0 | 203,C1 | 02,A3201 | 201,A0 | A3002, |
| 801,B4 | 502,C1 | ,B0801,B | 202,A0 | A3201, |
| 201,B5 | 701,A0 | 1301,B13 | 204,A0 | B1503, |
| 501,B5 | 201,A0 | 02,B1510 | 207,B1 | B2705, |
| 502,B5 | 202,A0 | ,B1517,B | 301,C0 | B4601, |
| 601,C0 | 203,A0 | 3501,B35 | 501,G0 | B5701, |
| 704,C0 | 204,A0 | 03,B3507 | 103,G0 | C0202, |
| 801,C1 | 207,B1 | ,B3801,C | 104,A0 | C0602, |

TABLE 9C-continued

| Estimated Population Coverage | | | | |
| --- | --- | --- | --- | --- |
| 701,un | 302,B0 | 0102,C03 | 201,A0 | C0701, |
| known, | 702,B0 | 02,C0303 | 202,A0 | C0702, |
| A0201, | 704,B0 | ,C0304,C | 203,A0 | unkno |
| A0202, | 801,B3 | 0401,C04 | 204,A0 | wn,A0 |
| A0203, | 503,B3 | 03,C0501 | 205,A0 | 201,A0 |
| A0204, | 507,B4 | ,C0602,C | 206,A0 | 202,A0 |
| A0205, | 201,B5 | 0701,C07 | 211,A6 | 203,A0 |
| A0206, | 501,B5 | 02,C0704 | 802,C1 | 204,A0 |
| A0211, | 502,B5 | ,C0801,C | 203,C1 | 207,A0 |
| A6802, | 601,C0 | 1402,C14 | 502,A0 | 201,A0 |
| B1302, | 704,C0 | 03,C1502 | 201,A0 | 202,A0 |
| B4006, | 801,C1 | ,C1601,C | 202,A0 | 204,A0 |
| B5101, | 701,un | 1701,G01 | 203,A0 | 207,B1 |
| B5201, | known, | 01,G0103 | 204,A0 | 301,C0 |
| B5401, | A0201, | ,G0104 | 205,A0 | 501,C0 |
| B5502, | A0202, | | 206,A0 | 802,G0 |
| B5601, | A0203, | | 207,A0 | 103,G0 |
| C0704, | A0204, | | 211,A2 | 104,A0 |
| C1203, | A0205, | | 501,A2 | 201,A0 |
| C1701, | A0206, | | 601,A6 | 202,A0 |
| G0101, | A0211, | | 802,B1 | 203,A0 |
| G0104, | A6802, | | 302,C0 | 204,A0 |
| A0201, | B1302, | | 202,C0 | 205,A0 |
| A0203, | B4006, | | 602,C1 | 206,A0 |
| A0205, | B5101, | | 203,C1 | 211,A6 |
| A0206, | B5201, | | 502,C1 | 802,C1 |
| A0207, | B5401, | | 701,A0 | 203,C1 |
| A2601, | B5502, | | 201,A0 | 502,A0 |
| A6802, | B5601, | | 202,A0 | 201,A0 |
| B5101, | C0704, | | 203,A0 | 202,A0 |
| B5201, | C1203, | | 204,A0 | 203,A0 |
| C0102, | C1701, | | 207,B1 | 204,A0 |
| C0403, | G0101, | | 301,B1 | 205,A0 |
| C0602, | G0104, | | 302,B3 | 206,A0 |
| A0201, | A0201, | | 801,C0 | 207,A0 |
| A0202, | A0203, | | 501,B0 | 211,A2 |
| A0203, | A0205, | | 702,B0 | 501,A2 |
| A0204, | A0206, | | 704,B0 | 601,A6 |
| A0205, | A0207, | | 801,B3 | 802,B1 |
| A0206, | A2601, | | 503,B3 | 302,C0 |
| A0207, | A6802, | | 507,B4 | 202,C0 |
| A0211, | B5101, | | 201,B5 | 602,C1 |
| A2902, | B5201, | | 501,B5 | 203,C1 |
| A3201, | C0102, | | 502,B5 | 502,C1 |
| B0801, | C0403, | | 601,C0 | 701,A0 |
| B1301, | C0602, | | 403,C0 | 201,A0 |
| B1302, | C0704, | | 704,C0 | 202,A0 |
| B1510, | A0201, | | 801,C1 | 203,A0 |
| B1517, | A0202, | | 701,unk | 204,A0 |
| B3501, | A0203, | | nown,A | 207,B1 |
| B3503, | A0204, | | 0201,A | 301,B1 |

TABLE 9C-continued

| Estimated Population Coverage | | | |
|---|---|---|---|
| B3801, | A0205, | 0202,A | 302,B3 |
| C0102, | A0206, | 0203,A | 801,C0 |
| C0302, | A0207, | 0204,A | 501,B0 |
| C0303, | A0211, | 0205,A | 702,B0 |
| C0304, | A2902, | 0206,A | 704,B0 |
| C0403, | A3201, | 0211,A | 801,B3 |
| C0602, | B0801, | 6802,B | 503,B3 |
| C0701, | B1301, | 1302,B | 507,B4 |
| C0702, | B1302, | 4006,B | 201,B5 |
| C0704, | B1510, | 5101,B | 501,B5 |
| C0801, | B1517, | 5201,B | 502,B5 |
| C1402, | B3501, | 5401,B | 601,C0 |
| C1403, | B3503, | 5501,B | 403,C0 |
| C1502, | B3507, | 5502,B | 704,C0 |
| C1601, | B3801, | 5601,C | 801,C1 |
| C1701, | C0102, | 0704,C | 701,un |
| G0101, | C0302, | 1203,C | known, |
| G0103, | C0303, | 1701,G | A0201, |
| G0104 | C0304, | 0101,G | A0202, |
| | C0401, | 0104,A | A0203, |
| | C0403, | 0201,A | A0204, |
| | C0501, | 0203,A | A0205, |
| | C0602, | 0205,A | A0206, |
| | C0701, | 0206,A | A0211, |
| | C0702, | 0207,A | A6802, |
| | C0704, | 2601,A | B1302, |
| | C0801, | 6802,B | B4006, |
| | C1402, | 5101,B | B5101, |
| | C1403, | 5201,C | B5201, |
| | C1502, | 0102,C | B5401, |
| | C1601, | 0403,C | B5501, |
| | C1701, | 0602,C | B5502, |
| | G0101, | 0704,G | B5601, |
| | G0103, | 0101,G | C0704, |
| | G0104 | 0103,G | C1203, |
| | | 0104,A | C1701, |
| | | 0201,A | G0101, |
| | | 0202,A | G0104, |
| | | 0203,A | A0201, |
| | | 0204,A | A0203, |
| | | 0205,A | A0205, |
| | | 0206,A | A0206, |
| | | 0207,A | A0207, |
| | | 0211,A | A2601, |
| | | 2407,A | A6802, |
| | | 2902,A | B5101, |
| | | 3201,B | B5201, |
| | | 0801,B | C0102, |
| | | 1301,B | C0403, |
| | | 1302,B | C0602, |
| | | 1502,B | C0704, |

TABLE 9C-continued

| Estimated Population Coverage | | |
|---|---|---|
| | 1510,B | G0101, |
| | 1517,B | G0103, |
| | 3501,B | G0104, |
| | 3503,B | A0201, |
| | 3507,B | A0202, |
| | 3801,B | A0203, |
| | 4601,C | A0204, |
| | 0102,C | A0205, |
| | 0302,C | A0206, |
| | 0303,C | A0207, |
| | 0304,C | A0211, |
| | 0401,C | A2407, |
| | 0403,C | A2902, |
| | 0501,C | A3201, |
| | 0602,C | B0801, |
| | 0701,C | B1301, |
| | 0702,C | B1302, |
| | 0704,C | B1502, |
| | 0801,C | B1510, |
| | 1402,C | B1517, |
| | 1403,C | B3501, |
| | 1502,C | B3503, |
| | 1601,C | B3507, |
| | 1701,G | B3801, |
| | 0101,G | B4601, |
| | 0103,G | B5201, |
| | 0104 | B5301, |
| | | C0102, |
| | | C0302, |
| | | C0303, |
| | | C0304, |
| | | C0401, |
| | | C0403, |
| | | C0501, |
| | | C0602, |
| | | C0701, |
| | | C0702, |
| | | C0704, |
| | | C0801, |
| | | C1402, |
| | | C1403, |
| | | C1502, |
| | | C1601, |
| | | C1701, |
| | | G0101, |
| | | G0103, |
| | | G0104 |

TABLE 9C-continued

| | Estimated Population Coverage | | | | | | | | | | | | | | |
|---|---|---|---|---|---|---|---|---|---|---|---|---|---|---|---|
| | Peptide | thr1.6_assign_alleles | thr1.6_num alleles | thr1.6_coverage | thr1.7_assign_alleles | thr1.7_num_alleles | thr1.7_coverage | thr1.8_assign_alleles | thr1.8_num_alleles | thr1.8_coverage | thr1.9_assign_alleles | thr1.9_num_alleles | thr1.9_coverage | thr2_assign_alleles | thr2_num_alleles | thr2_coverage |
| A549 | DEFVVVTV (SEQ ID NO: 11) | A6802, B1302, B1402, B1801, B3701, B4001, B4002, B4006, B4402, B4403, B4501, B4901, B5001, B5101, B5201, C0704 | 16 | 0.6072 | A6802, B1302, B1402, B1801, B3701, B4001, B4002, B4006, B4402, B4403, B4501, B4901, B5001, B5101, B5201, C0704 | 16 | 0.6072 | A6802,B1302,B1402,B1801,B3701,B4001,B4002,B4006,B4402,B4403,B4501,B4901,B5001,B5101,B5201,C0704 | 16 | 0.6072 | A6802, B1302, B1402, B1801, B3701, B4001, B4002, B4006, B4402, B4403, B4501, B4901, B5001, B5101, B5201, C0704 | 16 | 0.6072 | A6802, B1302, B1402, B1801, B3701, B4001, B4002, B4006, B4402, B4403, B4501, B4901, B5001, B5101, B5201, C0704 | 16 | 0.6072 |
| | LEDKAFQL (SEQ ID NO: 10) | A0101, A0202, A0207, A3601, B1301, B1510, B1517, B1801, B3503, B3701, B3801, B4001, B4002, B4402, B4403, B4501, B5001, B5703, C0704, C0802, G0101 | 21 | 0.5963 | A0101, A0202, A0207, A3601, B1301, B1510, B1517, B1801, B3503, B3507, B3701, B3801, B4001, B4002, B4402, B4403, B4501, B5001, B5703, B5801, C0704, C0802, G0101 | 23 | 0.6419 | A0101,A0202,A0207,A3601,B1301,B1510,B1517,B1801,B3503,B3507,B3701,B3801,B4001,B4002,B4402,B4403,B4501,B5001,B5703,B5801,C0704,C0802,G0101 | 23 | 0.6419 | A0101, A0202, A0207, A3601, B1301, B1510, B1517, B1801, B3503, B3507, B3701, B3801, B4001, B4002, B4402, B4403, B4501, B5001, B5703, B5801, C0501, C0704, C0802, G0101 | 24 | 0.6611 | A0101, A0202, A0206, A0207, A3601, B1301, B1510, B1517, B1801, B3503, B3507, B3701, B3801, B3802, B4001, B4002, B4402, B4403, B4501, B4901, B5001, B5301, B5703, B5801, C0501, C0704, C0802, G0101 | 28 | 0.7173 |

TABLE 9C-continued

| | Estimated Population Coverage | | | | | | | | | | | | | | |
|---|---|---|---|---|---|---|---|---|---|---|---|---|---|---|---|
| TVIEVQGY (SEQ ID NO: 22) | A0101, A0301, A2501, A2601, A2902, A3002, A3201, A3601, A6801, B1501, B1502, B3501, B5301 | 13 | 0.5045 | A0101, A0301, A2501, A2601, A2902, A3002, A3201, A3601, A6801, B1501, B1502, B3501, B5301 | 13 | 0.5045 | A0101,A0301,A2501,A2601,A2902,A3002,A3201,A3601,A6801,B1501,B1502,B3501,B5301 | 13 | 0.5045 | A0101, A0301, A2501, A2601, A2902, A3002, A3201, A3601, A6801, B1501, B1502, B3501, B5301 | 13 | 0.5045 | A0101, A0301, A2501, A2601, A2902, A3002, A3201, A3601, A6801, B1501, B1502, B3501, B5301 | 13 | 0.5045 |
| EIKESVQTF (SEQ ID NO: 15) | A2501, A2601, A3401, B1501, B1502, B4601, C1202 | 7 | 0.2766 | A2501, A2601, A3401, B1501, B1502, B4601, C1202 | 7 | 0.2766 | A2501,A2601,A3401,B1501,B1502,B4601,C1202 | 7 | 0.2766 | A2501, A2601, A3401, B1501, B1502, B4601, C1202 | 7 | 0.2766 | A2501, A2601, A3401, B1501, B1502, B4601, C1202 | 7 | 0.2766 |
| FASEAARVV (SEQ ID NO: 17) | B3503, B5101, C0202, C0302, C0303, C0304, C0501, C0602, C0704, C0801, C0802, C1202, C1203, C1502, C1601 | 15 | 0.7590 | B3503, B5101, C0202, C0302, C0303, C0304, C0501, C0602, C0704, C0801, C0802, C1202, C1203, C1502, C1601 | 15 | 0.7590 | B3503,B5101,C0202,C0302,C0303,C0304,C0501,C0602,C0704,C0801,C0802,C1202,C1203,C1502,C1601 | 15 | 0.7590 | B3503, B5101, C0202, C0302, C0303, C0304, C0501, C0602, C0704, C0801, C0802, C1202, C1203, C1502, C1601 | 15 | 0.7590 | B3503, B5101, C0202, C0302, C0303, C0304, C0501, C0602, C0704, C0801, C0802, C1202, C1203, C1502, C1601 | 15 | 0.7590 |
| FAVDAAKAY (SEQ ID NO: 28) | A2501, A2902, B1501, B1502, B1503, B3501, B3507, B4601, B5301, C0202, C0302, C0303, C0304, C0702, C1202, C1203, | 19 | 0.7960 | A2501, A2902, B1501, B1502, B1503, B3501, B3507, B4601, B5301, C0202, C0302, C0303, C0304, C0702, C1202, C1203, | 19 | 0.7960 | A2501,A2902,B1501,B1502,B1503,B3501,B3507,B4601,B5301,C0202,C0302,C0303,C0304,C0702,C1202,C1203,C1402,C1403,C1601 | 19 | 0.7960 | A2501, A2902, B1501, B1502, B1503, B3501, B3507, B4601, B5301, C0202, C0302, C0303, C0304, C0702, C1202, C1203, | 19 | 0.7960 | A2501, A2601, A2902, B1501, B1502, B1503, B3501, B3507, B4601, B5301, C0202, C0302, C0303, C0304, C0702, C1202, | 20 | 0.8098 |

TABLE 9C-continued

Estimated Population Coverage

| | | | | | | | | | | | | | | | |
|---|---|---|---|---|---|---|---|---|---|---|---|---|---|---|---|
| | C1402, C1403, C1601 | | | C1402, C1403, C1601 | | | | | | C1402, C1403, C1601 | | | C1203, C1402, C1403, C1601 | | |
| LATNNLVVM (SEQ ID NO: 16) | B3501, B3503, B3507, C0202, C0302, C0303, C0304, C0403, C0704, C0801, C1202, C1203, C1601, C1701 | 14 | 0.6655 | B3501, B3503, B3507, C0202, C0302, C0303, C0304, C0403, C0704, C0801, C1202, C1203, C1601, C1701 | 14 | 0.6655 | B3501,B3503,B3507,C0202,C0302,C0303,C0304,C0403,C0704,C0801,C1202,C1203,C1601,C1701 | 14 | 0.6655 | B3501, B3503, B3507, C0202, C0302, C0303, C0304, C0403, C0704, C0801, C1202, C1203, C1601, C1701 | 14 | 0.6655 | B3501, B3503, B3507, C0202, C0302, C0303, C0304, C0403, C0704, C0801, C1202, C1203, C1601, C1701 | 14 | 0.6655 |
| NATNVVIKV (SEQ ID NO: 37) | A0201, A0205, A0206, A6802, B1302, B5101, B5301, C0202, C0602, C0704, C0801, C1203, C1502, C1601, C1701 | 15 | 0.7006 | A0201, A0205, A0206, A6802, B1302, B5101, B5301, C0202, C0602, C0704, C0801, C1203, C1502, C1601, C1701 | 15 | 0.7006 | A0201,A0205,A0206,A6802,B1302,B5101,B5301,C0202,C0602,C0704,C0801,C1203,C1502,C1601,C1701 | 15 | 0.7006 | A0201, A0205, A0206, A6802, B1302, B5101, B5301, C0202, C0602, C0704, C0801, C1203, C1502, C1601, C1701 | 15 | 0.7006 | A0201, A0205, A0206, A6802, B1302, B5101, B5301, C0202, C0602, C0704, C0801, C1203, C1502, C1601, C1701 | 15 | 0.7006 |
| QLTPTWRVY (SEQ ID NO: 38) | A0101, A3002, B1501, B1502, C1203, C1601 | 6 | 0.2722 | A0101, A0301, A3002, B1501, B1502, C1203, C1601 | 7 | 0.3371 | A0101,A0301,A3002,B1501,B1502,C1203,C1601 | 7 | 0.3371 | A0101, A0301, A2501, A3002, B1501, B1502, C1203, C1601 | 8 | 0.3437 | A0101, A0301, A2501, A3002, A3601, B1501, B1502, C1203, C1601 | 9 | 0.3495 |
| SEFSSLPSY (SEQ ID NO: 27) | B1503, B1801, B4002, B4006, B4402, B4403 | 6 | 0.2959 | B1502, B1503, B1801, B4002, B4006, B4402, B4403 | 7 | 0.3179 | B1502,B1503,B1801,B4002,B4006,B4402,B4403 | 7 | 0.3179 | B1502, B1503, B1801, B4002, B4006, B4402, B4403 | 7 | 0.3179 | B1502, B1503, B1801, B4002, B4006, B4402, B4403 | 7 | 0.3179 |

TABLE 9C-continued

| Estimated Population Coverage | | | | | | | | | | | | | | | |
|---|---|---|---|---|---|---|---|---|---|---|---|---|---|---|---|
| TA QNS VR VL (SEQ ID NO: 18) | B0704, B3503, B4201, B5802, C0102, C0303, C0304, C0602, C0701, C0704, C0802, C1202, C1203, C1601 | 14 | 0.7542 | B0704, B3503, B4201, B5802, C0102, C0303, C0304, C0602, C0701, C0704, C0802, C1202, C1203, C1601 | 14 | 0.7542 | B0704,B3 503,B420 1,B5802, C0102,C0 303,C030 4,C0602, C0701,C0 704,C080 1,C0802, C1202,C1 203,C160 1 | 15 | 0.7946 | B0704, B3503, B4201, B5802, C0102, C0303, C0304, C0602, C0701, C0704, C0801, C0802, C1202, C1203, C1601 | 15 | 0.7946 | B0704, B3503, B4201, B5802, C0102, C0303, C0304, C0602, C0701, C0704, C0801, C0802, C1202, C1203, C1601 | 15 | 0.7946 |
| TTT IKP VT Y (SEQ ID NO: 21) | A0101, A0301, A2902, A3002, A3601, B1501, B1502, B1517, B1801, B5701, B5703, B5801, C0202, C1202, C1203, C1601 | 16 | 0.5220 | A0101, A0301, A2902, A3002, A3601, B1501, B1502, B1517, B1801, B5701, B5703, B5801, C0202, C1202, C1203, C1601 | 16 | 0.5220 | A0101,A 0301,A29 02,A3002 ,A3601,B 1501,B15 02,B1517 ,B1801,B 5701,B57 03,B5801 ,C0202,C 1202,C12 03,C1601 | 16 | 0.5220 | A0101, A0301, A2902, A3002, A3601, B1501, B1502, B1517, B1801, B5701, B5703, B5801, C0202, C1202, C1203, C1601 C1203, | 16 | 0.5220 | A0101, A0301, A2501, A2902, A3002, A3201, A3601, B1501, B1502, B1517, B1801, B5701, B5703, B5801, C0202, C1202, C1601 | 18 | 0.5424 |
| VA TSR TLS Y (SEQ ID NO: 41) | A0101, A2902, A3601, B1501, B1517, B3507, B4601, C0202, C0302, C1202, C1203, C1601 C1203, C1601 | 12 | 0.4344 | A0101, A2902, A3601, B1501, B1517, B3507, B4601, B5301, B5801, C0202, C0302, C1202, | 14 | 0.4882 | A0101,A 2902,A36 01,B1501 ,B1517,B 3507,B46 01,B5301 ,B5801,C 0202,C03 02,C1202 ,C1203,C 1601 | 14 | 0.4882 | A0101, A2601, A2902, A3601, B1501, B1517, B3507, B4601, B5301, B5801, C0202, C0302, C1202, C1203, C1601 | 15 | 0.5244 | A0101, A2601, A2902, A3601, B1501, B1517, B3507, B4601, B5301, B5801, C0202, C0302, C1202, C1203, C1601 | 15 | 0.5244 |

TABLE 9C-continued

| Estimated Population Coverage | | | | | | | | | | | | | | | |
|---|---|---|---|---|---|---|---|---|---|---|---|---|---|---|---|
| VG YL QPR TF (SEQ ID NO: 39) | B1503, B5701, B5802, C1601 | 4 | 0.1048 | B1503, B5701, B5802, C1601 | 4 | 0.1048 | B1503,B5701,B5802,C1601 | 4 | 0.1048 | B1503, B5101, B5701, B5802, C1601 | 5 | 0.1986 | B1503, B5101, B5701, B5802, C1601 | 5 | 0.1986 |
| EIL DIT PCS F (SEQ ID NO: 33) | A0211, A2301, A2407, A2501, A2601, A2902, A3201, A3402, A6802, B1502, B1801, B3507, B4601, C0202, C1202, C1402, C1403, G0101, G0104 | 19 | 0.4585 | A0211, A2301, A2407, A2501, A2601, A2902, A3201, A3402, A6802, B1502, B1801, B3501, B3507, B4601, C0202, C1202, C1402, C1403, G0101, G0104 | 20 | 0.5205 | A0211,A2301,A2407,A2501,A2601,A2902,A3201,A3402,A6802,B1502,B1801,B3501,B3507,B4601,C0202,C0302,C1202,C1402,C1403,G0101,G0104 | 21 | 0.5463 | A0211, A2301, A2407, A2501, A2601, A2902, A3201, A3401, A3402, A6802, B1502, B1801, B3501, B3507, B4601, C0202, C0302, C1202, C1402, C1403, G0101, G0104 | 22 | 0.5628 | A0211, A2301, A2407, A2501, A2601, A2902, A3201, A3401, A3402, A6802, B1502, B1801, B3501, B3507, B4601, C0202, C0302, C0403, C1202, C1402, C1403, G0101, G0104 | 23 | 0.5820 |
| KNI DG YFK IY (SEQ ID NO: 36) | A2601, A3002, A3201, A3601, B1503, B1517, B1801, B2705, B4403, B4601, B5001, B5701, B5802, C0701, C0702, C0704, C1202, C1502, C1601, C1701 | 20 | 0.7091 | A2601, A3002, A3201, A3601, B1503, B1517, B1801, B2705, B4402, B4403, B4601, B5001, B5701, B5802, C0202, C0602, C0701, C0702, C0704, C1202, | 23 | 0.7920 | A2601,A3002,A3201,A3601,B1503,B1517,B1801,B2705,B4402,B4403,B4601,B5001,B5701,B5802,C0202,C0602,C0701,C0702,C0704,C1202,C1502,C1601,C1701 | 23 | 0.7920 | A2601, A3002, A3201, A3601, B1503, B1517, B1801, B2705, B4402, B4403, B4601, B5001, B5701, B5802, C0202, C0602, C0701, C0702, C0704, C1202, | 26 | 0.8156 | A2601, A3002, A3201, A3601, B1503, B1517, B1801, B2705, B4402, B4403, B4601, B5001, B5701, B5802, C0202, C0602, C0701, C0702, C0704, C1202, | 27 | 0.8321 |

TABLE 9C-continued

| | | Estimated Population Coverage | | | | | | | | | | | | | | |
|---|---|---|---|---|---|---|---|---|---|---|---|---|---|---|---|---|
| | | | | | C1502, C1601, C1701 | | | | | | C1203, C1403, C1502, C1601, C1701, G0103 | | | C1203, C1402, C1403, C1502, C1601, C1701, G0103 | | |
| | EEFEPSTQYEY (SEQ ID NO: 20) | A2501, A2601, A2902, A3002, A3201, B1501, B1503, B1801, B3501, B3507, B4402, B4403, C0202, C1202, C1402, C1403 | 16 | 0.5679 | A2501, A2601, A2902, A3002, A3201, B1501, B1503, B1801, B3501, B3507, B4402, B4403, B4501, C0202, C1202, C1402, C1403 | 17 | 0.5786 | A2501,A2601,A2902,A3002,A3201,B1501,B1503,B1801,B3501,B3507,B4402,B4403,B4501,B5001,C0202,C1202,C1402,C1403 | 18 | 0.5885 | A2501, A2601, A2902, A3002, A3201, B1501, B1503, B1801, B3501, B3507, B4402, B4403, B4501, B5001, C0202, C1202, C1402, C1403 | 18 | 0.5885 | A2501, A2601, A2902, A3002, A3201, B1501, B1503, B1801, B3501, B3507, B4402, B4403, B4501, B5001, C0202, C1202, C1402, C1403 | 18 | 0.5885 |
| | EILDITPCSFG (SEQ ID NO: 47) | unknown | 0 | 0.0000 | unknown | 0 | 0.0000 | unknown | 0 | 0.0000 | unknown | 0 | 0.0000 | unknown | 0 | 0.0000 |
| HEK293 | AGTDTTITV (SEQ ID NO: 26) | C0704 | 1 | 0.0291 | C0704 | 1 | 0.0291 | C0704,C1502 | 2 | 0.0942 | C0704, C1502 | 2 | 0.0942 | B1302, C0704, C1502 | 3 | 0.1198 |
| | APRITFGGP (SEQ ID NO: 42) | unknown | 0 | 0.0000 | unknown | 0 | 0.0000 | unknown | 0 | 0.0000 | unknown | 0 | 0.0000 | unknown | 0 | 0.0000 |

TABLE 9C-continued

| Estimated Population Coverage | | | | | | | | | | | | | | | |
|---|---|---|---|---|---|---|---|---|---|---|---|---|---|---|---|
| ELPDEFVVV (SEQ ID NO: 12) | A0201, A0206, A0207, A6802, G0101, G0103, G0104 | 7 | 0.3948 | A0201, A0206, A0207, A6802, G0101, G0103, G0104 | 7 | 0.3948 | A0201,A0206,A0207,A6802,G0101,G0103,G0104 | 7 | 0.3948 | A0201, A0206, A0207, A6802, G0101, G0103, G0104 | 7 | 0.3948 | A0201, A0206, A0207, A6802, G0101, G0103, G0104 | 7 | 0.3948 |
| FGDDTVIEV (SEQ ID NO: 23) | A0101, A0201, A0206, A0207, C0303, C0304, C0401, C0403, C0501, C0704, C0801, C0802, C1502 | 13 | 0.8132 | A0101, A0201, A0206, A0207, C0303, C0304, C0401, C0403, C0501, C0704, C0801, C0802, C1203, C1502, C1701 | 15 | 0.8370 | A0101,A0201,A0206,A0207,B5101,C0303,C0304,C0401,C0403,C0501,C0602,C0704,C0801,C0802,C1203,C1502,C1701 | 17 | 0.8849 | A0101, A0201, A0206, A0207, B5101, C0303, C0304, C0401, C0403, C0501, C0602, C0704, C0801, C0802, C1203, C1502, C1701 | 17 | 0.8849 | A0101, A0201, A0206, A0207, B5101, C0303, C0304, C0401, C0403, C0501, C0602, C0704, C0801, C0802, C1203, C1502, C1701 | 17 | 0.8849 |
| GLITLSYHL (SEQ ID NO: 5) | A0201, A0202, A0204, A0205, A0211, A2301 | 6 | 0.3581 | A0201, A0202, A0204, A0205, A0211, A2301, B1301 | 7 | 0.3907 | A0201,A0202,A0204,A0205,A0211,A2301,B1301 | 7 | 0.3907 | A0201, A0202, A0204, A0205, A0207, A0211, A2301, B1301 | 8 | 0.4226 | A0201, A0202, A0204, A0205, A0207, A0211, A2301, B1301 | 8 | 0.4226 |
| IRQEEVQEL (SEQ ID NO: 31) | B1402, B3801, C0602, C0701, C0702 | 5 | 0.4764 | B1402, B3801, C0602, C0701, C0702 | 5 | 0.4764 | B1402,B3801,C0602,C0701, C0702 | 5 | 0.4764 | B1402, B3801, C0602, C0701, C0702 | 5 | 0.4764 | B1402, B3801, C0602, C0701, C0702 | 5 | 0.4764 |
| KRVDWTIEY | A2902, A3002, A3201, B1503, | 12 | 0.5919 | A2902, A3002, A3201, B1503, | 13 | 0.6141 | A2902,A3002,A3201,B1503,B1517,B | 14 | 0.6165 | A2902, A3002, A3201, B1501, | 15 | 0.6440 | A0301, A2902, A3002, A3201, | 16 | 0.6751 |

TABLE 9C-continued

| Estimated Population Coverage | | | | | | | | | | | | | | | |
|---|---|---|---|---|---|---|---|---|---|---|---|---|---|---|---|
| (SEQ ID NO: 29) | B2705, B4601, B5701, C0202, C0602, C0701, C0702, G0104 | | | B2705, B4601, B5701, C0202, C0602, C0701, C0702, C1203, G0104 | | | 2705,B46 01,B5701 ,C0202,C 0602,C07 01,C0702 ,C1203,G 0104 | | | B1503, B1517, B2705, B4601, B5701, C0202, C0602, C0701, C0702, C1203, G0104 | | | B1501, B1503, B1517, B2705, B4601, B5701, C0202, C0602, C0701, C0702, C1203, G0104 | | |
| ML LGS ML YM (SEQ ID NO: 4) | unknown | 0 | 0.0000 | unknown | 0 | 0.0000 | unknown | 0 | 0.0000 | unknown | 0 | 0.0000 | unknown | 0 | 0.0000 |
| NL NES LID L (SEQ ID NO: 40) | A0201, A0202, A0203, A0204, A0207 | 5 | 0.3603 | A0201, A0202, A0203, A0204, A0207 | 5 | 0.3603 | A0201,A 0202,A02 03,A0204 ,A0205,A 0207 | 6 | 0.3738 | A0201, A0202, A0203, A0204, A0205, A0207, C0102 | 7 | 0.4755 | A0201, A0202, A0203, A0204, A0205, A0207, C0102 | 7 | 0.4755 |
| SLE DK AFQ L (SEQ ID NO: 7) | A0201, A0202, A0204, A0207, A0211, B1301, C0501, C0802, G0101, G0103, G0104 | 11 | 0.4311 | A0201, A0202, A0204, A0207, A0211, B0801, B1301, C0501, C0802, G0101, G0103, G0104 | 12 | 0.4651 | A0201,A 0202,A02 04,A0207 ,A0211,B 0801,B13 01,C0501 ,C0802,G 0101,G01 03,G0104 | 12 | 0.4651 | A0201, A0202, A0204, A0205, A0207, A0211, B0801, B1301, C0501, C0802, G0101, G0103, G0104 | 13 | 0.4763 | A0201, A0202, A0204, A0205, A0207, A0211, B0801, B1301, C0501, C0802, G0101, G0103, G0104 | 13 | 0.4763 |
| STS AFV ETV | A0201, A0202, A0203, | 10 | 0.4802 | A0201, A0202, A0203, | 11 | 0.5041 | A0201,A 0202,A02 03,A0204 | 12 | 0.5184 | A0201, A0202, A0203, | 12 | 0.5184 | A0201, A0202, A0203, | 12 | 0.5184 |

TABLE 9C-continued

| Estimated Population Coverage | | | | | | | | | | | | | | | |
|---|---|---|---|---|---|---|---|---|---|---|---|---|---|---|---|
| (SEQ ID NO: 19) | A0204, A0205, A0206, A0211, A6802, C1203, C1502 | | | A0204, A0205, A0206, A0211, A6802, B5201, C1203, C1502 | | | ,A0205,A0206,A0211,A6802,B1302,B5201,C1203,C1502 | | | A0204, A0205, A0206, A0211, A6802, B1302, B5201, C1203, C1502 | | | A0204, A0205, A0206, A0211, A6802, B1302, B5201, C1203, C1502 | | |
| SVV SKY VK V (SEQ ID NO: 30) | A0201, A0202, A0203, A0204, A0205, A0206, A0207, A0211, A2501, A2601, A6802, B1302, C0202, C0602, C1203, C1502, C1701 | 17 | 0.6632 | A0201, A0202, A0203, A0204, A0205, A0206, A0207, A0211, A2501, A2601, A6802, B1302, C0202, C0602, C1203, C1502, C1701 | 17 | 0.6632 | A0201,A0202,A0203,A0204,A0205,A0206,A0207,A0211,A2501,A2601,A6802,B1302,C0202,C0602,C1203,C1502,C1701 | 17 | 0.6632 | A0201, A0202, A0203, A0204, A0205, A0206, A0207, A0211, A2501, A2601, A6802, B1302, C0202, C0602, C1203, C1502, C1701 | 17 | 0.6632 | A0201, A0202, A0203, A0204, A0205, A0206, A0207, A0211, A2501, A2601, A6802, B1302, C0202, C0602, C1203, C1502, C1701 | 17 | 0.6632 |
| YL NST NV TI (SEQ ID NO: 24) | A0201, A0202, A0203, A0204, A0207, B1301, B1302, B3801, C0501 | 9 | 0.4499 | A0201, A0202, A0203, A0204, A0207, B1301, B1302, B3801, C0501 | 9 | 0.4499 | A0201,A0202,A0203,A0204,A0207,B1301,B1302,B3801,C0501 | 9 | 0.4499 | A0201, A0202, A0203, A0204, A0207, B1301, B1302, B3801, C0102, C0501 | 10 | 0.5415 | A0201, A0202, A0203, A0204, A0207, B1301, B1302, B3801, C0102, C0501 | 10 | 0.5415 |
| APH GH VM VEL (SEQ ID NO: 14) | B0702, B0704, B0801, B1510, B3503, B3507, B4201, B5501, B5502, B5601, C0403, C0704, | 14 | 0.4409 | B0702, B0704, B0801, B1510, B3501, B3503, B3507, B4001, B4201, B5501, B5502, B5601, | 17 | 0.6508 | B0702,B0704,B0801,B1510,B3501,B3503,B3507,B4001,B4201,B5501,B5502,B5601,C0102,C0403,C0704,C0801, | 17 | 0.6508 | B0702, B0704, B0801, B1510, B3501, B3503, B3507, B4001, B4201, B5501, B5502, B5601, | 17 | 0.6508 | B0702, B0704, B0801, B1510, B3501, B3503, B3507, B4001, B4201, B5501, B5502, B5601, | 17 | 0.6508 |

TABLE 9C-continued

| Estimated Population Coverage | | | | | | | | | | | | | | | |
|---|---|---|---|---|---|---|---|---|---|---|---|---|---|---|---|
| | C0801, C1701 | | | C0102, C0403, C0704, C0801, C1701 | | | C1701 | | | C0102, C0403, C0704, C0801, C1701 | | | C0102, C0403, C0704, C0801, C1701 | | |
| GP MV LRG LIT (SEQ ID NO: 6) | unknown | 0 | 0.0000 | unknown | 0 | 0.0000 | unknown | 0 | 0.0000 | unknown | 0 | 0.0000 | unknown | 0 | 0.0000 |
| KAF QLT PIA V (SEQ ID NO: 13) | A0201, A0202, A0203, A0204, A0205, A0206, A0211, A6802, B1302, B4006, B5101, B5201, B5401, B5501, B5502, B5601, C0304, C0704, C1203, C1701, G0101, G0104 | 22 | 0.6947 | A0201, A0202, A0203, A0204, A0205, A0206, A0211, A6802, B1302, B4006, B5101, B5201, B5401, B5501, B5502, B5601, C0304, C0704, C1203, C1701, G0101, G0103, G0104 | 23 | 0.6947 | A0201,A0202,A0203,A0204,A0205,A0206,A0211,A6802,B1302,B4006,B5101,B5201,B5401,B5501,B5502,B5601,C0304,C0704,C1203,C1701,G0101,G0103,G0104 | 23 | 0.6947 | A0201, A0202, A0203, A0204, A0205, A0206, A0211, A6802, B1302, B4006, B5101, B5201, B5401, B5501, B5502, B5601, C0304, C0704, C1203, C1701, G0101, G0103, G0104 | 23 | 0.6947 | A0201, A0202, A0203, A0204, A0205, A0206, A0211, A6802, B1302, B4006, B5101, B5201, B5401, B5501, B5502, B5601, C0304, C0704, C0801, C1203, C1701, G0101, G0103, G0104 | 24 | 0.7261 |
| ELP DEF VV VT V (SEQ ID NO: 8) | A0201, A0203, A0205, A0206, A0207, A2601, A6802, B0801, B5101, B5201, C0102, C0403, C0602, C0704, | 17 | 0.7206 | A0201, A0203, A0205, A0206, A0207, A2601, A6802, B0801, B1302, B5101, B5201, C0102, C0403, C0501, | 19 | 0.7463 | A0201,A0203,A0205,A0206,A0207,A2601,A6802,B0801,B1302,B5101,B5201,C0102,C0403,C0501,C0602,C0704,G0101,G0103,G01 | 19 | 0.7463 | A0201, A0202, A0203, A0204, A0205, A0206, A0207, A0211, A2601, A6802, B0801, B1302, B5101, B5201, | 22 | 0.7562 | A0201, A0202, A0203, A0204, A0205, A0206, A0207, A0211, A2501, A2601, A6802, B0801, B1302, B5101, | 23 | 0.7593 |

TABLE 9C-continued

| Estimated Population Coverage | | | | | | | | | | | | | | | |
|---|---|---|---|---|---|---|---|---|---|---|---|---|---|---|---|
| | G0101,<br>G0103,<br>G0104 | | | C0602,<br>C0704,<br>G0101,<br>G0103,<br>G0104 | | | 04 | | | C0102,<br>C0403,<br>C0501,<br>C0602,<br>C0704,<br>G0101,<br>G0103,<br>G0104 | | | B5201,<br>C0102,<br>C0403,<br>C0501,<br>C0602,<br>C0704,<br>G0101,<br>G0103,<br>G0104 | | |
| YLF<br>DES<br>GEF<br>KL<br>(SEQ<br>ID<br>NO:<br>25) | A0201,<br>A0202,<br>A0203,<br>A0204,<br>A0205,<br>A0206,<br>A0207,<br>A0211,<br>A2407,<br>A2902,<br>A3201,<br>B0801,<br>B1301,<br>B1302,<br>B1502,<br>B1510,<br>B1517,<br>B3501,<br>B3503,<br>B3507,<br>B3801,<br>B3802,<br>B4601,<br>B5201,<br>B5301,<br>C0102,<br>C0202,<br>C0302,<br>C0303,<br>C0304,<br>C0401,<br>C0403,<br>C0501,<br>C0602,<br>C0701,<br>C0702,<br>C0704,<br>C0801,<br>C1402,<br>C1403,<br>C1502,<br>C1601, | 46 | 0.9958 | A0201,<br>A0202,<br>A0203,<br>A0204,<br>A0205,<br>A0206,<br>A0207,<br>A0211,<br>A2407,<br>A2902,<br>A3201,<br>B0801,<br>B1301,<br>B1302,<br>B1502,<br>B1510,<br>B1517,<br>B3501,<br>B3503,<br>B3507,<br>B3801,<br>B3802,<br>B4601,<br>B5201,<br>B5301,<br>C0102,<br>C0202,<br>C0302,<br>C0303,<br>C0304,<br>C0401,<br>C0403,<br>C0501,<br>C0602,<br>C0701,<br>C0702,<br>C0704,<br>C0801,<br>C1402,<br>C1403,<br>C1502,<br>C1601, | 46 | 0.9958 | A0201,A<br>0202,A02<br>03,A0204<br>,A0205,A<br>0206,A02<br>07,A0211<br>,A2407,A<br>2902,A32<br>01,A6802<br>,B0801,B<br>1301,B13<br>02,B1502<br>,B1510,B<br>1517,B35<br>01,B3503<br>,B3507,B<br>3801,B38<br>02,B4601<br>,B5201,B<br>5301,C01<br>02,C0202<br>,C0302,C<br>0303,C03<br>04,C0401<br>,C0403,C<br>0501,C06<br>02,C0701<br>,C0702,C<br>0704,C08<br>01,C1402<br>,C1403,C<br>1502,C16<br>01,C1701<br>,G0101,G<br>0103,G01<br>04 | 47 | 0.9960 | A0201,<br>A0202,<br>A0203,<br>A0204,<br>A0205,<br>A0206,<br>A0207,<br>A0211,<br>A2407,<br>A2902,<br>A3201,<br>A6802,<br>B0801,<br>B1301,<br>B1302,<br>B1502,<br>B1510,<br>B1517,<br>B3501,<br>B3503,<br>B3507,<br>B3801,<br>B3802,<br>B4601,<br>B5201,<br>B5301,<br>C0102,<br>C0202,<br>C0302,<br>C0303,<br>C0304,<br>C0401,<br>C0403,<br>C0501,<br>C0602,<br>C0701,<br>C0702,<br>C0704,<br>C0801,<br>C1203,<br>C1402,<br>C1403, | 48 | 0.9972 | A0201,<br>A0202,<br>A0203,<br>A0204,<br>A0205,<br>A0206,<br>A0207,<br>A0211,<br>A2301,<br>A2407,<br>A2902,<br>A3201,<br>A6802,<br>B0801,<br>B1301,<br>B1302,<br>B1502,<br>B1510,<br>B1517,<br>B3501,<br>B3503,<br>B3507,<br>B3801,<br>B3802,<br>B4601,<br>B4901,<br>B5201,<br>B5301,<br>C0102,<br>C0202,<br>C0302,<br>C0303,<br>C0304,<br>C0401,<br>C0403,<br>C0501,<br>C0602,<br>C0701,<br>C0702,<br>C0704,<br>C0801,<br>C1203, | 50 | 0.9974 |

TABLE 9C-continued

| Estimated Population Coverage | | | | | | | | | | | | | | | |
|---|---|---|---|---|---|---|---|---|---|---|---|---|---|---|---|
| | C1701,<br>G0101,<br>G0103,<br>G0104 | | | C1701,<br>G0101,<br>G0103,<br>G0104 | | | | | | C1502,<br>C1601,<br>C1701,<br>G0101,<br>G0103,<br>G0104 | | | C1402,<br>C1403,<br>C1502,<br>C1601,<br>C1701,<br>G0101,<br>G0103,<br>G0104 | | |
| Peps Comb-ined | A6802,<br>B1302,<br>B1402,<br>B1801,<br>B3701,<br>B4001,<br>B4002,<br>B4006,<br>B4402,<br>B4403,<br>B4501,<br>B4901,<br>B5001,<br>B5101,<br>B5201,<br>C0704,<br>A0101,<br>A0202,<br>A0207,<br>A3601,<br>B1301,<br>B1510,<br>B1517,<br>B1801,<br>B3503,<br>B3701,<br>B3801,<br>B4001,<br>B4002,<br>B4402,<br>B4403,<br>B4501,<br>B5001,<br>B5703,<br>C0704,<br>C0802,<br>G0101,<br>A0101,<br>A0301,<br>A2501,<br>A2601,<br>A2902,<br>A3002, | 86 | 1.0000 | A6802,<br>B1302,<br>B1402,<br>B1801,<br>B3701,<br>B4001,<br>B4002,<br>B4006,<br>B4402,<br>B4403,<br>B4501,<br>B4901,<br>B5001,<br>B5101,<br>B5201,<br>C0704,<br>A0101,<br>A0202,<br>A0207,<br>A3601,<br>B1301,<br>B1510,<br>B1517,<br>B1801,<br>B3503,<br>B3507,<br>B3701,<br>B3801,<br>B4001,<br>B4002,<br>B4402,<br>B4403,<br>B4501,<br>B5001,<br>B5703,<br>B5801,<br>C0704,<br>C0802,<br>G0101,<br>A0101,<br>A0301,<br>A2501,<br>A2601, | 86 | 1.0000 | A6802,B<br>1302,B14<br>02,B1801<br>,B3701,B<br>4001,B40<br>02,B4006<br>,B4402,B<br>4403,B45<br>01,B4901<br>,B5001,B<br>5101,B52<br>01,C0704<br>,A0101,A<br>0202,A02<br>07,A3601<br>,B1301,B<br>1510,B15<br>17,B1801<br>,B3503,B<br>3507,B37<br>01,B3801<br>,B4001,B<br>4002,B44<br>02,B4403<br>,B4501,B<br>5001,B57<br>03,B5801<br>,C0704,C<br>0802,G01<br>01,A0101<br>,A0301,A<br>2501,A26<br>01,A2902<br>,A3002,A<br>3201,A36<br>01,A6801<br>,B1501,B<br>1502,B35<br>01,B5301<br>,A2501,A<br>2601,A34<br>01,B1501<br>,B1502,B | 86 | 1.0000 | A6802,<br>B1302,<br>B1402,<br>B1801,<br>B3701,<br>B4001,<br>B4002,<br>B4006,<br>B4402,<br>B4403,<br>B4501,<br>B4901,<br>B5001,<br>B5101,<br>B5201,<br>C0704,<br>A0101,<br>A0202,<br>A0207,<br>A3601,<br>B1301,<br>B1510,<br>B1517,<br>B1801,<br>B3503,<br>B3507,<br>B3701,<br>B3801,<br>B4001,<br>B4002,<br>B4402,<br>B4403,<br>B4501,<br>B5001,<br>B5703,<br>B5801,<br>C0501,<br>C0704,<br>C0802,<br>G0101,<br>A0101,<br>A0301,<br>A2501, | 86 | 1.0000 | A6802,<br>B1302,<br>B1402,<br>B1801,<br>B3701,<br>B4001,<br>B4002,<br>B4006,<br>B4402,<br>B4403,<br>B4501,<br>B4901,<br>B5001,<br>B5101,<br>B5201,<br>C0704,<br>A0101,<br>A0202,<br>A0206,<br>A0207,<br>A3601,<br>B1301,<br>B1510,<br>B1517,<br>B1801,<br>B3503,<br>B3507,<br>B3701,<br>B3801,<br>B3802,<br>B4001,<br>B4002,<br>B4402,<br>B4403,<br>B4501,<br>B4901,<br>B5001,<br>B5301,<br>B5703,<br>B5801,<br>C0501,<br>C0704,<br>C0802, | 86 | 1.0000 |

TABLE 9C-continued

| Estimated Population Coverage | | | | |
|---|---|---|---|---|
| A3201, | A2902, | 4601,C12 | A2601, | G0101, |
| A3601, | A3002, | 02,B3503 | A2902, | A0101, |
| A6801, | A3201, | ,B5101,C | A3002, | A0301, |
| B1501, | A3601, | 0202,C03 | A3201, | A2501, |
| B1502, | A6801, | 02,C0303 | A3601, | A2601, |
| B3501, | B1501, | ,C0304,C | A6801, | A2902, |
| B5301, | B1502, | 0501,C06 | B1501, | A3002, |
| A2501, | B3501, | 02,C0704 | B1502, | A3201, |
| A2601, | B5301, | ,C0801,C | B3501, | A3601, |
| A3401, | A2501, | 0802,C12 | B5301, | A6801, |
| B1501, | A2601, | 02,C1203 | A2501, | B1501, |
| B1502, | A3401, | ,C1502,C | A2601, | B1502, |
| B4601, | B1501, | 1601,A25 | A3401, | B3501, |
| C1202, | B1502, | 01,A2902 | B1501, | B5301, |
| B3503, | B4601, | ,B1501,B | B1502, | A2501, |
| B5101, | C1202, | 1502,B15 | B4601, | A2601, |
| C0202, | B3503, | 03,B3501 | C1202, | A3401, |
| C0302, | B5101, | ,B3507,B | B3503, | B1501, |
| C0303, | C0202, | 4601,B53 | B5101, | B1502, |
| C0304, | C0302, | 01,C0202 | C0202, | B4601, |
| C0501, | C0303, | ,C0302,C | C0302, | C1202, |
| C0602, | C0304, | 0303,C03 | C0303, | B3503, |
| C0704, | C0501, | 04,C0702 | C0304, | B5101, |
| C0801, | C0602, | ,C1202,C | C0501, | C0202, |
| C0802, | C0704, | 1203,C14 | C0602, | C0302, |
| C1202, | C0801, | 02,C1403 | C0704, | C0303, |
| C1203, | C0802, | ,C1601,B | C0801, | C0304, |
| C1502, | C1202, | 3501,B35 | C0802, | C0501, |
| C1601, | C1203, | 03,B3507 | C1202, | C0602, |
| A2501, | C1502, | ,C0202,C | C1203, | C0704, |
| A2902, | C1601, | 0302,C03 | C1502, | C0801, |
| B1501, | A2501, | 03,C0304 | C1601, | C0802, |
| B1502, | A2902, | ,C0403,C | A2501, | C1202, |
| B1503, | B1501, | 0704,C08 | A2902, | C1203, |
| B3501, | B1502, | 01,C1202 | B1501, | C1502, |
| B3507, | B1503, | ,C1203,C | B1502, | C1601, |
| B4601, | B3501, | 1601,C17 | B1503, | A2501, |
| B5301, | B3507, | 01,A0201 | B3501, | A2601, |
| C0202, | B4601, | ,A0205,A | B3507, | A2902, |
| C0302, | B5301, | 0206,A68 | B4601, | B1501, |
| C0303, | C0202, | 02,B1302 | B5301, | B1502, |
| C0304, | C0302, | ,B5101,B | C0202, | B1503, |
| C0702, | C0303, | 5301,C02 | C0302, | B3501, |
| C1202, | C0304, | 02,C0602 | C0303, | B3507, |
| C1203, | C0702, | ,C0704,C | C0304, | B4601, |
| C1402, | C1202, | 0801,C12 | C0702, | B5301, |
| C1403, | C1203, | 03,C1502 | C1202, | C0202, |
| C1601, | C1402, | ,C1601,C | C1203, | C0302, |
| B3501, | C1403, | 1701,A01 | C1402, | C0303, |
| B3503, | C1601, | 01,A0301 | C1403, | C0304, |
| B3507, | B3501, | ,A3002,B | C1601, | C0702, |

TABLE 9C-continued

| Estimated Population Coverage | | | | |
|---|---|---|---|---|
| C0202, | B3503, | 1501,B15 | B3501, | C1202, |
| C0302, | B3507, | 02,C1203 | B3503, | C1203, |
| C0303, | C0202, | ,C1601,B | B3507, | C1402, |
| C0304, | C0302, | 1502,B15 | C0202, | C1403, |
| C0403, | C0303, | 03,B1801 | C0302, | C1601, |
| C0704, | C0304, | ,B4002,B | C0303, | B3501, |
| C0801, | C0403, | 4006,B44 | C0304, | B3503, |
| C1202, | C0704, | 02,B4403 | C0403, | B3507, |
| C1203, | C0801, | ,B0704,B | C0704, | C0202, |
| C1601, | C1202, | 3503,B42 | C0801, | C0302, |
| C1701, | C1203, | 01,B5802 | C1202, | C0303, |
| A0201, | C1601, | ,C0102,C | C1203, | C0304, |
| A0205, | C1701, | 0303,C03 | C1601, | C0403, |
| A0206, | A0201, | 04,C0602 | C1701, | C0704, |
| A6802, | A0205, | ,C0701,C | A0201, | C0801, |
| B1302, | A0206, | 0704,C08 | A0205, | C1202, |
| B5101, | A6802, | 01,C0802 | A0206, | C1203, |
| B5301, | B1302, | ,C1202,C | A6802, | C1601, |
| C0202, | B5101, | 1203,C16 | B1302, | C1701, |
| C0602, | B5301, | 01,A0101 | B5101, | A0201, |
| C0704, | C0202, | ,A0301,A | B5301, | A0205, |
| C0801, | C0602, | 2902,A30 | C0202, | A0206, |
| C1203, | C0704, | 02,A3601 | C0602, | A6802, |
| C1502, | C0801, | ,B1501,B | C0704, | B1302, |
| C1601, | C1203, | 1502,B15 | C0801, | B5101, |
| C1701, | C1502, | 17,B1801 | C1203, | B5301, |
| A0101, | C1601, | ,B5701,B | C1502, | C0202, |
| A3002, | C1701, | 5703,B58 | C1601, | C0602, |
| B1501, | A0101, | 01,C0202 | C1701, | C0704, |
| B1502, | A0301, | ,C1202,C | A0101, | C0801, |
| C1203, | A3002, | 1203,C16 | A0301, | C1203, |
| C1601, | B1501, | 01,A0101 | A2501, | C1502, |
| B1503, | B1502, | ,A2902,A | A3002, | C1601, |
| B1801, | C1203, | 3601,B15 | B1501, | C1701, |
| B4002, | C1601, | 01,B1517 | B1502, | A0101, |
| B4006, | B1502, | ,B3507,B | C1203, | A0301, |
| B4402, | B1503, | 4601,B53 | C1601, | A2501, |
| B4403, | B1801, | 01,B5801 | B1502, | A3002, |
| B0704, | B4002, | ,C0202,C | B1503, | A3601, |
| B3503, | B4006, | 0302,C12 | B1801, | B1501, |
| B4201, | B4402, | 02,C1203 | B4002, | B1502, |
| B5802, | B4403, | ,C1601,B | B4006, | C1203, |
| C0102, | B0704, | 1503,B57 | B4402, | C1601, |
| C0303, | B3503, | 01,B5802 | B4403, | B1502, |
| C0304, | B4201, | ,C1601,A | B0704, | B1503, |
| C0602, | B5802, | 0211,A23 | B3503, | B1801, |
| C0701, | C0102, | 01,A2407 | B4201, | B4002, |
| C0704, | C0303, | ,A2501,A | B5802, | B4006, |
| C0802, | C0304, | 2601,A29 | C0102, | B4402, |
| C1202, | C0602, | 02,A3201 | C0303, | B4403, |
| C1203, | C0701, | ,A3402,A | C0304, | B0704, |

TABLE 9C-continued

| Estimated Population Coverage | | | | |
|---|---|---|---|---|
| C1601, | C0704, | 6802,B15 | C0602, | B3503, |
| A0101, | C0802, | 02,B1801 | C0701, | B4201, |
| A0301, | C1202, | ,B3501,B | C0704, | B5802, |
| A2902, | C1203, | 3507,B46 | C0801, | C0102, |
| A3002, | C1601, | 01,C0202 | C0802, | C0303, |
| A3601, | A0101, | ,C0302,C | C1202, | C0304, |
| B1501, | A0301, | 1202,C14 | C1203, | C0602, |
| B1502, | A2902, | 02,C1403 | C1601, | C0701, |
| B1517, | A3002, | ,G0101,G | A0101, | C0704, |
| B1801, | A3601, | 0104,A26 | A0301, | C0801, |
| B5701, | B1501, | 01,A3002 | A2902, | C0802, |
| B5703, | B1502, | ,A3201,A | A3002, | C1202, |
| B5801, | B1517, | 3601,B15 | A3601, | C1203, |
| C0202, | B1801, | 03,B1517 | B1501, | C1601, |
| C1202, | B5701, | ,B1801,B | B1502, | A0101, |
| C1203, | B5703, | 2705,B44 | B1517, | A0301, |
| C1601, | B5801, | 02,B4403 | B1801, | A2501, |
| A0101, | C0202, | ,B4601,B | B5701, | A2902, |
| A2902, | C1202, | 5001,B57 | B5703, | A3002, |
| A3601, | C1203, | 01,B5802 | B5801, | A3201, |
| B1501, | C1601, | ,C0202,C | C0202, | A3601, |
| B1517, | A0101, | 0602,C07 | C1202, | B1501, |
| B3507, | A2902, | 01,C0702 | C1203, | B1502, |
| B4601, | A3601, | ,C0704,C | C1601, | B1517, |
| C0202, | B1501, | 1202,C15 | A0101, | B1801, |
| C0302, | B1517, | 02,C1601 | A2601, | B5701, |
| C1202, | B3507, | ,C1701,A | A2902, | B5703, |
| C1203, | B4601, | 2501,A26 | A3601, | B5801, |
| C1601, | B5301, | 01,A2902 | B1501, | C0202, |
| B1503, | B5801, | ,A3002,A | B1517, | C1202, |
| B5701, | C0202, | 3201,B15 | B3507, | C1203, |
| B5802, | C0302, | 01,B1503 | B4601, | C1601, |
| C1601, | C1202, | ,B1801,B | B5301, | A0101, |
| A0211, | C1203, | 3501,B35 | B5801, | A2601, |
| A2301, | C1601, | 07,B4402 | C0202, | A2902, |
| A2407, | B1503, | ,B4403,B | C0302, | A3601, |
| A2501, | B5701, | 4501,B50 | C1202, | B1501, |
| A2601, | B5802, | 01,C0202 | C1203, | B1517, |
| A2902, | C1601, | ,C1202,C | C1601, | B3507, |
| A3201, | A0211, | 1402,C14 | B1503, | B4601, |
| A3402, | A2301, | 03,unkno | B5101, | B5301, |
| A6802, | A2407, | wn,C070 | B5701, | B5801, |
| B1502, | A2501, | 4,C1502, | B5802, | C0202, |
| B1801, | A2601, | unknown, | C1601, | C0302, |
| B3507, | A2902, | A0201,A | A0211, | C1202, |
| B4601, | A3201, | 0206,A02 | A2301, | C1203, |
| C0202, | A3402, | 07,A6802 | A2407, | C1601, |
| C1202, | A6802, | ,G0101,G | A2501, | B1503, |
| C1402, | B1502, | 0103,G01 | A2601, | B5101, |
| C1403, | B1801, | 04,A0101 | A2902, | B5701, |
| G0101, | B3501, | ,A0201,A | A3201, | B5802, |

TABLE 9C-continued

| Estimated Population Coverage | | | | |
|---|---|---|---|---|
| G0104, | B3507, | 0206,A02 | A3401, | C1601, |
| A2601, | B4601, | 07,B5101 | A3402, | A0211, |
| A3002, | C0202, | ,C0303,C | A6802, | A2301, |
| A3201, | C1202, | 0304,C04 | B1502, | A2407, |
| A3601, | C1402, | 01,C0403 | B1801, | A2501, |
| B1503, | C1403, | ,C0501,C | B3501, | A2601, |
| B1517, | G0101, | 0602,C07 | B3507, | A2902, |
| B1801, | G0104, | 04,C0801 | B4601, | A3201, |
| B2705, | A2601, | ,C0802,C | C0202, | A3401, |
| B4403, | A3002, | 1203,C15 | C0302, | A3402, |
| B4601, | A3201, | 02,C1701 | C1202, | A6802, |
| B5001, | A3601, | ,A0201,A | C1402, | B1502, |
| B5701, | B1503, | 0202,A02 | C1403, | B1801, |
| B5802, | B1517, | 04,A0205 | G0101, | B3501, |
| C0701, | B1801, | ,A0211,A | G0104, | B3507, |
| C0702, | B2705, | 2301,B13 | A2601, | B4601, |
| C0704, | B4402, | 01,B1402 | A3002, | C0202, |
| C1202, | B4403, | ,B3801,C | A3201, | C0302, |
| C1502, | B4601, | 0602,C07 | A3601, | C0403, |
| C1601, | B5001, | 01,C0702 | B1503, | C1202, |
| C1701, | B5701, | ,A2902,A | B1517, | C1402, |
| A2501, | B5802, | 3002,A32 | B1801, | C1403, |
| A2601, | C0202, | 01,B1503 | B2705, | G0101, |
| A2902, | C0602, | ,B1517,B | B4402, | G0104, |
| A3002, | C0701, | 2705,B46 | B4403, | A2601, |
| A3201, | C0702, | 01,B5701 | B4601, | A3002, |
| B1501, | C0704, | ,C0202,C | B5001, | A3201, |
| B1503, | C1202, | 0602,C07 | B5701, | A3601, |
| B1801, | C1502, | 01,C0702 | B5802, | B1503, |
| B3501, | C1601, | ,C1203,G | C0202, | B1517, |
| B3507, | C1701, | 0104,unk | C0602, | B1801, |
| B4402, | A2501, | nown,A0 | C0701, | B2705, |
| B4403, | A2601, | 201,A020 | C0702, | B4402, |
| C0202, | A2902, | 2,A0203, | C0704, | B4403, |
| C1202, | A3002, | A0204,A | C1202, | B4601, |
| C1402, | A3201, | 0205,A02 | C1203, | B5001, |
| C1403, | B1501, | 07,A0201 | C1403, | B5701, |
| unkno | B1503, | ,A0202,A | C1502, | B5802, |
| wn,C0 | B1801, | 0204,A02 | C1601, | C0202, |
| 704,un | B3501, | 07,A0211 | C1701, | C0602, |
| known, | B3507, | ,B0801,B | G0103, | C0701, |
| A0201, | B4402, | 1301,C05 | A2501, | C0702, |
| A0206, | B4403, | 01,C0802 | A2601, | C0704, |
| A0207, | B4501, | ,G0101,G | A2902, | C1202, |
| A6802, | C0202, | 0103,G01 | A3002, | C1203, |
| G0101, | C1202, | 04,A0201 | A3201, | C1402, |
| G0103, | C1402, | ,A0202,A | B1501, | C1403, |
| G0104, | C1403, | 0203,A02 | B1503, | C1502, |
| A0101, | unkno | 04,A0205 | B1801, | C1601, |
| A0201, | wn,C07 | ,A0206,A | B3501, | C1701, |
| A0206, | 04,unk | 0211,A68 | B3507, | G0103, |

TABLE 9C-continued

| Estimated Population Coverage | | | | |
|---|---|---|---|---|
| A0207, | nown, | 02,B1302 | B4402, | A2501, |
| C0303, | A0201, | ,B5201,C | B4403, | A2601, |
| C0304, | A0206, | 1203,C15 | B4501, | A2902, |
| C0401, | A0207, | 02,A0201 | B5001, | A3002, |
| C0403, | A6802, | ,A0202,A | C0202, | A3201, |
| C0501, | G0101, | 0203,A02 | C1202, | B1501, |
| C0704, | G0103, | 04,A0205 | C1402, | B1503, |
| C0801, | G0104, | ,A0206,A | C1403, | B1801, |
| C0802, | A0101, | 0207,A02 | unknow | B3501, |
| C1502, | A0201, | 11,A2501 | n,C070 | B3507, |
| A0201, | A0206, | ,A2601,A | 4,C150 | B4402, |
| A0202, | A0207, | 6802,B13 | 2,unkno | B4403, |
| A0204, | C0303, | 02,C0202 | wn,A02 | B4501, |
| A0205, | C0304, | ,C0602,C | 01,A02 | B5001, |
| A0211, | C0401, | 1203,C15 | 06,A02 | C0202, |
| A2301, | C0403, | 02,C1701 | 07,A68 | C1202, |
| B1402, | C0501, | ,A0201,A | 02,G01 | C1402, |
| B3801, | C0704, | 0202,A02 | 01,G01 | C1403, |
| C0602, | C0801, | 03,A0204 | 03,G01 | unkno |
| C0701, | C0802, | ,A0207,B | 04,A01 | wn,B13 |
| C0702, | C1203, | 1301,B13 | 01,A02 | 02,C07 |
| A2902, | C1502, | 02,B3801 | 01,A02 | 04,C15 |
| A3002, | C1701, | ,C0501,B | 06,A02 | 02,unk |
| A3201, | A0201, | 0702,B07 | 07,B51 | nown, |
| B1503, | A0202, | 04,B0801 | 01,C03 | A0201, |
| B2705, | A0204, | ,B1510,B | 03,C03 | A0206, |
| B4601, | A0205, | 3501,B35 | 04,C04 | A0207, |
| B5701, | A0211, | 03,B3507 | 01,C04 | A6802, |
| C0202, | A2301, | ,B4001,B | 03,C05 | G0101, |
| C0602, | B1301, | 4201,B55 | 01,C06 | G0103, |
| C0701, | B1402, | 01,B5502 | 02,C07 | G0104, |
| C0702, | B3801, | ,B5601,C | 04,C08 | A0101, |
| G0104, | C0602, | 0102,C04 | 01,C08 | A0201, |
| unkno | C0701, | 03,C0704 | 02,C12 | A0206, |
| wn,A0 | C0702, | ,C0801,C | 03,C15 | A0207, |
| 201,A0 | A2902, | 1701,unk | 02,C17 | B5101, |
| 202,A0 | A3002, | nown,A0 | 01,A02 | C0303, |
| 203,A0 | A3201, | 201,A020 | 01,A02 | C0304, |
| 204,A0 | B1503, | 2,A0203, | 02,A02 | C0401, |
| 207,A0 | B2705, | A0204,A | 04,A02 | C0403, |
| 201,A0 | B4601, | 0205,A02 | 05,A02 | C0501, |
| 202,A0 | B5701, | 06,A0211 | 07,A02 | C0602, |
| 204,A0 | C0202, | ,A6802,B | 11,A23 | C0704, |
| 207,A0 | C0602, | 1302,B40 | 01,B13 | C0801, |
| 211,B1 | C0701, | 06,B5101 | 01,B14 | C0802, |
| 301,C0 | C0702, | ,B5201,B | 02,B38 | C1203, |
| 501,C0 | C1203, | 5401,B55 | 01,C06 | C1502, |
| 802,G0 | G0104, | 01,B5502 | 02,C07 | C1701, |
| 101,G0 | unkno | ,B5601,C | 01,C07 | A0201, |
| 103,G0 | wn,A0 | 0304,C07 | 02,A29 | A0202, |
| 104,A0 | 201,A0 | 04,C1203 | 02,A30 | A0204, |

TABLE 9C-continued

| Estimated Population Coverage | | | | |
|---|---|---|---|---|
| 201,A0 | 202,A0 | ,C1701,G | 02,A32 | A0205, |
| 202,A0 | 203,A0 | 0101,G01 | 01,B15 | A0207, |
| 203,A0 | 204,A0 | 03,G0104 | 01,B15 | A0211, |
| 204,A0 | 207,A0 | ,A0201,A | 03,B15 | A2301, |
| 205,A0 | 201,A0 | 0203,A02 | 17,B27 | B1301, |
| 206,A0 | 202,A0 | 05,A0206 | 05,B46 | B1402, |
| 211,A6 | 204,A0 | ,A0207,A | 01,B57 | B3801, |
| 802,C1 | 207,A0 | 2601,A68 | 01,C02 | C0602, |
| 203,C1 | 211,B0 | 02,B0801 | 02,C06 | C0701, |
| 502,A0 | 801,B1 | ,B1302,B | 02,C07 | C0702, |
| 201,A0 | 301,C0 | 5101,B52 | 01,C07 | A0301, |
| 202,A0 | 501,C0 | 01,C0102 | 02,C12 | A2902, |
| 203,A0 | 802,G0 | ,C0403,C | 03,G01 | A3002, |
| 204,A0 | 101,G0 | 0501,C06 | 04,unkn | A3201, |
| 205,A0 | 103,G0 | 02,C0704 | own,A0 | B1501, |
| 206,A0 | 104,A0 | ,G0101,G | 201,A0 | B1503, |
| 207,A0 | 201,A0 | 0103,G01 | 202,A0 | B1517, |
| 211,A2 | 202,A0 | 04,A0201 | 203,A0 | B2705, |
| 501,A2 | 203,A0 | ,A0202,A | 204,A0 | B4601, |
| 601,A6 | 204,A0 | 0203,A02 | 205,A0 | B5701, |
| 802,B1 | 205,A0 | 04,A0205 | 207,C0 | C0202, |
| 302,C0 | 206,A0 | ,A0206,A | 102,A0 | C0602, |
| 202,C0 | 211,A6 | 0207,A02 | 201,A0 | C0701, |
| 602,C1 | 802,B5 | 11,A2407 | 202,A0 | C0702, |
| 203,C1 | 201,C1 | ,A2902,A | 204,A0 | C1203, |
| 502,C1 | 203,C1 | 3201,A68 | 205,A0 | G0104, |
| 701,A0 | 502,A0 | 02,B0801 | 207,A0 | unkno |
| 201,A0 | 201,A0 | ,B1301,B | 211,B0 | wn,A0 |
| 202,A0 | 202,A0 | 1302,B15 | 801,B1 | 201,A0 |
| 203,A0 | 203,A0 | 02,B1510 | 301,C0 | 202,A0 |
| 204,A0 | 204,A0 | ,B1517,B | 501,C0 | 203,A0 |
| 207,B1 | 205,A0 | 3501,B35 | 802,G0 | 204,A0 |
| 301,B1 | 206,A0 | 03,B3507 | 101,G0 | 205,A0 |
| 302,B3 | 207,A0 | ,B3801,B | 103,G0 | 207,C0 |
| 801,C0 | 211,A2 | 3802,B46 | 104,A0 | 102,A0 |
| 501,B0 | 501,A2 | 01,B5201 | 201,A0 | 201,A0 |
| 702,B0 | 601,A6 | ,B5301,C | 202,A0 | 202,A0 |
| 704,B0 | 802,B1 | 0102,C02 | 203,A0 | 204,A0 |
| 801,B1 | 302,C0 | 02,C0302 | 204,A0 | 205,A0 |
| 510,B3 | 202,C0 | ,C0303,C | 205,A0 | 207,A0 |
| 503,B3 | 602,C1 | 0304,C04 | 206,A0 | 211,B0 |
| 507,B4 | 203,C1 | 01,C0403 | 211,A6 | 801,B1 |
| 201,B5 | 502,C1 | ,C0501,C | 802,B1 | 301,C0 |
| 501,B5 | 701,A0 | 0602,C07 | 302,B5 | 501,C0 |
| 502,B5 | 201,A0 | 01,C0702 | 201,C1 | 802,G0 |
| 601,C0 | 202,A0 | ,C0704,C | 203,C1 | 101,G0 |
| 403,C0 | 203,A0 | 0801,C14 | 502,A0 | 103,G0 |
| 704,C0 | 204,A0 | 02,C1403 | 201,A0 | 104,A0 |
| 801,C1 | 207,B1 | ,C1502,C | 202,A0 | 201,A0 |
| 701,un | 301,B1 | 1601,C17 | 203,A0 | 202,A0 |
| known, | 302,B3 | 01,G0101 | 204,A0 | 203,A0 |

TABLE 9C-continued

| Estimated Population Coverage | | | | |
|---|---|---|---|---|
| A0201, | 801,C0 | ,G0103,G | 205,A0 | 204,A0 |
| A0202, | 501,B0 | 0104 | 206,A0 | 205,A0 |
| A0203, | 702,B0 | | 207,A0 | 206,A0 |
| A0204, | 704,B0 | | 211,A2 | 211,A6 |
| A0205, | 801,B1 | | 501,A2 | 802,B1 |
| A0206, | 510,B3 | | 601,A6 | 302,B5 |
| A0211, | 501,B3 | | 802,B1 | 201,C1 |
| A6802, | 503,B3 | | 302,C0 | 203,C1 |
| B1302, | 507,B4 | | 202,C0 | 502,A0 |
| B4006, | 001,B4 | | 602,C1 | 201,A0 |
| B5101, | 201,B5 | | 203,C1 | 202,A0 |
| B5201, | 501,B5 | | 502,C1 | 203,A0 |
| B5401, | 502,B5 | | 701,A0 | 204,A0 |
| B5501, | 601,C0 | | 201,A0 | 205,A0 |
| B5502, | 102,C0 | | 202,A0 | 206,A0 |
| B5601, | 403,C0 | | 203,A0 | 207,A0 |
| C0304, | 704,C0 | | 204,A0 | 211,A2 |
| C0704, | 801,C1 | | 207,B1 | 501,A2 |
| C1203, | 701,un | | 301,B1 | 601,A6 |
| C1701, | known, | | 302,B3 | 802,B1 |
| G0101, | A0201, | | 801,C0 | 302,C0 |
| G0104, | A0202, | | 102,C0 | 202,C0 |
| A0201, | A0203, | | 501,B0 | 602,C1 |
| A0203, | A0204, | | 702,B0 | 203,C1 |
| A0205, | A0205, | | 704,B0 | 502,C1 |
| A0206, | A0206, | | 801,B1 | 701,A0 |
| A0207, | A0211, | | 510,B3 | 201,A0 |
| A2601, | A6802, | | 501,B3 | 202,A0 |
| A6802, | B1302, | | 503,B3 | 203,A0 |
| B0801, | B4006, | | 507,B4 | 204,A0 |
| B5101, | B5101, | | 001,B4 | 207,B1 |
| B5201, | B5201, | | 201,B5 | 301,B1 |
| C0102, | B5401, | | 501,B5 | 302,B3 |
| C0403, | B5501, | | 502,B5 | 801,C0 |
| C0602, | B5502, | | 601,C0 | 102,C0 |
| C0704, | B5601, | | 102,C0 | 501,B0 |
| G0101, | C0304, | | 403,C0 | 702,B0 |
| G0103, | C0704, | | 704,C0 | 704,B0 |
| G0104, | C1203, | | 801,C1 | 801,B1 |
| A0201, | C1701, | | 701,unk | 510,B3 |
| A0202, | G0101, | | nown,A | 501,B3 |
| A0203, | G0103, | | 0201,A | 503,B3 |
| A0204, | G0104, | | 0202,A | 507,B4 |
| A0205, | A0201, | | 0203,A | 001,B4 |
| A0206, | A0203, | | 0204,A | 201,B5 |
| A0207, | A0205, | | 0205,A | 501,B5 |
| A0211, | A0206, | | 0206,A | 502,B5 |
| A2407, | A0207, | | 0211,A | 601,C0 |
| A2902, | A2601, | | 6802,B | 102,C0 |
| A3201, | A6802, | | 1302,B | 403,C0 |
| B0801, | B0801, | | 4006,B | 704,C0 |

TABLE 9C-continued

| Estimated Population Coverage | | | |
|---|---|---|---|
| B1301, | B1302, | 5101,B | 801,C1 |
| B1302, | B5101, | 5201,B | 701,un |
| B1502, | B5201, | 5401,B | known, |
| B1510, | C0102, | 5501,B | A0201, |
| B1517, | C0403, | 5502,B | A0202, |
| B3501, | C0501, | 5601,C | A0203, |
| B3503, | C0602, | 0304,C | A0204, |
| B3507, | C0704, | 0704,C | A0205, |
| B3801, | G0101, | 1203,C | A0206, |
| B3802, | G0103, | 1701,G | A0211, |
| B4601, | G0104, | 0101,G | A6802, |
| B5201, | A0201, | 0103,G | B1302, |
| B5301, | A0202, | 0104,A | B4006, |
| C0102, | A0203, | 0201,A | B5101, |
| C0202, | A0204, | 0202,A | B5201, |
| C0302, | A0205, | 0203,A | B5401, |
| C0303, | A0206, | 0204,A | B5501, |
| C0304, | A0207, | 0205,A | B5502, |
| C0401, | A0211, | 0206,A | B5601, |
| C0403, | A2407, | 0207,A | C0304, |
| C0501, | A2902, | 0211,A | C0704, |
| C0602, | A3201, | 2601,A | C0801, |
| C0701, | B0801, | 6802,B | C1203, |
| C0702, | B1301, | 0801,B | C1701, |
| C0704, | B1302, | 1302,B | G0101, |
| C0801, | B1502, | 5101,B | G0103, |
| C1402, | B1510, | 5201,C | G0104, |
| C1403, | B1517, | 0102,C | A0201, |
| C1502, | B3501, | 0403,C | A0202, |
| C1601, | B3503, | 0501,C | A0203, |
| C1701, | B3507, | 0602,C | A0204, |
| G0101, | B3801, | 0704,G | A0205, |
| G0103, | B3802, | 0101,G | A0206, |
| G0104 | B4601, | 0103,G | A0207, |
| | B5201, | 0104,A | A0211, |
| | B5301, | 0201,A | A2501, |
| | C0102, | 0202,A | A2601, |
| | C0202, | 0203,A | A6802, |
| | C0302, | 0204,A | B0801, |
| | C0303, | 0205,A | B1302, |
| | C0304, | 0206,A | B5101, |
| | C0401, | 0207,A | B5201, |
| | C0403, | 0211,A | C0102, |
| | C0501, | 2407,A | C0403, |
| | C0602, | 2902,A | C0501, |
| | C0701, | 3201,A | C0602, |
| | C0702, | 6802,B | C0704, |
| | C0704, | 0801,B | G0101, |
| | C0801, | 1301,B | G0103, |
| | C1402, | 1302,B | G0104, |
| | C1403, | 1502,B | A0201, |

TABLE 9C-continued

| Estimated Population Coverage | | |
|---|---|---|
| C1502, | 1510,B | A0202, |
| C1601, | 1517,B | A0203, |
| C1701, | 3501,B | A0204, |
| G0101, | 3503,B | A0205, |
| G0103, | 3507,B | A0206, |
| G0104 | 3801,B | A0207, |
| | 3802,B | A0211, |
| | 4601,B | A2301, |
| | 5201,B | A2407, |
| | 5301,C | A2902, |
| | 0102,C | A3201, |
| | 0202,C | A6802, |
| | 0302,C | B0801, |
| | 0303,C | B1301, |
| | 0304,C | B1302, |
| | 0401,C | B1502, |
| | 0403,C | B1510, |
| | 0501,C | B1517, |
| | 0602,C | B3501, |
| | 0701,C | B3503, |
| | 0702,C | B3507, |
| | 0704,C | B3801, |
| | 0801,C | B3802, |
| | 1203,C | B4601, |
| | 1402,C | B4901, |
| | 1403,C | B5201, |
| | 1502,C | B5301, |
| | 1601,C | C0102, |
| | 1701,G | C0202, |
| | 0101,G | C0302, |
| | 0103,G | C0303, |
| | 0104 | C0304, |
| | | C0401, |
| | | C0403, |
| | | C0501, |
| | | C0602, |
| | | C0701, |
| | | C0702, |
| | | C0704, |
| | | C0801, |
| | | C1203, |
| | | C1402, |
| | | C1403, |
| | | C1502, |
| | | C1601, |
| | | C1701, |
| | | G0101, |
| | | G0103, |
| | | G0104 |

Figure 11C:
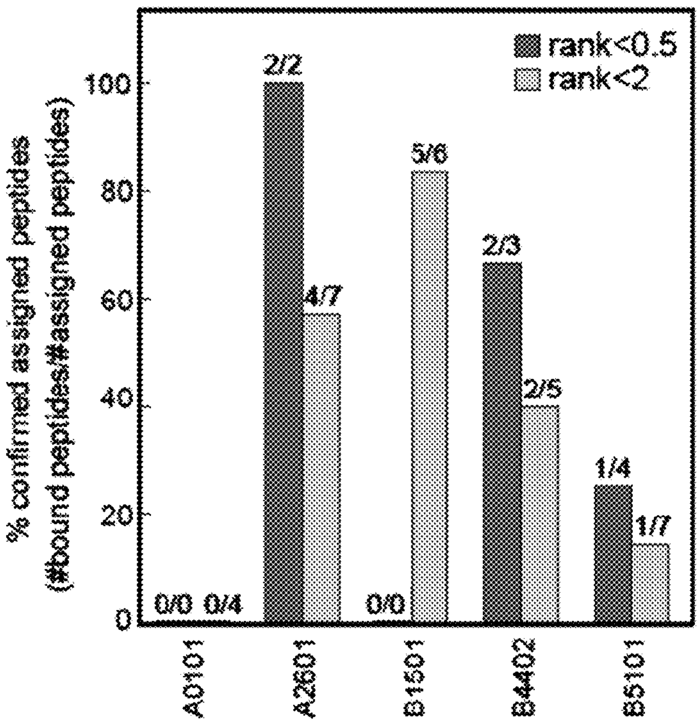
Figure 11D:
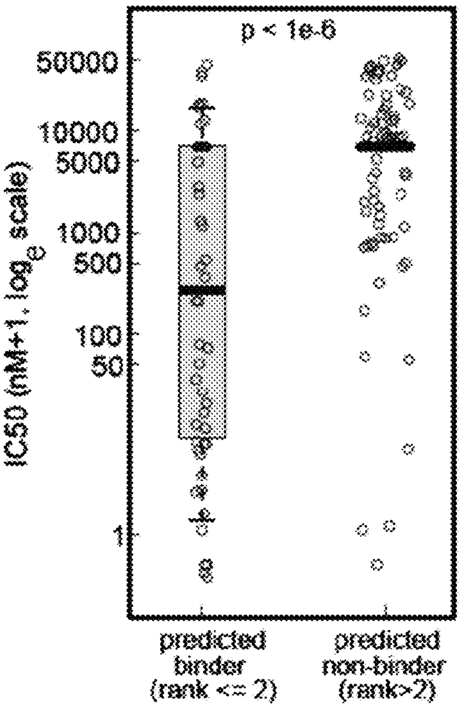

To validate the binding of the HLA-I peptides to the predicted alleles, biochemical binding measurement with 30 synthetic peptides and 5 purified HLA alleles not present in the two profiled cell lines was performed. These measurements confirmed binding for 5 of 9 (56%) HLA-I peptides predicted at a threshold of % rank <=0.5 and 12 of 29 (41%) peptides predicted at a threshold of % rank <=2 (FIG. 11C), with significantly higher measured affinities for predicted binders vs non-binders (FIG. 11D). Moreover, two peptides for which presentation was predicted on HLA alleles not profiled in the cell lines here, were recently found to elicit T cell responses in convalescent COVID-19 patients expressing the predicted alleles (EILDITPCSF (SEQ ID NO: 33) and QLTPTWRVY (SEQ ID NO: 38) detected on A*25:01 and C*16:01, were predicted to bind A*26:01 and A*30:02 at % rank <=0.5, respectively, (Tarke et al. 2020)). These results indicate that HLA-I immunopeptidomics on only two cell lines combined with epitope prediction tools can help prioritize CD8+ T cell epitopes with high population coverage for COVID-19 immune monitoring and vaccine development.

Discussion

This Example at least provides a view of SARS-COV-2 HLA-I peptides that are endogenously processed and presented by infected cells. Although this Example profiled two cell lines, it uncovers multiple insights into SARS-COV-2 antigen presentation that can extend beyond the nine HLA alleles tested here: (i) A substantial fraction, 9 of 36 (25%), of viral peptides detected are derived from internal out-of-frame ORFs in S (S.iORF1/2) and N (ORF9b). Remarkably, HLA-I peptides from the non-canonical ORFs were more immunogenic than the canonical HLA-I peptides in immunized mice and convalescence COVID-19 patients shown by both pooled ELISpot assays and multiplexed tetramer experiments. These observations imply that current interrogation of T cell responses in COVID-19 patients, which focus on the canonical viral ORFs (Grifoni et al., 2020a; Weiskopf et al., 2020), exclude an important source of virus-derived HLA-I epitopes. (ii) A large fraction of HLA-I peptides detected were from non-structural proteins (nsps). Earlier studies focused mostly on T cell responses toward S, N, M and E, which biased results toward structural proteins. Together with recent studies that expanded their epitope pools to include non-structural proteins (Dan et al., 2020; Kared et al., 2021; Tarke et al., 2020), it is shown that nsps are an integral part of the T cell response to SARS-COV-2. (iii) The timing of SARS-COV-2 protein expression appears to be a key determinant for antigen presentation and immunogenicity. Proteins expressed earlier in infection (3hpi) were more likely to be presented on the HLA-I complex and elicit a T cell response in COVID-19 patients. Together, these insights can inform the design of future peptide pools to allow more comprehensive characterization of T cell responses in COVID-19 patients.

Recent findings in the field highlights the need to look beyond antibodies for strategies to lasting protection from COVID-19 (Ledford, 2021), and to consider T cell epitopes. Several SARS-COV-2 variants have emerged associated with a reported reduction in neutralizing antibodies efficiencies. Importantly, recent studies found however that CD8+ T cell responses in convalescent patients and mRNA vaccines are not substantially affected by mutations found in prominent SARS-COV-2 variants (Redd et al., 2021; Tarke et al., 2021). Thus, integrating T cell epitopes into the next generation of vaccines has the potential to provide prolonged protection in the presence of an evolving virus. This work reveals that ORF9b is an important source for T cell epitopes that remained not well characterized for months of intensive research of SARS-COV-2 T cell immunity. Although relatively short (97 aa), we detected six HLA-I peptides (16%) from ORF9b in both A549 and HEK293T cells and found that ORF9b derived HLA-I peptides bind to at least four different alleles in the population using biochemical affinity measurements (A*02:01, B*18:01, B*44:03 and A*26:01). In this Example, two A*02:01 peptides, ELPDEFVVVTV (SEQ ID NO: 8) and SLEDKAFQL (SEQ ID NO: 7), were identified which elicit CD8+ T cell responses in convalescent patients, demonstrating that ORF9b is translated and presented on HLA-I in-vivo during the course of COVID-19. Moreover, ORF9b is among the few viral proteins that are detected early in infection and achieve high expression, two traits that correlate with HLA-I presentation and immunogenicity. In addition, this study highlights ELPDEFVVVTV (SEQ ID NO: 8) as a promising T cell epitope. It binds both A*02:01 and A*26:01 ($IC_{50}$=1.6 nM and $IC_{50}$=72, respectively, Table 4), elicits strong T cell responses in immunized mice and COVID-19 patients (FIGS. 10A, 10B, 10F, and 10G), and is being recognized by TCRs from different patients sharing a mutual CDR3 motif (FIGS. 16A-16D). Importantly, ELPDEFVVVTV (SEQ ID NO: 8) elicits stronger T cell responses than the three most commonly recognized A*02:01 SARS-COV-2 epitopes (Ferretti et al., 2020) including YLQPRTELL (SEQ ID NO: 207), which was recorded as the most potent SARS-COV-2 epitope in three independent studies (Ferretti et al., 2020; Habel et al., 2020; Shomuradova et al., 2020) and is the target of commercial monomer and tetramer assays.

These analyses demonstrate that synthetic approaches aiming at enhancing the expression of canonical ORFs, some of which are utilized in current vaccine strategies, can inadvertently eliminate or alter the production of HLA-I peptides derived from overlapping reading frames. Several of these findings—the large fraction of HLA-I peptides detected from internal out-of-frame ORFs, their strong affinity to biochemically purified HLA, the observed immunogenicity in mice and COVID-19 patients, the detection of memory and effector T cells reacting to ELPDEFVVVTV (SEQ ID NO: 8) from ORF9b and the homology of its TCR sequences across different patients—suggest that accounting for these ORFs may considerably contribute to the induction of effective memory T cells in response to SARS-COV-2 vaccines. Researchers may need to carefully examine the effects of sequence manipulation and codon optimization on the amino acids encoded by these ORFs with emphasis on the regions encoding the HLA-I peptides. In broader terms, many viral genomes have evolved to increase their coding capacity by utilizing overlapping ORFs and programmed frameshifting (Ketteler, 2012). Thus, these findings suggest a more general principle in vaccine design according to which optimizing expression of desired antigens using codon optimization can be at the expense of CD8+ response if the same region encodes a source protein for T cell epitopes in an alternative frame. Combining insights from ribosome profiling and HLA-I immunopeptidomics can uncover the presence of non-canonical peptides that will enable more informed decisions in vaccine design.

Figures 19A, 19B, 19C:
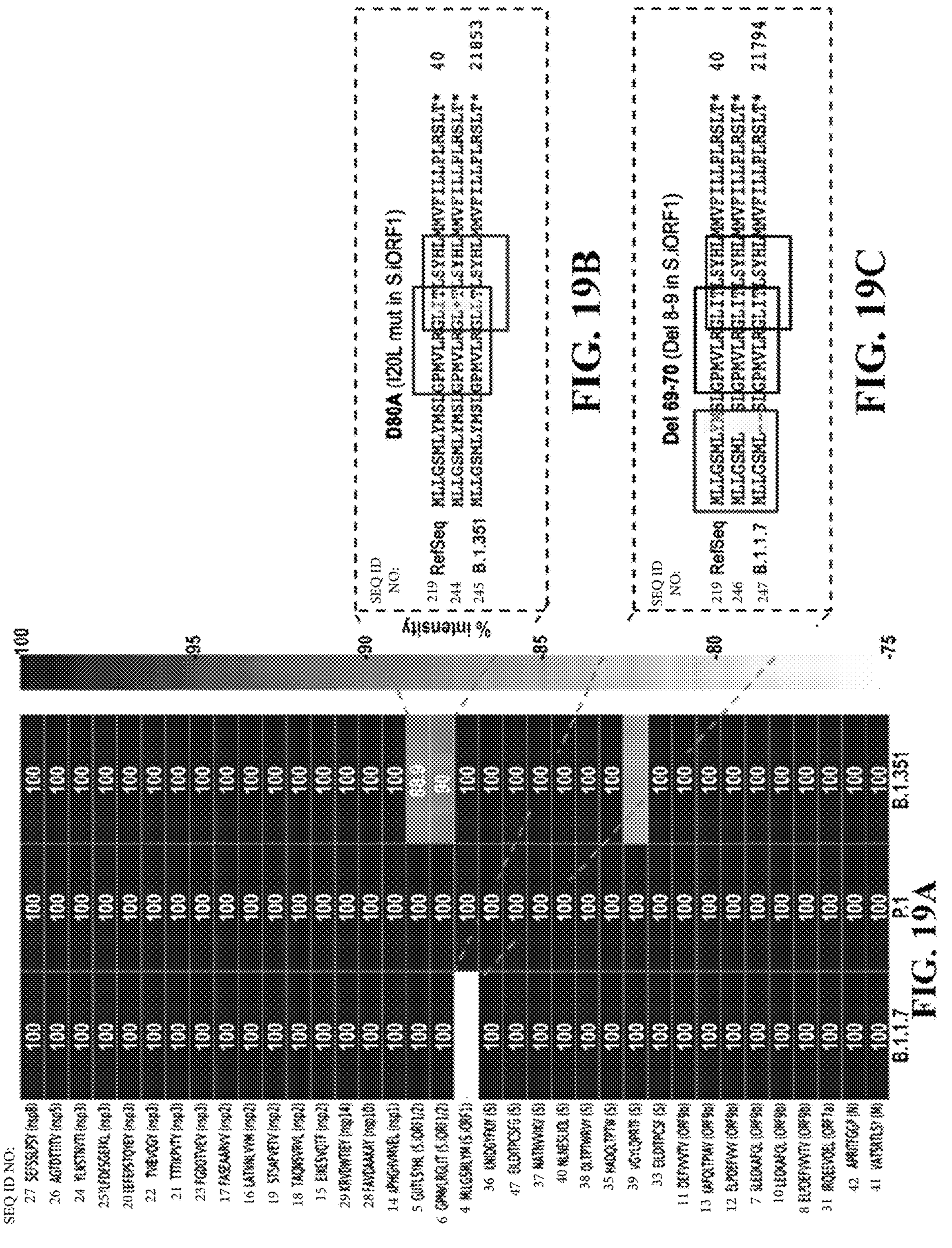
FIGS. 19A-19C. HLA-I peptide sequences in B.1.1.7, P.1 and B.1.351 SARS-COV-2 variants (FIG. 19A (SEQ ID NO: 4-8, 10-31, 33, 35-42, 47)) The sequence of the HLA-I peptides detected in our study was mapped to the genomes of SARS-COV-2 variants B.1.1.7, P.1 and B.1.351 using the BLAST tool tblastn. Identity scores for each peptide in each variant are shown in the heatmap.

In contrast to ORF9b, the T cell assays did not uncover significant reactivity to peptides from S.iORF1/2 in convalescent COVID-19 patients. This finding is surprising given that GLITLSYHL (SEQ ID NO: 5) and MLLGSMLYM (SEQ ID NO: 4) had the highest affinity to HLA-A*02:01 among all HLA-I peptides tested (<0.5 nM, FIG. 3E and Table 4) and were both immunogenic in a humanized HLA-A2 mouse model, demonstrating that they can be successfully presented on A*02:01 and elicit T cell responses in-vivo (FIGS. 10A-10B). Moreover, GLITLSYHL (SEQ ID NO: 5) immunogenicity in mice was 10-fold higher than ELPDEFVVVTV (SEQ ID NO: 8), the most potent SARS-COV-2 epitope detected in COVID-19 patients with comparable responses only to the Influenza epitope. The intriguing discrepancy between S.iORF1/2 derived peptides immunogenicity in mice and COVID-19 patients could suggest an immune evasion mechanism to attenuate the translation and/or antigen processing of this non-canonical ORFs in patients. It should be noted that testing T cell responses in convalescent samples, as done in our study, is biased toward symptomatic patients and perhaps T cell reactivity to these peptides is associated with asymptomatic infection. Interestingly, the sequence of the detected HLA-I peptides remained unchanged in the recent emerging SARS-COV-2 variants B.1.1.7, P.1 and B.1.351 (originally detected in the UK, Brazil and South Africa, respectively) but the three HLA-I peptides derived from S.iORF1/2 (FIGS. 19A-19C). Spike 69-70 deletion in the B.1.1.7 variant results in the deletion of the last two amino acids of the S.iORF1-derived MLLGSMLYM (SEQ ID NO: 4) epitope; and D80A substitution in canonical S of the B.1.351 variant results in I to L substitution in S.iORF1/2, which impacts both GPMVLRGLIT (SEQ ID NO: 6) and GLITLSYHL (SEQ ID NO: 5). While this could be due to relaxed selective pressure allowing for mutations to emerge, it could alternatively point to potential positive selective pressure on the three T cell epitopes encoded from the alternative out-of-frame ORFs in S.

These results hint that viruses may evolve to attenuate HLA-I presentation of highly abundant proteins. While N is among the most immunogenic proteins in COVID-19 patients, it elicits lower T cell responses than S (Grifoni et al., 2020a; Tarke et al., 2020) even though its source protein abundance is about 100-fold higher (FIG. 7C). In a similar trend, these experiments detected only one HLA-I peptide derived from N and eight peptides derived from S. Using epitope predictions from 92 frequent HLA-A,-B, and -C alleles, we show that N is less likely to generate presentable peptides in comparison to other ORFs of SARS-COV-2. An intriguing hypothesis is that viruses have evolved to attenuate HLA-I presentation of highly abundant proteins as an immune evasion mechanism. Yet, evidence suggests that SARS-COV-2 has only recently spilled over to humans from bats, so human HLA-I should not have played a significant role in its evolution. Studying MHC-I presentation of SARS-COV-2 in bats as well as expanding the relative presentability analysis to other human Coronaviruses are needed in order to evaluate the selective pressure shaping the evolution of N and whether it was adapted to attenuate HLA-I presentation.

Proteomics analyses of infected cells show that SARS-COV-2 may interfere with the presentation of HLA-I peptides and the expression of ubiquitination and immune signaling pathway proteins. It was found that SARS-COV-2 infection leads to a significant decrease in POMP and of ubiquitination pathway protein expression. By impacting ubiquitin mediated proteasomal degradation and immune signaling proteins, SARS-COV-2 may reduce the precursors for downstream processing and HLA-I presentation and alter the immune response. Moreover, it has been shown in vitro that disrupted IFN signaling can result from SARS-COV-2 infection (Chen et al., 2020a), which aligns with our observations of JAK1 depletion in both cell lines post infection and reports of a delayed IFN response observed in COVID-19 patients (Acharya et al., 2020).

In summary, this Example at least uncovers not previously characterized SARS-COV-2 HLA-I peptides from out-of-frame ORFs in SARS-COV-2 genome and highlights the contribution of these viral epitopes to the immune response in a mouse model and convalescent COVID-19 patients. These new CD8+ T cell targets and the insights into HLA-I presentation in infected cells will enable a more precise selection of peptides for COVID-19 immune monitoring and vaccine development.

Methods

Cell Culture

Human embryonic kidney HEK293T cells, human lung A549 cells, and African green monkey kidney Vero E6 cells were maintained at 37° C. and 5% CO2 in DMEM containing 10% FBS. Stable HEK293T and A549 cells expressing human ACE2 and TMPRSS2 were generated by transducing them with lentivirus particles carrying these two cDNAs.

SARS-COV-2 Virus Stock Preparation

The 2019-nCOV/USA-WA1/2020 isolate (NCBI accession number: MN985325) of SARS-COV-2 was obtained from the Centers for Disease Control and Prevention and BEI Resources. To generate the virus P1 stock, Vero E6 cells were infected with this isolate for 1 h at 37° C., removed the virus inoculum, rinsed the cell monolayer with 1×PBS, and added DMEM supplemented with 2% FBS. Three days later, when the cytopathic effect of the virus became visible, the culture medium was harvested, passed through a 0.2u filter, and stored at −80° C. To generate the virus P2 stock, Vero E6 cells were infected with the P1 stock at a multiplicity of infection (MOI) of 0.1 plaque forming units (PFU)/cell and the culture medium was harvested three days later using the same protocol as for the P1 stock. All experiments in this study were performed using the P2 stock.

Quantification of Virus Infectivity by Immunofluorescence

A549 and 293T cells expressing ACE2 and TMPRSS2 were infected with SARS-COV-2 (Washington isolate) at an MOI of 3 for indicated times (3, 6, 12, 18, and 24 hpi). After infection, supernatants were removed, and cells were fixed with 4% paraformaldehyde for 30 minutes at room temperature. Cells were then permeabilized with 0.1% of triton-X100 in PBS for 10 minutes and hybridized with Anti-SARS-COV Nucleocapsid (N) Protein (RABBIT) polyclonal antibody (1:2000, Rockland, #200-401-A50) at 4° C. overnight. Alexa Fluor 568 goat anti rabbit antibody (Invitrogen, A11011) were used as the secondary antibody for labelling virus infected cells. Finally, DAPI was added to label the nuclei. Immunofluorescent images were taken using an EVOS microscope with 10× lens and infection rates were calculated with ImageJ.

Plaque Assay

Vero E6 cells were used to determine the titer of our virus stock and to evaluate SARS-CoV-2 inactivation following lysis of infected cells in our HLA-IP buffer. Briefly, Vero E6 cells were seeded into a 12-well plate at a density of $2.5\times10^5$ cells per well, and the next day, infected them with serial 10-fold dilutions of the virus stock (for titration) or the A549 lysates (for the inactivation assay) for 1 h at 37° C. 1 ml per well of the overlay medium containing 2×DMEM (Gibco: #12800017) supplemented with 4% FBS was added and mixed at a 1:1 ratio with 1.2% Avicel (DuPont; RC-581) to obtain the final concentrations of 2% and 0.6% for FBS and Avicel, respectively. Three days later, the overlay medium was removed, the cell monolayer was removed with 1×PBS and the cells were fixed with 4% paraformaldehyde for 30 minutes at room temperature. 0.1% crystal violet was used to visualize the plaques.

Immunoprecipitation of HLA-I Peptide Complexes

Cells engineered to express SARS-COV-2 entry factors were seeded into nine 15 cm dishes (three dishes per time point) at a density of 15 million cells per dish for A549 cells and 20 million cells per dish for HEK293T cells. The next day, the cells were infected with SARS-COV-2 at a multiplicity of infection (MOI) of 3. To synchronize infection, the virus was bound to target cells in a small volume of opti-MEM on ice for one hour, followed by addition of DMEM/2% FBS and switching to 37° C. At 3, 6, 12, 18, and 24 h post-infection, the cells from three dishes were scraped into 2.5 ml/dish of cold lysis buffer (20 mM Tris, pH 8.0, 100 mM NaCl, 6 mM $MgCl_2$, 1 mM EDTA, 60 mM Octyl β-d-glucopyranoside, 0.2 mM Iodoacetamide, 1.5% Triton X-100, 50×Complete Protease Inhibitor Tablet-EDTA free and PMSF) obtaining a total of 9 ml lysate. This lysate was split into 6 eppendorf tubes, with each tube receiving 1.5 ml volume, and incubated on ice for 15 min with 1 ul of Benzonase (Thomas Scientific, E1014-25KU) to degrade nucleic acid. The lysates were then centrifuged at 4,000 rpm for 22 min at 4° C. and the supernatants were transferred to another set of six eppendorf tubes containing a mixture of pre-washed beads (Millipore Sigma, GE17-0886-01) and 50 ul of an MHC class I antibody (W6/32) (Santa Cruz Biotechnology, sc-32235). The immune complexes were captured on the beads by incubating on a rotor at 4° C. for 3 hr. The unbound lysates were kept for whole proteomics analysis while the beads were washed to remove non-specifically bound material. In total, nine washing steps were performed; one wash with 1 mL of cold lysis wash buffer (20 mM Tris, pH 8.0, 100 mM NaCl, 6 mM $MgCl_2$, 1 mM EDTA, 60 mM Octyl β-d-glucopyranoside, 0.2 mM Iodoacetamide, 1.5% Triton X-100), four washes with 1 mL of cold complete wash buffer (20 mM Tris, pH 8.0, 100 mM NaCl, 1 mM EDTA, 60 mM Octyl β-d-glucopyranoside, 0.2 mM Iodoacetamide), and four washes with 20 mM Tris pH 8.0 buffer. Dry beads were stored at −80° C. until mass-spectrometry analysis was performed.

HLA-I Immunopeptidome LC-MS/MS Data Generation

HLA peptides were eluted and desalted from beads as described previously (Sarkizova et al., 2020). After the primary elution step, HLA peptides were reconstituted in 3% ACN/5% FA and subjected to microscaled basic reverse phase separation. Briefly, peptides were loaded on Stage-tips with 2 punches of SDB-XC material (Empore 3M) and eluted in three fractions with increasing concentrations of ACN (5%, 10% and 30% in 0.1% $NH_4OH$, pH 10). For the time course experiment, one third of a pool of 6 IPs (for 12|18|24 h) or a pool of 2 IPs (for 3|6|24hpi) was also labeled with TMT6 (Thermo Fisher Scientific, lot #UC280588, A549: 12 h: 126, 3 h: 127, 18 h: 128, 129: 6 h, 24 h: 130, HEK293T: 3 h: 126, 12 h: 127, 6 h: 128, 18 h: 129, 24 h: 131) (Thompson et al., 2003), combined and desalted on a C18 Stage-tip, and then eluted into three fractions using basic reversed phase fractionation with increasing concentrations of ACN (10%, 15% and 50%) in 5 mM ammonium formate (pH 10). Peptides were reconstituted in 3% ACN/5% FA prior to loading onto an analytical column (25-30 cm, 1.9 μm C18 (Dr. Maisch HPLC GmbH), packed in-house PicoFrit 75 μm inner diameter, 10 μm emitter (New Objective)). Peptides were eluted with a linear gradient (EasyNanoLC 1200, Thermo Fisher Scientific) ranging from 6-30% Solvent B (0.1% FA in 90% ACN) over 84 min, 30-90% B over 9 min and held at 90% B for 5 min at 200 nl/min. MS/MS were acquired on a Thermo Orbitrap Exploris 480 equipped with FAIMS (Thermo Fisher Scientific) in data dependent acquisition. FAIMS CVs were set to −50 and −70 with a cycle time of 1.5s per FAIMS experiment. MS2 fill time was set to 100 ms, collision energy was 29CE or 32CE for TMT respectively.

Whole Proteome LC-MS/MS Data Generation

200 μL aliquot of HLA IP supernatants were reduced for 30 minutes with 5 mM DTT (Pierce DTT: A39255) and alkylated with 10 mM IAA (Sigma IAA: A3221-10VL) for 45 minutes both at 25° C. on a shaker (1000 rpm). Protein precipitation using methanol/chloroform was then performed. Briefly, methanol was added at a volume of 4× that of HLA IP supernatant aliquot. This was followed by a 1× volume of chloroform and 3× volume of water. The sample was mixed by vortexing and incubated at −20° C. for 1.5 hours. Samples were then centrifuged at 14,000 rpm for 10 minutes and the upper liquid layer was removed leaving a protein pellet. The pellet was rinsed with 3× volume of methanol, vortexed lightly, and centrifuged at 14,000 rpm for 10 minutes. Supernatant was removed and discarded without disturbing the pellet. Pellets were resuspended in 100 mM triethylammonium bicarbonate (pH 8.5) (TEAB). Samples were digested with LysC (1:50) for 2 h on a shaker (1000 rpm) at 25° C., followed by trypsin (1:50) overnight. Samples were acidified by 1% formic acid final concentration and dried. Samples were reconstituted 4.5 mM ammonium formate (pH 10) in 2% (vol/vol) acetonitrile and separated into four fractions using basic reversed phase fractionation on a C-18 Stage-tip. Fractions were eluted at 5%, 12.5%, 15%, and 50% ACN/4.5 mM ammonium formate (pH 10) and dried. Fractions were reconstituted in 3% ACN/5% FA, and 1 μg was used for LC-MS/MS analysis. MS/MS were acquired on a Thermo Orbitrap Exploris 480 (Thermo Fisher Scientific) in data dependent acquisition with FAIMS (MS2 isolation width 0.7m/z, cycle time 0.8, collision energy 30% for each CV) and without (MS2 isolation width 0.7m/z, top20 scans, collision energy 30%). Uninfected 1 μg single shot samples were analyzed similarly. For the time course experiment, the samples (12 h, 18 h, 24 h) were not fractionated and 1 μg was used for LC-MS/MS analysis, as described above except that FAIMS with −50, −65, and −85 CV was applied.

LC-MS/MS Data Interpretation

Peptide sequences were interpreted from MS/MS spectra using Spectrum Mill (v 7.1 pre-release) to search against a RefSeq-based sequence database containing 41,457 proteins mapped to the human reference genome (hg38) obtained via the UCSC Table Browser (https://genome.ucsc.edu/cgi-bin/hgTables) on Jun. 29, 2018, with the addition of 13 proteins encoded in the human mitochondrial genome, 264 common laboratory contaminant proteins, 553 human non-canonical small open reading frames, 28 SARS-COV2 proteins obtained from RefSeq derived from the original Wuhan-Hu-1 China isolate NC_045512.2 (https://www.ncbi.nlm-.nih.gov/nuccore/1798174254) (Wu et al., 2020), and 23 novel unannotated virus ORFs whose translation is supported by Ribo-seq (Finkel et al., 2020b) for a total of 42,337 proteins. Amongst the 28 annotated SARS-COV2 proteins we opted to omit the full length polyproteins ORF1a and ORF1ab, to simplify peptide-to-protein assignment, and instead represented ORF1ab as the mature 16 individual non-structural proteins that result from proteolytic processing of the 1a and 1ab polyproteins. The D614G variant of the SARS-Cov2 Spike protein that is commonly observed in European and American virus isolates was further added.

For immunopeptidome data MS/MS spectra were excluded from searching if they did not have a precursor MH+ in the range of 600-4000, had a precursor charge >5, or had a minimum of <5 detected peaks. Merging of similar spectra with the same precursor m/z acquired in the same chromatographic peak was disabled. Prior to searches, all MS/MS spectra had to pass the spectral quality filter with a sequence tag length >1 (i.e., minimum of 3 masses separated by the in-chain masses of 2 amino acids) based on HLA v3 peak detection. MS/MS search parameters included: ESI-QEXACTIVE-HCD-HLA-v3 scoring parameters; no-enzyme specificity; fixed modification: carbamidomethylation of cysteine; variable modifications: cysteinylation of cysteine, oxidation of methionine, deamidation of asparagine, acetylation of protein N-termini, and pyroglutamic acid at peptide N-terminal glutamine; precursor mass shift range of −18 to 81 Da; precursor mass tolerance of ±10 ppm; product mass tolerance of ±10 ppm, and a minimum matched peak intensity of 30%. Peptide spectrum matches (PSMs) for individual spectra were automatically designated as confidently assigned using the Spectrum Mill auto-validation module to apply target-decoy based FDR estimation at the PSM level of <1.5% FDR. For the TMT-labeled time course experiments, two parameters were revised: the MH+ range filter was 800-6000, and TMT labeling was required at lysine, but peptide N-termini were allowed to be either labeled or unlabeled. Relative abundances of peptides in the time-course experiments were determined in Spectrum Mill using TMT reporter ion intensity ratios from each PSM. TMT reporter ion intensities for the 3 time points split across two plexes were not corrected for isotopic impurities because the respective adjacent intervening labels were not included. Each peptide-level TMT ratio was calculated as the median of all PSMs contributing to that peptide. PSMs were excluded from the calculation that lacked a TMT label, or had a negative delta forward-reverse identification score (half of all false-positive identifications). Intensity values for each time point were normalized to the 24 h time point to compare between the 12|18|24 h and 3|6|24 h plex.

For whole proteome data MS/MS spectra were excluded from searching if they did not have a precursor MH+ in the range of 600-6000, had a precursor charge >5, had a minimum of <5 detected peaks, or failed the spectral quality filter with a sequence tag length >0 (i.e., minimum of 2 masses separated by the in-chain masses of 1 amino acid) based on ESI-QEXACTIVE-HCD-v4-30-20 peak detection. Similar spectra with the same precursor m/z acquired in the same chromatographic peak were merged. MS/MS search parameters included: ESI-QEXACTIVE-HCD-v4-30-20 scoring parameters; Trypsin allow P specificity with a maximum of 4 missed cleavages; fixed modification: carbamidomethylation of cysteine and seleno-cysteine; variable modifications: oxidation of methionine, deamidation of asparagine, acetylation of protein N-termini, pyroglutamic acid at peptide N-terminal glutamine, and pyro-carbamidomethylation at peptide N-terminal cysteine; precursor mass shift range of −18 to 64 Da; precursor mass tolerance of ±20 ppm; product mass tolerance of ±20 ppm, and a minimum matched peak intensity of 30%. Peptide spectrum matches (PSMs) for individual spectra were automatically designated as confidently assigned using the Spectrum Mill auto-validation module to apply target-decoy based FDR estimation at the PSM level of <1.0% FDR. Protein level data was summarized by top uses shared (SGT) peptide grouping and non-human contaminants were removed. SARS-COV-2 derived proteins were manually filtered to include identifications with >6% sequence coverage and at least 2 or more unique peptides. Postfiltering, intensity-based absolute quantification (iBAQ) was performed on the whole proteome LC-MS/MS as described in (Schwanhäusser et al., 2011). Briefly, iBAQ values were calculated as follows: log 10 (totalIntensity/numObservableTrypticPeptides), the total precursor ion intensity for each protein was calculated in Spectrum Mill as the sum of the precursor ion chromatographic peak areas (in MS1 spectra) for each precursor ion with a peptide spectrum match (MS/MS spectrum) to the protein, and the numObservableTrypticPeptides for each protein was calculated using the Spectrum Mill Protein Database utility as the number of tryptic peptides with length 8-40 amino acids, with no missed cleavages allowed. Of note, S coverage was 55% in the HEK293T and 44% in the A549 post 24 hour fractionated data, which may be due to the high levels of glycosylation. Lower peptide coverage may lead to underestimation of S protein in our data. Both log 10 transformed total intensity and iBAQ values were median normalized by subtracting sample specific medians and adding global medians for each abundance metrics and reported in Tables 6A-6B and data not shown.

To evaluate post infection protein level changes for a large set of proteins across cell lines and timepoints (FIGS. 9E-9F and 15E), all proteins detected in at least 6 out of 8 samples (A549 and HEK293T, each profiled at the 0, 3, 6, and 24 hpi) were retained in the analysis, with missing values imputed to the lowest $10^{th}$ percentile of the log 10iBAQ value distribution (Tyanova et al., 2016). A similar approach was used for the reanalysis of PXD020019 with values of proteins observed in eight of the twelve samples considered for imputation, and zero values replaced with a value below the minimum LFQ value reported.

Validation of Peptide Identifications

Peptide identifications were validated using synthetic peptides. Synthetic peptides were obtained from Genscript, at purity >90% purity and dissolved to 10 mM in DMSO. For LC-MS/MS measurements, peptides were pooled and further diluted with 0.1% FA/3% ACN to load 120 fmol/μl on column. One aliquot of synthetic peptides was also TMT labeled as described above. LC-MS/MS measurements were performed as described above. For plots, peak intensities in the experimental and the synthetic spectrum were normalized to the highest peak.

RNA-Seq of SARS-COV-2 Infected Cells

A549 and HEK293T cells were seeded into 6-well plates at a density of $5\times10^5$ cells per well (one well per condition). After 11-24 h, the cells were infected with SARS-COV-2 at an MOI of 3. At 12, 18 and 24 h post-infection, the cells were lysed in Trizol (Thermo, 15596026), and the total RNA was isolated using standard phenol chloroform extraction. Standard Illumina TruSeq Stranded mRNA (LT) was performed using 500 ng of total RNA (illumina, FC-122-2101). Oligo-dT beads were used to capture polyA-tailed RNA, followed by fragmentation and priming of the captured RNA (8 minutes at 94° C.). Immediately first strand cDNA synthesis was performed. Second strand cDNA synthesis was performed using second strand marking master and DNA polymerase 1 and RNase H. cDNA was adenylated at the 3' ends followed immediately by RNA end ligation single-index adapters (AR001-AR012). Library amplification was performed for 12-15 cycles under standard illumina library PCR conditions. Library quantitation was performed using Agilent 2200 TapeStation D1000 ScreenTape (Agilent, 5067-5582). RNA sequencing was performed on the NextSeq 550 System using a NextSeq V2.5 High Output 75 cycle kit (illumina, 20024906) or 150 cycles kit (illumina, 20024907) for paired-end sequencing (70nt of each end).

RNA Sequencing Reads Alignment

Sequencing reads were mapped to SARS-COV-2 genome (RefSeq NC_045512.2) and human transcriptome (Gencode v32). Alignment was performed using Bowtie version 1.2.2 (Langmead et al., 2009) with a maximum of two mismatches per read. The fraction of human and viral reads was determined based on the total number of reads aligned to either SARS-COV-2 or human transcripts.

In-Vitro MHC-Peptide Binding Assay

Classical competition assays, based on the inhibition of binding of a high affinity radiolabeled ligand to purified MHC molecules, were utilized to quantitatively measure peptide binding to HLA-A and -B class I MHC molecules. The assays were performed, and MHC purified, as detailed previously (Sidney et al., 2013). Briefly, 0.1-1 nM of radiolabeled peptide was co-incubated at room temperature with 1 μM to 1 nM of purified MHC in the presence of a cocktail of protease inhibitors and 1 μM B2-microglobulin. MHC bound radioactivity was determined following a two-day incubation by capturing MHC/peptide complexes on W6/32 (anti-class I) antibody coated Lumitrac 600 plates (Greiner Bio-one, Frickenhausen, Germany), and measuring bound cpm on the TopCount (Packard Instrument Co., Meriden, CT) microscintillation counter. The concentration of peptide yielding 50% inhibition of the binding of the radiolabeled peptide was calculated. Under the conditions utilized, where [label]< [MHC] and $IC_{50}$≥[MHC], the measured $IC_{50}$ values are reasonable approximations of the true Kd values (Cheng and Prusoff, 1973; Gulukota et al., 1997). Each competitor peptide was tested at six different concentrations covering a 100,000-fold dose range, and in three or more independent experiments. As a positive control, the unlabeled version of the radiolabeled probe was also tested in each experiment.

HLA-A02 Transgenic Mice Immunization

Mice. HLA-A2 transgenic AAD mice were used in the experiments (B6. Cg-Immp2 [$^{Tg(HLA-A/H2-D)2Enge}$/J). These animals express a chimeric molecule, which contains peptide-binding α1 and α2 domains of the HLA-A2.1 molecule and the α3 domain of the mouse H-2 $D^d$ molecule, under the control of the HLA-A2.1 promoter in addition to mouse MHC H-$2^b$. These animals allow the testing of human T cell immune responses to HLA-A2 presented antigens. Animals were maintained and bred in the animal facility at Dana Farber Cancer Institute in compliance with the Institutional Animal Care and Use Committee.

Vaccinations. Five mice were immunized subcutaneously in the flank with a vaccine. The vaccine contained nine COVID19 peptides (50 μg each peptide per mice) emulsified in Complete Freunds Adjuvant (CFA BD Bioscience/Difco) supplemented with 20 μg PolyIC/LC (Hiltonol/Oncovir). 10 days post-vaccination, animals were euthanized using CO2, and Spleens were removed for Elispot assays.

Mouse Interferon-gamma Elispot assays. Elispot was performed using red blood cell-depleted mouse splenocytes (200,000 cells/well) co-incubated with the individual COVID19 peptides (10 μg/ml) in triplicate in Elispot plates (Millipore, Billerica, MA) for 18 h. Interferon-γ (IFNγ) secretion was detected using capture and detection antibodies as described (Mabtech AB, Nacka Strand, Sweden) and imaged using an ImmunoSpot Series Analyzer (Cellular Technology, Ltd, Cleveland, OH). HLA-A*02:01 restricted HIV-GAG peptide and non-stimulated wells were used as negative controls. Spot numbers were normalized by removing the average background spot numbers calculated from negative control wells. AntiCD3 (2C11 BD BioScience) and PHA was used as a positive control. 55 spot-forming units/$10^6$ cells and a ≥3-fold increase over baseline is used as a threshold for positive responses. Methods were described in detail previously (Keskin et al., 2015).

Pooled Peptides IFNγ ELISPOT Assay with Convalescent COVID-19 PBMCs

Peripheral blood samples were collected from COVID-19 convalescent patients and PBMC were isolated using ficoll density gradient centrifugation. PBMC were plated out in serum free T cell assay media at 2.5e5 cells per well in a Human IFNg single color ELISpot plate (ImmunoSpot). The canonical and non canonical pools (Table 7) and a commercial nucleocapsid overlapping peptide pool (JPT peptide Technologies) were added to duplicate wells at a concentration of 2 ug/ml of each peptide. A negative control well (to which just the equivalent concentration of DMSO was added) was used to assess background IFNg secretion. Cells were incubated for 16-20 hours at 37 degrees C. before developing according to manufacturer's instructions. Spots were counted using an ImmunoSpot CoreS6 ELISpot counter (ImmunoSpot). The negative control background was subtracted from the antigen wells and the results are shown as spot forming units (SFU) per 2.5e5 PBMC. A spot cut off of 8 after background subtraction is used here to denote a positive response.

Multiplexed Tetramer Assay and Single Cell Sequencing

Production of tetramer library pools. HLA-A*02:01, and HLA-B*07:02 extracellular domains were expressed in *E. coli* and refolded along with beta-2-microglobulin and UV-labile place-holder peptides KILGFVFJV (SEQ ID NO: 213), and AARGJTLAM (SEQ ID NO: 214), respectively (Altman and Davis, 2016). The MHC monomer was then purified by size exclusion chromatography (SEC). MHC tetramers were produced by mixing alkylated MHC monomers and azidylated streptavidin in 0.5 mM copper sulfate, 2.5 mM BTTAA and 5 mM ascorbic acid for up to 4 h on ice, followed by purification of highly multimeric fractions by SEC. Individual peptide exchange reactions containing 500 nM MHC tetramer and 60 μM peptide were exposed to long-wave UV (366 nm) at a distance of 2-5 cm for 30 min at 4° C., followed by 30 min incubation at 30° C. A biotinylated oligonucleotide barcode (Integrated DNA Technologies) was added to each individual reaction followed by 30 minute incubation at 4° C. Individual tetramer reactions were then pooled and concentrated using 30 kDa molecular weight cut-off centrifugal filter units (Amicon).

Cell Staining. Peripheral blood mononuclear cells (PBMCs) from convalescent COVID-19 positive donors or unexposed donors were obtained from Precision 4 Medicine (USA), the Massachusetts Consortium on Pathogen Readiness (MassCPR), or CTL (USA), all under appropriate informed consent. PBMCs were thawed, and CD8+ T cells were enriched by magnetic-activated cell sorting (MACS) using a CD8+ T Cell Isolation Kit (Miltenyi) following the manufacturer's protocol. The CD8+ T cells were then stained with 1 nM final concentration tetramer library in the presence of 2 mg/mL salmon sperm DNA in PBS with 0.5% BSA solution for 20 minutes. Cells were then labeled with anti-TCR ADT (IP26, BioLegend) for 15 minutes followed by washing. Tetramer bound cells were then labeled with PE conjugated anti-DKDDDDK-Flag antibody (BioLegend) followed by dead cell discrimination using 7-amino-actinomycin D (7-AAD). The live, tetramer positive cells were sorted using a Sony MA900 Sorter (Sony).

Single-cell Sequencing. Tetramer positive cells were counted by Nexcelom Cellometer (Lawrence, MA, USA) using AOPI stain following manufacturer's recommended conditions. Single-cell encapsulations were generated utilizing 5' v1 Gem beads from 10× Genomics (Pleasanton, CA, USA) on a 10× Chromium controller and downstream TCR, and Surface marker libraries were made following manufacturer recommended conditions. All libraries were quantified on a BioRad CFX 384 (Hercules, CA, USA) using Kapa Biosystems (Wilmington, MA, USA) library quantified kits and pooled at an equimolar ratio. TCRs, surface markers, and tetramer generated libraries were sequenced on Illumina (San Diego, CA, USA) NextSeq550 instruments.

Initial analysis and preprocessing. Hydrogel-based RNA-seq data were analyzed using the Cell Ranger package from 10× Genomics (v3.1.0) with the GRCh38 human expression reference (v3.0.0). Except where noted, Scanpy (v1.6.0, (Wolf et al., 2018)) was used to perform the subsequent single cell analyses. Any exogenous control cells identified by TCR clonotype were removed before further gene expression processing. Hydrogels that contain UMIs for less than 300 genes were excluded. Genes that were detected in less than 3 cells were also excluded from further analysis. The following additional quality control thresholds were also enforced. To remove data generated from cells likely to be damaged, upper thresholds were set for percent UMIs arising from mitochondrial genes (13%). To exclude data likely arising from multiple cells captured in a single drop, upper thresholds were set for total UMI counts based on individual distributions from each encapsulation (from 1500 to 3000 UMIs). A lower threshold of 10% was set for UMIs arising from ribosomal protein genes. Finally, an upper threshold of 5% of UMIs was set for the MALAT1 gene. Any hydrogel outside of any of the thresholds was omitted from further analysis. A total of 15,683 hydrogels were carried forward. Gene expression data were normalized to counts per 10,000 UMIs per cell (CP10K) followed by log 1p transformation: In (CP10K+1).

Scoring pMHC-TCR interactions. Tetramer data analysis was performed using Python 3.7.3. For each single-cell encapsulation, tetramer UMI counts (columns) were matrixed by cell (rows) and log-transformed. The matrix was then Z-score transformed row-wise and subsequently, median-centered by column. Means were calculated by clonotype, and those with a value greater than 4 were characterized as positive interactions.

Clustering and Automated Annotation. Highly variable genes were identified (1,567) and scaled to have a mean of zero and unit variance. They were then provided to scanorama (v1.7, (Hie et al., 2019)) to perform batch integration and dimension reduction. These data were used to generate the nearest neighbor graph which was in turn used to generate a UMAP representation that was used for Leiden clustering. The hydrogel data (not scaled to mean zero, unit variance, and before extraction of highly variable genes) were labeled with cluster membership and provided to SingleR (v1.4.0, (Aran et al., 2019)) using the following references from Celldex (v1.0.0, (Aran et al., 2019)): MonacoImmuneData, DatabaseImmuneCellExpressionData, and BlueprintEncodeData. SingleR was used to annotate the clusters with their best-fit match from the cell types in the references. Clusters that yielded cell types other than types of the T Cell lineage were removed from consideration and the process was repeated starting from the batch integration step. The best-fit annotations from SingleR after the second round of clustering and annotation were assigned as putative labels for each Leiden cluster.

Scoring Clusters with Functional Gene Panels. In order to provide corroboration for the SingleR best-fit annotations and further evidence as to the phenotype of the clusters, gene panels representing functional categories (Naïve, Effector, Memory, Exhaustion, Proliferation) were used to score each hydrogel's expression profiles using scanpy's "score_genes" function (Wolf et al., 2018) which compares the mean expression values of the target gene set against a larger set of randomly chosen genes that represent background expression levels. The gene panels for each class were (Su et al., 2020): Naïve-TCF7, LEF1, CCR7; Effector-GZMB, PRF1, GNLY; Memory—AQP3, CD69, GZMK; Exhaustion-PDCD1, TIGIT, LAG3; Proliferation—MKI67, TYMS. The gene expression matrix for all hydrogels were first imputed using the MAGIC algorithm (v2.0.4, (van Dijk et al., 2018)). These functional scores were the only data generated from imputed expression values.

HLA-I Antigen Presentation Prediction

HLAthena, a prediction tool trained on endogenous LC-MS/MS-identified epitope data, was used to predict HLA class I presentation for all unique 8-11mer SARS-Cov-2 peptides across 31 HLA-A, 40 HLA-B and 21 HLA-C alleles (Sarkizova et al., 2020).

HLA Allele Frequencies and Coverage Estimates

World frequencies of HLA-A,-B, and -C allele in Table 8B are based on a meta-analysis of high-resolution HLA allele frequency data describing 497 population samples representing approximately 66,800 individuals from throughout the world (Solberg et al., 2008), downloaded from http://pypop.org/popdata/2008/byfreq-A.php.html, http://pypop.org/popdata/2008/byfreq-B.php.html, http://www.pypop.org/popdata/2008/byfreq-C.php. Subpopulation frequencies for AFA, API, EUR, HIS, and USA were obtained from supplementary data in (Poran et al., 2020).

The cumulative phenotypic frequency (CPF) of peptides was calculated using $CPF=1-(1-\Sigma_{i \in C} p_i)^2$, assuming Hardy-Weinberg proportions for the HLA genotypes (Dawson et al., 2001), where $p_i$ is the population frequency of the $i^{th}$ alleles within a subset of HLA-A,-B, or C alleles, denoted C. Coverage across HLA-A,-B, and -C alleles was calculated similarly: $CPF=1-(1-\Sigma_{i \in A} p_i)^2*(1-\Sigma_{i \in B} p_i)^2*(1-\Sigma_{i \in C} p_i)^2$, where A, B, and C denote a subset of HLA-A, -B, and/or -C alleles for which the coverage is computed, as recently done in (Poran et al., 2020).

References for Example 2

Abelin, J. G., Keskin, D. B., Sarkizova, S., Hartigan, C. R., Zhang, W., Sidney, J., Stevens, J., Lane, W., Zhang, G. L., Eisenhaure, T. M., et al. (2017). Mass Spectrometry Profiling of HLA-Associated Peptidomes in Mono-allelic Cells Enables More Accurate Epitope Prediction. Immunity 46, 315-326.

Abelin, J. G., Harjanto, D., Malloy, M., Suri, P., Colson, T., Goulding, S. P., Creech, A. L., Serrano, L. R., Nasir, G., Nasrullah, Y., et al. (2019). Defining HLA-II Ligand Processing and Binding Rules with Mass Spectrometry Enhances Cancer Epitope Prediction. Immunity 51, 766-779.e17.

Acharya, D., Liu, G., and Gack, M. U. (2020). Dysregulation of type I interferon responses in COVID-19. Nat. Rev. Immunol. 20, 397-398.

Altman, J. D., and Davis, M. M. (2016). MHC-Peptide Tetramers to Visualize Antigen-Specific T Cells. Curr. Protoc. Immunol. 115, 17.3.1-17.3.44.

Altmann, D. M., and Boyton, R. J. (2020). SARS-COV-2 T cell immunity: Specificity, function, durability, and role in protection. Sci Immunol 5.

Aran, D., Looney, A. P., Liu, L., Wu, E., Fong, V., Hsu, A., Chak, S., Naikawadi, R. P., Wolters, P. J., Abate, A. R., et al. (2019). Reference-based analysis of lung single-cell sequencing reveals a transitional profibrotic macrophage. Nat. Immunol. 20, 163-172.

Bassani-Sternberg, M., and Gfeller, D. (2016). Unsupervised HLA Peptidome Deconvolution Improves Ligand Prediction Accuracy and Predicts Cooperative Effects in Peptide-HLA Interactions. The Journal of Immunology 197, 2492-2499.

Burdette, D. L., Monroe, K. M., Sotelo-Troha, K., Iwig, J. S., Eckert, B., Hyodo, M., Hayakawa, Y., and Vance, R. E. (2011). STING is a direct innate immune sensor of cyclic di-GMP. Nature 478, 515-518.

Callaway, E. (2020). The race for coronavirus vaccines: a graphical guide. Nature 580, 576-577.

Campbell, K. M., Steiner, G., Wells, D. K., Ribas, A., and Kalbasi, A. (2020). Prediction of SARS-CoV-2 epitopes across 9360 HLA class I alleles. bioRxiv.

Chen, D.-Y., Khan, N., Close, B. J., Goel, R. K., Blum, B., Tavares, A. H., Kenney, D., Conway, H. L., Ewoldt, J. K., Kapell, S., et al. (2020a). SARS-COV-2 desensitizes host cells to interferon through inhibition of the JAK-STAT pathway. bioRxiv.

Chen, J., Brunner, A.-D., Cogan, J. Z., Nuñez, J. K., Fields, A. P., Adamson, B., Itzhak, D. N., Li, J. Y., Mann, M., Leonetti, M. D., et al. (2020b). Pervasive functional translation of noncanonical human open reading frames. Science 367, 1140-1146.

Cheng, Y., and Prusoff, W. H. (1973). Relationship between the inhibition constant (K1) and the concentration of inhibitor which causes 50 percent inhibition (150) of an enzymatic reaction. Biochem. Pharmacol. 22, 3099-3108.

Chong, C., Marino, F., Pak, H., Racle, J., Daniel, R. T., Müller, M., Gfeller, D., Coukos, G., and Bassani-Sternberg, M. (2018). High-throughput and Sensitive Immunopeptidomics Platform Reveals Profound Interferony-Mediated Remodeling of the Human Leukocyte Antigen (HLA) Ligandome. Mol. Cell. Proteomics 17, 533-548.

Croft, N. P., Smith, S. A., Wong, Y. C., Tan, C. T., Dudek, N. L., Flesch, I. E. A., Lin, L. C. W., Tscharke, D. C., and Purcell, A. W. (2013). Kinetics of antigen expression and epitope presentation during virus infection. PLOS Pathog. 9, e1003129.

Dan, J. M., Mateus, J., Kato, Y., Hastie, K. M., Yu, E. D., Faliti, C. E., Grifoni, A., Ramirez, S. I., Haupt, S., Frazier, A., et al. (2020). Immunological memory to SARS-COV-2 assessed for up to eight months after infection. bioRxiv.

Dawson, D. V., Ozgur, M., Sari, K., Ghanayem, M., and Kostyu, D. D. (2001). Ramifications of HLA class I polymorphism and population genetics for vaccine development. Genet. Epidemiol. 20, 87-106.

Demmers, L. C., Heck, A. J. R., and Wu, W. (2019). Pre-fractionation Extends but also Creates a Bias in the Detectable HLA Class I Ligandome. J. Proteome Res. 18, 1634-1643.

van Dijk, D., Sharma, R., Nainys, J., Yim, K., Kathail, P., Carr, A. J., Burdziak, C., Moon, K. R., Chaffer, C. L., Pattabiraman, D., et al. (2018). Recovering Gene Interactions from Single-Cell Data Using Data Diffusion. Cell 174, 716-729.e27.

Dominguez Andres, A., Feng, Y., Campos, A. R., Yin, J., Yang, C.-C., James, B., Murad, R., Kim, H., Deshpande, A. J., Gordon, D. E., et al. (2020). SARS-COV-2 ORF9c Is a Membrane-Associated Protein that Suppresses Antiviral Responses in Cells. bioRxiv.

Dutta, N. K., Mazumdar, K., and Gordy, J. T. (2020). The Nucleocapsid Protein of SARS-COV-2: a Target for Vaccine Development. J. Virol. 94.

Erhard, F., Halenius, A., Zimmermann, C., L'Hernault, A., Kowalewski, D. J., Weekes, M. P., Stevanovic, S., Zimmer, R., and Dölken, L. (2018). Improved Ribo-seq enables identification of cryptic translation events. Nat. Methods 15, 363-366.

Ferretti, A. P., Kula, T., Wang, Y., Nguyen, D. M. V., Weinheimer, A., Dunlap, G. S., Xu, Q., Nabilsi, N., Perullo, C. R., Cristofaro, A. W., et al. (2020). Unbiased Screens Show CD8+ T Cells of COVID-19 Patients Recognize Shared Epitopes in SARS-COV-2 that Largely Reside outside the Spike Protein. Immunity 53, 1095-1107.e3.

Finkel, Y., Schmiedel, D., Tai-Schmiedel, J., Nachshon, A., Winkler, R., Dobesova, M., Schwartz, M., Mandelboim, O., and Stern-Ginossar, N. (2020a). Comprehensive annotations of human herpesvirus 6A and 6B genomes reveal novel and conserved genomic features. Elife 9.

Finkel, Y., Mizrahi, O., and Nachshon, A. (2020b). The coding capacity of SARS-COV-2. bioRxiv.

Gallagher, K., and Maus, M. V. Evaluation of SARS-COV-2-specific T cell responses against wild type and spike variants using standardized IFNg release assays. In Preparation.

Girdlestone, J. (1995). Regulation of HLA class I loci by interferons. Immunobiology 193, 229-237.

Gordon, D. E., Jang, G. M., Bouhaddou, M., Xu, J., Obernier, K., White, K. M., O'Meara, M. J., Rezelj, V. V., Guo, J. Z., Swaney, D. L., et al. (2020). A SARS-COV-2 protein interaction map reveals targets for drug repurposing. Nature 583, 459-468.

Gragert, L., Madbouly, A., Freeman, J., and Maiers, M. (2013). Six-locus high resolution HLA haplotype frequencies derived from mixed-resolution DNA typing for the entire US donor registry. Hum. Immunol. 74, 1313-1320.

Grifoni, A., Weiskopf, D., Ramirez, S. I., Mateus, J., Dan, J. M., Moderbacher, C. R., Rawlings, S. A., Sutherland, A., Premkumar, L., Jadi, R. S., et al. (2020a). Targets of T Cell Responses to SARS-COV-2 Coronavirus in Humans with COVID-19 Disease and Unexposed Individuals. Cell 181, 1489-1501.e15.

Grifoni, A., Sidney, J., Zhang, Y., Scheuermann, R. H., Peters, B., and Sette, A. (2020b). A Sequence Homology and Bioinformatic Approach Can Predict Candidate Targets for Immune Responses to SARS-COV-2. Cell Host Microbe 27, 671-680.e2.

Gulukota, K., Sidney, J., Sette, A., and DeLisi, C. (1997). Two complementary methods for predicting peptides binding major histocompatibility complex molecules. J. Mol. Biol. 267, 1258-1267.

Habel, J. R., Nguyen, T. H. O., van de Sandt, C. E., Juno, J. A., Chaurasia, P., Wragg, K., Koutsakos, M., Hensen, L., Jia, X., Chua, B., et al. (2020). Suboptimal SARS-COV-2-specific CD8+ T cell response associated with the prominent HLA-A*02:01 phenotype. Proceedings of the National Academy of Sciences 117, 24384-24391.

Hansen, T. H., and Bouvier, M. (2009). MHC class I antigen presentation: learning from viral evasion strategies. Nat. Rev. Immunol. 9, 503-513.

Hickman, H. D., Mays, J. W., Gibbs, J., Kosik, I., Magadán, J. G., Takeda, K., Das, S., Reynoso, G. V., Ngudiankama, B. F., Wei, J., et al. (2018). Influenza A Virus Negative Strand RNA Is Translated for CD8+ T Cell Immunosurveillance. J. Immunol. 201, 1222-1228.

Hie, B., Bryson, B., and Berger, B. (2019). Efficient integration of heterogeneous single-cell transcriptomes using Scanorama. Nat. Biotechnol. 37, 685-691.

Ingolia, N. T., Ghaemmaghami, S., Newman, J. R. S., and Weissman, J. S. (2009). Genome-wide analysis in vivo of translation with nucleotide resolution using ribosome profiling. Science 324, 218-223.

Ingolia, N. T., Lareau, L. F., and Weissman, J. S. (2011). Ribosome profiling of mouse embryonic stem cells reveals the complexity and dynamics of mammalian proteomes. Cell 147, 789-802.

Ingolia, N. T., Brar, G. A., Stern-Ginossar, N., Harris, M. S., Talhouarne, G. J. S., Jackson, S. E., Wills, M. R., and Weissman, J. S. (2014). Ribosome profiling reveals pervasive translation outside of annotated protein-coding genes. Cell Rep. 8, 1365-1379.

Jackson, L. A., Anderson, E. J., Rouphael, N. G., Roberts, P. C., Makhene, M., Coler, R. N., Mccullough, M. P., Chappell, J. D., Denison, M. R., Stevens, L. J., et al. (2020). An mRNA vaccine against SARS-COV-2-preliminary report. N. Engl. J. Med.

Javitt, A., Barnea, E., Kramer, M. P., Wolf-Levy, H., Levin, Y., Admon, A., and Merbl, Y. (2019). Pro-inflammatory Cytokines Alter the Immunopeptidome Landscape by Modulation of HLA-B Expression. Front. Immunol. 10, 141.

Kared, H., Redd, A. D., Bloch, E. M., Bonny, T. S., Sumatoh, H. R., Kairi, F., Carbajo, D., Abel, B., Newell, E. W., Bettinotti, M., et al. (2021). SARS-COV-2-specific CD8+ T cell responses in convalescent COVID-19 individuals. J. Clin. Invest.

Keskin, D. B., Reinhold, B. B., Zhang, G. L., Ivanov, A. R., Karger, B. L., and Reinherz, E. L. (2015). Physical detection of influenza A epitopes identifies a stealth subset on human lung epithelium evading natural CD8 immunity. Proc. Natl. Acad. Sci. U.S.A 112, 2151-2156.

Ketteler, R. (2012). On programmed ribosomal frameshifting: the alternative proteomes. Front. Genet. 3, 242.

Kim, D., Lee, J.-Y., Yang, J.-S., Kim, J. W., Kim, V. N., and Chang, H. (2020). The Architecture of SARS-COV-2 Transcriptome. Cell 181, 914-921.e10.

Langmead, B., Trapnell, C., Pop, M., and Salzberg, S. L. (2009). Ultrafast and memory-efficient alignment of short DNA sequences to the human genome. Genome Biol. 10, R25.

Le Bert, N., Tan, A. T., Kunasegaran, K., Tham, C. Y. L., Hafezi, M., Chia, A., Chng, M. H. Y., Lin, M., Tan, N., Linster, M., et al. (2020). SARS-COV-2-specific T cell immunity in cases of COVID-19 and SARS, and uninfected controls. Nature.

Ledford, H. (2021). How "killer" T cells could boost COVID immunity in face of new variants. Nature.

Lu, R., Zhao, X., Li, J., Niu, P., Yang, B., Wu, H., Wang, W., Song, H., Huang, B., Zhu, N., et al. (2020). Genomic characterisation and epidemiology of 2019 novel coronavirus: implications for virus origins and receptor binding. Lancet 395, 565-574.

Lunemann, S., Schöbel, A., Kah, J., Fittje, P., Hölzemer, A., Langeneckert, A. E., Hess, L. U., Poch, T., Martrus, G., Garcia-Beltran, W. F., et al. (2018). Interactions Between KIR3DS1 and HLA-F Activate Natural Killer Cells to Control HCV Replication in Cell Culture. Gastroenterology 155, 1366-1371.e3.

Maness, N.J., Walsh, A. D., Piaskowski, S. M., Furlott, J., Kolar, H. L., Bean, A. T., Wilson, N. A., and Watkins, D. I. (2010). CD8+ T cell recognition of cryptic epitopes is a ubiquitous feature of AIDS virus infection. J. Virol. 84, 11569-11574.

McMurtrey, C. P., Lelic, A., Piazza, P., Chakrabarti, A. K., Yablonsky, E. J., Wahl, A., Bardet, W., Eckerd, A., Cook, R. L., Hess, R., et al. (2008). Epitope discovery in West Nile virus infection: Identification and immune recognition of viral epitopes. Proc. Natl. Acad. Sci. U.S.A 105, 2981-2986.

Moderbacher, C. R., Ramirez, S. I., Dan, J. M., Grifoni, A., Hastie, K. M., Weiskopf, D., Belanger, S., Abbott, R. K., Kim, C., Choi, J., et al. (2020). Antigen-specific adaptive immunity to SARS-CoV-2 in acute COVID-19 and associations with age and disease severity. Cell.

Monteil, V., Kwon, H., Prado, P., Hagelkrüys, A., Wimmer, R. A., Stahl, M., Leopoldi, A., Garreta, E., Hurtado Del Pozo, C., Prosper, F., et al. (2020). Inhibition of SARS-COV-2 Infections in Engineered Human Tissues Using Clinical-Grade Soluble Human ACE2. Cell 181, 905-913.e7.

Mulligan, M. J., Lyke, K. E., Kitchin, N., Absalon, J., Gurtman, A., Lockhart, S., Neuzil, K., Raabe, V., Bailey, R., Swanson, K. A., et al. (2020). Phase 1/2 study of COVID-19 RNA vaccine BNT162b1 in adults. Nature.

Neefjes, J., Jongsma, M. L. M., Paul, P., and Bakke, O. (2011). Towards a systems understanding of MHC class I and MHC class II antigen presentation. Nat. Rev. Immunol. 11, 823-836.

Nguyen, A., David, J. K., Maden, S. K., Wood, M. A., Weeder, B. R., Nellore, A., and Thompson, R. F. (2020). Human leukocyte antigen susceptibility map for SARS-COV-2. J. Virol.

Ouspenskaia, T., Law, T., Clauser, K. R., and Klaeger, S. (2020). Thousands of novel unannotated proteins expand the MHC I immunopeptidome in cancer. bioRxiv.

Poran, A., Harjanto, D., Malloy, M., Arieta, C. M., Rothenberg, D. A., Lenkala, D., van Buuren, M. M., Addona, T. A., Rooney, M. S., Srinivasan, L., et al. (2020). Sequence-based prediction of SARS-COV-2 vaccine targets using a mass spectrometry-based bioinformatics predictor identifies immunogenic T cell epitopes. Genome Med. 12, 70.

Puelles, V. G., Lütgehetmann, M., Lindenmeyer, M. T., Sperhake, J. P., Wong, M. N., Allweiss, L., Chilla, S., Heinemann, A., Wanner, N., Liu, S., et al. (2020). Multiorgan and Renal Tropism of SARS-COV-2. N. Engl. J. Med. 383, 590-592.

Redd, A. D., Nardin, A., Kared, H., Bloch, E. M., Pekosz, A., Laeyendecker, O., Abel, B., Fehlings, M., Quinn, T. C., and Tobian, A. A. (2021). CD8+ T cell responses in COVID-19 convalescent individuals target conserved epitopes from multiple prominent SARS-COV-2 circulating variants. medRxiv.

Rucevic, M., Kourjian, G., Boucau, J., Blatnik, R., Garcia Bertran, W., Berberich, M. J., Walker, B. D., Riemer, A. B., and Le Gall, S. (2016). Analysis of Major Histocompatibility Complex-Bound HIV Peptides Identified from Various Cell Types Reveals Common Nested Peptides and Novel T Cell Responses. J. Virol. 90, 8605-8620.

Ruiz Cuevas, M. V., Hardy, M.-P., Hollý, J., Bonneil, É., Durette, C., Courcelles, M., Lanoix, J., Côté, C., Staudt, L. M., Lemieux, S., et al. (2021). Most non-canonical proteins uniquely populate the proteome or immunopeptidome. Cell Rep. 34, 108815.

Sarkizova, S., Klaeger, S., Le, P. M., Li, L. W., Oliveira, G., Keshishian, H., Hartigan, C. R., Zhang, W., Braun, D. A., Ligon, K. L., et al. (2020). A large peptidome dataset improves HLA class I epitope prediction across most of the human population. Nat. Biotechnol. 38, 199-209.

Schellens, I. M., Meiring, H. D., Hoof, I., Spijkers, S. N., Poelen, M. C. M., van Gaans-van den Brink, J. A. M., Costa, A. I., Vennema, H., Keşmir, C., van Baarle, D., et al. (2015). Measles Virus Epitope Presentation by HLA:

Novel Insights into Epitope Selection, Dominance, and Microvariation. Front. Immunol. 6, 546.

Schmidt, N., Lareau, C. A., Keshishian, H., Ganskih, S., Schneider, C., Hennig, T., Melanson, R., Werner, S., Wei, Y., Zimmer, M., et al. (2020). The SARS-COV-2 RNA-protein interactome in infected human cells. Nat Microbiol.

Schwanhäusser, B., Busse, D., Li, N., Dittmar, G., Schuchhardt, J., Wolf, J., Chen, W., and Selbach, M. (2011). Global quantification of mammalian gene expression control. Nature 473, 337-342.

Sekine, T., Perez-Potti, A., Rivera-Ballesteros, O., Strålin, K., Gorin, J.-B., Olsson, A., Llewellyn-Lacey, S., Kamal, H., Bogdanovic, G., Muschiol, S., et al. (2020). Robust T cell immunity in convalescent individuals with asymptomatic or mild COVID-19.

Shomuradova, A. S., Vagida, M. S., Sheetikov, S. A., Zornikova, K. V., Kiryukhin, D., Titov, A., Peshkova, J. O., Khmelevskaya, A., Dianov, D. V., Malasheva, M., et al. (2020). Zornikova, Dmitry Kiryukhin, Aleksei Titov, Iuliia O. Peshkova, Alexandra Khmelevskaya, Dmitry V. Dianov, Maria Malasheva, Anton Shmelev, Yana Serdyuk, Dmitry V. Bagaev, Anastasia Pivnyuk, Dmitrii S. Shcherbinin, Alexandra V. Maleeva, Naina T. Shakirova, Artem Pilunov, Dmitry B. Malko, Ekaterina G. Khamaganova, Bella Biderman, Alexander Ivanov, Mikhail Shugay, Grigory A. Efimov SARS-COV-2 Epitopes Are Recognized by a Public and Diverse Repertoire of Human T Cell Receptors. Immunity 53, 1245-12575.

Sidney, J., Southwood, S., Moore, C., Oseroff, C., Pinilla, C., Grey, H. M., and Sette, A. (2013). Measurement of MHC/peptide interactions by gel filtration or monoclonal antibody capture. Curr. Protoc. Immunol. Chapter 18, Unit 18.3.

Solberg, O.D., Mack, S., Lancaster, A. K., Single, R. M., Tsai, Y., Sanchez-Mazas, A., and Thomson, G. (2008). Balancing selection and heterogeneity across the classical human leukocyte antigen loci: a meta-analytic review of 497 population studies. Hum. Immunol. 69, 443-464.

Sonenberg, N., and Hinnebusch, A. G. (2009). Regulation of translation initiation in eukaryotes: mechanisms and biological targets. Cell 136, 731-745.

Starck, S. R., and Shastri, N. (2016). Nowhere to hide: unconventional translation yields cryptic peptides for immune surveillance. Immunol. Rev. 272, 8-16.

Stern-Ginossar, N., Weisburd, B., Michalski, A., Le, V. T. K., Hein, M. Y., Huang, S.-X., Ma, M., Shen, B., Qian, S.-B., Hengel, H., et al. (2012). Decoding human cytomegalovirus. Science 338, 1088-1093.

Stukalov, A., Girault, V., Grass, V., Bergant, V., Karayel, O., Urban, C., Haas, D. A., Huang, Y., Oubraham, L., Wang, A., et al. (2020). Multi-level proteomics reveals host-perturbation strategies of SARS-COV-2 and SARS-COV.

Su, Y., Chen, D., Yuan, D., Lausted, C., Choi, J., Dai, C. L., Voillet, V., Duvvuri, V. R., Scherler, K., Troisch, P., et al. (2020). Multi-Omics Resolves a Sharp Disease-State Shift between Mild and Moderate COVID-19. Cell 183, 1479-1495.e20.

Takagi, A., and Matsui, M. (2020). Identification of HLA-A*02:01-Restricted Candidate Epitopes Derived from the Nonstructural Polyprotein la of SARS-COV-2 That May Be Natural Targets of CD8 T Cell Recognition In Vivo. Journal of Virology 95.

Tarke, A., Sidney, J., Kidd, C. K., Dan, J. M., Ramirez, S. I., Yu, E. D., Mateus, J., da Silva Antunes, R., Moore, E., Rubiro, P., et al. (2020). Comprehensive analysis of T cell immunodominance and immunoprevalence of SARS-COV-2 epitopes in COVID-19 cases. bioRxiv.

Tarke, A., Sidney, J., Methot, N., Zhang, Y., Dan, J. M., Goodwin, B., Rubiro, P., Sutherland, A., da Silva Antunes, R., Frazier, A., et al. (2021). Negligible impact of SARS-COV-2 variants on CD4+ and CD8+ T cell reactivity in COVID-19 exposed donors and vaccinees.

Ternette, N., Yang, H., Partridge, T., Llano, A., Cedeño, S., Fischer, R., Charles, P. D., Dudek, N. L., Mothe, B., Crespo, M., et al. (2016). Defining the HLA class I-associated viral antigen repertoire from HIV-1-infected human cells. Eur. J. Immunol. 46, 60-69.

Thompson, A., Schäfer, J., Kuhn, K., Kienle, S., Schwarz, J., Schmidt, G., Neumann, T., Johnstone, R., Mohammed, A. K. A., and Hamon, C. (2003). Tandem mass tags: a novel quantification strategy for comparative analysis of complex protein mixtures by MS/MS. Anal. Chem. 75, 1895-1904.

Tyanova, S., Temu, T., Sinitcyn, P., Carlson, A., Hein, M. Y., Geiger, T., Mann, M., and Cox, J. (2016). The Perseus computational platform for comprehensive analysis of (prote) omics data. Nat. Methods 13, 731-740.

Wainwright, S. D., Biro, P. A., and Holmes, C. H. (2000). HLA-F is a predominantly empty, intracellular, TAP-associated MHC class Ib protein with a restricted expression pattern. J. Immunol. 164, 319-328.

Weiskopf, D., Schmitz, K. S., Raadsen, M. P., Grifoni, A., Okba, N. M. A., Endeman, H., van den Akker, J. P. C., Molenkamp, R., Koopmans, M. P. G., van Gorp, E. C. M., et al. (2020). Phenotype and kinetics of SARS-COV-2-specific T cells in COVID-19 patients with acute respiratory distress syndrome. Science Immunology 5, eabd2071.

Wolf, F. A., Angerer, P., and Theis, F. J. (2018). SCANPY: large-scale single-cell gene expression data analysis. Genome Biol. 19, 15.

Wu, F., Zhao, S., Yu, B., Chen, Y.-M., Wang, W., Song, Z.-G., Hu, Y., Tao, Z.-W., Tian, J.-H., Pei, Y.-Y., et al. (2020). A new coronavirus associated with human respiratory disease in China. Nature 579, 265-269.

Wu, T., Guan, J., Handel, A., Tscharke, D. C., Sidney, J., Sette, A., Wakim, L. M., Sng, X. Y. X., Thomas, P. G., Croft, N. P., et al. (2019). Quantification of epitope abundance reveals the effect of direct and cross-presentation on influenza CTL responses. Nat. Commun. 10, 2846.

Yang, N., Gibbs, J. S., Hickman, H. D., Reynoso, G. V., Ghosh, A. K., Bennink, J. R., and Yewdell, J. W. (2016). Defining Viral Defective Ribosomal Products: Standard and Alternative Translation Initiation Events Generate a Common Peptide from Influenza A Virus M2 and Ml mRNAs. The Journal of Immunology 196, 3608-3617.

Zhu, M.-S., Pan, Y., Chen, H.-Q., Shen, Y., Wang, X.-C., Sun, Y.-J., and Tao, K.-H. (2004). Induction of SARS-nucleoprotein-specific immune response by use of DNA vaccine. Immunol. Lett. 92, 237-243.

***

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. An immunogenic composition comprising:

one or more vectors each comprising one or more polynucleotides encoding one or more polypeptides, wherein the one or more polypeptides:

a. is capable of binding to Major Histocompatibility Complex (MHC) class I, b. is derived from one or more proteins of SARS-COV-2 by expression of an internal out-of-frame open reading frame (ORF) of SARS-COV-2, wherein the internal out-of-frame ORF is S.iORF1 or S.iORF2, and c. wherein at least one polypeptide of the one or more polypeptides derived from expression of S.iORF1 is MLLGSMLYM (SEQ ID NO: 4); or wherein at least one polypeptide of the one or more polypeptides is derived from expression of S.iORF1 or S.iORF2 is GPMVLRGLIT (SEQ ID NO: 6) or GLITLSYHL (SEQ ID NO: 5).

2. The immunogenic composition of claim 1, wherein the MHC class I is Human Leukocyte Antigen class I (HLA-I).

3. The immunogenic composition of claim 2, wherein the HLA-I is encoded by an HLA allele having a prediction rank score ranking cut-off of 0.1% or greater as determined with HLAthena.

4. The immunogenic composition of claim 2, wherein the HLA-1 is encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, HLA-C*07:02; HLA-A*01:01; HLA-A*02:06; HLA-A*26:01; HLA-A*02:07; HLA-A*29:02; HLA-A*02:03; HLA-A*30:02; HLA-A*32:01; HLA-A*68:02; HLA-A*02:05; HLA-A*02:02; HLA-A*36:01; HLA-A*02:11; HLA-A*02:04; HLA-B*35:01; HLA-B*51:01; HLA-B*40:01; HLA-B*40:02; HLA-B*07:02; HLA-B*07:04; HLA-B*08:01; HLA-B*13:01; HLA-B*46:01; HLA-B*52:01; HLA-B*44:02; HLA-B*40:06; HLA-B*13:02; HLA-B*56:01; HLA-B*54:01; HLA-B*15:02; HLA-B*35:07; HLA-B*27:05; HLA-B*15:03; HLA-B*42:01; HLA-B*55:02; HLA-B*45:01; HLA-B*50:01; HLA-B*35:03; HLA-B*49:01; HLA-B*58:02; HLA-B*15:17; HLA-C*57:02; HLA-C*04:01; HLA-C*03:04; HLA-C*01:02; HLA-C*07:01; HLA-C*06:02; HLA-C*03:03; HLA-C*08:01; HLA-C*15:02; HLA-C*12:02; HLA-C*02:02; HLA-C*05:01; HLA-C*03:02; HLA-C*16:01; HLA-C*08:02; HLA-C*04:03; HLA-C*17:01; or HLA-C*17:04.

5. The immunogenic composition of claim 2, wherein the HLA-1 is encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, or HLA-C*07:02.

6. The immunogenic composition of claim 1, wherein one or more of the one or more polypeptides is capable of stimulating a T-cell response.

7. The immunogenic composition of claim 1, wherein at least one polypeptide of the one or more polypeptides derived from expression of S.iORF1 or S.iORF2 comprises one or more oxidized methionines.

8. The immunogenic composition of claim 7, wherein the at least one polypeptide is SEQ ID NO: 193 or 204.

9. The immunogenic composition of claim 1, wherein the one or more polypeptides are expressed and/or is bound by MHC-I 0-12, 0-11, 0-10, 0-9, 0-8, 0-7, 0-6, 0-5, 0-4, 0-3, 0-2, or 0-1 hours post infection.

10. The immunogenic composition of claim 1, wherein the immunogenic composition is a synthetic mRNA vaccine.

11. The immunogenic composition of claim 1, further comprising one or more SARS-COV-2 antigenic polypeptides capable of stimulating production of an antibody targeting SARS-COV-2, or one or more polynucleotides encoding the one or more SARS-COV-2 antigenic polypeptides.

12. The composition of claim 11, wherein the one or more SARS-CoV-2 antigenic polypeptides are from a nucleocapsid phosphoprotein of SARS-COV-2, a spike glycoprotein of SARS-COV-2, or a combination thereof.

13. A therapeutic composition comprising:

the immunogenic composition of claim 1;

one or more SARS-COV-2 antigenic polypeptides capable of stimulating production of an antibody targeting SARS-COV-2, or one or more polynucleotides encoding the one or more SARS-COV-2 antigenic polypeptides; and an anti-viral therapeutic.

14. The composition of claim 13, wherein the immunogenetic composition is formulated as a synthetic mRNA vaccine and wherein one or more polynucleotides encoding the one or more antigenic polypeptides are mRNA.

15. A method of treating or inhibiting a SARS-CoV-2 infection in a subject in need thereof comprising: administering, to the subject in need thereof, the immunogenic composition of claim 1 and one or more antigenic components capable of stimulating production of an antibody targeting SARS-COV-2; and an anti-viral therapeutic.

16. An immunogenic composition comprising:

a delivery vehicle comprising:

one or more polypeptides, one or more polynucleotides each encoding one or more of the one or more polypeptides, or any combination thereof, wherein the one or more polypeptides:

a. is capable of binding to Major Histocompatibility Complex (MHC) class I, and b. is derived from one or more proteins of SARS-COV-2 by expression of an internal out-of-frame open reading frame (ORF) of SARS-COV-2, wherein the internal out-of-frame ORF is S.iORF1 or S.iORF2, and wherein at least one polypeptide of the one or more polypeptides derived from expression of S.iORF1 is MLLGSMLYM (SEQ ID NO: 4); or wherein at least one polypeptide of the one or more polypeptides is derived from expression of S.iORF1 or S.iORF2 is GPMVLRGLIT (SEQ ID NO: 6) or GLITLSYHL (SEQ ID NO: 5).

17. The immunogenic composition of claim 16, wherein the MHC class I is Human Leukocyte Antigen class I (HLA-I).

18. The immunogenic composition of claim 17, wherein the HLA-1 is encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, HLA-C*07:02; HLA-A*01:01; HLA-A*02:06; HLA-A*26:01; HLA-A*02:07; HLA-A*29:02; HLA-A*02:03; HLA-A*30:02; HLA-A*32:01; HLA-A*68:02; HLA-A*02:05; HLA-A*02:02; HLA-A*36:01; HLA-A*02:11; HLA-A*02:04; HLA-B*35:01; HLA-B*51:01; HLA-B*40:01; HLA-B*40:02; HLA-B*07:02; HLA-B*07:04; HLA-B*08:01; HLA-B*13:01; HLA-B*46:01; HLA-B*52:01; HLA-B*44:02; HLA-B*40:06; HLA-B*13:02; HLA-B*56:01; HLA-B*54:01; HLA-B*15:02; HLA-B*35:07; HLA-B*27:05; HLA-B*15:03; HLA-B*42:01; HLA-B*55:02; HLA-B*45:01; HLA-B*50:01; HLA-B*35:03; HLA-B*49:01; HLA-B*58:02; HLA-B*15:17; HLA-C*57:02; HLA-C*04:01; HLA-C*03:04; HLA-C*01:02; HLA-C*07:01; HLA-C*06:02; HLA-C*03:03; HLA-C*08:01; HLA-C*15:02; HLA-C*12:02; HLA-C*02:02; HLA-C*05:01; HLA-C*03:02; HLA-C*16:01; HLA-C*08:02; HLA-C*04:03; HLA-C*17:01; or HLA-C*17:04.

19. The immunogenic composition of claim 17, wherein the HLA-1 is encoded by HLA-A*02:01, HLA-A*25:01, HLA-A*30:01, HLA-B*18:01, HLA-B*44:03, HLA-C*12:03, HLA-B*16:01, HLA-A*02:01, HLA-B*07:02, or HLA-C*07:02.

20. The immunogenic composition of claim 16, wherein one or more of the one or more polypeptides is capable of stimulating a T-cell response.

21. The immunogenic composition of claim 16, wherein at least one polypeptide of the one or more polypeptides derived from expression of S.iORF1 or S.iORF2 comprises one or more oxidized methionines.

22. The immunogenic composition of claim 21, wherein the at least one polypeptide is SEQ ID NO: 193 or 204.

23. The immunogenic composition of claim 16, further comprising one or more SARS-CoV-2 antigenic polypeptides capable of stimulating production of an antibody targeting SARS-CoV-2, or one or more polynucleotides encoding the one or more SARS-COV-2 antigenic polypeptides.

24. The immunogenic composition of claim 23, wherein the one or more SARS-COV-2 antigenic polypeptides are from a nucleocapsid phosphoprotein of SARS-COV-2, a spike glycoprotein of SARS-COV-2, or a combination thereof.

25. The immunogenic composition of claim 16, wherein the one or more polypeptides are expressed and/or is bound by MHC-I 0-12, 0-11, 0-10, 0-9, 0-8, 0-7, 0-6, 0-5, 0-4, 0-3, 0-2, or 0-1 hours post infection.

26. The immunogenic composition of claim 16, wherein the immunogenic composition is a synthetic mRNA vaccine.

27. The immunogenic composition of claim 26, wherein the immunogenetic composition is formulated as a synthetic mRNA vaccine and wherein one or more polynucleotides encoding the one or more antigenic polypeptides are mRNA.

28. A therapeutic composition comprising:

the immunogenic composition of claim 16;

one or more SARS-COV-2 antigenic polypeptides capable of stimulating production of an antibody targeting SARS-COV-2, or one or more polynucleotides encoding the one or more SARS-CoV-2 antigenic polypeptides; and an anti-viral therapeutic.

29. A method of treating or inhibiting a SARS-CoV-2 infection in a subject in need thereof comprising: administering, to the subject in need thereof, the immunogenic composition of claim 16 and one or more antigenic components capable of stimulating production of an antibody targeting SARS-COV-2; and an anti-viral therapeutic.

* * * * *